(12) United States Patent  (10) Patent No.: US 7,935,491 B2
Raitano et al.  (45) Date of Patent: May 3, 2011

(54) NUCLEIC ACID AND CORRESPONDING PROTEIN ENTITLED 24P4C12 USEFUL IN TREATMENT AND DETECTION OF CANCER

(75) Inventors: Arthur B. Raitano, Los Angeles, CA (US); Karen Jane Meyrick Morrison, Santa Monica, CA (US); Wangmao Ge, Los Angeles, CA (US); Pia M. Challita-Eid, Encino, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 11/518,610

(22) Filed: Sep. 8, 2006

(65) Prior Publication Data

US 2007/0053921 A1  Mar. 8, 2007

Related U.S. Application Data

(63) Continuation of application No. 10/306,631, filed on Nov. 27, 2002, now Pat. No. 7,244,827, which is a continuation-in-part of application No. 09/547,789, filed on Apr. 12, 2000, now Pat. No. 6,943,235.

(60) Provisional application No. 60/128,858, filed on Apr. 12, 1999.

(51) Int. Cl.
*G01N 33/53* (2006.01)
(52) U.S. Cl. .......................................................... 435/7.1
(58) Field of Classification Search .......................... None
See application file for complete search history.

(56) References Cited

U.S. PATENT DOCUMENTS

| | | | |
|---|---|---|---|
| 4,742,000 A | 5/1988 | Greene |
| 5,693,762 A | 12/1997 | Queen et al. |
| 6,312,922 B1 | 11/2001 | Edwards et al. |
| 6,551,795 B1 | 4/2003 | Rubenfield et al. |
| 6,682,736 B1 | 1/2004 | Hanson et al. |
| 6,747,137 B1 | 6/2004 | Weinstock et al. |
| 6,913,919 B2 | 7/2005 | Botstein et al. |
| 6,930,170 B2 | 8/2005 | Desnoyers et al. |
| 6,943,235 B1 | 9/2005 | Afar et al. |
| 6,953,836 B2 | 10/2005 | Desnoyers et al. |
| 6,965,108 B2 | 11/2005 | Bynum et al. |
| 6,972,185 B2 | 12/2005 | Desnoyers et al. |
| 7,018,811 B2 | 3/2006 | Botstein et al. |
| 7,019,116 B2 | 3/2006 | Desnoyers et al. |
| 7,029,873 B2 | 4/2006 | Desnoyers et al. |
| 7,034,106 B2 | 4/2006 | Desnoyers et al. |
| 7,034,122 B2 | 4/2006 | Desnoyers et al. |
| 7,034,136 B2 | 4/2006 | Goddard et al. |
| 7,244,827 B2 | 7/2007 | Raitano et al. |
| 7,288,251 B2 | 10/2007 | Bedian et al. |
| 7,303,895 B1 | 12/2007 | O'Regan et al. |
| 7,378,492 B2 | 5/2008 | Chawla et al. |
| 2002/0022248 A1 | 2/2002 | Xu et al. |
| 2002/0103125 A1 | 8/2002 | Ashkenazi et al. |
| 2002/0119130 A1 | 8/2002 | Eaton et al. |
| 2002/0123463 A1 | 9/2002 | Ashkenazi et al. |
| 2002/0127576 A1 | 9/2002 | Ashkenazi et al. |
| 2002/0132252 A1 | 9/2002 | Ashkenazi et al. |
| 2002/0142961 A1 | 10/2002 | Ashkenazi et al. |
| 2002/0160384 A1 | 10/2002 | Ashkenazi et al. |
| 2002/0177164 A1 | 11/2002 | Ashkenazi et al. |
| 2002/0182638 A1 | 12/2002 | Eaton et al. |
| 2002/0183493 A1 | 12/2002 | Eaton et al. |
| 2002/0183494 A1 | 12/2002 | Eaton et al. |
| 2002/0192763 A1 | 12/2002 | Xu et al. |
| 2002/0193299 A1 | 12/2002 | Ashkenazi et al. |
| 2002/0193300 A1 | 12/2002 | Ashkenazi et al. |
| 2002/0197615 A1 | 12/2002 | Ashkenazi et al. |
| 2002/0198148 A1 | 12/2002 | Ashkenazi et al. |
| 2003/0003531 A1 | 1/2003 | Ashkenazi et al. |
| 2003/0008297 A1 | 1/2003 | Ashkenazi et al. |
| 2003/0009012 A1 | 1/2003 | Eaton et al. |
| 2003/0009013 A1 | 1/2003 | Eaton et al. |
| 2003/0013855 A1 | 1/2003 | Eaton et al. |
| 2003/0017476 A1 | 1/2003 | Ashkenazi et al. |
| 2003/0017981 A1 | 1/2003 | Ashkenazi et al. |
| 2003/0017982 A1 | 1/2003 | Ashkenazi et al. |
| 2003/0018168 A1 | 1/2003 | Eaton et al. |
| 2003/0018172 A1 | 1/2003 | Eaton et al. |
| 2003/0018173 A1 | 1/2003 | Eaton et al. |
| 2003/0018183 A1 | 1/2003 | Eaton et al. |

(Continued)

FOREIGN PATENT DOCUMENTS

EP  1 033 401  6/2000

(Continued)

OTHER PUBLICATIONS

Greenbaum et al (Genome Biology, 2003, (4):9, 117.1-117.8).*

(Continued)

*Primary Examiner* — Sean E Aeder
(74) *Attorney, Agent, or Firm* — Morrison & Foerster LLP

(57) ABSTRACT

A novel gene 024P4C12 (also designated 24P4C12) and its encoded protein, and variants thereof, are described wherein 24P4C12 exhibits tissue specific expression in normal adult tissue, and is aberrantly expressed in the cancers listed in Table I. Consequently, 24P4C12 provides a diagnostic, prognostic, prophylactic and/or therapeutic target for cancer. The 24P4C12 gene or fragment thereof, or its encoded protein, or variants thereof, or a fragment thereof, can be used to elicit a humoral or cellular immune response; antibodies or T cells reactive with 24P4C12 can be used in active or passive immunization.

6 Claims, 58 Drawing Sheets

U.S. PATENT DOCUMENTS

| | | | |
|---|---|---|---|
| 2003/0022187 A1 | 1/2003 | Ashkenazi et al. |
| 2003/0023042 A1 | 1/2003 | Eaton et al. |
| 2003/0027162 A1 | 2/2003 | Ashkenazi et al. |
| 2003/0027163 A1 | 2/2003 | Ashkenazi et al. |
| 2003/0027212 A1 | 2/2003 | Eaton et al. |
| 2003/0027754 A1 | 2/2003 | Ashkenazi et al. |
| 2003/0027985 A1 | 2/2003 | Ashkenazi et al. |
| 2003/0027986 A1 | 2/2003 | Eaton et al. |
| 2003/0027992 A1 | 2/2003 | Eaton et al. |
| 2003/0027993 A1 | 2/2003 | Eaton et al. |
| 2003/0032023 A1 | 2/2003 | Ashkenazi et al. |
| 2003/0036634 A1 | 2/2003 | Eaton et al. |
| 2003/0040473 A1 | 2/2003 | Ashkenazi et al. |
| 2003/0044806 A1 | 3/2003 | Ashkenazi et al. |
| 2003/0045463 A1 | 3/2003 | Ashkenazi et al. |
| 2003/0045684 A1 | 3/2003 | Eaton et al. |
| 2003/0049638 A1 | 3/2003 | Ashkenazi et al. |
| 2003/0049681 A1 | 3/2003 | Ashkenazi et al. |
| 2003/0049682 A1 | 3/2003 | Ashkenazi et al. |
| 2003/0049735 A1 | 3/2003 | Eaton et al. |
| 2003/0050462 A1 | 3/2003 | Eaton et al. |
| 2003/0050465 A1 | 3/2003 | Eaton et al. |
| 2003/0054359 A1 | 3/2003 | Ashkenazi et al. |
| 2003/0054403 A1 | 3/2003 | Ashkenazi et al. |
| 2003/0054404 A1 | 3/2003 | Ashkenazi et al. |
| 2003/0054987 A1 | 3/2003 | Ashkenazi et al. |
| 2003/0059780 A1 | 3/2003 | Ashkenazi et al. |
| 2003/0059782 A1 | 3/2003 | Ashkenazi et al. |
| 2003/0059783 A1 | 3/2003 | Ashkenazi et al. |
| 2003/0059831 A1 | 3/2003 | Ashkenazi et al. |
| 2003/0059832 A1 | 3/2003 | Ashkenazi et al. |
| 2003/0059833 A1 | 3/2003 | Ashkenazi et al. |
| 2003/0060407 A1 | 3/2003 | Ashkenazi et al. |
| 2003/0060600 A1 | 3/2003 | Eaton et al. |
| 2003/0060601 A1 | 3/2003 | Eaton et al. |
| 2003/0060602 A1 | 3/2003 | Eaton et al. |
| 2003/0064375 A1 | 4/2003 | Ashkenazi et al. |
| 2003/0065143 A1 | 4/2003 | Eaton et al. |
| 2003/0065161 A1 | 4/2003 | Eaton et al. |
| 2003/0068623 A1 | 4/2003 | Ashkenazi et al. |
| 2003/0068647 A1 | 4/2003 | Ashkenazi et al. |
| 2003/0069394 A1 | 4/2003 | Eaton et al. |
| 2003/0069403 A1 | 4/2003 | Ashkenazi et al. |
| 2003/0073090 A1 | 4/2003 | Ashkenazi et al. |
| 2003/0073623 A1 | 4/2003 | Drmanac et al. |
| 2003/0078387 A1 | 4/2003 | Eaton et al. |
| 2003/0082546 A1 | 5/2003 | Ashkenazi et al. |
| 2003/0083461 A1 | 5/2003 | Ashkenazi et al. |
| 2003/0083473 A1 | 5/2003 | Eaton et al. |
| 2003/0087304 A1 | 5/2003 | Ashkenazi et al. |
| 2003/0087305 A1 | 5/2003 | Ashkenazi et al. |
| 2003/0099974 A1 | 5/2003 | Lillie et al. |
| 2003/0147904 A1 | 8/2003 | Afar et al. |
| 2003/0211100 A1 | 11/2003 | Bedian et al. |
| 2004/0228858 A1 | 11/2004 | Hanson et al. |
| 2005/0019870 A1 | 1/2005 | Afar et al. |
| 2007/0004910 A1 | 1/2007 | Sexton et al. |
| 2007/0027308 A1 | 2/2007 | Milne Edwards et al. |
| 2007/0160617 A1 | 7/2007 | Ma et al. |
| 2008/0311107 A1 | 12/2008 | Bollinger et al. |

FOREIGN PATENT DOCUMENTS

| | | |
|---|---|---|
| EP | 1 074 617 | 2/2001 |
| WO | WO-99/06548 | 2/1999 |
| WO | WO-99/06549 | 2/1999 |
| WO | WO-99/06550 | 2/1999 |
| WO | WO-99/40189 | 8/1999 |
| WO | WO-99/63088 | 12/1999 |
| WO | WO-00/04149 | 1/2000 |
| WO | WO-00/61746 | 10/2000 |
| WO | WO-00/73454 | 12/2000 |
| WO | WO-00/77021 | 12/2000 |
| WO | WO-01/16318 | 3/2001 |
| WO | WO-01/25272 | 4/2001 |
| WO | WO-01/34802 | 5/2001 |
| WO | WO-01/46258 | 6/2001 |
| WO | WO-01/51628 | 7/2001 |
| WO | WO-01/51633 | 7/2001 |
| WO | WO-01/53836 | 7/2001 |
| WO | WO-01/57270 | 8/2001 |
| WO | WO-01/57271 | 8/2001 |
| WO | WO-01/57272 | 8/2001 |
| WO | WO-01/57273 | 8/2001 |
| WO | WO-01/57274 | 8/2001 |
| WO | WO-01/57275 | 8/2001 |
| WO | WO-01/57276 | 8/2001 |
| WO | WO-01/57277 | 8/2001 |
| WO | WO-01/57278 | 8/2001 |
| WO | WO-01/60860 | 8/2001 |
| WO | WO-01/73027 | 10/2001 |
| WO | WO-01/73032 | 10/2001 |
| WO | WO-01/75067 | 10/2001 |
| WO | WO-01/86003 | 11/2001 |
| WO | WO-01/90304 | 11/2001 |
| WO | WO-01/96388 | 12/2001 |
| WO | WO-01/96390 | 12/2001 |
| WO | WO-02/12328 | 2/2002 |
| WO | WO-02/058534 | 8/2002 |
| WO | WO-02/074961 | 9/2002 |
| WO | WO-02/083876 | 10/2002 |
| WO | WO-02/089747 | 11/2002 |
| WO | WO-02/097031 | 12/2002 |
| WO | WO 2009/033094 | * 3/2009 |

OTHER PUBLICATIONS

Chang et al (The Journal of Histochemistry and Cytochemistry, Sep. 1991, 39(9): 1281-1287).*
Tockman et al (Cancer Res., 1992, 52:2711s-2718s).*
Greenbaum et al. (Genome Biology, 2003, vol. 4, Issue 9, pp. 117.1-117.8).*
Stites et al (Basic and Clinical Immunology, Seventh Edition, 1991, 102/Chapter 8, Appleton and Lange, East Norwalk, Connecticut).*
Alberts et al., Molecular Biology of the Cell, 3rd. ed. (1994) p. 465.
Benedict et al., J. Exp. Medicine (2001) 193(1):89-99.
Boehringer Mannheim Biochemicals, 1994 Catalog, p. 93.
Bowie et al., Science (1990) 247:1306-1310.
Brennan et al., Journal of Autoimmunity (1989) 2(suppl.):177-186.
Craft et al., Cancer Res. (1999) 59:5030-5036.
Dulcert et al., Accession No. AAY12282, 1999.
Ericksson et al., Diabetologia (1992) 35:143-147.
Ezzell, Journal of NIH Research (1995) 7:46-49.
Fu et al., EMBO Journal (1996) 15:4392-4401.
Gura, Science (1997) 278:1041-1042.
Hirashima et al., Int. Arch. Allergy Immunol. (2000) Suppl.1:6-9.
'Huang, G.M. et al., "Prostate cancer expression profiling by cDNA sequencing analysis," EMBL Database entry AI557659, Accession No. AI557659, Mar. 25, 1999, EP002144281, & Huang, G.M. et al., Genomics, vol. 59, No. 2, Jul. 1999, pp. 178-186.
Huang, Guyang Matthew, Aug. 9, 1999, dbEST Id 2373824, GenBank Acc. AI557660.
Inoko, Hidetoshi, Mar. 30, 2000, NCBI Accession No. AP000502.
International Search Report for PCT/US02/38264, mailed on Oct. 20, 2004, 3 pages.
Jiang et al., JBC (2003) 278(7):4763-4769.
Kerlavage, A. R, Apr. 21, 1997, dbEST Id 1008183, GenBank Acc. AA 366876.
Kilty and Amara, Curr. Opin. Biotechnology (1992) 3:675-682.
Klein et al., Nature Med. (1997) 3:402-408.
Lewin et al., Genes VI, Oxford University Press, Inc., New York, (1997) Chapter 29.
Mallampalli et al., Biochem. J. (1996) 318:333-341.
Mcclean and Hill, Eur. J. Cancer (1993) 29A:2243-2248.
Morton and Myszka, Methods in Enzymology (1998) 295:268.
Muller et al., MCB (1991) 11:1785.
NCI-CGAP, "National Cancer Institute, Cancer Genome Anatomy Project (CGAP)", Oct. 7,1997, EMBLDatabase Entry AA612666, Accession No. AA612666, XP002144282.
Pemberton et al., J. of Histochemistry and Cytochemistry (1997) 45:1697-1706.
Reiter, Robert E. et al., Prostate stem cell antigen: a cell surface marker overexpressed in prostate cancer:, Proc. Natl. Acad. Sci., Feb. 1998, vol. 95, pp. 1735-1740, XP-002078363.

Rowen, L. et al., "Sequence of the human major histocompatibility complex class III region", Mar. 29, 1999, EMBL Database Entry AF134726, Accession No. AF134726, XP002144283.
Rowen, L. et al., "Sequence of the human major histocompatibility complex class III region", Nov. 1, 1999, EMBL Database Entry Q9Y332, XP002144284.
Rowen, L., Mar. 24, 1999, NCBI Accession No. AAD21813.
Simpson, A.J.G., Mar. 16, 2000, dbEST Id 4011587, GenBank Acc. AW579065.
Simpson, A. J. G., Mar. 23, 2000, dbEST Id 4036649, GenBank Acc. AW603383.
Simpson, A. J. G., Mar. 23, 2000, dbEST Id 4035408, GenBank Acc. AW602142.
Simpson, A.J.G., Feb. 4, 2000, dbEST Id 3787048, GenBank Acc. AW393065.
Spitler, Cancer Biotherapy (1995) 10:1-3.
Storrie et al., Methods Enzymol. (1990) 182:203-225.
Strausberg, Robert, Sep. 6, 1999, dbEST Id 3075200, GenBank Acc. AI951815.
Strausberg, Robert, Mar. 9, 2000, dbEST Id 3079479, GenBank Acc. AI956094.
Strausberg, Robert, Jun. 21, 1999, dbEST Id 2655196, GenBank Acc. AI745450.
Strausberg, Robert, Mar. 7, 2000, dbEST Id 2893738, GenBank Acc. AI813886.
Strausberg, Robert, Aug. 14, 1997, dbEST Id 1112901, GenBank Acc. AA468365.
Strausberg, Robert, Aug. 21, 1997, dbEST Id 1178186, GenBank Acc. AA533783.
Strausberg, Robert, Feb. 16, 1999, dbEST Id 2101871, GenBank Acc. AI318311.
Strausberg, Robert, Oct. 30,1999, dbEST Id 3291479, GenBank Acc. AW139432.
Strausberg, Robert, Feb. 24, 2000, dbEST Id 3880006, GenBank Acc. AW469133.
Strausberg, Robert, Mar. 7, 2000, dbEST Id 2947457, GenBank Acc. AI858987.
Strausberg, Robert, May 13, 1999, dbEST Id 2376359, GenBank Acc. AI560195.
Strausberg, Robert, Mar. 7, 2000, dbEST Id 2946846, GenBank Acc. AI858299.
Strausberg, Robert, May 14, 1999, dbEST Id 2390443, GenBank Acc. AI572115.
Strausberg, Robert, May 14, 1999; dbEST Id 2381301, GenBank Acc. AI565097.
Strausberg, Robert, Dec. 14, 1999, dbEST Id 2443929, GenBank Acc. AI625125.
Strausberg, Robert, Mar. 8, 2000, dbEST Id 3055029, GenBank Acc. AI932443.
Takeda, Jun, Sep. 9, 1997, dbEST Id 1241269, GenBank Acc. C75094.
Welch et al., Int. J. Cancer (1989) 43:449-457.
Welford, Opt. Quant. Elect. (1991) 23:1.
White et al., Ann. Rev. Med. (2001) 52:125-145.
Wilson, R. K., Jun. 10, 1999, dbEST Id 2629269, GenBank Acc. AI721101.
Wilson, R. K., Jul. 7, 1995, dbEST Id 285541, GenBank Acc. H25030.
Wilson, R. K., Apr. 20, 1995, dbEST Id 194186, GenBank Acc. R24141.
Zimmer, Cell Motility and the Cytoskeleton (1991) 20:325-337.
Busken et al., Digestive Disease Week Abstracts and Itinerary Planner (2003) Abstract No. 850.
Freshney, Culture of Animal Cells, A Manual of Basic Technique, Alan R. Liss, Inc., New York (1983) p. 4.
Dermer, Bio/Technology (1994) 12:320.
Drexler et al., Leukemia and Lymphoma (1993) 9:1-25.
Zellner et al., Clin. Can. Res. (1998) 4:1797-1802.
Hsu, in Tissue Culture Methods and Applications, Kruse and Patterson, eds. (1973) Academic Press, Abstract p. 764.
Johnstone and Thorpe, Immunochemistry in Practice, $2^{nd}$ ed edition, Blackwell Scientific Publications, Oxford (1987) pp. 113-130.
Harlow and Lane (eds.), Antibodies: A Laboratory Manual, Cold Spring Harbor (1988) pp. 591-598.
Morrison et al., Proc. Natl. Acad. Sci. USA (1984) 81:6851-6855.
Gussow and Seemann, Methods in Enzymology (1991) 203:99-121.
Huston et al., Proc. Natl. Acad. Sci. USA (1988) 85:5879-5883.
Jakobovits, Expert Opinion on Investigational Drugs (1998) 7(4):607-614.
Slootstra et al., Molecular Diversity (1996) 2:156-164.
Paul, W.E., ed., Fundamental Immunology, Raven Press (1984) pp. 615-617.
Klein, Immunology: the Science of Self-Nonself Discrimination, John Wiley & Sons, New York, (1982) p. 355.
Alzari et al., Annual Rev Immunol (1988) 6:555-580.
Bruggemann et al., PNAS USA (1989) 86:6709-6713.
Hubert et al., PNAS USA (1999) 96(25):14523-14528.
Kohler and Milstein, Nature (1975) 256:495-497.
Pinto et al., Clin Cancer Res (1996) 2(9):1445-1451.
Su et al., PNAS USA (1996) 93:7252-7257.
Supplementary European Search Report for 02789937.6, mailed May 25, 2009, 7 pages.
International Search Report for PCT/US08/75488, mailed on Feb. 13, 2009, 5 pages.
Non-Final Office Action for U.S. Patent Application No. 11/842,016, mailed Dec. 30, 2008, 9 pages.
Written Opinion of the International Searching Authority for PCT/US0875488, mailed on Feb. 13, 2009, 7 pages.
Gress et al., Oncogene (1996) 13:1818-1830.
Muller-Pillasch et al., Gene (1998) 208:25-30.
Casset et al., Biochem. Biophys. Res. Commun. (2003) 307:198-205.
Pascalis et al., Journal of Immunology (2002) 169:3076-3084.
Rudikoff et al., PNAS USA (1982) 79:1979-1983.
Dictionary Definition of "coupled to" from Merriam-Webster online, visited Jan. 16, 2010.
Sequence Search Result (enablement), searched Jan. 24, 2010.
Sequence Search Result (ODP-'827), searched Jan. 18, 2010.
Sequence Search Result (ODP-'823), searched Jan. 24, 2010.
Sequence Search Result (ODP-'138), searched Feb. 2, 2010.
Sequence Search Result (Ashkenazi), searched Jan. 11, 2010.
International Search Report for PCT/US10/26429, mailed on Jun. 10, 2010, 3 pages.
Written Opinion of the International Searching Authority for PCT/US10/26429, mailed on Jun. 10, 2010, 3 pages.

* cited by examiner

Figure 1: 24P4C12 SSH sequence of 160 nucleotides. (SEQ ID NO: 1)

```
  1 GATCAGGGCG GCCAGCCAGG TCTCCTGCAC GCTCTGGTAG GCACTGAGGT TGGTGGTGAA
 61 ACCCAGCTGG GAGATGGAGG CGCCCTCGTC CCGCAGCACT CGGTACTCCT CCCAGCAGTA
121 GTAGATGCCA TATGCCAGCA CGCCCAGCAC TCCCAGGATC
```

Figure 2:

Figure 2A. The cDNA (SEQ ID. NO. : 2) and amino acid sequence (SEQ ID. NO. : 3) of 24P4C12 v.1. The start methionine is underlined. The open reading frame extends from nucleic acid 6-2138 including the stop codon.

Figure 2A-1

```
  1      M   G   G   K   Q   R   D   E   D   D   E   A   Y   G   K   P   V   K   Y
  1    gagccATGGGGGGAAAGCAGCGGGACGAGGATGACGAGGCCTACGGGAAGCCAGTCAAAT
 20      D   P   S   F   R   G   P   I   K   N   R   S   C   T   D   V   I   C   C   V
 61    ACGACCCCTCCTTTCGAGGCCCCATCAAGAACAGAAGCTGCACAGATGTCATCTGCTGCG
 40      L   F   L   L   F   I   L   G   Y   I   V   V   G   I   V   A   W   L   Y   G
121    TCCTCTTCCTGCTCTTCATTCTAGGTTACATCGTGGTGGGGATTGTGGCCTGGTTGTATG
 60      D   P   R   Q   V   L   Y   P   R   N   S   T   G   A   Y   C   M   G   E
181    GAGACCCCCGGCAAGTCCTCTACCCCAGGAACTCTACTGGGGCCTACTGTGGCATGGGGG
 80      N   K   D   K   P   Y   L   L   Y   F   N   I   F   S   C   I   L   S   S   N
241    AGAACAAAGATAAGCCGTATCTCCTGTACTTCAACATCTTCAGCTGCATCCTGTCCAGCA
100      I   I   S   V   A   E   N   G   L   Q   C   P   T   P   Q   V   C   V   S   S
301    ACATCATCTCAGTTGCTGAGAACGGCCTACAGTGCCCCACACCCCAGGTGTGTGTGTCCT
120      C   P   E   D   P   W   T   V   G   K   N   E   F   S   Q   T   V   G   E   V
361    CCTGCCCGGAGGACCCATGGACTGTGGGAAAAAACGAGTTCTCACAGACTGTTGGGGAAG
140      F   Y   T   K   N   R   N   F   C   L   P   G   V   P   W   N   M   T   V   I
421    TCTTCTATACAAAAAACAGGAACTTTTGTCTGCCAGGGGTACCCTGGAATATGACGGTGA
160      T   S   L   Q   Q   E   L   C   P   S   F   L   L   P   S   A   P   A   L   G
481    TCACAAGCCTGCAACAGGAACTCTGCCCCAGTTTCCTCCTCCCCTCTGCTCCAGCTCTGG
180      R   C   F   P   W   T   N   V   T   P   P   A   L   P   G   I   T   N   D   T
541    GGCGCTGCTTTCCATGGACCAACGTTACTCCACCGGCGCTCCCAGGGATCACCAATGACA
200      T   I   Q   Q   G   I   S   G   L   I   D   S   L   N   A   R   D   I   S   V
601    CCACCATACAGCAGGGGATCAGCGGTCTTATTGACAGCCTCAATGCCCGAGACATCAGTG
220      K   I   F   E   D   F   A   Q   S   W   Y   W   I   L   V   A   L   G   V   A
661    TTAAGATCTTTGAAGATTTTGCCCAGTCCTGGTATTGGATTCTTGTTGCCCTGGGGGTGG
240      L   V   L   S   L   L   F   I   L   L   L   R   L   V   A   G   P   L   V   L
721    CTCTGGTCTTGAGCCTACTGTTTATCTTGCTTCTGCGCCTGGTGGCTGGGCCCCTGGTGC
260      V   L   I   L   G   V   L   G   V   L   A   Y   G   I   Y   Y   C   W   E   E
781    TGGTGCTGATCCTGGGAGTGCTGGGCGTGCTGGCATACGGCATCTACTACTGCTGGGAGG
280      Y   R   V   L   R   D   K   G   A   S   I   S   Q   L   G   F   T   T   N   L
841    AGTACCGAGTGCTGCGGGACAAGGGCGCCTCCATCTCCCAGCTGGGTTTCACCACCAACC
300      S   A   Y   Q   S   V   Q   E   T   W   L   A   A   L   I   V   L   A   V   L
901    TCAGTGCCTACCAGAGCGTGCAGGAGACCTGGCTGGCCGCCCTGATCGTGTTGGCGGTGC
320      E   A   I   L   L   M   L   I   F   L   R   Q   R   I   R   I   A   I   A
961    TTGAAGCCATCCTGCTGCTGATGCTCATCTTCCTGCGGCAGCGGATTCGTATTGCCATCG
340      L   L   K   E   A   S   K   A   V   G   Q   M   M   S   T   M   F   Y   P   L
```

Figure 2A-2

```
1021 CCCTCCTGAAGGAGGCCAGCAAGGCTGTGGGACAGATGATGTCTACCATGTTCTACCCAC
 360   V  T  F  V  L  L  L  I  C  I  A  Y  W  A  M  T  A  L  Y  L
1081 TGGTCACCTTTGTCCTCCTCCTCATCTGCATTGCCTACTGGGCCATGACTGCTCTGTACC
 380   A  T  S  G  Q  P  Q  Y  V  L  W  A  S  N  I  S  S  P  G  C
1141 TGGCTACATCGGGGCAACCCCAGTATGTGCTCTGGGCATCCAACATCAGCTCCCCCGGCT
 400   E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
 420   P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
 440   F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
 460   L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
 480   Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
 500   G  S  L  A  F  G  A  L  I  L  T  L  V  Q  I  A  R  V  I  L
1501 CTGGGTCATTGGCATTTGGAGCCCTCATCCTGACCCTTGTGCAGATAGCCCGGGTCATCT
 520   E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
 540   C  F  K  C  C  L  W  C  L  E  K  F  I  K  F  L  N  R  N  A
1621 GCTGTTTCAAGTGCTGCCTCTGGTGTCTGGAAAAATTTATCAAGTTCCTAAACCGCAATG
 560   Y  I  M  I  A  I  Y  G  K  N  F  C  V  S  A  K  N  A  F  M
1681 CATACATCATGATCGCCATCTACGGGAAGAATTTCTGTGTCTCAGCCAAAAATGCGTTCA
 580   L  L  M  R  N  I  V  R  V  V  V  L  D  K  V  T  D  L  L  L
1741 TGCTACTCATGCGAAACATTGTCAGGGTGGTCGTCCTGGACAAAGTCACAGACCTGCTGC
 600   F  F  G  K  L  L  V  V  G  G  V  G  V  L  S  F  F  F  F  S
1801 TGTTCTTTGGGAAGCTGCTGGTGGTCGGAGGCGTGGGGGTCCTGTCCTTCTTTTTTTTCT
 620   G  R  I  P  G  L  G  K  D  F  K  S  P  H  L  N  Y  Y  W  L
1861 CCGGTCGCATCCCGGGGCTGGGTAAAGACTTTAAGAGCCCCCACCTCAACTATTACTGGC
 640   P  I  M  T  S  I  L  G  A  Y  V  I  A  S  G  F  F  S  V  F
1921 TGCCCATCATGACCTCCATCCTGGGGGCCTATGTCATCGCCAGCGGCTTCTTCAGCGTTT
 660   G  M  C  V  D  T  L  F  L  C  F  L  E  D  L  E  R  N  N  G
1981 TCGGCATGTGTGTGGACACGCTCTTCCTCTGCTTCCTGGAAGACCTGGAGCGGAACAACG
 680   S  L  D  R  P  Y  Y  M  S  K  S  L  L  K  I  L  G  K  K  N
2041 GCTCCCTGGACCGGCCCTACTACATGTCCAAGAGCCTTCTAAAGATTCTGGGCAAGAAGA
 700   E  A  P  P  D  N  K  K  R  K  K  *
2101 ACGAGGCGCCCCCGGACAACAAGAAGAGGAAGAAGTGAcagctccggccctgatccagga
2161 ctgcaccccaccccaccgtccagccatccaacctcacttcgccttacaggtctccattt
2221 tgtggtaaaaaaaggttttaggccaggcgccgtggctcacgcctgtaatccaacactttg
2281 agaggctgaggcgggcggatcacctgagtcaggagttcgagaccagcctggccaacatgg
```

Figure 2A-3

```
2341 tgaaacctccgtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaaacaaacaaacaaaaagatttattaaagatattttgttaactcagtaaaaaaaaaa
2581 aaaaaaa
```

Figure 2B. The cDNA (SEQ ID. NO. : 4) and amino acid sequence (SEQ ID. NO. : 5) of 24P4C12 v.2. The start methionine is underlined. The open reading frame extends from nucleic acid 6-2138 including the stop codon.

Figure 2B-1

```
  1     M  G  G  K  Q  R  D  E  D  D  E  A  Y  G  K  P  V  K  Y
  1   gagccATGGGGGGAAAGCAGCGGGACGAGGATGACGAGGCCTACGGGAAGCCAGTCAAAT
 20     D  P  S  F  R  G  P  I  K  N  R  S  C  T  D  V  I  C  C  V
 61   ACGACCCCTCCTTTCGAGGCCCCATCAAGAACAGAAGCTGCACAGATGTCATCTGCTGCG
 40     L  F  L  F  I  L  G  Y  I  V  V  G  I  V  A  W  L  Y  G
121   TCCTCTTCCTGCTCTTCATTCTAGGTTACATCGTGGTGGGGATTGTGGCCTGGTTGTATG
 60     D  P  R  Q  V  L  Y  P  R  N  S  T  G  A  Y  C  G  M  G  E
181   GAGACCCCCGGCAAGTCCTCTACCCCAGGAACTCTACTGGGGCCTACTGTGGCATGGGGG
 80     N  K  D  K  P  Y  L  L  Y  F  N  I  F  S  C  I  L  S  S  N
241   AGAACAAAGATAAGCCGTATCTCCTGTACTTCAACATCTTCAGCTGCATCCTGTCCAGCA
100     I  I  S  V  A  E  N  G  L  Q  C  P  T  P  Q  V  C  V  S  S
301   ACATCATCTCAGTTGCTGAGAACGGCCTACAGTGCCCCACACCCCAGGTGTGTGTGTCCT
120     C  P  E  D  P  W  T  V  G  K  N  E  F  S  Q  T  V  G  E  V
361   CCTGCCCGGAGGACCCATGGACTGTGGGAAAAAACGAGTTCTCACAGACTGTTGGGGAAG
140     F  Y  T  K  N  R  N  F  C  L  P  G  V  P  W  N  M  T  V  I
421   TCTTCTATACAAAAAACAGGAACTTTTGTCTGCCAGGGGTACCCTGGAATATGACGGTGA
160     T  S  L  Q  Q  E  L  C  P  S  F  L  L  P  S  A  P  A  L  G
481   TCACAAGCCTGCAACAGGAACTCTGCCCCAGTTTCCTCCTCCCCTCTGCTCCAGCTCTGG
180     R  C  F  P  W  T  N  V  T  P  P  A  L  P  G  I  T  N  D  T
541   GACGCTGCTTTCCATGGACCAACGTTACTCCACCGGCGCTCCCAGGGATCACCAATGACA
200     T  I  Q  Q  G  I  S  G  L  I  D  S  L  N  A  R  D  I  S  V
601   CCACCATACAGCAGGGGATCAGCGGTCTTATTGACAGCCTCAATGCCCGAGACATCAGTG
220     K  I  F  E  D  F  A  Q  S  W  Y  W  I  L  V  A  L  G  V  A
661   TTAAGATCTTTGAAGATTTTGCCCAGTCCTGGTATTGGATTCTTGTTGCCCTGGGGGTGG
240     L  V  L  S  L  L  F  I  L  L  R  L  V  A  G  P  L  V  L
721   CTCTGGTCTTGAGCCTACTGTTTATCTTGCTTCTGCGCCTGGTGGCTGGGCCCCTGGTGC
260     V  L  I  L  G  V  L  G  V  L  A  Y  G  I  Y  Y  C  W  E  E
781   TGGTGCTGATCCTGGGAGTGCTGGGCGTGCTGGCATACGGCATCTACTACTGCTGGGAGG
280     Y  R  V  L  R  D  K  G  A  S  I  S  Q  L  G  F  T  T  N  L
841   AGTACCGAGTGCTGCGGGACAAGGGCGCCTCCATCTCCCAGCTGGGTTTCACCACCAACC
```

Figure 2B-2

```
 300      S   A   Y   Q   S   V   Q   E   T   W   L   A   A   L   I   V   L   A   V   L
 901  TCAGTGCCTACCAGAGCGTGCAGGAGACCTGGCTGGCCGCCCTGATCGTGTTGGCGGTGC
 320      E   A   I   L   L   L   M   L   I   F   L   R   Q   R   I   R   I   A   I   A
 961  TTGAAGCCATCCTGCTGCTGATGCTCATCTTCCTGCGGCAGCGGATTCGTATTGCCATCG
 340      L   L   K   E   A   S   K   A   V   G   Q   M   M   S   T   M   F   Y   P   L
1021  CCCTCCTGAAGGAGGCCAGCAAGGCTGTGGGACAGATGATGTCTACCATGTTCTACCCAC
 360      V   T   F   V   L   L   L   I   C   I   A   Y   W   A   M   T   A   L   Y   L
1081  TGGTCACCTTTGTCCTCCTCCTCATCTGCATTGCCTACTGGGCCATGACTGCTCTGTACC
 380      A   T   S   G   Q   P   Q   Y   V   L   W   A   S   N   I   S   S   P   G   C
1141  TGGCTACATCGGGGCAACCCCAGTATGTGCTCTGGGCATCCAACATCAGCTCCCCCGGCT
 400      E   K   V   P   I   N   T   S   C   N   P   T   A   H   L   V   N   S   S   C
1201  GTGAGAAAGTGCCAATAAATACATCATGCAACCCCACGGCCCACCTTGTGAACTCCTCGT
 420      P   G   L   M   C   V   F   Q   G   Y   S   S   K   G   L   I   Q   R   S   V
1261  GCCCAGGGCTGATGTGCGTCTTCCAGGGCTACTCATCCAAAGGCCTAATCCAACGTTCTG
 440      F   N   L   Q   I   Y   G   V   L   G   L   F   W   T   L   N   W   V   L   A
1321  TCTTCAATCTGCAAATCTATGGGGTCCTGGGGCTCTTCTGGACCCTTAACTGGGTACTGG
 460      L   G   Q   C   V   L   A   G   A   F   A   S   F   Y   W   A   F   H   K   P
1381  CCCTGGGCCAATGCGTCCTCGCTGGAGCCTTTGCCTCCTTCTACTGGGCCTTCCACAAGC
 480      Q   D   I   P   T   F   P   L   I   S   A   F   I   R   T   L   R   Y   H   T
1441  CCCAGGACATCCCTACCTTCCCCTTAATCTCTGCCTTCATCCGCACACTCCGTTACCACA
 500      G   S   L   A   F   G   A   L   I   L   T   L   V   Q   I   A   R   V   I   L
1501  CTGGGTCATTGGCATTTGGAGCCCTCATCCTGACCCTTGTGCAGATAGCCCGGGTCATCT
 520      E   Y   I   D   H   K   L   R   G   V   Q   N   P   V   A   R   C   I   M   C
1561  TGGAGTATATTGACCACAAGCTCAGAGGAGTGCAGAACCCTGTAGCCCGCTGCATCATGT
 540      C   F   K   C   C   L   W   C   L   E   K   F   I   K   F   L   N   R   N   A
1621  GCTGTTTCAAGTGCTGCCTCTGGTGTCTGGAAAAATTTATCAAGTTCCTAAACCGCAATG
 560      Y   I   M   I   A   I   Y   G   K   N   F   C   V   S   A   K   N   A   F   M
1681  CATACATCATGATCGCCATCTACGGGAAGAATTTCTGTGTCTCAGCCAAAAATGCGTTCA
 580      L   L   M   R   N   I   V   R   V   V   V   L   D   K   V   T   D   L   L   L
1741  TGCTACTCATGCGAAACATTGTCAGGGTGGTCGTCCTGGACAAAGTCACAGACCTGCTGC
 600      F   F   G   K   L   L   V   V   G   G   V   G   V   L   S   F   F   F   F   S
1801  TGTTCTTTGGGAAGCTGCTGGTGGTCGGAGGCGTGGGGGTCCTGTCCTTCTTTTTTTTCT
 620      G   R   I   P   G   L   G   K   D   F   K   S   P   H   L   N   Y   Y   W   L
1861  CCGGTCGCATCCCGGGGCTGGGTAAAGACTTTAAGAGCCCCCACCTCAACTATTACTGGC
 640      P   I   M   T   S   I   L   G   A   Y   V   I   A   S   G   F   F   S   V   F
1921  TGCCCATCATGACCTCCATCCTGGGGGCCTATGTCATCGCCAGCGGCTTCTTCAGCGTTT
 660      G   M   C   V   D   T   L   F   L   C   F   L   E   D   L   E   R   N   N   G
1981  TCGGCATGTGTGTGGACACGCTCTTCCTCTGCTTCCTGGAAGACCTGGAGCGGAACAACG
 680      S   L   D   R   P   Y   Y   M   S   K   S   L   L   K   I   L   G   K   K   N
2041  GCTCCCTGGACCGGCCCTACTACATGTCCAAGAGCCTTCTAAAGATTCTGGGCAAGAAGA
```

Figure 2B-3

```
700  E  A  P  P  D  N  K  K  R  K  K  *
2101 ACGAGGCGCCCCCGGACAACAAGAAGAGGAAGAAGTGAcagctccggccctgatccagga
2161 ctgcaccccaccccaccgtccagccatccaacctcacttcgccttacaggtctccattt
2221 tgtggtaaaaaaaggttttaggccaggcgccgtggctcacgcctgtaatccaacactttg
2281 agaggctgaggcgggcggatcacctgagtcaggagttcgagaccagcctggccaacatgg
2341 tgaaaccteegtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaaacaaacaaacaaaaagattttattaaagatattttgttaactcagtaaaaaaaaaa
2581 aaaaaaa
```

Figure 2C. The cDNA (SEQ ID. NO. : 6) and amino acid sequence (SEQ ID. NO. : 7) of 24P4C12 v.3. The start methionine is underlined. The open reading frame extends from nucleic acid 6-2138 including the stop codon.

Figure 2C-1

```
1      M  G  G  K  Q  R  D  E  D  D  E  A  Y  G  K  P  V  K  Y
1    gagccATGGGGGGAAAGCAGCGGGACGAGGATGACGAGGCCTACGGGAAGCCAGTCAAAT
20     D  P  S  F  R  G  P  I  K  N  R  S  C  T  D  V  I  C  C  V
61   ACGACCCCTCCTTTCGAGGCCCCATCAAGAACAGAAGCTGCACAGATGTCATCTGCTGCG
40     L  F  L  L  F  I  L  G  Y  I  V  V  G  I  V  A  W  L  Y  G
121  TCCTCTTCCTGCTCTTCATTCTAGGTTACATCGTGGTGGGGATTGTGGCCTGGTTGTATG
60     D  P  R  Q  V  L  Y  P  R  N  S  T  G  A  Y  C  G  M  G  E
181  GAGACCCCCGGCAAGTCCTCTACCCCAGGAACTCTACTGGGGCCTACTGTGGCATGGGGG
80     N  K  D  K  P  Y  L  L  Y  F  N  I  F  S  C  I  L  S  S  N
241  AGAACAAAGATAAGCCGTATCTCCTGTACTTCAACATCTTCAGCTGCATCCTGTCCAGCA
100    I  I  S  V  A  E  N  G  L  Q  C  P  T  P  Q  V  C  V  S  S
301  ACATCATCTCAGTTGCTGAGAACGGCCTACAGTGCCCCACACCCCAGGTGTGTGTGTCCT
120    C  P  E  D  P  W  T  V  G  K  N  E  F  S  Q  T  V  G  E  V
361  CCTGCCCGGAGGACCCATGGACTGTGGGAAAAAACGAGTTCTCACAGACTGTTGGGGAAG
140    F  Y  T  K  N  R  N  F  C  L  P  G  V  P  W  N  M  T  V  I
421  TCTTCTATACAAAAAACAGGAACTTTTGTCTGCCAGGGGTACCCTGGAATATGACGGTGA
160    T  S  L  Q  Q  E  L  C  P  S  F  L  L  P  S  A  P  A  L  G
481  TCACAAGCCTGCAACAGGAACTCTGCCCCAGTTTCCTCCTCCCCTCTGCTCCAGCTCTGG
180    R  C  F  P  W  T  N  I  T  P  P  A  L  P  G  I  T  N  D  T
541  GGCGCTGCTTTCCATGGACCAACATTACTCCACCGGCGCTCCCAGGGATCACCAATGACA
200    T  I  Q  Q  G  I  S  G  L  I  D  S  L  N  A  R  D  I  S  V
601  CCACCATACAGCAGGGGATCAGCGGTCTTATTGACAGCCTCAATGCCCGAGACATCAGTG
220    K  I  F  E  D  F  A  Q  S  W  Y  W  I  L  V  A  L  G  V  A
661  TTAAGATCTTTGAAGATTTTGCCCAGTCCTGGTATTGGATTCTTGTTGCCCTGGGGGTGG
240    L  V  L  S  L  L  F  I  L  L  R  L  V  A  G  P  L  V  L
```

Figure 2C-2

```
 721 CTCTGGTCTTGAGCCTACTGTTTATCTTGCTTCTGCGCCTGGTGGCTGGGCCCCTGGTGC
 260   V  L  I  L  G  V  L  G  V  L  A  Y  G  I  Y  Y  C  W  E  E
 781 TGGTGCTGATCCTGGGAGTGCTGGGCGTGCTGGCATACGGCATCTACTACTGCTGGGAGG
 280   Y  R  V  L  R  D  K  G  A  S  I  S  Q  L  G  F  T  T  N  L
 841 AGTACCGAGTGCTGCGGGACAAGGGCGCCTCCATCTCCCAGCTGGGTTTCACCACCAACC
 300   S  A  Y  Q  S  V  Q  E  T  W  L  A  A  L  I  V  L  A  V  L
 901 TCAGTGCCTACCAGAGCGTGCAGGAGACCTGGCTGGCCGCCCTGATCGTGTTGGCGGTGC
 320   E  A  I  L  L  L  M  L  I  F  L  R  Q  R  I  R  I  A  I  A
 961 TTGAAGCCATCCTGCTGCTGATGCTCATCTTCCTGCGGCAGCGGATTCGTATTGCCATCG
 340   L  L  K  E  A  S  K  A  V  G  Q  M  M  S  T  M  F  Y  P  L
1021 CCCTCCTGAAGGAGGCCAGCAAGGCTGTGGGACAGATGATGTCTACCATGTTCTACCCAC
 360   V  T  F  V  L  L  L  I  C  I  A  Y  W  A  M  T  A  L  Y  L
1081 TGGTCACCTTTGTCCTCCTCCTCATCTGCATTGCCTACTGGGCCATGACTGCTCTGTACC
 380   A  T  S  G  Q  P  Q  Y  V  L  W  A  S  N  I  S  S  P  G  C
1141 TGGCTACATCGGGGCAACCCCAGTATGTGCTCTGGGCATCCAACATCAGCTCCCCCGGCT
 400   E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
 420   P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
 440   F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
 460   L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
 480   Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
 500   G  S  L  A  F  G  A  L  I  L  T  L  V  Q  I  A  R  V  I  L
1501 CTGGGTCATTGGCATTTGGAGCCCTCATCCTGACCCTTGTGCAGATAGCCCGGGTCATCT
 520   E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
 540   C  F  K  C  C  L  W  C  L  E  K  F  I  K  F  L  N  R  N  A
1621 GCTGTTTCAAGTGCTGCCTCTGGTGTCTGGAAAAATTTATCAAGTTCCTAAACCGCAATG
 560   Y  I  M  I  A  I  Y  G  K  N  F  C  V  S  A  K  N  A  F  M
1681 CATACATCATGATCGCCATCTACGGGAAGAATTTCTGTGTCTCAGCCAAAAATGCGTTCA
 580   L  L  M  R  N  I  V  R  V  V  V  L  D  K  V  T  D  L  L  L
1741 TGCTACTCATGCGAAACATTGTCAGGGTGGTCGTCCTGGACAAAGTCACAGACCTGCTGC
 600   F  F  G  K  L  L  V  V  G  G  V  G  V  L  S  F  F  F  F  S
1801 TGTTCTTTGGGAAGCTGCTGGTGGTCGGAGGCGTGGGGGTCCTGTCCTTCTTTTTTTTCT
 620   G  R  I  P  G  L  G  K  D  F  K  S  P  H  L  N  Y  Y  W  L
1861 CCGGTCGCATCCCGGGGCTGGGTAAAGACTTTAAGAGCCCCCACCTCAACTATTACTGGC
 640   P  I  M  T  S  I  L  G  A  Y  V  I  A  S  G  F  F  S  V  F
```

Figure 2C-3

```
1921 TGCCCATCATGACCTCCATCCTGGGGGCCTATGTCATCGCCAGCGGCTTCTTCAGCGTTT
 660   G  M  C  V  D  T  L  F  L  C  F  L  E  D  L  E  R  N  N  G
1981 TCGGCATGTGTGTGGACACGCTCTTCCTCTGCTTCCTGGAAGACCTGGAGCGGAACAACG
 680   S  L  D  R  P  Y  Y  M  S  K  S  L  L  K  I  L  G  K  K  N
2041 GCTCCCTGGACCGGCCCTACTACATGTCCAAGAGCCTTCTAAAGATTCTGGGCAAGAAGA
 700   E  A  P  P  D  N  K  K  R  K  K  *
2101 ACGAGGCGCCCCGGACAACAAGAAGAGGAAGAAGTGAcagctccggccctgatccagga
2161 ctgcacccacccccaccgtccagccatccaacctcacttcgccttacaggtctccattt
2221 tgtggtaaaaaaaggttttaggccaggcgccgtggctcacgcctgtaatccaacactttg
2281 agaggctgaggcgggcggatcacctgagtcaggagttcgagaccagcctggccaacatgg
2341 tgaaaccctccgtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaaacaaacaaacaaaaagatttttattaaagatattttgttaactcagtaaaaaaaaaa
2581 aaaaaaa
```

Figure 2D. The cDNA (SEQ ID. NO.: 8) and amino acid sequence (SEQ ID. NO.: 9) of 24P4C12 v.4. The start methionine is underlined. The open reading frame extends from nucleic acid 6-2138 including the stop codon.

Figure 2D-1

```
  1       M  G  G  K  Q  R  D  E  D  D  E  A  Y  G  K  P  V  K  Y
  1   gagccATGGGGGGAAAGCAGCGGGACGAGGATGACGAGGCCTACGGGAAGCCAGTCAAAT
 20       D  P  S  F  R  G  P  I  K  N  R  S  C  T  D  V  I  C  C  V
 61   ACGACCCCTCCTTTCGAGGCCCCATCAAGAACAGAAGCTGCACAGATGTCATCTGCTGCG
 40       L  F  L  L  F  I  L  G  Y  I  V  V  G  I  V  A  W  L  Y  G
121   TCCTCTTCCTGCTCTTCATTCTAGGTTACATCGTGGTGGGGATTGTGGCCTGGTTGTATG
 60       D  P  R  Q  V  L  Y  P  R  N  S  T  G  A  Y  C  G  M  G  E
181   GAGACCCCCGGCAAGTCCTCTACCCCAGGAACTCTACTGGGGCCTACTGTGGCATGGGGG
 80       N  K  D  K  P  Y  L  L  Y  F  N  I  F  S  C  I  L  S  S  N
241   AGAACAAAGATAAGCCGTATCTCCTGTACTTCAACATCTTCAGCTGCATCCTGTCCAGCA
100       I  I  S  V  A  E  N  G  L  Q  C  P  T  P  Q  V  C  V  S  S
301   ACATCATCTCAGTTGCTGAGAACGGCCTACAGTGCCCCACACCCCAGGTGTGTGTGTCCT
120       C  P  E  D  P  W  T  V  G  K  N  E  F  S  Q  T  V  G  E  V
361   CCTGCCCGGAGGACCCATGGACTGTGGGAAAAAACGAGTTCTCACAGACTGTTGGGGAAG
140       F  Y  T  K  N  R  N  F  C  L  P  G  V  P  W  N  M  T  V  I
421   TCTTCTATACAAAAAACAGGAACTTTTGTCTGCCAGGGGTACCCTGGAATATGACGGTGA
160       T  S  L  Q  Q  E  L  C  P  S  F  L  L  P  S  A  P  A  L  G
481   TCACAAGCCTGCAACAGGAACTCTGCCCCAGTTTCCTCCTCCCCTCTGCTCCAGCTCTGG
180       R  C  F  P  W  T  N  V  T  P  P  A  L  P  G  I  T  N  D  T
541   GGCGCTGCTTTCCATGGACCAACGTTACTCCACCGGCGCTCCCAGGGATCACCAATGACA
```

Figure 2D-2

```
200    T  I  Q  Q  G  I  S  G  L  I  D  S  L  N  A  R  D  I  S  V
601  CCACCATACAGCAGGGGATCAGCGGTCTTATTGACAGCCTCAATGCCCGAGACATCAGTG
220    K  I  F  E  D  F  A  Q  S  W  Y  W  I  L  V  A  L  G  V  A
661  TTAAGATCTTTGAAGATTTTGCCCAGTCCTGGTATTGGATTCTTGTTGCCCTGGGGGTGG
240    L  V  L  S  L  L  F  I  L  L  L  R  L  V  A  G  P  L  V  L
721  CTCTGGTCTTGAGCCTACTGTTTATCTTGCTTCTGCGCCTGGTGGCTGGGCCCCTGGTGC
260    V  L  I  L  G  V  L  G  V  L  A  Y  G  I  Y  Y  C  W  E  E
781  TGGTGCTGATCCTGGGAGTGCTGGGCGTGCTGGCATATGGCATCTACTACTGCTGGGAGG
280    Y  R  V  L  R  D  K  G  A  S  I  S  Q  L  G  F  T  T  N  L
841  AGTACCGAGTGCTGCGGGACAAGGGCGCCTCCATCTCCCAGCTGGGTTTCACCACCAACC
300    S  A  Y  Q  S  V  Q  E  T  W  L  A  A  L  I  V  L  A  V  L
901  TCAGTGCCTACCAGAGCGTGCAGGAGACCTGGCTGGCCGCCCTGATCGTGTTGGCGGTGC
320    E  A  I  L  L  L  M  L  I  F  L  R  Q  R  I  R  I  A  I  A
961  TTGAAGCCATCCTGCTGCTGATGCTCATCTTCCTGCGGCAGCGGATTCGTATTGCCATCG
340    L  L  K  E  A  S  K  A  V  G  Q  M  M  S  T  M  F  Y  P  L
1021 CCCTCCTGAAGGAGGCCAGCAAGGCTGTGGGACAGATGATGTCTACCATGTTCTACCCAC
360    V  T  F  V  L  L  L  I  C  I  A  Y  W  A  M  T  A  L  Y  L
1081 TGGTCACCTTTGTCCTCCTCCTCATCTGCATTGCCTACTGGGCCATGACTGCTCTGTACC
380    A  T  S  G  Q  P  Q  Y  V  L  W  A  S  N  I  S  S  P  G  C
1141 TGGCTACATCGGGGCAACCCCAGTATGTGCTCTGGGCATCCAACATCAGCTCCCCCGGCT
400    E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
420    P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
440    F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
460    L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
480    Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
500    G  S  L  A  F  G  A  L  I  L  T  L  V  Q  I  A  R  V  I  L
1501 CTGGGTCATTGGCATTTGGAGCCCTCATCCTGACCCTTGTGCAGATAGCCCGGGTCATCT
520    E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
540    C  F  K  C  C  L  W  C  L  E  K  F  I  K  F  L  N  R  N  A
1621 GCTGTTTCAAGTGCTGCCTCTGGTGTCTGGAAAAATTTATCAAGTTCCTAAACCGCAATG
560    Y  I  M  I  A  I  Y  G  K  N  F  C  V  S  A  K  N  A  F  M
1681 CATACATCATGATCGCCATCTACGGGAAGAATTTCTGTGTCTCAGCCAAAAATGCGTTCA
580    L  L  M  R  N  I  V  R  V  V  V  L  D  K  V  T  D  L  L  L
1741 TGCTACTCATGCGAAACATTGTCAGGGTGGTCGTCCTGGACAAAGTCACAGACCTGCTGC
```

Figure 2D-3

```
 600      F  F  G  K  L  L  V  V  G  G  V  G  V  L  S  F  F  F  F  S
1801    TGTTCTTTGGGAAGCTGCTGGTGGTCGGAGGCGTGGGGGTCCTGTCCTTCTTTTTTTCT
 620      G  R  I  P  G  L  G  K  D  F  K  S  P  H  L  N  Y  Y  W  L
1861    CCGGTCGCATCCCGGGGCTGGGTAAAGACTTTAAGAGCCCCCACCTCAACTATTACTGGC
 640      P  I  M  T  S  I  L  G  A  Y  V  I  A  S  G  F  F  S  V  F
1921    TGCCCATCATGACCTCCATCCTGGGGGCCTATGTCATCGCCAGCGGCTTCTTCAGCGTTT
 660      G  M  C  V  D  T  L  F  L  C  F  L  E  D  L  E  R  N  N  G
1981    TCGGCATGTGTGTGGACACGCTCTTCCTCTGCTTCCTGGAAGACCTGGAGCGGAACAACG
 680      S  L  D  R  P  Y  Y  M  S  K  S  L  L  K  I  L  G  K  K  N
2041    GCTCCCTGGACCGGCCCTACTACATGTCCAAGAGCCTTCTAAAGATTCTGGGCAAGAAGA
 700      E  A  P  P  D  N  K  K  R  K  K  *
2101    ACGAGGCGCCCCCGGACAACAAGAAGAGGAAGAAGTGAcagctccggccctgatccagga
2161    ctgcacccacccccaccgtccagccatccaacctcacttcgccttacaggtctccattt
2221    tgtggtaaaaaaaggttttaggccaggcgccgtggctcacgcctgtaatccaacactttg
2281    agaggctgaggcgggcggatcacctgagtcaggagttcgagaccagcctggccaacatgg
2341    tgaaacctccgtctctattaaaaatacaaaaattagccgagagtggtggcatgcacctgt
2401    catcccagctactcgggaggctgaggcaggagaatcgcttgaacccgggaggcagaggtt
2461    gcagtgagccgagatcgcgccactgcactccaacctgggtgacagactctgtctccaaaa
2521    caaaacaaacaaacaaaagatttttattaaagatatttttgttaactcagtaaaaaaaaaa
2581    aaaaaaa
```

Figure 2E. The cDNA (SEQ ID. NO. : 10) and amino acid sequence (SEQ ID. NO. : 11) of 24P4C12 v.5. The start methionine is underlined. The open reading frame extends from nucleic acid 6-2138 including the stop codon.

Figure 2E-1

```
  1        M  G  G  K  Q  R  D  E  D  D  E  A  Y  G  K  P  V  K  Y
  1     gagccATGGGGGGAAAGCAGCGGGACGAGGATGACGAGGCCTACGGGAAGCCAGTCAAAT
 20        D  P  S  F  R  G  P  I  K  N  R  S  C  T  D  V  I  C  C  V
 61     ACGACCCCTCCTTTCGAGGCCCCATCAAGAACAGAAGCTGCACAGATGTCATCTGCTGCG
 40        L  F  L  L  F  I  L  G  Y  I  V  V  G  I  V  A  W  L  Y  G
121     TCCTCTTCCTGCTCTTCATTCTAGGTTACATCGTGGTGGGGATTGTGGCCTGGTTGTATG
 60        D  P  R  Q  V  L  Y  P  R  N  S  T  G  A  Y  C  G  M  G  E
181     GAGACCCCCGGCAAGTCCTCTACCCCAGGAACTCTACTGGGGCCTACTGTGGCATGGGGG
 80        N  K  D  K  P  Y  L  L  Y  F  N  I  F  S  C  I  L  S  S  N
241     AGAACAAAGATAAGCCGTATCTCCTGTACTTCAACATCTTCAGCTGCATCCTGTCCAGCA
100        I  I  S  V  A  E  N  G  L  Q  C  P  T  P  Q  V  C  V  S  S
301     ACATCATCTCAGTTGCTGAGAACGGCCTACAGTGCCCCACACCCCAGGTGTGTGTGTCCT
120        C  P  E  D  P  W  T  V  G  K  N  E  F  S  Q  T  V  G  E  V
361     CCTGCCCGGAGGACCCATGGACTGTGGGAAAAAACGAGTTCTCACAGACTGTTGGGGAAG
140        F  Y  T  K  N  R  N  F  C  L  P  G  V  P  W  N  M  T  V  I
```

Figure 2E-2

```
421 TCTTCTATACAAAAAACAGGAACTTTTGTCTGCCAGGGGTACCCTGGAATATGACGGTGA
160   T  S  L  Q  Q  E  L  C  P  S  F  L  L  P  S  A  P  A  L  G
481 TCACAAGCCTGCAACAGGAACTCTGCCCCAGTTTCCTCCTCCCCTCTGCTCCAGCTCTGG
180   R  C  F  P  W  T  N  V  T  P  P  A  L  P  G  I  T  N  D  T
541 GGCGCTGCTTTCCATGGACCAACGTTACTCCACCGGCGCTCCCAGGGATCACCAATGACA
200   T  I  Q  Q  G  I  S  G  L  I  D  S  L  N  A  R  D  I  S  V
601 CCACCATACAGCAGGGGATCAGCGGTCTTATTGACAGCCTCAATGCCCGAGACATCAGTG
220   K  I  F  E  D  F  A  Q  S  W  Y  W  I  L  V  A  L  G  V  A
661 TTAAGATCTTTGAAGATTTTGCCCAGTCCTGGTATTGGATTCTTGTTGCCCTGGGGGTGG
240   L  V  L  S  L  L  F  I  L  L  L  R  L  V  A  G  P  L  V  L
721 CTCTGGTCTTGAGCCTACTGTTTATCTTGCTTCTGCGCCTGGTGGCTGGGCCCCTGGTGC
260   V  L  I  L  G  V  L  G  V  L  A  Y  G  I  Y  Y  C  W  E  E
781 TGGTGCTGATCCTGGGAGTGCTGGGCGTGCTGGCATACGGCATCTACTACTGCTGGGAGG
280   Y  R  V  L  R  D  K  G  A  S  I  S  Q  L  G  F  T  T  N  L
841 AGTACCGAGTGCTGCGGGACAAGGGCGCCTCCATCTCCCAGCTGGGTTTCACCACCAACC
300   S  A  Y  Q  S  V  Q  E  T  W  L  A  A  L  I  V  L  A  V  L
901 TCAGTGCCTACCAGAGCGTGCAGGAGACCTGGCTGGCCGCCCTGATCGTGTTGGCGGTGC
320   E  A  I  L  L  L  V  L  I  F  L  R  Q  R  I  R  I  A  I  A
961 TTGAAGCCATCCTGCTGCTGGTGCTCATCTTCCTGCGGCAGCGGATTCGTATTGCCATCG
340   L  L  K  E  A  S  K  A  V  G  Q  M  M  S  T  M  F  Y  P  L
1021 CCCTCCTGAAGGAGGCCAGCAAGGCTGTGGGACAGATGATGTCTACCATGTTCTACCCAC
360   V  T  F  V  L  L  L  I  C  I  A  Y  W  A  M  T  A  L  Y  L
1081 TGGTCACCTTTGTCCTCCTCCTCATCTGCATTGCCTACTGGGCCATGACTGCTCTGTACC
380   A  T  S  G  Q  P  Q  Y  V  L  W  A  S  N  I  S  S  P  G  C
1141 TGGCTACATCGGGGCAACCCCAGTATGTGCTCTGGGCATCCAACATCAGCTCCCCCGGCT
400   E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
420   P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
440   F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
460   L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
480   Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
500   G  S  L  A  F  G  A  L  I  L  T  L  V  Q  I  A  R  V  I  L
1501 CTGGGTCATTGGCATTTGGAGCCCTCATCCTGACCCTTGTGCAGATAGCCCGGGTCATCT
520   E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
540   C  F  K  C  C  L  W  C  L  E  K  F  I  K  F  L  N  R  N  A
```

Figure 2E-3

```
1621 GCTGTTTCAAGTGCTGCCTCTGGTGTCTGGAAAAATTTATCAAGTTCCTAAACCGCAATG
 560   Y   I   M   I   A   I   Y   G   K   N   F   C   V   S   A   K   N   A   F   M
1681 CATACATCATGATCGCCATCTACGGGAAGAATTTCTGTGTCTCAGCCAAAAATGCGTTCA
 580   L   L   M   R   N   I   V   R   V   V   L   D   K   V   T   D   L   L   L
1741 TGCTACTCATGCGAAACATTGTCAGGGTGGTCGTCCTGGACAAAGTCACAGACCTGCTGC
 600   F   F   G   K   L   L   V   V   G   G   V   G   V   L   S   F   F   F   S
1801 TGTTCTTTGGGAAGCTGCTGGTGGTCGGAGGCGTGGGGGTCCTGTCCTTCTTTTTTTTCT
 620   G   R   I   P   G   L   G   K   D   F   K   S   P   H   L   N   Y   Y   W   L
1861 CCGGTCGCATCCCGGGGCTGGGTAAAGACTTTAAGAGCCCCACCTCAACTATTACTGGC
 640   P   I   M   T   S   I   L   G   A   Y   V   I   A   S   G   F   F   S   V   F
1921 TGCCCATCATGACCTCCATCCTGGGGGCCTATGTCATCGCCAGCGGCTTCTTCAGCGTTT
 660   G   M   C   V   D   T   L   F   L   C   F   L   E   D   L   E   R   N   N   G
1981 TCGGCATGTGTGTGGACACGCTCTTCCTCTGCTTCCTGGAAGACCTGGAGCGGAACAACG
 680   S   L   D   R   P   Y   Y   M   S   K   S   L   L   K   I   L   G   K   K   N
2041 GCTCCCTGGACCGGCCCTACTACATGTCCAAGAGCCTTCTAAAGATTCTGGGCAAGAAGA
 700   E   A   P   P   D   N   K   K   R   K   K   *
2101 ACGAGGCGCCCCGGACAACAAGAAGAGGAAGAAGTGAcagctccggccctgatccagga
2161 ctgcaccccaccccaccgtccagccatccaacctcacttcgccttacaggtctccattt
2221 tgtggtaaaaaaggttttaggccaggcgccgtggctcacgcctgtaatccaacactttg
2281 agaggctgaggcgggcggatcacctgagtcaggagttcgagaccagcctggccaacatgg
2341 tgaaacctccgtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaaacaaacaaacaaaaagatttttattaaagatattttgttaactcagtaaaaaaaaa
2581 aaaaaaa
```

Figure 2F. The cDNA (SEQ ID. NO. : 12) and amino acid sequence (SEQ ID. NO. : 13) of 24P4C12 v.6. The start methionine is underlined. The open reading frame extends from nucleic acid 6-2138 including the stop codon.

Figure 2F-1

```
  1      M   G   G   K   Q   R   D   E   D   D   E   A   Y   G   K   P   V   K   Y
  1    gagccATGGGGGGAAAGCAGCGGGACGAGGATGACGAGGCCTACGGGAAGCCAGTCAAAT
 20      D   P   S   F   R   G   P   I   K   N   R   S   C   T   D   V   I   C   C   V
 61    ACGACCCCTCCTTTCGAGGCCCCATCAAGAACAGAAGCTGCACAGATGTCATCTGCTGCG
 40      L   F   L   L   F   I   L   G   Y   I   V   V   G   I   V   A   W   L   Y   G
121    TCCTCTTCCTGCTCTTCATTCTAGGTTACATCGTGGTGGGGATTGTGGCCTGGTTGTATG
 60      D   P   R   Q   V   L   Y   P   R   N   S   T   G   A   Y   C   G   M   G   E
181    GAGACCCCCGGCAAGTCCTCTACCCCAGGAACTCTACTGGGGCCTACTGTGGCATGGGGG
 80      N   K   D   K   P   Y   L   L   Y   F   N   I   F   S   C   I   L   S   S   N
241    AGAACAAAGATAAGCCGTATCTCCTGTACTTCAACATCTTCAGCTGCATCCTGTCCAGCA
```

Figure 2F-2

```
100    I  I  S  V  A  E  N  G  L  Q  C  P  T  P  Q  V  C  V  S  S
301  ACATCATCTCAGTTGCTGAGAACGGCCTACAGTGCCCCACACCCCAGGTGTGTGTGTCCT
120    C  P  E  D  P  W  T  V  G  K  N  E  F  S  Q  T  V  G  E  V
361  CCTGCCCGGAGGACCCATGGACTGTGGGAAAAAACGAGTTCTCACAGACTGTTGGGGAAG
140    F  Y  T  K  N  R  N  F  C  L  P  G  V  P  W  N  M  T  V  I
421  TCTTCTATACAAAAAACAGGAACTTTTGTCTGCCAGGGGTACCCTGGAATATGACGGTGA
160    T  S  L  Q  Q  E  L  C  P  S  F  L  L  P  S  A  P  A  L  G
481  TCACAAGCCTGCAACAGGAACTCTGCCCCAGTTTCCTCCTCCCCTCTGCTCCAGCTCTGG
180    R  C  F  P  W  T  N  V  T  P  P  A  L  P  G  I  T  N  D  T
541  GGCGCTGCTTTCCATGGACCAACGTTACTCCACCGGCGCTCCCAGGGATCACCAATGACA
200    T  I  Q  Q  G  I  S  G  L  I  D  S  L  N  A  R  D  I  S  V
601  CCACCATACAGCAGGGGATCAGCGGTCTTATTGACAGCCTCAATGCCCGAGACATCAGTG
220    K  I  F  E  D  F  A  Q  S  W  Y  W  I  L  V  A  L  G  V  A
661  TTAAGATCTTTGAAGATTTTGCCCAGTCCTGGTATTGGATTCTTGTTGCCCTGGGGGTGG
240    L  V  L  S  L  L  F  I  L  L  R  L  V  A  G  P  L  V  L
721  CTCTGGTCTTGAGCCTACTGTTTATCTTGCTTCTGCGCCTGGTGGCTGGGCCCCTGGTGC
260    V  L  I  L  G  V  L  G  V  L  A  Y  G  I  Y  Y  C  W  E  E
781  TGGTGCTGATCCTGGGAGTGCTGGGCGTGCTGGCATACGGCATCTACTACTGCTGGGAGG
280    Y  R  V  L  R  D  K  G  A  S  I  S  Q  L  G  F  T  T  N  L
841  AGTACCGAGTGCTGCGGGACAAGGGCGCCTCCATCTCCCAGCTGGGTTTCACCACCAACC
300    S  A  Y  Q  S  V  Q  E  T  W  L  A  A  L  I  V  L  A  V  L
901  TCAGTGCCTACCAGAGCGTGCAGGAGACCTGGCTGGCCGCCCTGATCGTGTTGGCGGTGC
320    E  A  I  L  L  L  M  L  I  F  L  R  Q  R  I  R  I  A  I  A
961  TTGAAGCCATCCTGCTGCTGATGCTCATCTTCCTGCGGCAGCGGATTCGTATTGCCATCG
340    L  L  K  E  A  S  K  A  V  G  Q  M  M  S  T  M  F  Y  P  L
1021 CCCTCCTGAAGGAGGCCAGCAAGGCTGTGGGACAGATGATGTCTACCATGTTCTACCCAC
360    V  T  F  V  L  L  I  C  I  A  Y  W  A  M  T  A  L  Y  L
1081 TGGTCACCTTTGTCCTCCTCCTCATCTGCATTGCCTACTGGGCCATGACTGCTCTGTACC
380    A  T  S  G  Q  P  Q  Y  V  L  W  A  S  N  I  S  S  P  G  C
1141 TGGCTACATCGGGGCAACCCCAGTATGTGCTCTGGGCATCCAACATCAGCTCCCCCGGCT
400    E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
420    P  G  L  M  C  V  F  Q  G  Y  S  S  K  G  L  I  P  R  S  V
1261 GCCCAGGGCTGATGTGCGTCTTCCAGGGCTACTCATCCAAAGGCCTAATCCCACGTTCTG
440    F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
460    L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
480    Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
```

Figure 2F-3

```
500       G   S   L   A   F   G   A   L   I   L   T   L   V   Q   I   A   R   V   I   L
1501 CTGGGTCATTGGCATTTGGAGCCCTCATCCTGACCCTTGTGCAGATAGCCCGGGTCATCT
520       E   Y   I   D   H   K   L   R   G   V   Q   N   P   V   A   R   C   I   M   C
1561 TGGAGTATATTGACCACAAGCTCAGAGGAGTGCAGAACCCTGTAGCCCGCTGCATCATGT
540       C   F   K   C   C   L   W   C   L   E   K   F   I   K   F   L   N   R   N   A
1621 GCTGTTTCAAGTGCTGCCTCTGGTGTCTGGAAAAATTTATCAAGTTCCTAAACCGCAATG
560       Y   I   M   I   A   I   Y   G   K   N   F   C   V   S   A   K   N   A   F   M
1681 CATACATCATGATCGCCATCTACGGGAAGAATTTCTGTGTCTCAGCCAAAAATGCGTTCA
580       L   L   M   R   N   I   V   R   V   V   V   L   D   K   V   T   D   L   L   L
1741 TGCTACTCATGCGAAACATTGTCAGGGTGGTCGTCCTGGACAAAGTCACAGACCTGCTGC
600       F   F   G   K   L   L   V   V   G   G   V   G   V   L   S   F   F   F   F   S
1801 TGTTCTTTGGGAAGCTGCTGGTGGTCGGAGGCGTGGGGGTCCTGTCCTTCTTTTTTTTCT
620       G   R   I   P   G   L   G   K   D   F   K   S   P   H   L   N   Y   Y   W   L
1861 CCGGTCGCATCCCGGGGCTGGGTAAAGACTTTAAGAGCCCCCACCTCAACTATTACTGGC
640       P   I   M   T   S   I   L   G   A   Y   V   I   A   S   G   F   F   S   V   F
1921 TGCCCATCATGACCTCCATCCTGGGGGCCTATGTCATCGCCAGCGGCTTCTTCAGCGTTT
660       G   M   C   V   D   T   L   F   L   C   F   L   E   D   L   E   R   N   N   G
1981 TCGGCATGTGTGTGGACACGCTCTTCCTCTGCTTCCTGGAAGACCTGGAGCGGAACAACG
680       S   L   D   R   P   Y   Y   M   S   K   S   L   L   K   I   L   G   K   K   N
2041 GCTCCCTGGACCGGCCCTACTACATGTCCAAGAGCCTTCTAAAGATTCTGGGCAAGAAGA
700       E   A   P   P   D   N   K   K   R   K   K   *
2101 ACGAGGCGCCCCCGGACAACAAGAAGAGGAAGAAGTGAcagctccggccctgatccagga
2161 ctgcaccccaccccaccgtccagccatccaacctcacttcgccttacaggtctccattt
2221 tgtggtaaaaaaggttttaggccaggcgccgtggctcacgcctgtaatccaacactttg
2281 agaggctgaggcgggcggatcacctgagtcaggagttcgagaccagcctggccaacatgg
2341 tgaaacctccgtctctattaaaaatacaaaaattagccgagagtggtggcatgcacctgt
2401 catcccagctactcgggaggctgaggcaggagaatcgcttgaacccgggaggcagaggtt
2461 gcagtgagccgagatcgcgccactgcactccaacctgggtgacagactctgtctccaaaa
2521 caaaacaaacaaacaaaaagattttattaaagatattttgttaactcagtaaaaaaaaa
2581 aaaaaaa
```

Figure 2G. The cDNA (SEQ ID. NO. : 14) and amino acid sequence (SEQ ID. NO. : 15) of 24P4C12 v.7. The start methionine is underlined. The open reading frame extends from nucleic acid 6-1802 including the stop codon.

Figure 2G-1

```
1         M   G   G   K   Q   R   D   E   D   D   E   A   Y   G   K   P   V   K   Y
1    gagccATGGGGGGAAAGCAGCGGGACGAGGATGACGAGGCCTACGGGAAGCCAGTCAAAT
20        D   P   S   F   R   G   P   I   K   N   R   S   C   T   D   V   I   C   C   V
61   ACGACCCCTCCTTTCGAGGCCCCATCAAGAACAGAAGCTGCACAGATGTCATCTGCTGCG
```

Figure 2G-2

```
 40      L  F  L  L  F  I  L  G  Y  I  V  V  G  I  V  A  W  L  Y  G
121   TCCTCTTCCTGCTCTTCATTCTAGGTTACATCGTGGTGGGGATTGTGGCCTGGTTGTATG
 60      D  P  R  Q  V  L  Y  P  R  N  S  T  G  A  Y  C  G  M  G  E
181   GAGACCCCCGGCAAGTCCTCTACCCCAGGAACTCTACTGGGGCCTACTGTGGCATGGGGG
 80      N  K  D  K  P  Y  L  L  Y  F  N  I  F  S  C  I  L  S  S  N
241   AGAACAAAGATAAGCCGTATCTCCTGTACTTCAACATCTTCAGCTGCATCCTGTCCAGCA
100      I  I  S  V  A  E  N  G  L  Q  C  P  T  P  Q  V  C  V  S  S
301   ACATCATCTCAGTTGCTGAGAACGGCCTACAGTGCCCCACACCCCAGGTGTGTGTGTCCT
120      C  P  E  D  P  W  T  V  G  K  N  E  F  S  Q  T  V  G  E  V
361   CCTGCCCGGAGGACCCATGGACTGTGGGAAAAACGAGTTCTCACAGACTGTTGGGGAAG
140      F  Y  T  K  N  R  N  F  C  L  P  G  V  P  W  N  M  T  V  I
421   TCTTCTATACAAAAAACAGGAACTTTTGTCTGCCAGGGGTACCCTGGAATATGACGGTGA
160      T  S  L  Q  Q  E  L  C  P  S  F  L  L  P  S  A  P  A  L  G
481   TCACAAGCCTGCAACAGGAACTCTGCCCCAGTTTCCTCCTCCCCTCTGCTCCAGCTCTGG
180      R  C  F  P  W  T  N  V  T  P  P  A  L  P  G  I  T  N  D  T
541   GGCGCTGCTTTCCATGGACCAACGTTACTCCACCGGCGCTCCCAGGGATCACCAATGACA
200      T  I  Q  Q  G  I  S  G  L  I  D  S  L  N  A  R  D  I  S  V
601   CCACCATACAGCAGGGGATCAGCGGTCTTATTGACAGCCTCAATGCCCGAGACATCAGTG
220      K  I  F  E  D  F  A  Q  S  W  Y  W  I  L  V  A  V  G  Q  M
661   TTAAGATCTTTGAAGATTTTGCCCAGTCCTGGTATTGGATTCTTGTGGCTGTGGGACAGA
240      M  S  T  M  F  Y  P  L  V  T  F  V  L  L  L  I  C  I  A  Y
721   TGATGTCTACCATGTTCTACCCACTGGTCACCTTTGTCCTCCTCCTCATCTGCATTGCCT
260      W  A  M  T  A  L  Y  L  A  T  S  G  Q  P  Q  Y  V  L  W  A
781   ACTGGGCCATGACTGCTCTGTACCTGGCTACATCGGGGCAACCCCAGTATGTGCTCTGGG
280      S  N  I  S  S  P  G  C  E  K  V  P  I  N  T  S  C  N  P  T
841   CATCCAACATCAGCTCCCCCGGCTGTGAGAAAGTGCCAATAAATACATCATGCAACCCCA
300      A  H  L  V  N  S  S  C  P  G  L  M  C  V  F  Q  G  Y  S  S
901   CGGCCCACCTTGTGAACTCCTCGTGCCCAGGGCTGATGTGCGTCTTCCAGGGCTACTCAT
320      K  G  L  I  Q  R  S  V  F  N  L  Q  I  Y  G  V  L  G  L  F
961   CCAAAGGCCTAATCCAACGTTCTGTCTTCAATCTGCAAATCTATGGGGTCCTGGGGCTCT
340      W  T  L  N  W  V  L  A  L  G  Q  C  V  L  A  G  A  F  A  S
1021  TCTGGACCCTTAACTGGGTACTGGCCCTGGGCCAATGCGTCCTCGCTGGAGCCTTTGCCT
360      F  Y  W  A  F  H  K  P  Q  D  I  P  T  F  P  L  I  S  A  F
1081  CCTTCTACTGGGCCTTCCACAAGCCCCAGGACATCCCTACCTTCCCCTTAATCTCTGCCT
380      I  R  T  L  R  Y  H  T  G  S  L  A  F  G  A  L  I  L  T  L
1141  TCATCCGCACACTCCGTTACCACACTGGGTCATTGGCATTTGGAGCCCTCATCCTGACCC
400      V  Q  I  A  R  V  I  L  E  Y  I  D  H  K  L  R  G  V  Q  N
1201  TTGTGCAGATAGCCCGGGTCATCTTGGAGTATATTGACCACAAGCTCAGAGGAGTGCAGA
420      P  V  A  R  C  I  M  C  C  F  K  C  C  L  W  C  L  E  K  F
1261  ACCCTGTAGCCCGCTGCATCATGTGCTGTTTCAAGTGCTGCCTCTGGTGTCTGGAAAAAT
```

Figure 2G-3

```
440   I  K  F  L  N  R  N  A  Y  I  M  I  A  I  Y  G  K  N  F  C
1321  TTATCAAGTTCCTAAACCGCAATGCATACATCATGATCGCCATCTACGGGAAGAATTTCT
460   V  S  A  K  N  A  F  M  L  L  M  R  N  I  V  R  V  V  V  L
1381  GTGTCTCAGCCAAAAATGCGTTCATGCTACTCATGCGAAACATTGTCAGGGTGGTCGTCC
480   D  K  V  T  D  L  L  L  F  F  G  K  L  L  V  V  G  G  V  G
1441  TGGACAAAGTCACAGACCTGCTGCTGTTCTTTGGAAGCTGCTGGTGGTCGGAGGCGTGG
500   V  L  S  F  F  F  F  S  G  R  I  P  G  L  G  K  D  F  K  S
1501  GGGTCCTGTCCTTCTTTTTTTTCTCCGGTCGCATCCCGGGGCTGGGTAAAGACTTTAAGA
520   P  H  L  N  Y  Y  W  L  P  I  M  T  S  I  L  G  A  Y  V  I
1561  GCCCCCACCTCAACTATTACTGGCTGCCCATCATGACCTCCATCCTGGGGGCCTATGTCA
540   A  S  G  F  F  S  V  F  G  M  C  V  D  T  L  F  L  C  F  L
1621  TCGCCAGCGGCTTCTTCAGCGTTTTCGGCATGTGTGTGGACACGCTCTTCCTCTGCTTCC
560   E  D  L  E  R  N  N  G  S  L  D  R  P  Y  Y  M  S  K  S  L
1681  TGGAAGACCTGGAGCGGAACAACGGCTCCCTGGACCGGCCCTACTACATGTCCAAGAGCC
580   L  K  I  L  G  K  K  N  E  A  P  P  D  N  K  K  R  K  K  *
1741  TTCTAAAGATTCTGGGCAAGAAGAACGAGGCGCCCCCGGACAACAAGAAGAGGAAGAAGT
1801  GAcagctccggccctgatccaggactgcaccccaccccaccgtccagccatccaacctc
1861  acttcgccttacaggtctccattttgtggtaaaaaaggttttaggccaggcgccgtggc
1921  tcacgcctgtaatccaacactttgagaggctgaggcgggcggatcacctgagtcaggagt
1981  tcgagaccagcctggccaacatggtgaaaccccgtctctattaaaaatacaaaaattag
2041  ccgagagtggtggcatgcacctgtcatcccagctactcgggaggctgaggcaggagaatc
2101  gcttgaacccggggaggcagaggttgcagtgagccgagatcgcgccactgcactccaacct
2161  gggtgacagactctgtctccaaaacaaaacaaacaaacaaaaagatttattaaagatat
2221  tttgttaactcagtaaaaaaaaaaaaaaaaa
```

Figure 2H. The cDNA (SEQ ID. NO.: 16) and amino acid sequence (SEQ ID. NO.: 17) of 24P4C12 v.8. The start methionine is underlined. The open reading frame extends from nucleic acid 6-2174 including the stop codon.

Figure 2H-1

```
  1      M   G   G   K   Q   R   D   E   D   D   E   A   Y   G   K   P   V   K   Y
  1    gagccATGGGGGGAAAGCAGCGGGACGAGGATGACGAGGCCTACGGGAAGCCAGTCAAAT
 20      D   P   S   F   R   G   P   I   K   N   R   S   C   T   D   V   I   C   C   V
 61    ACGACCCCTCCTTTCGAGGCCCCATCAAGAACAGAAGCTGCACAGATGTCATCTGCTGCG
 40      L   F   L   L   F   I   L   G   Y   I   V   V   G   I   V   A   W   L   Y   G
121    TCCTCTTCCTGCTCTTCATTCTAGGTTACATCGTGGTGGGGATTGTGGCCTGGTTGTATG
 60      D   P   R   Q   V   L   Y   P   R   N   S   T   G   A   Y   C   G   M   G   E
181    GAGACCCCCGGCAAGTCCTCTACCCCAGGAACTCTACTGGGGCCTACTGTGGCATGGGGG
 80      N   K   D   K   P   Y   L   L   Y   F   N   I   F   S   C   I   L   S   S   N
241    AGAACAAAGATAAGCCGTATCTCCTGTACTTCAACATCTTCAGCTGCATCCTGTCCAGCA
100      I   I   S   V   A   E   N   G   L   Q   C   P   T   P   Q   V   C   V   S   S
301    ACATCATCTCAGTTGCTGAGAACGGCCTACAGTGCCCCACACCCCAGGTGTGTGTGTCCT
120      C   P   E   D   P   W   T   V   G   K   N   E   F   S   Q   T   V   G   E   V
361    CCTGCCCGGAGGACCCATGGACTGTGGGAAAAAACGAGTTCTCACAGACTGTTGGGGAAG
140      F   Y   T   K   N   R   N   F   C   L   P   G   V   P   W   N   M   T   V   I
421    TCTTCTATACAAAAAACAGGAACTTTTGTCTGCCAGGGGTACCCTGGAATATGACGGTGA
160      T   S   L   Q   Q   E   L   C   P   S   F   L   L   P   S   A   P   A   L   G
481    TCACAAGCCTGCAACAGGAACTCTGCCCCAGTTTCCTCCTCCCCTCTGCTCCAGCTCTGG
180      R   C   F   P   W   T   N   V   T   P   P   A   L   P   G   I   T   N   D   T
541    GGCGCTGCTTTCCATGGACCAACGTTACTCCACCGGCGCTCCCAGGGATCACCAATGACA
200      T   I   Q   Q   G   I   S   G   L   I   D   S   L   N   A   R   D   I   S   V
601    CCACCATACAGCAGGGGATCAGCGGTCTTATTGACAGCCTCAATGCCCGAGACATCAGTG
220      K   I   F   E   D   F   A   Q   S   W   Y   W   I   L   V   A   L   G   V   A
661    TTAAGATCTTTGAAGATTTTGCCCAGTCCTGGTATTGGATTCTTGTTGCCCTGGGGGTGG
240      L   V   L   S   L   L   F   I   L   L   L   R   L   V   A   G   P   L   V   L
721    CTCTGGTCTTGAGCCTACTGTTTATCTTGCTTCTGCGCCTGGTGGCTGGGCCCCTGGTGC
260      V   L   I   L   G   V   L   G   V   L   A   Y   G   I   Y   Y   C   W   E   E
781    TGGTGCTGATCCTGGGAGTGCTGGGCGTGCTGGCATACGGCATCTACTACTGCTGGGAGG
280      Y   R   V   L   R   D   K   G   A   S   I   S   Q   L   G   F   T   T   N   L
841    AGTACCGAGTGCTGCGGGACAAGGGCGCCTCCATCTCCCAGCTGGGTTTCACCACCAACC
300      S   A   Y   Q   S   V   Q   E   T   W   L   A   A   L   I   V   L   A   V   L
901    TCAGTGCCTACCAGAGCGTGCAGGAGACCTGGCTGGCCGCCCTGATCGTGTTGGCGGTGC
320      E   A   I   L   L   M   L   I   F   L   R   Q   R   I   R   I   A   I   A
961    TTGAAGCCATCCTGCTGCTGATGCTCATCTTCCTGCGGCAGCGGATTCGTATTGCCATCG
340      L   L   K   E   A   S   K   A   V   G   Q   M   M   S   T   M   F   Y   P   L
1021   CCCTCCTGAAGGAGGCCAGCAAGGCTGTGGGACAGATGATGTCTACCATGTTCTACCCAC
360      V   T   F   V   L   L   L   I   C   I   A   Y   W   A   M   T   A   L   Y   L
```

Figure 2H-2

```
1081 TGGTCACCTTTGTCCTCCTCCTCATCTGCATTGCCTACTGGGCCATGACTGCTCTGTACC
 380   A  T  S  G  Q  P  Q  Y  V  L  W  A  S  N  I  S  S  P  G  C
1141 TGGCTACATCGGGGCAACCCCAGTATGTGCTCTGGGCATCCAACATCAGCTCCCCCGGCT
 400   E  K  V  P  I  N  T  S  C  N  P  T  A  H  L  V  N  S  S  C
1201 GTGAGAAAGTGCCAATAAATACATCATGCAACCCCACGGCCCACCTTGTGAACTCCTCGT
 420   P  G  L  M  C  V  F  Q  G  Y  S  S  K  G  L  I  Q  R  S  V
1261 GCCCAGGGCTGATGTGCGTCTTCCAGGGCTACTCATCCAAAGGCCTAATCCAACGTTCTG
 440   F  N  L  Q  I  Y  G  V  L  G  L  F  W  T  L  N  W  V  L  A
1321 TCTTCAATCTGCAAATCTATGGGGTCCTGGGGCTCTTCTGGACCCTTAACTGGGTACTGG
 460   L  G  Q  C  V  L  A  G  A  F  A  S  F  Y  W  A  F  H  K  P
1381 CCCTGGGCCAATGCGTCCTCGCTGGAGCCTTTGCCTCCTTCTACTGGGCCTTCCACAAGC
 480   Q  D  I  P  T  F  P  L  I  S  A  F  I  R  T  L  R  Y  H  T
1441 CCCAGGACATCCCTACCTTCCCCTTAATCTCTGCCTTCATCCGCACACTCCGTTACCACA
 500   G  S  L  A  F  G  A  L  I  L  T  L  V  Q  I  A  R  V  I  L
1501 CTGGGTCATTGGCATTTGGAGCCCTCATCCTGACCCTTGTGCAGATAGCCCGGGTCATCT
 520   E  Y  I  D  H  K  L  R  G  V  Q  N  P  V  A  R  C  I  M  C
1561 TGGAGTATATTGACCACAAGCTCAGAGGAGTGCAGAACCCTGTAGCCCGCTGCATCATGT
 540   C  F  K  C  C  L  W  C  L  E  K  F  I  K  F  L  N  R  N  A
1621 GCTGTTTCAAGTGCTGCCTCTGGTGTCTGGAAAAATTTATCAAGTTCCTAAACCGCAATG
 560   Y  I  M  I  A  I  Y  G  K  N  F  C  V  S  A  K  N  A  F  M
1681 CATACATCATGATCGCCATCTACGGGAAGAATTTCTGTGTCTCAGCCAAAAATGCGTTCA
 580   L  L  M  R  N  I  V  R  V  V  V  L  D  K  V  T  D  L  L  L
1741 TGCTACTCATGCGAAACATTGTCAGGGTGGTCGTCCTGGACAAAGTCACAGACCTGCTGC
 600   F  F  G  K  L  L  V  V  G  G  V  G  V  L  S  F  F  F  F  S
1801 TGTTCTTTGGGAAGCTGCTGGTGGTCGGAGGCGTGGGGGTCCTGTCCTTCTTTTTTTTCT
 620   G  R  I  P  G  L  G  K  D  F  K  S  P  H  L  N  Y  Y  W  L
1861 CCGGTCGCATCCCGGGGCTGGGTAAAGACTTTAAGAGCCCCCACCTCAACTATTACTGGC
 640   P  I  M  R  N  P  I  T  P  T  G  H  V  F  Q  T  S  I  L  G
1921 TGCCCATCATGAGGAACCCAATAACCCCAACGGGTCATGTCTTCCAGACCTCCATCCTGG
 660   A  Y  V  I  A  S  G  F  F  S  V  F  G  M  C  V  D  T  L  F
1981 GGGCCTATGTCATCGCCAGCGGCTTCTTCAGCGTTTTCGGCATGTGTGTGGACACGCTCT
 680   L  C  F  L  E  D  L  E  R  N  N  G  S  L  D  R  P  Y  Y  M
2041 TCCTCTGCTTCCTGGAAGACCTGGAGCGGAACAACGGCTCCCTGGACCGGCCCTACTACA
 700   S  K  S  L  L  K  I  L  G  K  K  N  E  A  P  P  D  N  K  K
2101 TGTCCAAGAGCCTTCTAAAGATTCTGGGCAAGAAGAACGAGGCGCCCCCGGACAACAAGA
 720   R  K  K  *
2161 AGAGGAAGAAGTGAcagctccggccctgatccaggactgcaccccaccccaccgtccag
2221 ccatccaacctcacttcgccttacaggtctccattttgtggtaaaaaaggttttaggcc
2281 aggcgccgtggctcacgcctgtaatccaacactttgagaggctgaggcgggcggatcacc
```

Figure 2H-3

```
2341 tgagtcaggagttcgagaccagcctggccaacatggtgaaacctccgtctctattaaaaa
2401 tacaaaaattagccgagagtggtggcatgcacctgtcatcccagctactcgggaggctga
2461 ggcaggagaatcgcttgaacccggggaggcagaggttgcagtgagccgagatcgcgccact
2521 gcactccaacctgggtgacagactctgtctccaaaacaaaacaaacaaacaaaagattt
2581 tattaaagatattttgttaactcagtaaaaaaaaaaaaaaaa
```

Figure 2I. The cDNA (SEQ ID. NO. : 18) and amino acid sequence (SEQ ID. NO. : 19) of 24P4C12 v.9. The start methionine is underlined. The open reading frame extends from nucleic acid 6-2144 including the stop codon.

Figure 2I-1

```
  1     M   G   G   K   Q   R   D   E   D   D   E   A   Y   G   K   P   V   K   Y
  1   gagccATGGGGGGAAAGCAGCGGGACGAGGATGACGAGGCCTACGGGAAGCCAGTCAAAT
 20     D   P   S   F   R   G   P   I   K   N   R   S   C   T   D   V   I   C   C   V
 61   ACGACCCCTCCTTTCGAGGCCCCATCAAGAACAGAAGCTGCACAGATGTCATCTGCTGCG
 40     L   F   L   L   F   I   L   G   Y   I   V   V   G   I   V   A   W   L   Y   G
121   TCCTCTTCCTGCTCTTCATTCTAGGTTACATCGTGGTGGGGATTGTGGCCTGGTTGTATG
 60     D   P   R   Q   V   L   Y   P   R   N   S   T   G   A   Y   C   G   M   G   E
181   GAGACCCCCGGCAAGTCCTCTACCCCAGGAACTCTACTGGGGCCTACTGTGGCATGGGGG
 80     N   K   D   K   P   Y   L   L   Y   F   N   I   F   S   C   I   L   S   S   N
241   AGAACAAAGATAAGCCGTATCTCCTGTACTTCAACATCTTCAGCTGCATCCTGTCCAGCA
100     I   I   S   V   A   E   N   G   L   Q   C   P   T   P   Q   V   C   V   S   S
301   ACATCATCTCAGTTGCTGAGAACGGCCTACAGTGCCCCACACCCCAGGTGTGTGTGTCCT
120     C   P   E   D   P   W   T   V   G   K   N   E   F   S   Q   T   V   G   E   V
361   CCTGCCCGGAGGACCCATGGACTGTGGGAAAAAACGAGTTCTCACAGACTGTTGGGGAAG
140     F   Y   T   K   N   R   N   F   C   L   P   G   V   P   W   N   M   T   V   I
421   TCTTCTATACAAAAAACAGGAACTTTTGTCTGCCAGGGGTACCCTGGAATATGACGGTGA
160     T   S   L   Q   Q   E   L   C   P   S   F   L   L   P   S   A   P   A   L   G
481   TCACAAGCCTGCAACAGGAACTCTGCCCCAGTTTCCTCCTCCCCTCTGCTCCAGCTCTGG
180     R   C   F   P   W   T   N   V   T   P   P   A   L   P   G   I   T   N   D   T
541   GGCGCTGCTTTCCATGGACCAACGTTACTCCACCGGCGCTCCCAGGGATCACCAATGACA
200     T   I   Q   Q   G   I   S   G   L   I   D   S   L   N   A   R   D   I   S   V
601   CCACCATACAGCAGGGGATCAGCGGTCTTATTGACAGCCTCAATGCCCGAGACATCAGTG
220     K   I   F   E   D   F   A   Q   S   W   Y   W   I   L   V   A   L   G   V   A
661   TTAAGATCTTTGAAGATTTTGCCCAGTCCTGGTATTGGATTCTTGTTGCCCTGGGGGTGG
240     L   V   L   S   L   L   F   I   L   L   L   R   L   V   A   G   P   L   V   L
721   CTCTGGTCTTGAGCCTACTGTTTATCTTGCTTCTGCGCCTGGTGGCTGGGCCCCTGGTGC
260     V   L   I   L   G   V   L   G   V   L   A   Y   G   I   Y   Y   C   W   E   E
781   TGGTGCTGATCCTGGGAGTGCTGGGCGTGCTGGCATACGGCATCTACTACTGCTGGGAGG
280     Y   R   V   L   R   D   K   G   A   S   I   S   Q   L   G   F   T   T   N   L
841   AGTACCGAGTGCTGCGGGACAAGGGCGCCTCCATCTCCCAGCTGGGTTTCACCACCAACC
```

Figure 2I-2

```
300  S   A   Y   Q   S   V   Q   E   T   W   L   A   A   L   I   V   L   A   V   L
901  TCAGTGCCTACCAGAGCGTGCAGGAGACCTGGCTGGCCGCCCTGATCGTGTTGGCGGTGC
320  E   A   I   L   L   L   M   L   I   F   L   R   Q   R   I   R   I   A   I   A
961  TTGAAGCCATCCTGCTGCTGATGCTCATCTTCCTGCGGCAGCGGATTCGTATTGCCATCG
340  L   L   K   E   A   S   K   A   V   G   Q   M   M   S   T   M   F   Y   P   L
1021 CCCTCCTGAAGGAGGCCAGCAAGGCTGTGGGACAGATGATGTCTACCATGTTCTACCCAC
360  V   T   F   V   L   L   L   I   C   I   A   Y   W   A   M   T   A   L   Y   P
1081 TGGTCACCTTTGTCCTCCTCCTCATCTGCATTGCCTACTGGGCCATGACTGCTCTGTATC
380  L   P   T   Q   P   A   T   L   G   Y   V   L   W   A   S   N   I   S   S   P
1141 CTCTGCCCACGCAGCCAGCCACTCTTGGATATGTGCTCTGGGCATCCAACATCAGCTCCC
400  G   C   E   K   V   P   I   N   T   S   C   N   P   T   A   H   L   V   N   S
1201 CCGGCTGTGAGAAAGTGCCAATAAATACATCATGCAACCCCACGGCCCACCTTGTGAACT
420  S   C   P   G   L   M   C   V   F   Q   G   Y   S   S   K   G   L   I   Q   R
1261 CCTCGTGCCCAGGGCTGATGTGCGTCTTCCAGGGCTACTCATCCAAAGGCCTAATCCAAC
440  S   V   F   N   L   Q   I   Y   G   V   L   G   L   F   W   T   L   N   W   V
1321 GTTCTGTCTTCAATCTGCAAATCTATGGGGTCCTGGGGCTCTTCTGGACCCTTAACTGGG
460  L   A   L   G   Q   C   V   L   A   G   F   A   S   F   Y   W   A   F   H
1381 TACTGGCCCTGGGCCAATGCGTCCTCGCTGGAGCCTTTGCCTCCTTCTACTGGGCCTTCC
480  K   P   Q   D   I   P   T   F   P   L   I   S   A   F   I   R   T   L   R   Y
1441 ACAAGCCCCAGGACATCCCTACCTTCCCCTTAATCTCTGCCTTCATCCGCACACTCCGTT
500  H   T   G   S   L   A   F   G   A   L   I   L   T   L   V   Q   I   A   R   V
1501 ACCACACTGGGTCATTGGCATTTGGAGCCCTCATCCTGACCCTTGTGCAGATAGCCCGGG
520  I   L   E   Y   I   D   H   K   L   R   G   V   Q   N   P   V   A   R   C   I
1561 TCATCTTGGAGTATATTGACCACAAGCTCAGAGGAGTGCAGAACCCTGTAGCCCGCTGCA
540  M   C   C   F   K   C   C   L   W   C   L   E   K   F   I   K   F   L   N   R
1621 TCATGTGCTGTTTCAAGTGCTGCCTCTGGTGTCTGGAAAAATTTATCAAGTTCCTAAACC
560  N   A   Y   I   M   I   A   I   Y   G   K   N   F   C   V   S   A   K   N   A
1681 GCAATGCATACATCATGATCGCCATCTACGGGAAGAATTTCTGTGTCTCAGCCAAAAATG
580  F   M   L   L   M   R   N   I   V   R   V   V   V   L   D   K   V   T   D   L
1741 CGTTCATGCTACTCATGCGAAACATTGTCAGGGTGGTCGTCCTGGACAAAGTCACAGACC
600  L   L   F   F   G   K   L   L   V   V   G   G   V   G   V   L   S   F   F   F
1801 TGCTGCTGTTCTTTGGGAAGCTGCTGGTGGTCGGAGGCGTGGGGGTCCTGTCCTTCTTTT
620  F   S   G   R   I   P   G   L   G   K   D   F   K   S   P   H   L   N   Y   Y
1861 TTTTCTCCGGTCGCATCCCGGGGCTGGGTAAAGACTTTAAGAGCCCCCACCTCAACTATT
640  W   L   P   I   M   T   S   I   L   G   A   Y   V   I   A   S   G   F   F   S
1921 ACTGGCTGCCCATCATGACCTCCATCCTGGGGGCCTATGTCATCGCCAGCGGCTTCTTCA
660  V   F   G   M   C   V   D   T   L   F   L   C   F   L   E   D   L   E   R   N
1981 GCGTTTTCGGCATGTGTGTGGACACGCTCTTCCTCTGCTTCCTGGAAGACCTGGAGCGGA
680  N   G   S   L   D   R   P   Y   Y   M   S   K   S   L   L   K   I   L   G   K
2041 ACAACGGCTCCCTGGACCGGCCCTACTACATGTCCAAGAGCCTTCTAAAGATTCTGGGCA
```

Figure 2I-3

```
 700   K  N  E  A  P  P  D  N  K  K  R  K  K  *
2101  AGAAGAACGAGGCGCCCCCGGACAACAAGAAGAGGAAGAAGTGAcagctccggccctgat
2161  ccaggactgcaccccaccccaccgtccagccatccaacctcacttcgccttacaggtct
2221  ccatttgtggtaaaaaaaggttttaggccaggcgccgtggctcacgcctgtaatccaac
2281  actttgagaggctgaggcgggcggatcacctgagtcaggagttcgagaccagcctggcca
2341  acatggtgaaaccctccgtctctattaaaaatacaaaaattagccgagagtggtggcatgc
2401  acctgtcatcccagctactcgggaggctgaggcaggagaatcgcttgaacccgggaggca
2461  gaggttgcagtgagccgagatcgcgccactgcactccaacctgggtgacagactctgtct
2521  ccaaaacaaaacaaacaaacaaaagatttattaaagatatttgttaactcagtaaaa
2581  aaaaaaaaaaaa
```

Figure 3:

Figure 3A. Amino acid sequence of 24P4C12 v.1 (SEQ ID. NO. : 20). The 24P4C12 v.1 protein has 710 amino acids.

```
  1 MGGKQRDEDD EAYGKPVKYD PSFRGPIKNR SCTDVICCVL FLLFILGYIV VGIVAWLYGD
 61 PRQVLYPRNS TGAYCGMGEN KDKPYLLYFN IFSCILSSNI ISVAENGLQC PTPQVCVSSC
121 PEDPWTVGKN EFSQTVGEVF YTKNRNFCLP GVPWNMTVIT SLQQELCPSF LLPSAPALGR
181 CFPWTNVTPP ALPGITNDTT IQQGISGLID SLNARDISVK IFEDFAQSWY WILVALGVAL
241 VLSLLFILLL RLVAGPLVLV LILGVLGVLA YGIYYCWEEY RVLRDKGASI SQLGFTTNLS
301 AYQSVQETWL AALIVLAVLE AILLLMLIFL RQRIRIAIAL LKEASKAVGQ MMSTMFYPLV
361 TFVLLLICIA YWAMTALYLA TSGQPQYVLW ASNISSPGCE KVPINTSCNP TAHLVNSSCP
421 GLMCVFQGYS SKGLIQRSVF NLQIYGVLGL FWTLNWVLAL GQCVLAGAFA SFYWAFHKPQ
481 DIPTFPLISA FIRTLRYHTG SLAFGALILT LVQIARVILE YIDHKLRGVQ NPVARCIMCC
541 FKCCLWCLEK FIKFLNRNAY IMIAIYGKNF CVSAKNAFML LMRNIVRVVV LDKVTDLLLF
601 FGKLLVVGGV GVLSFFFFSG RIPGLGKDFK SPHLNYYWLP IMTSILGAYV IASGFFSVFG
661 MCVDTLFLCF LEDLERNNGS LDRPYYMSKS LLKILGKKNE APPDNKKRKK
```

Figure 3B. Amino acid sequence of 24P4C12 v.3 (SEQ ID. NO. : 21). The 24P4C12 v.3 protein has 710 amino acids.

```
  1 MGGKQRDEDD EAYGKPVKYD PSFRGPIKNR SCTDVICCVL FLLFILGYIV VGIVAWLYGD
 61 PRQVLYPRNS TGAYCGMGEN KDKPYLLYFN IFSCILSSNI ISVAENGLQC PTPQVCVSSC
121 PEDPWTVGKN EFSQTVGEVF YTKNRNFCLP GVPWNMTVIT SLQQELCPSF LLPSAPALGR
181 CFPWTNITPP ALPGITNDTT IQQGISGLID SLNARDISVK IFEDFAQSWY WILVALGVAL
241 VLSLLFILLL RLVAGPLVLV LILGVLGVLA YGIYYCWEEY RVLRDKGASI SQLGFTTNLS
301 AYQSVQETWL AALIVLAVLE AILLLMLIFL RQRIRIAIAL LKEASKAVGQ MMSTMFYPLV
361 TFVLLLICIA YWAMTALYLA TSGQPQYVLW ASNISSPGCE KVPINTSCNP TAHLVNSSCP
421 GLMCVFQGYS SKGLIQRSVF NLQIYGVLGL FWTLNWVLAL GQCVLAGAFA SFYWAFHKPQ
481 DIPTFPLISA FIRTLRYHTG SLAFGALILT LVQIARVILE YIDHKLRGVQ NPVARCIMCC
541 FKCCLWCLEK FIKFLNRNAY IMIAIYGKNF CVSAKNAFML LMRNIVRVVV LDKVTDLLLF
601 FGKLLVVGGV GVLSFFFFSG RIPGLGKDFK SPHLNYYWLP IMTSILGAYV IASGFFSVFG
661 MCVDTLFLCF LEDLERNNGS LDRPYYMSKS LLKILGKKNE APPDNKKRKK
```

Figure 3C. Amino acid sequence of 24P4C12 v.5 (SEQ ID. NO. : 22). The 24P4C12 v.5 protein has 710 amino acids.

Figure 3C-1

```
  1 MGGKQRDEDD EAYGKPVKYD PSFRGPIKNR SCTDVICCVL FLLFILGYIV VGIVAWLYGD
 61 PRQVLYPRNS TGAYCGMGEN KDKPYLLYFN IFSCILSSNI ISVAENGLQC PTPQVCVSSC
121 PEDPWTVGKN EFSQTVGEVF YTKNRNFCLP GVPWNMTVIT SLQQELCPSF LLPSAPALGR
181 CFPWTNVTPP ALPGITNDTT IQQGISGLID SLNARDISVK IFEDFAQSWY WILVALGVAL
241 VLSLLFILLL RLVAGPLVLV LILGVLGVLA YGIYYCWEEY RVLRDKGASI SQLGFTTNLS
301 AYQSVQETWL AALIVLAVLE AILLLVLIFL RQRIRIAIAL LKEASKAVGQ MMSTMFYPLV
361 TFVLLLICIA YWAMTALYLA TSGQPQYVLW ASNISSPGCE KVPINTSCNP TAHLVNSSCP
421 GLMCVFQGYS SKGLIQRSVF NLQIYGVLGL FWTLNWVLAL GQCVLAGAFA SFYWAFHKPQ
```

Figure 3C-2

```
481 DIPTFPLISA FIRTLRYHTG SLAFGALILT LVQIARVILE YIDHKLRGVQ NPVARCIMCC
541 FKCCLWCLEK FIKFLNRNAY IMIAIYGKNF CVSAKNAFML LMRNIVRVVV LDKVTDLLLF
601 FGKLLVVGGV GVLSFFFFSG RIPGLGKDFK SPHLNYYWLP IMTSILGAYV IASGFFSVFG
661 MCVDTLFLCF LEDLERNNGS LDRPYYMSKS LLKILGKKNE APPDNKKRKK
```

Figure 3D. Amino acid sequence of 24P4C12 v.6 (SEQ ID. NO. : 23). The 24P4C12 v.6 protein has 710 amino acids.

```
  1 MGGKQRDEDD EAYGKPVKYD PSFRGPIKNR SCTDVICCVL FLLFILGYIV VGIVAWLYGD
 61 PRQVLYPRNS TGAYCGMGEN KDKPYLLYFN IFSCILSSNI ISVAENGLQC PTPQVCVSSC
121 PEDPWTVGKN EFSQTVGEVF YTKNRNFCLP GVPWNMTVIT SLQQELCPSF LLPSAPALGR
181 CFPWTNVTPP ALPGITNDTT IQQGISGLID SLNARDISVK IFEDFAQSWY WILVALGVAL
241 VLSLLFILLL RLVAGPLVLV LILGVLGVLA YGIYYCWEEY RVLRDKGASI SQLGFTTNLS
301 AYQSVQETWL AALIVLAVLE AILLLMLIFL RQRIRIAIAL LKEASKAVGQ MMSTMFYPLV
361 TFVLLLICIA YWAMTALYLA TSGQPQYVLW ASNISSPGCE KVPINTSCNP TAHLVNSSCP
421 GLMCVFQGYS SKGLIPRSVF NLQIYGVLGL FWTLNWVLAL GQCVLAGAFA SFYWAFHKPQ
481 DIPTFPLISA FIRTLRYHTG SLAFGALILT LVQIARVILE YIDHKLRGVQ NPVARCIMCC
541 FKCCLWCLEK FIKFLNRNAY IMIAIYGKNF CVSAKNAFML LMRNIVRVVV LDKVTDLLLF
601 FGKLLVVGGV GVLSFFFFSG RIPGLGKDFK SPHLNYYWLP IMTSILGAYV IASGFFSVFG
661 MCVDTLFLCF LEDLERNNGS LDRPYYMSKS LLKILGKKNE APPDNKKRKK
```

Figure 3E. Amino acid sequence of 24P4C12 v.7 (SEQ ID. NO. : 24). The 24P4C12 v.7 protein has 598 amino acids.

```
  1 MGGKQRDEDD EAYGKPVKYD PSFRGPIKNR SCTDVICCVL FLLFILGYIV VGIVAWLYGD
 61 PRQVLYPRNS TGAYCGMGEN KDKPYLLYFN IFSCILSSNI ISVAENGLQC PTPQVCVSSC
121 PEDPWTVGKN EFSQTVGEVF YTKNRNFCLP GVPWNMTVIT SLQQELCPSF LLPSAPALGR
181 CFPWTNVTPP ALPGITNDTT IQQGISGLID SLNARDISVK IFEDFAQSWY WILVAVGQMM
241 STMFYPLVTF VLLLICIAYW AMTALYLATS GQPQYVLWAS NISSPGCEKV PINTSCNPTA
301 HLVNSSCPGL MCVFQGYSSK GLIQRSVFNL QIYGVLGLFW TLNWVLALGQ CVLAGAFASF
361 YWAFHKPQDI PTFPLISAFI RTLRYHTGSL AFGALILTLV QIARVILEYI DHKLRGVQNP
421 VARCIMCCFK CCLWCLEKFI KFLNRNAYIM IAIYGKNFCV SAKNAFMLLM RNIVRVVVLD
481 KVTDLLLFFG KLLVVGGVGV LSFFFFSGRI PGLGKDFKSP HLNYYWLPIM TSILGAYVIA
541 SGFFSVFGMC VDTLFLCFLE DLERNNGSLD RPYYMSKSLL KILGKKNEAP PDNKKRKK
```

Figure 3F. Amino acid sequence of 24P4C12 v.8 (SEQ ID. NO. : 25). The 24P4C12 v.8 protein has 722 amino acids.

Figure 3F-1

```
  1 MGGKQRDEDD EAYGKPVKYD PSFRGPIKNR SCTDVICCVL FLLFILGYIV VGIVAWLYGD
 61 PRQVLYPRNS TGAYCGMGEN KDKPYLLYFN IFSCILSSNI ISVAENGLQC PTPQVCVSSC
121 PEDPWTVGKN EFSQTVGEVF YTKNRNFCLP GVPWNMTVIT SLQQELCPSF LLPSAPALGR
```

Figure 3F-2

```
181 CFPWTNVTPP ALPGITNDTT IQQGISGLID SLNARDISVK IFEDFAQSWY WILVALGVAL
241 VLSLLFILLL RLVAGPLVLV LILGVLGVLA YGIYYCWEEY RVLRDKGASI SQLGFTTNLS
301 AYQSVQETWL AALIVLAVLE AILLLMLIFL RQRIRIAIAL LKEASKAVGQ MMSTMFYPLV
361 TFVLLLICIA YWAMTALYLA TSGQPQYVLW ASNISSPGCE KVPINTSCNP TAHLVNSSCP
421 GLMCVFQGYS SKGLIQRSVF NLQIYGVLGL FWTLNWVLAL GQCVLAGAFA SFYWAFHKPQ
481 DIPTFPLISA FIRTLRYHTG SLAFGALILT LVQIARVILE YIDHKLRGVQ NPVARCIMCC
541 FKCCLWCLEK FIKFLNRNAY IMIAIYGKNF CVSAKNAFML LMRNIVRVVV LDKVTDLLLF
601 FGKLLVVGGV GVLSFFFFSG RIPGLGKDFK SPHLNYYWLP IMRNPITPTG HVFQTSILGA 2
661 YVIASGFFSV FGMCVDTLFL CFLEDLERNN GSLDRPYYMS KSLLKILGKK NEAPPDNKKR
721 KK
```

Figure 3G. Amino acid sequence of 24P4C12 v.9 (SEQ ID. NO. : 26). The 24P4C12 v.9 protein has 712 amino acids.

```
  1 MGGKQRDEDD EAYGKPVKYD PSFRGPIKNR SCTDVICCVL FLLFILGYIV VGIVAWLYGD
 61 PRQVLYPRNS TGAYCGMGEN KDKPYLLYFN IFSCILSSNI ISVAENGLQC PTPQVCVSSC
121 PEDPWTVGKN EFSQTVGEVF YTKNRNFCLP GVPWNMTVIT SLQQELCPSF LLPSAPALGR
181 CFPWTNVTPP ALPGITNDTT IQQGISGLID SLNARDISVK IFEDFAQSWY WILVALGVAL
241 VLSLLFILLL RLVAGPLVLV LILGVLGVLA YGIYYCWEEY RVLRDKGASI SQLGFTTNLS
301 AYQSVQETWL AALIVLAVLE AILLLMLIFL RQRIRIAIAL LKEASKAVGQ MMSTMFYPLV
361 TFVLLLICIA YWAMTALYPL PTQPATLGYV LWASNISSPG CEKVPINTSC NPTAHLVNSS
421 CPGLMCVFQG YSSKGLIQRS VFNLQIYGVL GLFWTLNWVL ALGQCVLAGA FASFYWAFHK
481 PQDIPTFPLI SAFIRTLRYH TGSLAFGALI LTLVQIARVI LEYIDHKLRG VQNPVARCIM
541 CCFKCCLWCL EKFIKFLNRN AYIMIAIYGK NFCVSAKNAF MLLMRNIVRV VVLDKVTDLL
601 LFFGKLLVVG GVGVLSFFFF SGRIPGLGKD FKSPHLNYYW LPIMTSILGA YVIASGFFSV
661 FGMCVDTLFL CFLEDLERNN GSLDRPYYMS KSLLKILGKK NEAPPDNKKR KK
```

Figure 4: Alignment or 24P4C12 (SEQ ID NO: 27) with human choline transporter-like protein 4 (CTL4) (gi|14249468) (SEQ ID NO: 28)

```
Score = 1323 bits (3423), Expect = 0.0
 Identities = 706/710 (99%), Positives = 709/710 (99%)

24P4C12: 1    MGGKQRDEDDEAYGKPVKYDPSFRGPIKNRSCTDVICCVLFLLFILGYIVVGIVAWLYGD 60
              MGGKQRDEDDEAYGKPVKYDPSFRGPIKNRSCTDVICCVLFLLFILGYIVVGIVAWLYGD
CTL-4  : 1    MGGKQRDEDDEAYGKPVKYDPSFRGPIKNRSCTDVICCVLFLLFILGYIVVGIVAWLYGD 60

Query: 61     PRQVLYPRNSTGAYCGMGENKDKPYLLYFNIFSCILSSNIISVAENGLQCPTPQVCVSSC 120
              PRQVLYPRNSTGAYCGMGENKDKPYLLYFNIFSCILSSNIISVAENGLQCPTPQVCVSSC
Sbjct: 61     PRQVLYPRNSTGAYCGMGENKDKPYLLYFNIFSCILSSNIISVAENGLQCPTPQVCVSSC 120

Query: 121    PEDPWTVGKNEFSQTVGEVFYTKNRNFCLPGVPWNMTVITSLQQELCPSFLLPSAPALGR 180
              PEDPWTVGKNEFSQTVGEVFYTK+ NFCLPGVPWNMTVITSLQQELCPSFLLPSAPALGR
Sbjct: 121    PEDPWTVGKNEFSQTVGEVFYTKSSNFCLPGVPWNMTVITSLQQELCPSFLLPSAPALGR 180

Query: 181    CFPWTNVTPPALPGITNDTTIQQGISGLIDSLNARDISVKIFEDFAQSWYWILVALGVAL 240
              CFPWTN+TPPALPGITNDTTIQQGISGLIDSLNARDISVKIFEDFAQSWYWILVALGVAL
Sbjct: 181    CFPWTNITPPALPGITNDTTIQQGISGLIDSLNARDISVKIFEDFAQSWYWILVALGVAL 240

Query: 241    VLSLLFILLLRLVAGPLVLVLILGVLGVLAYGIYYCWEEYRVLRDKGASISQLGFTTNLS 300
              VLSLLFILLLRLVAGPLVLVLILGVLGVLAYGIYYCWEEYRVLRDKGASISQLGFTTNLS
Sbjct: 241    VLSLLFILLLRLVAGPLVLVLILGVLGVLAYGIYYCWEEYRVLRDKGASISQLGFTTNLS 300

Query: 301    AYQSVQETWLAALIVLAVLEAILLLMLIFLRQRIRIAIALLKEASKAVGQMMSTMFYPLV 360
              AYQSVQETWLAALIVLAVLEAILLL+LIFLRQRIRIAIALLKEASKAVGQMMSTMFYPLV
Sbjct: 301    AYQSVQETWLAALIVLAVLEAILLLVLIFLRQRIRIAIALLKEASKAVGQMMSTMFYPLV 360

Query: 361    TFVLLLICIAYWAMTALYLATSGQPQYVLWASNISSPGCEKVPINTSCNPTAHLVNSSCP 420
              TFVLLLICIAYWAMTALYLATSGQPQYVLWASNISSPGCEKVPINTSCNPTAHLVNSSCP
Sbjct: 361    TFVLLLICIAYWAMTALYLATSGQPQYVLWASNISSPGCEKVPINTSCNPTAHLVNSSCP 420

Query: 421    GLMCVFQGYSSKGLIQRSVFNLQIYGVLGLFWTLNWVLALGQCVLAGAFASFYWAFHKPQ 480
              GLMCVFQGYSSKGLIQRSVFNLQIYGVLGLFWTLNWVLALGQCVLAGAFASFYWAFHKPQ
Sbjct: 421    GLMCVFQGYSSKGLIQRSVFNLQIYGVLGLFWTLNWVLALGQCVLAGAFASFYWAFHKPQ 480

Query: 481    DIPTFPLISAFIRTLRYHTGSLAFGALILTLVQIARVILEYIDHKLRGVQNPVARCIMCC 540
              DIPTFPLISAFIRTLRYHTGSLAFGALILTLVQIARVILEYIDHKLRGVQNPVARCIMCC
Sbjct: 481    DIPTFPLISAFIRTLRYHTGSLAFGALILTLVQIARVILEYIDHKLRGVQNPVARCIMCC 540

Query: 541    FKCCLWCLEKFIKFLNRNAYIMIAIYGKNFCVSAKNAFMLLMRNIVRVVVLDKVTDLLLF 600
              FKCCLWCLEKFIKFLNRNAYIMIAIYGKNFCVSAKNAFMLLMRNIVRVVVLDKVTDLLLF
Sbjct: 541    FKCCLWCLEKFIKFLNRNAYIMIAIYGKNFCVSAKNAFMLLMRNIVRVVVLDKVTDLLLF 600

Query: 601    FGKLLVVGGVGVLSFFFFSGRIPGLGKDFKSPHLNYYWLPIMTSILGAYVIASGFFSVFG 660
              FGKLLVVGGVGVLSFFFFSGRIPGLGKDFKSPHLNYYWLPIMTSILGAYVIASGFFSVFG
Sbjct: 601    FGKLLVVGGVGVLSFFFFSGRIPGLGKDFKSPHLNYYWLPIMTSILGAYVIASGFFSVFG 660

Query: 661    MCVDTLFLCFLEDLERNNGSLDRPYYMSKSLLKILGKKNEAPPDNKKRKK 710
              MCVDTLFLCFLEDLERNNGSLDRPYYMSKSLLKILGKKNEAPPDNKKRKK
Sbjct: 661    MCVDTLFLCFLEDLERNNGSLDRPYYMSKSLLKILGKKNEAPPDNKKRKK 710
```

Figure 5: 24P4C12 variant 1 Hydrophilicity profile
(Hopp T.P., Woods K.R., 1981.
Proc. Natl. Acad. Sci. U.S.A. 78:3824-3828)
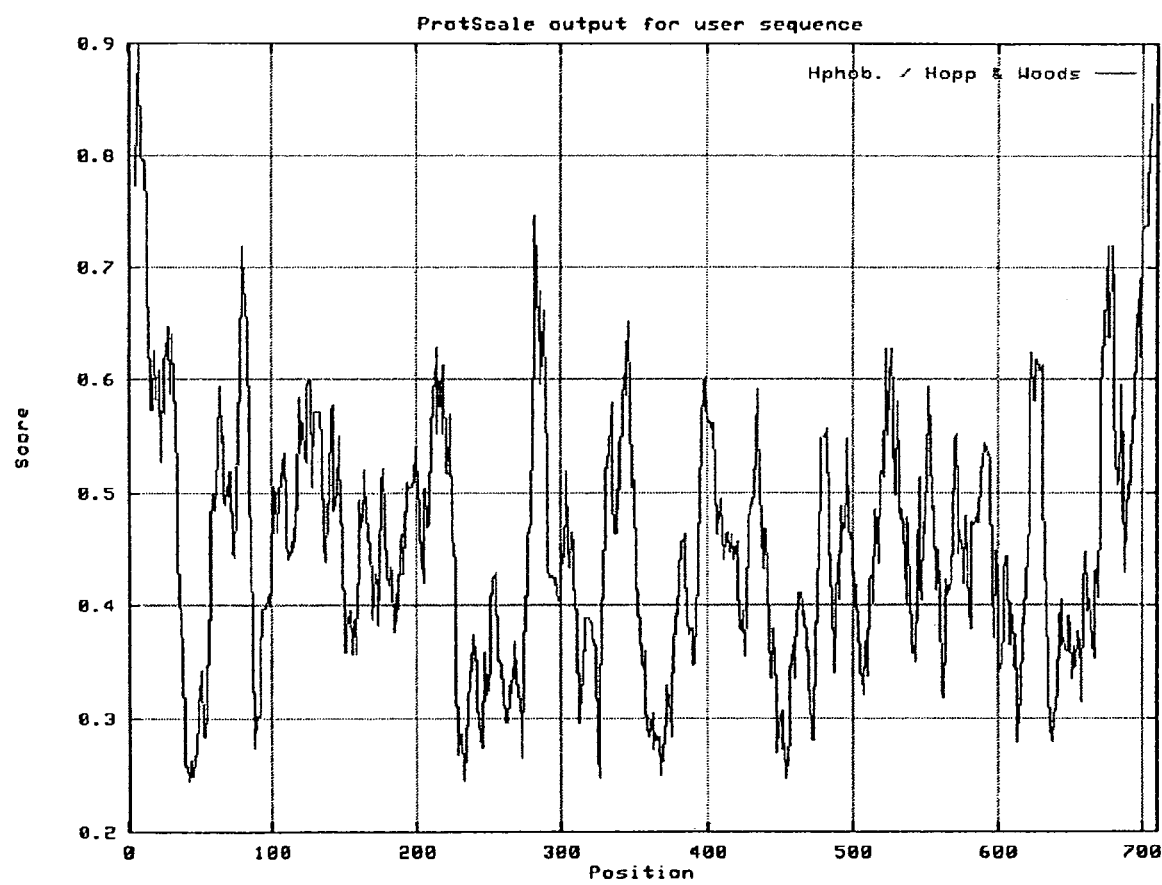

Figure 6: 24P4C12 variant 1 Hydropathicity Profile
(Kyte J., Doolittle R.F., 1982. J. Mol. Biol. 157:105-132)
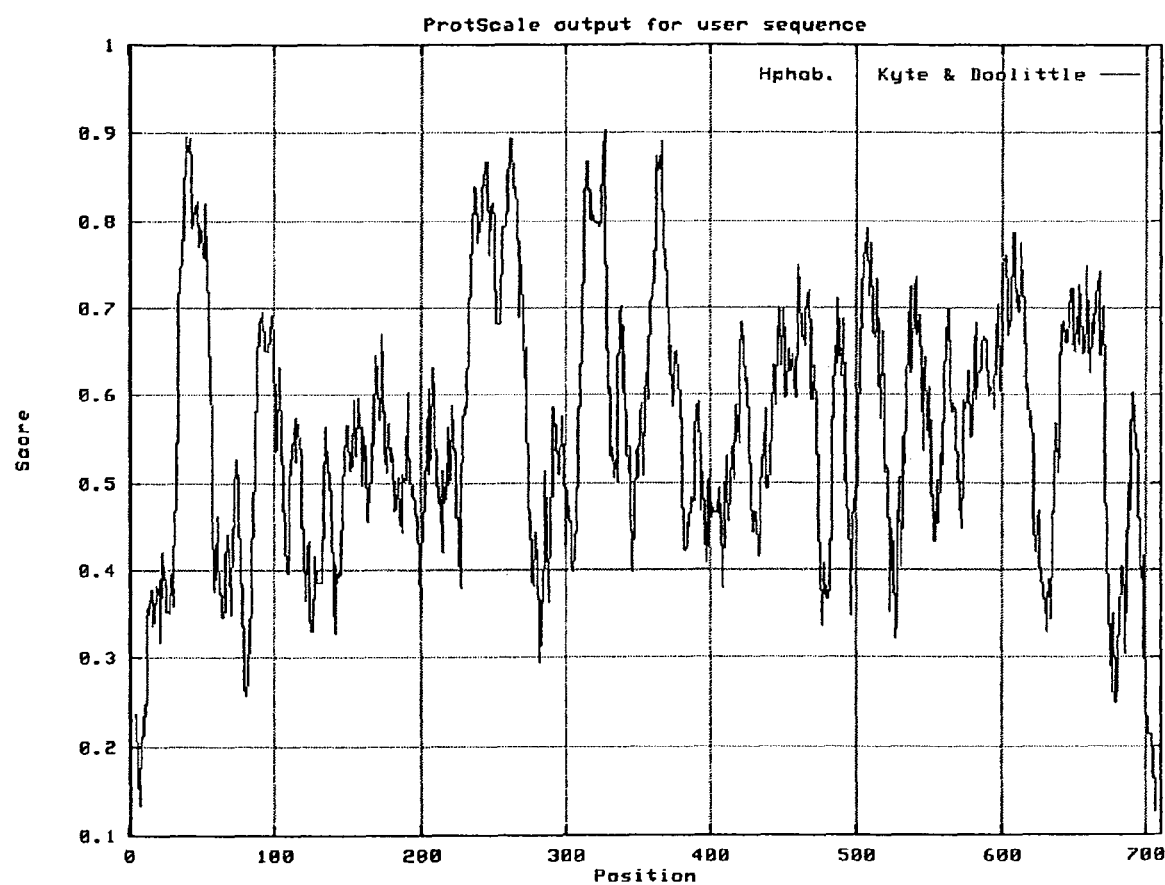

Figure 7: 24P4C12 variant 1 % Accessible Residues Profile (Janin J., 1979. Nature 277:491-492)
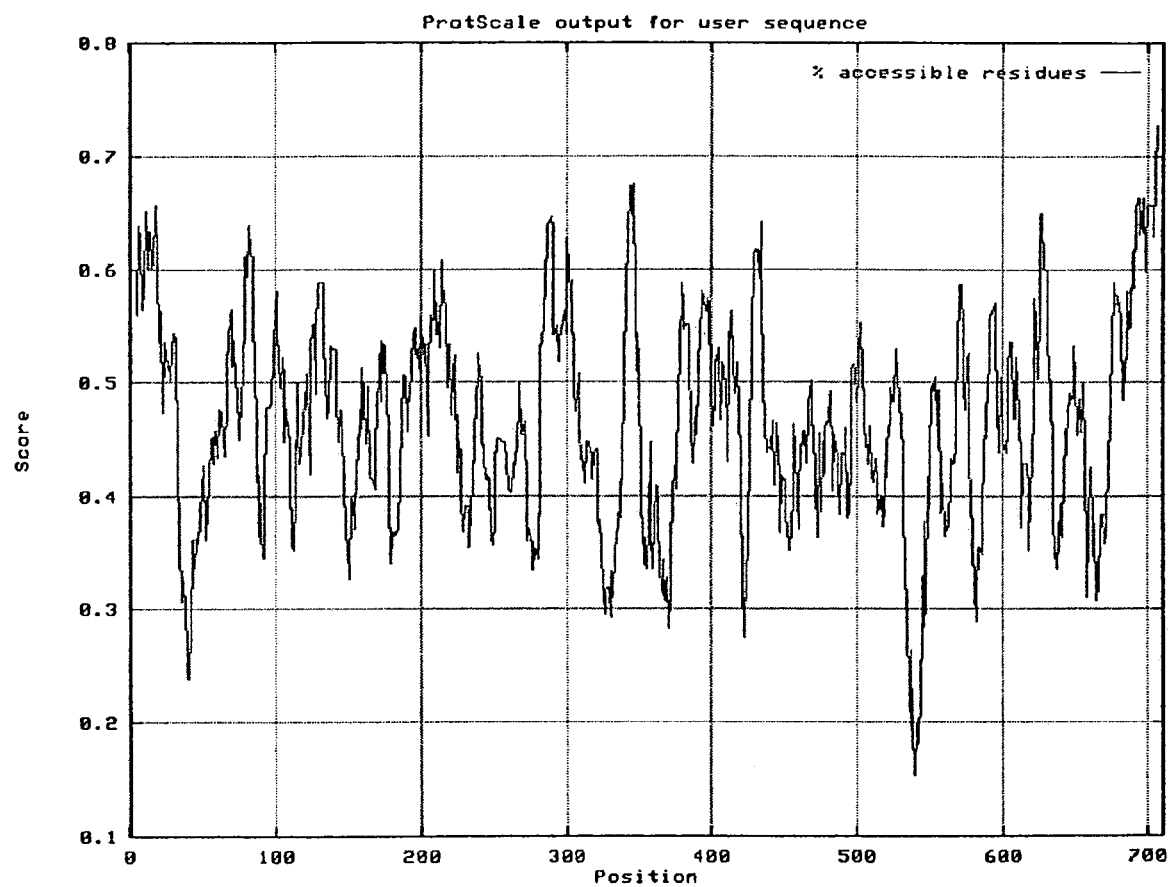

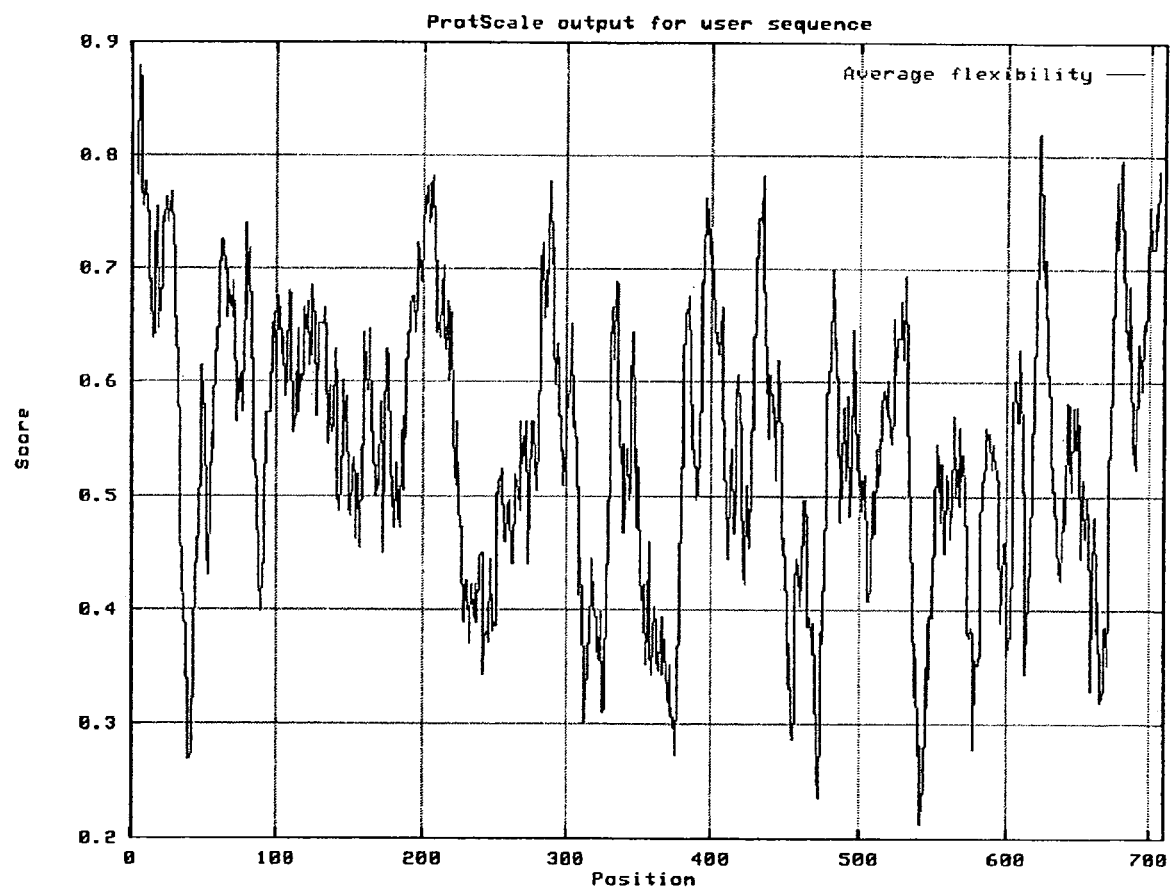
Figure 8: 24P4C12 variant 1 Average Flexibility Profile
(Bhaskaran R., Ponnuswamy P.K., 1988.
Int. J. Pept. Protein Res. 32:242-255)

Figure 9: 24P4C12 variant 1 Beta-turn Profile
(Deleage, G., Roux B. 1987. Protein Engineering 1:289-294)
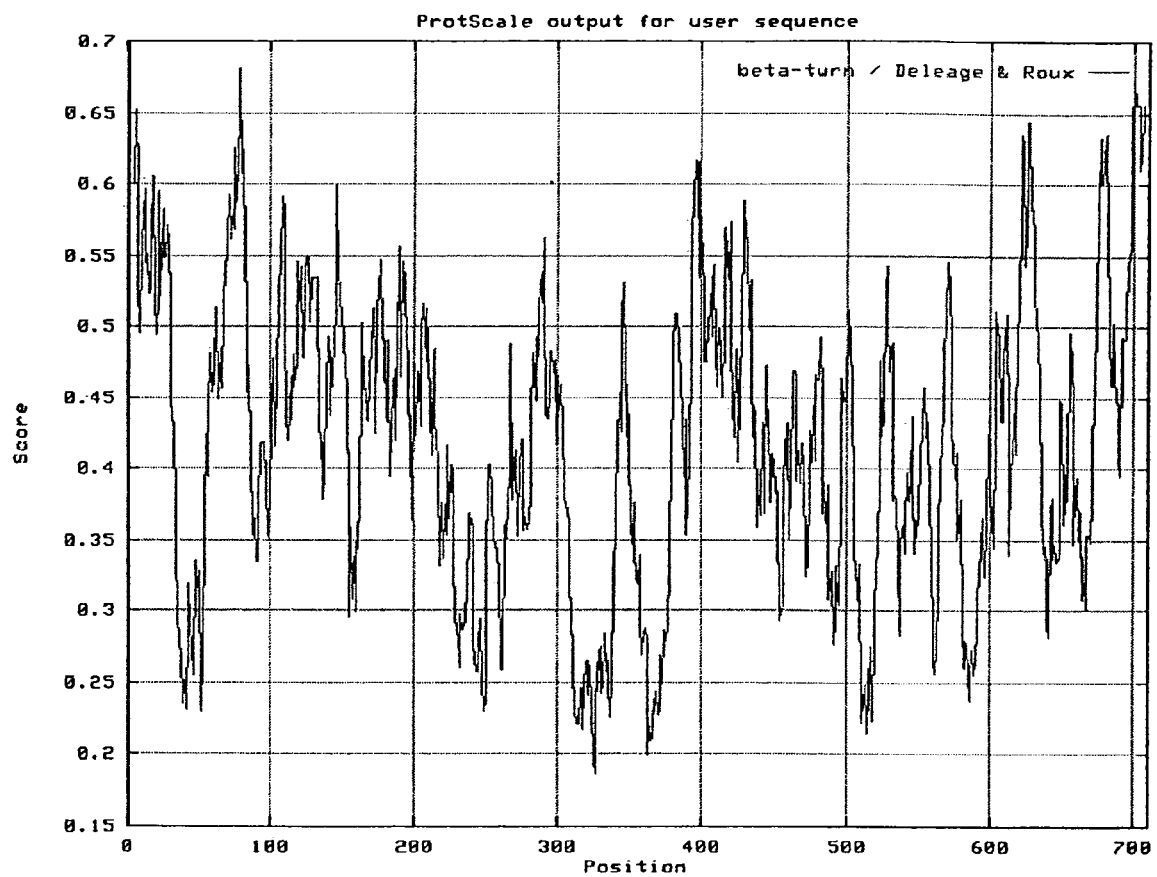

Fig. 13A: Secondary structure prediction of 24P4C12 variant 1

```
          10        20        30        40        50        60        70
          |         |         |         |         |         |         |
MGGKQRDEDDEAYGKPVKYDPSFRGPIKNRSCTDVICCVLFLLFILGYIVVGIVAWLYGDPRQVLYPRNS
cccccccccccccccccccccccccccccchhhhhhhhhhhhhhhhhhhhhhheccccceeeecccc
TGAYCGMGENKDKPYLLYFNIFSCILSSNIISVAENGLQCPTPQVCVSSCPEDPWTVGKNEFSQTVGEVF
ccccccccccccceeeehhhhhhhhcchhheccccccccceeeccccccccccccchchcceee
YTKNRNFCLPGVPWNMTVITSLQQELCPSFLLPSAPALGRCFPWTNVTPPALPGITNDTTIQQGISGLID
eecccceeccccceeeeehcccccccccccccccccccccccccccccccccchhhhhhhhhh
SLNARDISVKIFEDFAQSWYWILVALGVALVLSLLFILLLRLVAGPLVLVLILGVLGVLAYGIYYCWEEY
hccccchhhhhhhhhhhhhhhhhhhhhhhhhhhhhhhhhhhhhhcchhhhhhhhhhhhhhhcheeeechh
RVLRDKGASISQLGFTTNLSAYQSVQETWLAALIVLAVLEAILLLMLIFLRQRIRIAIALLKEASKAVGQ
hhhhhcccceeeeccccccchhhhhhhhhhhhhhhhhhhhhhhhhhhhhhhhhhhhhhhhhhhhhhhhh
MMSTMFYPLVTFVLLLICIAYWAMTALYLATSGQPQYVLWASNISSPGCEKVPINTSCNPTAHLVNSSCP
hhhhhhhhhhhhhhhhhhhhhhhhhhhhhhhhhccceeeeeeccccccccccccccccccceecccccc
GLMCVFQGYSSKGLIQRSVFNLQIYGVLGLFWTLNWVLALGQCVLAGAFASFYWAFHKPQDIPTFPLISA
ceeeeeecccchhhhhhhhhhhhhhhhhhhhhhhhhhhhhhhhhhhhhhhhhhhhhhccccccccchhhh
FIRTLRYHTGSLAFGALILTLVQIARVILEYIDHKLRGVQNPVARCIMCCFKCCLWCLEKFIKFLNRNAY
hhhhhhhccccchhhhhhhhhhhhhhhhhhhhhhhhhhhccccchhhhhhhhhhhhhhhhhhhhhhccce
IMIAIYGKNFCVSAKNAFMLLMRNIVRVVVLDKVTDLLLFFGKLLVVGGVGVLSFFFFSGRIPGLGKDFK
eeeeeeccchhhhhhhhhhhhhhhhhhhhhhhhhhhhhhhhhcceeeeccchheeeeeccccccccccc
SPHLNYYWLPIMTSILGAYVIASGFFSVFGMCVDTLFLCFLEDLERNNGSLDRPYYMSKSLLKILGKKNE
ccccchhhhhhhhhhhchhehhhhhhhhhhhhhhhhhhhhhhhhhhhhccccccchhhhhhhhhhccccc
APPDNKKRKK
cccccccccc
```

| | | |
|---|---|---|
| Alpha helix | (h) : | 53.94% |
| Extended strand | (e) : | 9.44% |
| Random coil | (c) : | 36.62% |

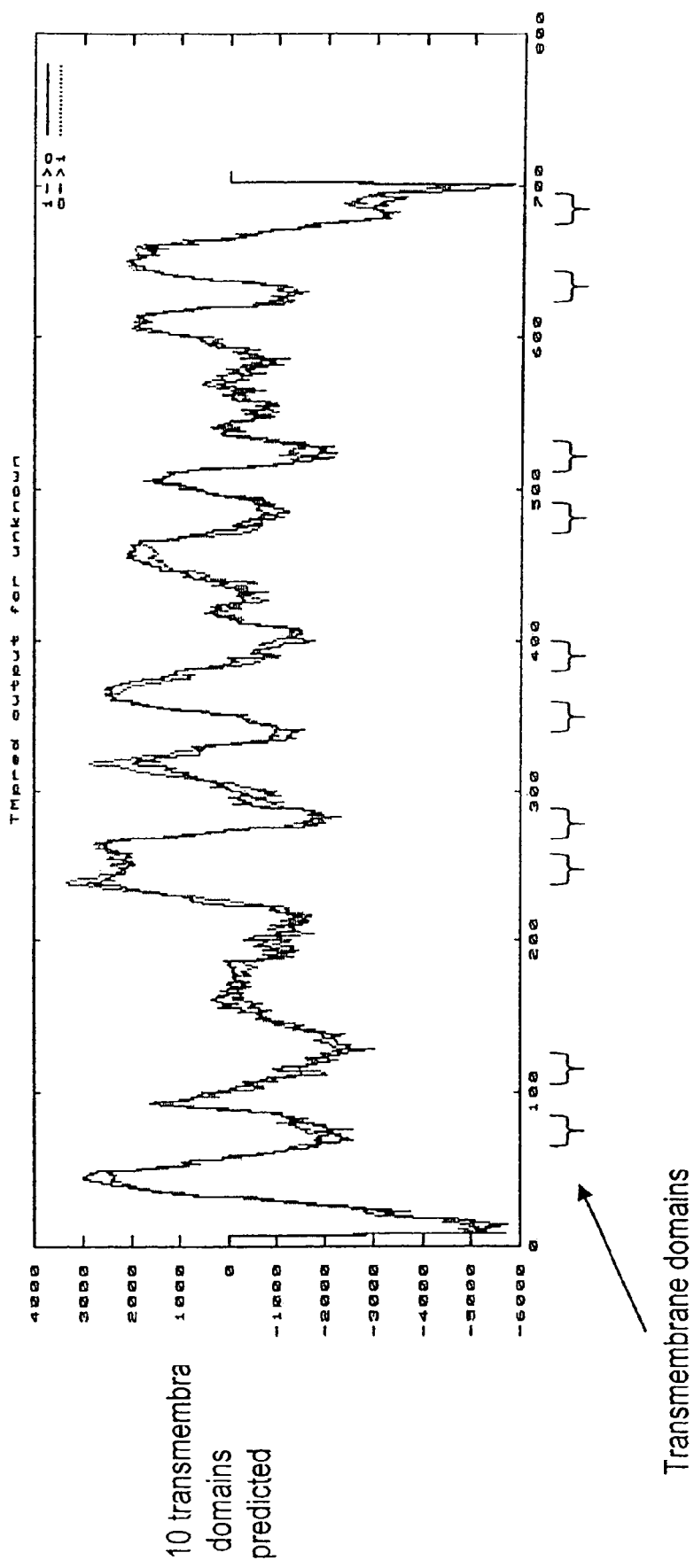
Figure 13B Transmembrane prediction for 24P4C12 variant 1

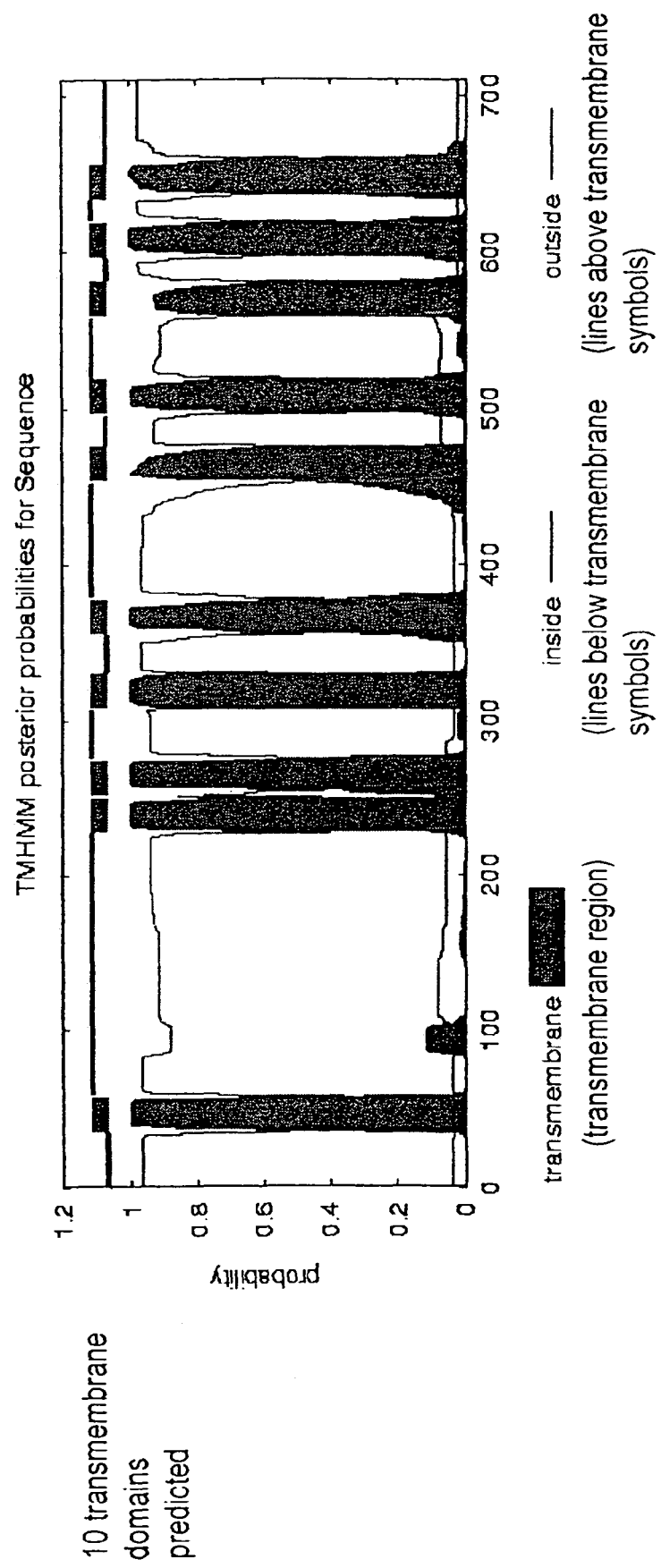
Fig. 13C Transmembrane prediction for 24P4C12 variant 1

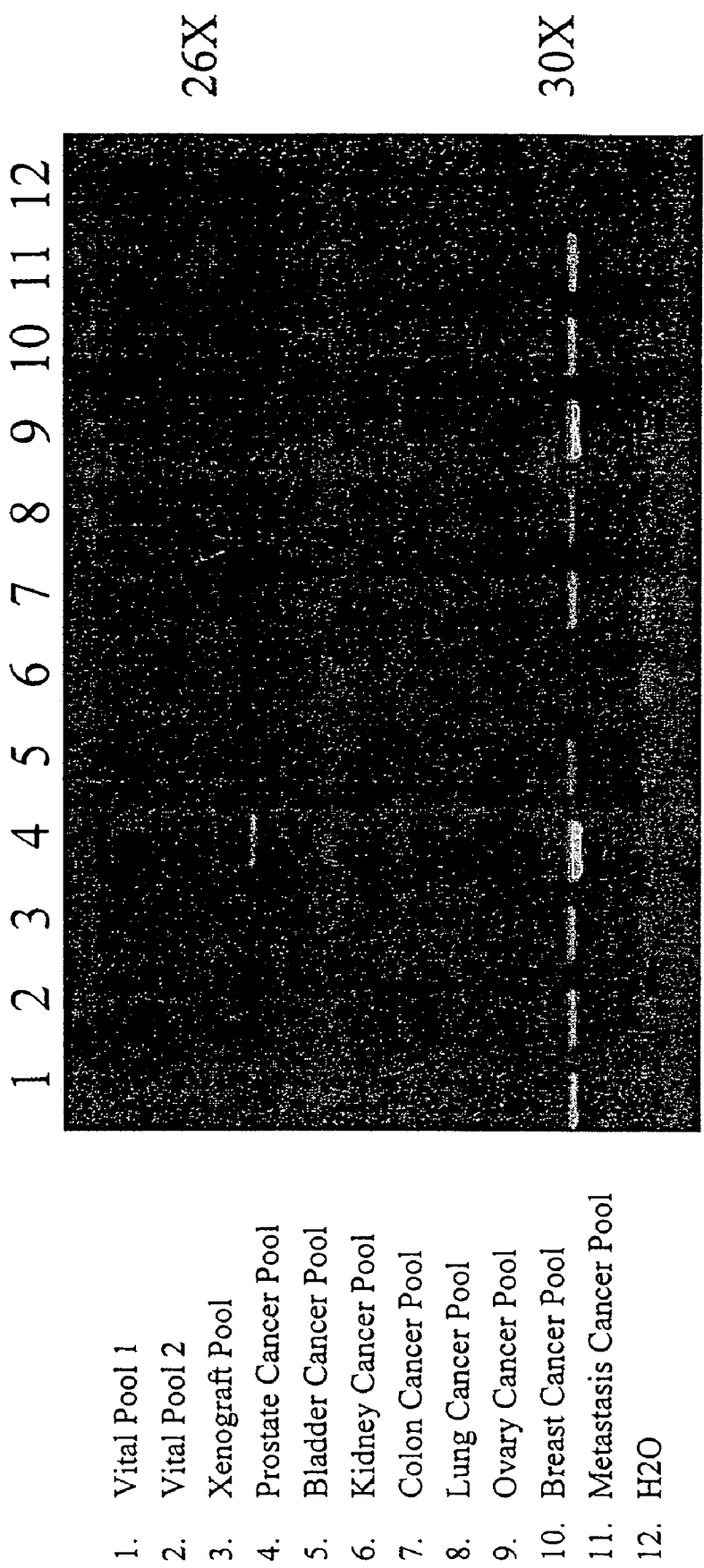
Figure 14: 24P4C12 Expression by RT-PCR
1. Vital Pool 1
2. Vital Pool 2
3. Xenograft Pool
4. Prostate Cancer Pool
5. Bladder Cancer Pool
6. Kidney Cancer Pool
7. Colon Cancer Pool
8. Lung Cancer Pool
9. Ovary Cancer Pool
10. Breast Cancer Pool
11. Metastasis Cancer Pool
12. H2O

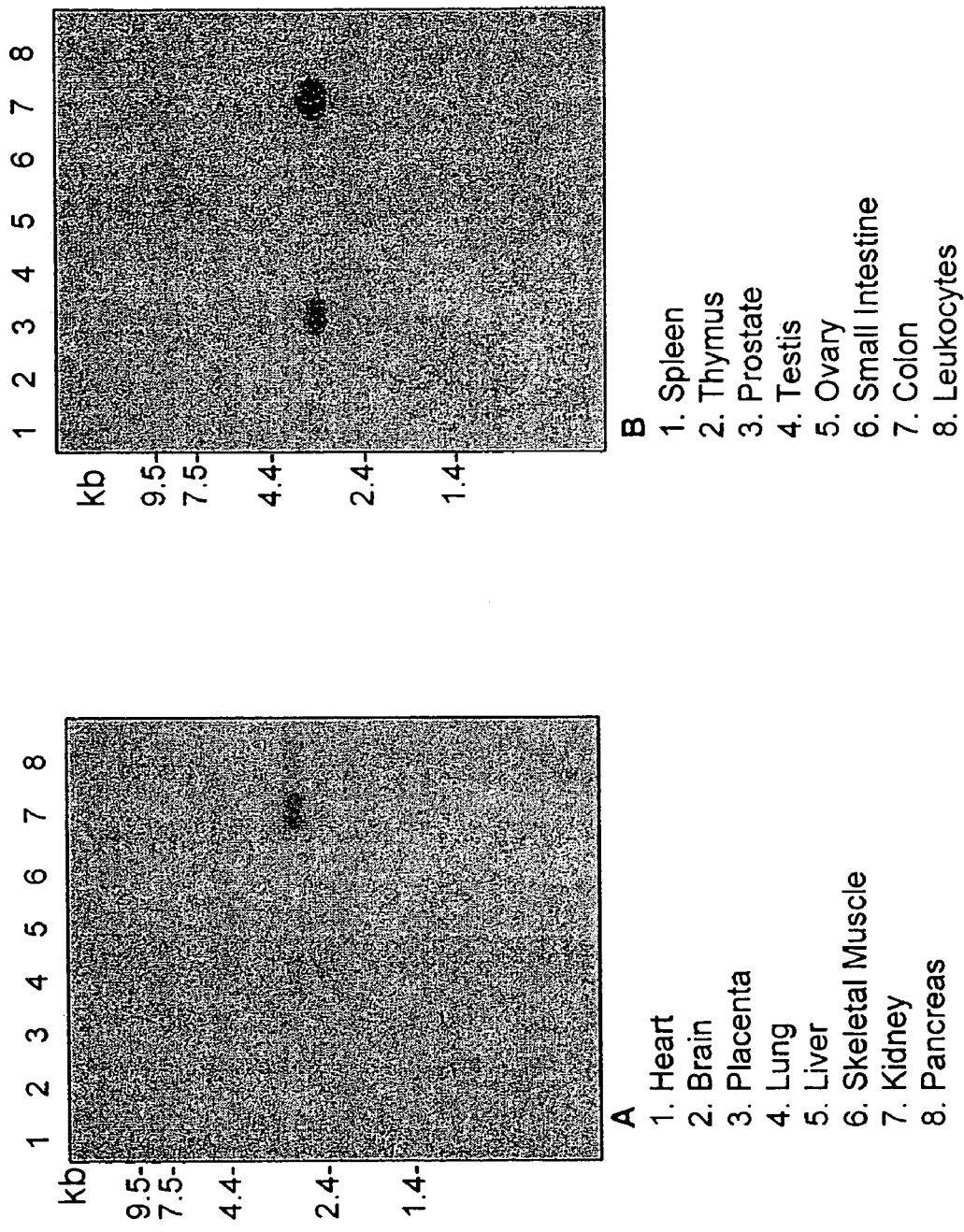
Figure 15: Expression of 24P4C12 in Normal Tissues

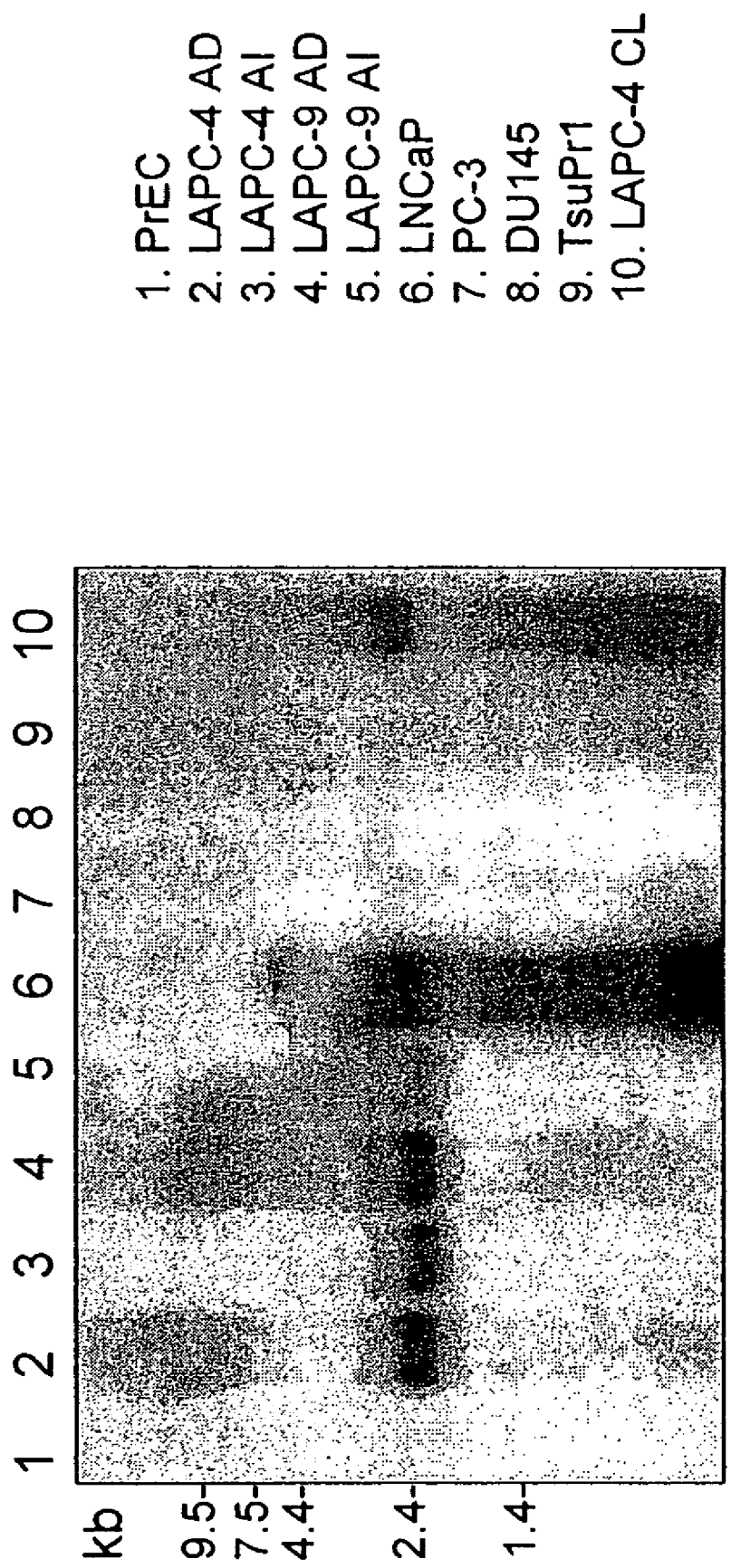
Figure 16: Expression of 24P4C12 in Prostate Cancer Xenografts and Cell Lines

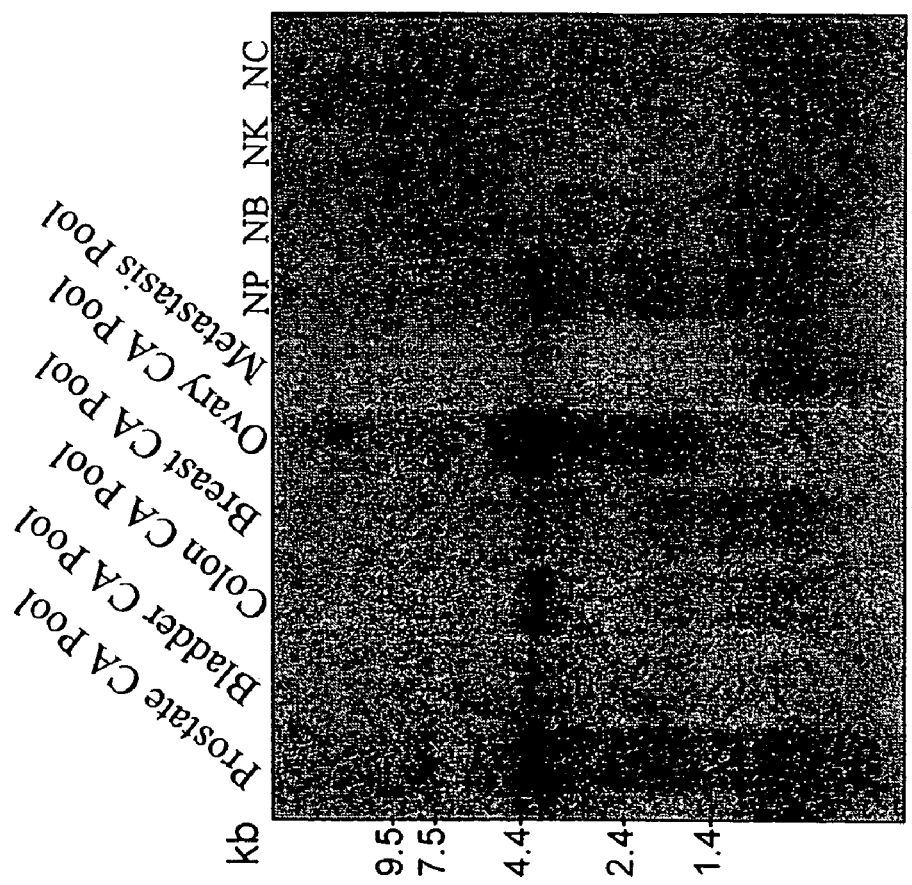

Figure 17: Expression of 24P4C12 in Human Patient Cancer Specimens

10μg total RNA/per lane from a pool of 3 tumors as follows:

Prostate Cancer Pool = gleason 6, 8, 9
Bladder Cancer Pool = grade 2, 3
Colon Cancer Pool = stage II, III, IV
Breast Cancer Pool = grade 1, 2, 3
Ovary Cancer Pool = grade 2, 2, 3
Metastasis Pool = colon to lung, colon to liver, ovary to fall. tube NP = Normal Prostate
NB = Normal Bladder
NK = Normal Kidney
NC = Normal Colon

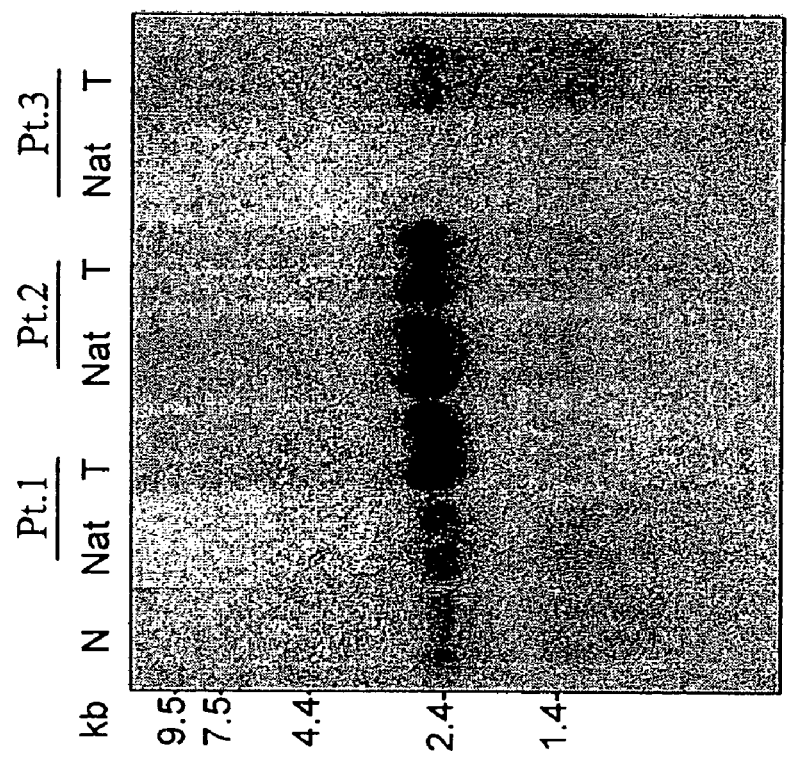
Figure 18: Expression of 24P4C12 in Prostate Cancer Patient Specimens
N = Normal prostate
Nat = Normal adjacent tissue
T = Tumor
Patient 1- Gleason Score 4+5
Patient 2- Gleason Score 3+4
Patient 3- Gleason Score 4+3

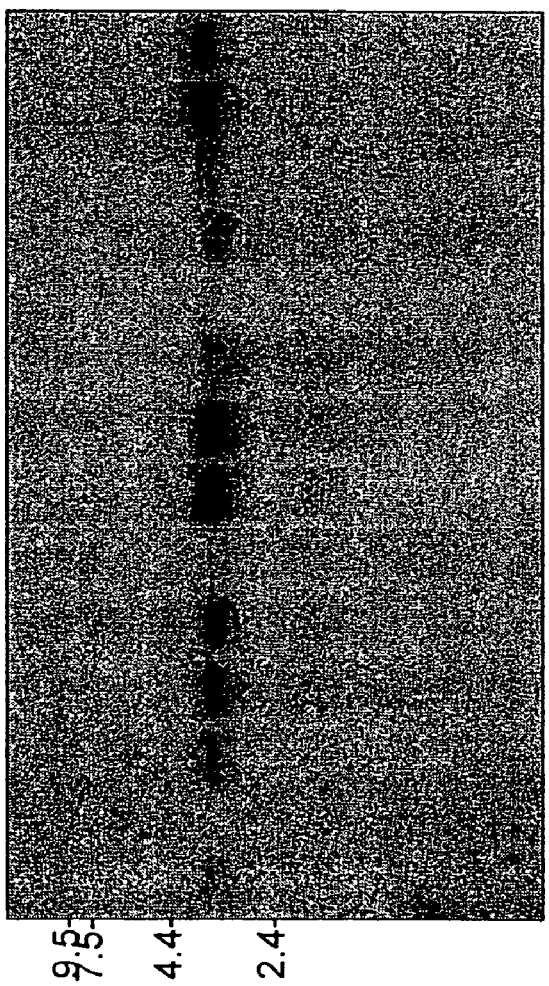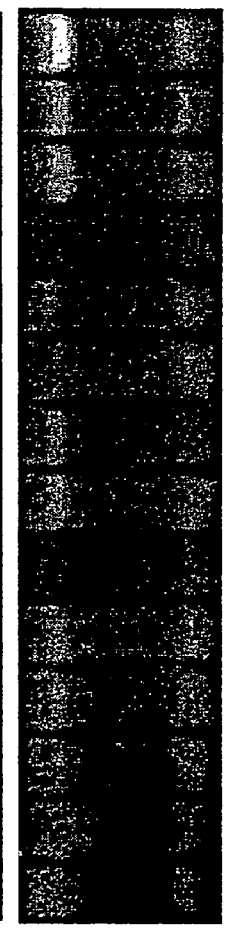
Figure 19: Expression of 24P4C12 in Colon Cancer Patient Samples
Pt.1, stage I
Pt.2, stage II
Pt.3, stage II
Pt.4, stage III
Pt.5, stage IV
N = Normal colon
Nat = Normal Adjacent Tissue
T = Tumor
CL = Cell lines (Colo 205, LoVo, SK-CO-1)

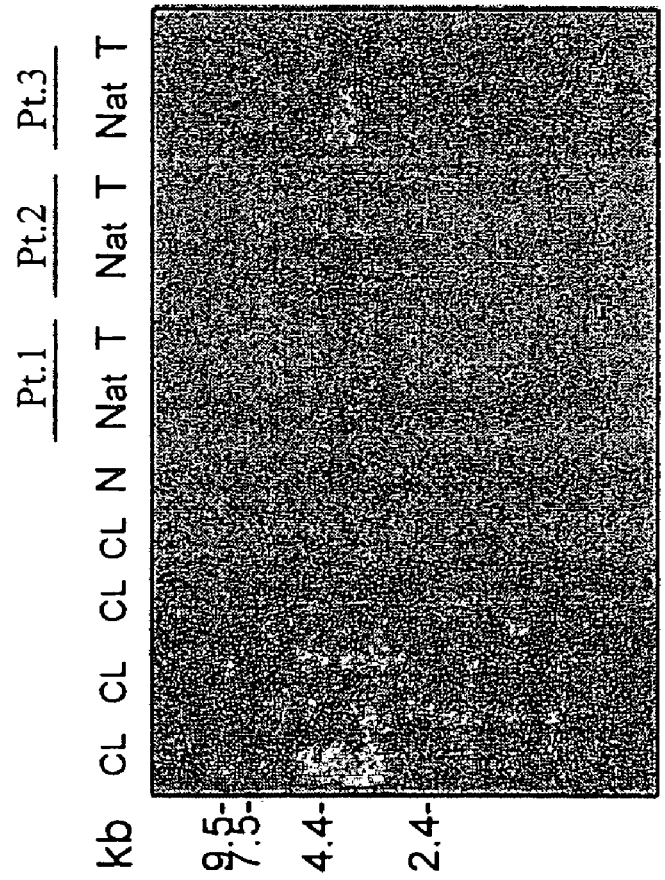
Figure 20: Expression of 24P4C12 in Lung Cancer Patient Samples

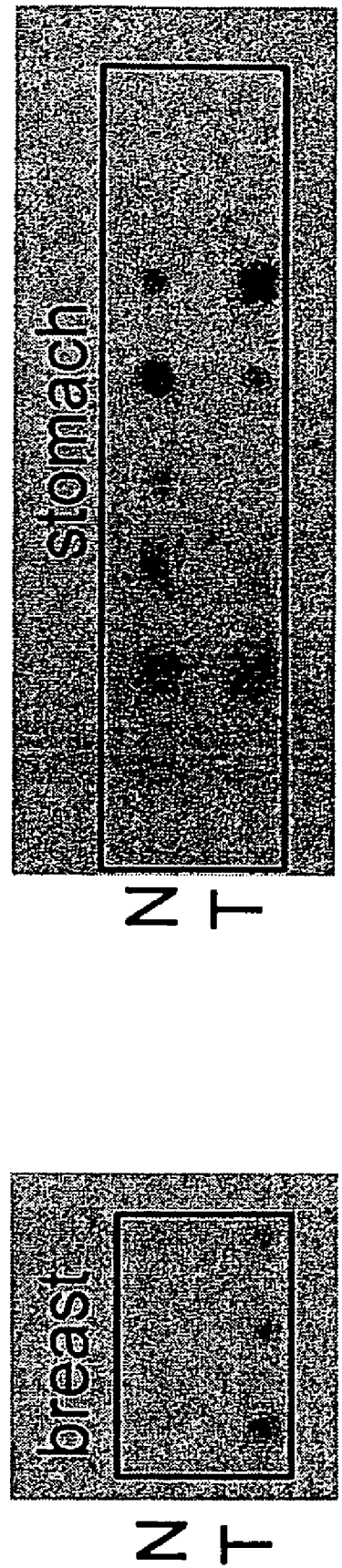
Figure 21: Expression of 24P4C12 in Patient Cancer Specimens
T = tumor RNA
N = normal adjacent tissue RNA

Figure 22-1: 24P4C12 Expression in Patient Cancer Specimens
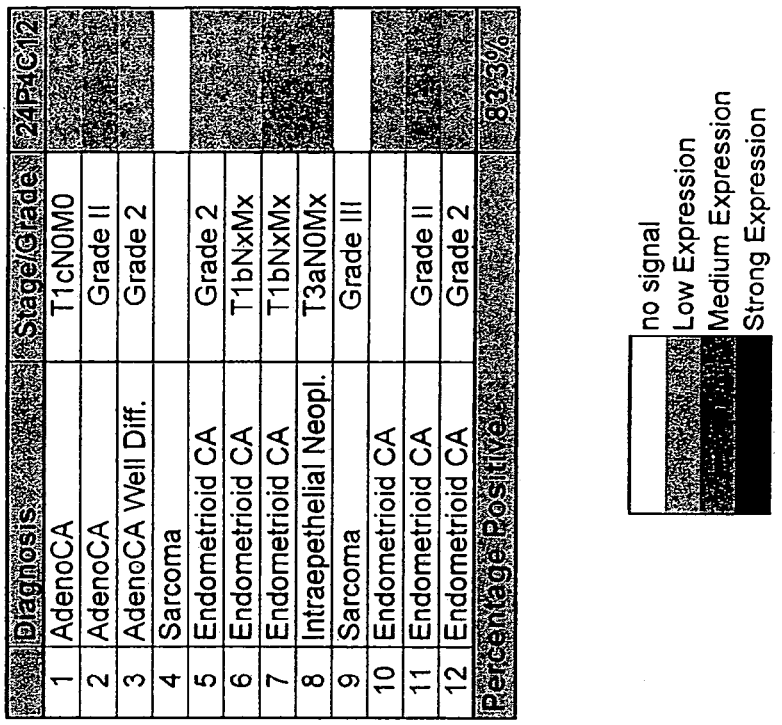
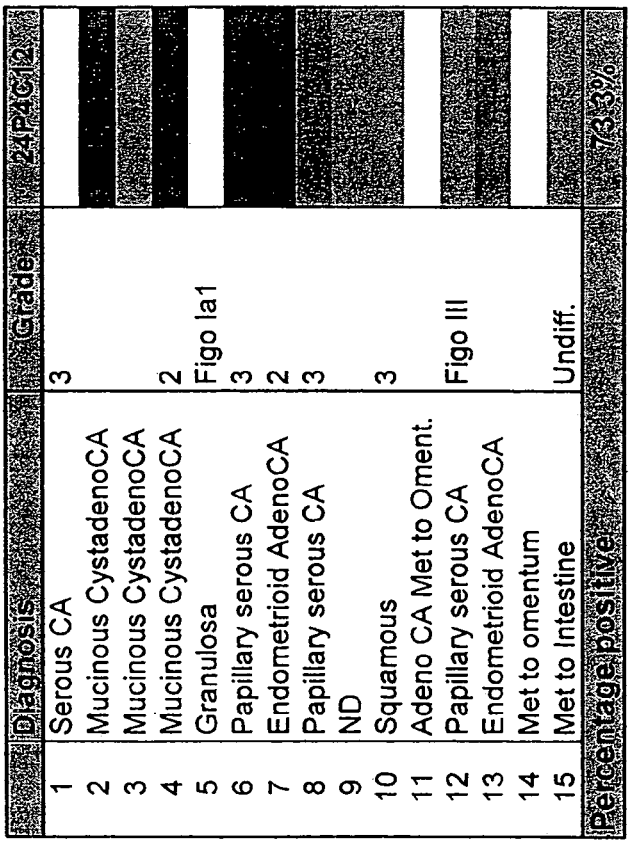

Figure 22-2: 24P4C12 Expression in Patient Cancer Specimens
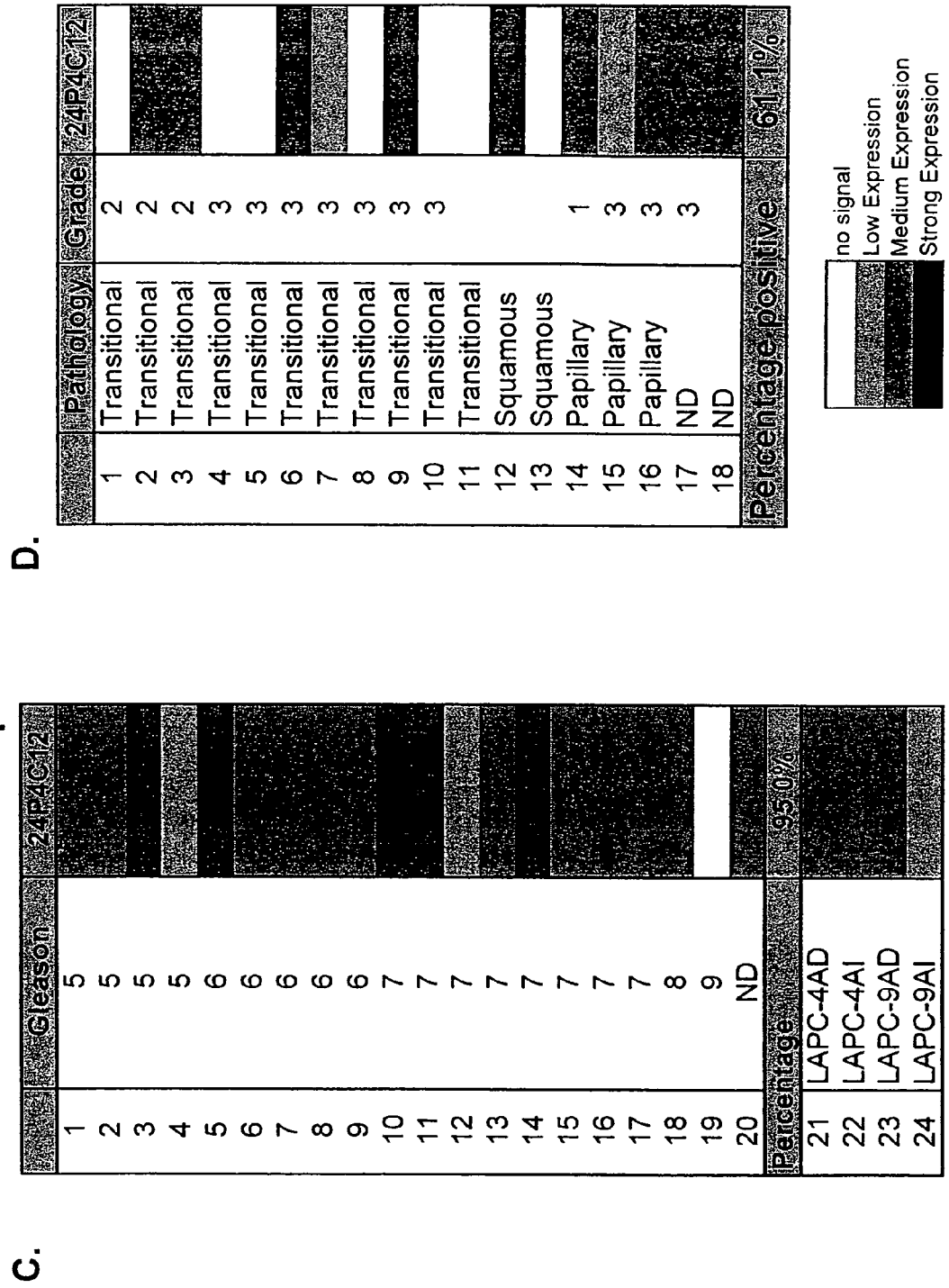

Figure 22-3: 24P4C12 Expression in Patient Cancer Specimens
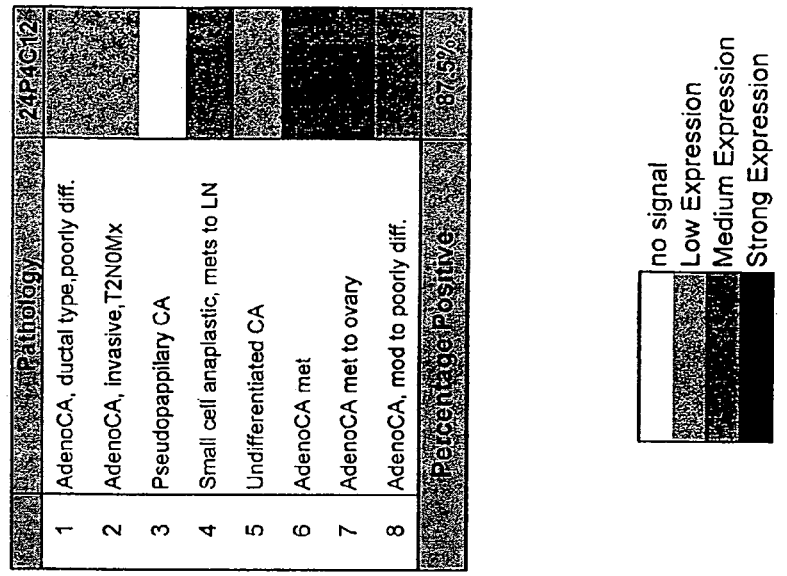

Figure 22-4: 24P4C12 Expression in Patient Cancer Specimens
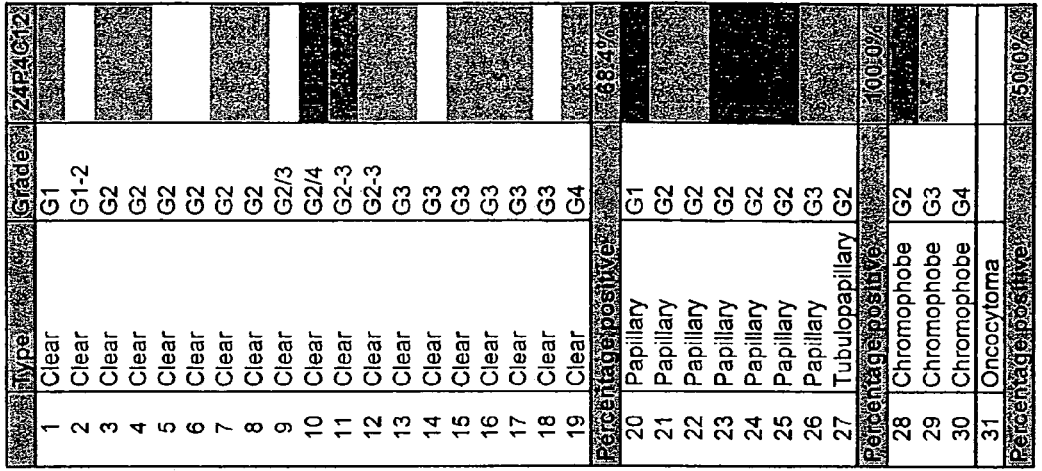
H.
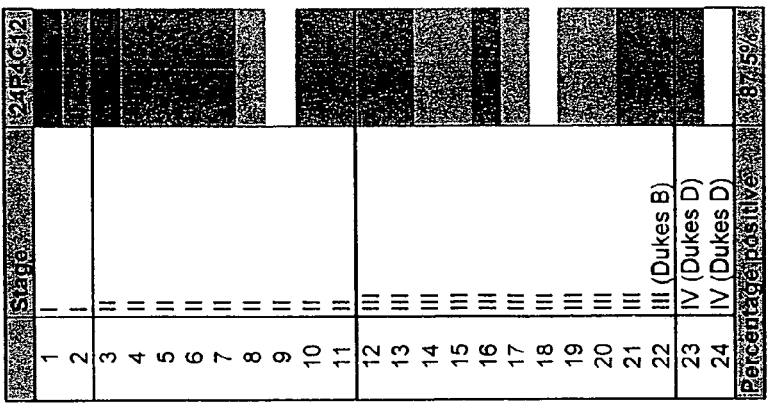
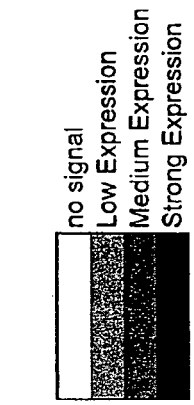
G.

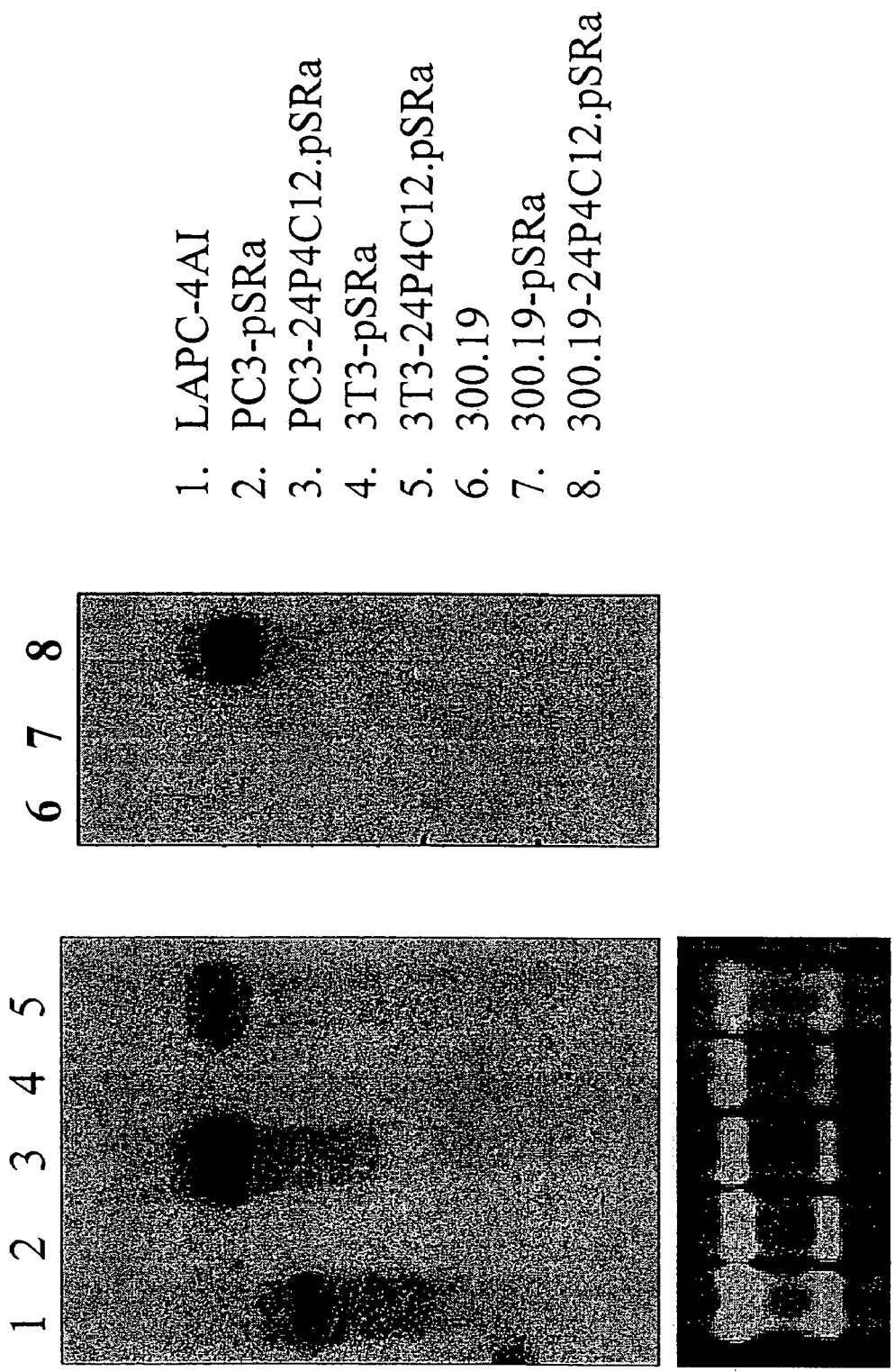
Figure 23: Expression of 24P4C12 in Transduced Cells

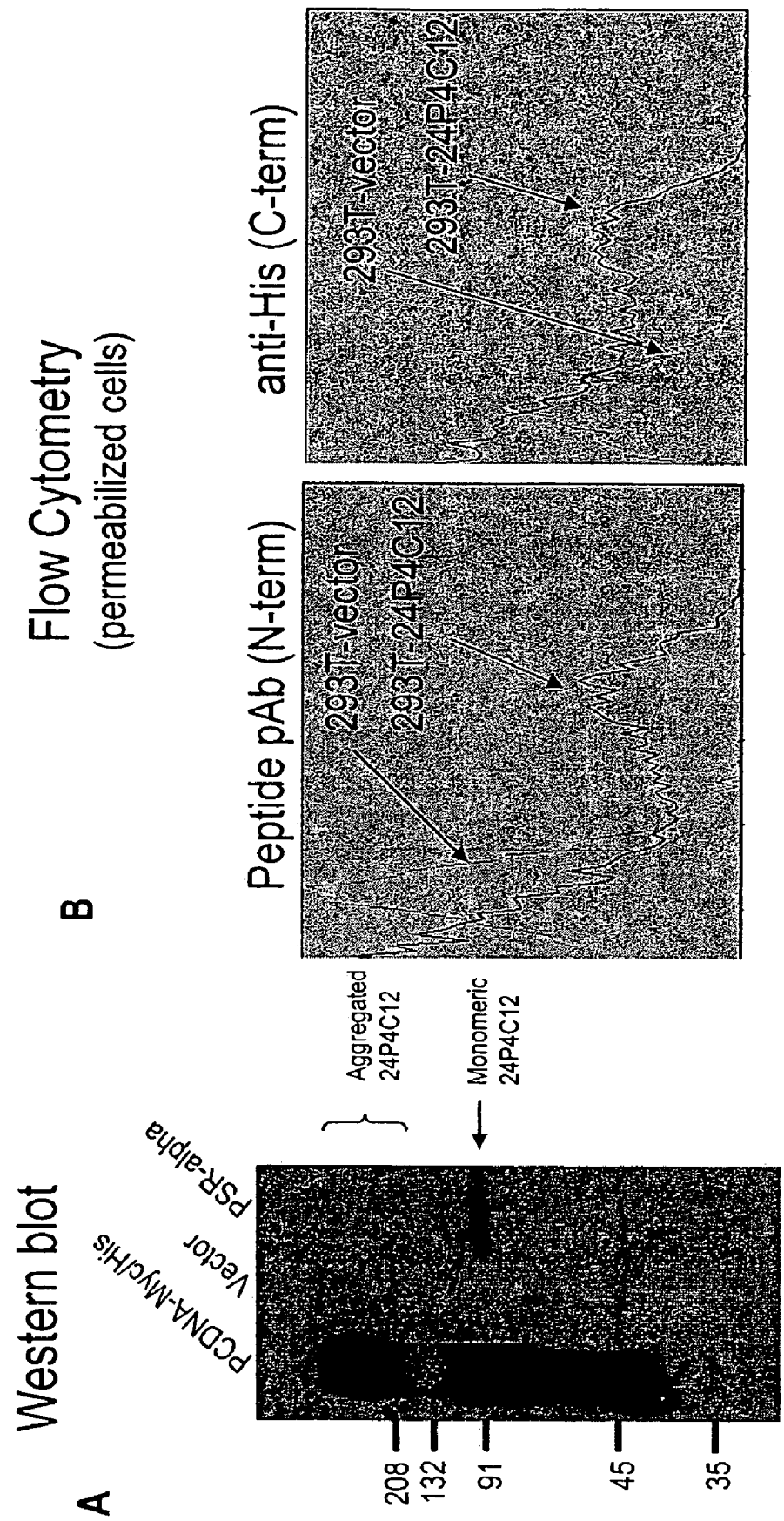
Figure 24: Expression of 24P4C12 in 293T cells

Figure 25: Expression and detection of 24P4C12 in stably transduced PC3 cells
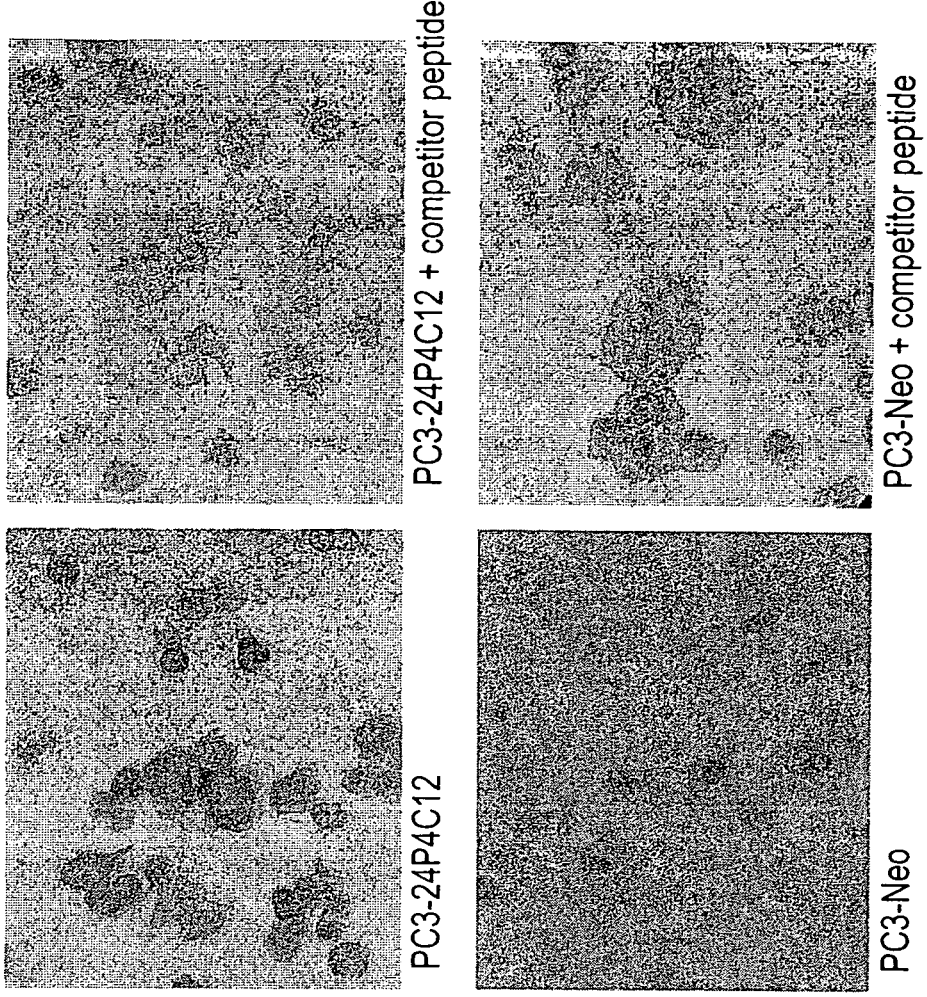

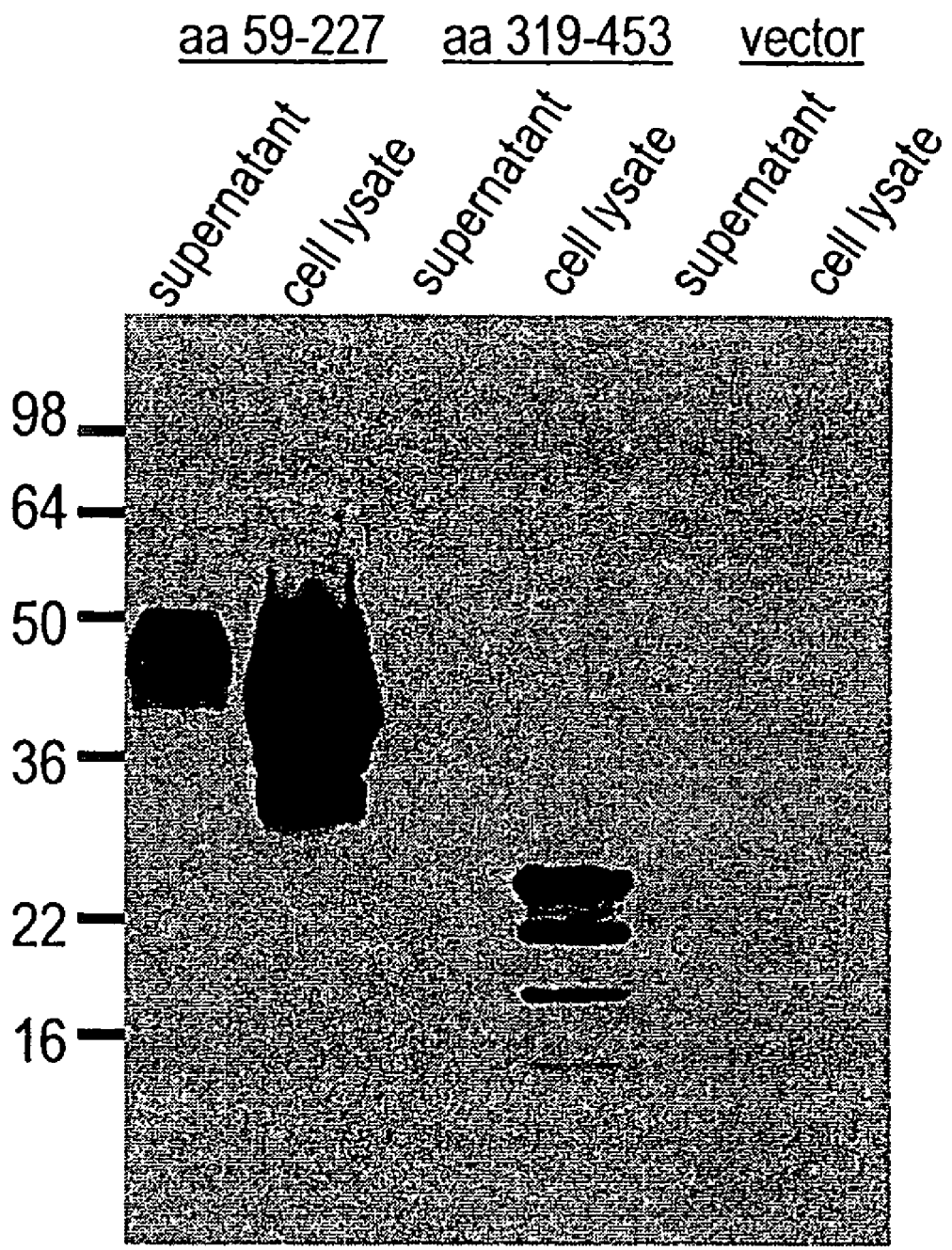
Figure 26: Expression of recombinant 24P4C12 antigens in 293T cells

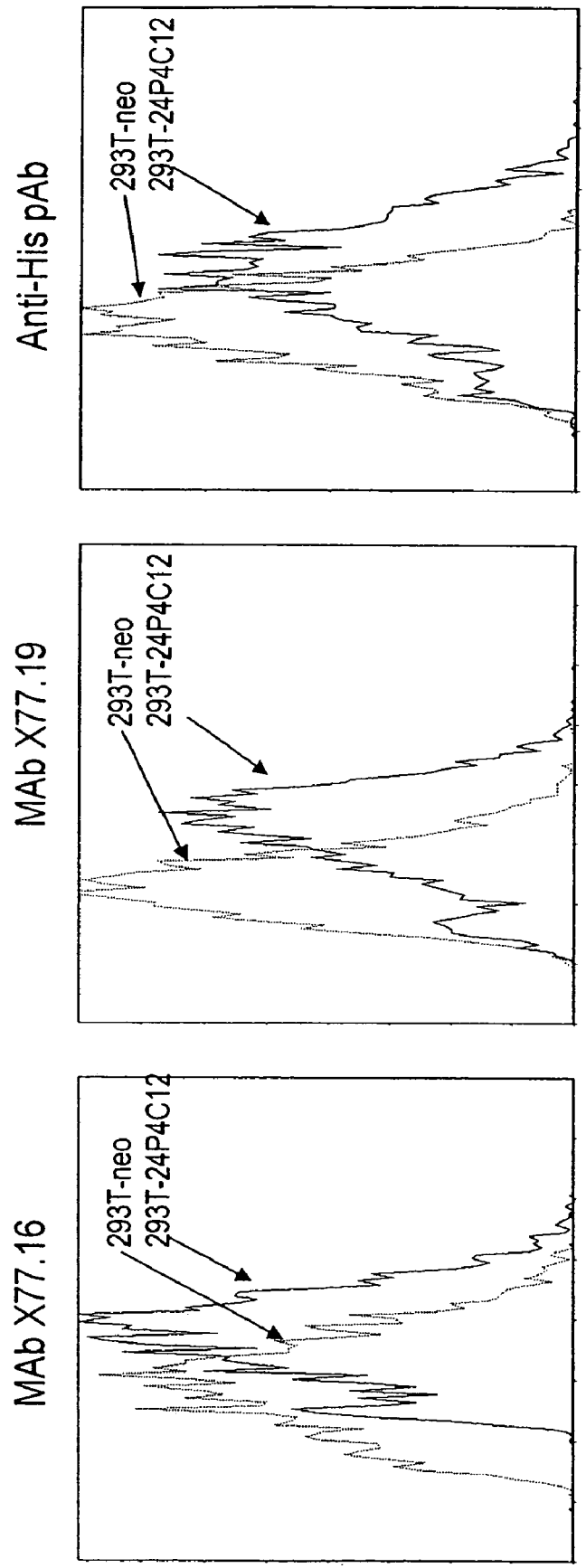
Figure 27: Monoclonal antibodies detect 24P4C12 protein expression in 293T cells by flow cytometry

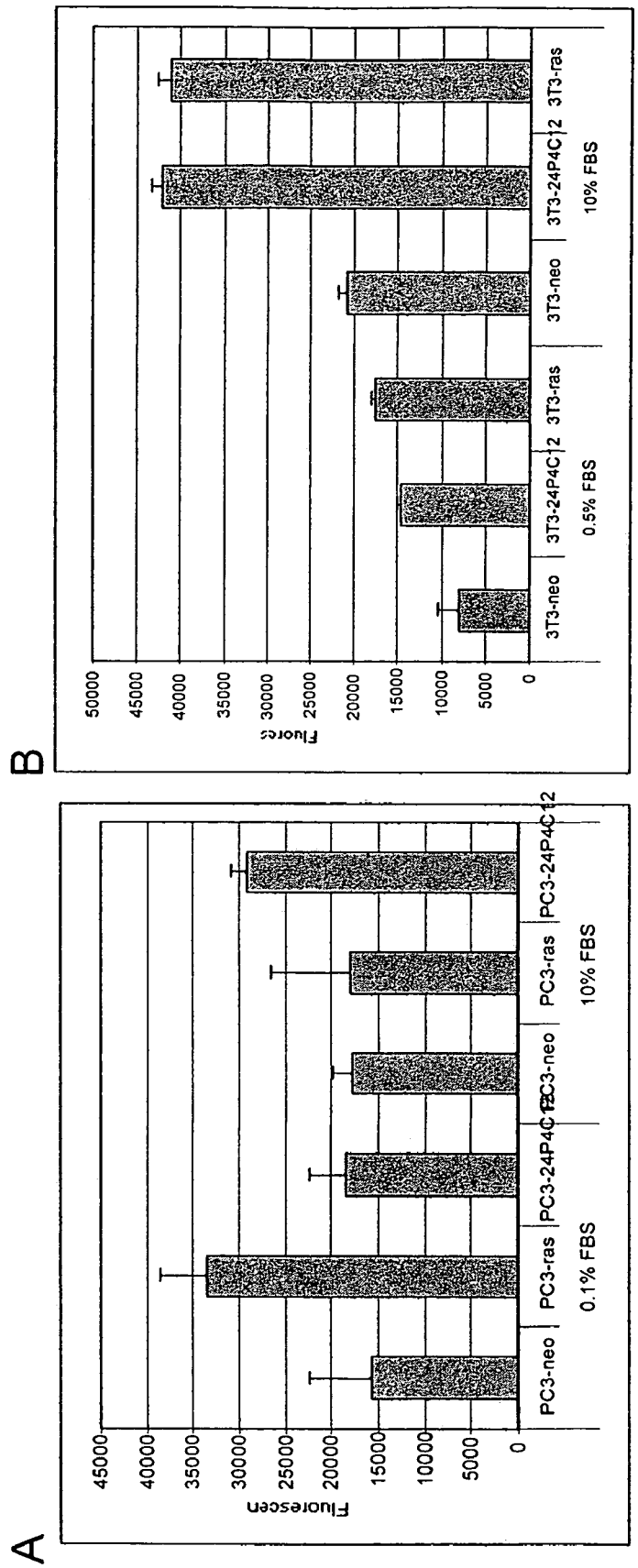
Figure 28: Expression of 24P4C12 Enhances Proliferation
Enhance Proliferation in PC3 cells after 48 hr
Enhance Proliferation in 3T3 cells after 72 hr
- PC3 and 3T3 were grown overnight in low FBS. Cells were then incubated in low or 10% FBS as indicated. Proliferation was measured by Alamar Blue.
- Experiments were performed in triplicate

Figure 29: Detection of 24P4C12 protein by immunohistochemistry in prostate cancer patient specimens.
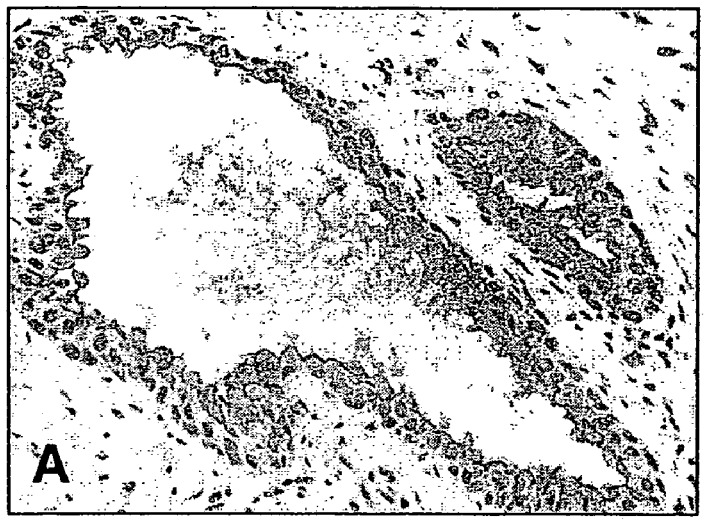
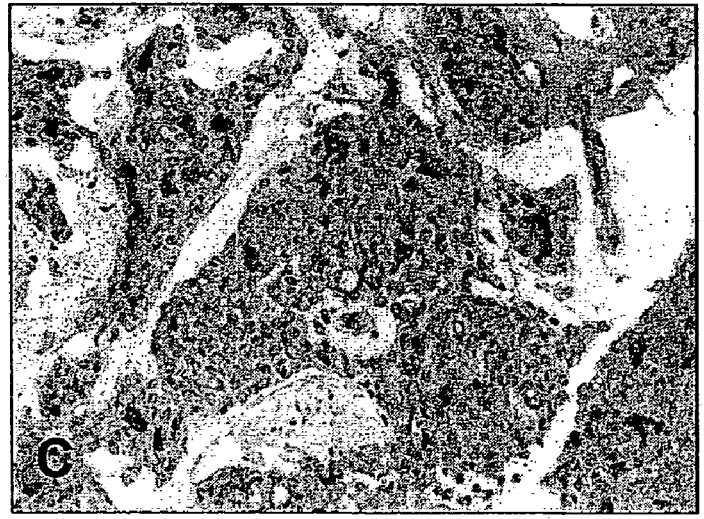

Figure 30: Detection of 24P4C12 protein by immunohistochemistry in various cancer patient specimens.
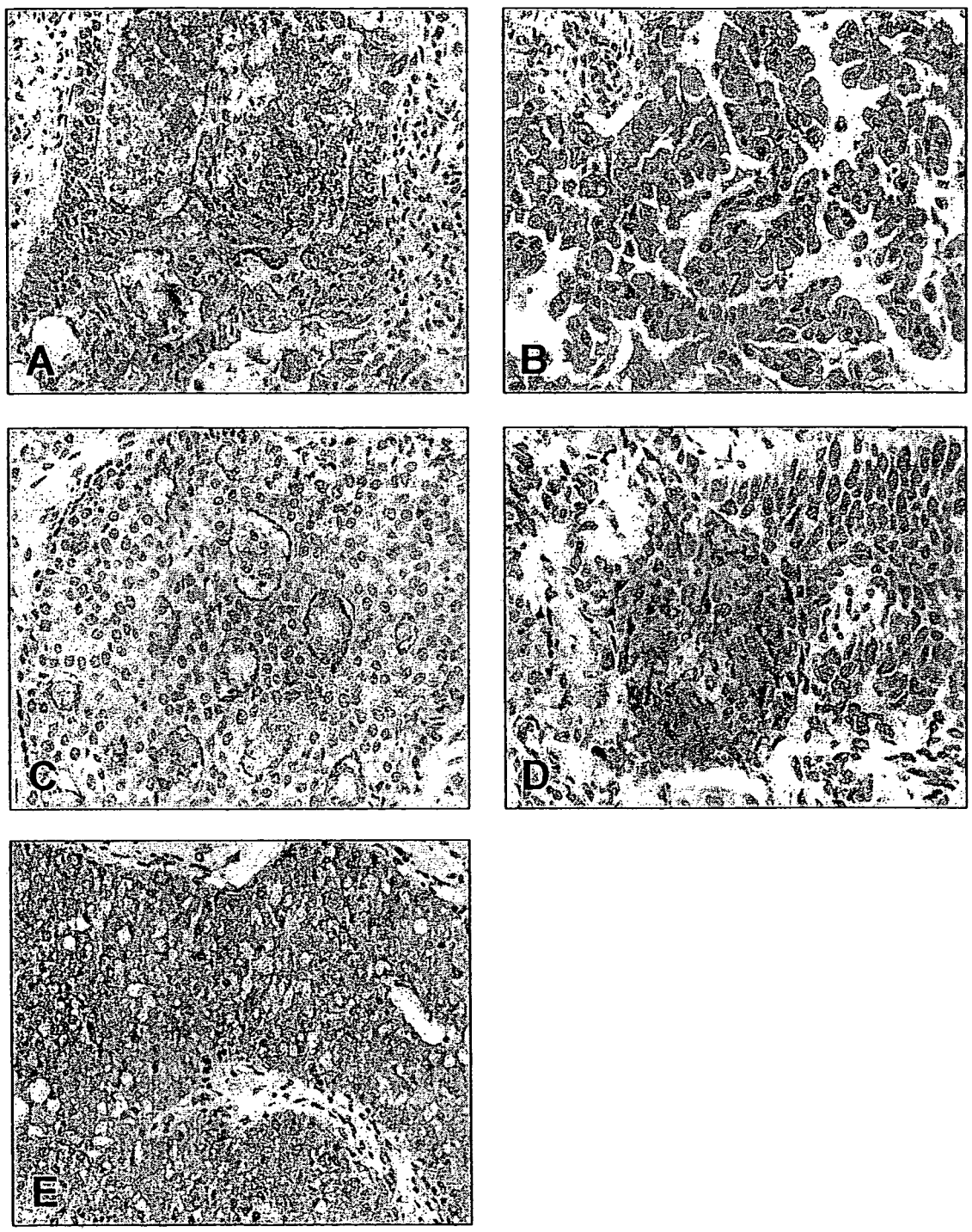

Figure 31: 24P4C12 Enhances Tumor Growth in SCID Mice
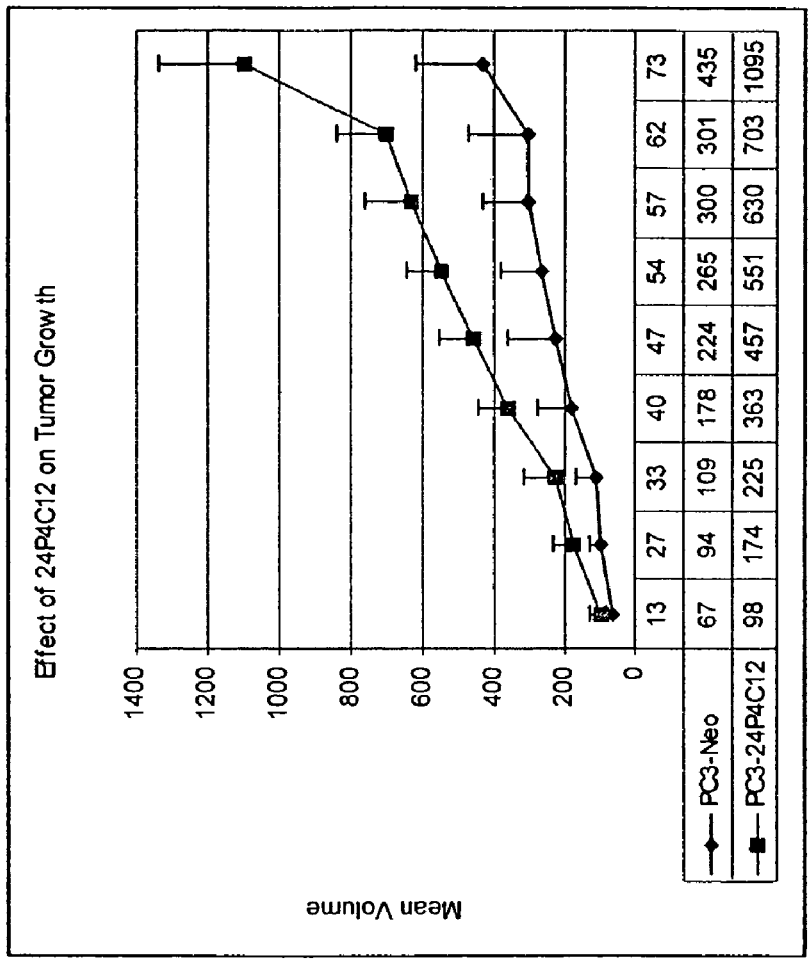
- $1 \times 10^6$ PC3-24P4C12 cells were mixed with Matrigel and injected on the right and left subcutaneous flanks of 4 male SCID mice per group.
- Each data point represents mean tumor volume (n=8).

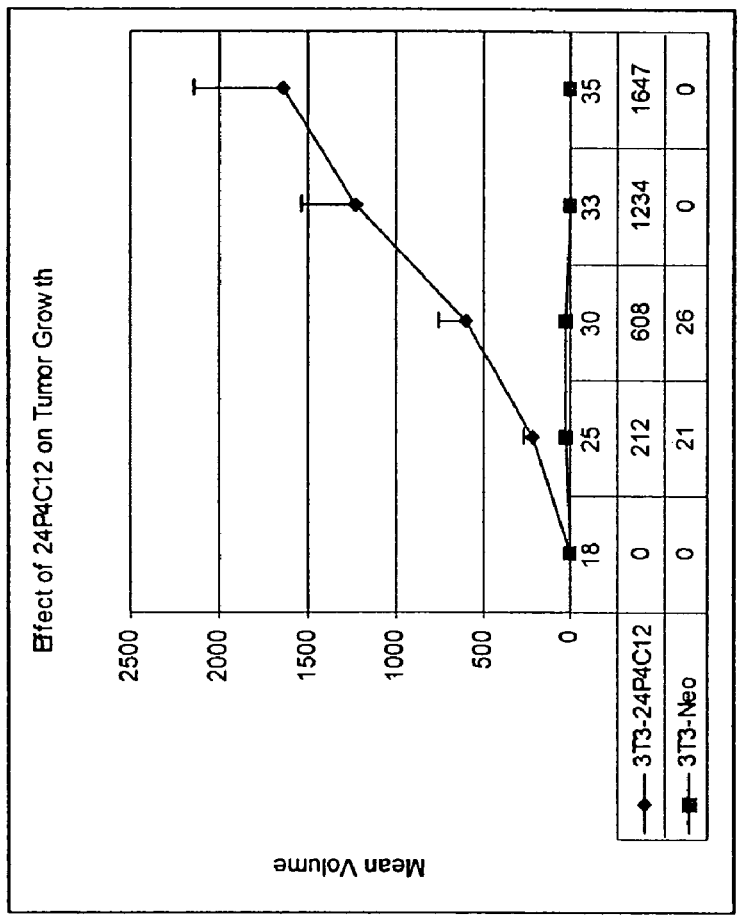
Figure 32: 24P4C12 Enhances Tumor Growth in SCID Mice
- 1 x 10⁶ 3T3-24P4C12 cells were mixed with Matrigel and injected on the right subcutaneous flanks of 7 male SCID mice per group.
- Each data point represents mean tumor volume (n=6).

NUCLEIC ACID AND CORRESPONDING PROTEIN ENTITLED 24P4C12 USEFUL IN TREATMENT AND DETECTION OF CANCER

CROSS-REFERENCE TO RELATED APPLICATIONS

This application is a continuation of U.S. patent application Ser. No. 10/306,631, filed 27 Nov. 2002, which is a continuation-in-part of U.S. patent application Ser. No. 09/547,789, filed 12 Apr. 2000, now U.S. Pat. No. 6,943,235, issued 13 Sep. 2005, and claims priority to U.S. provisional patent application No. 60/128,858, filed 12 Apr. 1999.

STATEMENT OF RIGHTS TO INVENTIONS MADE UNDER FEDERALLY SPONSORED RESEARCH

Not applicable.

FIELD OF THE INVENTION

The invention described herein relates to a gene and its encoded protein, termed 24P4C12, expressed in certain cancers, and to diagnostic and therapeutic methods and compositions useful in the management of cancers that express 24P4C12.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 Sep. 2 (9): 1445-51), STEAP (Hubert, et al., Proc Natl Acad Sci USA. 1999 Dec. 7; 96(25): 14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women.

According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF THE INVENTION

The present invention relates to a gene, designated 24P4C12, that has now been found to be over-expressed in the cancer(s) listed in Table I. Northern blot expression analysis of 24P4C12 gene expression in normal tissues shows a restricted expression pattern in adult tissues. The nucleotide (FIG. 2) and amino acid (FIG. 2, and FIG. 3) sequences of 24P4C12 are provided. The tissue-related profile of 24P4C12 in normal adult tissues, combined with the over-expression observed in the tissues listed in Table I, shows that 24P4C12 is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 24P4C12 genes, mRNAs, and/or coding sequences, preferably in isolated form, including polynucleotides encoding 24P4C12-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 24P4C12-related protein, as well as the peptides/proteins themselves; DNA, RNA, DNA/RNA hybrids, and related molecules, polynucleotides or oligonucleotides complementary or having at least a 90% homology to the 24P4C12 genes or mRNA sequences or parts thereof, and polynucleotides or oligonucleotides that hybridize to the 24P4C12 genes, mRNAs, or to 24P4C12-encoding polynucleotides. Also provided are means for isolating cDNAs and the genes encoding 24P4C12. Recombinant DNA molecules containing 24P4C12 polynucleotides, cells transformed or transduced with such molecules, and host-vector systems for the expression of 24P4C12 gene products are also provided. The invention further provides antibodies that bind to 24P4C12 proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 24P4C12 polynucleotides and proteins in various biological samples, as well as methods for identifying cells that express 24P4C12. A typical embodiment of this invention provides methods for monitoring 24P4C12 gene products in a tissue or hematology sample having or suspected of having some form of growth dysregulation such as cancer.

The invention further provides various immunogenic or therapeutic compositions and strategies for treating cancers that express 24P4C12 such as cancers of tissues listed in Table I, including therapies aimed at inhibiting the transcription, translation, processing or function of 24P4C12 as well as cancer vaccines. In one aspect, the invention provides compositions, and methods comprising them, for treating a cancer that expresses 24P4C12 in a human subject wherein the composition comprises a carrier suitable for human use and a human unit dose of one or more than one agent that inhibits the production or function of 24P4C12. Preferably, the carrier is a uniquely human carrier. In another aspect of the invention, the agent is a moiety that is immunoreactive with 24P4C12 protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to 24P4C12 and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 24P4C12 as described above. The one or more than one nucleic acid molecule may also be, or encodes, a molecule that inhibits production of 24P4C12. Non-limiting examples of such molecules include, but are not limited to, those complementary to a nucleotide sequence essential for production of 24P4C12 (e.g. antisense sequences or molecules that form a triple helix with a nucleotide double helix essential for 24P4C12 production) or a ribozyme effective to lyse 24P4C12 mRNA.

Note that to determine the starting position of any peptide set forth in Tables VIII-XXI and XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides in Table VII. Generally, a unique Search Peptide is used to obtain HLA peptides of a particular for a particular variant. The position of each Search Peptide relative to its respective parent molecule is listed in Table VII. Accordingly, if a Search Peptide begins at position "X", one must add the value "X-1" to each position in Tables VIII-XXI and XXII to XLIX to obtain the actual position of the HLA peptides in their parental molecule. For example, if a particular Search Peptide begins at position 150 of its parental molecule, one must add 150-1, i.e., 149 to each HLA peptide amino acid position to calculate the position of that amino acid in the parent molecule.

One embodiment of the invention comprises an HLA peptide, that occurs at least twice in Tables VIII-XXI and XXII to XLIX collectively, or an oligonucleotide that encodes the HLA peptide. Another embodiment of the invention comprises an HLA peptide that occurs at least once in Tables VIII-XXI and at least once in tables XXII to XLIX, or an oligonucleotide that encodes the HLA peptide.

Another embodiment of the invention is antibody epitopes, which comprise a peptide regions, or an oligonucleotide encoding the peptide region, that has one two, three, four, or five of the following characteristics:

i) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a peptide region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or v) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9.

BRIEF DESCRIPTION OF THE FIGURES

FIG. 1. The 24P4C12 SSH sequence of 160 nucleotides.

FIG. 2. A) The cDNA and amino acid sequence of 24P4C12 variant 1 (also called "24P4C12 v.1" or "24P4C2 variant 1") is shown in FIG. 2A. The start methionine is underlined. The open reading frame extends from nucleic acid 6-2138 including the stop codon.

Figure 10:
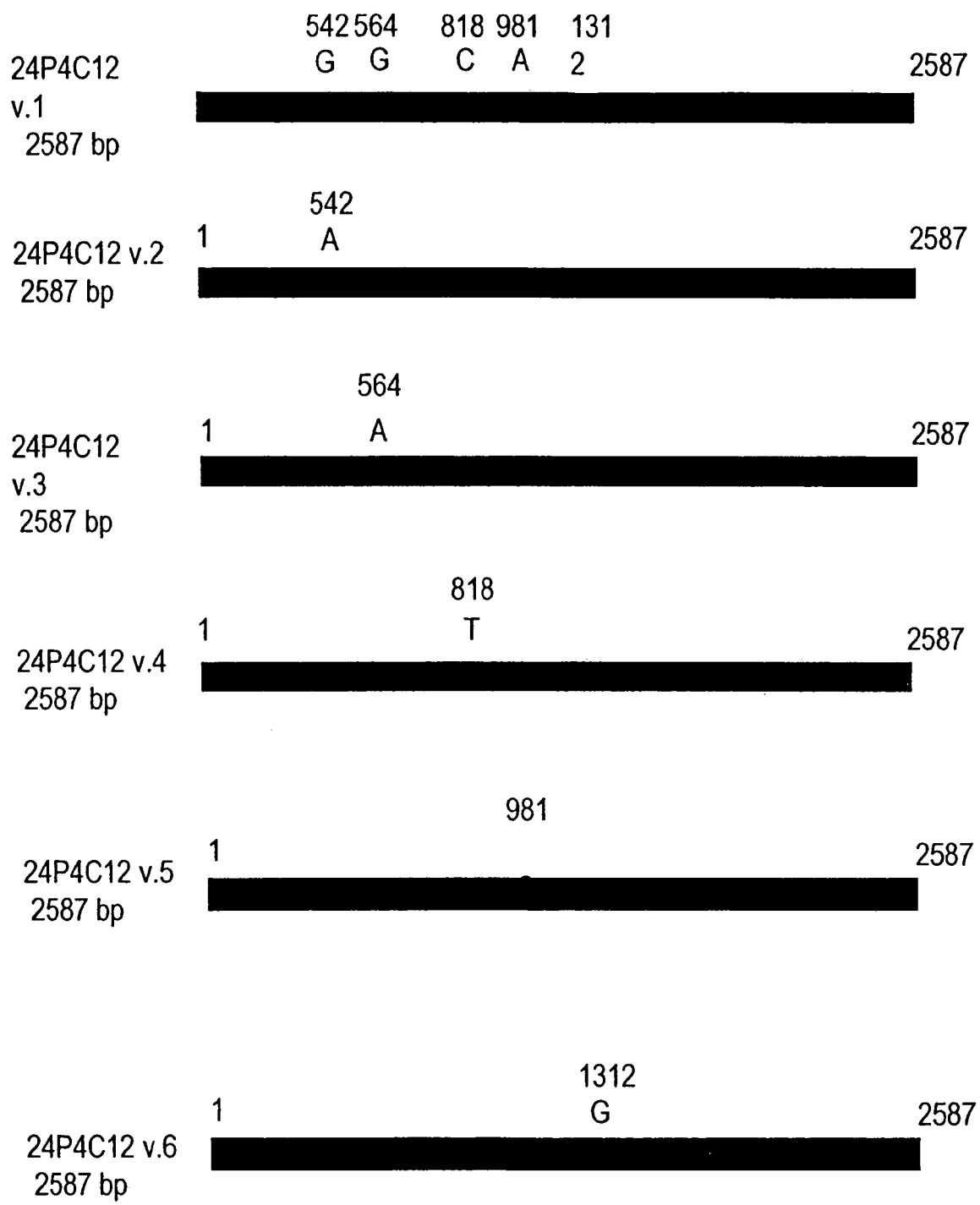

B) The cDNA and amino acid sequence of 24P4C12 variant 2 (also called "24P4C12 v.2") is shown in FIG. 2B. The codon for the start methionine is underlined. The open reading frame extends from nucleic acid 6-2138 including the stop codon.

C) The cDNA and amino acid sequence of 24P4C12 variant 3 (also called "24P4C12 v.3") is shown in FIG. 2C. The codon for the start methionine is underlined. The open reading frame extends from nucleic acid 6-2138 including the stop codon.

D) The cDNA and amino acid sequence of 24P4C12 variant 4 (also called "24P4C12 v.4") is shown in FIG. 2D. The codon for the start methionine is underlined. The open reading frame extends from nucleic acid 6-2138 including the stop codon.

E) The cDNA and amino acid sequence of 24P4C12 variant 5 (also called "24P4C12 v.5") is shown in FIG. 2E. The codon for the start methionine is underlined. The open reading frame extends from nucleic acid 6-2138 including the stop codon.

F) The cDNA and amino acid sequence of 24P4C12 variant 6 (also called "24P4C12 v.6") is shown in FIG. 2F. The codon for the start methionine is underlined. The open reading frame extends from nucleic acid 6-2138 including the stop codon.

G) The cDNA and amino acid sequence of 24P4C12 variant 7 (also called "24P4C12 v.7") is shown in FIG. 2G. The codon for the start methionine is underlined. The open reading frame extends from nucleic acid 6-1802 including the stop codon.

H) The cDNA and amino acid sequence of 24P4C12 variant 8 (also called "24P4C12 v.8") is shown in FIG. 2H. The codon for the start methionine is underlined. The open reading frame extends from nucleic acid 6-2174 including the stop codon.

I) The cDNA and amino acid sequence of 24P4C12 variant 9 (also called "24P4C12 v.9") is shown in FIG. 2I. The codon for the start methionine is underlined. The open reading frame extends from nucleic acid 6-2144 including the stop codon.

FIG. 3.

A) Amino acid sequence of 24P4C12 v.1 is shown in FIG. 3A; it has 710 amino acids.

B) The amino acid sequence of 24P4C12 v.3 is shown in FIG. 3B; it has 710 amino acids.

C) The amino acid sequence of 24P4C12 v.5 is shown in FIG. 3C; it has 710 amino acids.

D) The amino acid sequence of 24P4C12 v.6 is shown in FIG. 3D; it has 710 amino acids.

E) The amino acid sequence of 24P4C12 v.7 is shown in FIG. 3E; it has 598 amino acids.

F) The amino acid sequence of 24P4C12 v.8 is shown in FIG. 3F; it has 722 amino acids.

G) The amino acid sequence of 24P4C12 v.9 is shown in FIG. 3G; it has 712 amino acids. As used herein, a reference to 24P4C12 includes all variants thereof, including those shown in FIGS. 2, 3, 10, and 11, unless the context clearly indicates otherwise.

FIG. 4. Alignment or 24P4C12 with human choline transporter-like protein 4 (CTL4) (gi114249468).

FIG. 5. Hydrophilicity amino acid profile of 24P4C12 determined by computer algorithm sequence analysis using the method of Hopp and Woods (Hopp T. P., Woods K. R., 1981. Proc. Natl. Acad. Sci. U.S.A. 78:3824-3828) accessed on the Protscale website located on the World Wide Web at (.expasy.ch/cgi-bin/protscale.pl) through the ExPasy molecular biology server.

FIG. 6. Hydropathicity amino acid profile of 24P4C12 determined by computer algorithm sequence analysis using the method of Kyte and Doolittle (Kyte J., Doolittle R. F., 1982. J. Mol. Biol. 157:105-132) accessed on the ProtScale website located on the World Wide Web at (.expasy.ch/cgi-bin/protscale.pl) through the ExPasy molecular biology server.

FIG. 7. Percent accessible residues amino acid profile of 24P4C12 determined by computer algorithm sequence analysis using the method of Janin (Janin J., 1979 Nature 277:491-492) accessed on the ProtScale website located on the World Wide Web at (.expasy.ch/cgi-bin/protscale.pl) through the ExPasy molecular biology server.

FIG. 8. Average flexibility amino acid profile of 24P4C12 determined by computer algorithm sequence analysis using the method of Bhaskaran and Ponnuswamy (Bhaskaran R., and Ponnuswamy P. K., 1988. Int. J. Pept. Protein Res. 32:242-255) accessed on the ProtScale website located on the World Wide Web at (.expasy.ch/cgi-bin/protscale.pl) through the ExPasy molecular biology server.

FIG. 9. Beta-turn amino acid profile of 24P4C12 determined by computer algorithm sequence analysis using the method of Deleage and Roux (Deleage, G., Roux B. 1987 Protein Engineering 1:289-294) accessed on the ProtScale website located on the World Wide Web at (.expasy.ch/cgi-bin/protscale.pl) through the ExPasy molecular biology server.

FIG. 10. Schematic alignment of SNP variants of 24P4C12. Variants 24P4C12 v.2 through v.6 are variants with single nucleotide differences. Though these SNP variants are shown separately, they could also occur in any combinations and in any transcript variants that contains the base pairs. Numbers correspond to those of 24P4C12 v.1. Black box shows the same sequence as 24P4C12 v.1. SNPs are indicated above the box.

Figure 11:
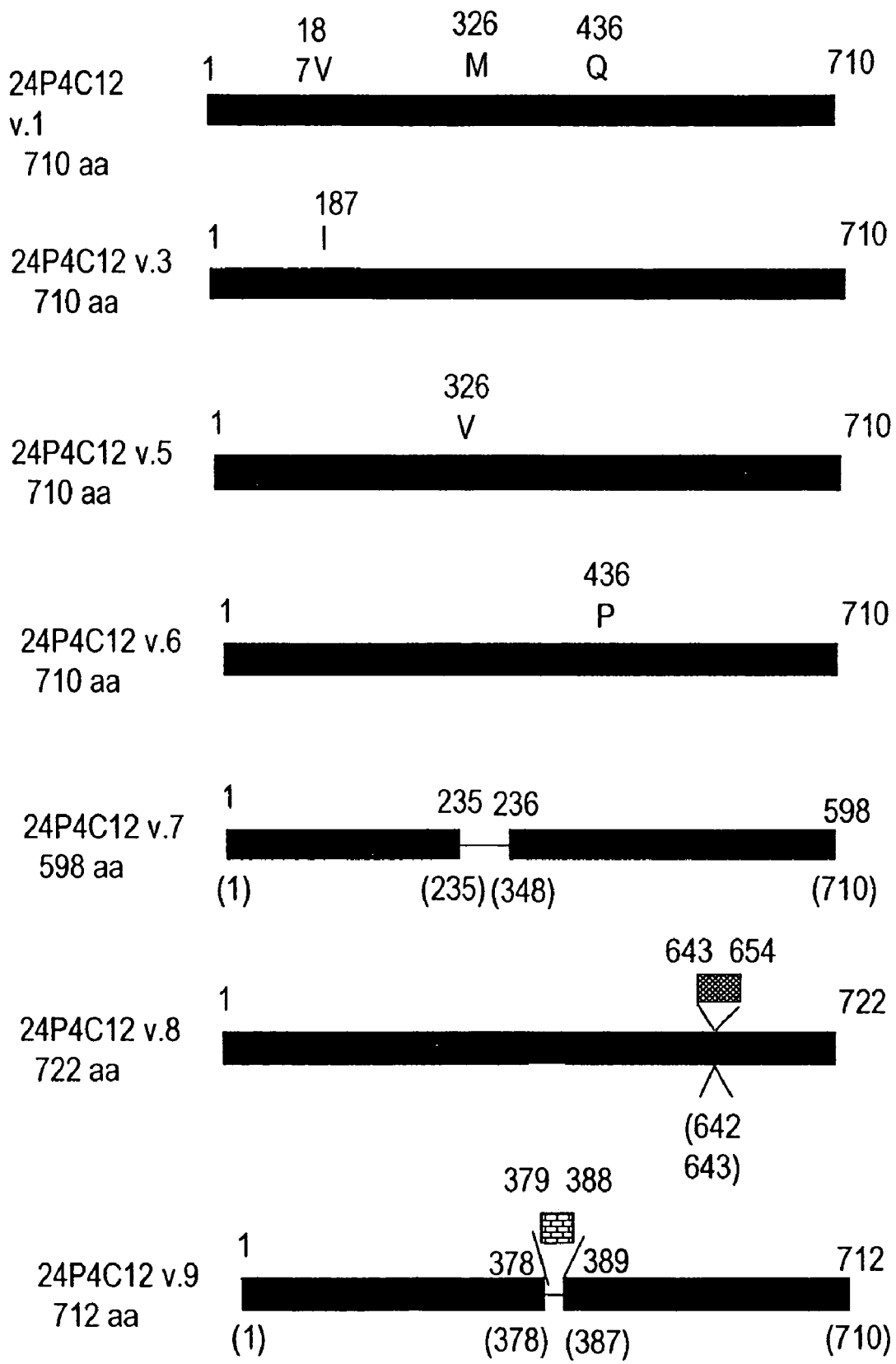
Figure 12:
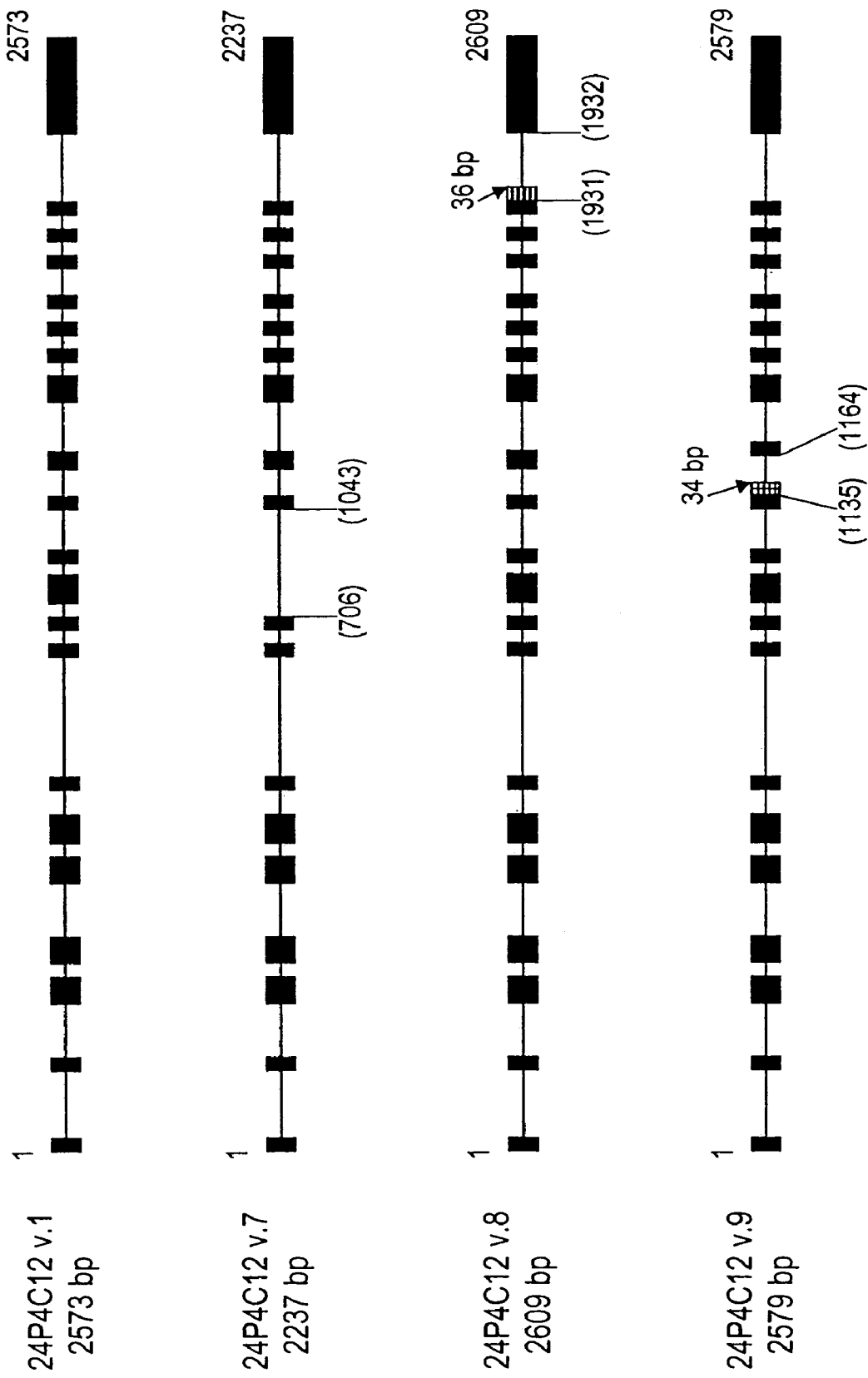

FIG. 11. Schematic alignment of protein variants of 24P4C12. Protein variants correspond to nucleotide variants. Nucleotide variants 24P4C12 v.2, v.4 in FIG. 10 code for the same protein as 24P4C12 v.1. Nucleotide variants 24P4C12 v.7, v.8 and v.9 are splice variants of v.1, as shown in FIG. 12. Single amino acid differences were indicated above the boxes. Black boxes represent the same sequence as 24P4C12 v.1. Numbers underneath the box correspond to 24P4C12 v.1.

FIG. 12. Exon compositions of transcript variants of 24P4C12. Variant 24P4C12 v.7, v.8 and v.9 are transcript variants of 24P4C12 v.1. Variant 24P4C12 v.7 does not have exons 10 and 11 of variant 24P4C12 v.1. Variant 24P4C12 v.8 extended 36 bp at the 3' end of exon 20 of variant 24P4C12 v.1. Variant 24P4C12 v.9 had a longer exon 12 and shorter exon 13 as compared to variant 24P4C12 v.1. Numbers in "( )" underneath the boxes correspond to those of 24P4C12 v.1. Lengths of introns and exons are not proportional.

FIG. 13. Secondary structure and transmembrane domains prediction for 24P4C12 protein variant 1 (SEQ ID NO: 112). A: The secondary structure of 24P4C12 protein variant 1 was predicted using the HNN—Hierarchical Neural Network method (Guermeur, 1997, located on the World Wide Web at pbil.ibcp.fr/cgi-bin/npsa_automat.pl?page=npsa_nn.html), accessed from the ExPasy molecular biology server at expasy.ch/tools/). This method predicts the presence and location of alpha helices, extended strands, and random coils from the primary protein sequence. The percent of the protein in a given secondary structure is also listed. B: Schematic representation of the probability of existence of transmembrane regions and orientation of 24P4C12 variant 1 based on the TMpred algorithm of Hofmann and Stoffel which utilizes TMBASE (K. Hofmann, W. Stoffel. TMBASE—A database of membrane spanning protein segments Biol. Chem. Hoppe-Seyler 374:166, 1993). C: Schematic representation of the probability of the existence of transmembrane regions and the extracellular and intracellular orientation of 24P4C12 variant 1 based on the TMHMM algorithm of Sonnhammer, von Heijne, and Krogh (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998). The TMpred and TMHMM algorithms are accessed from the ExPasy molecular biology server at expasy.ch/tools/).

FIG. 14. 24P4C12 Expression by RT-PCR. First strand cDNA was generated from vital pool 1 (kidney, liver and lung), vital pool 2 (colon, pancreas and stomach), a pool of prostate cancer xenografts (LAPC-4AD, LAPC-4AI, LAPC-9AD and LAPC-9AI), prostate cancer pool, bladder cancer pool, kidney cancer pool, colon cancer pool, ovary cancer pool, breast cancer pool, and cancer metastasis pool. Normalization was performed by PCR using primers to actin. Semi-quantitative PCR, using primers to 24P4C12, was performed at 26 and 30 cycles of amplification. Results show strong expression of 24P4C12 in prostate cancer pool and ovary cancer pool. Expression was also detected in prostate cancer xenografts, bladder cancer pool, kidney cancer pool, colon cancer pool, breast cancer pool, cancer metastasis pool, vital pool 1, and vital pool 2.

FIG. 15. Expression of 24P4C12 in normal tissues. Two multiple tissue northern blots (Clontech) both with 2 ug of mRNA/lane were probed with the 24P4C12 sequence. Size standards in kilobases (kb) are indicated on the side. Results show expression of 24P4C12 in prostate, kidney and colon. Lower expression is detected in pancreas, lung and placenta amongst all 16 normal tissues tested.

FIG. 16. Expression of 24P4C12 in Prostate Cancer Xenografts and Cell Lines. RNA was extracted from a panel of cell lines and prostate cancer xenografts (PrEC, LAPC-4AD, LAPC-4AI, LAPC-9AD, LAPC-9AI, LNCaP, PC-3, DU145, TsuPr, and LAPC-4CL). Northern blot with 10 ug of total RNA/lane was probed with 24P4C12 SSH sequence. Size standards in kilobases (kb) are indicated on the side. The 24P4C12 transcript was detected in LAPC-4AD, LAPC-4AI, LAPC-9AD, LAPC-9AI, LNCaP, and LAPC-4 CL.

FIG. 17. Expression of 24P4C12 in Patient Cancer Specimens and Normal Tissues. RNA was extracted from a pool of prostate cancer specimens, bladder cancer specimens, colon cancer specimens, ovary cancer specimens, breast cancer specimens and cancer metastasis specimens, as well as from normal prostate (NP), normal bladder (NB), normal kidney (NK), and normal colon (NC). Northern blot with 10 μg of total RNA/lane was probed with 24P4C12 SSH sequence. Size standards in kilobases (kb) are indicated on the side. Strong expression of 24P4C12 transcript was detected in the patient cancer pool specimens, and in normal prostate but not in the other normal tissues tested.

FIG. 18. Expression of 24P4C12 in Prostate Cancer Patient Specimens. RNA was extracted from normal prostate (N), prostate cancer patient tumors (T) and their matched normal adjacent tissues (Nat). Northern blots with 10 ug of total RNA were probed with the 24P4C12 SSH fragment. Size standards in kilobases are on the side. Results show expression of 24P4C12 in normal prostate and all prostate patient tumors tested.

FIG. 19. Expression of 24P4C12 in Colon Cancer Patient Specimens. RNA was extracted from colon cancer cell lines (CL: Colo 205, LoVo, and SK-CO-), normal colon (N), colon cancer patient tumors (T) and their matched normal adjacent tissues (Nat). Northern blots with 10 ug of total RNA were probed with the 24P4C12 SSH fragment. Size standards in kilobases are on the side. Results show expression of 24P4C12 in normal colon and all colon patient tumors tested. Expression was detected in the cell lines Colo 205 and SK-CO-, but not in LoVo.

FIG. 20. Expression of 24P4C12 in Lung Cancer Patient Specimens. RNA was extracted from lung cancer cell lines (CL: CALU-1, A427, NCI-H82, NCI-H146), normal lung (N), lung cancer patient tumors (T) and their matched normal adjacent tissues (Nat). Northern blots with 10 ug of total RNA were probed with the 24P4C12 SSH fragment. Size standards in kilobases are on the side. Results show expression of 24P4C12 in lung patient tumors tested, but not in normal lung. Expression was also detected in CALU-1, but not in the other cell lines A427, NCI-H82, and NCI-H146.

FIG. 21. Expression of 24P4C12 in breast and stomach human cancer specimens. Expression of 24P4C12 was assayed in a panel of human stomach and breast cancers (T) and their respective matched normal tissues (N) on RNA dot blots. 24P4C12 expression was seen in both stomach and breast cancers. The expression detected in normal adjacent tissues (isolated from diseased tissues) but not in normal tissues (isolated from healthy donors) may indicate that these tissues are not fully normal and that 24P4C12 may be expressed in early stage tumors.

FIG. 22. 24P4C12 Expression in a large panel of Patient Cancer Specimens. First strand cDNA was prepared from a panel of ovary patient cancer specimens (A), uterus patient cancer specimens (B), prostate cancer specimens (C), bladder cancer patient specimens (D), lung cancer patient specimens (E), pancreas cancer patient specimens (F), colon cancer specimens (G), and kidney cancer specimens (H). Normalization was performed by PCR using primers to actin. Semi-quantitative PCR, using primers to 24P4C12, was performed at 26 and 30 cycles of amplification. Samples were run on an agarose gel, and PCR products were quantitated using the Alphalmager software. Expression was recorded as absent, low, medium or strong. Results show expression of 24P4C12 in the majority of patient cancer specimens tested, 73.3% of ovary patient cancer specimens, 83.3% of uterus patient cancer specimens, 95.0% of prostate cancer specimens, 61.1% of bladder cancer patient specimens, 80.6% of lung cancer patient specimens, 87.5% of pancreas cancer patient specimens, 87.5% of colon cancer specimens, 68.4% of clear cell renal carcinoma, 100% of papillary renal cell carcinoma.

FIG. 23. 24P4C12 expression in transduced cells. PC3 prostate cancer cells, NIH-3T3 mouse cells and 300.19 mouse cells were transduced with 24P4C12.pSRa retroviral vector. Cells were selected in neomycin for the generation of stable cell lines. RNA was extracted following selection in neomycin. Northern blots with 10 ug of total RNA were probed with the 24P4C12 SSH fragment. Results show strong expression of 24P4C12 in 24P4C12.pSRa transduced PC3, 3T3 and 300.19 cells, but not in the control cells transduced with the parental pSRa construct.

FIG. 24. Expression of 24P4C12 in 293T cells. 293T cell were transiently transfected with either pCDNA3.1 Myc-His tagged expression vector, the pSR☐ expression vector each encoding the 24P4C12 variant 1 cDNA or a control neo vector. Cells were harvested 2 days later and analyzed by Western blot with anti-24P4C12 pAb (A) or by Flow cytometry (B) on fixed and permeabilized 293T cells with either the anti-24P4C12 pAb or anti-His pAb followed by a PE-conjugated anti-rabbit IgG secondary Ab. Shown is expression of the monomeric and aggregated forms of 24P4C12 by Western blot and a fluorescent shift of 24P4C12-293T cells compared to control neo cells when stained with the anti-24P4C12 and anti-His pAbs which are directed to the intracellular NH3 and COOH termini, respectively.

FIG. 25. Expression and detection of 24P4C12 in stably transduced PC3 cells. PC3 cells were infected with retrovirus encoding the 24P4C12 variant 1 cDNA and stably transduced cells were derived by G418 selection. Cells were then analyzed by Western blot (A) or immunohistochemistry (B) with anti-24P4C12 pAb. Shown with an arrow on the Western blot is expression of a ~94 kD band representing 24P4C12 expressed in $PC_{3-24}P4C12$ cells but not in control neo cells. Immunohistochemical analysis shows specific staining of 24P4C12-PC3 cells and not PC3-neo cells which is competed away competitor peptide to which the pAb was derived.

FIG. 26. Expression of recombinant 24P4C12 antigens in 293T cells. 293T cells were transiently transfected with Tag5 His-tagged expression vectors encoding either amino acids 59-227 or 319-453 of 24P4C12 variant 1 or a control vector. 2 days later supernatants were collected and cells harvested and lysed. Supernatants and lysates were then subjected to Western blot analysis using an anti-His pAb. Shown is expression of the recombinant Tag5 59-227 protein in both the supernatant and lysate and the Tag5 319-453 protein in the cell lysate. These proteins are purified and used as antigens for generation of 24P4C12-specific antibodies.

FIG. 27. Monoclonal antibodies detect 24P4C12 protein expression in 293T cells by flow cytometry. 293T cells were transfected with either pcDNA 3.1 His-tagged expression vector for 24P4C12 or a control neo vector and harvested 2 days later. Cells were fixed, permeabilized, and stained with a 1:2 dilution of supernatants of the indicated hybridomas generated from mice immunized with 300.19-24P4C12 cells or with anti-His pAb. Cells were then stained with a PE-conjugated secondary Ab and analyzed by flow cytometry. Shown is a fluorescent shift of 293T-24P4C12 cells but not control neo cells demonstrating specific recognition of 24P4C12 protein by the hybridoma supernatants.

FIG. 28. Shows expression of 24P4C12 Enhances Proliferation. PC3 and 3T3 were grown overnight in low FBS. Cells were then incubated in low or 10% FBS as indicated. Proliferation was measured by Alamar Blue.

FIG. 29. Detection of 24P4C12 protein by immunohistochemistry in prostate cancer patient specimens. Prostate adenocarcinoma tissue and its matched normal adjacent tissue were obtained from prostate cancer patients. The results showed strong expression of 24P4C12 in the tumor cells and normal epithelium of the prostate cancer patients' tissue (panels (A) low grade prostate adenocarcinoma, (B) high grade prostate adenocarcinoma, (C) normal tissue adjacent to tumor). The expression was detected mostly around the cell membrane indicating that 24P4C12 is membrane associated in prostate tissues.

FIG. 30. Detection of 24P4C12 protein by immunohistochemistry in various cancer patient specimens. Tissue was obtained from patients with colon adenocarcinoma, breast ductal carcinoma, lung adenocarcinoma, bladder transitional cell carcinoma, renal clear cell carcinoma and pancreatic adenocarcinoma. The results showed expression of 24P4C12 in the tumor cells of the cancer patients' tissue (panel (A) colon adenocarcinoma, (B) lung adenocarcinoma, (C) breast ductal carcinoma, (D) bladder transitional carcinoma, (E) renal clear cell carcinoma, (F) pancreatic adenocarcinoma).

FIG. 31. Shows 24P4C12 Enhances Tumor Growth in SCID Mice. 1×106 PC3-24P4C12 cells were mixed with Matrigel and injected on the right and left subcutaneous flanks of 4 male SCID mice per group. Each data point represents mean tumor volume (n=8).

FIG. 32. Shows 24P4C12 Enhances Tumor Growth in SCID Mice. 1×106 3T3-24P4C12 cells were mixed with Matrigel and injected on the right subcutaneous flanks of 7 male SCID mice per group. Each data point represents mean tumor volume (n=6).

DETAILED DESCRIPTION OF THE INVENTION

Outline of Sections

I.) Definitions
II.) 24P4C12 Polynucleotides
II.A.) Uses of 24P4C12 Polynucleotides
II.A.1.) Monitoring of Genetic Abnormalities
II.A.2.) Antisense Embodiments
II.A.3.) Primers and Primer Pairs
II.A.4.) Isolation of 24P4C12-Encoding Nucleic Acid Molecules
II.A.5.) Recombinant Nucleic Acid Molecules and Host-Vector Systems
III.) 24P4C12-related Proteins
III.A.) Motif-bearing Protein Embodiments
III.B.) Expression of 24P4C12-related Proteins
III.C.) Modifications of 24P4C12-related Proteins
III.D.) Uses of 24P4C12-related Proteins
IV.) 24P4C12 Antibodies
V.) 24P4C12 Cellular Immune Responses
VI.) 24P4C12 Transgenic Animals
VII.) Methods for the Detection of 24P4C12
VIII.) Methods for Monitoring the Status of 24P4C12-related Genes and Their Products
IX.) Identification of Molecules That Interact With 24P4C12
X.) Therapeutic Methods and Compositions
X.A.) Anti-Cancer Vaccines
X.B.) 24P4C12 as a Target for Antibody-Based Therapy
X.C.) 24P4C12 as a Target for Cellular Immune Responses
X.C.1. Minigene Vaccines X.C.2. Combinations of CTL Peptides with Helper Peptides X.C.3. Combinations of CTL Peptides with T Cell Priming Agents X.C.4. Vaccine Compositions Comprising DC Pulsed with CTL and/or HTL Peptides X.D.) Adoptive Immunotherapy X.E.) Administration of Vaccines for Therapeutic or Prophylactic Purposes XI.) Diagnostic and Prognostic Embodiments of 24P4C12.

XII.) Inhibition of 24P4C12 Protein Function

XII.A.) Inhibition of 24P4C12 With Intracellular Antibodies

XII.B.) Inhibition of 24P4C12 with Recombinant Proteins

XII.C.) Inhibition of 24P4C12 Transcription or Translation

XII.D.) General Considerations for Therapeutic Strategies

XIII.) Identification, Characterization and Use of Modulators of 24P4C12

XIV.) KITS/Articles of Manufacture

I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 24P4C12 (either by removing the underlying glycosylation site or by deleting the glycosylation by chemical and/or enzymatic means), and/or adding one or more glycosylation sites that are not present in the native sequence 24P4C12. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 24P4C12-related protein). For example, an analog of a 24P4C12 protein can be specifically bound by an antibody or T cell that specifically binds to 24P4C12.

The term "antibody" is used in the broadest sense. Therefore, an "antibody" can be naturally occurring or man-made such as monoclonal antibodies produced by conventional hybridoma technology. Anti-24P4C12 antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-24P4C12 antibodies and clones thereof (including agonist, antagonist and neutralizing antibodies) and anfi-24P4C12 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Numerous chemical compounds are synthesized through such combinatorial mixing of chemical building blocks (Gallop et al., J. Med. Chem. 37(9): 1233-1251 (1994)).

Preparation and screening of combinatorial libraries is well known to those of skill in the art. Such combinatorial chemical libraries include, but are not limited to, peptide libraries (see, e.g., U.S. Pat. No. 5,010,175, Furka, Pept. Prot. Res. 37:487-493 (1991), Houghton et al., Nature, 354:84-88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with a Beta-D-Glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho, et al., Science 261: 1303 (1993)), and/or peptidyl phosphonates (Campbell et al., J. Org. Chem. 59:658 (1994)). See, generally, Gordon et al., J. Med. Chem. 37:1385 (1994), nucleic acid libraries (see, e.g., Stratagene, Corp.), peptide nucleic acid libraries (see, e.g., U.S. Pat. No. 5,539,083), antibody libraries (see, e.g., Vaughn et al., Nature Biotechnology 14(3): 309-314 (1996), and PCT/US96/10287), carbohydrate libraries (see, e.g., Liang et al., Science 274:1520-1522 (1996), and U.S. Pat. No. 5,593,853), and small organic molecule libraries (see, e.g., benzodiazepines, Baum, C&EN, January 18, page 33 (1993); isoprenoids, U.S. Pat. Nos. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford, NIA). A number of well-known robotic systems have also been developed for solution phase chemistries. These systems include automated workstations such as the automated synthesis apparatus developed by Takeda Chemical Industries, LTD. (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tripos, Inc., St. Louis, Mo.; ChemStar, Ltd, Moscow, RU; 3D Pharmaceuticals, Exton, Pa.; Martek Biosciences, Columbia, Md.; etc.).

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auromycins, maytansinoids, yttrium, bismuth, ricin, ricin A-chain, combrestatin, duocarmycins, dolostatins, doxorubicin, daunorubicin, taxol, cisplatin, cc1065, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, Sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212\ or\ 213}$, $P^{32}$ and radioactive isotopes of Lu including $Lu^{177}$. Antibodies may also be conjugated to an anti-cancer pro-drug activating enzyme capable of converting the pro-drug to its active form.

The "gene product" is sometimes referred to herein as a protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I, etc. In one embodiment, the cancer protein is encoded by a nucleic acid of FIG. 2. The cancer protein can be a fragment, or alternatively, be the full-length protein to the fragment encoded by the nucleic acids of FIG. 2. In one embodiment, a cancer amino acid sequence is used to determine sequence identity or similarity. In another embodiment, the sequences are naturally occurring allelic variants of a protein encoded by a nucleic acid of FIG. 2. In another embodiment, the sequences are sequence variants as further described herein.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,576,220 and 5,541,061 disclose high throughput methods of screening for ligand/antibody binding.

In addition, high throughput screening systems are commercially available (see, e.g., Amersham Biosciences, Piscataway, N.J.; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detector (s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/ 100 µg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 24P4C12 genes or that encode polypeptides other than 24P4C12 gene product or fragments thereof. A skilled artisan can readily employ nucleic acid isolation procedures to obtain an isolated 24P4C12 polynucleotide. A protein is said to be "isolated," for example, when physical, mechanical or chemical methods are employed to remove the 24P4C12 proteins from cellular constituents that are normally associated with the protein. A skilled artisan can readily employ standard purification methods to obtain an isolated 24P4C12 protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage T×N×M+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of a 24P4C12-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

"Radioisotopes" include, but are not limited to the following (non-limiting exemplary uses are also set forth):

| Examples of Medical Isotopes: | |
|---|---|
| Isotope | Description of use |
| Actinium-225 (AC-225) | See Thorium-229 (Th-229) |
| Actinium-227 (AC-227) | Parent of Radium-223 (Ra-223) which is an alpha emitter used to treat metastases in the skeleton resulting from cancer (i.e., breast and prostate cancers), and cancer radioimmunotherapy |
| Bismuth-212 (Bi-212) | See Thorium-228 (Th-228) |
| Bismuth-213 (Bi-213) | See Thorium-229 (Th-229) |
| Cadmium-109 (Cd-109) | Cancer detection |
| Cobalt-60 (Co-60) | Radiation source for radiotherapy of cancer, for food irradiators, and for sterilization of medical supplies |
| Copper-64 (Cu-64) | A positron emitter used for cancer therapy and SPECT imaging |
| Copper-67 (Cu-67) | Beta/gamma emitter used in cancer radioimmunotherapy and diagnostic studies (i.e., breast and colon cancers, and lymphoma) |
| Dysprosium-166 (Dy-166) | Cancer radioimmunotherapy |
| Erbium-169 (Er-169) | Rheumatoid arthritis treatment, particularly for the small joints associated with fingers and toes |
| Europium-152 (Eu-152) | Radiation source for food irradiation and for sterilization of medical supplies |
| Europium-154 (Eu-154) | Radiation source for food irradiation and for sterilization of medical supplies |
| Gadolinium-153 (Gd-153) | Osteoporosis detection and nuclear medical quality assurance devices |
| Gold-198 (Au-198) | Implant and intracavity therapy of ovarian, prostate, and brain cancers |
| Holmium-166 (Ho-166) | Multiple myeloma treatment in targeted skeletal therapy, cancer radioimmunotherapy, bone marrow ablation, and rheumatoid arthritis treatment |
| Iodine-125 (I-125) | Osteoporosis detection, diagnostic imaging, tracer drugs, brain cancer treatment, radiolabeling, tumor imaging, mapping of receptors in the brain, interstitial radiation therapy, brachytherapy for treatment of prostate cancer, determination of glomerular filtration rate (GFR), determination of plasma volume, detection of deep vein thrombosis of the legs |
| Iodine-131 (I-131) | Thyroid function evaluation, thyroid disease detection, treatment of thyroid cancer as well as other non-malignant thyroid diseases (i.e., Graves disease, goiters, and hyperthyroidism), treatment of leukemia, lymphoma, and other forms of cancer (e.g., breast cancer) using radioimmunotherapy |
| Iridium-192 (Ir-192) | Brachytherapy, brain and spinal cord tumor treatment, treatment of blocked arteries (i.e., arteriosclerosis and restenosis), and implants for breast and prostate tumors |
| Lutetium-177 (Lu-177) | Cancer radioimmunotherapy and treatment of blocked arteries (i.e., arteriosclerosis and restenosis) |
| Molybdenum-99 (Mo-99) | Parent of Technetium-99m (Tc-99m) which is used for imaging the brain, liver, lungs, heart, and other organs. Currently, Tc-99m is the most widely used radioisotope used for diagnostic imaging of various cancers and diseases involving the brain, heart, liver, lungs; also used in detection of deep vein thrombosis of the legs |
| Osmium-194 (Os-194) | Cancer radioimmunotherapy |
| Palladium-103 (Pd-103) | Prostate cancer treatment |
| Platinum-195m (Pt-195m) | Studies on biodistribution and metabolism of cisplatin, a chemotherapeutic drug |
| Phosphorus-32 (P-32) | Polycythemia rubra vera (blood cell disease) and leukemia treatment, bone cancer diagnosis/treatment; colon, pancreatic, and liver cancer treatment; radiolabeling nucleic acids for in vitro research, diagnosis of superficial tumors, treatment of blocked arteries (i.e., arteriosclerosis and restenosis), and intracavity therapy |

-continued

Examples of Medical Isotopes:

| Isotope | Description of use |
|---|---|
| Phosphorus-33 (P-33) | Leukemia treatment, bone disease diagnosis/treatment, radiolabeling, and treatment of blocked arteries (i.e., arteriosclerosis and restenosis) |
| Radium-223 (Ra-223) | See Actinium-227 (Ac-227) |
| Rhenium-186 (Re-186) | Bone cancer pain relief, rheumatoid arthritis treatment, and diagnosis and treatment of lymphoma and bone, breast, colon, and liver cancers using radioimmunotherapy |
| Rhenium-188 (Re-188) | Cancer diagnosis and treatment using radioimmunotherapy, bone cancer pain relief, treatment of rheumatoid arthritis, and treatment of prostate cancer |
| Rhodium-105 (Rh-105) | Cancer radioimmunotherapy |
| Samarium-145 (Sm-145) | Ocular cancer treatment |
| Samarium-153 (Sm-153) | Cancer radioimmunotherapy and bone cancer pain relief |
| Scandium-47 (Sc-47) | Cancer radioimmunotherapy and bone cancer pain relief |
| Selenium-75 (Se-75) | Radiotracer used in brain studies, imaging of adrenal cortex by gamma-scintigraphy, lateral locations of steroid secreting tumors, pancreatic scanning, detection of hyperactive parathyroid glands, measure rate of bile acid loss from the endogenous pool |
| Strontium-85 (Sr-85) | Bone cancer detection and brain scans |
| Strontium-89 (Sr-89) | Bone cancer pain relief, multiple myeloma treatment, and osteoblastic therapy |
| Technetium-99m (Tc-99m) | See Molybdenum-99 (Mo-99) |
| Thorium-228 (Th-228) | Parent of Bismuth-212 (Bi-212) which is an alpha emitter used in cancer radioimmunotherapy |
| Thorium-229 (Th-229) | Parent of Actinium-225 (Ac-225) and grandparent of Bismuth-213 (Bi-213) which are alpha emitters used in cancer radioimmunotherapy |
| Thulium-170 (Tm-170) | Gamma source for blood irradiators, energy source for implanted medical devices |
| Tin-117m (Sn-117m) | Cancer immunotherapy and bone cancer pain relief |
| Tungsten-188 (W-188) | Parent for Rhenium-188 (Re-188) which is used for cancer diagnostics/treatment, bone cancer pain relief, rheumatoid arthritis treatment, and treatment of blocked arteries (i.e., arteriosclerosis and restenosis) |
| Xenon-127 (Xe-127) | Neuroimaging of brain disorders, high resolution SPECT studies, pulmonary function tests, and cerebral blood flow studies |
| Ytterbium-175 (Yb-175) | Cancer radioimmunotherapy |
| Yttrium-90 (Y-90) | Microseeds obtained from irradiating Yttrium-89 (Y-8g) for liver cancer treatment |
| Yttrium-91 (Y-91) | A gamma-emitting label for Yttrium-90 (Y-90) which is used for cancer radioimmunotherapy (i.e., lymphoma, breast, colon, kidney, lung, ovarian, prostate, pancreatic, and inoperable liver cancers) |

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant" DNA or RNA molecule is a DNA or RNA molecule that has been subjected to molecular manipulation in vitro.

Non-limiting examples of small molecules include compounds that bind or interact with 24P4C12, ligands including hormones, neuropeptides, chemokines, odorants, phospholipids, and functional equivalents thereof that bind and preferably inhibit 24P4C12 protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 24P4C12 protein; are not found in naturally occurring metabolic pathways; and/or are more soluble in aqueous than non-aqueous solutions "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficol/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (F). The non-limiting constituents of various supetypes are as follows:

A2: A*0201, A*0202, A*0203, A*0204, A*0205, A*0206, A*6802, A*6901, A*0207

A3: A3, A11, A31, A*3301, A*6801, A*0301, A*1101, A*3101

B7: B7, B*3501-03, B*51, B*5301, B*5401, B*5501, B*5502, B*5601, B*6701, B*7801, B*0702, B*5101, B*5602

B44: B*3701, B*4402, B*4403, B*60 (B*4001), B61 (B*4006)

A1: A*0102, A*2604, A*3601, A*4301, A*8001

A24: A*24, A*30, A*2403, A*2404, A*3002, A*3003

B27: B*1401-02, 8*1503, B*1509, B*1510, B*1518, B*3801-02, B*3901, B*3902, B*3903-04, B*4801-02, B*7301, B*2701-08

B58: B*1516, B*1517, B*5701, B*5702, B58

B62: B*4601, B52, B*1501 (B62), B*1502 (B75), B*1513 (B77)

Calculated population coverage afforded by different HLA-supertype combinations are set forth in Table IV (G).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 24P4C12 protein shown in FIG. 2 or FIG. 3. An analog is an example of a variant protein. Splice isoforms and single nucleotides polymorphisms (SNPs) are further examples of variants.

The "24P4C12-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 24P4C12 proteins or fragments thereof, as well as fusion proteins of a 24P4C12 protein and a heterologous polypeptide are also included. Such 24P4C12 proteins are collectively referred to as the 24P4C12-related proteins, the proteins of the invention, or 24P4C12. The term "24P4C12-related protein" refers to a polypeptide fragment or a 24P4C12 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, or 664 or more amino acids.

II.) 24P4C12 Polynucleotides

One aspect of the invention provides polynucleotides corresponding or complementary to all or part of a 24P4C12 gene, mRNA, and/or coding sequence, preferably in isolated form, including polynucleotides encoding a 24P4C12-related protein and fragments thereof, DNA, RNA, DNA/RNA hybrid, and related molecules, polynucleotides or oligonucleotides complementary to a 24P4C12 gene or mRNA sequence or a part thereof, and polynucleotides or oligonucleotides that hybridize to a 24P4C12 gene, mRNA, or to a 24P4C12 encoding polynucleotide (collectively, "24P4C12 polynucleotides"). In all instances when referred to in this section, T can also be U in FIG. 2.

Embodiments of a 24P4C12 polynucleotide include: a 24P4C12 polynucleotide having the sequence shown in FIG. 2, the nucleotide sequence of 24P4C12 as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 24P4C12 nucleotides comprise, without limitation:

(I) a polynucleotide comprising, consisting essentially of, or consisting of a sequence as shown in FIG. 2, wherein T can also be U;

(II) a polynucleotide comprising, consisting essentially of, or consisting of the sequence as shown in FIG. 2A, from nucleotide residue number 6 through nucleotide residue number 2138, including the stop codon, wherein T can also be U;

(III) a polynucleotide comprising, consisting essentially of, or consisting of the sequence as shown in FIG. 2B, from nucleotide residue number 6 through nucleotide residue number 2138, including the stop codon, wherein T can also be U;

(IV) a polynucleotide comprising, consisting essentially of, or consisting of the sequence as shown in FIG. 2C, from nucleotide residue number 6 through nucleotide residue number 2138, including the a stop codon, wherein T can also be U;

(V) a polynucleotide comprising, consisting essentially of, or consisting of the sequence as shown in FIG. 2D, from nucleotide residue number 6 through nucleotide residue number 2138, including the stop codon, wherein T can also be U;

(VI) a polynucleotide comprising, consisting essentially of, or consisting of the sequence as shown in FIG. 2E, from nucleotide residue number 6 through nucleotide residue number 2138, including the stop codon, wherein T can also be U;

(VII) a polynucleotide comprising, consisting essentially of, or consisting of the sequence as shown in FIG. 2F, from nucleotide residue number 6 through nucleotide residue number 2138, including the stop codon, wherein T can also be U;

(VIII) a polynucleotide comprising, consisting essentially of, or consisting of the sequence as shown in FIG. 2G, from nucleotide residue number 6 through nucleotide residue number 1802, including the stop codon, wherein T can also be U;

(IX) a polynucleotide comprising, consisting essentially of, or consisting of the sequence as shown in FIG. 2H, from nucleotide residue number 6 through nucleotide residue number 2174, including the stop codon, wherein T can also be U;

(X) a polynucleotide comprising, consisting essentially of, or consisting of the sequence as shown in FIG. 2I, from nucleotide residue number 6 through nucleotide residue number 2144, including the stop codon, wherein T can also be U;

(XI) a polynucleotide that encodes a 24P4C12-related protein that is at least 90, 91, 92, 93, 94, 95, 96, 97, 98, 99 or 100% homologous to an entire amino acid sequence shown in FIG. 2A-I;

(XII) a polynucleotide that encodes a 24P4C12-related protein that is at least 90, 91, 92, 93, 94, 95, 96, 97, 98, 99 or 100% identical to an entire amino acid sequence shown in FIG. 2A-I;

(XIII) a polynucleotide that encodes at least one peptide set forth in Tables VIII-XXI and XXII-XLIX;

(XIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 710 that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 710 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 710 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XVII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 710 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XVIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A-D in any whole number increment up to 710 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 598 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 598 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 598 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 598 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 598 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XXIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment upto 722 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment up to 722 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment up to 722 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXVII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment up to 722 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXVIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment up to 722 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XXIX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 712 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 712 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXXI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 712 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXXII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 712 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXXIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 712 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XXXIV) a polynucleotide that is fully complementary to a polynucleotide of any one of (I) -(XXXIII).

(XXXV) a peptide that is encoded by any of (I) to (XXXIII); and (XXXVI) a composition comprising a polynucleotide of any of (I)-(XXXIV) or peptide of (XXXV) together with a pharmaceutical excipient and/or in a human unit dose form.

(XXXVII) a method of using a polynucleotide of any (I)-(XXXIV) or peptide of (XXXV) or a composition of (XXXVI) in a method to modulate a cell expressing 24P4C12, (XXXVIII) a method of using a polynucleotide of any (I)-(XXXIV) or peptide of (XXXV) or a composition of (XXXVI) in a method to diagnose, prophylax, prognose, or treat an individual who bears a cell expressing 24P4C12

(XXXIX) a method of using a polynucleotide of any (I)-(XXXIV) or peptide of (XXXV) or a composition of (XXXVI) in a method to diagnose, prophylax, prognose, or treat an individual who bears a cell expressing 24P4C12, said cell from a cancer of a tissue listed in Table I;

(XL) a method of using a polynucleotide of any (I)-(XXXIV) or peptide of (XXXV) or a composition of (XXXVI) in a method to diagnose, prophylax, prognose, or treat a cancer;

(XLI) a method of using a polynucleotide of any (I)-(XXXIV) or peptide of (XXXV) or a composition of (XXXVI) in a method to diagnose, prophylax, prognose, or treat a cancer of a tissue listed in Table I; and, (XLII) a method of using a polynucleotide of any (I)-(XXXIV) or peptide of (XXXV) or a composition of (XXXVI) in a method to identify or characterize a modulator of a cell expressing 24P4C12.

As used herein, a range is understood to disclose specifically all whole unit positions thereof.

Typical embodiments of the invention disclosed herein include 24P4C12 polynucleotides that encode specific portions of 24P4C12 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 710 or more contiguous amino acids of 24P4C12 variant 1; the maximal lengths relevant for other variants are: variant 3, 710 amino acids; variant 5, 710 amino acids, variant 6, 710 amino acids, variant 7, 598 amino acids, variant 8, 722 amino acids, and variant 9, 712 amino acids.

For example, representative embodiments of the invention disclosed herein include: polynucleotides and their encoded peptides themselves encoding about amino acid 1 to about amino acid 10 of the 24P4C12 protein shown in FIG. 2 or FIG. 3, polynucleotides encoding about amino acid 10 to about amino acid 20 of the 24P4C12 protein shown in FIG. 2 or FIG. 3, polynucleotides encoding about amino acid 20 to about amino acid 30 of the 24P4C12 protein shown in FIG. 2 or FIG. 3, polynucleotides encoding about amino acid 30 to about amino acid 40 of the 24P4C12 protein shown in FIG. 2 or FIG. 3, polynucleotides encoding about amino acid 40 to about amino acid 50 of the 24P4C12 protein shown in FIG. 2 or FIG. 3, polynucleotides encoding about amino acid 50 to about amino acid 60 of the 24P4C12 protein shown in FIG. 2 or FIG. 3, polynucleotides encoding about amino acid 60 to about amino acid 70 of the 24P4C12 protein shown in FIG. 2 or FIG. 3, polynucleotides encoding about amino acid 70 to about amino acid 80 of the 24P4C12 protein shown in FIG. 2 or FIG. 3, polynucleotides encoding about amino acid 80 to about amino acid 90 of the 24P4C12 protein shown in FIG. 2 or FIG. 3, polynucleotides encoding about amino acid 90 to about amino acid 100 of the 24P4C12 protein shown in FIG. 2 or FIG. 3, in increments of about 10 amino acids, ending at the carboxyl terminal amino acid set forth in FIG. 2 or FIG. 3. Accordingly, polynucleotides encoding portions of the amino acid sequence (of about 10 amino acids), of amino acids, 100 through the carboxyl terminal amino acid of the 24P4C12 protein are embodiments of the invention. Wherein it is understood that each particular amino acid position discloses that position plus or minus five amino acid residues.

Polynucleotides encoding relatively long portions of a 24P4C12 protein are also within the scope of the invention. For example, polynucleotides encoding from about amino acid 1 (or 20 or 30 or 40 etc.) to about amino acid 20, (or 30, or 40 or 50 etc.) of the 24P4C12 protein "or variant" shown in FIG. 2 or FIG. 3 can be generated by a variety of techniques well known in the art. These polynucleotide fragments can include any portion of the 24P4C12 sequence as shown in FIG. 2.

Additional illustrative embodiments of the invention disclosed herein include 24P4C12 polynucleotide fragments encoding one or more of the biological motifs contained within a 24P4C12 protein "or variant" sequence, including one or more of the motif-bearing subsequences of a 24P4C12 protein or variant set forth in Tables VIII-XXI and XXII-XLIX. In another embodiment, typical polynucleotide fragments of the invention encode one or more of the regions of 24P4C12 protein or variant that exhibit homology to a known molecule. In another embodiment of the invention, typical polynucleotide fragments can encode one or more of the 24P4C12 protein or variant N-glycosylation sites, cAMP and cGMP-dependent protein kinase phosphorylation sites, casein kinase 11 phosphorylation sites or N-myristoylation site and amidation sites.

Note that to determine the starting position of any peptide set forth in Tables VIII-XXI and Tables XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides listed in Table LVII. Generally, a unique Search Peptide is used to obtain HLA peptides for a particular variant. The position of each Search Peptide relative to its respective parent molecule is listed in Table VII. Accordingly, if a Search Peptide begins at position "X", one must add the value "X minus 1" to each position in Tables VIII-XXI and Tables XXII-IL to obtain the actual position of the HLA peptides in their parental molecule. For example if a particular Search Peptide begins at position 150 of its parental molecule, one must add 150-1, i.e., 149 to each HLA peptide amino acid position to calculate the position of that amino acid in the parent molecule.

II.A.) Uses of 24P4C12 Polynucleotides

II.A.1.) Monitoring of Genetic Abnormalities

The polynucleotides of the preceding paragraphs have a number of different specific uses. The human 24P4C12 gene maps to the chromosomal location set forth in the Example entitled "Chromosomal Mapping of 24P4C12." For example, because the 24P4C12 gene maps to this chromosome, polynucleotides that encode different regions of the 24P4C12 proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83(1998); Johansson et al., Blood 86(10): 3905-3914(1995) and Finger et al., P.N.A.S. 85(23): 9158-9162 (1988)). Thus, polynucleotides encoding specific regions of the 24P4C12 proteins provide new tools that can be used to delineate, with greater precision than previously possible, cytogenetic abnormalities in the chromosomal region that encodes 24P4C12 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 24P4C12 was shown to be highly expressed in bladder and other cancers, 24P4C12 polynucleotides are used in methods assessing the status of 24P4C12 gene products in normal versus cancerous tissues. Typically, polynucleotides that encode specific regions of the 24P4C12 proteins are used to assess the presence of perturbations (such as deletions, insertions, point mutations, or alterations resulting in a loss of an antigen etc.) in specific regions of the 24P4C12 gene, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 24P4C12. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the 24P4C12 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 24P4C12. See for example, Jack Cohen, Oligodeoxynucleotides, Antisense Inhibitors of Gene Expression, CRC Press, 1989; and Synthesis 1:1-5 (1988). The 24P4C12 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. Soc. 112:1253-1254 (1990). Additional 24P4C12 antisense oligonucleotides of the present invention include morpholino antisense oligonucleotides known in the art (see, e.g., Partridge et al., 1996, Antisense & Nucleic Acid Drug Development 6:169-175).

The 24P4C12 antisense oligonucleotides of the present invention typically can be RNA or DNA that is complementary to and stably hybridizes with the first 100 5' codons or last 100 3' codons of a 24P4C12 genomic sequence or the corresponding mRNA. Absolute complementarity is not required, although high degrees of complementarity are preferred. Use of an oligonucleotide complementary to this region allows for the selective hybridization to 24P4C12 mRNA and not to mRNA specifying other regulatory subunits of protein kinase. In one embodiment, 24P4C12 antisense oligonucleotides of the present invention are 15 to 30-mer fragments of the antisense DNA molecule that have a sequence that hybridizes to 24P4C12 mRNA. Optionally, 24P4C12 antisense oligonucleotide is a 30-mer oligonucleotide that is complementary to a region in the first 10 5' codons or last 10 3' codons of 24P4C12. Alternatively, the antisense molecules are modified to employ ribozymes in the inhibition of 24P4C12 expression, see, e.g., L. A. Couture & D. T. Stinchcomb; Trends Genet 12: 510-515 (1996).

II.A.3.) Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 24P4C12 polynucleotide in a sample and as a means for detecting a cell expressing a 24P4C12 protein.

Examples of such probes include polypeptides comprising all or part of the human 24P4C12 cDNA sequence shown in FIG. 2. Examples of primer pairs capable of specifically amplifying 24P4C12 mRNAs are also described in the Examples. As will be understood by the skilled artisan, a great many different primers and probes can be prepared based on the sequences provided herein and used effectively to amplify and/or detect a 24P4C12 mRNA.

The 24P4C12 polynucleotides of the invention are useful for a variety of purposes, including but not limited to their use as probes and primers for the amplification and/or detection of the 24P4C12 gene(s), mRNA(s), or fragments thereof; as reagents for the diagnosis and/or prognosis of prostate cancer and other cancers; as coding sequences capable of directing the expression of 24P4C12 polypeptides; as tools for modulating or inhibiting the expression of the 24P4C12 gene(s) and/or translation of the 24P4C12 transcript(s); and as therapeutic agents.

The present invention includes the use of any probe as described herein to identify and isolate a 24P4C12 or 24P4C12 related nucleic acid sequence from a naturally occurring source, such as humans or other mammals, as well as the isolated nucleic acid sequence per se, which would comprise all or most of the sequences found in the probe used.

II.A.4.) Isolation of 24P4C12-Encoding Nucleic Acid Molecules

The 24P4C12 cDNA sequences described herein enable the isolation of other polynucleotides encoding 24P4C12 gene product(s), as well as the isolation of polynucleotides encoding 24P4C12 gene product homologs, alternatively spliced isoforms, allelic variants, and mutant forms of a 24P4C12 gene product as well as polynucleotides that encode analogs of 24P4C12-related proteins. Various molecular cloning methods that can be employed to isolate full length cDNAs encoding a 24P4C12 gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 24P4C12 gene cDNAs can be identified by probing with a labeled 24P4C12 cDNA or a fragment thereof. For example, in one embodiment, a 24P4C12 cDNA (e.g., FIG. 2) or a portion thereof can be synthesized and used as a probe to retrieve overlapping and full-length cDNAs corresponding to a 24P4C12 gene. A 24P4C12 gene itself can be isolated by screening genomic DNA libraries, bacterial artificial chromosome libraries (BACs), yeast artificial chromosome libraries (YACs), and the like, with 24P4C12 DNA probes or primers.

II.A.5.) Recombinant Nucleic Acid Molecules and Host-Vector Systems

The invention also provides recombinant DNA or RNA molecules containing a 24P4C12 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al, 1989, supra).

The invention further provides a host-vector system comprising a recombinant DNA molecule containing a 24P4C12 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 24P4C12 or a fragment, analog or homolog thereof can be used to generate 24P4C12 proteins or fragments thereof using any number of host-vector systems routinely used and widely known in the art.

A wide range of host-vector systems suitable for the expression of 24P4C12 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 24P4C12 can be expressed in several prostate cancer and non-prostate cell lines, including for example 293, 293T, rat-1, NIH 3T3 and TsuPr1. The host-vector systems of the invention are useful for the production of a 24P4C12 protein or fragment thereof. Such host-vector systems can be employed to study the functional properties of 24P4C12 and 24P4C12 mutations or analogs.

Recombinant human 24P4C12 protein or an analog or homolog or fragment thereof can be produced by mammalian cells transfected with a construct encoding a 24P4C12-related nucleotide. For example, 293T cells can be transfected with an expression plasmid encoding 24P4C12 or fragment, analog or homolog thereof, a 24P4C12-related protein is expressed in the 293T cells, and the recombinant 24P4C12 protein is isolated using standard purification methods (e.g., affinity purification using anti-24P4C12 antibodies). In another embodiment, a 24P4C12 coding sequence is subcloned into the retroviral vector pSRαMSVtkneo and used to infect various mammalian cell lines, such as NIH 3T3, TsuPr1, 293 and rat-1 in order to establish 24P4C12 expressing cell lines. Various other expression systems well known in the art can also be employed. Expression constructs encoding a leader peptide joined in frame to a 24P4C12 coding sequence can be used for the generation of a secreted form of recombinant 24P4C12 protein.

As discussed herein, redundancy in the genetic code permits variation in 24P4C12 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL dna.affrc.go.jp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell. Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 24P4C12-related Proteins

Another aspect of the present invention provides 24P4C12-related proteins. Specific embodiments of 24P4C12 proteins comprise a polypeptide having all or part of the amino acid sequence of human 24P4C12 as shown in FIG. 2 or FIG. 3. Alternatively, embodiments of 24P4C12 proteins comprise variant, homolog or analog polypeptides that have alterations in the amino acid sequence of 24P4C12 shown in FIG. 2 or FIG. 3.

Embodiments of a 24P4C12 polypeptide include: a 24P4C12 polypeptide having a sequence shown in FIG. 2, a peptide sequence of a 24P4C12 as shown in FIG. 2 wherein T is U; at least 10 contiguous nucleotides of a polypeptide having the sequence as shown in FIG. 2; or, at least 10 contiguous peptides of a polypeptide having the sequence as shown in FIG. 2 where T is U. For example, embodiments of 24P4C12 peptides comprise, without limitation:

(I) a protein comprising, consisting essentially of, or consisting of an amino acid sequence as shown in FIG. 2A-I or FIG. 3A-G;

(II) a 24P4C12-related protein that is at least 90, 91, 92, 93, 94, 95, 96, 97, 98, 99 or 100% homologous to an entire amino acid sequence shown in FIG. 2A-I;

(III) a 24P4C12-related protein that is at least 90, 91, 92, 93, 94, 95, 96, 97, 98, 99 or 100% identical to an entire amino acid sequence shown in FIG. 2A-1 or 3A-G;

(IV) a protein that comprises at least one peptide set forth in Tables VIII to XLIX, optionally with a proviso that it is not an entire protein of FIG. 2;

(V) a protein that comprises at least one peptide set forth in Tables VIII-XXI, collectively, which peptide is also set forth in Tables XXII to XLIX, collectively, optionally with a proviso that it is not an entire protein of FIG. 2;

(VI) a protein that comprises at least two peptides selected from the peptides set forth in Tables VIII-XLIX, optionally with a proviso that it is not an entire protein of FIG. 2;

(VII) a protein that comprises at least two peptides selected from the peptides set forth in Tables VIII to XLIX collectively, with a proviso that the protein is not a contiguous sequence from an amino acid sequence of FIG. 2;

(VIII) a protein that comprises at least one peptide selected from the peptides set forth in Tables VIII-XXI; and at least one peptide selected from the peptides set forth in Tables XXII to XLIX, with a proviso that the protein is not a contiguous sequence from an amino acid sequence of FIG. 2;

(IX) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, 3E, 3F, or 3G in any whole number increment up to 710, 710, 710, 710, 598, 722, or 712 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(x) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, 3E, 3F, or 3G in any whole number increment up to 710, 710, 710, 710, 598, 722, or 712 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, 3E, 3F, or 3G in any whole number increment up to 710, 710, 710, 710, 598, 722, or 712 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, 3E, 3F, or 3G in any whole number increment up to 710, 710, 710, 710, 598, 722, or 712 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XIII) a polypeptide comprising at least 5, 6, 7, 8, 9, 10, 11 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, 3E, 3F, or 3G in any whole number increment up to 710, 710, 710, 710, 598, 722, or 712 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIV) a peptide that occurs at least twice in Tables VIII-XXI and XXII to XLIX, collectively;

(XV) a peptide that occurs at least three times in Tables VIII-XXI and XXII to XLIX, collectively;

(XVI) a peptide that occurs at least four times in Tables VIII-XXI and XXII to XLIX, collectively;

(XVII) a peptide that occurs at least five times in Tables VIII-XXI and XXII to XLIX, collectively;

(XVIII) a peptide that occurs at least once in Tables VIII-XXI, and at least once in tables XXII to XLIX;

(XIX) a peptide that occurs at least once in Tables VIII-XXI, and at least twice in tables XXII to XLIX;

(XX) a peptide that occurs at least twice in Tables VIII-XXI, and at least once in tables XXII to XLIX;

(XXI) a peptide that occurs at least twice in Tables VIII-XXI, and at least twice in tables XXII to XLIX;

(XXII) a peptide which comprises one two, three, four, or five of the following characteristics, or an oligonucleotide encoding such peptide:

i) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or, v) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9;

(XXIII) a composition comprising a peptide of (I)-(XXII) or an antibody or binding region thereof together with a pharmaceutical excipient and/or in a human unit dose form.

(XXIV) a method of using a peptide of (I)-(XXII), or an antibody or binding region thereof or a composition of (XXIII) in a method to modulate a cell expressing 24P4C12, (XXV) a method of using a peptide of (I)-(XXII) or an antibody or binding region thereof or a composition of (XXIII) in a method to diagnose, prophylax, prognose, or treat an individual who bears a cell expressing 24P4C12

(XXVI) a method of using a peptide of (I)-(XXII) or an antibody or binding region thereof or a composition (XXIII) in a method to diagnose, prophylax, prognose, or treat an individual who bears a cell expressing 24P4C12, said cell from a cancer of a tissue listed in Table I;

(XXVII) a method of using a peptide of (I)-(XXII) or an antibody or binding region thereof or a composition of (XXIII) in a method to diagnose, prophylax, prognose, or treat a cancer;

(XXVIII) a method of using a peptide of (I)-(XXII) or an antibody or binding region thereof or a composition of (XXIII) in a method to diagnose, prophylax, prognose, or treat a cancer of a tissue listed in Table I; and, (XXIX) a method of using a peptide of (I)-(XXII) or an antibody or binding region thereof or a composition (XXIII) in a method to identify or characterize a modulator of a cell expressing 24P4C12.

As used herein, a range is understood to specifically disclose all whole unit positions thereof.

Typical embodiments of the invention disclosed herein include 24P4C12 polynucleotides that encode specific portions of 24P4C12 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 710 or more contiguous amino acids of 24P4C12 variant 1; the maximal lengths relevant for other variants are: variant 3, 710 amino acids; variant 5, 710 amino acids, variant 6, 710, variant 7, 598 amino acids, variant 8, 722 amino acids, and variant 9, 712 amino acids.

In general, naturally occurring allelic variants of human 24P4C12 share a high degree of structural identity and homology (e.g., 90% or more homology). Typically, allelic variants of a 24P4C12 protein contain conservative amino acid substitutions within the 24P4C12 sequences described herein or contain a substitution of an amino acid from a corresponding position in a homologue of 24P4C12. One class of 24P4C12 alelic variants are proteins that share a high degree of homology with at least a small region of a particular 24P4C12 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" $2^{nd}$ ED. Lubert Stryer ed (Stanford University); Henikoff et al., PNAS 1992 Vol 89 10915-10919; Lei et al., J Biol Chem 1995 May 19; 270(20):11882-6).

Embodiments of the invention disclosed herein include a wide variety of art-accepted variants or analogs of 24P4C12 proteins such as polypeptides having amino acid insertions, deletions and substitutions. 24P4C12 variants can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., Gene, 34:315 (1985)), restriction selection mutagenesis (Wells et al., *Philos. Trans. R. Soc. London SerA,* 317:415 (1986)) or other known techniques can be performed on the cloned DNA to produce the 24P4C12 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, 24P4C12 variants, analogs or homologs, have the distinguishing attribute of having at least one epitope that is "cross reactive" with a 24P4C12 protein having an amino acid sequence of FIG. 3. As used in this sentence, "cross reactive" means that an antibody or T cell that specifically binds to a 24P4C12 variant also specifically binds to a 24P4C12 protein having an amino acid sequence set forth in FIG. 3. A polypeptide ceases to be a variant of a protein shown in FIG. 3, when it no longer contains any epitope capable of being recognized by an antibody or T cell that specifically binds to the starting 24P4C12 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165(12): 6949-6955; Hebbes et al., Mol Immunol (1989) 26(9):865-73; Schwartz et al., J Immunol (1985) 135(4):2598-608.

Other classes of 24P4C12-related protein variants share 70%, 75%, 80%, 85% or 90% or more similarity with an amino acid sequence of FIG. 3, or a fragment thereof. Another specific class of 24P4C12 protein variants or analogs comprises one or more of the 24P4C12 biological motifs described herein or presently known in the art. Thus, encompassed by the present invention are analogs of 24P4C12 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a 24P4C12 protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a 24P4C12 protein shown in FIG. 2 or FIG. 3.

Moreover, representative embodiments of the invention disclosed herein include polypeptides consisting of about amino acid 1 to about amino acid 10 of a 24P4C12 protein shown in FIG. 2 or FIG. 3, polypeptides consisting of about amino acid 10 to about amino acid 20 of a 24P4C12 protein shown in FIG. 2 or FIG. 3, polypeptides consisting of about amino acid 20 to about amino acid 30 of a 24P4C12 protein shown in FIG. 2 or FIG. 3, polypeptides consisting of about amino acid 30 to about amino acid 40 of a 24P4C12 protein shown in FIG. 2 or FIG. 3, polypeptides consisting of about amino acid 40 to about amino acid 50 of a 24P4C12 protein shown in FIG. 2 or FIG. 3, polypeptides consisting of about amino acid 50 to about amino acid 60 of a 24P4C12 protein shown in FIG. 2 or FIG. 3, polypeptides consisting of about amino acid 60 to about amino acid 70 of a 24P4C12 protein shown in FIG. 2 or FIG. 3, polypeptides consisting of about amino acid 70 to about amino acid 80 of a 24P4C12 protein shown in FIG. 2 or FIG. 3, polypeptides consisting of about amino acid 80 to about amino acid 90 of a 24P4C12 protein shown in FIG. 2 or FIG. 3, polypeptides consisting of about amino acid 90 to about amino acid 100 of a 24P4C12 protein shown in FIG. 2 or FIG. 3, etc. throughout the entirety of a 24P4C12 amino acid sequence. Moreover, polypeptides consisting of about amino acid 1 (or 20 or 30 or 40 etc.) to about amino acid 20, (or 130, or 140 or 150 etc.) of a 24P4C12 protein shown in FIG. 2 or FIG. 3 are embodiments of the invention. It is to be appreciated that the starting and stopping positions in this paragraph refer to the specified position as well as that position plus or minus 5 residues.

24P4C12-related proteins are generated using standard peptide synthesis technology or using chemical cleavage methods well known in the art. Alternatively, recombinant methods can be used to generate nucleic acid molecules that encode a 24P4C12-related protein. In one embodiment, nucleic acid molecules provide a means to generate defined fragments of a 24P4C12 protein (or variants, homologs or analogs thereof).

III.A.) Motif-bearing Protein Embodiments

Additional illustrative embodiments of the invention disclosed herein include 24P4C12 polypeptides comprising the amino acid residues of one or more of the biological motifs contained within a 24P4C12 polypeptide sequence set forth in FIG. 2 or FIG. 3. Various motifs are known in the art, and a protein can be evaluated for the presence of such motifs by a number of publicly available Internet sites (see, e.g., URL addresses: pfam.wustl.edu/; searchlauncher.bcm.tmc.edu/ seq-search/struc-predict.html; psort.ims.u-tokyo.ac.jp/; cbs-.dtu.dk/; ebi.ac.uk/interpro/scan.html; expasy.ch/tools/ scnpsit1.html; Epimatrix™ and Epimer™, Brown University, brown.edu/Research/TB-HIV_Lab/epimatrix/ epimatrix.html; and BIMAS, bimas.dcrt.nih.gov/.).

Motif bearing subsequences of all 24P4C12 variant proteins are set forth and identified in Tables VIII-XXI and XXII-XLIX.

Table V sets forth several frequently occurring motifs based on pfam searches (see URL address pfam.wustl.edu/). The columns of Table V list (1) motif name abbreviation, (2) percent identity found amongst the different member of the motif family, (3) motif name or description and (4) most common function; location information is included if the motif is relevant for location.

Polypeptides comprising one or more of the 24P4C12 motifs discussed above are useful in elucidating the specific characteristics of a malignant phenotype in view of the observation that the 24P4C12 motifs discussed above are associated with growth dysregulation and because 24P4C12 is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al, J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables VIII-XXI and XXII-XLIX. CTL epitopes can be determined using specific algorithms to identify peptides within a 24P4C12 protein that are capable of optimally binding to specified HLA alleles (e.g., Table IV; Epimatrix™ and Epimer™, Brown University, URL brown.edu/Research/ TB-HIV_Lab/epimatrix/epimatrix.html; and BIMAS, URL bimas.dcrt.nih.gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/ supermotifs of Table IV). The epitope is analoged by substituting out an amino acid at one of the specified positions, and replacing it with another amino acid specified for that position. For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al, Immunol. Res. 1998 18(2): 79-92.

Related embodiments of the invention include polypeptides comprising combinations of the different motifs set forth in Table VI, and/or, one or more of the predicted CTL epitopes of Tables VIII-XXI and XXII-XLIX, and/or, one or more of the predicted HTL epitopes of Tables XLVI-XLIX, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 50 amino acid residues.

24P4C12-related proteins are embodied in many forms, preferably in isolated form. A purified 24P4C12 protein molecule will be substantially free of other proteins or molecules that impair the binding of 24P4C12 to antibody, T cell or other ligand. The nature and degree of isolation and purification will depend on the intended use. Embodiments of a 24P4C12-related proteins include purified 24P4C12-related proteins and functional, soluble 24P4C12-related proteins. In one embodiment, a functional, soluble 24P4C12 protein or fragment thereof retains the ability to be bound by antibody, T cell or other ligand.

The invention also provides 24P4C12 proteins comprising biologically active fragments of a 24P4C12 amino acid sequence shown in FIG. 2 or FIG. 3. Such proteins exhibit properties of the starting 24P4C12 protein, such as the ability to elicit the generation of antibodies that specifically bind an epitope associated with the starting 24P4C12 protein; to be bound by such antibodies; to elicit the activation of HTL or CTL; and/or, to be recognized by HTL or CTL that also specifically bind to the starting protein.

24P4C12-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schuftz or Jameson-Wolf analysis, or based on immunogenicity. Fragments that contain such structures are particularly useful in generating subunit-specific anti-24P4C12 antibodies or T cells or in identifying cellular factors that bind to 24P4C12. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a 24P4C12 protein that are capable of optimally binding to specified HLA alleles (e.g., by using the SYFPEITHI site at World Wide Web URL syfpeithi.bmi-heidelberg.com/; the listings in Table IV(A)-(E); Epimatrix™ and Epimer™, Brown University, URL (brown.edu/Research/TB-HIV_Lab/epimatrix/epimatrix.html); and BIMAS, URL bimas.dcrt.nih.gov/). Illustrating this, peptide epitopes from 24P4C12 that are presented in the context of human MHC Class I molecules, e.g., HLA-A1, A2, A3, A11, A24, B7 and B35 were predicted (see, e.g., Tables VIII-XXI, XXII-XLIX). Specifically, the complete amino acid sequence of the 24P4C12 protein and relevant portions of other variants, i.e., for HLA Class I predictions 9 flanking residues on either side of a point mutation or exon junction, and for HLA Class II predictions 14 flanking residues on either side of a point mutation or exon junction corresponding to that variant, were entered into the HLA Peptide Motif Search algorithm found in the Bioinformatics and Molecular Analysis Section (BIMAS) web site listed above; in addition to the site SYFPEITHI, at URL syfpeithi.bmi-heidelberg.com/.

The HLA peptide motif search algorithm was developed by Dr. Ken Parker based on binding of specific peptide sequences in the groove of HLA Class I molecules, in particular HLA-A2 (see, e.g., Falk et al, Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992)). Selected results of 24P4C12 predicted binding peptides are shown in Tables VIII-XXI and XXII-XLIX herein. In Tables VIII-XXI and XXII-XLVII, selected candidates, 9-mers and 10-mers, for each family member are shown along with their location, the amino acid sequence of each specific peptide, and an estimated binding score. In Tables XLVI-XLIX, selected candidates, 15-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/, or BIMAS, bimas.dcrt.nih.gov/) are to be "applied" to a 24P4C12 protein in accordance with the invention. As used in this context "applied" means that a 24P4C12 protein is evaluated, e.g., visually or by computer-based patterns finding methods, as appreciated by those of skill in the relevant art. Every subsequence of a 24P4C12 protein of 8, 9, 10, or 11 amino acid residues that bears an HLA Class I motif, or a subsequence of 9 or more amino acid residues that bear an HLA Class II motif are within the scope of the invention.

III.B.) Expression of 24P4C12-related Proteins

In an embodiment described in the examples that follow, 24P4C12 can be conveniently expressed in cells (such as 293T cells) transfected with a commercially available expression vector such as a CMV -driven expression vector encoding 24P4C12 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 24P4C12 protein in transfected cells. The secreted HIS-tagged 24P4C12 in the culture media can be purified, e.g., using a nickel column using standard techniques.

III.C.) Modifications of 24P4C12-related Proteins

Modifications of 24P4C12-related proteins such as covalent modifications are included within the scope of this invention. One type of covalent modification includes reacting targeted amino acid residues of a 24P4C12 polypeptide with an organic derivatizing agent that is capable of reacting with selected side chains or the N- or C-terminal residues of a 24P4C12 protein. Another type of covalent modification of a 24P4C12 polypeptide included within the scope of this invention comprises altering the native glycosylation pattern of a protein of the invention. Another type of covalent modification of 24P4C12 comprises linking a 24P4C12 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 24P4C12-related proteins of the present invention can also be modified to form a chimeric molecule comprising 24P4C12 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 24P4C12 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 24P4C12. A chimeric molecule can comprise a fusion of a 24P4C12-related protein with a polyhistidine epitope tag, which provides an epitope to which immobilized nickel can selectively bind, with cytokines or with growth factors. The epitope tag is generally placed at the amino- or carboxyl-terminus of a 24P4C12 protein. In an alternative embodiment, the chimeric molecule can comprise a fusion of a 24P4C12-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 24P4C12 polypeptide in place of at least one variable region within an Og molecule. In a preferred embodiment, the immunoglobulin fusion includes the hinge, CH2 and CH3, or the hinge, CHI, CH2 and CH3 regions of an IgGl molecule. For the production of immunoglobulin fusions see, e.g., U.S. Pat. No. 5,428, 130 issued Jun. 27, 1995.

III.D.) Uses of 24P4C12-related Proteins

The proteins of the invention have a number of different specific uses. As 24P4C12 is highly expressed in prostate and other cancers, 24P4C12-related proteins are used in methods that assess the status of 24P4C12 gene products in normal versus cancerous tissues, thereby elucidating the malignant phenotype. Typically, polypeptides from specific regions of a 24P4C12 protein are used to assess the presence of perturbations (such as deletions, insertions, point mutations etc.) in those regions (such as regions containing one or more motifs). Exemplary assays utilize antibodies or T cells targeting 24P4C12-related proteins comprising the amino acid residues of one or more of the biological motifs contained within a 24P4C12 polypeptide sequence in order to evaluate the characteristics of this region in normal versus cancerous tissues or to elicit an immune response to the epitope. Alternatively, 24P4C12-related proteins that contain the amino acid residues of one or more of the biological motifs in a 24P4C12 protein are used to screen for factors that interact with that region of 24P4C12.

24P4C12 protein fragments/subsequences are particularly useful in generating and characterizing domain-specific antibodies (e.g., antibodies recognizing an extracellular or intracellular epitope of a 24P4C12 protein), for identifying agents or cellular factors that bind to 24P4C12 or a particular structural domain thereof, and in various therapeutic and diagnostic contexts, including but not limited to diagnostic assays, cancer vaccines and methods of preparing such vaccines.

Proteins encoded by the 24P4C12 genes, or by analogs, homologs or fragments thereof, have a variety of uses, including but not limited to generating antibodies and in methods for identifying ligands and other agents and cellular constituents that bind to a 24P4C12 gene product. Antibodies raised against a 24P4C12 protein or fragment thereof are useful in diagnostic and prognostic assays, and imaging methodologies in the management of human cancers characterized by expression of 24P4C12 protein, such as those listed in Table I. Such antibodies can be expressed intracellularly and used in methods of treating patients with such cancers. 24P4C12-related nucleic acids or proteins are also used in generating HTL or CTL responses.

Various immunological assays useful for the detection of 24P4C12 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 24P4C12-expressing cells (e.g., in radioscintigraphic imaging methods). 24P4C12 proteins are also particularly useful in generating cancer vaccines, as further described herein.

IV.) 24P4C12 Antibodies

Another aspect of the invention provides antibodies that bind to 24P4C12-related proteins. Preferred antibodies specifically bind to a 24P4C12-related protein and do not bind (or bind weakly) to peptides or proteins that are not 24P4C12-related proteins. For example, antibodies that bind 24P4C12 can bind 24P4C12-related proteins such as the homologs or analogs thereof.

24P4C12 antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 24P4C12 is also expressed or overexpressed in these other cancers. Moreover, intracellularly expressed antibodies (e.g., single chain antibodies) are therapeutically useful in treating cancers in which the expression of 24P4C12 is involved, such as advanced or metastatic prostate cancers.

The invention also provides various immunological assays useful for the detection and quantification of 24P4C12 and mutant 24P4C12-related proteins. Such assays can comprise one or more 24P4C12 antibodies capable of recognizing and binding a 24P4C12-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 24P4C12 are also provided by the invention, including but not limited to radioscintigraphic imaging methods using labeled 24P4C12 antibodies. Such assays are clinically useful in the detection, monitoring, and prognosis of 24P4C12 expressing cancers such as prostate cancer.

24P4C12 antibodies are also used in methods for purifying a 24P4C12-related protein and for isolating 24P4C12 homologues and related molecules. For example, a method of purifying a 24P4C12-related protein comprises incubating a 24P4C12 antibody, which has been coupled to a solid matrix, with a lysate or other solution containing a 24P4C12-related protein under conditions that permit the 24P4C12 antibody to bind to the 24P4C12-related protein; washing the solid matrix to eliminate impurities; and eluting the 24P4C12-related protein from the coupled antibody. Other uses of 24P4C12 antibodies in accordance with the invention include generating anti-idiotypic antibodies that mimic a 24P4C12 protein.

Various methods for the preparation of antibodies are well known in the art. For example, antibodies can be prepared by immunizing a suitable mammalian host using a 24P4C12-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 24P4C12 can also be used, such as a 24P4C12 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 24P4C12-related protein is synthesized and used as an immunogen.

In addition, naked DNA immunization techniques known in the art are used (with or without purified 24P4C12-related protein or 24P4C12 expressing cells) to generate an immune response to the encoded immunogen (for review, see Donnelly et al., 1997, Ann. Rev. Immunol. 15: 617-648).

The amino acid sequence of a 24P4C12 protein as shown in FIG. 2 or FIG. 3 can be analyzed to select specific regions of the 24P4C12 protein for generating antibodies. For example, hydrophobicity and hydrophilicity analyses of a 24P4C12 amino acid sequence are used to identify hydrophilic regions in the 24P4C12 structure. Regions of a 24P4C12 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson -Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Methods for the generation of 24P4C12 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 24P4C12 immunogen is often conducted by injection over a suitable time period and with use of a suitable adjuvant, as is understood in the art. During the immunization schedule, titers of antibodies can be taken to determine adequacy of antibody formation.

24P4C12 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 24P4C12-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 24P4C12 protein can also be produced in the context of chimeric or complementarity-determining region (CDR) grafted antibodies of multiple species origin. Humanized or human 24P4C12 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al, 1988, Science 239: 1534-1536). See also, Carter et al., 1993, Proc. Natl. Acad. Sci. USA 89: 4285 and Sims et al, 1993, J. Immunol. 151: 2296.

Methods for producing fully human monoclonal antibodies include phage display and transgenic methods (for review, see Vaughan et al., 1998, Nature Biotechnology 16: 535-539). Fully human 24P4C12 monoclonal antibodies can be generated using cloning technologies employing large human 19 gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 24P4C12 monoclonal antibodies can also be produced using transgenic mice engineered to contain human immunoglobulin gene loci as described in PCT Patent Application WO98/24893, Kucherlapati and Jakobovits et al, published Dec. 3, 1997 (see also, Jakobovfts, 1998, Exp. Opin. Invest. Drugs 7(4): 607-614; U.S. Pat. No. 6,162,963 issued 19 Dec. 2000; U.S. Pat. No. 6,150,584 issued 12 Nov. 2000; and, U.S. Pat. No. 6,114,598 issued 5 Sep. 2000). This method avoids the in vitro manipulation required with phage display technology and efficiently produces high affinity authentic human antibodies.

Reactivity of 24P4C12 antibodies with a 24P4C12-related protein can be established by a number of well known means, including Western blot, immunoprecipitation, ELISA, and FACS analyses using, as appropriate, 24P4C12-related proteins, 24P4C12-expressing cells or extracts thereof. A 24P4C12 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 24P4C12 epitopes are generated using methods generally known in the art. Homodimeric antibodies can also be generated by cross-linking techniques known in the art (e.g., Wolff et al., Cancer Res. 53: 2560-2565).

V.) 24P4C12 Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA -restricted T cells (Buus, S. et al., *Cell* 47:1071, 1986; Babbitt, B. P. et al., *Nature* 317: 359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., *J. Immunol.* 160: 3363, 1998; Rammensee, et al., *Immunogenetics* 41:178, 1995; Rammensee et al., SYFPEITHI, access via World Wide Web at URL (134.2.96.221/scripts.hlaserver.dll/home.htm); Sette, A. and Sidney, *J. Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52, 1994; Ruppert et al., *Cell* 74:929-937, 1993; Kondo et al., *J. Immunol.* 155: 4307-4312, 1995; Sidney et al., *J. Immunol.* 157:3480-3490, 1996; Sidney et al., *Human Immunol.* 45:79-93, 1996; Sette, A. and Sidney, *J. Immunogenetics* 1999 November; 50(3-4): 201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide -sensitized targets, T cell proliferation, or lymphokine release.

VI.) 24P4C12 Transgenic Animals

Nucleic acids that encode a 24P4C12-related protein can also be used to generate either transgenic animals or "knock out" animals that, in turn, are useful in the development and screening of therapeutically useful reagents. In accordance with established techniques, cDNA encoding 24P4C12 can be used to clone genomic DNA that encodes 24P4C12. The cloned genomic sequences can then be used to generate transgenic animals containing cells that express DNA that encode 24P4C12. Methods for generating transgenic animals, particularly animals such as mice or rats, have become conventional in the art and are described, for example, in U.S. Pat. No. 4,736,866 issued 12 Apr. 1988, and U.S. Pat. No. 4,870,009 issued 26 Sep. 1989. Typically, particular cells would be targeted for 24P4C12 transgene incorporation with tissue-specific enhancers.

Transgenic animals that include a copy of a transgene encoding 24P4C12 can be used to examine the effect of increased expression of DNA that encodes 24P4C12. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 24P4C12 can be used to construct a 24P4C12 "knock out" animal that has a defective or altered gene encoding 24P4C12 as a result of homologous recombination between the endogenous gene encoding 24P4C12 and altered genomic DNA encoding 24P4C12 introduced into an embryonic cell of the animal. For example, cDNA that encodes 24P4C12 can be used to clone genomic DNA encoding 24P4C12 in accordance with established techniques. A portion of the genomic DNA encoding 24P4C12 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell,* 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell,* 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 24P4C12 polypeptide.

VII.) Methods for the Detection of 24P4C12

Another aspect of the present invention relates to methods for detecting 24P4C12 polynucleotides and 24P4C12-related proteins, as well as methods for identifying a cell that expresses 24P4C12. The expression profile of 24P4C12 makes it a diagnostic marker for metastasized disease. Accordingly, the status of 24P4C12 gene products provides information useful for predicting a variety of factors including susceptibility to advanced stage disease, rate of progression, and/or tumor aggressiveness. As discussed in detail herein, the status of 24P4C12 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 24P4C12 polynucleotides in a biological sample, such as serum, bone, prostate, and other tissues, urine, semen, cell preparations, and the like. Detectable 24P4C12 polynucleotides include, for example, a 24P4C12 gene or fragment thereof, 24P4C12 mRNA, alternative splice variant 24P4C12 mRNAS, and recombinant DNA or RNA molecules that contain a 24P4C12 polynucleotide. A number of methods for amplifying and/or detecting the presence of 24P4C12 polynucleotides are well known in the art and can be employed in the practice of this aspect of the invention.

In one embodiment, a method for detecting a 24P4C12 mRNA in a biological sample comprises producing cDNA from the sample by reverse transcription using at least one primer; amplifying the cDNA so produced using a 24P4C12 polynucleotides as sense and antisense primers to amplify 24P4C12 cDNAs therein; and detecting the presence of the amplified 24P4C12 cDNA. Optionally, the sequence of the amplified 24P4C12 cDNA can be determined.

In another embodiment, a method of detecting a 24P4C12 gene in a biological sample comprises first isolating genomic DNA from the sample; amplifying the isolated genomic DNA using 24P4C12 polynucleotides as sense and antisense primers; and detecting the presence of the amplified 24P4C12 gene. Any number of appropriate sense and antisense probe combinations can be designed from a 24P4C12 nucleotide sequence (see, e.g., FIG. 2) and used for this purpose.

The invention also provides assays for detecting the presence of a 24P4C12 protein in a tissue or other biological sample such as serum, semen, bone, prostate, urine, cell preparations, and the like. Methods for detecting a 24P4C12-related protein are also well known and include, for example, immunoprecipitation, immunohistochemical analysis, Western blot analysis, molecular binding assays, ELISA, ELIFA and the like. For example, a method of detecting the presence of a 24P4C12-related protein in a biological sample comprises first contacting the sample with a 24P4C12 antibody, a 24P4C12-reactive fragment thereof, or a recombinant protein containing an antigen-binding region of a 24P4C12 antibody; and then detecting the binding of 24P4C12-related protein in the sample.

Methods for identifying a cell that expresses 24P4C12 are also within the scope of the invention. In one embodiment, an assay for identifying a cell that expresses a 24P4C12 gene comprises detecting the presence of 24P4C12 mRNA in the cell. Methods for the detection of particular mRNAs in cells are well known and include, for example, hybridization assays using complementary DNA probes (such as in situ hybridization using labeled 24P4C12 riboprobes, Northern blot and related techniques) and various nucleic acid amplification assays (such as RT-PCR using complementary primers specific for 24P4C12, and other amplification type detection methods, such as, for example, branched DNA, SISBA, TMA and the like). Alternatively, an assay for identifying a cell that expresses a 24P4C12 gene comprises detecting the presence of 24P4C12-related protein in the cell or secreted by the cell. Various methods for the detection of proteins are well known in the art and are employed for the detection of 24P4C12-related proteins and cells that express 24P4C12-related proteins.

24P4C12 expression analysis is also useful as a tool for identifying and evaluating agents that modulate 24P4C12 gene expression. For example, 24P4C12 expression is significantly upregulated in prostate cancer, and is expressed in cancers of the tissues listed in Table I. Identification of a molecule or biological agent that inhibits 24P4C12 expression or over-expression in cancer cells is of therapeutic value. For example, such an agent can be identified by using a screen that quantifies 24P4C12 expression by RT-PCR, nucleic acid hybridization or antibody binding.

VIII.) Methods for Monitoring the Status of 24P4C12-related Genes and their Products Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant 24P4C12 expression in cancers) allows for early detection of such aberrant physiology, before a pathologic state such as cancer has progressed to a stage that therapeutic options are more limited and or the prognosis is worse. In such examinations, the status of 24P4C12 in a biological sample of interest can be compared, for example, to the status of 24P4C12 in a corresponding normal sample (e.g. a sample from that individual or alternatively another individual that is not affected by a pathology). An alteration in the status of 24P4C12 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306-14 and U.S. Pat. No. 5,837,501) to compare 24P4C12 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 24P4C12 expressing cells) as well as the level, and biological activity of expressed gene products (such as 24P4C12 mRNA, polynucleotides and polypeptides). Typically, an alteration in the status of 24P4C12 comprises a change in the location of 24P4C12 and/or 24P4C12 expressing cells and/or an increase in 24P4C12 mRNA and/or protein expression.

24P4C12 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a 24P4C12 gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 24P4C12 in a biological sample is evaluated by various methods utilized by skilled artisans including, but not limited to genomic Southern analysis (to examine, for example perturbations in a 24P4C12 gene), Northern analysis and/or PCR analysis of 24P4C12 mRNA (to examine, for example alterations in the polynucleotide sequences or expression levels of 24P4C12 mRNAs), and, Western and/or immunohistochemical analysis (to examine, for example alterations in polypeptide sequences, alterations in polypeptide localization within a sample, alterations in expression levels of 24P4C12 proteins and/or associations of 24P4C12 proteins with polypeptide binding partners). Detectable 24P4C12 polynucleotides include, for example, a 24P4C12 gene or fragment thereof, 24P4C12 mRNA, alternative splice variants, 24P4C12 mRNAs, and recombinant DNA or RNA molecules containing a 24P4C12 polynucleotide.

The expression profile of 24P4C12 makes it a diagnostic marker for local and/or metastasized disease, and provides information on the growth or oncogenic potential of a biological sample. In particular, the status of 24P4C12 provides information useful for predicting susceptibility to particular disease stages, progression, and/or tumor aggressiveness. The invention provides methods and assays for determining 24P4C12 status and diagnosing cancers that express 24P4C12, such as cancers of the tissues listed in Table I. For example, because 24P4C12 mRNA is so highly expressed in prostate and other cancers relative to normal prostate tissue, assays that evaluate the levels of 24P4C12 mRNA transcripts or proteins in a biological sample can be used to diagnose a disease associated with 24P4C12 dysregulation, and can provide prognostic information useful in defining appropriate therapeutic options.

The expression status of 24P4C12 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 24P4C12 in biological samples such as those from individuals suffering from, or suspected of suffering from a pathology characterized by dysregulated cellular growth, such as cancer.

As described above, the status of 24P4C12 in a biological sample can be examined by a number of well-known procedures in the art. For example, the status of 24P4C12 in a biological sample taken from a specific location in the body can be examined by evaluating the sample for the presence or absence of 24P4C12 expressing cells (e.g. those that express 24P4C12 mRNAs or proteins). This examination can provide evidence of dysregulated cellular growth, for example, when 24P4C12-expressing cells are found in a biological sample that does not normally contain such cells (such as a lymph node), because such alterations in the status of 24P4C12 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000); Su et al., Semin. Surg. Oncol. 18(1): 17-28 (2000) and Freeman et al., J Urol 1995 August 154(2 Pt 1):474-8).

In one aspect, the invention provides methods for monitoring 24P4C12 gene products by determining the status of 24P4C12 gene products expressed by cells from an individual suspected of having a disease associated with dysregulated cell growth (such as hyperplasia or cancer) and then comparing the status so determined to the status of 24P4C12 gene products in a corresponding normal sample. The presence of aberrant 24P4C12 gene products in the test sample relative to the normal sample provides an indication of the presence of dysregulated cell growth within the cells of the individual.

In another aspect, the invention provides assays useful in determining the presence of cancer in an individual, comprising detecting a significant increase in 24P4C12 mRNA or protein expression in a test cell or tissue sample relative to expression levels in the corresponding normal cell or tissue. The presence of 24P4C12 mRNA can, for example, be evaluated in tissues including but not limited to those listed in Table I. The presence of significant 24P4C12 expression in any of these tissues is useful to indicate the emergence, presence and/or severity of a cancer, since the corresponding normal tissues do not express 24P4C12 mRNA or express it at lower levels.

In a related embodiment, 24P4C12 status is determined at the protein level rather than at the nucleic acid level. For example, such a method comprises determining the level of 24P4C12 protein expressed by cells in a test tissue sample and comparing the level so determined to the level of 24P4C12 expressed in a corresponding normal sample. In one embodiment, the presence of 24P4C12 protein is evaluated, for example, using immunohistochemical methods. 24P4C12 antibodies or binding partners capable of detecting 24P4C12 protein expression are used in a variety of assay formats well known in the art for this purpose.

In a further embodiment, one can evaluate the status of 24P4C12 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 24P4C12 may be indicative of the presence or promotion of a tumor. Such assays therefore have diagnostic and predictive value where a mutation in 24P4C12 indicates a potential loss of function or increase in tumor growth.

A wide variety of assays for observing perturbations in nucleotide and amino acid sequences are well known in the art. For example, the size and structure of nucleic acid or amino acid sequences of 24P4C12 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. No. 5,382,510 issued 7 Sep. 1999, and U.S. Pat. No. 5,952, 170 issued 17 Jan. 1995).

Additionally, one can examine the methylation status of a 24P4C12 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al, Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 24P4C12. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA -protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 24P4C12 expression. The presence of RT-PCR amplifiable 24P4C12 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al, 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 24P4C12 mRNA or 24P4C12 protein in a tissue sample, its presence indicating susceptibility to cancer, wherein the degree of 24P4C12 mRNA expression correlates to the degree of susceptibility. In a specific embodiment, the presence of 24P4C12 in prostate or other tissue is examined, with the presence of 24P4C12 in the sample providing an indication of prostate cancer susceptibility (or the emergence or existence of a prostate tumor). Similarly, one can evaluate the integrity 24P4C12 nucleotide and amino acid sequences in a biological sample, in order to identify perturbations in the structure of these molecules such as insertions, deletions, substitutions and the like. The presence of one or more perturbations in 24P4C12 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 24P4C12 mRNA or 24P4C12 protein expressed by tumor cells, comparing the level so determined to the level of 24P4C12 mRNA or 24P4C12 protein expressed in a corresponding normal tissue taken from the same individual or a normal tissue reference sample, wherein the degree of 24P4C12 mRNA or 24P4C12 protein expression in the tumor sample relative to the normal sample indicates the degree of aggressiveness. In a specific embodiment, aggressiveness of a tumor is evaluated by determining the extent to which 24P4C12 is expressed in the tumor cells, with higher expression levels indicating more aggressive tumors. Another embodiment is the evaluation of the integrity of 24P4C12 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 24P4C12 mRNA or 24P4C12 protein expressed by cells in a sample of the tumor, comparing the level so determined to the level of 24P4C12 mRNA or 24P4C12 protein expressed in an equivalent tissue sample taken from the same individual at a different time, wherein the degree of 24P4C12 mRNA or 24P4C12 protein expression in the tumor sample over time provides information on the progression of the cancer. In a specific embodiment, the progression of a cancer is evaluated by determining 24P4C12 expression in the tumor cells over time, where increased expression over time indicates a progression of the cancer. Also, one can evaluate the integrity 24P4C12 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 24P4C12 gene and 24P4C12 gene products (or perturbations in 24P4C12 gene and 24P4C12 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Epstein, 1995, Hum. Pathol. 26(2): 223-9; Thorson et al., 1998, Mod. Pathol. 11(6):543-51; Baisden et al., 1999, Am. J. Surg. Pathol. 23(8):918-24). Methods for observing a coincidence between the expression of 24P4C12 gene and 24P4C12 gene products (or perturbations in 24P4C12 gene and 24P4C12 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 24P4C12 gene and 24P4C12 gene products (or perturbations in 24P4C12 gene and 24P4C12 gene products) and another factor associated with malignancy entails detecting the overexpression of 24P4C12 mRNA or protein in a tissue sample, detecting the overexpression of PSA mRNA or protein in a tissue sample (or PSCA or PSM expression), and observing a coincidence of 24P4C12 mRNA or protein and PSA mRNA or protein overexpression (or PSCA or PSM expression). In a specific embodiment, the expression of 24P4C12 and PSA mRNA in prostate tissue is examined, where the coincidence of 24P4C12 and PSA mRNA overexpression in the sample indicates the existence of prostate cancer, prostate cancer susceptibility or the emergence or status of a prostate tumor.

Methods for detecting and quantifying the expression of 24P4C12 mRNA or protein are described herein, and standard nucleic acid and protein detection and quantification technologies are well known in the art. Standard methods for the detection and quantification of 24P4C12 mRNA include in situ hybridization using labeled 24P4C12 riboprobes, Northern blot and related techniques using 24P4C12 polynucleotide probes, RT-PCR analysis using primers specific for 24P4C12, and other amplification type detection methods, such as, for example, branched DNA, SISBA, TMA and the like. In a specific embodiment, semi-quantitative RT-PCR is used to detect and quantify 24P4C12 mRNA expression. Any number of primers capable of amplifying 24P4C12 can be used for this purpose, including but not limited to the various primer sets specifically described herein. In a specific embodiment, polyclonal or monoclonal antibodies specifically reactive with the wild-type 24P4C12 protein can be used in an immunohistochemical assay of biopsied tissue.

IX.) Identification of Molecules that Interact with 24P4C12

The 24P4C12 protein and nucleic acid sequences disclosed herein allow a skilled artisan to identify proteins, small molecules and other agents that interact with 24P4C12, as well as pathways activated by 24P4C12 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. No. 5,955,280 issued 21 Sep. 1999, U.S. Pat. No. 5,925,523 issued 20 Jul. 1999, U.S. Pat. No. 5,846,722 issued 8 Dec. 1998 and U.S. Pat. No. 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 24P4C12 protein sequences. In such methods, peptides that bind to 24P4C12 are identified by screening libraries that encode a random or controlled collection of amino acids. Peptides encoded by the libraries are expressed as fusion proteins of bacteriophage coat proteins, the bacteriophage particles are then screened against the 24P4C12 protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 24P4C12 protein sequences are disclosed for example in U.S. Pat. No. 5,723,286 issued 3 Mar. 1998 and U.S. Pat. No. 5,733,731 issued 31 Mar. 1998.

Alternatively, cell lines that express 24P4C12 are used to identify protein-protein interactions mediated by 24P4C12. Such interactions can be examined using immunoprecipitation techniques (see, e.g., Hamilton B. J., et al. Biochem. Biophys. Res. Commun. 1999, 261:646-51). 24P4C12 protein can be immunoprecipitated from 24P4C12-expressing cell lines using anti-24P4C12 antibodies. Alternatively, antibodies against His-tag can be used in a cell line engineered to express fusions of 24P4C12 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 24P4C12 can be identified through related embodiments of such screening assays. For example, small molecules can be identified that interfere with protein function, including molecules that interfere with 24P4C12's ability to mediate phosphorylation and de-phosphorylation, interaction with DNA or RNA molecules as an indication of regulation of cell cycles, second messenger signaling or tumorigenesis. Similarly, small molecules that modulate 24P4C12-related ion channel, protein pump, or cell communication functions are identified and used to treat patients that have a cancer that expresses 24P4C12 (see, e.g., Hille, B., Ionic Channels of Excitable Membranes 2nd Ed., Sinauer Assoc., Sunderland, Mass., 1992). Moreover, ligands that regulate 24P4C12 function can be identified based on their ability to bind 24P4C12 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 24P4C12 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit 24P4C12.

An embodiment of this invention comprises a method of screening for a molecule that interacts with a 24P4C12 amino acid sequence shown in FIG. 2 or FIG. 3, comprising the steps of contacting a population of molecules with a 24P4C12 amino acid sequence, allowing the population of molecules and the 24P4C12 amino acid sequence to interact under conditions that facilitate an interaction, determining the presence of a molecule that interacts with the 24P4C12 amino acid sequence, and then separating molecules that do not interact with the 24P4C12 amino acid sequence from molecules that do. In a specific embodiment, the method further comprises purifying, characterizing and identifying a molecule that interacts with the 24P4C12 amino acid sequence. The identified molecule can be used to modulate a function performed by 24P4C12. In a preferred embodiment, the 24P4C12 amino acid sequence is contacted with a library of peptides.

X.) Therapeutic Methods and Compositions

The identification of 24P4C12 as a protein that is normally expressed in a restricted set of tissues, but which is also expressed in prostate and other cancers, opens a number of therapeutic approaches to the treatment of such cancers. As contemplated herein, 24P4C12 functions as a transcription factor involved in activating tumor-promoting genes or repressing genes that block tumorigenesis.

Accordingly, therapeutic approaches that inhibit the activity of a 24P4C12 protein are useful for patients suffering from a cancer that expresses 24P4C12. These therapeutic approaches generally fall into two classes. One class comprises various methods for inhibiting the binding or association of a 24P4C12 protein with its binding partner or with other proteins. Another class comprises a variety of methods for inhibiting the transcription of a 24P4C12 gene or translation of 24P4C12 mRNA.

X.A.) Anti-Cancer Vaccines

The invention provides cancer vaccines comprising a 24P4C12-related protein or 24P4C12-related nucleic acid. In view of the expression of 24P4C12, cancer vaccines prevent and/or treat 24P4C12-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a 24P4C12-related protein, or a 24P4C12-encoding nucleic acid molecule and recombinant vectors capable of expressing and presenting the 24P4C12 immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 February 31(1):66-78; Maruyama et al., Cancer Immunol Immunother 2000 June 49(3):123-32) Briefly, such methods of generating an immune response (e.g. humoral and/or cell-mediated) in a mammal, comprise the steps of: exposing the mammal's immune system to an immunoreactive epitope (e.g. an epitope present in a 24P4C12 protein shown in FIG. 3 or analog or homolog thereof) so that the mammal generates an immune response that is specific for that epitope (e.g. generates antibodies that specifically recognize that epitope). In a preferred method, a 24P4C12 immunogen contains a biological motif, see e.g., Tables VIII-XXI and XXII-XLIX, or a peptide of a size range from 24P4C12 indicated in FIG. 5, FIG. 6, FIG. 7, FIG. 8, and FIG. 9.

The entire 24P4C12 protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32,1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148: 1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 24P4C12-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 24P4C12 protein that bind corresponding HLA alleles (see e.g., Table IV; Epimer™ and Epimatrix™, Brown University (URL brown.edu/Research/TB-HIV_Lab/epimatrix/epimatrix.html); and, BIMAS, (URL bimas.dcrt.nih.gov/; SYFPEITHI at URL syfpeithi.bmi-heidelberg.com/). In a preferred embodiment, a 24P4C12 immunogen contains one or more amino acid sequences identified using techniques well known in the art, such as the sequences shown in Tables VIII-XXI and XXII-XLIX or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 24P4C12 protein) so that an immune response is generated. A typical embodiment consists of a method for generating an immune response to 24P4C12 in a host, by contacting the host with a sufficient amount of at least one 24P4C12 B cell or cytotoxic T-cell epitope or analog thereof; and at least one periodic interval thereafter re-contacting the host with the 24P4C12 B cell or cytotoxic T-cell epitope or analog thereof. A specific embodiment consists of a method of generating an immune response against a 24P4C12-related protein or a man-made multiepitopic peptide comprising: administering 24P4C12 immunogen (e.g. a 24P4C12 protein or a peptide fragment thereof, a 24P4C12 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 24P4C12 immunogen by: administering in vivo to muscle or skin of the individual's body a DNA molecule that comprises a DNA sequence that encodes a 24P4C12 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 24P4C12, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 24P4C12. Constructs comprising DNA encoding a 24P4C12-related protein/immunogen and appropriate regulatory sequences can be injected directly into muscle or skin of an individual, such that the cells of the muscle or skin take-up the construct and express the encoded 24P4C12 protein/immunogen. Alternatively, a vaccine comprises a 24P4C12-related protein. Expression of the 24P4C12-related protein immunogen results in the generation of prophylactic or therapeutic humoral and cellular immunity against cells that bear a 24P4C12 protein. Various prophylactic and therapeutic genetic immunization techniques known in the art can be used (for review, see information and references published at Internet address genweb.com). Nucleic acid-based delivery is described, for instance, in Wolff et al., *Science* 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. *J. Natl. Cancer Inst.* 87:982-990 (1995)). Non-viral delivery systems can also be employed by introducing naked DNA encoding a 24P4C12-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 24P4C12-related nucleic acid molecule. In one embodiment, the full-length human 24P4C12 cDNA is employed. In another embodiment, 24P4C12 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 24P4C12 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 24P4C12 peptides to T cells in the context of MHC class I or II molecules. In one embodiment, autologous dendritic cells are pulsed with 24P4C12 peptides capable of binding to MHC class I and/or class II molecules. In another embodiment, dendritic cells are pulsed with the complete 24P4C12 protein. Yet another embodiment involves engineering the overexpression of a 24P4C12 gene in dendritic cells using various implementing vectors known in the art, such as adenovirus (Arthur etaaL, 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186:1177-1182). Cells that express 24P4C12 can also be engineered to express immune modulators, such as GM-CSF, and used as immunizing agents.

X.B.) 24P4C12 as a Target for Antibody-based Therapy

24P4C12 is an attractive target for antibody-based therapeutic strategies. A number of antibody strategies are known in the art for targeting both extracellular and intracellular molecules (see, e.g., complement and ADCC mediated killing as well as the use of intrabodies). Because 24P4C12 is expressed by cancer cells of various lineages relative to corresponding normal cells, systemic administration of 24P4C12-immunoreactive compositions are prepared that exhibit excellent sensitivity without toxic, non-specific and/or non-target effects caused by binding of the immunoreactive composition to non-target organs and tissues. Antibodies specifically reactive with domains of 24P4C12 are useful to treat 24P4C12-expressing cancers systemically, either as conjugates with a toxin or therapeutic agent, or as naked antibodies capable of inhibiting cell proliferation or function.

24P4C12 antibodies can be introduced into a patient such that the antibody binds to 24P4C12 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 24P4C12, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 24P4C12 sequence shown in FIG. 2 or FIG. 3. In addition, skilled artisans understand that it is routine to conjugate antibodies to cytotoxic agents (see, e.g., Slevers et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. 24P4C12), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-24P4C12 antibody) that binds to a marker (e.g. 24P4C12) expressed, accessible to binding or localized on the cell surfaces. A typical embodiment is a method of delivering a cytotoxic and/or therapeutic agent to a cell expressing 24P4C12, comprising conjugating the cytotoxic agent to an antibody that immunospecifically binds to a 24P4C12 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-24P4C12 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). The antibodies can be conjugated to a therapeutic agent. To treat prostate cancer, for example, 24P4C12 antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized $IgG_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although 24P4C12 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although 24P4C12 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 24P4C12 expression, preferably using immunohistochemical assessments of tumor tissue, quantitative 24P4C12 imaging, or other techniques that reliably indicate the presence and degree of 24P4C12 expression. Immunohistochemical analysis of tumor biopsies or surgical specimens is preferred for this purpose. Methods for immunohistochemical analysis of tumor tissues are well known in the art.

Anti-24P4C12 monoclonal antibodies that treat prostate and other cancers include those that initiate a potent immune response against the tumor or those that are directly cytotoxic. In this regard, anti -24P4C12 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-24P4C12 mAbs that exert a direct biological effect on tumor growth are useful to treat cancers that express 24P4C12. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-24P4C12 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 24P4C12 antigen with high affinity but exhibit low or no antigenicity in the patient.

Therapeutic methods of the invention contemplate the administration of single anti-24P4C12 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-24P4C12 mAbs can be administered concomitantly with other therapeutic modalities, including but not limited to various chemotherapeutic agents, androgen-blockers, immune modulators (e.g., IL-2, GM-CSF), surgery or radiation. The anti-24P4C12 mAbs are administered in their "naked" or unconjugated form, or can have a therapeutic agent(s) conjugated to them.

Anti-24P4C12 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti -24P4C12 antibody preparation, via an acceptable route of administration such as intravenous injection (IV), typically at a dose in the range of about 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg mAb per week are effective and well tolerated.

Based on clinical experience with the Herceptin™ mAb in the treatment of metastatic breast cancer, an initial loading dose of approximately 4 mg/kg patient body weight IV, followed by weekly doses of about 2 mg/kg IV of the anti-24P4C12 mAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 24P4C12 expression in the patient, the extent of circulating shed 24P4C12 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 24P4C12 in a given sample (e.g. the levels of circulating 24P4C12 antigen and/or 24P4C12 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-24P4C12 antibodies can also be used in anti-cancer therapy as a vaccine for inducing an immune response to cells expressing a 24P4C12-related protein. In particular, the generation of anti-idiotypic antibodies is well known in the art; this methodology can readily be adapted to generate anti-idiotypic anti-24P4C12 antibodies that mimic an epitope on a 24P4C12-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

X.C.) 24P4C12 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis, J. Immunol. 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 24P4C12 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915-3925, 1999; An, L. and Whitton, J. L., *J. Virol.* 71:2292, 1997; Thomson, S. A. et al., J. Immunol. 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 24P4C12, the PADRE® universal helper T cell epitope or multiple HTL epitopes from 24P4C12 (see e.g., Tables VIII-XXI and XXII to XLIX), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide -loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 (QYIKANSKFIGITE; SEQ ID NO: 29), *Plasmodium falciparum* circumsporozoite (CS) protein at positions 378-398 (DIEKKIAKMEKASS-VFNVVNS; SEQ ID NO: 30), and *Streptococcus* 18 kD protein at positions 116-131 (GAVDSILGGVATYGAA; SEQ ID NO: 31). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed, most preferably, to bind most HLA-DR (human HLA class II) molecules. For instance, a pan-DR-binding epitope peptide having the formula: AKXVAAWTLKAAA (SEQ ID NO: 32), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the ϵ- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ϵ- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinly-seryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to prime specifically an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 24P4C12. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 24P4C12.

X.D. Adoptive Immunotherapy

Antigenic 24P4C12-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 24P4C12. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 24P4C12. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 24P4C12-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 24P4C12, a vaccine comprising 24P4C12-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 μg and the higher value is about 10,000; 20,000; 30,000; or 50,000 μg. Dosage values for a human typically range from about 500 μg to about 50,000 μg per 70 kilogram patient. Boosting dosages of between about 1.0 μg to about 50,000 μg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 μg and the higher value is about 10,000; 20,000; 30,000; or 50,000 μg. Dosage values for a human typically range from about 500 μg to about 50,000 μg per 70 kilogram patient. This is followed by boosting dosages of between about 1.0 μg to about 50,000 μg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, $17^{th}$ Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5-10^7$ to $5\times10^9$ pfu.

For antibodies, a treatment generally involves repeated administration of the anti-24P4C12 antibody preparation, via an acceptable route of administration such as intravenous injection (IV), typically at a dose in the range of about 0.1 to about 10 mg/kg body weight. In general, doses in the range of 10-500 mg mAb per week are effective and well tolerated. Moreover, an initial loading dose of approximately 4 mg/kg patient body weight IV, followed by weekly doses of about 2 mg/kg IV of the anti-24P4C12 mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 24P4C12 expression in the patient, the extent of circulating shed 24P4C12 antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg-1 mg, 1 mg-50 mg, 50 mg-100 mg, 100 mg-200 mg, 200 mg-300 mg, 400 mg-500 mg, 500 mg-600 mg, 600 mg-700 mg; 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg $m^2$ of body area weekly; 1-600 mg $m^2$ of body area weekly; 225-400 mg $m^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5\times10^{10}$ cells. A dose may also about $10^6$ cells/$m^2$ to about $10^{10}$ cells/$m^2$, or about $10^6$ cells/$m^2$ to about $10^8$ cells/$m^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) Diagnostic and Prognostic Embodiments of 24P4C12.

As disclosed herein, 24P4C12 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of 24P4C12 in normal tissues, and patient specimens").

24P4C12 can be analogized to a prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August; 162(2):293-306 (1999) and Fortier et al., J. Nat. Cancer Inst. 91(19): 1635-1640(1999)). A variety of other diagnostic markers are also used in similar contexts including p53 and K-ras (see, e.g., Tulchinsky et al., Int J Mol Med 1999 Jul. 4(1):99-102 and Minimoto et al., Cancer Detect Prev 2000;24(1):1-12). Therefore, this disclosure of 24P4C12 polynucleotides and polypeptides (as well as 24P4C12 polynucleotide probes and anti-24P4C12 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 24P4C12 polynucleotides, polypeptides, reactive T cells and antibodies are analogous to those methods from well-established diagnostic assays, which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74(1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 24P4C12 polynucleotides described herein can be utilized in the same way to detect 24P4C12 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 24P4C12 polypeptides described herein can be utilized to generate antibodies for use in detecting 24P4C12 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 24P4C12 polynucleotides and/or polypeptides can be used to provide evidence of metastasis. For example, when a biological sample from tissue that does not normally contain 24P4C12-expressing cells (lymph node) is found to contain 24P4C12-expressing cells such as the 24P4C12 expression seen in LAPC4 and LAPC9, xenografts isolated from lymph node and bone metastasis, respectively, this finding is indicative of metastasis.

Alternatively 24P4C12 polynucleotides and/or polypeptides can be used to provide evidence of cancer, for example, when cells in a biological sample that do not normally express 24P4C12 or express 24P4C12 at a different level are found to express 24P4C12 or have an increased expression of 24P4C12 (see, e.g., the 24P4C12 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 24P4C12) such as PSA, PSCA etc. (see, e.g., Alanen et al., Pathol. Res. Pract. 192(3): 233-237 (1996)).

Just as PSA polynucleotide fragments and polynucleotide variants are employed by skilled artisans for use in methods of monitoring PSA, 24P4C12 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson etaaL, Methods Mol. Biol. 98:121-154 (1998)). An additional illustration of the use of such fragments is provided in the Example entitled "Expression analysis of 24P4C12 in normal tissues, and patient specimens," where a 24P4C12 polynucleotide fragment is used as a probe to show the expression of 24P4C12 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 Nov.-Dec. 11 (6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a 24P4C12 polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. 24P4C12 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and 5,939,533). For example it may be preferable to utilize a polypeptide comprising one of the 24P4C12 biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a 24P4C12 polypeptide shown in FIG. 3).

As shown herein, the 24P4C12 polynucleotides and polypeptides (as well as the 24P4C12 polynucleotide probes and anti-24P4C12 antibodies or T cells used to identify the presence of these molecules) exhibit specific properties that make them useful in diagnosing cancers such as those listed in Table I. Diagnostic assays that measure the presence of 24P4C12 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as 24P4C12 polynucleotides and polypeptides (as well as the 24P4C12 polynucleotide probes and anti-24P4C12 antibodies used to identify the presence of these molecules) need to be employed to confirm a metastases of prostatic origin.

Finally, in addition to their use in diagnostic assays, the 24P4C12 polynucleotides disclosed herein have a number of other utilities such as their use in the identification of oncogenetic associated chromosomal abnormalities in the chromosomal region to which the 24P4C12 gene maps (see the Example entitled "Chromosomal Mapping of 24P4C12" below). Moreover, in addition to their use in diagnostic assays, the 24P4C12-related proteins and polynucleotides disclosed herein have other utilities such as their use in the forensic analysis of tissues of unknown origin (see, e.g., Takahama K Forensic Sci Int 1996 Jun. 28;80(1-2): 63-9).

Additionally, 24P4C12-related proteins or polynucleotides of the invention can be used to treat a pathologic condition characterized by the over-expression of 24P4C12. For example, the amino acid or nucleic acid sequence of FIG. 2 or FIG. 3, or fragments of either, can be used to generate an immune response to a 24P4C12 antigen. Antibodies or other molecules that react with 24P4C12 can be used to modulate the function of this molecule, and thereby provide a therapeutic benefit.

XII.) Inhibition of 24P4C12 Protein Function

The invention includes various methods and compositions for inhibiting the binding of 24P4C12 to its binding partner or its association with other protein(s) as well as methods for inhibiting 24P4C12 function.

XII.A.) Inhibition of 24P4C12 with Intracellular Antibodies

In one approach, a recombinant vector that encodes single chain antibodies that specifically bind to 24P4C12 are introduced into 24P4C12 expressing cells via gene transfer technologies. Accordingly, the encoded single chain anti-24P4C12 antibody is expressed intracellularly, binds to 24P4C12 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 24P4C12 in the nucleus, thereby preventing its activity within the nucleus. Nuclear targeting signals are engineered into such 24P4C12 intrabodies in order to achieve the desired targeting. Such 24P4C12 intrabodies are designed to bind specifically to a particular 24P4C12 domain. In another embodiment, cytosolic intrabodies that specifically bind to a 24P4C12 protein are used to prevent 24P4C12 from gaining access to the nucleus, thereby preventing it from exerting any biological activity within the nucleus (e.g., preventing 24P4C12 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 24P4C12 with Recombinant Proteins

In another approach, recombinant molecules bind to 24P4C12 and thereby inhibit 24P4C12 function. For example, these recombinant molecules prevent or inhibit 24P4C12 from accessing/binding to its binding partner(s) or associating with other protein(s). Such recombinant molecules can, for example, contain the reactive part(s) of a 24P4C12 specific antibody molecule. In a particular embodiment, the 24P4C12 binding domain of a 24P4C12 binding partner is engineered into a dimeric fusion protein, whereby the fusion protein comprises two 24P4C12 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 24P4C12, whereby the dimeric fusion protein specifically binds to 24P4C12 and blocks 24P4C12 interaction with a binding partner. Such dimeric fusion proteins are further combined into multimeric proteins using known antibody linking technologies.

XII.C.) Inhibition of 24P4C12 Transcription or Translation

The present invention also comprises various methods and compositions for inhibiting the transcription of the 24P4C12 gene. Similarly, the invention also provides methods and compositions for inhibiting the translation of 24P4C12 mRNA into protein.

In one approach, a method of inhibiting the transcription of the 24P4C12 gene comprises contacting the 24P4C12 gene with a 24P4C12 antisense polynucleotide. In another approach, a method of inhibiting 24P4C12 mRNA translation comprises contacting a 24P4C12 mRNA with an antisense polynucleotide. In another approach, a 24P4C12 specific ribozyme is used to cleave a 24P4C12 message, thereby inhibiting translation. Such antisense and ribozyme based methods can also be directed to the regulatory regions of the 24P4C12 gene, such as 24P4C12 promoter and/or enhancer elements. Similarly, proteins capable of inhibiting a 24P4C12 gene transcription factor are used to inhibit 24P4C12 mRNA transcription. The various polynucleotides and compositions useful in the aforementioned methods have been described above. The use of antisense and ribozyme molecules to inhibit transcription and translation is well known in the art.

Other factors that inhibit the transcription of 24P4C12 by interfering with 24P4C12 transcriptional activation are also useful to treat cancers expressing 24P4C12. Similarly, factors that interfere with 24P4C12 processing are useful to treat cancers that express 24P4C12. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 24P4C12 (i.e., antisense, ribozyme, polynucleotides encoding intrabodies and other 24P4C12 inhibitory molecules). A number of gene therapy approaches are known in the art. Recombinant vectors encoding 24P4C12 antisense polynucleotides, ribozymes, factors capable of interfering with 24P4C12 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 24P4C12 to a binding partner, etc.

In vivo, the effect of a 24P4C12 therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Identification, Characterization and Use of Modulators of 24P4C12

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state; screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression pattern, or a modulator of a cancer gene that leads to expression of the gene as in normal tissue) a screen is performed to identify genes that are specifically modulated in response to the agent. Comparing expression profiles between normal tissue and agent-treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cells. In addition, antibodies are raised against the agent-induced proteins and used to target novel therapeutics to the treated cancer tissue sample.

Modulator-related Identification and Screening Assays:
Gene Expression-related Assays Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al, J Biol Screen 7:69 (2002); Zlokarnik, et al., Science 279:84-8 (1998); Heid, Genome Res 6:986-94,1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokarmik, supra.

A variety of assays are executed directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100-300%, and in some embodiments 300-1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10-fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 2. In this embodiment, e.g., cancer nucleic acid probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 2. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g., a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus, it can be desirable to perform certain steps at higher stringency conditions to reduce non-specific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents that otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-related Assays

The invention provides methods identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way, compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (e.g., inhibiting) cancer cell division is provided; the method comprises administration of a cancer modulator. In another embodiment, a method of modulating (e.g., inhibiting) cancer is provided; the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc. of a cell. In one embodiment, a cancer inhibitor is an antibody as discussed above. In another embodiment, the cancer inhibitor is an antisense molecule. A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation in assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, Culture of Animal Cells a Manual of Basic Technique (3rd ed., 1994). See also, the methods section of Garkavtsev et al. (1996), supra.

Evaluation of Contact Inhibition and Growth Density Limitation to Identify and Characterize Modulators Normal cells typically grow in a flat and organized pattern in cell culture until they touch other cells. When the cells touch one another, they are contact inhibited and stop growing. Transformed cells, however, are not contact inhibited and continue to grow to high densities in disorganized foci. Thus, transformed cells grow to a higher saturation density than corresponding normal cells. This is detected morphologically by the formation of a disoriented monolayer of cells or cells in foci. Alternatively, labeling index with ($^3$H)-thymidine at saturation density is used to measure density limitation of growth, similarly an MTT or Alamar blue assay will reveal proliferation capacity of cells and the ability of modulators to affect same. See Freshney (1994), supra. Transformed cells, when transfected with tumor suppressor genes, can regenerate a normal phenotype and become contact inhibited and would grow to a lower density.

In this assay, labeling index with $^3$H)-thymidine at saturation density is a preferred method of measuring density limitation of growth. Transformed host cells are transfected with a cancer-associated sequence and are grown for 24 hours at saturation density in non-limiting medium conditions. The percentage of cells labeling with ($^3$H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Temin, J. Natl. Cancer Inst. 37:167-175 (1966); Eagle et al., J. Exp. Med 131:836-879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-specific Marker Levels to Identify and Characterize Modulators

Tumor cells release an increased amount of certain factors (hereinafter "tumor specific markers") than their normal counterparts. For example, plasminogen activator (PA) is released from human glioma at a higher level than from normal brain cells (see, e.g., Gullino, Angiogenesis, Tumor Vascularization, and Potential Interference with Tumor Growth, in Biological Responses in Cancer, pp. 178-184 (Mihich (ed.) 1985)). Similarly, Tumor Angiogenesis Factor (TAF) is released at a higher level in tumor cells than their normal counterparts. See, e.g., Folkman, Angiogenesis and Cancer, Sem Cancer Biol. (1992)), while bFGF is released from endothelial tumors (Ensoli, B et al).

Various techniques which measure the release of these factors are described in Freshney (1994), supra. Also, see, Unkless et al., J. Biol. Chem. 249:4295-4305 (1974); Strickland & Beers, J. Biol. Chem. 251:5694-5702 (1976); Whur et al., Br. J. Cancer 42:305 312 (1980); Gullino, Angiogenesis, Tumor Vascularization, and Potential Interference with Tumor Growth, in Biological Responses in Cancer, pp. 178-184 (Mihich (ed.) 1985); Freshney, Anticancer Res. 5:111-130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Techniques described in Cancer Res. 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$1 and counting the radioactivity on the distal side of the filter or bottom of the dish. See, e.g., Freshney (1984), supra.

Evaluation of Tumor Growth In Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., Science 244:1288 (1989)). Chimeric mice can be derived according to U.S. Pat. No. 6,365,797, issued 2 Apr. 2002; U.S. Pat. No. 6,107,540 issued 22 Aug. 2000; Hogan et al., Manipulating the Mouse Embryo: A laboratory Manual, Cold Spring Harbor Laboratory (1988) and Teratocarcinomas and Embryonic Stem Cells: A Practical Approach, Robertson, ed., IRL Press, Washington, D.C., (1987).

Alternatively, various immune-suppressed or immune-deficient host animals can be used. For example, a genetically athymic "nude" mouse (see, e.g., Giovanella et al., J. Natl. Cancer Inst. 52:921 (1974)), a SCID mouse, a thymectornized mouse, or an irradiated mouse (see, e.g., Bradley et al., Br. J. Cancer 38:263 (1978); Selby et al., Br. J. Cancer 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4-8 weeks, tumor growth is measured (e.g., by volume or by its two largest dimensions, or weight) and compared to the control. Tumors that have statistically significant reduction (using, e.g., Student's T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA. The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e.g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or P-gal. The reporter construct is typically transfected into a cell. After treatment with a potential modulator, the amount of reporter gene transcription, translation, or activity is measured according to standard techniques known to those of skill in the art (Davis G F, supra; Gonzalez, J. & Negulescu, P. Curr. Opin. Biotechnol. 1998: 9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

Binding Assays to Identify and Characterize Modulators

In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can, e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon™, etc. Microtiter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vitro protein-protein binding assays, electrophoretic mobility shift assays, immunoassays for protein binding, functional assays (phosphorylation assays, etc.) and the like.

A determination of binding of the test compound (ligand, binding agent, modulator, etc.) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$, for the proteins and a fluorophor for the compound. Proximity reagents, e.g., quenching or energy transfer reagents are also useful.

Competitive Binding to Identify and Characterize Modulators

In one embodiment, the binding of the "test compound" is determined by competitive binding assay with a "competitor." The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays. Preferably control and test samples are performed in at least triplicate to obtain statistically significant results. Incubation of all samples occurs for a time sufficient to allow for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g. albumin, detergents, etc. which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-regulate or Inhibit a Protein of the Invention.

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein &Cohen (Cancer Res. 48:2659 (1988 and van der Krol et al. (BioTechniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al., Adv. in Pharmacology 25: 289-317 (1994) for a general review of the properties of different ribozymes).

The general features of hairpin ribozymes are described, e.g., in Hampel et al., Nucl. Acids Res. 18:299-304 (1990); European Patent Publication No. 0360257; U.S. Pat. No. 5,254,678. Methods of preparing are well known to those of skill in the art (see, e.g., WO 94/26877; Ojwang et al., Proc. Natl. Acad. Sci. USA 90:6340-6344 (1993); Yamada et al., Human Gene Therapy 1:39-45 (1994); Leavitt et al., Proc. Natl. Acad. Sci. USA 92:699-703 (1995); Leavitt et al., Human Gene Therapy 5: 1151-120 (1994); and Yamada et al., Virology 205: 121-126 (1994)).

Use of Modulators in Phenotypic Screening

In one embodiment, a test compound is administered to a population of cancer cells, which have an associated cancer expression profile. By "administration" or "contacting" herein is meant that the modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining all or part of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Besffit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome. The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XIV.) Kits/Articles of Manufacture

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a FIG. 2-*related* protein or a FIG. 2 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequences in FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes; carrier, package, container, vial and/or tube labels listing contents and/or instructions for use, and package inserts with instructions for use.

A label can be present on the container to indicate that the composition is used for a specific therapy or non-therapeutic application, such as a diagnostic or laboratory application, and can also indicate directions for either in vivo or in vitro use, such as those described herein. Directions and or other information can also be included on an insert(s) or label(s) which is included with or on the kit.

The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass or plastic. The container can hold amino acid sequence(s), small molecule(s), nucleic acid sequence(s), and/or antibody(s), in one embodiment the container holds a polynucleotide for use in examining the mRNA expression profile of a cell, together with reagents used for this purpose.

The container can alternatively hold a composition which is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 24P4C12 and modulating the function of 24P4C12.

The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I. The article of manufacture can further comprise a second container comprising a pharmaceutically-acceptable buffer, such as phosphate-buffered saline, Ringer's solution and/ordextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which are intended to limit the scope of the invention.

Example 1

SSH-Generated Isolation of cDNA Fragment of the 24P4C12 Gene

Suppression Subtractive Hybridization (SSH) was used to identify cDNAs corresponding to genes that may be differentially expressed in prostate cancer. The SSH reaction utilized cDNA from the LAPC-9 AD prostate cancer xenograft. The gene 24P4C12 was derived from an LAPC-9 AD minus benign prostatic hyperplasia experiment.

The 24P4C12 SSH cDNA of 160 bp is listed in FIG. 1. The full length 24P4C12 cDNAs and ORFs are described in FIG. 2 with the protein sequences listed in FIG. 3.

Materials and Methods

Human Tissues:

The patient cancer and normal tissues were purchased from different sources such as the NDR1 (Philadelphia, Pa.). mRNA for some normal tissues were purchased from Clontech, Palo Alto, Calif.

RNA Isolation:

Tissues were homogenized in Trizol reagent (Life Technologies, Gibco BRL) using 10 ml/g tissue isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
DPNCDN (cDNA synthesis primer):
                                      (SEQ ID NO: 33)
5'TTTTGATCAAGCTT₃₀3'

Adaptor 1:
                                      (SEQ ID NO: 34)
5'CTAATACGACTCACTATAGGGCTCGAGCGGCCGCCCGGGCAG3'

(SEQ ID NO: 35)
3'GGCCCGTCCTAG5'

Adaptor 2:
                                      (SEQ ID NO: 36)
5'GTAATACGACTCACTATAGGGCAGCGTGGTCGCGGCCGAG3'

(SEQ ID NO: 37)
3'CGGCTCCTAG5'

PCR primer 1:
                                      (SEQ ID NO: 38)
5'CTAATACGACTCACTATAGGGC3'

Nested primer (NP)1:
                                      (SEQ ID NO: 39)
5'TCGAGCGGCCGCCCGGGCAGGA3'

Nested primer (NP)2:
                                      (SEQ ID NO: 40)
5'AGCGTGGTCGCGGCCGAGGA3'
```

Suppression Subtractive Hybridization:

Suppression Subtractive Hybridization (SSH) was used to identify cDNAs corresponding to genes that may be differentially expressed in prostate cancer. The SSH reaction utilized cDNA from prostate cancer and normal tissues.

The gene 24P4C12 sequence was derived from LAPC-4AD prostate cancer xenograft minus begnin prostatic hyperplasia cDNA subtraction. The SSH DNA sequence (FIG. 1) was identified.

The cDNA derived from a pool of normal tissues and benign prostatic hyperplasia was used as the source of the "driver" cDNA, while the cDNA from LAPC-4AD xenograft was used as the source of the "tester" cDNA. Double stranded cDNAs corresponding to tester and driver cDNAs were synthesized from 2 µg of poly(A)⁺ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Driver cDNA was generated by combining in a 1:1 ratio Dpn II digested cDNA from the relevant tissue source (see above) with a mix of digested cDNAs derived from the nine normal tissues: stomach, skeletal muscle, lung, brain, liver, kidney, pancreas, small intestine, and heart.

Tester cDNA was generated by diluting 1 µl of Dpn II digested cDNA from the relevant tissue source (see above) (400 ng) in 5 µl of water. The diluted cDNA (2 µl, 160 ng) was then ligated to 2 µl of Adaptor 1 and Adaptor 2 (10 µM), in separate ligation reactions, in a total volume of 10 µl at 16° C. overnight, using 400 u of T4 DNA ligase (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) Adaptor 1- and Adaptor 2-ligated tester cDNA. In a final volume of 4 µl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5 µl 10× reaction buffer (CLONTECH) and 0.5 µl 50× Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ul of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 µg of mRNA with oligo (dT)12-18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 µl with water prior to normalization. First strand cDNAs from 16 different normal human tissues can be obtained from Clontech.

Normalization of the first strand cDNAs from multiple tissues was performed by using the primers 5'atatcgccgcgctcgtcgtcgacaa3' (SEQ ID NO: 41) and 5'agccacacgcagctcattgtagaagg 3' (SEQ ID NO: 42) to amplify β-actin. First strand cDNA (5 µl) were amplified in a total volume of 50 µl containing 0.4 µM primers, 0.2 µM each dNTPs, 1×PCR buffer (Clontech, 10 mM Tris-HCL, 1.5 mM MgCl2, 50 mM KCl, pH8.3) and 1× Klentaq DNA polymerase (Clontech). Five µl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 b.p. β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 24P4C12 gene, 5 µl of normalized first strand cDNA were analyzed by PCR using 26, and 30 cycles of amplification. Semi-quantitative expression analysis can be achieved by comparing the PCR products at cycle numbers that give light band intensities. The primers used for RT-PCR were designed using the 24P4C12 SSH sequence and are listed below:

```
24P4C12.1
5'-AGATGAGGAGGAGGACAAAGGTG-3'      (SEQ ID NO: 43)

24P4C12.2
5'-ACTGCTGGGAGGAGTACCGAGTG-3'      (SEQ ID NO: 44)
```

Example 2

Isolation of Full Length 24P4C12 Encoding cDNA

The 24P4C12 SSH cDNA sequence was derived from a subtraction consisting of LAPC-4AD xenograft minus benign prostatic hyperplasia. The SSH cDNA sequence (FIG. 1) was designated 24P4C12.

The isolated gene fragment of 160 bp encodes a putative open reading frame (ORF) of 53 amino acids and exhibits significant homology to an EST derived from a colon tumor library. Two larger cDNA clones were obtained by gene trapper experiments, GTE9 and GTF8. The ORF revealed a significant homology to the mouse gene NG22 and the *C. elegans* gene CEESB82F. NG22 was recently identified as one of many ORFs within a genomic BAC clone that encompasses the MHC class III in the mouse genome. Both NG22 and CEESB82F appear to be genes that contain 12 transmembrane domains. This suggests that the gene encoding 24P4C12 contains 12 transmembrane domains and is the human homologue of mouse NG22 and *C. elegans* CEESB82F. Functional studies in *C. elegans* may reveal the biological role of these homologs. If 24P4C12 is a cell surface marker, then it may have an application as a potential imaging reagent and/or therapeutic target in prostate cancer.

The 24P4C12 v.1 of 2587 bp codes for a protein of 710 amino acids (FIG. 2 and FIG. 3). Other variants of 24P4C12 were also identified and these are listed in FIG. 2 and 3. 24P4C12 v.1, v.3, v.5 and v.6 proteins are 710 amino acids in length and differ from each other by one amino acid as shown in FIG. 11. 24P4C12 v.2 and v.4 code for the same protein as 24P4C12 v.1. 24P4C12 v.7, v.8 and v.9 are alternative splice variants and code for proteins of 598, 722 and 712 amino acids in length, respectively.

Example 3

Chromosomal Mapping of 24P4C12

Chromosomal localization can implicate genes in disease pathogenesis. Several chromosome mapping approaches are available including fluorescent in situ hybridization (FISH), human/hamster radiation hybrid (RH) panels (Walter et al., 1994; Nature Genetics 7:22; Research Genetics, Huntsville Ala.), human-rodent somatic cell hybrid panels such as is available from the Coriell Institute (Camden, N.J.), and genomic viewers utilizing BLAST homologies to sequenced and mapped genomic clones (NCBI, Bethesda, Md.). 24P4C12 maps to chromosome 6p21.3 using 24P4C12 sequence and the NCBI BLAST tool located on the World Wide Web at (.ncbi.nlm.nih.gov/genome/seq/page.cgi?F=HsBlast.html&&ORG=Hs).

Example 4

Expression Analysis of 24P4C12

Expression analysis by RT-PCR demonstrated that 24P4C12 is strongly expressed in prostate and ovary cancer patient specimens (FIG. 14). First strand cDNA was generated from vital pool 1 (kidney, liver and lung), vital pool 2 (colon, pancreas and stomach), a pool of prostate cancer xenografts (LAPC-4AD, LAPC-4AI, LAPC-9AD and LAPC-9AI), prostate cancer pool, bladder cancer pool, kidney cancer pool, colon cancer pool, ovary cancer pool, breast cancer pool, and cancer metastasis pool. Normalization was performed by PCR using primers to actin. Semi-quantitative PCR, using primers to 24P4C12, was performed at 26 and 30 cycles of amplification. Results show strong expression of 24P4C12 in prostate cancer pool and ovary cancer pool. Expression was also detected in prostate cancer xenografts, bladder cancer pool, kidney cancer pool, colon cancer pool, breast cancer pool, cancer metastasis pool, vital pool 1, and vital pool 2.

Extensive northern blot analysis of 24P4C12 in multiple human normal tissues is shown in FIG. 15. Two multiple tissue northern blots (Clontech) both with 2 μg of mRNA/lane were probed with the 24P4C12 SSH sequence. Expression of 24P4C12 was detected in prostate, kidney and colon. Lower expression is detected in pancreas, lung and placenta amongst all 16 normal tissues tested.

Expression of 24P4C12 was tested in prostate cancer xenografts and cell lines. RNA was extracted from a panel of cell lines and prostate cancer xenografts (PrEC, LAPC-4AD, LAPC-4AI, LAPC-9AD, LAPC-9AI, LNCaP, PC-3, DU145, TsuPr, and LAPC-4CL). Northern blot with 10 μg of total RNA/lane was probed with 24P4C12 SSH sequence. Size standards in kilobases (kb) are indicated on the side. The 24P4C12 transcript was detected in LAPC-4AD, LAPC-4AI, LAPC-9AD, LAPC-9AI, LNCaP, and LAPC-4 CL Expression of 24P4C12 in patient cancer specimens and human normal tissues is shown in FIG. 16. RNA was extracted from a pool of prostate cancer specimens, bladder cancer specimens, colon cancer specimens, ovary cancer specimens, breast cancer specimens and cancer metastasis specimens, as well as from normal prostate (NP), normal bladder (NB), normal kidney (NK), and normal colon (NC). Northern blot with 10 μg of total RNA/ane was probed with 24P4C12 SSH sequence. Size standards in kilobases (kb) are indicated on the side. Strong expression of 24P4C12 transcript was detected in the patient cancer pool specimens, and in normal prostate but not in the other normal tissues tested.

Expression of 24P4C12 was also detected in individual prostate cancer patient specimens (FIG. 17). RNA was extracted from normal prostate (N), prostate cancer patient tumors (T) and their matched normal adjacent tissues (Nat). Northern blots with 10 μg of total RNA were probed with the 24P4C12 SSH fragment. Size standards in kilobases are on the side. Results show expression of 24P4C12 in normal prostate and all prostate patient tumors tested.

Expression of 24P4C12 in colon cancer patient specimens is shown in FIG. 18. RNA was extracted from colon cancer cell lines (CL: Colo 205, LoVo, and SK-CO-), normal colon (N), colon cancer patient tumors (T) and their matched normal adjacent tissues (Nat). Northern blots with 10 μg of total RNA were probed with the 24P4C12 SSH fragment. Size standards in kilobases are on the side. Results show expression of 24P4C12 in normal colon and all colon patient tumors tested. Expression was detected in the cell lines Colo 205 and SK-CO-, but not in LoVo.

FIG. 20 displays expression results of 24P4C12 in lung cancer patient specimens. Ma was extracted from lung cancer cell lines (CL: CALU-1, A427, NCI-H82, NCI-H146), normal lung (N), lung cancer patient tumors (T) and their matched normal adjacent tissues (Nat). Northern blots with 10 μg of total RNA were probed with the 24P4C12 SSH fragment. Size standards in kilobases are on the side. Results show expression of 24P4C12 in lung patient tumors tested, but not in normal lung. Expression was also detected in CALU-1, but not in the other cell lines A427, NCI-H82, and NCI-H146.

24P4C12 was assayed in a panel of human stomach and breast cancers (T) and their respective matched normal tissues (N) on RNA dot blots. 24P4C12 expression was seen in both stomach and breast cancers. The expression detected in normal adjacent tissues (isolated from diseased tissues) but not in normal tissues (isolated from healthy donors) may indicate that these tissues are not fully normal and that 24P4C12 may be expressed in early stage tumors.

The level of expression of 24P4C12 was analyzed and quantitated in a panel of patient cancer tissues. First strand cDNA was prepared from a panel of ovary patient cancer specimens (A), uterus patient cancer specimens (B), prostate cancer specimens (C), bladder cancer patient specimens (D), lung cancer patient specimens (E), pancreas cancer patient specimens (F), colon cancer specimens (G), and kidney cancer specimens (H). Normalization was performed by PCR using primers to actin. Semi-quantitative PCR, using primers to 24P4C12, was performed at 26 and 30 cycles of amplification. Samples were run on an agarose gel, and PCR products were quantitated using the AlphaImager software. Expression was recorded as absent, low, medium or strong. Results show expression of 24P4C12 in the majority of patient cancer specimens tested, 73.3% of ovary patient cancer specimens, 83.3% of uterus patient cancer specimens, 95.0% of prostate cancer specimens, 61.1% of bladder cancer patient specimens, 80.6% of lung cancer patient specimens, 87.5% of pancreas cancer patient specimens, 87.5% of colon cancer specimens, 68.4% of clear cell renal carcinoma, 100% of papillary renal cell carcinoma. The restricted expression of 24P4C12 in normal tissues and the expression detected in prostate cancer, ovary cancer, bladder cancer, colon cancer, lung cancer pancreas cancer, uterus cancer, kidney cancer, stomach cancer and breast cancer suggest that 24P4C12 is a potential therapeutic target and a diagnostic marker for human cancers.

Example 5

Transcript Variants of 24P4C12

Transcript variants are variants of mature mRNA from the same gene which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different cellular or extracellular localizations, e.g., secreted versus intracellular.

Transcript variants are identified by a variety of art-accepted methods. For example, alternative transcripts and splice variants are identified by full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not a full-length clone, that portion of the variant is very useful for antigen generation and for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in *Drosophila* genomic DNA," Genome Research. 2000 April; 10(4):516-22); Grail (URL at compbio.ornl.gov/Grail-bin/EmptyGrailForm) and GenScan (URL at genes.mit.edu/GENSCAN.html). For a general discussion of splice variant identification protocols see., e.g., Southan, C., A genomic perspective on human proteases, FEBS Lett. 2001 Jun. 8; 498(2-3):214-8; de Souza, S. J., Identification of human chromosome 22 transcribed sequences with ORF expressed sequence tags, Proc. Natl Acad Sci USA. 2000 Nov. 7; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., Albumin banks peninsula: a new termination variant characterized by electrospray mass spectrometry, Biochem Biophys Acta. 1999 Aug. 17; 1433(1-2):321-6; Ferranti P, et al., Differential splicing of pre-messenger RNA produces multiple forms of mature caprine alpha(s1)-casein, Eur J Biochem. 1997 Oct. 1; 249(1):1-7. For PCR-based Validation: Wellmann S, et al., Specific reverse transcription-PCR quantification of vascular endothelial growth factor (VEGF) splice variants by LightCycler technology, Clin Chem. 2001 April; 47(4):654-60; Jia, H. P., Discovery of new human beta-defensins using a genomics-based approach, Gene. 2001 Jan. 24; 263(1-2):211-8. For PCR-based and 5' RACE Validation: Brigle, K. E., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that 24P4C12 has a particular expression profile related to cancer. Alternative transcripts and splice variants of 24P4C12 may also be involved in cancers in the same or different tissues, thus serving as tumor-associated markers/antigens.

The exon composition of the original transcript, designated as 24P4C12 v.1, is shown in Table LI. Using the full-length gene and EST sequences, three transcript variants were identified, designated as 24P4C12 v.7, v.8 and v.9. Compared with 24P4C12 v.1, transcript variant 24P4C12 v.7 has spliced out exons 10 and 11 from variant 24P4C12 v.1, as shown in FIG. 12. Variant 24P4C12 v.8 inserted 36 bp in between 1931 and 1932 of variant 24P4C12 v.1 and variant 24P4C12 v.9 replaced with 36 bp the segment 1136-1163 of variant 24P4C12 v.1. Theoretically, each different combination of exons in spatial order, e.g. exons 2 and 3, is a potential splice variant. FIG. 12 shows the schematic alignment of exons of the four transcript variants.

Tables LII through LXIII are set forth on a variant by variant basis. Tables LII, LVI, and LX show nucleotide sequences of the transcript variant. Tables LII, LVII, and LXI show the alignment of the transcript variant with the nucleic acid sequence of 24P4C12 v.1. Tables LIV, LVIII, and LXII lay out the amino acid translation of the transcript variant for the identified reading frame orientation. Tables LV, LIX, and LXIII display alignments of the amino acid sequence encoded by the splice variant with that of 24P4C12 v.1.

Example 6

Single Nucleotide Polymorphisms of 24P4C12

A Single Nucleotide Polymorphism (SNP) is a single base pair variation in a nucleotide sequence at a specific location. At any given point of the genome, there are four possible nucleotide base pairs: A/T, C/G, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several tightly linked genes. SNPs that occur on a cDNA are called cSNPs. These cSNPs may change amino acids of the protein encoded by the gene and thus change the functions of the protein. Some SNPs cause inherited diseases; others contribute to quantitative variations in phenotype and reactions to environmental factors including diet and drugs among individuals. Therefore, SNPs and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," Curr. Opin. Neurobiol. 2001 October; 11 (5):637-641; M. Pirmohamed and B. K. Park, "Genetic susceptibility to adverse drug reactions," Trends Pharmacol. Sci. 2001 June; 22(6):298-305; J. H. Riley, C. J. Allan, E. Lai and A. Roses, "The use of single nucleotide polymorphisms in the isolation of common disease genes," Pharmacogenomics. 2000 February; 1(1):39-47; R. Judson, J. C. Stephens and A. Windemuth, "The predictive power of haplotypes in clinical response," Pharmacogenomics. 2000 February; 1(1):15-26).

SNPs are identified by a variety of art-accepted methods (P. Bean, "The promising voyage of SNP target discovery," Am. Clin. Lab. 2001 October-November; 20(9):18-20; K. M. Weiss, "In search of human variation," Genome Res. 1998 July; 8(7):691-697; M. M. She, "Enabling large-scale pharmacogenetic studies by high-throughput mutation detection and genotyping technologies," Clin. Chem. 2001 February; 47(2):164-172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221-225). SNPs can be verified and genotype or haplotype of an individual can be determined by a variety of methods including direct sequencing and high throughput microarrays (P. Y. Kwok, "Methods for genotyping single nucleotide polymorphisms,"Annu. Rev. Genomics Hum. Genet. 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. 2000 December; 5(4):329-340).

Using the methods described above, five SNPs were identified in the original transcript, 24P4C12 v.1, at positions 542 (G/A), 564 (G/A), 818 (C/T), 981(ANG) and 1312 (A/C). The transcripts or proteins with alternative alleles were designated as variants 24P4C12 v.2, v.3, v.4, v.5 and v.6, respectively. FIG. 10 shows the schematic alignment of the SNP variants. FIG. 11 shows the schematic alignment of protein variants, corresponding to nucleotide variants. Nucleotide variants that code for the same amino acid sequence as variant 1 are not shown in FIG. 11. These alleles of the SNPs, though shown separately here, can occur in different combinations (haplotypes) and in any one of the transcript variants (such as 24P4C12 v.7) that contains the sequence context of the SNPs.

Example 7

Production of Recombinant 24P4C12 in Prokaryotic Systems

To express recombinant 24P4C12 and 24P4C12 variants in prokaryotic cells, the full or partial length 24P4C12 and 24P4C12 variant cDNA sequences are cloned into any one of a variety of expression vectors known in the art. The full length cDNA, or any 8, 9, 10, 11, 12, 13, 14, 15, 16, 17, 18, 19, 20, 21, 22, 23, 24, 25, 26, 27, 28, 29, 30 or more contiguous amino acids from 24P4C12, variants, or analogs thereof are used.

A. In vitro Transcription and Translation Constructs:

pCRII: To generate 24P4C12 sense and anti-sense RNA probes for RNA in situ investigations, pCRII constructs (Invitrogen, Carlsbad Calif.) are generated encoding either all or fragments of the 24P4C12 cDNA. The pCR11 vector has Sp6 and T7 promoters flanking the insert to drive the transcription of 24P4C12 RNA for use as probes in RNA in situ hybridization experiments. These probes are used to analyze the cell and tissue expression of 24P4C12 at the RNA level. Transcribed 24P4C12 RNA representing the cDNA amino acid coding region of the 24P4C12 gene is used in vitro translation systems such as the TnT™ Coupled Reticulolysate System (Promega, Corp., Madison, Wis.) to synthesize 24P4C12 protein.

B. Bacterial Constructs:

pGEX Constructs: To generate recombinant 24P4C12 proteins in bacteria that are fused to the Glutathione S-transferase (GST) protein, all or parts of the 24P4C12 cDNA or variants are cloned into the GST-fusion vector of the pGEX family (Amersham Pharmacia Biotech, Piscataway, N.J.). These constructs allow controlled expression of recombinant 24P4C12 protein sequences with GST fused at the amino-terminus and a six histidine epitope (6×His) at the carboxyl-terminus. The GST and 6×His tags permit purification of the recombinant fusion protein from induced bacteria with the appropriate affinity matrix and allow recognition of the fusion protein with anti-GST and anti-His antibodies. The 6×His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 24P4C12-related protein. The ampicillin resistance gene and pBR322 origin permits selection and maintenance of the pGEX plasmids in *E. coli*.

pMAL Constructs: To generate, in bacteria, recombinant 24P4C12 proteins that are fused to maltose-binding protein (MBP), all or parts of the 24P4C12 cDNA protein coding sequence are fused to the MBP gene by cloning into the pMAL-c2X and pMAL-p2X vectors (New England Biolabs, Beverly, Mass.). These constructs allow controlled expression of recombinant 24P4C12 protein sequences with MBP fused at the amino-terminus and a 6×His epitope tag at the carboxyl-terminus. The MBP and 6×His tags permit purification of the recombinant protein from induced bacteria with the appropriate affinity matrix and allow recognition of the fusion protein with anti-MBP and anti-His antibodies. The 6×His epitope tag is generated by adding 6 histidine codons to the 3' cloning primer. A Factor Xa recognition site permits cleavage of the pMAL tag from 24P4C12. The pMAL-c2X and pMAL-p2X vectors are optimized to express the recombinant protein in the cytoplasm or periplasm respectively. Periplasm expression enhances folding of proteins with disulfide bonds.

pET Constructs: To express 24P4C12 in bacterial cells, all or parts of the 24P4C12 cDNA protein coding sequence are cloned into the pET family of vectors (Novagen, Madison, Wis.). These vectors allow tightly controlled expression of recombinant 24P4C12 protein in bacteria with and without fusion to proteins that enhance solubility, such as NusA and thioredoxin (Trx), and epitope tags, such as 6×His and S-Tag™ that aid purification and detection of the recombinant protein. For example, constructs are made utilizing pET NusA fusion system 43.1 such that regions of the 24P4C12 protein are expressed as amino-terminal fusions to NusA.

C. Yeast Constructs:

pESC Constructs: To express 24P4C12 in the yeast species *Saccharomyces cerevisiae* for generation of recombinant protein and functional studies, all or parts of the 24P4C12 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of 24P4C12. In addition, expression in yeast yields similar post-translational modifications, such as glycosylations and phosphorylations, that are found when expressed in eukaryotic cells.

pESP Constructs: To express 24P4C12 in the yeast species *Saccharomyces pombe*, all or parts of the 24P4C12 cDNA protein coding sequence are cloned into the pESP family of vectors. These vectors allow controlled high level of expression of a 24P4C12 protein sequence that is fused at either the amino terminus or at the carboxyl terminus to GST which aids purification of the recombinant protein. A Flag™ epitope tag allows detection of the recombinant protein with anti-Flag™ antibody.

Example 8

Production of Recombinant 24P4C12 in Higher Eukaryotic Systems

A. Mammalian Constructs:

To express recombinant 24P4C12 in eukaryotic cells, the full or partial length 24P4C12 cDNA sequences can be cloned into any one of a variety of expression vectors known in the art. One or more of the following regions of 24P4C12 are expressed in these constructs, amino acids 1 to 710, or any 8, 9, 10, 11, 12, 13, 14, 15, 16, 17, 18, 19, 20, 21, 22, 23, 24, 25, 26, 27, 28, 29, 30 or more contiguous amino acids from 24P4C12 v.1 through v.6; amino acids 1 to 598, or any 8, 9, 10, 11, 12, 13, 14, 15, 16, 17, 18, 19, 20, 21, 22, 23, 24, 25, 26, 27, 28, 29, 30 or more contiguous amino acids from 24P4C12 v.7, amino acids 1 to 722, or any 8, 9, 10, 11, 12, 13, 14, 15, 16, 17, 18, 19, 20, 21, 22, 23, 24, 25, 26, 27, 28, 29, 30 or more contiguous amino acids from 24P4C12 v.8, amino acids 1 to 712, or any 8, 9, 10, 11, 12, 13, 14, 15, 16, 17, 18, 19, 20, 21, 22, 23, 24, 25, 26, 27, 28, 29, 30 or more contiguous amino acids from 24P4C12 v.9, variants, or analogs thereof.

The constructs can be transfected into any one of a wide variety of mammalian cells such as 293T cells. Transfected 293T cell lysates can be probed with the anti-24P4C12 polyclonal serum, described herein.

pcDNA3.1/MycHis Constructs: To express 24P4C12 in mammalian cells, a 24P4C12 ORF, or portions thereof, of 24P4C12 with a consensus Kozak translation initiation site was cloned into pcDNA3.1/MycHis Version A (Invitrogen, Carlsbad, Calif.). Protein expression is driven from the cytomegalovirus (CMV) promoter. The recombinant proteins have the myc epitope and 6xHis epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli*. Figure Art-1 demonstrates expression of 24P4C12 from the pcDNA3.1/MycHis construct in transiently transfected 293T cells.

pcDNA4/HisMax Constructs: To express 24P4C12 in mammalian cells, a 24P4C12 ORF, or portions thereof, of 24P4C12 are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6xHis) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

pcDNA3.1/CT-GFP-TOPO Construct: To express 24P4C12 in mammalian cells and to allow detection of the recombinant proteins using fluorescence, a 24P4C12 ORF, or portions thereof, with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein and the ampicillin resistance gene and ColE1 origin permits selection and maintenance of the plasmid in *E. coli*. Additional constructs with an amino-terminal GFP fusion are made in pcDNA3.1/NT-GFP-TOPO spanning the entire length of a 24P4C12 protein.

pTag5: A 24P4C12 ORF, or portions thereof, were cloned into pTag-5. This vector is similar to pAPtag but without the alkaline phosphatase fusion. This construct generates 24P4C12 protein with an amino-terminal IgGκ signal sequence and myc and 6xHis epitope tags at the carboxyl-terminus that facilitate detection and affinity purification. The resulting recombinant 24P4C12 protein were optimized for secretion into the media of transfected mammalian cells, and is used as immunogen or ligand to identify proteins such as ligands or receptors that interact with the 24P4C12 proteins. Protein expression is driven from the CMV promoter. The Zeocin resistance gene present in the vector allows for selection of mammalian cells expressing the protein, and the ampicillin resistance gene permits selection of the plasmid in *E. coli*. Figure Art-3 shows expression of 24P4C12 from two different pTag5 constructs.

PAPtag: A 24P4C12 ORF, or portions thereof, is cloned into pAPtag-5 (GenHunter Corp. Nashville, Tenn.). This construct generates an alkaline phosphatase fusion at the carboxyl-terminus of a 24P4C12 protein while fusing the IgGκ signal sequence to the amino-terminus. Constructs are also generated in which alkaline phosphatase with an amino-terminal IgGκ signal sequence is fused to the amino-terminus of a 24P4C12 protein. The resulting recombinant 24P4C12 proteins are optimized for secretion into the media of transfected mammalian cells and can be used to identify proteins such as ligands or receptors that interact with 24P4C12 proteins. Protein expression is driven from the CMV promoter and the recombinant proteins also contain myc and 6xHis epitopes fused at the carboxyl-terminus that facilitates detection and purification. The Zeocin resistance gene present in the vector allows for selection of mammalian cells expressing the recombinant protein and the ampicillin resistance gene permits selection of the plasmid in E. coli.

PsecFc: A 24P4C12 ORF, or portions thereof, is also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 24P4C12 proteins, while fusing the IgGK signal sequence to N-terminus. 24P4C12 fusions utilizing the murine IgG1 Fc region are also used. The resulting recombinant 24P4C12 proteins are optimized for secretion into the media of transfected mammalian cells, and can be used as immunogens or to identify proteins such as ligands or receptors that interact with 24P4C12 protein. Protein expression is driven from the CMV promoter. The hygromycin resistance gene present in the vector allows for selection of mammalian cells that express the recombinant protein, and the ampicillin resistance gene permits selection of the plasmid in E. coli.

pSRα Constructs: To generate mammalian cell lines that express 24P4C12 constitutively, 24P4C12 ORF, or portions thereof, of 24P4C12 were cloned into pSRα constructs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 24P4C12, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in E. coli. The retroviral vectors can thereafter be used for infection and generation of various cell lines using, for example, PC3, NIH 3T3, TsuPr1, 293 or rat-1 cells. FIG. 23 shows RNA expression of 24P4C12 driven from the 24P4C12.pSRa construct in stably transduced PC3, 3T3 and 300.19 cells. Figure Art-2 shows 24P4C12 protein expression in PC3 cells stably transduced with 24P4C12.pSRa construct.

Additional pSRα constructs are made that fuse an epitope tag such as the FLAG™ tag to the carboxyl-terminus of 24P4C12 sequences to allow detection using anti-Flag antibodies. For example, the FLAG™ sequence 5' gat tac aag gat gac gac gat aag 3' (SEQ ID NO: 45) is added to cloning primer at the 3' end of the ORF. Additional pSRα constructs are made to produce both amino-terminal and carboxyl-terminal GFP and myc/6xHis fusion proteins of the full-length 24P4C12 proteins.

Additional Viral Vectors: Additional constructs are made for viral-mediated delivery and expression of 24P4C12. High virus titer leading to high level expression of 24P4C12 is achieved in viral delivery systems such as adenoviral vectors and herpes amplicon vectors. A 24P4C12 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 24P4C12 coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 24P4C12 in mammalian cells, coding sequences of 24P4C12, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 24P4C12. These vectors are thereafter used to control expression of 24P4C12 in various cell lines such as PC3, NIH 3T3, 293 or rat-1 cells.

B. Baculovirus Expression Systems

To generate recombinant 24P4C12 proteins in a baculovirus expression system, 24P4C12 ORF, or portions thereof, are cloned into the baculovirus transfer vector pBlueBac 4.5 (Invitrogen), which provides a His-tag at the N-terminus. Specifically, pBlueBac-24P4C12 is co-transfected with helper plasmid pBac-N-Blue (Invitrogen) into SF9 (Spodoptera frugiperda) insect cells to generate recombinant baculovirus (see Invitrogen instruction manual for details). Baculovirus is then collected from cell supernatant and purified by plaque assay.

Recombinant 24P4C12 protein is then generated by infection of HighFive insect cells (Invitrogen) with purified baculovirus. Recombinant 24P4C12 protein can be detected using anti-24P4C12 or anti-His-tag antibody. 24P4C12 protein can be purified and used in various cell-based assays or as immunogen to generate polyclonal and monoclonal antibodies specific for 24P4C12.

Example 9

Antigenicity Profiles and Secondary Structure

FIGS. 5-9 depict graphically five amino acid profiles of the 24P4C12 variant 1, assessment available by accessing the ProtScale website located on the World Wide Web at (.expasy.ch/cgi-bin/protscale.pl) on the ExPasy molecular biology server.

These profiles: FIG. 5, Hydrophilicity, (Hopp T. P., Woods K. R., 1981. Proc. Natl. Acad. Sci. U.S.A. 78:3824-3828); FIG. 6, Hydropathicity, (Kyte J., Doolittle R. F., 1982. J. Mol. Biol. 157:105-132); FIG. 7, Percentage Accessible Residues (Janin J., 1979 Nature 277:491-492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of the 24P4C12 protein. Each of the above amino acid profiles of 24P4C12 were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 24P4C12 protein and of the variant proteins indicated, e.g., by the profiles set forth in FIG. 5, FIG. 6, FIG. 7, FIG. 8, and/or FIG. 9 are used to prepare immunogens, either peptides or nucleic acids that encode them, to generate therapeutic and diagnostic anti-24P4C12 antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 24P4C12 protein variants listed in FIGS. 2 and 3. In particular, peptide immunogens of the invention can comprise, a peptide region of at least 5 amino acids of FIGS. 2 and 3 in any whole number increment that includes an amino acid position having a value greater than 0.5 in the Hydrophilicity profile of FIG. 5; a peptide region of at least 5 amino acids of FIGS. 2 and 3 in any whole number increment that includes an amino acid position having a value less than 0.5 in the Hydropathicity profile of FIG. 6; a peptide region of at least 5 amino acids of FIGS. 2 and 3 in any whole number increment that includes an amino acid position having a value greater than 0.5 in the Percent Accessible Residues profile of FIG. 7; a peptide region of at least 5 amino acids of FIGS. 2 and 3 in any whole number increment that includes an amino acid position having a value greater than 0.5 in the Average Flexibility profile on FIG. 8; and, a peptide region of at least 5 amino acids of FIGS. 2 and 3 in any whole number increment that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 24P4C12 variant 1, namely the predicted presence and location of alpha helices, extended strands, and random coils, are predicted from the respective primary amino acid sequences using the HNN—Hierarchical Neural Network method (Guermeur, 1997, located on the World Wide Web at pbil.ibcp.fr/cgi-bin/npsa_automat.pl?page=npsa_nn.html), accessed from the ExPasy molecular biology server at expasy.ch/tools/). The analysis indicates that 24P4C12 variant 1 is composed of 53.94% alpha helix, 9.44% extended strand, and 36.62% random coil (FIG. 13a). Analysis for the potential presence of transmembrane domains in 24P4C12 variants were carried out using a variety of transmembrane prediction algorithms accessed from the ExPasy molecular biology server (at expasy.ch/tools/). Shown graphically are the results of analysis of variant 1 depicting the presence and location of 10 transmembrane domains using the TMpred program (FIG. 13b) and TMHMM program (FIG. 13c). The results of each program, namely the amino acids encoding the transmembrane domains are summarized in Table L.

Example 10

Generation of 24P4C12 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with the full length 24P4C12 protein, computer algorithms are employed in design of immunogens that, based on amino acid sequence analysis contain characteristics of being antigenic and available for recognition by the immune system of the immunized host (see the Example entitled "Antigenicity Profiles"). Such regions would be predicted to be hydrophilic, flexible, in beta-turn conformations, and be exposed on the surface of the protein (see, e.g., FIG. 5, FIG. 6, FIG. 7, FIG. 8, or FIG. 9 for amino acid profiles that indicate such regions of 24P4C12 and variants).

For example, 24P4C12 recombinant bacterial fusion proteins or peptides containing hydrophilic, flexible, beta-turn regions of 24P4C12 variant proteins are used as antigens to generate polyclonal antibodies in New Zealand White rabbits. For example, such regions include, but are not limited to, amino acids 1-34, amino acids 118-135, amino acids 194-224, amino acids 280-290, and amino acids 690-710, of 24P4C12 variants 1. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 1-14 of 24P4C12 variant 1 was conjugated to KLH and used to immunize a rabbit. This antiserum exhibited a high titer to the peptide (>10,000) and recognized 24P4C12 in transfected 293T cells by Western blot and flow cytometry (FIG. 24) and in stable recombinant PC3 cells by Western blot and immunohistochemistry (FIG. 25). Alternatively the immunizing agent may include all or portions of the 24P4C12 variant proteins, analogs or fusion proteins thereof. For example, the 24P4C12 variant 1 amino acid sequence can be fused using recombinant DNA techniques to any one of a variety of fusion protein partners that are well known in the art, such as glutathione-5-transferase (GST) and HIS tagged fusion proteins. Such fusion proteins are purified from induced bacteria using the appropriate affinity matrix.

In one embodiment, a GST-fusion protein encoding amino acids 379-453, encompassing the third predicted extracellular loop of variant 1, is produced, purified, and used as immunogen. Other recombinant bacterial fusion proteins that may be employed include maltose binding protein, LacZ, thioredoxin, NusA, or an immunoglobulin constant region (see the section entitled "Production of 24P4C12 in Prokaryotic Systems" and Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L. (1991) J. Exp. Med. 174, 561-566).

In addition to bacterial derived fusion proteins, mammalian expressed protein antigens are also used. These antigens are expressed from mammalian expression vectors such as the Tag5 and Fc-fusion vectors (see the Example entitled "Production of Recombinant 24P4C12 in Eukaryotic Systems"), and retains post-translational modifications such as glycosylations found in native protein. In two embodiments, the predicted 1st and third extracellular loops of variant 1, amino acids 59-227 and 379-453 respectively, were each cloned into the Tag5 mammalian secretion vector and expressed in 293T cells (FIG. 26). Each recombinant protein is then purified by metal chelate chromatography from tissue culture supernatants and/or lysates of 293T cells stably expressing the recombinant vector. The purified Tag5 24P4C12 protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 µg, typically 100-200 µg, of fusion protein or peptide conjugated to KLH mixed in complete Freund's adjuvant (CFA). Rabbits are then injected subcutaneously every two weeks with up to 200 µg, typically 100-200 µg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as the rabbit serum derived from immunization with a KLH-conjugated peptide encoding amino acids 1-14 of variant 1, the full-length 24P4C12 variant 1 cDNA is cloned into pcDNA 3.1 myc-his or retroviral expression vectors (Invitrogen, see the Example entitled "Production of Recombinant 24P4C12 in Eukaryotic Systems"). After transfection of the constructs into 293T cells or transduction of PC3 with 24P4C12 retrovirus, cell lysates are probed with the anti-24P4C12 serum and with anti-His antibody (Santa Cruz Biotechnologies, Santa Cruz, Calif.) to determine specific reactivity to denatured 24P4C12 protein using the Western blot technique. As shown in FIGS. 24 and 25 the antiserum specifically recognizes 24P4C12 protein in 293T and PC3 cells. In addition, the immune serum is tested by fluorescence microscopy, flow cytometry, and immunohistochemistry (FIG. 25) and immunoprecipitation against 293T and other recombinant 24P4C12-expressing cells to determine specific recognition of native protein. Western blot, immunoprecipitation, fluorescent microscopy, immunohistochemistry and flow cytometric techniques using cells that endogenously express 24P4C12 are also carried out to test reactivity and specificity.

Anti-serum from rabbits immunized with 24P4C12 variant fusion proteins, such as GST and MBP fusion proteins, are purified by depletion of antibodies reactive to the fusion partner sequence by passage over an affinity column containing the fusion partner either alone or in the context of an irrelevant fusion protein. For example, antiserum derived from a GST-24P4C12 fusion protein encoding amino acids 379-453 of variant 1 is first purified by passage over a column of GST protein covalently coupled to AffiGel matrix (BioRad, Hercules, Calif.). The antiserum is then affinity purified by passage over a column composed of a MBP-fusion protein also encoding amino acids 379-453 covalently coupled to Affigel matrix. The serum is then further purified by protein G affinity chromatography to isolate the IgG fraction. Sera from other His-tagged antigens and peptide immunized rabbits as well as fusion partner depleted sera are affinity purified by passage over a column matrix composed of the original protein immunogen or free peptide.

Example 11

Generation of 24P4C12 Monoclonal Antibodies (mAbs)

In one embodiment, therapeutic mAbs to 24P4C12 variants comprise those that react with epitopes specific for each variant protein or specific to sequences in common between the variants that would disrupt or modulate the biological function of the 24P4C12 variants, for example those that would disrupt the interaction with ligands and substrates or disrupt its biological activity. Immunogens for generation of such mAbs include those designed to encode or contain the entire 24P4C12 protein variant sequence, regions of the 24P4C12 protein variants predicted to be antigenic from computer analysis of the amino acid sequence (see, e.g., FIG. 5, FIG. 6, FIG. 7, FIG. 8, or FIG. 9, and the Example entitled "Antigenicity Profiles"). Immunogens include peptides, recombinant bacterial proteins, and mammalian expressed Tag 5 proteins and human and murine IgG FC fusion proteins. In addition, cells engineered to express high levels of a respective 24P4C12 variant, such as 293T-24P4C12 variant 1 or 300.19-24P4C12 variant 1 murine Pre-B cells, are used to immunize mice.

To generate mAbs to a 24P4C12 variant, mice are first immunized intraperitoneally (IP) with, typically, 10-50 µg of protein immunogen or $10^7$ $^{24}$P4C12-expressing cells mixed in complete Freund's adjuvant. Mice are then subsequently immunized IP every 2-4 weeks with, typically, 10-50 µg of protein immunogen or $10^7$ cells mixed in incomplete Freund's adjuvant. Alternatively, MPL-TDM adjuvant is used in immunizations. In one embodiment, mice were immunized as above with 300.19-24P4C12 cells in complete and then incomplete Freund's adjuvant, and subsequently sacrificed and the spleens harvested and used for fusion and hybridoma generation. As is can be seen in FIG. 27, 2 hybridomas were generated whose antibodies specifically recognize 24P4C12 protein expressed in 293T cells by flow cytometry. In addition to the above protein and cell-based immunization strategies, a DNA-based immunization protocol is employed in which a mammalian expression vector encoding a 24P4C12 variant sequence is used to immunize mice by direct injection of the plasmid DNA. In one embodiment, a Tag5 mammalian secretion vector encoding amino acids 59-227 of the variant 1 sequence (FIG. 26) was used to immunize mice. Subsequent booster immunizations are then carried out with the purified protein. In another example, the same amino acids are cloned into an Fc-fusion secretion vector in which the 24P4C12 variant 1 sequence is fused at the amino-terminus to an IgK leader sequence and at the carboxyl-terminus to the coding sequence of the human or murine IgG Fc region. This recombinant vector is then used as immunogen. The plasmid immunization protocols are used in combination with purified proteins as above and with cells expressing the respective 24P4C12 variant.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, immunohistochemistry, and flow cytometric analyses, fusion and hybridoma generation is then carried out with established procedures well known in the art (see, e.g., Harlow and Lane, 1988).

In one embodiment for generating 24P4C12 variant 8 specific monoclonal antibodies, a peptide encoding amino acids 643-654 (RNPITPTGHVFQ) (SEQ ID NO: 46) of 24P4C12 variant 8 is synthesized, coupled to KLH and used as immunogen. Balb C mice are initially immunized intraperitoneally with 25 µg of the KLH-24P4C12 variant 8 peptide mixed in complete Freund's adjuvant. Mice are subsequently immunized every two weeks with 25 µg of the antigen mixed in incomplete Freund's adjuvant for a total of three immunizations. ELISA using the free peptide determines the reactivity of serum from immunized mice. Reactivity and specificity of serum to full length 24P4C12 variant 8 protein is monitored by Western blotting, immunoprecipitation and flow cytometry using 293T cells transfected with an expression vector encoding the 24P4C12 variant 8 cDNA compared to cells transfected with the other 24P4C12 variants (see e.g., the Example entitled "Production of Recombinant 24P4C12 in Eukaryotic Systems"). Other recombinant 24P4C12 variant 8-expressing cells or cells endogenously expressing 24P4C12 variant 8 are also used. Mice showing the strongest specific reactivity to 24P4C12 variant 8 are rested and given a final injection of antigen in PBS and then sacrificed four days later. The spleens of the sacrificed mice are harvested and fused to SPO/2 myeloma cells using standard procedures (Harlow and Lane, 1988). Supernatants from HAT selected growth wells are screened by ELISA, Western blot, immunoprecipitation, fluorescent microscopy, and flow cytometry to identify 24P4C12 variant 8-specific antibody-producing clones. A similar strategy is also used to derive 24P4C12 variant 9-specific antibodies using a peptide encompassing amino acids 379-388 (PLPTQPATLG) (SEQ ID NO: 47).

The binding affinity of a 24P4C12 monoclonal antibody is determined using standard technologies. Affinity measurements quantify the strength of antibody to epitope binding and are used to help define which 24P4C12 monoclonal antibodies preferred for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor bimolecular interactions in real time. BIAcore analysis conveniently generates association rate constants, dissociation rate constants, equilibrium dissociation constants, and affinity constants.

Example 12

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geq$ [HLA], the measured $IC_{50}$ values are reasonable approximations of the true $K_D$ values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides (see Table IV).

Example 13

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-bearing Epitopes The searches performed to identify the motif-bearing peptide sequences in the Example entitled "Antigenicity Profiles" and Tables VIII-XXI and XXII-XLIX employ the protein sequence data from the gene product of 24P4C12 set forth in FIGS. 2 and 3, the specific search peptides used to generate the tables are listed in Table VII.

Computer searches for epitopes bearing HLA Class I or Class II supermotifs or motifs are performed as follows. All translated 24P4C12 protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or $\Delta G$) of peptide-HLA molecule interactions can be approximated as a linear polynomial function of the type:

$$"\Delta G" = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide.

The method of derivation of specific algorithm coefficients has been described in Gulukota et al., *J. Mol. Biol.* 267:1258-126, 1997; (see also Sidney et al, *Human Immunol.* 45:79-93, 1996; and Southwood et al., *J. Immunol.* 160:3363-3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-reactive Peptides

Protein sequences from 24P4C12 are scanned utilizing motif identification software, to identify 8-, 9- 10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-bearing Epitopes

The 24P4C12 protein sequence(s) scanned above is also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of ≦500 nM, often ≦200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 24P4C12 protein(s) scanned above is also analyzed for the presence of 8-, 9-10-, or 11-mer peptides with the HLA-B7-supermotif. Corresponding peptides are synthesized and tested for binding to HLA -B*0702, the molecule encoded by the most common B7-supertype allele (i.e., the prototype B7 supertype allele). Peptides binding B*0702 with $IC_{50}$ of ≦500 nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-bearing Epitopes

To further increase population coverage, HLA-A1 and -A24 epitopes can also be incorporated into vaccine compositions. An analysis of the 24P4C12 protein can also be performed to identify HLA-A1- and A24-motif-containing sequences.

High affinity and/or cross-reactive binding epitopes that bear other motif and/or supermotifs are identified using analogous methodology.

Example 14

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The 221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 µg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10 \times 10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dynal immunomagnetic beads (Dynabeads® M-450) and the detacha-bead® reagent. Typically about $200\text{-}250 \times 10^6$ PBMC are processed to obtain $24 \times 10^6$ CD8$^+$ T-cells (enough for a 48-well plate culture). Briefly, the PBMCs are thawed in RPMI with 30 µg/ml DNAse, washed once with PBS containing 1% human AB serum and resuspended in PBS/1% AB serum at a concentration of $20 \times 10^6$ cells/ml. The magnetic beads are washed 3 times with PBS/AB serum, added to the cells (140 µl beads/$20 \times 10^6$ cells) and incubated for 1 hour at 4° C. with continuous mixing. The beads and cells are washed 4× with PBS/AB serum to remove the nonadherent cells and resuspended at $100 \times 10^6$ cells/ml (based on the original cell number) in PBS/AB serum containing 100 µl/ml detacha-bead® reagent and 30 µg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 µg/ml of peptide at a cell concentration of $1\text{-}2 \times 10^6$/ml in the presence of 3 µg/ml $\beta_2$-microglobulin for 4 hours at 20° C. The DC are then irradiated (4,200 rads), washed 1 time with medium and counted again.

Setting up induction cultures: 0.25 ml cytokine-generated DC (at $1 \times 10^5$ cells/ml) are co-cultured with 0.25 ml of CD8+ T-cells (at $2 \times 10^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at $5 \times 10^6$ cells/ml and irradiated at ~4200 rads. The PBMCs are plated at $2 \times 10^6$ in 0.5 ml complete medium per well and incubated for 2 hours at 37° C. The plates are washed twice with RPMI by tapping the plate gently to remove the nonadherent cells and the adherent cells pulsed with 10 µg/ml of peptide in the presence of 3 µg/ml $\beta_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2-3 days later at 50 IU/ml (Tsai et al., *Critical Reviews in Immunology* 18(1-2):65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labeled with 200 μCi of $^{51}$Cr sodium chromate (Dupont, Wilmington, Del.) for 1 hour at 37° C. Labeled target cells are resuspended at $10^6$ per ml and diluted 1:10 with K562 cells at a concentration of $3.3\times10^6$/ml (an NK-sensitive erythroblastoma cell line used to reduce non-specific lysis). Target cells (100 μl) and effectors (100 μl) are plated in 96 well round-bottom plates and incubated for 5 hours at 37° C. At that time, 100 μl of supernatant are collected from each well and percent lysis is determined according to the formula:

[(cpm of the test sample–cpm of the spontaneous $^{51}$Cr release sample)/(cpm of the maximal $^{51}$Cr release sample–cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-specific and Endogenous Recognition Immulon 2 plates are coated with mouse anti-human IFNγ monoclonal antibody (4 μg/ml 0.1M NaHCO$_3$, pH8.2) overnight at 4° C. The plates are washed with Ca$^{2+}$, Mg$^{2+}$-free PBS/0.05% Tween 20 and blocked with PBS/10% FCS for two hours, after which the CTLs (100 pt/well) and targets (100 μl/well) are added to each well, leaving empty wells for the standards and blanks (which received media only). The target cells, either peptide-pulsed or endogenous targets, are used at a concentration of 1×10$^6$ cells/ml. The plates are incubated for 48 hours at 37° C. with 5% CO$_2$.

Recombinant human IFN-gamma is added to the standard wells starting at 400 μg or 1200 μg/100 microliter/well and the plate incubated for two hours at 37° C. The plates are washed and 100 μl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5-15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, 5×10$^4$ CD8+ cells are added to a T25 flask containing the following: 1×10$^6$ irradiated (4,200 rad) PBMC (autologous or allogeneic) per ml, 2×10$^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 μM 2-mercapto-ethanol, L-glutamine and penicillin/streptomycin. Recombinant human 112 is added 24 hours later at a final concentration of 200 IU/ml and every three days thereafter with fresh media at 50 IU/ml. The cells are split if the cell concentration exceeds 1×10$^6$/ml and the cultures are assayed between days 13 and 15 at E:T ratios of 30, 10, 3 and 1:1 in the $^{51}$Cr release assay or at 1×10$^6$/ml in the in situ IFNγ assay using the same targets as before the expansion.

Cultures are expanded in the absence of anti-CD3+ as follows. Those cultures that demonstrate specific lytic activity against peptide and endogenous targets are selected and 5×10$^4$ CD8$^+$ cells are added to a T25 flask containing the following: 1×10$^6$ autologous PBMC per ml which have been peptide-pulsed with 10 μg/ml peptide for two hours at 37° C. and irradiated (4,200 rad); 2×10$^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 24P4C12. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology Example 15

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 5000 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., J. Immunol. 157:2539, 1996; and Pogue et al., *Proc. Natl. Acad. Sci. USA* 92:8166,1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 24P4C12-expressing tumors.

Other Analoging Strategies

Another form of peptide analoging, unrelated to anchor positions, involves the substitution of a cysteine with $\alpha$-amino butyric acid. Due to its chemical nature, cysteine has the propensity to form disulfide bridges and sufficiently alter the peptide structurally so as to reduce binding capacity. Substitution of $\alpha$-amino butyric acid for cysteine not only alleviates this problem, but has been shown to improve binding and crossbinding capabilities in some instances (see, e.g., the review by Sette et al., In: Persistent Viral Infections, Eds. R. Ahmed and 1. Chen, John Wiley & Sons, England, 1999).

Thus, by the use of single amino acid substitutions, the binding properties and/or cross-reactivity of peptide ligands for HLA supertype molecules can be modulated.

Example 16

Identification and Confirmation of 24P4C12-Derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 24P4C12-derived, HLA class II HTL epitopes, a 24P4C12 antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160:3363-3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 24P4C12-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 $\beta 1$, DR2w2 $\beta 2$, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 24P4C12-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 24P4C12 antigens are analyzed for sequences carrying one of the two DR3-specific binding motifs reported by Geluk et al. (J. Immunol. 152:5742-5748, 1994). The corresponding peptides are then synthesized and confirmed as having the ability to bind DR3 with an affinity of 1 µM or better, i.e., less than 1 µM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 17

Immunogenicity of 24P4C12-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 24P4C12-expressing tumors.

Example 18

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1-(SQRT(1-af) (see, e.g., Sidney et al., Human Immunol. 45:79-93, 1996). To obtain overall phenotypic frequencies, cumulative gene frequencies are calculated, and the cumulative antigen frequencies derived by the use of the inverse formula [af=1-(1-Cgf)$^2$].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1−A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%, see, e.g., Table IV (G). An analogous approach can be used to estimate population coverage achieved with combinations of class II motif-bearing epitopes.

Immunogenicity studies in humans (e.g., Bertoni et al., J. Clin. Invest. 100:503, 1997; Doolan et al., Immunity 7:97, 1997; and Threlkeld et al., J. Immunol. 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 19

CTL Recognition of Endogenously Processed Antigens After Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with 24P4C12 expression vectors.

The results demonstrate that CTL lines obtained from animals primed with peptide epitope recognize endogenously synthesized 24P4C12 antigen. The choice of transgenic mouse model to be used for such an analysis depends upon the epitope(s) that are being evaluated. In addition to HLA-A*0201/K$^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 20

Activity of CTL-HTL Conjugated Epitopes in Transgenic Mice

This example illustrates the induction of CTLs and HTLs in transgenic mice, by use of a 24P4C12-derived CTL and HTL peptide vaccine compositions. The vaccine composition used herein comprise peptides to be administered to a patient with a 24P4C12-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures: Immunization of transgenic mice is performed as described (Alexander et al., *J. Immunol.* 159:4753-4761, 1997). For example, A2/K$^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/K$^b$ chimeric gene (e.g., Vitiello et al., *J. Exp. Med.* 173:1007, 1991)

In vitro CTL activation: One week after priming, spleen cells (30×10$^6$ cells/flask) are co-cultured at 37° C. with syngeneic, irradiated (3000 rads), peptide coated lymphoblasts (10×10$^6$ cells/flask) in 10 ml of culture medium/T25 flask. After six days, effector cells are harvested and assayed for cytotoxic activity.

Assay for cytotoxic activity: Target cells (1.0 to 1.5×10$^6$) are incubated at 37° C. in the presence of 200 μl of $^{51}$Cr. After 60 minutes, cells are washed three times and resuspended in R10 medium. Peptide is added where required at a concentration of 1 μg/ml. For the assay, 10$^4$ $^{51}$Cr-labeled target cells are added to different concentrations of effector cells (final volume of 200 μl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/10$^6$ cells. One lytic unit is arbitrarily defined as the number of effector cells required to achieve 30% lysis of 10,000 target cells in a six hour $^{51}$Cr release assay. To obtain specific lytic units/10$^6$, the lytic units/10$^6$ obtained in the absence of peptide is subtracted from the lytic units/10$^6$ obtained in the presence of peptide. For example, if 30% $^{51}$Cr release is obtained at the effector (E): target (T) ratio of 50:1 (i.e., 5×10$^5$ effector cells for 10,000 targets) in the absence of peptide and 5:1 (i.e., 5×10$^4$ effector cells for 10,000 targets) in the presence of peptide, the specific lytic units would be: [(1/50,000)−(1/500,000)]×10$^6$=18 LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity." Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 21

Selection of CTL and HTL Epitopes for Inclusion in a 24P4C12-Specific Vaccine

This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 24P4C12 clearance. The number of epitopes used depends on observations of patients who spontaneously clear 24P4C12. For example, if it has been observed that patients who spontaneously clear 24P4C12-expressing cells generate an immune response to at least three (3) epitopes from 24P4C12 antigen, then at least three epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site, at URL bimas.dcrt.nih.gov/.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 24P4C12, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 24P4C12.

Example 22

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 24P4C12, are selected such that multiple supermotifs/motifs are represented to ensure broad population coverage. Similarly, HLA class II epitopes are selected from 24P4C12 to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (50 below the lowest calculated Tm of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 23

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751-761, 1994.

For example, to confirm the capacity of a DNA minigene construct containing at least one HLA-A2 supermotif peptide to induce CTLs in vivo, HLA-A2.1/$K^b$ transgenic mice, for example, are immunized intramuscularly with 100 μg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}Cr$ release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-$A^b$-restricted mice, for example, are immunized intramuscularly with 100 μg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3H$-thymidine incorporation proliferation assay, (see, e.g., Alexander et al. Immunity 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299-S309, 1998) or recombinant vaccinia, for example, expressing a minigene or DNA encoding the complete protein of interest (see, e.g., Hanke et al., *Vaccine* 16:439-445,1998; Sedegah et al., *Proc. Natl. Acad. Sci USA* 95:7648-53,1998; Hanke and McMichael, *Immunol. Letters* 66:177-181, 1999; and Robinson et al., *Nature Med.* 5:526-34,1999).

For example, the efficacy of the DNA minigene used in a prime boost protocol is initially evaluated in transgenic mice. In this example, A2.1/$K^b$ transgenic mice are immunized IM with 100 μg of a DNA minigene encoding the immunogenic peptides including at least one HLA-A2 supermotif-bearing peptide. After an incubation period (ranging from 3-9 weeks), the mice are boosted IP with $10^7$ pfu/mouse of a recombinant vaccinia virus expressing the same sequence encoded by the DNA minigene. Control mice are immunized with 100 μg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 24

Peptide Compositions for Prophylactic Uses

Vaccine compositions of the present invention can be used to prevent 24P4C12 expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 24P4C12-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 μg, generally 100-5,000 μg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 24P4C12-associated disease.

Alternatively, a composition typically comprising transfecting agents is used for the administration of a nucleic acid-based vaccine in accordance with methodologies known in the art and disclosed herein.

Example 25

Polyepitopic Vaccine Compositions Derived from Native 24P4C12 Sequences

A native 24P4C12 polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 24P4C12 antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally, such an embodiment provides for the possibility of motif-bearing epitopes for an HLA makeup(s) that is presently unknown. Furthermore, this embodiment (excluding an analoged embodiment) directs the immune response to multiple peptide sequences that are actually present in native 24P4C12, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 26

Polyepitopic Vaccine Compositions from Multiple Antigens

The 24P4C12 peptide epitopes of the present invention are used in conjunction with epitopes from other target tumor-associated antigens, to create a vaccine composition that is useful for the prevention or treatment of cancer that expresses 24P4C12 and such other antigens. For example, a vaccine composition can be provided as a single polypeptide that incorporates multiple epitopes from 24P4C12 as well as tumor-associated antigens that are often expressed with a target cancer associated with 24P4C12 expression, or can be administered as a composition comprising a cocktail of one or more discrete epitopes. Alternatively, the vaccine can be administered as a minigene construct or as dendritic cells which have been loaded with the peptide epitopes in vitro.

Example 27

Use of Peptides to Evaluate an Immune Response

Peptides of the invention may be used to analyze an immune response for the presence of specific antibodies, CTL or HTL directed to 24P4C12. Such an analysis can be performed in a manner described by Ogg et al., *Science* 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 24P4C12 HLA-A*0201-specific CTL frequencies from HLA A*0201-positive individuals at different stages of disease or following immunization comprising a 24P4C12 peptide containing an A*0201 motif. Tetrameric complexes are synthesized as described (Musey et al., *N. Engl. J. Med.* 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tri-color analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 24P4C12 epitope, and thus the status of exposure to 24P4C12, or exposure to a vaccine that elicits a protective or therapeutic response.

Example 28

Use of Peptide Epitopes to Evaluate Recall Responses

The peptide epitopes of the invention are used as reagents to evaluate T cell responses, such as acute or recall responses, in patients. Such an analysis may be performed on patients who have recovered from 24P4C12-associated disease or who have been vaccinated with a 24P4C12 vaccine.

For example, the class I restricted CTL response of persons who have been vaccinated may be analyzed. The vaccine may be any 24P4C12 vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI) and plated using microculture formats. A synthetic peptide comprising an epitope of the invention is added at 10 µg/ml to each well and HBV core 128-140 epitope is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 µl of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}Cr$ release, based on comparison with non-diseased control subjects as previously described (Rehermann, et al., *Nature Med.* 2:1104,1108, 1996; Rehermann et al., *J. Clin. Invest.* 97:1655-1665, 1996; and Rehermann et al. *J. Clin. Invest* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670-2678,1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 µM, and labeled with 100 µCi of $^{51}Cr$ (Amersham Corp., Arlington Heights, Ill.) for 1 hour after which they are washed four times with HBSS.

Cytolytic activity is determined in a standard 4-h, split well $^{51}Cr$ release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release−spontaneous release)/maximum release−spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 24P4C12 or a 24P4C12 vaccine.

Similarly, Class II restricted HTL responses may also be analyzed. Purified PBMC are cultured in a 96-well flat bottom plate at a density of $1.5 \times 10^5$ cells/well and are stimulated with 10 g/ml synthetic peptide of the invention, whole 24P4C12 antigen, or PHA. Cells are routinely plated in replicates of 4-6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of 3H-thymidine incorporation in the presence of antigen divided by the $^3$H-thymidine incorporation in the absence of antigen.

Example 29

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 30

Phase II Trials in Patients Expressing 24P4C12

Phase II trials are performed to study the effect of administering the CTL-HTL peptide compositions to patients having cancer that expresses 24P4C12. The main objectives of the trial are to determine an effective dose and regimen for inducing CTLs in cancer patients that express 24P4C12, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them have a tumor that expresses 24P4C12.

Clinical manifestations or antigen-specific T-cell responses are monitored to assess the effects of administering the peptide compositions. The vaccine composition is found to be both safe and efficacious in the treatment of 24P4C12-associated disease.

Example 31

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of "Minigene" Multi-Epitope DNA Plasmids" in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowlpox virus administered at a dose of $5\text{-}10^7$ to $5\times10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 24P4C12 is generated.

Example 32

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 24P4C12 protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., *Nature Med.* 4:328, 1998; *Nature Med.* 2:52, 1996 and *Prostate* 32:272, 1997). Although $2\text{-}50\times10^6$ DC per patient are typically administered, larger number of DC, such as $10^7$ or $10^8$ can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5\times10^6$ DC, then the patient will be injected with a total of $2.5\times10^8$ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to 24P4C12 antigens can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 33

An Alternative Method of Identifying and Confirming Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 24P4C12. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., *J. Immunol.* 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 24P4C12 to isolate peptides corresponding to 24P4C12 that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 34

Complementary Polynucleotides

Sequences complementary to the 24P4C12-encoding sequences, or any parts thereof, are used to detect, decrease, or inhibit expression of naturally occurring 24P4C12. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 24P4C12. To inhibit transcription, a complementary oligonucleotide is designed from the most unique 5' sequence and used to prevent promoter binding to the coding sequence. To inhibit translation, a complementary oligonucleotide is designed to prevent ribosomal binding to a 24P4C12-encoding transcript.

Example 35

Purification of Naturally-occurring or Recombinant 24P4C12 Using 24P4C12-Specific Antibodies Naturally occurring or recombinant 24P4C12 is substantially purified by immunoaffinity chromatography using antibodies specific for 24P4C12. An immunoaffinity column is constructed by covalently coupling anti-24P4C12 antibody to an activated chromatographic resin, such as CNBr-activated SEPHAROSE (Amersham Pharmacia Biotech). After the coupling, the resin is blocked and washed according to the manufacturer's instructions.

Media containing 24P4C12 are passed over the immunoaffinity column, and the column is washed under conditions that allow the preferential absorbance of 24P4C12 (e.g., high ionic strength buffers in the presence of detergent). The column is eluted under conditions that disrupt antibody/24P4C12 binding (e.g., a buffer of pH 2 to pH 3, or a high concentration of a chaotrope, such as urea or thiocyanate ion), and GCR.P is collected.

Example 36

Identification of Molecules which Interact with 24P4C12

24P4C12, or biologically active fragments thereof, are labeled with 1211 Bolton-Hunter reagent. (See, e.g., Bolton et al. (1973) Biochem. J. 133:529.) Candidate molecules previously arrayed in the wells of a multi-well plate are incubated with the labeled 24P4C12, washed, and any wells with labeled 24P4C12 complex are assayed. Data obtained using different concentrations of 24P4C12 are used to calculate values for the number, affinity, and association of 24P4C12 with the candidate molecules.

Example 37

In Vivo Assay for 24P4C12 Tumor Growth Promotion

The effect of the 24P4C12 protein on tumor cell growth is evaluated in vivo by evaluating tumor development and growth of cells expressing or lacking 24P4C12. For example, SCID mice are injected subcutaneously on each flank with $1 \times 10^6$ of either 3T3, prostate, colon, ovary, lung, or bladder cancer cell lines (e.g. PC3, Caco, PA-1, CaLu or J82 cells) containing tkNeo empty vector or 24P4C12. At least two strategies may be used: (1) Constitutive 24P4C12 expression under regulation of a promoter, such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tetracycline, etc., provided such promoters are compatible with the host cell systems. Tumor volume is then monitored by caliper measurement at the appearance of palpable tumors and followed over time to determine if 24P4C12-expressing cells grow at a faster rate and whether tumors produced by 24P4C12-expressing cells demonstrate characteristics of altered aggressiveness (e.g. enhanced metastasis, vascularization, reduced responsiveness to chemotherapeutic drugs). As shown in FIG. 31 and FIG. 32, 24P4C12 has a profound effect on tumor growth in SCID mice. The prostate cancer cells PC3 and PC3-24P4C12 were injected subcutaneously in the right flank of SCID mice. Tumor growth was evaluated by caliper measurements. An increase in tumor growth was observed in PC3-24P4C12 tumors within 47 days of injection (FIG. 31). In addition, subcutaneous injection of 3T3-24P4C12 induced tumor formation in SCID mice (FIG. 32). This finding is significant as control 3T3 cells fail to form tumors, indicating that 24P4C12 has several tumor enhancing capabilities, including transformation, as well as tumor initiation and promotion.

Example 38

24P4C12 Monoclonal Antibody-Mediated Inhibition of Prostate Tumors In Vivo

The significant expression of 24P4C12 in cancer tissues, together with its restrictive expression in normal tissues and cell surface localization, make 24P4C12 a good target for antibody therapy. Similarly, 24P4C12 is a target for T cell-based immunotherapy. Thus, the therapeutic efficacy of anti-24P4C12 mAbs in human prostate cancer xenograft mouse models is evaluated by using recombinant cell lines such as PC3-24P4C12, and 3T3-24P4C12 (see, e.g., Kaighn, M., Invest Urol, 1979. 17(1): p. 16-23), as well as human prostate xenograft models such as LAPC9 (Saffran et al, Proc Natl Acad Sci USA. 2001, 98:2658). Similarly, anti-24P4C12 mAbs are evaluated in xenograft models of human bladder cancer colon cancer, ovarian cancer or lung cancer using recombinant cell lines such as J82-24P4C12, Caco-24P4C12, PA-24P4C1 or CaLu-24P4C12, respectively.

Antibody efficacy on tumor growth and metastasis formation is studied, e.g., in a mouse orthotopic bladder cancer xenograft model, and a mouse prostate cancer xenograft model. The antibodies can be unconjugated, as discussed in this Example, or can be conjugated to a therapeutic modality, as appreciated in the art. Anti-24P4C12 mAbs inhibit formation of prostate and bladder xenografts. Anti-24P4C12 mAbs also retard the growth of established orthotopic tumors and prolonged survival of tumor-bearing mice. These results indicate the utility of anti-24P4C12 mAbs in the treatment of local and advanced stages of prostate, colon, ovarian, lung and bladder cancer. (See, e.g., Saffran, D., et al., PNAS 10:1073-1078 located on the World Wide Web at pnas.org/cgi/doi/10.1073/pnas.051624698).

Administration of the anti-24P4C12 mAbs led to retardation of established orthotopic tumor growth and inhibition of metastasis to distant sites, resulting in a significant prolongation in the survival of tumor-bearing mice. These studies indicate that 24P4C12 as an attractive target for immunotherapy and demonstrate the therapeutic potential of anti-24P4C12 mAbs for the treatment of local and metastatic cancer. This example demonstrates that unconjugated 24P4C12 monoclonal antibodies are effective to inhibit the growth of human prostate, colon, ovarian, lung and bladder cancer tumor xenografts grown in SCID mice; accordingly a combination of such efficacious monoclonal antibodies is also effective.

Tumor Inhibition Using Multiple Unconjugated 24P4C12 mAbs

Materials and Methods

24P4C12 Monoclonal Antibodies:

Monoclonal antibodies are raised against 24P4C12 as described in the Example entitled "Generation of 24P4C12 Monoclonal Antibodies (mAbs)." The antibodies are characterized by ELISA, Western blot, FACS, and immunoprecipitation for their capacity to bind 24P4C12. Epitope mapping data for the anti-24P4C12 mAbs, as determined by ELISA and Western analysis, recognize epitopes on the 24P4C12 protein. Immunohistochemical analysis of prostate cancer tissues and cells with these antibodies is performed.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of SCABER, J82, A498, 769P, CaOv1 or PA1 tumor xenografts.

Cell Lines

The prostate, colon, ovarian, lung and bladder cancer carcinoma cell lines, Caco, PA-1, CaLu or J82 cells as well as the fibroblast line NIH 3T3 (American Type Culture Collection) are maintained in media supplemented with L-glutamine and 10% FBS.

PC3-24P4C12, Caco-24P4C12, PA-24P4C12, CaLu-24P4C12 or J82-24P4C12 cells and 3T3-24P4C12 cell populations are generated by retroviral gene transfer as described in Hubert, R., Proc Natl Acad Sci USA, 1999. 96(25): 14523.

Xenograft Mouse Models.

Subcutaneous (s.c.) tumors are generated by injection of $1 \times 10^6$ cancer cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. Tumor sizes are determined by caliper measurements, and the tumor volume is calculated as: Length×Width×Height. Mice with s.c. tumors greater than 1.5 cm in diameter are sacrificed.

Orthotopic injections are performed under anesthesia by using ketamine/xylazine. For bladder orthotopic studies, an incision is made through the abdomen to expose the bladder, and tumor cells ($5 \times 10^5$) mixed with Matrigel are injected into the bladder wall in a 10-µl volume. To monitor tumor growth, mice are palpated and blood is collected on a weekly basis to measure BTA levels. For prostate orthopotic models, an incision is made through the abdominal muscles to expose the bladder and seminal vesicles, which then are delivered through the incision to expose the dorsal prostate. Tumor cells e.g. LAPC-9 cells ($5 \times 10^5$) mixed with Matrigel are injected into the prostate in a 10-µl volume (Yoshida Y et al, Anticancer Res. 1998, 18:327; Ahn et al, Tumour Biol. 2001, 22:146). To monitor tumor growth, blood is collected on a weekly basis measuring PSA levels. Similar procedures are followed for lung and ovarian xenograft models. The mice are segregated into groups for the appropriate treatments, with anti-24P4C12 or control mAbs being injected i.p.

Anti-24P4C12 mAbs Inhibit Growth of 24P4C12-Expressing Xenograft-Cancer Tumors

The effect of anti-24P4C12 mAbs on tumor formation is tested on the growth and progression of bladder, and prostate cancer xenografts using PC3-24P4C12, Caco-24P4C12, PA-24P4C12, CaLu-24P4C12 or J82-24P4C12 orthotopic models. As compared with the s.c. tumor model, the orthotopic model, which requires injection of tumor cells directly in the mouse prostate, colon, ovary, lung and bladder, respectively, results in a local tumor growth, development of metastasis in distal sites, deterioration of mouse health, and subsequent death (Saffran, D., et al., PNAS supra; Fu, X., et al., Int J Cancer, 1992. 52(6): p. 987-90; Kubota, T., J Cell Biochem, 1994. 56(1): p. 4-8). The features make the orthotopic model more representative of human disease progression and allowed us to follow the therapeutic effect of mAbs on clinically relevant end points.

Accordingly, tumor cells are injected into the mouse organs, and 2 days later, the mice are segregated into two groups and treated with either: a) 200-500 µg, of anti-24P4C12 Ab, or b) PBS three times per week for two to five weeks.

A major advantage of the orthotopic cancer models is the ability to study the development of metastases. Formation of metastasis in mice bearing established orthotopic tumors is studies by IHC analysis on lung sections using an antibody against a tumor-specific cell-surface protein such as anti-CK20 for bladder cancer, anti-STEAP-1 for prostate cancer models (Lin S et al, Cancer Detect Prev. 2001;25:202; Saffran, D., et al., PNAS supra).

Mice bearing established orthotopic tumors are administered 1000 µg injections of either anti-24P4C12 mAb or PBS over a 4-week period. Mice in both groups are allowed to establish a high tumor burden, to ensure a high frequency of metastasis formation in mouse lungs. Mice then are killed and their bladders, livers, bone and lungs are analyzed for the presence of tumor cells by IHC analysis.

These studies demonstrate a broad anti-tumor efficacy of anti-24P4C12 antibodies on initiation and progression of prostate and kidney cancer in xenograft mouse models. Anti-24P4C12 antibodies inhibit tumor formation of tumors as well as retarding the growth of already established tumors and prolong the survival of treated mice. Moreover, anti-24P4C12 mAbs demonstrate a dramatic inhibitory effect on the spread of local bladder and prostate tumor to distal sites, even in the presence of a large tumor burden. Thus, anti-24P4C12 mAbs are efficacious on major clinically relevant end points (tumor growth), prolongation of survival, and health.

Example 39

Therapeutic and Diagnostic Use of Anti-24P4C12 Antibodies in Humans

Anti-24P4C12 monoclonal antibodies are safely and effectively used for diagnostic, prophylactic, prognostic and/or therapeutic purposes in humans. Western blot and immunohistochemical analysis of cancer tissues and cancer xenografts with anti-24P4C12 mAb show strong extensive staining in carcinoma but significantly lower or undetectable levels in normal tissues. Detection of 24P4C12 in carcinoma and in metastatic disease demonstrates the usefulness of the mAb as a diagnostic and/or prognostic indicator. Anti-24P4C12 antibodies are therefore used in diagnostic applications such as immunohistochemistry of kidney biopsy specimens to detect cancer from suspect patients.

As determined by flow cytometry, anti-24P4C12 mAb specifically binds to carcinoma cells. Thus, anti-24P4C12 antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of 24P4C12. Shedding or release of an extracellular domain of 24P4C12 into the extracellular milieu, such as that seen for alkaline phosphodiesterase B10 (Meerson, N. R., Hepatology 27:563-568 (1998)), allows diagnostic detection of 24P4C12 by anti-24P4C12 antibodies in serum and/or urine samples from suspect patients.

Anti-24P4C12 antibodies that specifically bind 24P4C12 are used in therapeutic applications for the treatment of cancers that express 24P4C12. Anti-24P4C12 antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-24P4C12 antibodies are tested for efficacy of tumor prevention and growth inhibition in the SCID mouse cancer xenograft models, e.g., kidney cancer models AGS-K3 and AGS-K6, (see, e.g., the Example entitled "24P4C12 Monoclonal Antibody-mediated Inhibition of Bladder and Lung Tumors In Vivo"). Either conjugated and unconjugated anti-24P4C12 antibodies are used as a therapeutic modality in human clinical trials either alone or in combination with other treatments as described in following Examples.

Example 40

Human Clinical Trials for the Treatment and Diagnosis of Human Carcinomas through Use of Human Anti-24P4C12 Antibodies In Vivo Antibodies are used in accordance with the present invention which recognize an epitope on 24P4C12, and are used in the treatment of certain tumors such as those listed in Table I. Based upon a number of factors, including 24P4C12 expression levels, tumors such as those listed in Table I are presently preferred indications. In connection with each of these indications, three clinical approaches are successfully pursued.

I.) Adjunctive therapy: In adjunctive therapy, patients are treated with anti-24P4C12 antibodies in combination with a chemotherapeutic or antineoplastic agent and/or radiation therapy. Primary cancer targets, such as those listed in Table I, are treated under standard protocols by the addition anti-24P4C12 antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-24P4C12 antibodies are utilized in several adjunctive clinical trials in combination with the chemotherapeutic or antineoplastic agents adriamycin (advanced prostate carcinoma), cisplatin (advanced head and neck and lung carcinomas), taxol (breast cancer), and doxorubicin (preclinical).

II.) Monotherapy: In connection with the use of the anti-24P4C12 antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-24P4C12 antibodies, the radiolabeled antibodies are utilized as a diagnostic and/or imaging agent. In such a role, the labeled antibodies localize to both solid tumors, as well as, metastatic lesions of cells expressing 24P4C12. In connection with the use of the anti-24P4C12 antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-24P4C12 antibody is used as an imaging agent in a Phase I human clinical trial in patients having a carcinoma that expresses 24P4C12 (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified Dose and Route of Administration As appreciated by those of ordinary skill in the art, dosing considerations can be determined through comparison with the analogous products that are in the clinic. Thus, anti-24P4C12 antibodies can be administered with doses in the range of 5 to 400 mg/m$^2$, with the lower doses used, e.g., in connection with safety studies. The affinity of anti-24P4C12 antibodies relative to the affinity of a known antibody for its target is one parameter used by those of skill in the art for determining analogous dose regimens. Further, anti-24P4C12 antibodies that are fully human antibodies, as compared to the chimeric antibody, have slower clearance; accordingly, dosing in patients with such fully human anti-24P4C12 antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-24P4C12 antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-24P4C12 antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-24P4C12 antibodies. As will be appreciated, one criteria that can be utilized in connection with enrollment of patients is 24P4C12 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 24P4C12. Standard tests and follow-up are utilized to monitor each of these safety concerns. Anti-24P4C12 antibodies are found to be safe upon human administration.

Example 41

Human Clinical Trial Adjunctive Therapy with Human Anti-24P4C12 Antibody and Chemotherapeutic Agent A phase I human clinical trial is initiated to assess the safety of six intravenous doses of a human anti-24P4C12 antibody in connection with the treatment of a solid tumor, e.g., a cancer of a tissue listed in Table I. In the study, the safety of single doses of anti-24P4C12 antibodies when utilized as an adjunctive therapy to an antineoplastic or chemotherapeutic agent as defined herein, such as, without limitation: cisplatin, topotecan, doxorubicin, adriamycin, taxol, or the like, is assessed. The trial design includes delivery of six single doses of an anti-24P4C12 antibody with dosage of antibody escalating from approximately about 25 mg/m$^2$ to about 275 mg/m$^2$ over the course of the treatment in accordance with the following schedule:

|  | Day 0 | Day 7 | Day 14 | Day 21 | Day 28 | Day 35 |
| --- | --- | --- | --- | --- | --- | --- |
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express 24P4C12. Standard tests and follow-up are utilized to monitor each of these safety concerns. Patients are also assessed for clinical outcome, and particularly reduction in tumor mass as evidenced by MRI or other imaging.

The anti-24P4C12 antibodies are demonstrated to be safe and efficacious, Phase II trials confirm the efficacy and refine optimum dosing.

Example 42

Human Clinical Trial: Monotherapy with Human Anti-24P4C12 Antibody

Anti-24P4C12 antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-24P4C12 antibodies.

Example 43

Human Clinical Trial: Diagnostic Imaging with Anti-24P4C12 Antibody

Once again, as the adjunctive therapy discussed above is safe within the safety criteria discussed above, a human clinical trial is conducted concerning the use of anti-24P4C12 antibodies as a diagnostic imaging agent. The protocol is designed in a substantially similar manner to those described in the art, such as in Divgi et al. *J. Natl. Cancer Inst* 83:97-104 (1991). The antibodies are found to be both safe and efficacious when used as a diagnostic modality.

Example 44

Homology Comparison of 24P4C12 to Known Sequences

The 24P4C12 protein of FIG. 3 has 710 amino acids with calculated molecular weight of 79.3 kDa, and pI of 8.9. Several variants of 24P4C12 have been identified, including 4 SNPs (namely v.1, v.3, v.5, v.6) and 3 splice variants (namely v.7, v.8 and v.9) (FIGS. 10 and 11). 24P4C12 variants v.3, v.5, and v.6 differ from 24P4C12 v.1 by 1 amino acid each, at aa positions 187, 326 and 436, respectively. Variant v.7 carries a deletion of 111 aa long starting at aa 237, while variant v.8 and v.9 contain insertions at aa 642 and 378, respectively. The 24P4C12 protein exhibits homology to a previously cloned human gene, namely NG22 also known as chorine transporter-like protein 4 (gi 14249468). It shows 99% identity and 99% homology to the CTL4 protein over the length of that protein (FIG. 4). 24P4C12 is a multi-transmembrane protein, predicted to carry 10, 11 or 13 transmembrane domains. Bioinformatic analysis indicates that the 24P4C12 protein localizes to the plasma membrane with some endoplasmic reticulum localization (see Table L). Recent evidence indicates that the 24P4C12 protein is a 10 transmembrane protein that localizes to the cell surface (O'Regan S et al PNAS 2000, 97:1835).

Choline as an essential component of cell membranes that plays an important role in cell integrity, growth and survival of normal and tumor cells. Choline accumulates at increased concentration in tumor cells relative to their normal counterparts and as such constitutes a tool for the detection of cancer cells by magnetic resonance imaging (Kurhanewicz J et al, J Magn Reson Imaging. 2002.). In addition to its role in maintaining membrane integrity, choline mediates signal transduction event from the membrane to the nucleus (Spiegel S, Milstien S. J Membr Biol. 1995, 146:225). Choline metabolites include sphingosylphosphorylcholine and lysophosphatidylcholine, both of which activate G-protein coupled receptors (Xu F et al Biochim Biophys Acta 2002, 1582:81). In addition, choline results in the activation of kinase pathways including Raf-1 (Lee M, Han S S, Cell Signal 2002, 14:373.). Choline also plays a role in regulating DNA methylation and regulation of gene expression. For example, choline methabolites regulate the expression of cytokines and chemokines essential for tumor growth (Schwartz B M et al, Gynecol Oncol. 2001, 81:291; Denda A et al, Carcinogenesis. 2002, 23:245). Due to its effect on cell signaling and gene expression, choline controls cell growth and survival (Holmes-McNary M Q et al, J Biol. Chem. 2001, 276:41197; Albright et al, FASEB 1996,10:510). Choline deficiency results in cell death, apoptosis and transformation, while accumulation of choline is associated with tumor growth (Zeisel S et al, Carcinogenesis 1997, 18:731). Accordingly, when 24P4C12 functions as a regulator of tumor formation, cell proliferation, invasion or cell signaling, 24P4C12 is used for therapeutic, diagnostic, prognostic and/or preventative purposes.

Example 45

Identification and Confirmation of Potential Signal Transduction Pathways

Many mammalian proteins have been reported to interact with signaling molecules and to participate in regulating signaling pathways. (J Neurochem. 2001; 76:217-223). In particular, choline have been reported to activate MAK cascades as well as G proteins, and been associated with the DAG and ceramide and sphingophosphorylcholine signaling pathway (Cummings et al, above). In addition, choline transmit its signals by regulating choline-kinase and phospholipase activity, resulting in enhance tumorigenic effect (Ramirez et al, Oncogene. 2002, 21:4317; Lucas et al, Oncogene. 2001, 20:1110; Chung T et al, Cell Signal. 2000,12:279).

Using immunoprecipitation and Western blotting techniques, proteins are identified that associate with 24P4C12 and mediate signaling events. Several pathways known to play a role in cancer biology can be regulated by 24P4C12, including phospholipid pathways such as P13K, AKT, etc, adhesion and migration pathways, including FAK, Rho, Rac-1, etc, as well as mitogenic/survival cascades such as ERK, p38, etc (Cell Growth Differ. 2000, 11:279; J Biol. Chem. 1999, 274:801; Oncogene. 2000, 19:3003; J. Cell Biol. 1997, 138:913). Using Western blotting and other techniques, the ability of 24P4C12 to regulate these pathways is confirmed. Cells expressing or lacking 24P4C12 are either left untreated or stimulated with cytokines, androgen and anti-integrin antibodies. Cell lysates are analyzed using anti-phospho-specific antibodies (Cell Signaling, Santa Cruz Biotechnology) in order to detect phosphorylation and regulation of ERK, p38, AKT, P13K, PLC and other signaling molecules.

To confirm that 24P4C12 directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress
7. TCF-luc, TCF/Lef; □-catenin, Adhesion/invasion Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by 24P4C12 are mapped and used for the identification and validation of therapeutic targets. When 24P4C12 is involved in cell signaling, it is used as target for diagnostic, prognostic, preventative and/or therapeutic purposes.

Example 46

24P4C12 Functions as a Choline transporter

Sequence and homology analysis of 24P4C12 indicate that 24P4C12 carries a transport domain and that 24P4C12 functions as a choline transporter. In order to confirm that 24P4C12 transports choline, primary and tumor cells, including prostate, colon, bladder and lung lines, are grown in the presence and absence of $^3$H-choline. Radioactive choline uptake is measured by counting incorporated counts per minutes (cpm). Parental 24P4C12 negative cells are compared to 24P4C12-expressing cells using this and similar assays. Similarly, parental and 24P4C12-expressing cells can be compared for choline content using NMR spectroscopy. These assay systems can be used to identify small molecules and antibodies that interfere with choline uptake and/or with the function of 24P4C12.

Thus, compounds and small molecules designed to inhibit 24P4C12 function and downstream signaling events are used for therapeutic diagnostic, prognostic and/or preventative purposes.

Example 47

Regulation of Transcription

The cell surface localization of 24P4C12 and its ability to regulate DNA methylation indicate that it is effectively used as a modulator of the transcriptional regulation of eukaryotic genes. Regulation of gene expression is confirmed, e.g., by studying gene expression in cells expressing or lacking 24P4C12. For this purpose, two types of experiments are performed.

In the first set of experiments, RNA from parental and 24P4C12-expressing cells are extracted and hybridized to commercially available gene arrays (Clontech) (Smid-Koopman E et al. Br J Cancer. 2000. 83:246). Resting cells as well as cells treated with FBS, pheromones, or growth factors are compared. Differentially expressed genes are identified in accordance with procedures known in the art. The differentially expressed genes are then mapped to biological pathways (Chen K et al. Thyroid. 2001. 11:41.).

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation.

Thus, 24P4C12 plays a role in gene regulation, and it is used as a target for diagnostic, prognostic, preventative and/or therapeutic purposes.

Example 48

Involvement in Tumor Progression

The 24P4C12 gene can contribute to the growth of cancer cells. The role of 24P4C12 in tumor growth is confirmed in a variety of primary and transfected cell lines including prostate, and bladder cell lines, as well as NIH 3T3 cells engineered to stably express 24P4C12. Parental cells lacking 24P4C12 and cells expressing 24P4C12 are evaluated for cell growth using a well-documented proliferation assay (Fraser S P, et al., Prostate 2000;44:61, Johnson D E, Ochieng J, Evans S L. Anticancer Drugs. 1996, 7:288). Such a study was performed on prostate cancer cells and the results are shown in FIG. 28. The growth of parental PC3 and PC3-24P4C12 cells was compared in low (0.1%) and 10% FBS. Expression of 24P4C12 imparted a growth advantage to PC3 cells grown in 10% FBS. Similarly, expression of 24P4C12 in NIH-3T3 cells enhances the proliferation of these cells relative to control 3T3-neo cells. The effect of 24P4C12 can also be observed on cell cycle progression. Control and 24P4C12-expressing cells are grown in low serum overnight, and treated with 10% FBS for 48 and 72 hrs. Cells are analyzed for BrdU and propidium iodide incorporation by FACS analysis.

To confirm the role of 24P4C12 in the transformation process, its effect in colony forming assays is investigated. Parental NIH-3T3 cells lacking 24P4C12 are compared to NIH-3T3 cells expressing 24P4C12, using a soft agar assay under stringent and more permissive conditions (Song Z. et al. Cancer Res. 2000;60:6730).

To confirm the role of 24P4C12 in invasion and metastasis of cancer cells, a well-established assay is used. A non-limiting example is the use of an assay which provides a basement membrane or an analog thereof used to detect whether cells are invasive (e.g., a Transwell Insert System assay (Becton Dickinson) (Cancer Res. 1999; 59:6010)). Control cells, including prostate, and bladder cell lines lacking 24P4C12 are compared to cells expressing 24P4C12. Cells are loaded with the fluorescent dye, calcein, and plated in the top well of a support structure coated with a basement membrane analog (e.g. the Transwell insert) and used in the assay. Invasion is determined by fluorescence of cells in the lower chamber relative to the fluorescence of the entire cell population.

24P4C12 can also play a role in cell cycle and apoptosis. Parental cells and cells expressing 24P4C12 are compared for differences in cell cycle regulation using a well-established BrdU assay (Abdel-Malek Z A. J Cell Physiol. 1988, 136: 247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 24P4C12, including normal and tumor prostate, colon and lung cells. Engineered and parental cells are treated with various chemotherapeutic agents, such as etoposide, flutamide, etc, and protein synthesis inhibitors, such as cycloheximide. Cells are stained with annexin V-FITC and cell death is measured by FACS analysis. The modulation of cell death by 24P4C12 can play a critical role in regulating tumor progression and tumor load.

When 24P4C12 plays a role in cell growth, transformation, invasion or apoptosis, it is used as a target for diagnostic, prognostic, preventative and/or therapeutic purposes.

Example 49

Involvement in Angiocenesis

Angiogenesis or new capillary blood vessel formation is necessary for tumor growth (Hanahan D, Folkman J. Cell. 1996, 86:353; Folkman J. Endocrinology. 1998 139:441). Based on the effect of phsophodieseterase inhibitors on endothelial cells, 24P4C12 plays a role in angiogenesis (De-Fouw L et al, Microvasc Res 2001, 62:263). Several assays have been developed to measure angiogenesis in vitro and in vivo, such as the tissue culture assays endothelial cell tube formation and endothelial cell proliferation. Using these assays as well as in vitro neo-vascularization, the role of 24P4C12 in angiogenesis, enhancement or inhibition, is confirmed.

For example, endothelial cells engineered to express 24P4C12 are evaluated using tube formation and proliferation assays. The effect of 24P4C12 is also confirmed in animal models in vivo. For example, cells either expressing or lacking 24P4C12 are implanted subcutaneously in immunocompromised mice. Endothelial cell migration and angiogenesis are evaluated 5-15 days later using immunohistochemistry techniques. 24P4C12 affects angiogenesis and it is used as a target for diagnostic, prognostic, preventative and/or therapeutic purposes.

Example 50

Involvement in Adhesion

Cell adhesion plays a critical role in tissue colonization and metastasis. The presence of leucine rich and cysteine rich motifs in 24P4C12 is indicative of its role in cell adhesion. To confirm that 24P4C12 plays a role in cell adhesion, control cells lacking 24P4C12 are compared to cells expressing 24P4C12, using techniques previously described (see, e.g., Haier et al, Br. J. Cancer. 1999, 80:1867; Lehr and Pienta, J. Natl. Cancer Inst. 1998, 90:118). Briefly, in one embodiment, cells labeled with a fluorescent indicator, such as calcein, are incubated on tissue culture wells coated with media alone or with matrix proteins. Adherent cells are detected by fluorimetric analysis and percent adhesion is calculated. This experimental system can be used to identify proteins, antibodies and/or small molecules that modulate cell adhesion to extracellular matrix and cell-cell interaction. Since cell adhesion plays a critical role in tumor growth, progression, and, colonization, the gene involved in this process can serves as a diagnostic, preventative and therapeutic modality.

Example 51

Detection of 24P4C12 protein in cancer patient specimens

To determine the expression of 24P4C12 protein, specimens were obtained from various cancer patients and stained using an affinity purified polyclonal rabbit antibody raised against the peptide encoding amino acids 1-14 of 24P4C12 variant 1 and conjugated to KLH (See, Example 10: Generation of 24P4C12 Polyclonal Antibodies.) This antiserum exhibited a high titer to the peptide (>10,000) and recognized 24P4C12 in transfected 293T cells by Western blot and flow cytometry (FIG. 24) and in stable recombinant PC3 cells by Western blot and immunohistochemistry (FIG. 25). Formalin fixed, paraffin embedded tissues were cut into 4 micron sections and mounted on glass slides. The sections were dewaxed, rehydrated and treated with antigen retrieval solution (0.1M Tris, pH10) at high temperature. Sections were then incubated in polyclonal rabbit anti-24P4C12 antibody for 3 hours. The slides were washed three times in buffer and further incubated with DAKO EnVision+™ peroxidase-conjugated goat anti-rabbit immunoglobulin secondary antibody (DAKO Corporation, Carpenteria, Calif.) for 1 hour. The sections were then washed in buffer, developed using the DAB kit (SIGMA Chemicals), counterstained using hematoxylin, and analyzed by bright field microscopy. The results showed expression of 24P4C12 in cancer patients' tissue (FIGS. 29 and 30). Tissue from prostate cancer patients showed expression of 24P4C12 in the tumor cells and in the prostate epithelium of tissue normal adjacent to tumor (FIG. 29). Generally, expression of 24P4C12 was high in all prostate tumors and was expressed mainly around the cell membrane indicating that 24P4C12 is membrane associated in prostate tissues. All of the prostate samples tested were positive for 24P4C12. Other tumors that were positive for 24P4C12 included colon adenocarcinoma, breast ductal carcinoma, pancreatic adenocarcinoma, lung adenocarcinoma, bladder transitional cell carcinoma and renal clear cell carcinoma (FIG. 30). Normal tissues investigated for expression of 24P4C12 included heart, skeletal muscle, liver, brain, spinal cord, skin, adrenal, lymph node, spleen, salivary gland, small intestine and placenta. None demonstrated any expression of 24P4C12 by immunohistochemistry. Normal adjacent to tumor tissues were also studied to determine the presence of 24P4C12 protein by immunohistochemistry. These included breast, lung, colon, ileum, bladder, kidney and pancreas. In some of the tissues from these organs there was weak expression of 24P4C12. This expression may relate to the fact that the samples were not truly normal and may indicate a precancerous change. The ability to identify malignancy in tissue that has not undergone obvious morphological changes is an important diagnostic modality for cancerous and precancerous conditions.

These results indicate that 24P4C12 is a target for diagnostic, prophylactic, prognostic and therapeutic applications in cancer.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables:

TABLE I

Tissues that Express 24P4C12:
a. Malignant Tissues

Prostate
Bladder
Kidney
Lung
Colon
Ovary
Breast
Uterus
Stomach

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix
Adapted from the GCG Software 9.0 BLOSUM62 amino acid substitution matrix
(block substitution matrix). The higher the value, the more likely a substitution is found in related, natural proteins. (See world wide web URL ikp.unibe.ch/manual/blosum62.html)

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | -2 | -1 | -2 | 0 | -2 | -1 | -1 | -1 | -1 | -2 | -1 | -1 | -1 | 1 | 0 | 0 | -3 | -2 | A |
|   | 9 | -3 | -4 | -2 | -3 | -3 | -1 | -3 | -1 | -1 | -3 | -3 | -3 | -3 | -1 | -1 | -1 | -2 | -2 | C |
|   |   | 6 | 2 | -3 | -1 | -1 | -3 | -1 | -4 | -3 | 1 | -1 | 0 | -2 | 0 | -1 | -3 | -4 | -3 | D |
|   |   |   | 5 | -3 | -2 | 0 | -3 | 1 | -3 | -2 | 0 | -1 | 2 | 0 | 0 | -1 | -2 | -3 | -2 | E |
|   |   |   |   | 6 | -3 | -1 | 0 | -3 | 0 | 0 | -3 | -4 | -3 | -3 | -2 | -2 | -1 | 1 | 3 | F |
|   |   |   |   |   | 6 | -2 | -4 | -2 | -4 | -3 | 0 | -2 | -2 | -2 | 0 | -2 | -3 | -2 | -3 | G |
|   |   |   |   |   |   | 8 | -3 | -1 | -3 | -2 | 1 | -2 | 0 | 0 | -1 | -2 | -3 | -2 | 2 | H |
|   |   |   |   |   |   |   | 4 | -3 | 2 | 1 | -3 | -3 | -3 | -3 | -2 | -1 | 3 | -3 | -1 | I |
|   |   |   |   |   |   |   |   | 5 | -2 | -1 | 0 | -1 | 1 | 2 | 0 | -1 | -2 | -3 | -2 | K |
|   |   |   |   |   |   |   |   |   | 4 | 2 | -3 | -3 | -2 | -2 | -2 | -1 | 1 | -2 | -1 | L |
|   |   |   |   |   |   |   |   |   |   | 5 | -2 | -2 | 0 | -1 | -1 | -1 | 1 | -1 | -1 | M |
|   |   |   |   |   |   |   |   |   |   |   | 6 | -2 | 0 | 0 | 1 | 0 | -3 | -4 | -2 | N |
|   |   |   |   |   |   |   |   |   |   |   |   | 7 | -1 | -2 | -1 | -1 | -2 | -4 | -3 | P |
|   |   |   |   |   |   |   |   |   |   |   |   |   | 5 | 1 | 0 | -1 | -2 | -2 | -1 | Q |
|   |   |   |   |   |   |   |   |   |   |   |   |   |   | 5 | -1 | -1 | -3 | -3 | -2 | R |
|   |   |   |   |   |   |   |   |   |   |   |   |   |   |   | 4 | 1 | -2 | -3 | -2 | S |
|   |   |   |   |   |   |   |   |   |   |   |   |   |   |   |   | 5 | 0 | -2 | -2 | T |
|   |   |   |   |   |   |   |   |   |   |   |   |   |   |   |   |   | 4 | -3 | -1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

Table IV:
HLA Class I/II Motifs/Supermotifs

TABLE IV (A)

HLA Class I Supermotifs/Motifs

| | POSITION 2 (Primary Anchor) | POSITION 3 (Primary Anchor) | POSITION C Terminus (Primary Anchor) |
|---|---|---|---|
| SUPERMOTIF | | | |
| A1 | T*ILVMS* | | FWY |
| A2 | LIVM*ATQ* | | IVM*ATL* |
| A3 | VSM*ATLI* | | RK |
| A24 | YF*WIVLMT* | | FI*YWLM* |
| B7 | P | | VILF*MWYA* |
| B27 | RHK | | FYL*WMIVA* |
| B44 | ED | | FWYLIMVA |
| B58 | ATS | | FWY*LIVMA* |
| B62 | QL*IVMP* | | FWY*MIVLA* |
| MOTIFS | | | |
| A1 | TSM | DE*AS* | Y |
| A1 | | | Y |
| A2.1 | LM*VQIAT* | | V*LIMAT* |
| A3 | LMVISATF*CGD* | | KYR*HFA* |
| A11 | VTMLISAGN*CDF* | | KR*YH* |
| A24 | YF*WM* | | FLIW |

TABLE IV (A)-continued

HLA Class I Supermotifs/Motifs

| | POSITION 2 (Primary Anchor) | POSITION 3 (Primary Anchor) | POSITION C Terminus (Primary Anchor) |
|---|---|---|---|
| A*3101 | MVT*ALIS* | | RK |
| A*3301 | MVALF*IST* | | RK |
| A*6801 | AVT*MSLI* | | RK |
| B*0702 | P | | LMF*WYAIV* |
| B*3501 | P | | LMFWY*IVA* |
| B51 | P | | LIVF*WYAM* |
| B*5301 | P | | IMFWY*ALV* |
| B*5401 | P | | ATIV*LMFWY* |

Bolded residues are preferred, italicized residues are less preferred: A peptide is considered motif-bearing if it has primary anchors at each primary anchor position for a motif or supermotif as specified in the above table.

TABLE IV (B)

HLA Class II Supermotif

| 1 | 6 | 9 |
|---|---|---|
| W, F, Y, V, I, L | A, V, I, L, P, C, S, T | A, V, I, L, C, S, T, M, Y |

TABLE IV (C)

HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | T | | I | VSTC*PALIM* | MH | | MH |
| | deleterious | | | | W | | | R | | WDE |
| DR1 | preferred | MF*LIVWY* | | | PAMQ | | VMAT*SPLIC* | M | | AVM |
| | deleterious | | C | CH | FD | CWD | | GDE | D | |
| DR7 | preferred | MF*LIVWY* | M | W | A | | IVMSA*CTPL* | M | | IV |
| | deleterious | | C | | G | | | GRD | N | G |
| DR3 | MOTIFS | 1° anchor 1 | 2 | 3 | 1° anchor 4 | 5 | 1° anchor 6 | | | |
| Motif a preferred | | LIVMFY | | | D | | | | | |
| Motif b preferred | | LIVMFAY | | | DNQEST | | KRH | | | |
| DR Supermotif | | MF*LIVWY* | | | | | VMSTA*CPLI* | | | |

Italicized residues indicate less preferred or "tolerated" residues

TABLE IV (D)

| | | | | | | | | | | |
|---|---|---|---|---|---|---|---|---|---|---|
| SUPER-MOTIFS | POSITION: | 1 | 2 | 3 | 4 | 5 | 6 | 7 | 8 | C-terminus |
| A1 | | | 1° Anchor T*ILVMS* | | | | | | | 1° Anchor FWY |
| A2 | | | 1° Anchor LIVM*ATQ* | | | | | | | 1° Anchor LIVMAT |
| A3 | Preferred | | 1° Anchor VSMA*TLI* | YFW (4/5) | | | YFW (3/5) | YFW (4/5) | P (4/5) | 1° Anchor RK |
| | deleterious | DE (3/5); P (5/5) | | DE (4/5) | | | | | | |
| A24 | | | 1° Anchor YF*WIVLMT* | | | | | | | 1° Anchor FIY*WLM* |
| B7 | Preferred | FWY (5/5) LIVM (3/5) | 1° Anchor P | FWY (4/5) | | | | | FWY (3/5) | 1° Anchor VILF*MWYA* |
| | deleterious | DE (3/5); P(5/5); G(4/5); A(3/5); QN(3/5) | | | | DE (3/5) | G (4/5) | QN (4/5) | DE (4/5) | |
| B27 | | | 1° Anchor RHK | | | | | | | 1° Anchor FYL*WMIVA* |
| B44 | | | 1° Anchor ED | | | | | | | 1° Anchor FWYLIMVA |
| B58 | | | 1° Anchor ATS | | | | | | | 1° Anchor FWY*LIVMA* |
| B62 | | | 1° Anchor QL*IVMP* | | | | | | | 1° Anchor FWY*MIVLA* |

Italicized residues indicate less preferred or "tolerated" residues

TABLE IV (E)

| | | HLA Class I Motifs | | | | |
|---|---|---|---|---|---|---|
| | POSITION | 1 | 2 | 3 | 4 | 5 |
| A1 9-mer | preferred | GFYW | 1° Anchor STM | DEA | YFW | |
| | deleterious | DE | | RHKLIVMP | A | G |
| A1 9-mer | preferred | GRHK | ASTCLIVM | 1° Anchor DEAS | GSTC | |
| | deleterious | A | RHKDEPYFW | | DE | PQN |
| A1 10-mer | preferred | YFW | 1° Anchor STM | DEAQN | A | YFWQN |
| | deleterious | GP | | RHKGLIVM | DE | RHK |
| A1 10-mer | preferred | YFW | STCLIVM | 1° Anchor DEAS | A | YFW |
| | deleterious | RHK | RHKDEPYFW | | | P |
| A2.1 9-mer | preferred | YFW | 1° Anchor LM*IVQAT* | YFW | STC | YFW |
| | deleterious | DEP | | DERKH | | |
| A2.1 10-mer | preferred | AYFW | 1° Anchor LM*IVQAT* | LVIM | G | |
| | deleterious | DEP | | DE | RKHA | P |
| A3 | preferred | RHK | 1° Anchor LMVISATFCGD | YFW | PRHKYFW | A |
| | deleterious | DEP | | DE | | |
| A11 | preferred | A | 1° Anchor VTLMISAGN*CDF* | YFW | YFW | A |
| | deleterious | DEP | | | | |
| A24 9-mer | preferred | YFWRHK | 1° Anchor YF*WM* | | STC | |
| | deleterious | DEG | | DE | G | QNP |
| A24 10-mer | Preferred | | 1° Anchor YF*WM* | | P | YFWP |
| | Deleterious | | | GDE | QN | RHK |
| A3101 | Preferred | RHK | 1° Anchor MVT*ALIS* | YFW | P | |
| | Deleterious | DEP | | DE | | ADE |
| A3301 | Preferred | | 1° Anchor MVALF*IST* | YFW | | |
| | Deleterious | GP | | DE | | |
| A6801 | Preferred | YFWSTC | 1° Anchor AVT*MSLI* | | | YFWLIVM |
| | deleterious | GP | | DEG | | RHK |
| B0702 | Preferred | RHKFWY | 1° Anchor P | RHK | | RHK |
| | deleterious | DEQNP | | DEP | DE | DE |
| A1 9-mer | preferred | GFYW | 1° Anchor STM | DEA | YFW | |
| | deleterious | DE | | RHKLIVMP | A | G |
| A1 9-mer | preferred | GRHK | ASTCLIVM | 1° Anchor DEAS | GSTC | |
| | deleterious | A | RHKDEPYFW | | DE | PQN |
| B3501 | Preferred | FWYLIVM | 1° Anchor P | FWY | | |
| | deleterious | AGP | | | | G |
| B51 | Preferred | LIVMFWY | 1° Anchor P | FWY | STC | FWY |
| | deleterious | AGPDERHKSTC | | | | DE |
| B5301 | preferred | LIVMFWY | 1° Anchor P | FWY | STC | FWY |
| | deleterious | AGPQN | | | | |
| B5401 | preferred | FWY | 1° Anchor P | FWYLIVM | | LIVM |
| | deleterious | GPQNDE | | GDESTC | | RHKDE |

| | | | | | | 9 or C-terminus | C-terminus |
|---|---|---|---|---|---|---|---|
| | POSITION | 6 | 7 | 8 | | | |
| A1 9-mer | preferred | P | DEQN | YFW | | 1° Anchor Y | |
| | deleterious | A | | | | | |
| A1 9-mer | preferred | ASTC | LIVM | DE | | 1° Anchor Y | |
| | deleterious | RHK | PG | GP | | | |
| A1 10-mer | preferred | PASTC | GDE | | P | 1° Anchor Y | |
| | deleterious | QNA | RHKYFW | RHK | | A | |
| A1 | preferred | | PG | G | | YFW | 1° Anchor |

TABLE IV (E)-continued

HLA Class I Motifs

| Motif | | | | | | | |
|---|---|---|---|---|---|---|---|
| 10-mer A2.1 | deleterious | G | | | PRHK | QN | Y |
| | preferred | | A | | P | 1° Anchor V*LIMAT* | |
| 9-mer A2.1 | deleterious | RKH | DERKH | | | | |
| | preferred | G | | | FYWLVIM | | 1° Anchor V*LIMAT* |
| 10-mer A3 | deleterious | | RKH | | DERKHRKH | | |
| | preferred | YFW | | | P | 1° Anchor KYR*HFA* | |
| A11 | deleterious | | | | | | |
| | preferred | YFW | YFW | | P | 1° Anchor K*RYH* | |
| A24 9-mer | deleterious | | A | | G | | |
| | preferred | | YFW | | YFW | 1° Anchor FLIW | |
| A24 10-mer | deleterious | DERHKG | | | AQN | | |
| | Preferred | | P | | | 1° Anchor FLIW | |
| A3101 | Deleterious | DE | A | | QN | DEA | |
| | Preferred | YFW | YFW | | AP | 1° Anchor RK | |
| A3301 | Deleterious | DE | DE | | DE | | |
| | Preferred | | AYFW | | | 1° Anchor RK | |
| A6801 | Deleterious | | | | | | |
| | Preferred | | YFW | | P | 1° Anchor RK | |
| B0702 | deleterious | | | | A | | |
| | Preferred | RHK | RHK | | PA | 1° Anchor LMF*WYAIV* | |
| A1 9-mer | deleterious | GDE | QN | | DE | | |
| | preferred | P | DEQN | | YFW | 1° Anchor Y | |
| A1 9-mer | deleterious | A | | | | | |
| | preferred | ASTC | LIVM | | DE | 1° Anchor Y | |
| B3501 | deleterious | RHK | PG | | GP | | |
| | Preferred | | FWY | | | 1° Anchor LMFWY*IVA* | |
| B51 | deleterious | G | | | | | |
| | Preferred | | G | | FWY | 1° Anchor LIVF*WYAM* | |
| B5301 | deleterious | G | DEQN | | GDE | | |
| | preferred | | LIVMFWY | | FWY | 1° Anchor IMFWY*ALV* | |
| B5401 | deleterious | G | RHKQN | | DE | | |
| | preferred | | ALIVM | | FWYAP | 1° Anchor ATIV*LMFWY* | |
| | deleterious | DE | QNDGE | | DE | | |

TABLE IV (F)

Summary of HLA-supertypes
Overall phenotypic frequencies of HLA-supertypes in different ethnic populations

| | Specificity | | Phenotypic frequency | | | | | |
|---|---|---|---|---|---|---|---|---|
| Supertype | Position 2 | C-Terminus | Caucasian | N.A. Black | Japanese | Chinese | Hispanic | Average |
| B7 | P | AILMVFWY | 43.2 | 55.1 | 57.1 | 43.0 | 49.3 | 49.5 |
| A3 | AILMVST | RK | 37.5 | 42.1 | 45.8 | 52.7 | 43.1 | 44.2 |
| A2 | AILMVT | AILMVT | 45.8 | 39.0 | 42.4 | 45.9 | 43.0 | 42.2 |
| A24 | YF (WIVLMT) | FI (YWLM) | 23.9 | 38.9 | 58.6 | 40.1 | 38.3 | 40.0 |
| B44 | E (D) | FWYLIMVA | 43.0 | 21.2 | 42.9 | 39.1 | 39.0 | 37.0 |
| A1 | TI (LVMS) | FWY | 47.1 | 16.1 | 21.8 | 14.7 | 26.3 | 25.2 |
| B27 | RHK | FYL (WMI) | 28.4 | 26.1 | 13.3 | 13.9 | 35.3 | 23.4 |
| B62 | QL (IVMP) | FMY (MIV) | 12.6 | 4.8 | 36.5 | 25.4 | 11.1 | 18.1 |
| B58 | ATS | FWY (LIV) | 10.0 | 25.1 | 1.6 | 9.0 | 5.9 | 10.3 |

TABLE IV (G)

Calculated population coverage afforded by different HLA-supertype combinations

| HLA-supertypes | Phenotypic frequency | | | | | |
|---|---|---|---|---|---|---|
| | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, B44 and A1 | 99.5 | 98.1 | 100.0 | 99.5 | 99.4 | 99.3 |
| A2, A3, B7, A24, B44, A1, B27, B62, and B 58 | 99.9 | 99.6 | 100.0 | 99.8 | 99.9 | 99.8 |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE V

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE VI

Motifs and Post-translational Modifications of 24P4C12

N-glycosylation site

| | | |
|---|---|---|
| 29-32 | NRSC | (SEQ ID NO: 48) |
| 69-72 | NSTG | (SEQ ID NO: 49) |
| 155-158 | NMTV | (SEQ ID NO: 50) |
| 197-200 | NDTT | (SEQ ID NO: 51) |
| 298-301 | NLSA | (SEQ ID NO: 52) |
| 393-396 | NISS | (SEQ ID NO: 53) |
| 405-408 | NTSC | (SEQ ID NO: 54) |
| 416-419 | NSSC | (SEQ ID NO: 55) |
| 678-681 | NGSL | (SEQ ID NO: 56) |

Protein kinase C phosphorylation site

| | |
|---|---|
| 22-24 | SfR |
| 218-220 | SvK |
| 430-432 | SsK |

TABLE VI-continued

Motifs and Post-translational Modifications of 24P4C12

| | | |
|---|---|---|
| 494-496 | T1R | |
| 573-575 | SaK | |
| 619-621 | SgR | |

Casein kinase II phosphorylation site

| | | |
|---|---|---|
| 31-34 | SCTD | (SEQ ID NO: 57) |
| 102-105 | SVAE | (SEQ ID NO: 58) |
| 119-122 | SCPE | (SEQ ID NO: 59) |
| 135-138 | TVGE | (SEQ ID NO: 60) |
| 304-307 | SVQE | (SEQ ID NO: 61) |

Tyrosine kinase phosphorylation site

| | | |
|---|---|---|
| 6-13 | RDEDDEAY | (SEQ ID NO: 62) |

N-myristoylation site

| | | |
|---|---|---|
| 72-77 | GAYCGM | (SEQ ID NO: 63) |
| 76-81 | GMGENK | (SEQ ID NO: 64) |
| 151-156 | GVPWNM | (SEQ ID NO: 65) |
| 207-212 | GLIDSL | (SEQ ID NO: 66) |
| 272-277 | GIYYCW | (SEQ ID NO: 67) |
| 287-292 | GASISQ | (SEQ ID NO: 68) |
| 349-354 | GQMMST | (SEQ ID NO: 69) |
| 449-454 | GLFWTL | (SEQ ID NO: 70) |
| 467-472 | GAFASF | (SEQ ID NO: 71) |

Amidation site

| | | |
|---|---|---|
| 695-698 | IGKK | (SEQ ID NO: 72) |

Leucine zipper pattern

| | | |
|---|---|---|
| 245-266 | LFILLLRLVAGPLVLVLILGVL | (SEQ ID NO: 73) |

Cysteine-rich region

| | | |
|---|---|---|
| 536-547 | CIMCCFKCCLWC | (SEQ ID NO: 74) |

TABLE VII

Search Peptides
Variant 1,
9-mers, 10-mers, 15-mers
(SEQ ID NO: 75)

MGGKQRDEDD EAYGKPVKYD PSFRGPIKNR SCTDVICCVL
FLLFILGYIV VGIVAWLYGD

PRQVLYPRNS TGAYCGMGEN KDKPYLLYFN IFSCILSSNI
ISVAENGLQC PTPQVCVSSC

PEDPWTVGKN EFSQTVGEVF YTKNRNFCLP GVPWNMTVIT
SLQQELCPSF LLPSAPALGR

CFPWTNVTPP ALPGITNDTT IQQGISGLID SLNARDISVK
IFEDFAQSWY WILVALGVAL

VLSLLFILLL RLVAGPLVLV LILGVLGVLA YGIYYCWEEY
RVLRDKGASI SQLGFTTNLS

AYQSVQETWL AALIVLAVLE AILLLMLIFL RQRIRIAIAL
LKEASKAVGQ MMSTMFYPLV

TFVLLLICIA YWAMTALYLA TSGQPQYVLW ASNISSPGCE
KVPINTSCNP TAHLVNSSCP

GLMCVFQGYS SKGLIQRSVF NLQIYGVLGL FWTLNWVLAL
GQCVLAGAFA SFYWAFHKPQ

DIPTFPLISA FIRTLRYHTG SLAFGALILT LVQIARVILE
YIDHKLRGVQ NPVARCIMCC

FKCCLWCLEK FIKFLNRNAY IMIAIYGKNF CVSAKNAFML
LMRNIVRVVV LDKVTDLLLF

FGKLLVVGGV GVLSFFFFSG RIPGLGKDFK SPHLNYYWLP
IMTSILGAYV IASGFFSVFG

MCVDTLFLCF LEDLERNNGS LDRPYYMSKS LLKILGKKNE
APPDNKKRKK

Variant 3:
9-mers
(SEQ ID NO: 76)
GRCFPWTNITPPALPGI 10-mers
(SEQ ID NO: 77)
LGRCFPWTNITPPALPGIT 15-mers
(SEQ ID NO: 78)
PSAPALGRCFPWTNITPPALPGITNDTTI Variant 5:
9-mers
(SEQ ID NO: 79)
VLEAILLLVLIFLRQRI 10-mers
(SEQ ID NO: 80)
AVLEAILLLVLIFLRQRIR 15-mers
(SEQ ID NO: 81)
ALIVLAVLEAILLLVLIFLRQRIRIAIAL Variant 6:
9-mers
(SEQ ID NO: 82)
GYSSKGLIPRSVFNLQI 10-mers
(SEQ ID NO: 83)
QGYSSKGLIPRSVFNLQIY 15-mers
(SEQ ID NO: 84)
LMCVFQGYSSKGLIPRSVFNLQIYGVLGL Variant 7
9-mers
(SEQ ID NO: 85)
SWYWILVAVGQMMSTM 10-mers
(SEQ ID NO: 86)
QSWYWILVAVGQMMSTMF 15-mers
(SEQ ID NO: 87)
FEDFAQSWYWILVAVGQMMSTMFYPLVT Variant 8
9-mers
(SEQ ID NO: 88)
NYYWLPIMRNPITPTGHVFQTSILGAYV 10-mers

TABLE VII-continued

```
                                        (SEQ ID NO: 89)
LNYYWLPIMRNPITPTGHVFQTSILGAYVI 15-mers
                                        (SEQ ID NO: 90)
FKSPHLNYYWLPIMRNPITPTGHVFQTSILGAYVIASGFF Variant 9
9-mers
                                        (SEQ ID NO: 91)
YWAMTALYPLPTQPATLGYVLWASNI 10-mers
                                        (SEQ ID NO: 92)
AYWAMTALYPLPTQPATLGYVLWASNIS 15-mers
                                        (SEQ ID NO: 93)
LLICIAYWAMTALYPLPTQPATLGYVLWASNISSPGCE
```

Table VIII-XXI:

TABLE VIII-V1

HLA-A1-9mers-24P4C12
Each peptide is a portion of SEQ ID NO: 3; each start position is specified, the length of peptide is 9 amino acids, and the end position for each peptide is the start position plus eight.

| Start | Subsequence | Score |
|-------|-------------|-------|
| 58 | YGDPRQVLY | 125.000 |
| 662 | CVDTLFLCF | 25.000 |
| 77 | MGENKDKPY | 11.250 |
| 594 | VTDLLLFFG | 6.250 |
| 698 | KNEAPPDNK | 4.500 |
| 318 | VLEAILLLM | 4.500 |
| 363 | VLLLICIAY | 2.500 |
| 489 | SAFIRTLRY | 2.500 |
| 267 | GVLAYGIYY | 2.500 |
| 689 | KSLLKILGK | 1.500 |
| 470 | ASFYWAFHK | 1.500 |
| 222 | FEDFAQSWY | 1.250 |
| 32 | CTDVICCVL | 1.250 |
| 5 | QRDEDDEAY | 1.250 |
| 121 | PEDPWTVGK | 1.000 |
| 379 | LATSGQPQY | 1.000 |
| 700 | EAPPDNKKR | 1.000 |
| 558 | NAYIMIAIY | 1.000 |
| 542 | KCCLWCLEK | 1.000 |
| 7 | DEDDEAYGK | 1.000 |
| 11 | EAYGKPVKY | 1.000 |
| 670 | FLEDLERNN | 0.900 |
| 276 | CWEEYRVLR | 0.900 |

TABLE VIII-V1-continued

HLA-A1-9mers-24P4C12
Each peptide is a portion of SEQ ID NO: 3; each start position is specified, the length of peptide is 9 amino acids, and the end position for each peptide is the start position plus eight.

| Start | Subsequence | Score |
|-------|-------------|-------|
| 518 | ILEYIDHKL | 0.900 |
| 417 | SSCPGLMCV | 0.750 |
| 437 | RSVFNLQIY | 0.750 |
| 80 | NKDKPYLLY | 0.625 |
| 263 | LGVLGVLAY | 0.625 |
| 546 | WCLEKFIKF | 0.500 |
| 243 | SLLFILLLR | 0.500 |
| 238 | VALVLSLLF | 0.500 |
| 579 | MLLMRNIVR | 0.500 |
| 465 | LAGAFASFY | 0.500 |
| 421 | GLMCVFQGY | 0.500 |
| 508 | ILTLVQIAR | 0.500 |
| 593 | KVTDLLLFF | 0.500 |
| 321 | AILLLMLIF | 0.500 |
| 36 | ICCVLFLLF | 0.500 |
| 50 | VVGIVAWLY | 0.500 |
| 186 | NVTPPALPG | 0.500 |
| 609 | GVGVLSFFF | 0.500 |
| 287 | GASISQLGF | 0.500 |
| 187 | VTPPALPGI | 0.500 |
| 668 | LCFLEDLER | 0.500 |
| 323 | LLLMLIFLR | 0.500 |
| 272 | GIYYCWEEY | 0.500 |
| 521 | YIDHKLRGV | 0.500 |
| 253 | VAGPLVLVL | 0.500 |
| 398 | GCEKVPINT | 0.450 |
| 560 | YIMIAIYGK | 0.400 |
| 338 | IALLKEASK | 0.400 |
| 135 | TVGEVFYTK | 0.400 |
| 349 | GQMMSTMFY | 0.375 |
| 118 | SSCPEDPWT | 0.300 |
| 305 | VQETWLAAL | 0.270 |
| 629 | FKSPHLNYY | 0.250 |
| 214 | ARDISVKIF | 0.250 |
| 702 | PPDNKKRKK | 0.250 |

TABLE VIII-V1-continued

HLA-A1-9mers-24P4C12
Each peptide is a portion of SEQ ID NO: 3; each start position is specified, the length of peptide is 9 amino acids, and the end position for each peptide is the start position plus eight.

| Start | Subsequence | Score |
|---|---|---|
| 641 | IMTSILGAY | 0.250 |
| 678 | NGSLDRPYY | 0.250 |
| 513 | QIARVILEY | 0.250 |
| 483 | PTFPLISAF | 0.250 |
| 120 | CPEDPWTVG | 0.225 |
| 129 | KNEFSQTVG | 0.225 |
| 136 | VGEVFYTKN | 0.225 |
| 170 | FLLPSAPAL | 0.200 |
| 147 | FCLPGVPWN | 0.200 |
| 393 | NISSPGCEK | 0.200 |
| 464 | VLAGAFASF | 0.200 |
| 517 | VILEYIDHK | 0.200 |
| 424 | CVFQGYSSK | 0.200 |
| 394 | ISSPGCEKV | 0.150 |
| 133 | SQTVGEVFY | 0.150 |
| 613 | LSFFFFSGR | 0.150 |
| 132 | FSQTVGEVF | 0.150 |
| 488 | ISAFIRTLR | 0.150 |
| 163 | QQELCPSFL | 0.135 |
| 199 | TTIQQGISG | 0.125 |
| 485 | FPLISAFIR | 0.125 |
| 607 | VGGVGVLSF | 0.125 |
| 134 | QTVGEVFYT | 0.125 |
| 575 | KNAFMLLMR | 0.125 |
| 266 | LGVLAYGIY | 0.125 |
| 40 | LFLLFILGY | 0.125 |
| 196 | TNDTTIQQG | 0.125 |
| 610 | VGVLSFFFF | 0.125 |
| 360 | VTFVLLLIC | 0.125 |
| 156 | MTVITSLQQ | 0.125 |
| 677 | NNGSLDRPY | 0.125 |
| 498 | HTGSLAFGA | 0.125 |
| 172 | LPSAPALGR | 0.125 |
| 195 | ITNDTTIQQ | 0.125 |
| 452 | WTLNWVLAL | 0.125 |
| 353 | STMFYPLVT | 0.125 |

TABLE VIII-V1-continued

HLA-A1-9mers-24P4C12
Each peptide is a portion of SEQ ID NO: 3; each start position is specified, the length of peptide is 9 amino acids, and the end position for each peptide is the start position plus eight.

| Start | Subsequence | Score |
|---|---|---|
| 443 | QIYGVLGLF | 0.100 |
| 543 | CCLWCLEKF | 0.100 |
| 207 | GLIDSLNAR | 0.100 |
| 407 | SCNPTAHLV | 0.100 |
| 180 | RCFPWTNVT | 0.100 |
| 354 | TMFYPLVTF | 0.100 |

TABLE VIII-V3

HLA-A1-9mers-24P4C12
Each peptide is a portion of SEQ ID NO: 7; each start position is specified, the length of peptide is 9 amino acids, and the end position for each peptide is the start position plus eight.

| Start | Subsequence | Score |
|---|---|---|
| 9 | ITPPALPGI | 0.500 |
| 8 | NITPPALPG | 0.500 |
| 2 | RCFPWTNIT | 0.100 |
| 6 | WTNITPPAL | 0.050 |
| 7 | TNITPPALP | 0.001 |
| 1 | GRCFPWTNI | 0.001 |
| 3 | CFPWTNITP | 0.000 |
| 5 | PWTNITPPA | 0.000 |
| 4 | FPWTNITPP | 0.000 |

TABLE VIII-V5

HLA-A1-9mers-24P4C12
Each peptide is a portion of SEQ ID NO: 3; each start position is specified, the length of peptide is 9 amino acids, and the end position for each peptide is the start position plus eight.

| Start | Subsequence | Score |
|---|---|---|
| 1 | VLEAILLLV | 4.500 |
| 6 | LLLVLIFLR | 0.500 |
| 4 | AILLLVLIF | 0.500 |
| 8 | LVLIFLRQR | 0.100 |
| 7 | LLVLIFLRQ | 0.050 |
| 5 | ILLLVLIFL | 0.050 |
| 3 | EAILLLVLI | 0.020 |

TABLE VIII-V5-continued

HLA-A1-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 9 | VLIFLRQRI | 0.010 |
| 2 | LEAILLLVL | 0.003 |

TABLE VIII-V6

HLA-A1-9mers-24P4C12
Each peptide is a portion of SEQ ID NO: 13;
each start position is specified, the length
of peptide is 9 amino acids, and the end
position for each peptide is the start
position plus eight.

| Start | Subsequence | Score |
|---|---|---|
| 6 | GLIPRSVFN | 0.200 |
| 2 | YSSKGLIPR | 0.075 |
| 5 | KGLIPRSVF | 0.025 |
| 7 | LIPRSVFNL | 0.005 |
| 3 | SSKGLIPRS | 0.003 |
| 4 | SKGLIPRSV | 0.001 |
| 9 | PRSVFNLQI | 0.000 |
| 8 | IPRSVFNLQ | 0.000 |
| 1 | GYSSKGLIP | 0.000 |

TABLE VIII-V7

HLA-A1-9mers-24P4C12
Each peptide is a portion of SEQ ID NO: 15;
each start position is specified, the length
of peptide is 9 amino acids, and the end
position for each peptide is the start
position plus eight.

| Start | Subsequence | Score |
|---|---|---|
| 7 | VAVGQMMST | 0.050 |
| 6 | LVAVGQMMS | 0.050 |
| 8 | AVGQMMSTM | 0.010 |
| 5 | ILVAVGQMM | 0.010 |
| 4 | WILVAVGQM | 0.010 |
| 3 | YWILVAVGQ | 0.001 |
| 1 | SWYWILVAV | 0.001 |
| 2 | WYWILVAVG | 0.000 |

TABLE VIII-V8

HLA-A1-9mers-24P4C12
Each peptide is a portion of SEQ ID NO: 17;
each start position is specified, the length
of peptide is 9 amino acids, and the end
position for each peptide is the start
position plus eight.

| Start | Subsequence | Score |
|---|---|---|
| 11 | PITPTGHVF | 0.100 |
| 19 | FQTSILGAY | 0.075 |
| 20 | QTSILGAYV | 0.050 |
| 17 | HVFQTSILG | 0.050 |
| 12 | ITPTGHVFQ | 0.050 |
| 1 | NYYWLPIMR | 0.025 |
| 13 | TPTGHVFQT | 0.013 |
| 8 | MRNPITPTG | 0.010 |
| 4 | WLPIMRNPI | 0.010 |
| 5 | LPIMRNPIT | 0.005 |
| 18 | VFQTSILGA | 0.003 |
| 10 | NPITPTGHV | 0.003 |
| 15 | TGHVFQTSI | 0.003 |
| 9 | RNPITPTGH | 0.003 |
| 14 | PTGHVFQTS | 0.003 |
| 7 | IMRNPITPT | 0.001 |
| 3 | YWLPIMRNP | 0.001 |
| 16 | GHVFQTSIL | 0.001 |
| 2 | YYWLPIMRN | 0.000 |
| 6 | PIMRNPITP | 0.000 |

TABLE VIII-V9

HLA-A1-9mers-24P4C12
Each peptide is a portion of SEQ ID NO: 19;
each start position is specified, the length
of peptide is 9 amino acids, and the end
position for each peptide is the start
position plus eight.

| Start | Subsequence | Score |
|---|---|---|
| 11 | PTQPATLGY | 6.250 |
| 4 | MTALYPLPT | 0.125 |
| 15 | ATLGYVLWA | 0.125 |
| 8 | YPLPTQPAT | 0.050 |
| 5 | TALYPLPTQ | 0.020 |
| 2 | WAMTALYPL | 0.020 |
| 16 | TLGYVLWAS | 0.010 |
| 6 | ALYPLPTQP | 0.010 |
| 13 | QPATLGYVL | 0.005 |
| 17 | LGYVLWASN | 0.005 |

TABLE VIII-V9-continued

HLA-A1-9mers-24P4C12
Each peptide is a portion of SEQ ID NO: 19;
each start position is specified, the length
of peptide is 9 amino acids, and the end
position for each peptide is the start
position plus eight.

| Start | Subsequence | Score |
|---|---|---|
| 10 | LPTQPATLG | 0.003 |
| 9 | PLPTQPATL | 0.002 |
| 14 | PATLGYVLW | 0.002 |
| 12 | TQPATLGYV | 0.002 |
| 3 | AMTALYPLP | 0.001 |
| 18 | GYVLWASNI | 0.001 |
| 7 | LYPLPTQPA | 0.001 |
| 1 | YWAMTALYP | 0.000 |

TABLE IX-V1

HLA-A1-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 594 | VTDLLLFFGK | 125.000 |
| 32 | CTDVICCVLF | 25.000 |
| 120 | CPEDPWTVGK | 9.000 |
| 518 | ILEYIDHKLR | 9.000 |
| 680 | SLDRPYYMSK | 5.000 |
| 698 | KNEAPPDNKK | 4.500 |
| 318 | VLEAILLLML | 4.500 |
| 488 | ISAFIRTLRY | 3.750 |
| 39 | VLFLLFILGY | 2.500 |
| 262 | ILGVLGVLAY | 2.500 |
| 362 | FVLLLICIAY | 2.500 |
| 136 | VGEVFYTKNR | 2.250 |
| 221 | IFEDFAQSWY | 2.250 |
| 700 | EAPPDNKKRK | 2.000 |
| 9 | DDEAYGKPVK | 1.800 |
| 6 | RDEDDEAYGK | 1.800 |
| 417 | SSCPGLMCVF | 1.500 |
| 132 | FSQTVGEVFY | 1.500 |
| 134 | QTVGEVFYTK | 1.000 |
| 469 | FASFYWAFHK | 1.000 |
| 369 | IAYWAMTALY | 1.000 |

TABLE IX-V1-continued

HLA-A1-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 378 | YLATSGQPQY | 1.000 |
| 670 | FLEDLERNNG | 0.900 |
| 103 | VAENGLQCPT | 0.900 |
| 277 | WEEYRVLRDK | 0.900 |
| 242 | LSLLFILLLR | 0.750 |
| 163 | QQELCPSFLL | 0.675 |
| 58 | YGDPRQVLYP | 0.625 |
| 266 | LGVLAYGIYY | 0.625 |
| 348 | VGQMMSTMFY | 0.625 |
| 171 | LLPSAPALGR | 0.500 |
| 507 | LILTLVQIAR | 0.500 |
| 237 | GVALVLSLLF | 0.500 |
| 320 | EAILLLMLIF | 0.500 |
| 208 | LIDSLNARDI | 0.500 |
| 609 | GVGVLSFFFF | 0.500 |
| 353 | STMFYPLVTF | 0.500 |
| 464 | VLAGAFASFY | 0.500 |
| 322 | ILLLMLIFLR | 0.500 |
| 35 | VICCVLFLLF | 0.500 |
| 606 | VVGGVGVLSF | 0.500 |
| 521 | YIDHKLRGVQ | 0.500 |
| 662 | CVDTLFLCFL | 0.500 |
| 661 | MCVDTLFLCF | 0.500 |
| 265 | VLGVLAYGIY | 0.500 |
| 49 | IVVGIVAWLY | 0.500 |
| 667 | FLCFLEDLER | 0.500 |
| 407 | SCNPTAHLVN | 0.500 |
| 165 | ELCPSFLLPS | 0.500 |
| 77 | MGENKDKPYL | 0.450 |
| 547 | CLEKFIKFLN | 0.450 |
| 337 | AIALLKEASK | 0.400 |
| 512 | VQIARVILEY | 0.375 |
| 689 | KSLLKILGKK | 0.300 |
| 305 | VQETWLAALI | 0.270 |
| 18 | KYDPSFRGPI | 0.250 |

TABLE IX-V1-continued

HLA-A1-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 76 | GMGENKDKPY | 0.250 |
| 557 | RNAYIMIAIY | 0.250 |
| 590 | VLDKVTDLLL | 0.250 |
| 677 | NNGSLDRPYY | 0.250 |
| 578 | FMLLMRNIVR | 0.250 |
| 187 | VTPPALPGIT | 0.250 |
| 463 | CVLAGAFASF | 0.200 |
| 516 | RVILEYIDHK | 0.200 |
| 74 | YCGMGENKDK | 0.200 |
| 72 | GAYCGMGENK | 0.200 |
| 423 | MCVFQGYSSK | 0.200 |
| 621 | RIPGLGKDFK | 0.200 |
| 170 | FLLPSAPALG | 0.200 |
| 211 | SLNARDISVK | 0.200 |
| 161 | SLQQELCPSF | 0.200 |
| 253 | VAGPLVLVLI | 0.200 |
| 186 | NVTPPALPGI | 0.200 |
| 618 | FSGRIPGLGK | 0.150 |
| 173 | PSAPALGRCF | 0.150 |
| 118 | SSCPEDPWTV | 0.150 |
| 125 | WTVGKNEFSQ | 0.125 |
| 676 | RNNGSLDRPY | 0.125 |
| 608 | GGVGVLSFFF | 0.125 |
| 286 | KGASISQLGF | 0.125 |
| 80 | NKDKPYLLYF | 0.125 |
| 360 | VTFVLLLICI | 0.125 |
| 196 | TNDTTIQQGI | 0.125 |
| 198 | DTTIQQGISG | 0.125 |
| 293 | LGFTTNLSAY | 0.125 |
| 271 | YGIYYCWEEY | 0.125 |
| 382 | SGQPQYVLWA | 0.125 |
| 467 | GAFASFYWAF | 0.100 |
| 487 | LISAFIRTLR | 0.100 |
| 650 | VIASGFFSVF | 0.100 |
| 64 | VLYPRNSTGA | 0.100 |
| 347 | AVGQMMSTMF | 0.100 |

TABLE IX-V1-continued

HLA-A1-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 272 | GIYYCWEEYR | 0.100 |
| 333 | RIRIAIALLK | 0.100 |
| 612 | VLSFFFFSGR | 0.100 |
| 147 | FCLPGVPWNM | 0.100 |
| 216 | DISVKIFEDF | 0.100 |
| 53 | IVAWLYGDPR | 0.100 |
| 326 | MLIFLRQRIR | 0.100 |
| 544 | CLWCLEKFIK | 0.100 |

TABLE IX-V3

HLA-A1-10mers-24P4C12
Each peptide is a portion of SEQ ID NO: 7;
each start position is specified, the length
of peptide is 10 amino acids, and the end
position for each peptide is the start
position plus nine.

| Start | Subsequence | Score |
|---|---|---|
| 10 | ITPPALPGIT | 0.250 |
| 9 | NITPPALPGI | 0.200 |
| 3 | RCFPWTNITP | 0.050 |
| 8 | TNITPPALPG | 0.013 |
| 7 | WTNITPPALP | 0.005 |
| 5 | FPWTNITPPA | 0.001 |
| 2 | GRCFPWTNIT | 0.001 |
| 1 | LGRCFPWTNI | 0.000 |
| 6 | PWTNITPPAL | 0.000 |
| 4 | CFPWTNITPP | 0.000 |

TABLE IX-V5

HLA-A1-10mers-24P4C12
Each peptide is a portion of SEQ ID NO: 11;
each start position is specified, the length
of peptide is 10 amino acids, and the end
position for each peptide is the start
position plus nine.

| Start | Subsequence | Score |
|---|---|---|
| 2 | VLEAILLLVL | 4.500 |
| 6 | ILLLVLIFLR | 0.500 |
| 4 | EAILLLVLIF | 0.500 |
| 8 | LLVLIFLRQR | 0.100 |

TABLE IX-V5-continued

HLA-A1-10mers-24P4C12
Each peptide is a portion of SEQ ID NO: 11; each start position is specified, the length of peptide is 10 amino acids, and the end position for each peptide is the start position plus nine.

| Start | Subsequence | Score |
|---|---|---|
| 10 | VLIFLRQRIR | 0.100 |
| 7 | LLLVLIFLRQ | 0.050 |
| 1 | AVLEAILLLV | 0.050 |
| 5 | AILLLVLIFL | 0.050 |
| 9 | LVLIFLRQRI | 0.010 |
| 3 | LEAILLLVLI | 0.001 |

TABLE IX-V6

HLA-A1-10mers-24P4C12
Each peptide is a portion of SEQ ID NO: 13; each start position is specified, the length of peptide is 10 amino acids, and the end position for each peptide is the start position plus nine.

| Start | Subsequence | Score |
|---|---|---|
| 7 | GLIPRSVFNL | 0.500 |
| 2 | GYSSKGLIPR | 0.025 |
| 6 | KGLIPRSVFN | 0.005 |
| 5 | SKGLIPRSVF | 0.005 |
| 3 | YSSKGLIPRS | 0.003 |
| 10 | PRSVFNLQIY | 0.003 |
| 4 | SSKGLIPRSV | 0.002 |
| 9 | IPRSVFNLQI | 0.001 |
| 1 | QGYSSKGLIP | 0.001 |
| 8 | LIPRSVFNLQ | 0.001 |

TABLE IX-V7

HLA-A1-10mers-24P4C12
Each peptide is a portion of SEQ ID NO: 15; each start position is specified, the length of peptide is 10 amino acids, and the end position for each peptide is the start position plus nine.

| Start | Subsequence | Score |
|---|---|---|
| 9 | AVGQMMSTMF | 0.100 |
| 6 | ILVAVGQMMS | 0.050 |
| 7 | LVAVGQMMST | 0.050 |
| 8 | VAVGQMMSTM | 0.010 |
| 5 | WILVAVGQMM | 0.010 |
| 1 | QSWYWILVAV | 0.003 |

TABLE IX-V7-continued

HLA-A1-10mers-24P4C12
Each peptide is a portion of SEQ ID NO: 15; each start position is specified, the length of peptide is 10 amino acids, and the end position for each peptide is the start position plus nine.

| Start | Subsequence | Score |
|---|---|---|
| 2 | SWYWILVAVG | 0.001 |
| 4 | YWILVAVGQM | 0.001 |
| 3 | WYWILVAVGQ | 0.000 |

TABLE IX-V8

HLA-A1-10mers-24P4C12
Each peptide is a portion of SEQ ID NO: 17; each start position is specified, the length of peptide is 10 amino acids, and the end position for each peptide is the start position plus nine.

| Start | Subsequence | Score |
|---|---|---|
| 1 | LNYYWLPIMR | 0.125 |
| 13 | ITPTGHVFQT | 0.125 |
| 21 | QTSILGAYVI | 0.050 |
| 18 | HVFQTSILGA | 0.050 |
| 11 | NPITPTGHVF | 0.025 |
| 19 | VFQTSILGAY | 0.025 |
| 12 | PITPTGHVFQ | 0.020 |
| 5 | WLPIMRNPIT | 0.020 |
| 4 | YWLPIMRNPI | 0.005 |
| 9 | MRNPITPTGH | 0.005 |
| 20 | FQTSILGAYV | 0.003 |
| 15 | PTGHVFQTSI | 0.003 |
| 14 | TPTGHVFQTS | 0.003 |
| 10 | RNPITPTGHV | 0.003 |
| 2 | NYYWLPIMRN | 0.003 |
| 16 | TGHVFQTSIL | 0.003 |
| 17 | GHVFQTSILG | 0.003 |
| 6 | LPIMRNPITP | 0.001 |
| 8 | IMRNPTPTG | 0.001 |
| 7 | PIMRNPITPT | 0.000 |
| 3 | YYWLPIMRNP | 0.000 |

TABLE IX-V9

HLA-A1-10mers-24P4C12
Each peptide is a portion of SEQ ID NO: 19; each start position is specified, the length of peptide is 10 amino acids, and the end position for each peptide is the start position plus nine.

| Start | Subsequence | Score |
|---|---|---|
| 11 | LPTQPATLGY | 0.625 |
| 7 | ALYPLPTQPA | 0.100 |
| 9 | YPLPTQPATL | 0.050 |
| 5 | MTALYPLPTQ | 0.050 |
| 12 | PTQPATLGYV | 0.025 |
| 4 | AMTALYPLPT | 0.025 |
| 16 | ATLGYVLWAS | 0.025 |
| 17 | TLGYVLWASN | 0.020 |
| 15 | PATLGYVLWA | 0.005 |
| 14 | QPATLGYVLW | 0.005 |
| 13 | TQPATLGYVL | 0.003 |
| 18 | LGYVLWASNI | 0.003 |
| 3 | WAMTALYPLP | 0.002 |
| 2 | YWAMTALYPL | 0.001 |
| 10 | PLPTQPATLG | 0.001 |
| 6 | TALYPLPTQP | 0.001 |
| 8 | LYPLPTQPAT | 0.001 |
| 19 | GYVLWASNIS | 0.001 |
| 1 | AYWAMTALYP | 0.000 |

TABLE X-V1

HLA-A0201-9mers-24P4C12
Each peptide is a portion of SEQ ID NO: 3; each start position is specified, the length of peptide is 9 amino acids, and the end position for each peptide is the start position plus eight.

| Start | Subsequence | Score |
|---|---|---|
| 449 | GLFWTLNWV | 3255.381 |
| 322 | ILLLMLIFL | 1699.774 |
| 580 | LLMRNIVRV | 1006.209 |
| 597 | LLLFFGKLL | 510.604 |
| 544 | CLWCLEKFI | 476.257 |
| 598 | LLFFGKLLV | 437.482 |
| 170 | FLLPSAPAL | 363.588 |
| 86 | LLYFNIFSC | 360.526 |
| 578 | FMLLMRNIV | 350.529 |
| 244 | LLFILLLRL | 309.050 |
| 41 | FLLFILGYI | 292.008 |
| 95 | ILSSNIISV | 271.948 |
| 260 | VLILGVLGV | 271.948 |

TABLE X-V1-continued

HLA-A0201-9mers-24P4C12
Each peptide is a portion of SEQ ID NO: 3; each start position is specified, the length of peptide is 9 amino acids, and the end position for each peptide is the start position plus eight.

| Start | Subsequence | Score |
|---|---|---|
| 56 | WLYGDPRQV | 204.761 |
| 42 | LLFILGYIV | 179.368 |
| 650 | VIASGFFSV | 179.161 |
| 564 | AIYGKNFCV | 177.497 |
| 239 | ALVLSLLFI | 131.975 |
| 604 | LLVVGGVGV | 118.238 |
| 589 | VVLDKVTDL | 110.872 |
| 268 | VLAYGIYYC | 106.837 |
| 456 | WVLALGQCV | 103.580 |
| 537 | IMCCFKCCL | 99.667 |
| 446 | GVLGLFWTL | 98.554 |
| 257 | LVLVLILGV | 88.043 |
| 660 | GMCVDTLFL | 84.856 |
| 686 | YMSKSLLKI | 79.718 |
| 177 | ALGRCFPWT | 77.873 |
| 211 | SLNARDISV | 69.552 |
| 107 | GLQCPTPQV | 69.552 |
| 241 | VLSLLFILL | 69.001 |
| 434 | LIQRSVFNL | 66.613 |
| 35 | VICCVLFLL | 66.613 |
| 547 | CLEKFIKFL | 65.721 |
| 317 | AVLEAILLL | 65.219 |
| 240 | LVLSLLFIL | 64.306 |
| 302 | YQSVQETWL | 54.798 |
| 309 | WLAALIVLA | 52.561 |
| 351 | MMSTMFYPL | 49.834 |
| 365 | LLICIAYWA | 46.451 |
| 45 | ILGYIVVGI | 40.792 |
| 638 | WLPIMTSIL | 40.289 |
| 49 | IVVGIVAWL | 40.197 |
| 38 | CVLFLLFIL | 37.827 |
| 148 | CLPGVPWNM | 37.260 |
| 232 | ILVALGVAL | 36.316 |
| 291 | SQLGFTTNL | 30.453 |
| 85 | YLLYFNIFS | 26.508 |

TABLE X-V1-continued

HLA-A0201-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 506 | ALILTLVQI | 23.995 |
| 252 | LVAGPLVLV | 23.795 |
| 233 | LVALGVALV | 23.795 |
| 525 | KLRGVQNPV | 18.501 |
| 339 | ALLKEASKA | 18.382 |
| 265 | VLGVLAYGI | 17.736 |
| 326 | MLIFLRQRI | 17.736 |
| 340 | LLKEASKAV | 16.967 |
| 445 | YGVLGLFWT | 16.418 |
| 315 | VLAVLEAIL | 14.890 |
| 457 | VLALGQCVL | 14.890 |
| 509 | LTLVQIARV | 13.975 |
| 119 | SCPEDPWTV | 13.961 |
| 366 | LICIAYWAM | 13.064 |
| 226 | AQSWYWILV | 11.988 |
| 452 | WTLNWVLAL | 11.615 |
| 426 | FQGYSSKGL | 9.963 |
| 554 | FLNRNAYIM | 9.370 |
| 642 | MTSILGAYV | 9.032 |
| 164 | QELCPSFLL | 8.914 |
| 693 | KILGKKNEA | 8.846 |
| 251 | RLVAGPLVL | 8.759 |
| 501 | SLAFGALIL | 8.759 |
| 487 | LISAFIRTL | 8.729 |
| 442 | LQIYGVLGL | 8.469 |
| 262 | ILGVLGVLA | 8.446 |
| 521 | YIDHKLRGV | 8.094 |
| 373 | AMTALYLAT | 8.073 |
| 242 | LSLLFILLL | 7.666 |
| 134 | QTVGEVFYT | 7.594 |
| 191 | ALPGITNDT | 7.452 |
| 590 | VLDKVTDLL | 7.118 |
| 362 | FVLLLICIA | 6.977 |
| 200 | TIQQGISGL | 6.756 |
| 83 | KPYLLYFNI | 6.636 |
| 314 | IVLAVLEAI | 6.471 |

TABLE X-V1-continued

HLA-A0201-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 383 | GQPQYVLWA | 6.372 |
| 225 | FAQSWYWIL | 6.295 |
| 289 | SISQLGFTT | 5.943 |
| 364 | LLLICIAYW | 5.929 |
| 596 | DLLLFFGKL | 5.564 |
| 611 | GVLSFFFFS | 5.557 |
| 282 | VLRDKGASI | 5.526 |
| 154 | WNMTVITSL | 5.459 |
| 380 | ATSGQPQYV | 5.313 |
| 612 | VLSFFFFSG | 5.305 |
| 100 | IISVAENGL | 4.993 |
| 158 | VITSLQQEL | 4.993 |
| 504 | FGALILTLV | 4.804 |
| 536 | CIMCCFKCC | 4.802 |
| 246 | FILLLRLVA | 4.767 |
| 357 | YPLVTFVLL | 4.510 |

TABLE X-V3

HLA-A0201-9mers-24P4C12
Each peptide is a portion of SEQ ID NO: 7;
each start position is specified, the length
of peptide is 9 amino acids, and the end
position for each peptide is the start
position plus eight.

| Start | Subsequence | Score |
|---|---|---|
| 6 | WTNITPPAL | 1.365 |
| 9 | ITPPALPGI | 0.567 |
| 2 | RCFPWTNIT | 0.074 |
| 8 | NITPPALPG | 0.010 |
| 4 | FPWTNITPP | 0.009 |
| 1 | GRCFPWTNI | 0.002 |
| 7 | TNITPPALP | 0.000 |
| 5 | PWTNITPPA | 0.000 |
| 3 | CFPWTNITP | 0.000 |

TABLE X-V5

HLA-A0201-9mers-24P4C12
Each peptide is a portion of SEQ ID NO: 11;

each start position is specified, the length of peptide is 9 amino acids, and the end position for each peptide is the start position plus eight.

| Start | Subsequence | Score |
|---|---|---|
| 5 | ILLLVLIFL | 1699.774 |
| 9 | VLIFLRQRI | 17.736 |
| 1 | VLEAILLLV | 5 |
| 6 | LLLVLIFLR | 1.251 |
| 2 | LEAILLLVL | 0.666 |
| 7 | LLVLIFLRQ | 0.048 |
| 4 | AILLLVLIF | 0.036 |
| 3 | EAILLLVLI | 0.025 |
| 8 | LVLIFLRQR | 0.014 |

TABLE X-V6

HLA-A0201-9mers-24P4C12
Each peptide is a portion of SEQ ID NO: 13; each start position is specified, the length of peptide is 9 amino acids, and the end position for each peptide is the start position plus eight.

| Start | Subsequence | Score |
|---|---|---|
| 7 | LIPRSVFNL | 66.613 |
| 6 | GLIPRSVFN | 0.410 |
| 4 | SKGLIPRSV | 0.019 |
| 5 | KGLIPRSVF | 0.003 |
| 2 | YSSKGLIPR | 0.001 |
| 9 | PRSVFNLQI | 0.000 |
| 3 | SSKGLIPRS | 0.000 |
| 8 | IPRSVFNLQ | 0.000 |
| 1 | GYSSKGLIP | 0.000 |

TABLE X-V7

HLA-A0201-9mers-24P4C12
Each peptide is a portion of SEQ ID NO: 15; each start position is specified, the length of peptide is 9 amino acids, and the end position for each peptide is the start position plus eight.

| Start | Subsequence | Score |
|---|---|---|
| 5 | ILVAVGQMM | 8.446 |
| 4 | WILVAVGQM | 3.476 |
| 8 | AVGQMMSTM | 1.000 |
| 7 | VAVGQMMST | 0.405 |
| 1 | SWYWILVAV | 0.071 |
| 6 | LVAVGQMMS | 0.011 |

TABLE X-V7-continued

HLA-A0201-9mers-24P4C12
Each peptide is a portion of SEQ ID NO: 15; each start position is specified, the length of peptide is 9 amino acids, and the end position for each peptide is the start position plus eight.

| Start | Subsequence | Score |
|---|---|---|
| 2 | WYWILVAVG | 0.000 |
| 3 | YWILVAVGQ | 0.000 |

TABLE X-V8

HLA-A0201-9mers-24P4C12
Each peptide is a portion of SEQ ID NO: 17; each start position is specified, the length of peptide is 9 amino acids, and the end position for each peptide is the start position plus eight.

| Start | Subsequence | Score |
|---|---|---|
| 4 | WLPIMRNPI | 47.991 |
| 20 | QTSILGAYV | 5.313 |
| 7 | IMRNPITPT | 1.599 |
| 13 | TPTGHVFQT | 0.649 |
| 15 | TGHVFQTSI | 0.259 |
| 10 | NPITPTGHV | 0.059 |
| 5 | LPIMRNPIT | 0.034 |
| 18 | VFQTSILGA | 0.013 |
| 19 | FQTSILGAY | 0.010 |
| 16 | GHVFQTSIL | 0.006 |
| 12 | ITPTGHVFQ | 0.002 |
| 2 | YYWLPIMRN | 0.001 |
| 17 | HVFQTSILG | 0.001 |
| 9 | RNPITPTGH | 0.000 |
| 6 | PIMRNPITP | 0.000 |
| 11 | PITPTGHVF | 0.000 |
| 14 | PTGHVFQTS | 0.000 |
| 8 | MRNPITPTG | 0.000 |
| 3 | YWLPIMRNP | 0.000 |
| 1 | NYYWLPIMR | 0.000 |

TABLE X-V9

HLA-A0201-9mers-24P4C12
Each peptide is a portion of SEQ ID NO: 19; each start position is specified, the length of peptide is 9 amino acids, and the end position for each peptide is the start position plus eight.

| Start | Subsequence | Score |
|---|---|---|
| 2 | WAMTALYPL | 11.615 |
| 12 | TQPATLGYV | 11.597 |
| 15 | ATLGYVLWA | 3.230 |
| 16 | TLGYVLWAS | 1.285 |
| 8 | YPLPTQPAT | 0.828 |
| 9 | PLPTQPATL | 0.470 |
| 4 | MTALYPLPT | 0.176 |
| 13 | QPATLGYVL | 0.057 |
| 6 | ALYPLPTQP | 0.048 |
| 3 | AMTALYPLP | 0.016 |
| 17 | LGYVLWASN | 0.004 |
| 5 | TALYPLPTQ | 0.002 |
| 18 | GYVLWASNI | 0.001 |
| 7 | LYPLPTQPA | 0.001 |
| 10 | LPTQPATLG | 0.001 |
| 1 | YWAMTALYP | 0.000 |
| 14 | PATLGYVLW | 0.000 |
| 11 | PTQPATLGY | 0.000 |

TABLE XI-V1

HLA-A0201-10mers-24P4C12
Each peptide is a portion of SEQ ID NO: 3; each start position is specified, the length of peptide is 10 amino acids, and the end position for each peptide is the start position plus nine.

| Start | Subsequence | Score |
|---|---|---|
| 354 | TMFYPLVTFV | 2351.109 |
| 85 | YLLYFNIFSC | 1127.969 |
| 579 | MLLMRNIVRV | 1006.209 |
| 603 | KLLVVGGVGV | 900.698 |
| 309 | WLAALIVLAV | 735.860 |
| 351 | MMSTMFYPLV | 486.748 |
| 41 | FLLFILGYIV | 485.348 |
| 641 | IMTSILGAYV | 469.669 |
| 546 | WCLEKFIKFL | 467.771 |
| 597 | LLLFFGKLLV | 437.482 |
| 598 | LLFFGKLLVV | 412.546 |
| 665 | TLFLCFLEDL | 338.500 |
| 241 | VLSLLFILLL | 317.403 |
| 649 | YVIASGFFSV | 308.501 |
| 433 | GLIQRSVFNL | 284.974 |
| 508 | ILTLVQIARV | 271.948 |
| 232 | ILVALGVALV | 271.948 |
| 42 | LLFILGYIVV | 269.051 |
| 339 | ALLKEASKAV | 257.342 |
| 449 | GLFWTLNWVL | 243.051 |
| 244 | LLFILLLRLV | 201.242 |
| 243 | SLLFILLLRL | 181.794 |
| 364 | LLLICIAYWA | 171.868 |
| 48 | YIVVGIVAWL | 170.923 |
| 251 | RLVAGPLVLV | 159.970 |
| 321 | AILLLMLIFL | 137.482 |
| 56 | WLYGDPRQVL | 128.926 |
| 239 | ALVLSLLFIL | 116.840 |
| 350 | QMMSTMFYPL | 108.462 |
| 86 | LLYFNIFSCI | 107.833 |
| 365 | LLICIAYWAM | 95.013 |
| 259 | LVLILGVLGV | 88.043 |
| 162 | LQQELCPSFL | 83.030 |
| 580 | LLMRNIVRVV | 82.509 |
| 94 | CILSSNIISV | 81.385 |
| 517 | VILEYIDHKL | 75.751 |
| 554 | FLNRNAYIMI | 71.986 |
| 686 | YMSKSLLKIL | 66.925 |
| 44 | FILGYIVVGI | 56.155 |
| 133 | SQTVGEVFYT | 55.435 |
| 438 | SVFNLQIYGV | 51.790 |
| 231 | WILVALGVAL | 49.993 |
| 235 | ALGVALVLSL | 49.134 |
| 441 | NLQIYGVLGL | 49.134 |
| 660 | GMCVDTLFLC | 47.864 |
| 325 | LMLIFLRQRI | 47.394 |

TABLE XI-V1-continued

HLA-A0201-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 536 | CIMCCFKCCL | 41.299 |
| 315 | VLAVLEAILL | 36.316 |
| 448 | LGLFWTLNWV | 36.126 |
| 662 | CVDTLFLGFL | 35.941 |
| 64 | VLYPRNSTGA | 27.026 |
| 589 | VVLDKVTDLL | 23.620 |
| 596 | DLLLFFGKLL | 22.527 |
| 240 | LVLSLLFILL | 22.339 |
| 357 | YPLVTFVLLL | 20.744 |
| 267 | GVLAYGIYYC | 20.346 |
| 304 | SVQETWLAAL | 17.627 |
| 248 | LLLRLVAGPL | 17.468 |
| 302 | YQSVQETWLA | 17.378 |
| 501 | SLAFGALILT | 17.140 |
| 317 | AVLEAILLLM | 15.167 |
| 590 | VLDKVTDLLL | 14.526 |
| 45 | ILGYIVVGIV | 14.495 |
| 659 | FGMCVDTLFL | 13.054 |
| 456 | WVLALGQCVL | 13.044 |
| 148 | CLPGVPWNMT | 12.668 |
| 108 | LQCPTPQVCV | 11.988 |
| 478 | KPQDIPTFPL | 11.606 |
| 238 | VALVLSLLFI | 11.529 |
| 312 | ALIVLAVLEA | 11.426 |
| 459 | ALGQCVLAGA | 11.426 |
| 571 | CVSAKNAFML | 10.841 |
| 563 | IAIYGKNFCV | 9.525 |
| 445 | YGVLGLFWTL | 9.141 |
| 379 | LATSGQPQYV | 9.032 |
| 327 | LIFLRQRIRI | 9.023 |
| 249 | LLRLVAGPLV | 8.986 |
| 539 | CCFKCGLWCL | 8.900 |
| 513 | QIARVILEYI | 8.892 |
| 510 | TLVQIARVIL | 8.759 |
| 457 | VLALGQCVLA | 8.446 |
| 95 | ILSSNIISVA | 7.964 |

TABLE XI-V1-continued

HLA-A0201-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 657 | SVFGMCVDTL | 7.794 |
| 225 | FAQSWYWILV | 7.554 |
| 588 | VVVLDKVTDL | 7.309 |
| 593 | KVTDLLLFFG | 6.865 |
| 368 | CIAYWAMTAL | 6.756 |
| 562 | MIAIYGKNFC | 6.387 |
| 363 | VLLLICIAYW | 5.929 |
| 36 | ICCVLFLLFI | 5.565 |
| 318 | VLEAILLLML | 5.346 |
| 292 | QLGFTTNLSA | 4.968 |
| 314 | IVLAVLEAIL | 4.821 |
| 393 | NISSPGCEKV | 4.686 |
| 506 | ALILTLVQIA | 4.685 |
| 260 | VLILGVLGVL | 4.452 |
| 604 | LLVVGGVGVL | 4.452 |
| 261 | LILGVLGVLA | 4.297 |
| 502 | LAFGALILTL | 4.292 |
| 147 | FCLPGVPWNM | 4.140 |

TABLE XI-V3

HLA-A0201-10mers-24P4C12
Each peptide is a portion of SEQ ID NO: 7;
each start position is specified, the length
of peptide is 10 amino acids, and the end
position for each peptide is the start
position plus nine.

| Start | Subsequence | Score |
|---|---|---|
| 9 | NITPPALPGI | 3.299 |
| 5 | FPWTNITPPA | 1.238 |
| 1 | LGRCFPWTNI | 0.015 |
| 10 | ITPPALPGIT | 0.009 |
| 7 | WTNITPPALP | 0.001 |
| 8 | TNITPPALPG | 0.000 |
| 2 | GRCFPWTNIT | 0.000 |
| 3 | RCFPWTNITP | 0.000 |
| 6 | PWTNITPPAL | 0.000 |
| 4 | CFPWTNITPP | 0.000 |

TABLE XI-V5

HLA-A0201-10mers-24P4C12
Each peptide is a portion of SEQ ID NO: 11;
each start position is specified, the length
of peptide is 10 amino acids, and the end
position for each peptide is the start
position plus nine.

| Start | Subsequence | Score |
|---|---|---|
| 1 | AVLEAILLLV | 212.340 |
| 5 | AILLLVLIFL | 137.482 |
| 9 | LVLIFLRQRI | 5.742 |
| 2 | VLEAILLLVL | 2.192 |
| 6 | ILLLVLIFLR | 1.251 |
| 3 | LEAILLLVLI | 0.793 |
| 7 | LLLVLIFLRQ | 0.178 |
| 8 | LLVLIFLRQR | 0.044 |
| 10 | VLIFLRQRIR | 0.002 |
| 4 | EAILLLVLIF | 0.000 |

TABLE XI-V6

HLA-A0201-10mers-24P4C12
Each peptide is a portion of SEQ ID NO: 13;
each start position is specified, the length
of peptide is 10 amino acids, and the end
position for each peptide is the start
position plus nine.

| Start | Subsequence | Score |
|---|---|---|
| 7 | GLIPRSVFNL | 284.974 |
| 6 | KGLIPRSVFN | 0.035 |
| 9 | IPRSVFNLQI | 0.033 |
| 8 | LIPRSVFNLQ | 0.007 |
| 3 | YSSKGLIPRS | 0.005 |
| 4 | SSKGLIPRSV | 0.003 |
| 1 | QGYSSKGLIP | 0.000 |
| 5 | SKGLIPRSVF | 0.000 |
| 2 | GYSSKGLIPR | 0.000 |
| 10 | PRSVFNLQIY | 0.000 |

TABLE XI-V7

HLA-A0201-10mers-24P4C12
Each peptide is a portion of SEQ ID NO: 15;
each start position is specified, the length
of peptide is 10 amino acids, and the end
position for each peptide is the start
position plus nine.

| Start | Subsequence | Score |
|---|---|---|
| 5 | WILVAVGQMM | 11.626 |
| 1 | QSWYWILVAV | 8.667 |

TABLE XI-V7-continued

HLA-A0201-10mers-24P4C12
Each peptide is a portion of SEQ ID NO: 15;
each start position is specified, the length
of peptide is 10 amino acids, and the end
position for each peptide is the start
position plus nine.

| Start | Subsequence | Score |
|---|---|---|
| 7 | LVAVGQMMST | 2.550 |
| 8 | VAVGQMMSTM | 0.270 |
| 6 | ILVAVGQMMS | 0.127 |
| 9 | AVGQMMSTMF | 0.007 |
| 4 | YWILVAVGQM | 0.001 |
| 3 | WYWILVAVGQ | 0.000 |
| 2 | SWYWILVAVG | 0.000 |

TABLE XI-V8

HLA-A0201-10mers-24P4C12
Each peptide is a portion of SEQ ID NO: 17;
each start position is specified, the length
of peptide is 10 amino acids, and the end
position for each peptide is the start
position plus nine.

| Start | Subsequence | Score |
|---|---|---|
| 20 | FQTSILGAYV | 178.411 |
| 5 | WLPIMRNPIT | 14.054 |
| 13 | ITPTGHVFQT | 2.347 |
| 7 | PIMRNPITPT | 0.192 |
| 18 | HVFQTSILGA | 0.126 |
| 21 | QTSILGAYVI | 0.059 |
| 10 | RNPITPTGHV | 0.059 |
| 16 | TGHVFQTSIL | 0.057 |
| 4 | YWLPIMRNPI | 0.025 |
| 15 | PTGHVFQTSI | 0.012 |
| 8 | IMRNPITPTG | 0.007 |
| 14 | TPTGHVFQTS | 0.001 |
| 1 | LNYYWLPIMR | 0.001 |
| 12 | PITPTGHVFQ | 0.000 |
| 11 | NPITPTGHVF | 0.000 |
| 6 | LPIMRNPITP | 0.000 |
| 2 | NYYWLPIMRN | 0.000 |
| 17 | GHVFQTSILG | 0.000 |
| 3 | YYWLPIMRNP | 0.000 |
| 19 | VFQTSILGAY | 0.000 |
| 9 | MRNPITPTGH | 0.000 |

TABLE XI-V9

HLA-A0201-10mers-24P4C12
Each peptide is a portion of SEQ ID NO: 19;
each start position is specified, the length
of peptide is 10 amino acids, and the end
position for each peptide is the start
position plus nine.

| Start | Subsequence | Score |
|---|---|---|
| 7 | ALYPLPTQPA | 15.898 |
| 4 | AMTALYPLPT | 5.382 |
| 9 | YPLPTQPATL | 2.373 |
| 13 | TQPATLGYVL | 0.888 |
| 18 | LGYVLWASNI | 0.370 |
| 17 | TLGYVLWASN | 0.127 |
| 16 | ATLGYVLWAS | 0.066 |
| 12 | PTQPATLGYV | 0.035 |
| 2 | YWAMTALYPL | 0.031 |
| 15 | PATLGYVLWA | 0.019 |
| 3 | WAMTALYPLP | 0.005 |
| 8 | LYPLPTQPAT | 0.002 |
| 10 | PLPTQPATLG | 0.002 |
| 11 | LPTQPATLGY | 0.001 |
| 5 | MTALYPLPTQ | 0.001 |
| 6 | TALYPLPTQP | 0.001 |
| 14 | QPATLGYVLW | 0.001 |
| 1 | AYWAMTALYP | 0.000 |
| 19 | GYVLWASNIS | 0.000 |

TABLE XII-V1

HLA-A3-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 421 | GLMCVFQGY | 81.000 |
| 135 | TVGEVFYTK | 40.500 |
| 207 | GLIDSLNAR | 27.000 |
| 323 | LLLMLIFLR | 27.000 |
| 243 | SLLFILLLR | 27.000 |
| 354 | TMFYPLVTF | 22.500 |
| 690 | SLLKILGKK | 20.250 |
| 517 | VILEYIDHK | 20.250 |
| 363 | VLLLICIAY | 18.000 |
| 585 | IVRVVVLDK | 18.000 |

TABLE XII-V1-continued

HLA-A3-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 560 | YIMIAIYGK | 13.500 |
| 508 | ILTLVQIAR | 12.000 |
| 579 | MLLMRNIVR | 12.000 |
| 267 | GVLAYGIYY | 10.800 |
| 424 | CVFQGYSSK | 10.000 |
| 244 | LLFILLLRL | 9.000 |
| 464 | VLAGAFASF | 9.000 |
| 272 | GIYYCWEEY | 6.000 |
| 351 | MMSTMFYPL | 5.400 |
| 470 | ASFYWAFHK | 4.500 |
| 449 | GLFWTLNWV | 4.500 |
| 86 | LLYFNIFSC | 4.500 |
| 446 | GVLGLFWTL | 3.645 |
| 660 | GMCVDTLFL | 3.600 |
| 633 | HLNYYWLPI | 3.600 |
| 542 | KCCLWCLEK | 3.600 |
| 241 | VLSLLFILL | 3.600 |
| 42 | LLFILGYIV | 3.000 |
| 393 | NISSPGCEK | 3.000 |
| 325 | LMLIFLRQR | 2.700 |
| 45 | ILGYIVVGI | 2.700 |
| 322 | ILLLMLIFL | 2.700 |
| 239 | ALVLSLLFI | 2.700 |
| 641 | IMTSILGAY | 2.700 |
| 598 | LLFFGKLLV | 2.000 |
| 260 | VLILGVLGV | 1.800 |
| 265 | VLGVLAYGI | 1.800 |
| 513 | QIARVILEY | 1.800 |
| 609 | GVGVLSFFF | 1.800 |
| 537 | IMCCFKCCL | 1.800 |
| 50 | VVGIVAWLY | 1.800 |
| 686 | YMSKSLLKI | 1.800 |
| 251 | RLVAGPLVL | 1.800 |
| 593 | KVTDLLLFF | 1.800 |
| 358 | PLVTFVLLL | 1.620 |

TABLE XII-V1-continued

HLA-A3-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 544 | CLWCLEKFI | 1.500 |
| 689 | KSLLKILGK | 1.350 |
| 525 | KLRGVQNPV | 1.350 |
| 170 | FLLPSAPAL | 1.350 |
| 547 | CLEKFIKFL | 1.350 |
| 597 | LLLFFGKLL | 1.350 |
| 365 | LLICIAYWA | 1.350 |
| 506 | ALILTLVQI | 1.350 |
| 148 | CLPGVPWNM | 1.350 |
| 501 | SLAFGALIL | 1.200 |
| 662 | CVDTLFLCF | 1.200 |
| 349 | GQMMSTMFY | 1.080 |
| 443 | QIYGVLGLF | 1.012 |
| 321 | AILLLMLIF | 0.900 |
| 590 | VLDKVTDLL | 0.900 |
| 326 | MLIFLRQRI | 0.900 |
| 268 | VLAYGIYYC | 0.900 |
| 107 | GLQCPTPQV | 0.900 |
| 613 | LSFFFFSGR | 0.900 |
| 318 | VLEAILLLM | 0.900 |
| 232 | ILVALGVAL | 0.900 |
| 518 | ILEYIDHKL | 0.900 |
| 452 | WTLNWVLAL | 0.810 |
| 596 | DLLLFFGKL | 0.729 |
| 645 | ILGAYVIAS | 0.720 |
| 258 | VLVLILGVL | 0.608 |
| 49 | IVVGIVAWL | 0.608 |
| 41 | FLLFILGYI | 0.608 |
| 54 | VAWLYGDPR | 0.600 |
| 665 | TLFLCFLED | 0.600 |
| 95 | ILSSNIISV | 0.600 |
| 457 | VLALGQCVL | 0.600 |
| 282 | VLRDKGASI | 0.600 |
| 554 | FLNRNAYIM | 0.600 |
| 39 | VLFLLFILG | 0.600 |
| 315 | VLAVLEAIL | 0.600 |

TABLE XII-V1-continued

HLA-A3-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 638 | WLPIMTSIL | 0.600 |
| 434 | LIQRSVFNL | 0.540 |
| 612 | VLSFFFFSG | 0.540 |
| 611 | GVLSFFFFS | 0.486 |
| 647 | GAYVIASGF | 0.450 |
| 580 | LLMRNIVRV | 0.450 |
| 364 | LLLICIAYW | 0.450 |
| 564 | AIYGKNFCV | 0.450 |
| 237 | GVALVLSLL | 0.450 |
| 38 | CVLFLLFIL | 0.405 |
| 204 | GISGLIDSL | 0.405 |
| 35 | VICCVLFLL | 0.405 |
| 317 | AVLEAILLL | 0.405 |
| 240 | LVLSLLFIL | 0.405 |
| 668 | LCFLEDLER | 0.400 |
| 388 | VLWASNISS | 0.400 |
| 489 | SAFIRTLRY | 0.400 |
| 211 | SLNARDISV | 0.400 |
| 85 | YLLYFNIFS | 0.360 |

TABLE XII-V3

HLA-A3-9mers-24P4C12
Each peptide is a portion of SEQ ID NO: 7;
each start position is specified, the length
of peptide is 9 amino acids, and the end
position for each peptide is the start
position plus eight.

| Start | Subsequence | Score |
|---|---|---|
| 9 | ITPPALPGI | 0.068 |
| 6 | WTNITPPAL | 0.030 |
| 2 | RCFPWTNIT | 0.022 |
| 8 | NITPPALPG | 0.009 |
| 1 | GRCFPWTNI | 0.003 |
| 4 | FPWTNITPP | 0.002 |
| 7 | TNITPPALP | 0.000 |
| 3 | CFPWTNITP | 0.000 |
| 5 | PWTNITPPA | 0.000 |

TABLE XII-V5

HLA-A3-9mers-24P4C12
Each peptide is a portion of SEQ ID NO: 11;
each start position is specified, the length
of peptide is 9 amino acids, and the end
position for each peptide is the start
position plus eight.

| Start | Subsequence | Score |
|---|---|---|
| 6 | LLLVLIFLR | 27.000 |
| 5 | ILLLVLIFL | 4.050 |
| 4 | AILLLVLIF | 1.800 |
| 9 | VLIFLRQRI | 0.900 |
| 1 | VLEAILLLV | 0.900 |
| 7 | LLVLIFLRQ | 0.270 |
| 8 | LVLIFLRQR | 0.270 |
| 2 | LEAILLLVL | 0.005 |
| 3 | EAILLLVLI | 0.004 |

TABLE XII-V6

HLA-A3-9mers-24P4C12
Each peptide is a portion of SEQ ID NO: 13;
each start position is specified, the length
of peptide is 9 amino acids, and the end
position for each peptide is the start
position plus eight.

| Start | Subsequence | Score |
|---|---|---|
| 7 | LIPRSVFNL | 0.540 |
| 6 | GLIPRSVFN | 0.135 |
| 2 | YSSKGLIPR | 0.060 |
| 5 | KGLIPRSVF | 0.013 |
| 8 | IPRSVFNLQ | 0.001 |
| 3 | SSKGLIPRS | 0.000 |
| 9 | PRSVFNLQI | 0.000 |
| 1 | GYSSKGLIP | 0.000 |
| 4 | SKGLIPRSV | 0.000 |

TABLE XII-V7

HLA-A3-9mers-24P4C12
Each peptide is a portion of SEQ ID NO: 15;
each start position is specified, the length
of peptide is 9 amino acids, and the end
position for each peptide is the start
position plus eight.

| Start | Subsequence | Score |
|---|---|---|
| 5 | ILVAVGQMM | 0.450 |
| 8 | AVGQMMSTM | 0.030 |
| 4 | WILVAVGQM | 0.027 |
| 6 | LVAVGQMMS | 0.008 |

TABLE XII-V7-continued

HLA-A3-9mers-24P4C12
Each peptide is a portion of SEQ ID NO: 15;
each start position is specified, the length
of peptide is 9 amino acids, and the end
position for each peptide is the start
position plus eight.

| Start | Subsequence | Score |
|---|---|---|
| 7 | VAVGQMMST | 0.007 |
| 1 | SWYWILVAV | 0.002 |
| 2 | WYWILVAVG | 0.000 |
| 3 | YWILVAVGQ | 0.000 |

TABLE XII-V8

HLA-A3-9mers-24P4C12
Each peptide is a portion of SEQ ID NO: 17;
each start position is specified, the length
of peptide is 9 amino acids, and the end
position for each peptide is the start
position plus eight.

| Start | Subsequence | Score |
|---|---|---|
| 4 | WLPIMRNPI | 0.600 |
| 7 | IMRNPITPT | 0.225 |
| 19 | FQTSILGAY | 0.081 |
| 1 | NYYWLPIMR | 0.040 |
| 11 | PITPTGHVF | 0.030 |
| 17 | HVFQTSILG | 0.020 |
| 13 | TPTGHVFQT | 0.013 |
| 20 | QTSILGAYV | 0.010 |
| 16 | GHVFQTSIL | 0.003 |
| 15 | TGHVFQTSI | 0.002 |
| 5 | LPIMRNPIT | 0.002 |
| 10 | NPITPTGHV | 0.001 |
| 12 | ITPTGHVFQ | 0.001 |
| 14 | PTGHVFQTS | 0.001 |
| 18 | VFQTSILGA | 0.001 |
| 6 | PIMRNPITP | 0.001 |
| 2 | YYWLPIMRN | 0.000 |
| 9 | RNPITPTGH | 0.000 |
| 8 | MRNPITPTG | 0.000 |
| 3 | YWLPIMRNP | 0.000 |

TABLE XII-V9

HLA-A3-9mers-24P4C12
Each peptide is a portion of SEQ ID NO: 19;
each start position is specified, the length
of peptide is 9 amino acids, and the end
position for each peptide is the start

| Start | Subsequence | Score |
|---|---|---|
| 15 | ATLGYVLWA | 0.405 |
| 16 | TLGYVLWAS | 0.270 |
| 6 | ALYPLPTQP | 0.150 |
| 11 | PTQPATLGY | 0.060 |
| 9 | PLPTQPATL | 0.060 |
| 2 | WAMTALYPL | 0.041 |
| 4 | MTALYPLPT | 0.030 |
| 3 | AMTALYPLP | 0.020 |
| 13 | QPATLGYVL | 0.018 |
| 18 | GYVLWASNI | 0.008 |
| 12 | TQPATLGYV | 0.003 |
| 8 | YPLPTQPAT | 0.002 |
| 5 | TALYPLPTQ | 0.001 |
| 7 | LYPLPTQPA | 0.000 |
| 10 | LPTQPATLG | 0.000 |
| 14 | PATLGYVLW | 0.000 |
| 17 | LGYVLWASN | 0.000 |
| 1 | YWAMTALYP | 0.000 |

TABLE XIII-V1

HLA-A3-10mers-24P4C12
Each peptide is a portion of SEQ ID NO: 3; each start position is specified, the length of peptide is 10 amino acids, and the end position for each peptide is the start position plus nine.

| Start | Subsequence | Score |
|---|---|---|
| 544 | CLWCLEKFIK | 300.000 |
| 39 | VLFLLFILGY | 180.000 |
| 680 | SLDRPYYMSK | 120.000 |
| 612 | VLSFFFFSGR | 36.000 |
| 134 | QTVGEVFYTK | 30.375 |
| 211 | SLNARDISVK | 30.000 |
| 449 | GLFWTLNWVL | 27.000 |
| 322 | ILLLMLIFLR | 27.000 |
| 584 | NIVRVVVLDK | 27.000 |
| 433 | GLIQRSVFNL | 24.300 |
| 262 | ILGVLGVLAY | 24.000 |
| 272 | GIYYCWEEYR | 18.000 |
| 464 | VLAGAFASFY | 18.000 |
| 665 | TLFLCFLEDL | 13.500 |

TABLE XIII-V1-continued

HLA-A3-10mers-24P4C12
Each peptide is a portion of SEQ ID NO: 3; each start position is specified, the length of peptide is 10 amino acids, and the end position for each peptide is the start position plus nine.

| Start | Subsequence | Score |
|---|---|---|
| 516 | RVILEYIDHK | 13.500 |
| 86 | LLYFNIFSCI | 13.500 |
| 171 | LLPSAPALGR | 12.000 |
| 578 | FMLLMRNIVR | 12.000 |
| 76 | GMGENKDKPY | 9.000 |
| 594 | VTDLLLFFGK | 9.000 |
| 350 | QMMSTMFYPL | 8.100 |
| 667 | FKCFLEDLER | 8.000 |
| 56 | WLYGDPRQVL | 6.750 |
| 333 | RIRIAIALLK | 6.000 |
| 609 | GVGVLSFFFF | 5.400 |
| 241 | VLSLLFILLL | 5.400 |
| 561 | IMIAIYGKNF | 4.500 |
| 239 | ALVLSLLFIL | 4.050 |
| 49 | IVVGIVAWLY | 4.050 |
| 378 | YLATSGQPQY | 4.000 |
| 441 | NLQIYGVLGL | 3.600 |
| 235 | ALGVALVLSL | 3.600 |
| 598 | LLFFGKLLVV | 3.000 |
| 621 | RIPGLGKDFK | 3.000 |
| 354 | TMFYPLVTFV | 3.000 |
| 72 | GAYCGMGENK | 3.000 |
| 324 | LLMLIFLRQR | 2.700 |
| 660 | GMCVDTLFLC | 2.700 |
| 467 | GAFASFYWAF | 2.700 |
| 243 | SLLFILLLRL | 2.700 |
| 83 | KPYLLYFNIF | 2.700 |
| 42 | LLFILGYIVV | 2.000 |
| 518 | ILEYIDHKLR | 2.000 |
| 161 | SLQQELCPSF | 2.000 |
| 337 | AIALLKEASK | 2.000 |
| 362 | FVLLLICIAY | 1.800 |
| 650 | VIASGFFSVF | 1.800 |
| 606 | VVGGVGVLSF | 1.800 |
| 507 | LILTLVQIAR | 1.800 |
| 329 | FLRQRIRIAI | 1.800 |

TABLE XIII-V1-continued

HLA-A3-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 318 | VLEAILLLML | 1.800 |
| 624 | GLGKDFKSPH | 1.800 |
| 309 | WLAALIVLAV | 1.800 |
| 312 | ALIVLAVLEA | 1.800 |
| 469 | FASFYWAFHK | 1.800 |
| 64 | VLYPRNSTGA | 1.500 |
| 364 | LLLICIAYWA | 1.350 |
| 657 | SVFGMCVDTL | 1.350 |
| 85 | YLLYFNIFSC | 1.350 |
| 220 | KIFEDFAQSW | 1.350 |
| 264 | GVLGVLAYGI | 1.215 |
| 315 | VLAVLEAILL | 1.200 |
| 237 | GVALVLSLLF | 1.200 |
| 554 | FLNRNAYIMI | 1.200 |
| 590 | VLDKVTDLLL | 1.200 |
| 265 | VLGVLAYGIY | 1.200 |
| 35 | VICCVLFLLF | 1.200 |
| 53 | IVAWLYGDPR | 1.200 |
| 447 | VLGLFWTLNW | 1.200 |
| 268 | VLAYGIYYCW | 0.900 |
| 413 | HLVNSSCPGL | 0.900 |
| 275 | YCWEEYRVLR | 0.900 |
| 232 | ILVALGVALV | 0.900 |
| 325 | LMLIFLRQRI | 0.900 |
| 463 | CVLAGAFASF | 0.900 |
| 525 | KLRGVQNPVA | 0.900 |
| 506 | ALILTLVQIA | 0.900 |
| 603 | KLLVVGGVGV | 0.900 |
| 633 | HLNYYWLPIM | 0.900 |
| 510 | TLVQIARVIL | 0.900 |
| 365 | LLICIAYWAM | 0.900 |
| 41 | FLLFILGYIV | 0.900 |
| 512 | VQIARVILEY | 0.810 |
| 604 | LLVVGGVGVL | 0.810 |
| 251 | RLVAGPLVLV | 0.675 |

TABLE XIII-V1-continued

HLA-A3-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 260 | VLILGVLGVL | 0.608 |
| 44 | FILGYIVVGI | 0.608 |
| 107 | GLQCPTPQVC | 0.600 |
| 327 | LIFLRQRIRI | 0.600 |
| 326 | MLIFLRQRIR | 0.600 |
| 597 | LLLFFGKLLV | 0.600 |
| 487 | LISAFIRTLR | 0.600 |
| 120 | CPEDPWTVGK | 0.600 |
| 351 | MMSTMFYPLV | 0.600 |
| 240 | LVLSLLFILL | 0.540 |
| 252 | LVAGPLVLVL | 0.540 |
| 360 | VTFVLLLICI | 0.450 |
| 363 | VLLLICIAYW | 0.450 |
| 579 | MLLMRNIVRV | 0.450 |
| 95 | ILSSNIISVA | 0.450 |

TABLE XIII-V3

HLA-A3-10mers-24P4C12
Each peptide is a portion of SEQ ID NO: 7;
each start position is specified, the length
of peptide is 10 amino acids, and the end
position for each peptide is the start
position plus nine.

| Start | Subsequence | Score |
|---|---|---|
| 9 | NITPPALPGI | 0.135 |
| 5 | FPWTNITPPA | 0.015 |
| 3 | RCFPWTNITP | 0.003 |
| 10 | ITPPALPGIT | 0.002 |
| 7 | WTNITPPALP | 0.002 |
| 1 | LGRCFPWTNI | 0.001 |
| 2 | GRCFPWTNIT | 0.001 |
| 8 | TNITPPALPG | 0.000 |
| 6 | PWTNITPPAL | 0.000 |
| 4 | CFPWTNITPP | 0.000 |

TABLE XIII-V5

HLA-A3-10mers-24P4C12
Each peptide is a portion of SEQ ID NO: 11;
each start position is specified, the length of peptide is 10 amino acids, and the end position for each peptide is the start position plus nine.

| Start | Subsequence | Score |
|---|---|---|
| 6 | ILLLVLIFLR | 27.000 |
| 8 | LLVLIFLRQR | 2.700 |
| 2 | VLEAILLLVL | 1.800 |
| 10 | VLIFLRQRIR | 0.600 |
| 5 | AILLLVLIFL | 0.405 |
| 7 | LLLVLIFLRQ | 0.270 |
| 1 | AVLEAILLLV | 0.203 |
| 9 | LVLIFLRQRI | 0.090 |
| 4 | EAILLLVLIF | 0.054 |
| 3 | LEAILLLVLI | 0.003 |

TABLE XIII-V6

HLA-A3-10mers-24P4C12
Each peptide is a portion of SEQ ID NO: 13; each start position is specified, the length of peptide is 10 amino acids, and the end position for each peptide is the start position plus nine.

| Start | Subsequence | Score |
|---|---|---|
| 7 | GLIPRSVFNL | 36.450 |
| 2 | GYSSKGLIPR | 0.036 |
| 9 | IPRSVFNLQI | 0.036 |
| 8 | LIPRSVFNLQ | 0.009 |
| 5 | SKGLIPRSVF | 0.003 |
| 10 | PRSVFNLQIY | 0.001 |
| 3 | YSSKGLIPRS | 0.000 |
| 4 | SSKGLIPRSV | 0.000 |
| 1 | QGYSSKGLIP | 0.000 |
| 6 | KGLIPRSVFN | 0.000 |

TABLE XIII-V7

HLA-A3-10mers-24P4C12
Each peptide is a portion of SEQ ID NO: 15; each start position is specified, the length of peptide is 10 amino acids, and the end position for each peptide is the start position plus nine.

| Start | Subsequence | Score |
|---|---|---|
| 9 | AVGQMMSTMF | 0.200 |
| 6 | ILVAVGQMMS | 0.120 |
| 5 | WILVAVGQMM | 0.045 |
| 7 | LVAVGQMMST | 0.030 |
| 1 | QSWYWILVAV | 0.011 |

TABLE XIII-V7-continued

HLA-A3-10mers-24P4C12
Each peptide is a portion of SEQ ID NO: 15; each start position is specified, the length of peptide is 10 amino acids, and the end position for each peptide is the start position plus nine.

| Start | Subsequence | Score |
|---|---|---|
| 8 | VAVGQMMSTM | 0.007 |
| 2 | SWYWILVAVG | 0.000 |
| 4 | YWILVAVGQM | 0.000 |
| 3 | WYWILVAVGQ | 0.000 |

TABLE XIII-V8

HLA-A3-10mers-24P4C12
Each peptide is a portion of SEQ ID NO: 17; each start position is specified, the length of peptide is 10 amino acids, and the end position for each peptide is the start position plus nine.

| Start | Subsequence | Score |
|---|---|---|
| 18 | HVFQTSILGA | 0.300 |
| 5 | WLPIMRNPIT | 0.100 |
| 21 | QTSILGAYVI | 0.090 |
| 1 | LNYYWLPIMR | 0.080 |
| 13 | ITPTGHVFQT | 0.045 |
| 11 | NPITPTGHVF | 0.030 |
| 8 | IMRNPITPTG | 0.030 |
| 15 | PTGHVFQTSI | 0.009 |
| 20 | FQTSILGAYV | 0.006 |
| 7 | PIMRNPITPT | 0.003 |
| 14 | TPTGHVFQTS | 0.003 |
| 19 | VFQTSILGAY | 0.003 |
| 4 | YWLPIMRNPI | 0.001 |
| 6 | LPIMRNPITP | 0.001 |
| 16 | TGHVFQTSIL | 0.001 |
| 2 | NYYWLPIMRN | 0.000 |
| 9 | MRNPITPTGH | 0.000 |
| 12 | PITPTGHVFQ | 0.000 |
| 17 | GHVFQTSILG | 0.000 |
| 10 | RNPITPTGHV | 0.000 |
| 3 | YYWLPIMRNP | 0.000 |

TABLE XIII-V9

HLA-A3-10mers-24P4C12
Each peptide is a portion of SEQ ID NO: 19;

each start position is specified, the length of peptide is 10 amino acids, and the end position for each peptide is the start position plus nine.

| Start | Subsequence | Score |
|---|---|---|
| 7 | ALYPLPTQPA | 2.250 |
| 4 | AMTALYPLPT | 0.600 |
| 11 | LPTQPATLGY | 0.080 |
| 13 | TQPATLGYVL | 0.054 |
| 16 | ATLGYVLWAS | 0.030 |
| 17 | TLGYVLWASN | 0.020 |
| 9 | YPLPTQPATL | 0.013 |
| 18 | LGYVLWASNI | 0.009 |
| 15 | PATLGYVLWA | 0.004 |
| 10 | PLPTQPATLG | 0.003 |
| 2 | YWAMTALYPL | 0.003 |
| 5 | MTALYPLPTQ | 0.002 |
| 14 | QPATLGYVLW | 0.002 |
| 12 | PTQPATLGYV | 0.001 |
| 6 | TALYPLPTQP | 0.000 |
| 3 | WAMTALYPLP | 0.000 |
| 1 | AYWAMTALYP | 0.000 |
| 19 | GYVLWASNIS | 0.000 |
| 8 | LYPLPTQPAT | 0.000 |

TABLE XIV-V1

HLA-A1101-9mers-24P4C12
Each peptide is a portion of SEQ ID NO: 3; each start position is specified, the length of peptide is 9 amino acids, and the end position for each peptide is the start position plus nine.

| Start | Subsequence | Score |
|---|---|---|
| 135 | TVGEVFYTK | 4.000 |
| 585 | IVRVVVLDK | 4.000 |
| 424 | CVFQGYSSK | 4.000 |
| 560 | YIMIAIYGK | 1.600 |
| 685 | YYMSKSLLK | 1.600 |
| 542 | KCCLWCLEK | 1.200 |
| 690 | SLLKILGKK | 0.600 |
| 517 | VILEYIDHK | 0.600 |
| 73 | AYCGMGENK | 0.400 |
| 393 | NISSPGCEK | 0.400 |
| 207 | GLIDSLNAR | 0.360 |
| 323 | LLLMLIFLR | 0.360 |

TABLE XIV-V1-continued

HLA-A1101-9mers-24P4C12
Each peptide is a portion of SEQ ID NO: 3; each start position is specified, the length of peptide is 9 amino acids, and the end position for each peptide is the start position plus nine.

| Start | Subsequence | Score |
|---|---|---|
| 338 | IALLKEASK | 0.300 |
| 579 | MLLMRNIVR | 0.240 |
| 243 | SLLFILLLR | 0.240 |
| 622 | IPGLGKDFK | 0.200 |
| 689 | KSLLKILGK | 0.180 |
| 516 | RVILEYIDH | 0.180 |
| 609 | GVGVLSFFF | 0.180 |
| 485 | FPLISAFIR | 0.180 |
| 446 | GFLGLFWTL | 0.180 |
| 267 | GVLAYGIYY | 0.180 |
| 273 | IYYCWEEYR | 0.160 |
| 508 | ILTLVQIAR | 0.160 |
| 668 | LCFLEDLER | 0.160 |
| 698 | KNEAPPDNK | 0.120 |
| 470 | ASFYWAFHK | 0.120 |
| 593 | KVTDLLLFF | 0.120 |
| 701 | APPDNKKRK | 0.100 |
| 595 | TDLLLFFGK | 0.090 |
| 38 | CVLFLLFIL | 0.090 |
| 240 | LVLSLLFIL | 0.090 |
| 54 | VAWLYGDPR | 0.080 |
| 172 | LPSAPALGR | 0.080 |
| 349 | GQMMSTMFY | 0.072 |
| 334 | IRIAIALLK | 0.060 |
| 545 | LWCLEKFIK | 0.060 |
| 567 | GKNFCVSAK | 0.060 |
| 317 | AVLEAILLL | 0.060 |
| 699 | NEAPPDNKK | 0.060 |
| 151 | GVPWNMTVI | 0.060 |
| 237 | GVALVLSLL | 0.060 |
| 257 | LVLVLILGV | 0.060 |
| 20 | DPSFRGPIK | 0.060 |
| 575 | KNAFMLLMR | 0.048 |
| 212 | LNARDISVK | 0.040 |
| 359 | KVTFVLLLI | 0.040 |

TABLE XIV-V1-continued

HLA-A1101-9mers-24P4C12
Each peptide is a portion of SEQ ID NO: 3;
each start position is specified, the length
of peptide is 9 amino acids, and the end
position for each peptide is the start
position plus nine.

| Start | Subsequence | Score |
|---|---|---|
| 16 | PVKYDPSFR | 0.040 |
| 304 | SVQETWLAA | 0.040 |
| 619 | SGRIPGLGK | 0.040 |
| 50 | VVGIVAWLY | 0.040 |
| 681 | LDRPYYMSK | 0.040 |
| 662 | CVDTLFLCF | 0.040 |
| 7 | DEDDEAYGK | 0.036 |
| 83 | KPYLLYFNI | 0.036 |
| 47 | GYIVVGIVA | 0.036 |
| 251 | RLVAGPLVL | 0.036 |
| 383 | GQPQYVLWA | 0.036 |
| 49 | IVVGIVAWL | 0.030 |
| 314 | IVLAVLEAI | 0.030 |
| 456 | WVLALGQCV | 0.030 |
| 589 | VVLDKVTDL | 0.030 |
| 452 | WTLNWVLAL | 0.030 |
| 141 | YTKNRNFCL | 0.030 |
| 498 | HTGSLAFGA | 0.030 |
| 605 | LVVGGVGVL | 0.030 |
| 362 | FVLLLICIA | 0.030 |
| 611 | GVLSFFFFS | 0.027 |
| 137 | GEVFYTKNR | 0.027 |
| 564 | AIYGKNFCV | 0.024 |
| 272 | GIYYCWEEY | 0.024 |
| 60 | DPRQVLYPR | 0.024 |
| 421 | GLMCVFQGY | 0.024 |
| 467 | GAFASFYWA | 0.024 |
| 449 | GLFWTLNWV | 0.024 |
| 660 | GMCVDTLFL | 0.024 |
| 496 | RYHTGSLAF | 0.024 |
| 511 | LVQIARVIL | 0.020 |
| 218 | SVKIFEDFA | 0.020 |
| 233 | LVALGVALV | 0.020 |
| 22 | SFRGPIKNR | 0.020 |
| 75 | CGMGENKDK | 0.020 |
| 414 | LVNSSCPGL | 0.020 |

TABLE XIV-V1-continued

HLA-A1101-9mers-24P4C12
Each peptide is a portion of SEQ ID NO: 3;
each start position is specified, the length
of peptide is 9 amino acids, and the end
position for each peptide is the start
position plus nine.

| Start | Subsequence | Score |
|---|---|---|
| 252 | LVAGPLVLV | 0.020 |
| 571 | CVSAKNAFM | 0.020 |
| 347 | AVGQMMSTM | 0.020 |
| 534 | ARCIMCCFK | 0.020 |
| 527 | RGVQNPVAR | 0.018 |
| 34 | DVICCVLFL | 0.018 |
| 693 | KILGKKNEA | 0.018 |
| 461 | GQCVLAGAF | 0.018 |
| 4 | KQRDEDDEA | 0.018 |
| 331 | RQRIRIAIA | 0.018 |
| 10 | DEAYGKPVK | 0.018 |
| 442 | LQIYGVLGL | 0.018 |
| 255 | GPLVLVLIL | 0.018 |
| 598 | LLFFGKLLV | 0.016 |
| 42 | LLFILGYIV | 0.016 |
| 244 | LLFILLLRL | 0.016 |
| 327 | LIFLRQRIR | 0.016 |

TABLE XIV-V3

HLA-A1101-9mers-24P4C12
Each peptide is a portion of SEQ ID NO: 7;
each start position is specified, the length
of peptide is 9 amino acids, and the end
position for each peptide is the start
position plus eight.

| Start | Subsequence | Score |
|---|---|---|
| 9 | ITPPALPGI | 0.010 |
| 6 | WTNITPPAL | 0.010 |
| 2 | RCFPWTNIT | 0.001 |
| 8 | NITPPALPG | 0.001 |
| 1 | GRCFPWTNI | 0.001 |
| 4 | FPWTNITPP | 0.000 |
| 3 | CFPWTNITP | 0.000 |
| 7 | TNITPPALP | 0.000 |
| 5 | PWTNITPPA | 0.000 |

TABLE XIV-V5

HLA-A1101-9mers-24P4C12

TABLE XIV-V5 (continued)

Each peptide is a portion of SEQ ID NO: 11; each start position is specified, the length of peptide is 9 amino acids, and the end position for each peptide is the start position plus eight.

| Start | Subsequence | Score |
|---|---|---|
| 6 | LLLVLIFLR | 0.360 |
| 8 | LVLIFLRQR | 0.060 |
| 4 | AILLLVLIF | 0.012 |
| 5 | ILLLVLIFL | 0.012 |
| 1 | VLEAILLLV | 0.008 |
| 9 | VLIFLRQRI | 0.006 |
| 7 | LLVLIFLRQ | 0.001 |
| 2 | LEAILLLVL | 0.001 |
| 3 | EAILLLVLI | 0.001 |

TABLE XIV-V6

HLA-A1101-9mers-24P4C12
Each peptide is a portion of SEQ ID NO: 13; each start position is specitied, the length of peptide is 9 amino acids, and the end position for each peptide is the start position plus eight.

| Start | Subsequence | Score |
|---|---|---|
| 7 | LIPRSVFNL | 0.012 |
| 2 | YSSKGLIPR | 0.008 |
| 1 | GYSSKGLIP | 0.002 |
| 6 | GLIPRSVFN | 0.002 |
| 5 | KGLIPRSVF | 0.001 |
| 8 | IPRSVFNLQ | 0.000 |
| 9 | PRSVFNLQI | 0.000 |
| 4 | SKGLIPRSV | 0.000 |
| 3 | SSKGLIPRS | 0.000 |

TABLE XIV-V7

HLA-A1101-9mers-24P4C12
Each peptide is a portion of SEQ ID NO: 15; each start position is specified, the length of peptide is 9 amino acids, and the end position for each peptide is the start position plus eight.

| Start | Subsequence | Score |
|---|---|---|
| 8 | AVGQMMSTM | 0.020 |
| 5 | ILVAVGQMM | 0.006 |
| 4 | WILVAVGQM | 0.006 |
| 6 | LVAVGQMMS | 0.004 |
| 2 | WYWILVAVG | 0.001 |
| 7 | VAVGQMMST | 0.001 |

TABLE XIV-V7-continued

HLA-A1101-9mers-24P4C12
Each peptide is a portion of SEQ ID NO: 15; each start position is specified, the length of peptide is 9 amino acids, and the end position for each peptide is the start position plus eight.

| Start | Subsequence | Score |
|---|---|---|
| 1 | SWYWILVAV | 0.000 |
| 3 | YWILVAVGQ | 0.000 |

TABLE XIV-V8

HLA-A1101-9mers-24P4C12
Each peptide is a portion of SEQ ID NO: 17; each start position is specified, the length of peptide is 9 amino acids, and the end position for each peptide is the start position plus eight.

| Start | Subsequence | Score |
|---|---|---|
| 1 | NYYWLPIMR | 0.320 |
| 20 | QTSILGAYV | 0.010 |
| 17 | HVFQTSILG | 0.008 |
| 19 | FQTSILGAY | 0.006 |
| 18 | VFQTSILGA | 0.004 |
| 4 | WLPIMRNPI | 0.004 |
| 10 | NPITPTGHV | 0.003 |
| 2 | YYWLPIMRN | 0.002 |
| 9 | RNPITPTGH | 0.001 |
| 12 | ITPTGHVFQ | 0.001 |
| 16 | GHVFQTSIL | 0.001 |
| 13 | TPTGHVFQT | 0.001 |
| 11 | PITPTGHVF | 0.000 |
| 7 | IMRNPITPT | 0.000 |
| 5 | LPIMRNPIT | 0.000 |
| 15 | TGHVFQTSI | 0.000 |
| 6 | PIMRNPITP | 0.000 |
| 14 | PTGHVFQTS | 0.000 |
| 8 | MRNPITPTG | 0.000 |
| 3 | YWLPIMRNP | 0.000 |

TABLE XIV-V9

HLA-A1101-9mers-24P4C12
Each peptide is a portion of SEQ ID NO: 19; each start position is specified, the length of peptide is 9 amino acids, and the end position for each peptide is the start position plus eight.

| Start | Subsequence | Score |
|---|---|---|
| 15 | ATLGYVLWA | 0.030 |
| 18 | GYVLWASNI | 0.018 |
| 2 | WAMTALYPL | 0.008 |
| 12 | TQPATLGYV | 0.006 |
| 7 | LYPLPTQPA | 0.004 |
| 13 | QPATLGYVL | 0.004 |
| 4 | MTALYPLPT | 0.002 |
| 11 | PTQPATLGY | 0.002 |
| 6 | ALYPLPTQP | 0.001 |
| 16 | TLGYVLWAS | 0.001 |
| 3 | AMTALYPLP | 0.000 |
| 9 | PLPTQPATL | 0.000 |
| 8 | YPLPTQPAT | 0.000 |
| 5 | TALYPLPTQ | 0.000 |
| 10 | LPTQPATLG | 0.000 |
| 14 | PATLGYVLW | 0.000 |
| 17 | LGYVLWASN | 0.000 |
| 1 | YWAMTALYP | 0.000 |

TABLE XV-V1

A1101-10mers-24P4C12
Each peptide is a portion of SEQ ID NO: 3; each start position is specified, the length of peptide is 10 amino acids, and the end position for each peptide is the start position plus nine.

| Start | Subsequence | Score |
|---|---|---|
| 516 | RVILEYIDHK | 9.000 |
| 594 | VTDLLLFFGK | 3.000 |
| 134 | QTVGEVFYTK | 3.000 |
| 333 | RIRIAIALLK | 2.400 |
| 544 | CLWCLEKFIK | 2.400 |
| 621 | RIPGLGKDFK | 1.200 |
| 559 | AYIMIAIYGK | 1.200 |
| 72 | GAYCGMGENK | 1.200 |
| 584 | NIVRVVVLDK | 1.200 |
| 680 | SLDRPYYMSK | 0.800 |
| 469 | FASFYWAFHK | 0.600 |

TABLE XV-V1-continued

A1101-10mers-24P4C12
Each peptide is a portion of SEQ ID NO: 3; each start position is specified, the length of peptide is 10 amino acids, and the end position for each peptide is the start position plus nine.

| Start | Subsequence | Score |
|---|---|---|
| 272 | GIYYCWEEYR | 0.480 |
| 428 | GYSSKGLIQR | 0.480 |
| 337 | AIALLKEASK | 0.400 |
| 53 | IVAWLYGDPR | 0.400 |
| 211 | SLNARDISVK | 0.400 |
| 322 | ILLLMLIFLR | 0.360 |
| 423 | MCVFQGYSSK | 0.300 |
| 507 | LILTLVQIAR | 0.240 |
| 578 | FMLLMRNIVR | 0.240 |
| 120 | CPEDPWTVGK | 0.200 |
| 533 | VARCIMCCFK | 0.200 |
| 15 | KPVKYDPSFR | 0.180 |
| 264 | GVLGVLAYGI | 0.180 |
| 609 | GVGVLSFFFF | 0.180 |
| 684 | PYYMSKSLLK | 0.160 |
| 667 | FLCFLEDLER | 0.160 |
| 171 | LLPSAPALGR | 0.160 |
| 6 | RDEDDEAYGK | 0.120 |
| 698 | KNEAPPDNKK | 0.120 |
| 484 | TFPLISAFIR | 0.120 |
| 237 | GVALVLSLLF | 0.120 |
| 74 | YCGMGENKDK | 0.100 |
| 689 | KSLLKILGKK | 0.090 |
| 649 | YVIASGFFSV | 0.090 |
| 281 | RVLRDKGASI | 0.090 |
| 612 | VLSFFFFSGR | 0.080 |
| 487 | LISAFIRTLR | 0.080 |
| 275 | YCWEEYRVLR | 0.080 |
| 438 | SVFNLQIYGV | 0.080 |
| 697 | KKNEAPPDNK | 0.060 |
| 392 | SNISSPGCEK | 0.060 |
| 571 | GVSAKNAFML | 0.060 |
| 259 | LVLILGVLGV | 0.060 |
| 49 | IVVGIVAWLY | 0.060 |
| 240 | LVLSLLFILL | 0.060 |

TABLE XV-V1-continued

A1101-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 317 | AVLEAILLLM | 0.060 |
| 362 | FVLLLICIAY | 0.060 |
| 433 | GLIQRSVFNL | 0.054 |
| 449 | GLFWTLNWVL | 0.048 |
| 493 | RTLRYHTGSL | 0.045 |
| 518 | ILEYIDHKLR | 0.040 |
| 252 | LVAGPLVLVL | 0.040 |
| 618 | FSGRIPGLGK | 0.040 |
| 688 | SKSLLKILGK | 0.040 |
| 606 | VVGGVGVLSF | 0.040 |
| 541 | FKCCLWCLEK | 0.040 |
| 657 | SVFGMCVDTL | 0.040 |
| 360 | VTFVLLLICI | 0.040 |
| 233 | LVALGVALVL | 0.040 |
| 331 | RQRIRIAIAL | 0.036 |
| 589 | VVLDKVTDLL | 0.030 |
| 157 | TVITSLQQEL | 0.030 |
| 463 | CVLAGAFASF | 0.030 |
| 588 | VVVLDKVTDL | 0.030 |
| 700 | EAPPDNKKRK | 0.030 |
| 314 | IVLAVLEAIL | 0.030 |
| 456 | WVLALGQCVL | 0.030 |
| 257 | LVLVLILGVL | 0.030 |
| 34 | DVICCVLFLL | 0.027 |
| 611 | GVLSFFFFSG | 0.027 |
| 59 | GDPRQVLYPR | 0.024 |
| 220 | KIFEDFAQSW | 0.024 |
| 654 | GFFSVFGMCV | 0.024 |
| 548 | LEKFIKFLNR | 0.024 |
| 467 | GAFASFYWAF | 0.024 |
| 674 | LERNNGSLDR | 0.024 |
| 347 | AVGQMMSTMF | 0.020 |
| 566 | YGKNFCVSAK | 0.020 |
| 353 | STMFYPLVTF | 0.020 |
| 585 | IVRVVVLDKV | 0.020 |
| 701 | APPDNKKRKK | 0.020 |

TABLE XV-V1-continued

A1101-10mers-24P4C12
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 304 | SVQETWLAAL | 0.020 |
| 380 | ATSGQPQYVL | 0.020 |
| 662 | CVDTLFLCFL | 0.020 |
| 414 | LVNSSGPGLM | 0.020 |
| 19 | YDPSFRGPIK | 0.020 |
| 116 | CVSSCPEDPW | 0.020 |
| 186 | NVTPPALPGI | 0.020 |
| 642 | MTSILGAYVI | 0.020 |
| 512 | VQIARVILEY | 0.018 |
| 478 | KPQDIPTFPL | 0.018 |
| 47 | GYIVVGIVAW | 0.018 |
| 461 | GQCVLAGAFA | 0.018 |
| 239 | ALVLSLLFIL | 0.018 |
| 4 | KQRDEDDEAY | 0.018 |
| 603 | KLLVVGGVGV | 0.018 |
| 553 | KFLNRNAYIM | 0.018 |
| 163 | QQELCPSFLL | 0.018 |
| 267 | GVLAYGIYYC | 0.018 |

TABLE XV-V3

HLA-A1101-10mers-24P4C12
Each peptide is a portion of SEQ ID NO: 7;
each start position is specified, the length
of peptide is 10 amino acids, and the end
position for each peptide is the start
position plus nine.

| Start | Subsequence | Score |
|---|---|---|
| 9 | NITPPALPGI | 0.004 |
| 5 | FPWTNITPPA | 0.004 |
| 3 | RCFPWTNITP | 0.002 |
| 7 | WTNITPPALP | 0.001 |
| 10 | ITPPALPGIT | 0.001 |
| 4 | CFPWTNITPP | 0.000 |
| 1 | LGRCFPWTNI | 0.000 |
| 8 | TNITPPALPG | 0.000 |
| 2 | GRCFPWTNIT | 0.000 |
| 6 | PWTNITPPAL | 0.000 |

TABLE XV-V5

HLA-A1101-10mers-24P4C12
Each peptide is a portion of SEQ ID NO: 11;
each start position is specified, the length
of peptide is 10 amino acids, and the end
position for each peptide is the start
position plus nine.

| Start | Subsequence | Score |
|---|---|---|
| 6 | ILLLVLIFLR | 0.360 |
| 1 | AVLEAILLLV | 0.060 |
| 9 | LVLIFLRQRI | 0.030 |
| 8 | LLVLIFLRQR | 0.012 |
| 10 | VLIFLRQRIR | 0.012 |
| 5 | AILLLVLIFL | 0.012 |
| 2 | VLEAILLLVL | 0.008 |
| 4 | EAILLLVLIF | 0.002 |
| 7 | LLLVLIFLRQ | 0.001 |
| 3 | LEAILLLVLI | 0.001 |

TABLE XV-V6

HLA-A1101-10mers-24P4C12
Each peptide is a portion of SEQ ID NO: 13;
each start position is specified, the length
of peptide is 10 amino acids, and the end
position for each peptide is the start
position plus nine.

| Start | Subsequence | Score |
|---|---|---|
| 2 | GYSSKGLIPR | 0.480 |
| 7 | GLIPRSVFNL | 0.054 |
| 9 | IPRSVFNLQI | 0.004 |
| 8 | LIPRSVFNLQ | 0.000 |
| 5 | SKGLIPRSVF | 0.000 |
| 6 | KGLIPRSVFN | 0.000 |
| 1 | QGYSSKGLIP | 0.000 |
| 10 | PRSVFNLQIY | 0.000 |
| 4 | SSKGLIPRSV | 0.000 |
| 3 | YSSKGLIPRS | 0.000 |

TABLE XV-V7

HLA-A1101-10mers-24P4C12
Each peptide is a portion of SEQ ID NO: 15;
each start position is specified, the length
of peptide is 10 amino acids, and the end
position for each peptide is the start
position plus nine.

| Start | Subsequence | Score |
|---|---|---|
| 9 | AVGQMMSTMF | 0.020 |
| 5 | WILVAVGQMM | 0.006 |

TABLE XV-V7-continued

HLA-A1101-10mers-24P4C12
Each peptide is a portion of SEQ ID NO: 15;
each start position is specified, the length
of peptide is 10 amino acids, and the end
position for each peptide is the start
position plus nine.

| Start | Subsequence | Score |
|---|---|---|
| 7 | LVAVGQMMST | 0.004 |
| 8 | VAVGQMMSTM | 0.003 |
| 6 | ILVAVGQMMS | 0.001 |
| 3 | WYWILVAVGQ | 0.001 |
| 1 | QSWYWILVAV | 0.000 |
| 4 | YWILVAVGQM | 0.000 |
| 2 | SWYWILVAVG | 0.000 |

TABLE XV-V8

HLA-A1101-10mers-24P4C12
Each peptide is a portion of SEQ ID NO: 17;
each start position is specified, the length
of peptide is 10 amino acids, and the end
position for each peptide is the start
position plus nine.

| Start | Subsequence | Score |
|---|---|---|
| 18 | HVFQTSILGA | 0.080 |
| 1 | LNYYWLPIMR | 0.032 |
| 21 | QTSILGAYVI | 0.020 |
| 20 | FQTSILGAYV | 0.006 |
| 11 | NPITPTGHVF | 0.003 |
| 13 | ITPTGHVFQT | 0.003 |
| 19 | VFQTSILGAY | 0.002 |
| 2 | NYYWLPIMRN | 0.002 |
| 10 | RNPITPTGHV | 0.001 |
| 15 | PTGHVFQTSI | 0.001 |
| 6 | LPIMRNPITP | 0.001 |
| 8 | IMRNPITPTG | 0.000 |
| 5 | WLPIMRNPIT | 0.000 |
| 4 | YWLPIMRNPI | 0.000 |
| 9 | MRNPITPTGH | 0.000 |
| 14 | TPTGHVFQTS | 0.000 |
| 16 | TGHVFQTSIL | 0.000 |
| 17 | GHVFQTSILG | 0.000 |
| 7 | PIMRNPITPT | 0.000 |
| 3 | YYWLPIMRNP | 0.000 |
| 12 | PITPTGHVFQ | 0.000 |

TABLE XV-V9

HLA-A1101-10mers-24P4C12
Each peptide is a portion of SEQ ID NO: 19;
each start position is specified, the length
of peptide is 10 amino acids, and the end
position for each peptide is the start
position plus nine.

| Start | Subsequence | Score |
|---|---|---|
| 13 | TQPATLGYVL | 0.012 |
| 7 | ALYPLPTQPA | 0.008 |
| 11 | LPTQPATLGY | 0.004 |
| 9 | YPLPTQPATL | 0.003 |
| 16 | ATLGYVLWAS | 0.003 |
| 14 | QPATLGYVLW | 0.002 |
| 19 | GYVLWASNIS | 0.002 |
| 1 | AYWAMTALYP | 0.002 |
| 12 | PTQPATLGYV | 0.001 |
| 5 | MTALYPLPTQ | 0.001 |
| 4 | AMTALYPLPT | 0.001 |
| 8 | LYPLPTQPAT | 0.000 |
| 18 | LGYVLWASNI | 0.000 |
| 15 | PATLGYVLWA | 0.000 |
| 17 | TLGYVLWASN | 0.000 |
| 3 | WAMTALYPLP | 0.000 |
| 2 | YWAMTALYPL | 0.000 |
| 6 | TALYPLPTQP | 0.000 |
| 10 | PLPTQPATLG | 0.000 |

TABLE XVI-V1

HLA-A24-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 356 | FYPLVTFVL | 420.000 |
| 57 | LYGDPRQVL | 288.000 |
| 496 | RYHTGSLAF | 200.000 |
| 648 | AYVIASGFF | 150.000 |
| 87 | LYFNIFSCI | 84.000 |
| 386 | QYVLWASNI | 75.000 |
| 88 | YFNIFSCIL | 30.000 |
| 666 | LFLCFLEDL | 30.000 |
| 450 | LFWTLNWVL | 24.000 |
| 503 | AFGALILTL | 24.000 |

TABLE XVI-V1-continued

HLA-A24-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 84 | PYLLYFNIF | 21.600 |
| 540 | CFKCCLWCL | 20.000 |
| 684 | PYYMSKSLL | 20.000 |
| 617 | FFSGRIPGL | 20.000 |
| 658 | VFGMCVDTL | 20.000 |
| 553 | KFLNRNAYI | 15.000 |
| 251 | RLVAGPLVL | 12.000 |
| 583 | RNIVRVVVL | 12.000 |
| 484 | TFPLISAFI | 10.500 |
| 47 | GYIVVGIVA | 10.500 |
| 301 | AYQSVQETW | 10.500 |
| 468 | AFASFYWAF | 10.000 |
| 139 | VFYTKNRNF | 10.000 |
| 518 | ILEYIDHKL | 9.240 |
| 361 | TFVLLLICI | 9.000 |
| 577 | AFMLLMRNI | 9.000 |
| 446 | GVLGLFWTL | 8.640 |
| 258 | VLVLILGVL | 8.400 |
| 49 | IVVGIVAWL | 8.400 |
| 154 | WNMTVITSL | 8.400 |
| 311 | AALIVLAVL | 8.400 |
| 261 | LILGVLGVL | 8.400 |
| 440 | FNLQIYGVL | 8.400 |
| 234 | VALGVALVL | 8.400 |
| 683 | RPYYMSKSL | 8.000 |
| 333 | RIRIAIALL | 8.000 |
| 596 | DLLLFFGKL | 7.920 |
| 65 | LYPRNSTGA | 7.500 |
| 328 | IFLRQRIRI | 7.500 |
| 317 | AVLEAILLL | 7.200 |
| 255 | GPLVLVLIL | 7.200 |
| 38 | CVLFLLFIL | 7.200 |
| 240 | LVLSLLFIL | 7.200 |
| 232 | ILVALGVAL | 7.200 |
| 589 | VVLDKVTDL | 7.200 |

TABLE XVI-V1-continued

HLA-A24-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 170 | FLLPSAPAL | 7.200 |
| 357 | YPLVTFVLL | 7.200 |
| 236 | LGVALVLSL | 7.200 |
| 621 | RIPGLGKDF | 7.200 |
| 158 | VITSLQQEL | 6.336 |
| 305 | VQETWLAAL | 6.000 |
| 15 | KPVKYDPSF | 6.000 |
| 547 | CLEKFIKFL | 6.000 |
| 597 | LLLFFGKLL | 6.000 |
| 565 | IYGKNFCVS | 6.000 |
| 34 | DVICCVLFL | 6.000 |
| 308 | TWLAALIVL | 6.000 |
| 184 | WTNVTPPAL | 6.000 |
| 316 | LAVLEAILL | 6.000 |
| 200 | TIQQGISGL | 6.000 |
| 635 | NYYWLPIMT | 6.000 |
| 140 | FYTKNRNFC | 6.000 |
| 673 | DLERNNGSL | 6.000 |
| 442 | LQIYGVLGL | 6.000 |
| 414 | LVNSSCPGL | 6.000 |
| 444 | IYGVLGLFW | 6.000 |
| 452 | WTLNWVLAL | 6.000 |
| 242 | LSLLFILLL | 6.000 |
| 605 | LVVGGVGVL | 6.000 |
| 638 | WLPIMTSIL | 6.000 |
| 511 | LVQIARVIL | 6.000 |
| 163 | QQELCPSFL | 6.000 |
| 291 | SQLGFTTNL | 6.000 |
| 434 | LIQRSVFNL | 6.000 |
| 432 | KGLIQRSVF | 6.000 |
| 225 | FAQSWYWIL | 6.000 |
| 322 | ILLLMLIFL | 6.000 |
| 593 | KVTDLLLFF | 5.760 |
| 241 | VLSLLFILL | 5.760 |
| 253 | VAGPLVLVL | 5.760 |
| 237 | GVALVLSLL | 5.600 |

TABLE XVI-V1-continued

HLA-A24-9mers-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 228 | SWYWILVAL | 5.600 |
| 249 | LLRLVAGPL | 5.600 |
| 35 | VICCVLFLL | 5.600 |
| 32 | CTDVICCVL | 5.600 |
| 590 | VLDKVTDLL | 5.600 |
| 217 | ISVKIFEDF | 5.040 |
| 224 | DFAQSWYWI | 5.000 |
| 614 | SFFFFSGRI | 5.000 |
| 274 | YYCWEEYRV | 5.000 |
| 636 | YYWLPIMTS | 5.000 |
| 370 | AYWAMTALY | 5.000 |
| 573 | SAKNAFMLL | 4.800 |
| 351 | MMSTMFYPL | 4.800 |
| 315 | VLAVLEAIL | 4.800 |
| 100 | IISVAENGL | 4.800 |
| 204 | GISGLIDSL | 4.800 |
| 687 | MSKSLLKIL | 4.800 |
| 244 | LLFILLLRL | 4.800 |
| 499 | TGSLAFGAL | 4.800 |

TABLE XVI-V3

HLA-A24-9mers-24P4C12
Each peptide is a portion of SEQ ID NO: 7;
each start position is specified, the length
of peptide is 9 amino acids, and the end
position for each peptide is the start
position plus eight.

| Start | Subsequence | Score |
|---|---|---|
| 6 | WTNITPPAL | 6.000 |
| 9 | ITPPALPGI | 1.800 |
| 2 | RCFPWTNIT | 0.288 |
| 1 | GRCFPWTNI | 0.100 |
| 3 | CFPWTNITP | 0.075 |
| 7 | TNITPPALP | 0.015 |
| 5 | PWTNITPPA | 0.014 |
| 8 | NITPPALPG | 0.012 |
| 4 | FPWTNITPP | 0.010 |

TABLE XVI-V5

HLA-A24-9mers-24P4C12
Each peptide is a portion of
SEQ ID NO: 11; each start position
is specified, the length of peptide
is 9 amino acids, and the end
position for each peptide is the
start position plus eight.

| Start | Subsequence | Score |
|---|---|---|
| 5 | ILLLVLIFL | 8.400 |
| 4 | AILLLVLIF | 3.600 |
| 9 | VLIFLRQRI | 2.160 |
| 3 | EAILLLVLI | 1.800 |
| 2 | LEAILLLVL | 0.480 |
| 1 | VLEAILLLV | 0.210 |
| 7 | LLVLIFLRQ | 0.025 |
| 6 | LLLVLIFLR | 0.018 |
| 8 | LVLIFLRQR | 0.015 |

TABLE XVI-V6

HLA-A24-9mers-24P4C12
Each peptide is a portion of
SEQ ID NO: 13; each start position
is specified, the length of peptide
is 9 amino acids, and the end
position for each peptide is the
start position plus eight.

| Start | Subsequence | Score |
|---|---|---|
| 5 | KGLIPRSVF | 6.000 |
| 7 | LIPRSVFNL | 6.000 |
| 1 | GYSSKGLIP | 0.500 |
| 6 | GLIPRSVFN | 0.180 |
| 3 | SSKGLIPRS | 0.120 |
| 8 | IPRSVFNLQ | 0.020 |
| 4 | SKGLIPRSV | 0.014 |
| 2 | YSSKGLIPR | 0.010 |
| 9 | PRSVFNLQI | 0.010 |

TABLE XVI-V7

HLA-A24-9mers-24P4C12
Each peptide is a portion of
SEQ ID NO: 15; each start position
is specified, the length of peptide
is 9 amino acids, and the end
position for each peptide is the
start position plus eight.

| Start | Subsequence | Score |
|---|---|---|
| 5 | ILVAVGQMM | 1.260 |
| 4 | WILVAVGQM | 0.750 |
| 2 | WYWILVAVG | 0.600 |

TABLE XVI-V7-continued

HLA-A24-9mers-24P4C12
Each peptide is a portion of
SEQ ID NO: 15; each start position
is specified, the length of peptide
is 9 amino acids, and the end
position for each peptide is the
start position plus eight.

| Start | Subsequence | Score |
|---|---|---|
| 8 | AVGQMMSTM | 0.500 |
| 7 | VAVGQMMST | 0.150 |
| 1 | SWYWILVAV | 0.140 |
| 6 | LVAVGQMMS | 0.100 |
| 3 | YWILVAVGQ | 0.021 |

TABLE XVI-V8

HLA-A24-9mers-24P4C12
Each peptide is a portion of
SEQ ID NO: 17; each start position
is specified, the length of peptide
is 9 amino acids, and the end
position for each peptide is the
start position plus eight.

| Start | Subsequence | Score |
|---|---|---|
| 2 | YYWLPIMRN | 5.000 |
| 4 | WLPIMRNPI | 1.800 |
| 15 | TGHVFQTSI | 1.000 |
| 18 | VFQTSILGA | 0.750 |
| 16 | GHVFQTSIL | 0.600 |
| 1 | NYYWLPIMR | 0.600 |
| 11 | PITPTGHVF | 0.240 |
| 10 | NPITPTGHV | 0.150 |
| 5 | LPIMRNPIT | 0.150 |
| 19 | FQTSILGAY | 0.140 |
| 20 | QTSILGAYV | 0.120 |
| 13 | TPTGHVFQT | 0.100 |
| 7 | IMRNPITPT | 0.100 |
| 9 | RNPITPTGH | 0.030 |
| 3 | YWLPIMRNP | 0.025 |
| 14 | PTGHVFQTS | 0.020 |
| 12 | ITPTGHVFQ | 0.015 |
| 17 | HVFQTSILG | 0.010 |
| 8 | MRNPITPTG | 0.003 |
| 6 | PIMRNPITP | 0.002 |

TABLE XVI-V9

HLA-A24-9mers-24P4C12
Each peptide is a portion of
SEQ ID NO: 19; each start position
is specified, the length of peptide
is 9 amino acids, and the end
position for each peptide is the
start position plus eight.

| Start | Subsequence | Score |
|---|---|---|
| 18 | GYVLWASNI | 75.000 |
| 7 | LYPLPTQPA | 9.000 |
| 2 | WAMTALYPL | 6.000 |
| 13 | QPATLGYVL | 4.800 |
| 9 | PLPTQPATL | 0.600 |
| 8 | YPLPTQPAT | 0.180 |
| 15 | ATLGYVLWA | 0.150 |
| 12 | TQPATLGYV | 0.150 |
| 16 | TLGYVLWAS | 0.140 |
| 17 | LGYVLWASN | 0.120 |
| 4 | MTALYPLPT | 0.100 |
| 11 | PTQPATLGY | 0.018 |
| 5 | TALYPLPTQ | 0.015 |
| 6 | ALYPLPTQP | 0.014 |
| 3 | AMTALYPLP | 0.012 |
| 10 | LPTQPATLG | 0.010 |
| 14 | PATLGYVLW | 0.010 |
| 1 | YWAMTALYP | 0.010 |

TABLE XVII-V1

V1-HLA-A24-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 356 | FYPLVTFVLL | 360.000 |
| 301 | AYQSVQETWL | 300.000 |
| 87 | LYFNIFSCIL | 200.000 |
| 140 | FYTKNRNFCL | 200.000 |
| 274 | YYCWEEYRVL | 200.000 |
| 370 | AYWAMTALYL | 200.000 |
| 18 | KYDPSFRGPI | 120.000 |
| 685 | YYMSKSLLKI | 82.500 |
| 636 | YYWLPIMTSI | 70.000 |
| 439 | VFNLQIYGVL | 42.000 |
| 355 | MFYPLVTFVL | 33.600 |

TABLE XVII-V1-continued

V1-HLA-A24-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 169 | SFLLPSAPAL | 30.000 |
| 425 | VFQGYSSKGL | 30.000 |
| 616 | FFFSGRIPGL | 20.000 |
| 224 | DFAQSWYWIL | 20.000 |
| 478 | KPQDIPTFPL | 14.400 |
| 131 | EFSQTVGEVF | 14.000 |
| 658 | VFGMCVDTLF | 14.000 |
| 569 | NFCVSAKNAF | 12.000 |
| 630 | KSPHLNYYWL | 12.000 |
| 493 | RTLRYHTGSL | 12.000 |
| 331 | RQRIRIAIAL | 11.200 |
| 517 | VILEYIDHKL | 11.088 |
| 40 | LFLLFILGYI | 10.500 |
| 589 | VVLDKVTDLL | 10.080 |
| 157 | TVITSLQQEL | 9.504 |
| 520 | EYIDHKLRGV | 9.000 |
| 386 | QYVLWASNIS | 9.000 |
| 445 | YGVLGLFWTL | 8.640 |
| 240 | LVLSLLFILL | 8.640 |
| 248 | LLLRLVAGPL | 8.400 |
| 257 | LVLVLILGVL | 8.400 |
| 48 | YIVVGIVAWL | 8.400 |
| 260 | VLILGVLGVL | 8.400 |
| 236 | LGVALVLSLL | 8.400 |
| 34 | DVICCVLFLL | 8.400 |
| 683 | RPYYMSKSLL | 8.000 |
| 648 | AYVIASGFFS | 7.500 |
| 47 | GYIVVGIVAW | 7.500 |
| 65 | LYPRNSTGAY | 7.500 |
| 553 | KFLNRNAYIM | 7.500 |
| 254 | AGPLVLVLIL | 7.200 |
| 304 | SVQETWLAAL | 7.200 |
| 231 | WILVALGVAL | 7.200 |
| 637 | YWLPIMTSIL | 7.200 |
| 162 | LQQELCPSFL | 7.200 |

TABLE XVII-V1-continued

V1-HLA-A24-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 239 | ALVLSLLFIL | 7.200 |
| 318 | VLEAILLLML | 7.200 |
| 314 | IVLAVLEAIL | 7.200 |
| 37 | CCVLFLLFIL | 7.200 |
| 546 | WCLEKFIKFL | 7.200 |
| 350 | QMMSTMFYPL | 7.200 |
| 99 | NIISVAENGL | 7.200 |
| 203 | QGISGLIDSL | 7.200 |
| 243 | SLLFILLLRL | 7.200 |
| 229 | WYWILVALGV | 7.000 |
| 31 | SCTDVICCVL | 6.720 |
| 441 | NLQIYGVLGL | 6.000 |
| 357 | YPLVTFVLLL | 6.000 |
| 604 | LLVVGGVGVL | 6.000 |
| 510 | TLVQIARVIL | 6.000 |
| 596 | DLLLFFGKLL | 6.000 |
| 536 | CIMCCFKCCL | 6.000 |
| 588 | VVVLDKVTDL | 6.000 |
| 433 | GLIQRSVFNL | 6.000 |
| 659 | FGMCVDTLFL | 6.000 |
| 456 | WVLALGQCVL | 6.000 |
| 413 | HLVNSSCPGL | 6.000 |
| 290 | ISQLGFTTNL | 6.000 |
| 321 | AILLLMLIFL | 6.000 |
| 316 | LAVLEAILLL | 6.000 |
| 57 | LYGDPRQVLY | 6.000 |
| 91 | IFSCILSSNI | 6.000 |
| 77 | MGENKDKPYL | 6.000 |
| 163 | QQELCPSFLL | 6.000 |
| 199 | TTIQQGISGL | 6.000 |
| 500 | GSLAFGALIL | 6.000 |
| 83 | KPYLLYFNIF | 5.760 |
| 310 | LAALIVLAVL | 5.600 |
| 233 | LVALGVALVL | 5.600 |
| 227 | QSWYWILVAL | 5.600 |

TABLE XVII-V1-continued

V1-HLA-A24-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 611 | MCVDTLFLCF | 5.184 |
| 565 | IYGKNFCVSA | 5.000 |
| 279 | EYRVLRDKGA | 5.000 |
| 635 | NYYWLPIMTS | 5.000 |
| 273 | IYYCWEEYRV | 5.000 |
| 444 | IYGVLGLFWT | 5.000 |
| 686 | YMSKSLLKIL | 4.800 |
| 56 | WLYGDPRQVL | 4.800 |
| 235 | ALGVALVLSL | 4.800 |
| 252 | LVAGPLVLVL | 4.800 |
| 449 | GLFWTLNWVL | 4.800 |
| 502 | LAFGALILTL | 4.800 |
| 625 | LGKDFKSPHL | 4.800 |
| 498 | HTGSLAFGAL | 4.800 |
| 572 | VSAKNAFMLL | 4.800 |
| 542 | KCCLWCLEKF | 4.400 |
| 442 | LQIYGVLGLF | 4.200 |
| 368 | CIAYWAMTAL | 4.000 |
| 241 | VLSLLFILLL | 4.000 |

TABLE XVII-V3

HLA-A24-10mers-24P4C12
Each peptide is a portion of
SEQ ID NO: 7; each start position
is specified, the length of peptide
is 10 amino acids, and the end
position for each peptide is the
start position plus nine.

| Start | Subsequence | Score |
|---|---|---|
| 9 | NITPPALPGI | 1.200 |
| 1 | LGRCFPWTNI | 1.000 |
| 6 | PWTNITPPAL | 0.400 |
| 10 | ITPPALPGIT | 0.216 |
| 5 | FPWTNITPPA | 0.140 |
| 4 | CFPWTNITPP | 0.075 |
| 3 | RCFPWTNITP | 0.024 |
| 8 | TNITPPALPG | 0.015 |

TABLE XVII-V3-continued

HLA-A24-10mers-24P4C12
Each peptide is a portion of
SEQ ID NO: 7; each start position
is specified, the length of peptide
is 10 amino acids, and the end
position for each peptide is the
start position plus nine.

| Start | Subsequence | Score |
|---|---|---|
| 7 | WTNITPPALP | 0.015 |
| 2 | GRCFPWTNIT | 0.012 |

TABLE XVII-V5

HLA-A24-10mers-24P4C12
Each peptide is a portion of
SEQ ID NO: 11; each start position
is specified, the length of peptide
is 10 amino acids, and the end
position for each peptide is the
start position plus nine.

| Start | Subsequence | Score |
|---|---|---|
| 5 | AILLLVLIFL | 8.400 |
| 2 | VLEAILLLVL | 7.200 |
| 4 | EAILLLVLIF | 3.600 |
| 9 | LVLIFLRQRI | 2.160 |
| 1 | AVLEAILLLV | 0.252 |
| 3 | LEAILLLVLI | 0.120 |
| 7 | LLLVLIFLRQ | 0.025 |
| 6 | ILLLVLIFLR | 0.018 |
| 10 | VLIFLRQRIR | 0.015 |
| 8 | LLVLIFLRQR | 0.015 |

TABLE XVII-V6

HLA-A24-10mers-24P4C12
Each peptide is a portion of
SEQ ID NO: 13; each start position
is specified, the length of peptide
is 10 amino acids, and the end
position for each peptide is the
start position plus nine.

| Start | Subsequence | Score |
|---|---|---|
| 7 | GLIPRSVFNL | 7.200 |
| 9 | IPRSVFNLQI | 1.000 |
| 2 | GYSSKGLIPR | 0.500 |
| 6 | KGLIPRSVFN | 0.300 |
| 5 | SKGLIPRSVF | 0.200 |
| 4 | SSKGLIPRSV | 0.140 |
| 3 | YSSKGLIPRS | 0.120 |
| 8 | LIPRSVFNLQ | 0.030 |
| 1 | QGYSSKGLIP | 0.010 |

TABLE XVII-V6-continued

HLA-A24-10mers-24P4C12
Each peptide is a portion of
SEQ ID NO: 13; each start position
is specified, the length of peptide
is 10 amino acids, and the end
position for each peptide is the
start position plus nine.

| Start | Subsequence | Score |
|---|---|---|
| 10 | PRSVFNLQIY | 0.001 |

TABLE XVII-V7

HLA-A24-10mers-24P4C12
Each peptide is a portion of
SEQ ID NO: 15; each start position
is specified, the length of peptide
is 10 amino acids, and the end
position for each peptide is the
start position plus nine.

| Start | Subsequence | Score |
|---|---|---|
| 9 | AVGQMMSTMF | 2.000 |
| 5 | WILVAVGQMM | 1.260 |
| 4 | YWILVAVGQM | 0.750 |
| 8 | VAVGQMMSTM | 0.750 |
| 3 | WYWILVAVGQ | 0.700 |
| 6 | ILVAVGQMMS | 0.150 |
| 1 | QSWYWILVAV | 0.140 |
| 7 | LVAVGQMMST | 0.100 |
| 2 | SWYWILVAVG | 0.012 |

TABLE XVII-V8

HLA-A24-10mers-24P4C12
Each peptide is a portion of
SEQ ID NO: 17; each start position
is specified, the length of peptide
is 10 amino acids, and the end
position for each peptide is the
start position plus nine.

| Start | Subsequence | Score |
|---|---|---|
| 2 | NYYWLPIMRN | 5.000 |
| 16 | TGHVFQTSIL | 4.000 |
| 11 | NPITPTGHVF | 3.000 |
| 4 | YWLPIMRNPI | 2.160 |
| 19 | VFQTSILGAY | 1.050 |
| 21 | QTSILGAYVI | 1.000 |
| 3 | YYWLPIMRNP | 0.700 |
| 10 | RNPITPTGHV | 0.300 |
| 14 | TPTGHVFQTS | 0.202 |
| 5 | WLPIMRNPIT | 0.150 |

TABLE XVII-V8-continued

HLA-A24-10mers-24P4C12
Each peptide is a portion of
SEQ ID NO: 17; each start position
is specified, the length of peptide
is 10 amino acids, and the end
position for each peptide is the
start position plus nine.

| Start | Subsequence | Score |
|---|---|---|
| 13 | ITPTGHVFQT | 0.150 |
| 20 | FQTSILGAYV | 0.120 |
| 18 | HVFQTSILGA | 0.100 |
| 15 | PTGHVFQTSI | 0.100 |
| 6 | LPIMRNPITP | 0.015 |
| 7 | PIMRNPITPT | 0.015 |
| 8 | IMRNPITPTG | 0.014 |
| 1 | LNYYWLPIMR | 0.012 |
| 9 | MRNPITPTGH | 0.002 |
| 17 | GHVFQTSILG | 0.002 |
| 12 | PITPTGHVFQ | 0.001 |

TABLE XVII-V9

HLA-A24-10mers-24P4C12
Each peptide is a portion of
SEQ ID NO: 19; each start position
is specified, the length of peptide
is 10 amino acids, and the end
position for each peptide is the
start position plus nine.

| Start | Subsequence | Score |
|---|---|---|
| 19 | GYVLWASNIS | 9.000 |
| 8 | LYPLPTQPAT | 7.500 |
| 13 | TQPATLGYVL | 7.200 |
| 9 | YPLPTQPATL | 7.200 |
| 2 | YWAMTALYPL | 4.000 |
| 18 | LGYVLWASNI | 1.000 |
| 1 | AYWAMTALYP | 0.500 |
| 16 | ATLGYVLWAS | 0.210 |
| 7 | ALYPLPTQPA | 0.144 |
| 17 | TLGYVLWASN | 0.120 |
| 4 | AMTALYPLPT | 0.100 |
| 14 | QPATLGYVLW | 0.100 |
| 11 | LPTQPATLGY | 0.100 |
| 12 | PTQPATLGYV | 0.018 |
| 6 | TALYPLPTQP | 0.018 |
| 3 | WAMTALYPLP | 0.018 |
| 15 | PATLGYVLWA | 0.010 |

TABLE XVII-V9-continued

HLA-A24-10mers-24P4C12
Each peptide is a portion of
SEQ ID NO: 19; each start position
is specified, the length of peptide
is 10 amino acids, and the end
position for each peptide is the
start position plus nine.

| Start | Subsequence | Score |
|---|---|---|
| 5 | MTALYPLPTQ | 0.010 |
| 10 | PLPTQPATLG | 0.002 |

TABLE XVIII-V1

HLA-B7-9mers-24P4C12
Each peptide is a portion of
SEQ ID NO: 3; each start position
is specified, the length of peptide
is 9 amino acids, and the end
position for each peptide is the
start position plus eight.

| Start | Subsequence | Score |
|---|---|---|
| 255 | GPLVLVLIL | 80.000 |
| 631 | SPHLNYYWL | 80.000 |
| 357 | YPLVTFVLL | 80.000 |
| 683 | RPYYMSKSL | 80.000 |
| 317 | AVLEAILLL | 60.000 |
| 249 | LLRLVAGPL | 40.000 |
| 494 | TLRYHTGSL | 40.000 |
| 333 | RIRIAIALL | 40.000 |
| 311 | AALIVLAVL | 36.000 |
| 511 | LVQIARVIL | 30.000 |
| 414 | LVNSSCPGL | 20.000 |
| 38 | CVLFLLFIL | 20.000 |
| 49 | IVVGIVAWL | 20.000 |
| 446 | GVLGLFWTL | 20.000 |
| 237 | GVALVLSLL | 20.000 |
| 240 | LVLSLLFIL | 20.000 |
| 605 | LWGGVGVL | 20.000 |
| 34 | DVICCVLFL | 20.000 |
| 589 | VVLDKVTDL | 20.000 |
| 347 | AVGQMMSTM | 15.000 |
| 573 | SAKNAFMLL | 12.000 |
| 253 | VAGPLVLVL | 12.000 |
| 369 | IAYWAMTAL | 12.000 |
| 225 | FAQSNYWIL | 12.000 |
| 213 | NARDISVKI | 12.000 |

TABLE XVIII-V1-continued

HLA-B7-9mers-24P4C12
Each peptide is a portion of
SEQ ID NO: 3; each start position
is specified, the length of peptide
is 9 amino acids, and the end
position for each peptide is the
start position plus eight.

| Start | Subsequence | Score |
|---|---|---|
| 514 | IARVILEYI | 12.000 |
| 154 | WNMTVITSL | 12.000 |
| 316 | LAVLEAILL | 12.000 |
| 234 | VALGVALVL | 12.000 |
| 396 | SPGCEKVPI | 8.000 |
| 83 | KPYLLYFNI | 8.000 |
| 406 | TSCNPTAHL | 6.000 |
| 381 | TSGQPQYVL | 6.000 |
| 571 | CVSAKNAFM | 5.000 |
| 261 | LILGVLGVL | 4.000 |
| 315 | VLAVLEAIL | 4.000 |
| 291 | SQLGFTTNL | 4.000 |
| 638 | WLPIMTSIL | 4.000 |
| 258 | VLVLILGVL | 4.000 |
| 452 | WTLNWVLAL | 4.000 |
| 28 | KNRSCTDVI | 4.000 |
| 241 | VLSLLFILL | 4.000 |
| 236 | LGVALVLSL | 4.000 |
| 440 | FNLQIYGVL | 4.000 |
| 184 | WTNVTPPAL | 4.000 |
| 597 | LLLFFGKLL | 4.000 |
| 583 | RNIVRVVVL | 4.000 |
| 275 | YCWEEYRVL | 4.000 |
| 170 | FLLPSAPAL | 4.000 |
| 596 | DLLLFFGKL | 4.000 |
| 282 | VLRDKGASI | 4.000 |
| 158 | VITSLQQEL | 4.000 |
| 537 | IMCCFKCGL | 4.000 |
| 660 | GMCVDTLFL | 4.000 |
| 457 | VLALGQCVL | 4.000 |
| 499 | TGSLAFGAL | 4.000 |
| 66 | YPRNSTGAY | 4.000 |
| 141 | YTKNRNFCL | 4.000 |
| 55 | LNRNAYIMI | 4.000 |
| 426 | FQGYSSKGL | 4.000 |

TABLE XVIII-V1-continued

HLA-B7-9mers-24P4C12
Each peptide is a portion of
SEQ ID NO: 3; each start position
is specified, the length of peptide
is 9 amino acids, and the end
position for each peptide is the
start position plus eight.

| Start | Subsequence | Score |
|---|---|---|
| 244 | LLFILLLRL | 4.000 |
| 242 | LSLLFILLL | 4.000 |
| 487 | LISAFIRTL | 4.000 |
| 79 | ENKDKPYLL | 4.000 |
| 351 | MMSTMFYPL | 4.000 |
| 442 | LQIYGVLGL | 4.000 |
| 200 | TIQQGISGL | 4.000 |
| 434 | LIQRSVFNL | 4.000 |
| 501 | SLAFGALIL | 4.000 |
| 322 | ILLLMLIFL | 4.000 |
| 251 | RLVAGPLVL | 4.000 |
| 204 | GISGLIDSL | 4.000 |
| 572 | VSAKNAFML | 4.000 |
| 687 | MSKSLLKIL | 4.000 |
| 100 | IISVAENGL | 4.000 |
| 232 | ILVALGVAL | 4.000 |
| 302 | YQSVQETWL | 4.000 |
| 35 | VICCVLFLL | 4.000 |
| 25 | GPIKNRSCT | 3.000 |
| 482 | IPTFPLISA | 3.000 |
| 344 | ASKAVGQMM | 3.000 |
| 343 | EASKAVGQM | 3.000 |
| 149 | LPGVPWNMT | 3.000 |
| 581 | LMRNIVRVV | 2.000 |
| 152 | VPWNMTVIT | 2.000 |
| 531 | NPVARCIMC | 2.000 |
| 188 | TPPALPGIT | 2.000 |
| 112 | TPQVGVSSC | 2.000 |
| 60 | DPRQVLYPR | 2.000 |
| 525 | KLRGVQNPV | 2.000 |
| 314 | IVLAVLEAI | 2.000 |
| 167 | CPSFLLPSA | 2.000 |
| 151 | GVPWNMTVI | 2.000 |
| 192 | LPGITNDTT | 2.000 |
| 359 | LVTFVLLLI | 2.000 |

TABLE XVIII-V1-continued

HLA-B7-9mers-24P4C12
Each peptide is a portion of
SEQ ID NO: 3; each start position
is specified, the length of peptide
is 9 amino acids, and the end
position for each peptide is the
start position plus eight.

| Start | Subsequence | Score |
|---|---|---|
| 252 | LVAGPLVLV | 1.500 |
| 491 | FIRTLRYHT | 1.500 |
| 530 | QNPVARCIM | 1.500 |
| 239 | ALVLSLLFI | 1.200 |
| 305 | VQETWLAAL | 1.200 |

TABLE XVIII-V3

HLA-B7-9mers-24P4C12
Each peptide is a portion of
SEQ ID NO: 7; each start position
is specified, the length of peptide
is 9 amino acids, and the end
position for each peptide is the
start position plus eight.

| Start | Subsequence | Score |
|---|---|---|
| 6 | WTNITPPAL | 4.000 |
| 9 | ITPPALPGI | 0.400 |
| 4 | FPWTNITPP | 0.200 |
| 2 | RCFPWTNIT | 0.100 |
| 1 | GRCFPWTNI | 0.060 |
| 7 | TNITPPALP | 0.015 |
| 8 | NITPPALPG | 0.015 |
| 3 | CFPWTNITP | 0.001 |
| 5 | PWTNITPPA | 0.001 |

TABLE XVIII-V5

HLA-B7-9mers-24P4C12
Each peptide is a portion of
SEQ ID NO: 11; each start position
is specified, the length of peptide
is 9 amino acids, and the end
position for each peptide is the
start position plus eight.

| Start | Subsequence | Score |
|---|---|---|
| 5 | ILLLVLIFL | 4.000 |
| 3 | EAILLLVLI | 1.200 |
| 9 | VLIFLRQRI | 0.600 |
| 2 | LEAILLLVL | 0.400 |
| 4 | AILLLVLIF | 0.060 |
| 1 | VLEAILLLV | 0.060 |
| 8 | LVLIFLRQR | 0.050 |

TABLE XVIII-V5-continued

HLA-B7-9mers-24P4C12
Each peptide is a portion of
SEQ ID NO: 11; each start position
is specified, the length of peptide
is 9 amino acids, and the end
position for each peptide is the
start position plus eight.

| Start | Subsequence | Score |
|---|---|---|
| 7 | LLVLIFLRQ | 0.010 |
| 6 | LLLVLIFLR | 0.010 |

TABLE XVIII-V6

HLA-B7-9mers-24P4C12
Each peptide is a portion of
SEQ ID NO: 13; each start position
is specified, the length of peptide
is 9 amino acids, and the end
position for each peptide is the
start position plus eight.

| Start | Subsequence | Score |
|---|---|---|
| 7 | LIPRSVFNL | 4.000 |
| 8 | IPRSVFNLQ | 2.000 |
| 5 | KGLIPRSVF | 0.045 |
| 6 | GLIPRSVFN | 0.020 |
| 4 | SKGLIPRSV | 0.020 |
| 3 | SSKGLIPRS | 0.020 |
| 2 | YSSKGLIPR | 0.010 |
| 9 | PRSVFNLQI | 0.004 |
| 1 | GYSSKGLIP | 0.001 |

TABLE XVIII-V7

HLA-B7-9mers-24P4C12
Each peptide is a portion of
SEQ ID NO: 15; each start position
is specified, the length of peptide
is 9 amino acids, and the end
position for each peptide is the
start position plus eight.

| Start | Subsequence | Score |
|---|---|---|
| 8 | AVGQMMSTM | 15.000 |
| 5 | ILVAVGQMM | 1.000 |
| 4 | WILVAVGQM | 1.000 |
| 7 | VAVGQMMST | 0.300 |
| 6 | LVAVGQMMS | 0.100 |
| 1 | SWYWILVAV | 0.020 |
| 3 | YWILVAVGQ | 0.001 |
| 2 | WYWILVAVG | 0.001 |

TABLE XVIII-V8

HLA-B7-9mers-24P4C12
Each peptide is a portion of
SEQ ID NO: 17; each start position
is specified, the length of peptide
is 9 amino acids, and the end
position for each peptide is the
start position plus eight.

| Start | Subsequence | Score |
|---|---|---|
| 10 | NPITPTGHV | 6.000 |
| 5 | LPIMRNPIT | 2.000 |
| 13 | TPTGHVFQT | 2.000 |
| 7 | IMRNPITPT | 1.500 |
| 4 | WLPIMRNPI | 0.600 |
| 15 | TGHVFQTSI | 0.400 |
| 16 | GHVFQTSIL | 0.400 |
| 20 | QTSILGAYV | 0.200 |
| 17 | HVFQTSILG | 0.050 |
| 19 | FQTSILGAY | 0.020 |
| 18 | VFQTSILGA | 0.010 |
| 12 | ITPTGHVFQ | 0.010 |
| 9 | RNPITPTGH | 0.010 |
| 6 | PIMRNPITP | 0.003 |
| 2 | YYWLPIMRN | 0.003 |
| 11 | PITPTGHVF | 0.002 |
| 14 | PTGHVFQTS | 0.002 |
| 3 | YWLPIMRNP | 0.001 |
| 8 | MRNPITPTG | 0.001 |
| 1 | NYYWLPIMR | 0.001 |

TABLE XVIII-V9

HLA-B7-9mers-24P4C12
Each peptide is a portion of
SEQ ID NO: 19; each start position
is specified, the length of peptide
is 9 amino acids, and the end
position for each peptide is the
start position plus eight.

| Start | Subsequence | Score |
|---|---|---|
| 13 | QPATLGYVL | 80.000 |
| 2 | WAMTALYPL | 36.000 |
| 8 | YPLPTQPAT | 2.000 |
| 9 | PLPTQPATL | 0.400 |
| 10 | LPTQPATLG | 0.300 |
| 15 | ATLGYVLWA | 0.300 |
| 12 | TQPATLGYV | 0.200 |
| 4 | MTALYPLPT | 0.100 |

TABLE XVIII-V9-continued

HLA-B7-9mers-24P4C12
Each peptide is a portion of
SEQ ID NO: 19; each start position
is specified, the length of peptide
is 9 amino acids, and the end
position for each peptide is the
start position plus eight.

| Start | Subsequence | Score |
|---|---|---|
| 5 | TALYPLPTQ | 0.045 |
| 18 | GYVLWASNI | 0.040 |
| 3 | AMTALYPLP | 0.030 |
| 6 | ALYPLPTQP | 0.030 |
| 17 | LGYVLWASN | 0.020 |
| 16 | TLGYVLWAS | 0.020 |
| 7 | LYPLPTQPA | 0.015 |
| 14 | PATLGYVLW | 0.006 |
| 11 | PTQPATLGY | 0.002 |
| 1 | YWAMTALYP | 0.001 |

TABLE XIX-V1

HLA-B7-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 478 | KPQDIPTFPL | 120.000 |
| 683 | RPYYMSKSLL | 80.000 |
| 357 | YPLVTFVLLL | 80.000 |
| 331 | RQRIRIAIAL | 40.000 |
| 571 | CVSAKNAFML | 20.000 |
| 257 | LVLVLILGVL | 20.000 |
| 456 | WVLALGQCVL | 20.000 |
| 588 | VVVLDKVTDL | 20.000 |
| 157 | TVITSLQQEL | 20.000 |
| 240 | LVLSLLFILL | 20.000 |
| 66 | YPRNSTGAYC | 20.000 |
| 314 | IVLAVLEAIL | 20.000 |
| 589 | VVLDKVTDLL | 20.000 |
| 252 | LVAGPLVLVL | 20.000 |
| 657 | SVFGMCVDTL | 20.000 |
| 304 | SVQETWLAAL | 20.000 |
| 34 | DVICCVLFLL | 20.000 |

TABLE XIX-V1-continued

HLA-B7-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 233 | LVALGVALVL | 20.000 |
| 380 | ATSGQPQYVL | 18.000 |
| 317 | AVLEAILLLM | 15.000 |
| 321 | AILLLMLIFL | 12.000 |
| 502 | LAFGALILTL | 12.000 |
| 239 | ALVLSLLFIL | 12.000 |
| 659 | FGMCVDTLFL | 12.000 |
| 254 | AGPLVLVLIL | 12.000 |
| 350 | QMMSTMFYPL | 12.000 |
| 235 | ALGVALVLSL | 12.000 |
| 536 | CIMCCFKCCL | 12.000 |
| 316 | LAVLEAILLL | 12.000 |
| 310 | LAALIVLAVL | 12.000 |
| 585 | IVRVVVLDKV | 10.000 |
| 56 | WLYGDPRQVL | 9.000 |
| 192 | LPGITNDTTI | 8.000 |
| 510 | TLVQIARVIL | 6.000 |
| 662 | CVDTLFLCFL | 6.000 |
| 329 | FLRQRIRIAI | 6.000 |
| 405 | NTSCNPTAHL | 6.000 |
| 414 | LVNSSCPGLM | 5.000 |
| 413 | HLVNSSCPGL | 4.000 |
| 203 | QGISGLIDSL | 4.000 |
| 368 | CIAYWAMTAL | 4.000 |
| 686 | YMSKSLLKIL | 4.000 |
| 99 | NIISVAENGL | 4.000 |
| 665 | TLFLCFLEDL | 4.000 |
| 290 | ISQLGFTTNL | 4.000 |
| 441 | NLQIYGVLGL | 4.000 |
| 630 | KSPHLNYYWL | 4.000 |
| 315 | VLAVLEAILL | 4.000 |
| 236 | LGVALVLSLL | 4.000 |
| 596 | DLLLFFGKLL | 4.000 |
| 60 | DPRQVLYPRN | 4.000 |
| 243 | SLLFILLLRL | 4.000 |

TABLE XIX-V1-continued

HLA-B7-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 37 | CCVLFLLFIL | 4.000 |
| 449 | GLFWTLNWVL | 4.000 |
| 162 | LQQELCPSFL | 4.000 |
| 625 | LGKDFKSPHL | 4.000 |
| 227 | QSWYWILVAL | 4.000 |
| 498 | HTGSLAFGAL | 4.000 |
| 48 | YIVVGIVAWL | 4.000 |
| 604 | LLVVGGVGVL | 4.000 |
| 149 | LPGVPWNMTV | 4.000 |
| 260 | VLILGVLGVL | 4.000 |
| 493 | RTLRYHTGSL | 4.000 |
| 248 | LLLRLVAGPL | 4.000 |
| 231 | WILVALGVAL | 4.000 |
| 500 | GSLAFGALIL | 4.000 |
| 546 | WCLEKFIKFL | 4.000 |
| 241 | VLSLLFILLL | 4.000 |
| 539 | CCFKCCLWCL | 4.000 |
| 445 | YGVLGLFWTL | 4.000 |
| 307 | ETWLAALIVL | 4.000 |
| 435 | IQRSVFNLQI | 4.000 |
| 572 | VSAKNAFMLL | 4.000 |
| 433 | GLIQRSVFNL | 4.000 |
| 517 | VILEYIDHKL | 4.000 |
| 199 | TTIQQGISGL | 4.000 |
| 31 | SCTDVIGCVL | 4.000 |
| 178 | LGRCFPWTNV | 3.000 |
| 343 | EASKAVGQMM | 3.000 |
| 346 | KAVGQMMSTM | 3.000 |
| 581 | LMRNIVRVVV | 3.000 |
| 573 | SAKNAFMLLM | 3.000 |
| 652 | ASGFFSVFGM | 3.000 |
| 402 | VPINTSCNPT | 2.000 |
| 182 | FPWTNVTPPA | 2.000 |
| 528 | GVQNPVARCI | 2.000 |
| 281 | RVLRDKGASI | 2.000 |

TABLE XIX-V1-continued

HLA-B7-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 186 | NVTPPALPGI | 2.000 |
| 143 | KNRNFGLPGV | 2.000 |
| 639 | LPIMTSILGA | 2.000 |
| 249 | LLRLVAGPLV | 2.000 |
| 172 | LPSAPALGRC | 2.000 |
| 485 | FPLISAFIRT | 2.000 |
| 264 | GVLGVLAYGI | 2.000 |
| 531 | NPVARCIMCC | 2.000 |
| 163 | QQELCPSFLL | 1.800 |
| 529 | VQNPVARCIM | 1.500 |
| 576 | NAFMLLMRNI | 1.200 |
| 370 | AYWAMTALYL | 1.200 |
| 318 | VLEAILLLML | 1.200 |

TABLE XIX-V3

HLA-B7-10mers-24P4C12
Each peptide is a portion of
SEQ ID NO: 7; each start position
is specified, the length of peptide
is 10 amino acids, and the end
position for each peptide is the
start position plus nine.

| Start | Subsequence | Score |
|---|---|---|
| 1 | LGRCFPWTNI | 6.000 |
| 5 | FPWTNITPPA | 2.000 |
| 9 | NITPPALPGI | 0.400 |
| 10 | ITPPALPGIT | 0.100 |
| 6 | PWTNITPPAL | 0.040 |
| 8 | TNITPPALPG | 0.015 |
| 7 | WTNITPPALP | 0.015 |
| 3 | RCFPWTNITP | 0.010 |
| 2 | GRCFPWTNIT | 0.010 |
| 4 | CFPWTNITPP | 0.001 |

TABLE XIX-V5

HLA-B7-10mers-24P4C12
Each peptide is a portion of
SEQ ID NO: 11; each start position
is specified, the length of peptide
is 10 amino acids, and the end
position for each peptide is the
start position plus nine.

| Start | Subsequence | Score |
|---|---|---|
| 5 | AILLLVLIFL | 12.000 |
| 9 | LVLIFLRQRI | 3.000 |
| 1 | AVLEAILLLV | 3.000 |
| 2 | VLEAILLLVL | 1.200 |
| 4 | EAILLLVLIF | 0.060 |
| 3 | LEAILLLVLI | 0.040 |
| 7 | LLLVLIFLRQ | 0.010 |
| 6 | ILLLVLIFLR | 0.010 |
| 10 | VLIFLRQRIR | 0.010 |
| 8 | LLVLIFLRQR | 0.010 |

TABLE XIX-V6

HLA-B7-10mers-24P4C12
Each peptide is a portion of
SEQ ID NO: 13; each start position
is specified, the length of peptide
is 10 amino acids, and the end
position for each peptide is the
start position plus nine.

| Start | Subsequence | Score |
|---|---|---|
| 7 | GLIPRSVFNL | 4.000 |
| 4 | SSKGLIPRSV | 0.200 |
| 6 | KGLIPRSVFN | 0.020 |
| 3 | YSSKGLIPRS | 0.020 |
| 8 | LIPRSVFNLQ | 0.010 |
| 1 | QGYSSKGLIP | 0.010 |
| 5 | SKGLIPRSVF | 0.005 |
| 2 | GYSSKGLIPR | 0.001 |
| 10 | PRSVFNLQIY | 0.000 |

TABLE XIX-V7

HLA-B7-10mers-24P4C12
Each peptide is a portion of
SEQ ID NO: 15; each start position
is specified, the length of peptide
is 10 amino acids, and the end
position for each peptide is the
start position plus nine.

| Start | Subsequence | Score |
|---|---|---|
| 8 | VAVGQMMSTM | 3.000 |
| 5 | WILVAVGQMM | 1.000 |
| 7 | LVAVGQMMST | 0.500 |
| 9 | AVGQMMSTMF | 0.300 |
| 1 | QSWYWILVAV | 0.200 |

TABLE XIX-V7-continued

HLA-B7-10mers-24P4C12
Each peptide is a portion of
SEQ ID NO: 15; each start position
is specified, the length of peptide
is 10 amino acids, and the end
position for each peptide is the
start position plus nine.

| Start | Subsequence | Score |
|---|---|---|
| 4 | YWILVAVGQM | 0.100 |
| 6 | ILVAVGQMMS | 0.020 |
| 2 | SWYWILVAVG | 0.001 |
| 3 | WYWILVAVGQ | 0.001 |

TABLE XIX-V8

HLA-B7-10mers-24P4C12
Each peptide is a portion of
SEQ ID NO: 17; each start position
is specified, the length of peptide
is 10 amino acids, and the end
position for each peptide is the
start position plus nine.

| Start | Subsequence | Score |
|---|---|---|
| 16 | TGHVFQTSIL | 4.000 |
| 18 | HVFQTSILGA | 0.500 |
| 11 | NPITPTGHVF | 0.400 |
| 21 | QTSILGAYVI | 0.400 |
| 14 | TPTGHVFQTS | 0.400 |
| 10 | RNPITPTGHV | 0.300 |
| 20 | FQTSILGAYV | 0.200 |
| 6 | LPIMRNPITP | 0.200 |
| 13 | ITPTGHVFQT | 0.100 |
| 8 | IMRNPITPTG | 0.100 |
| 5 | WLPIMRNPIT | 0.100 |
| 4 | YWLPIMRNPI | 0.060 |
| 7 | PIMRNPITPT | 0.045 |
| 15 | PTGHVFQTSI | 0.040 |
| 1 | LNYYWLPIMR | 0.010 |
| 2 | NYYWLPIMRN | 0.003 |
| 19 | VFQTSILGAY | 0.002 |
| 17 | GHVFQTSILG | 0.001 |
| 3 | YYWLPIMRNP | 0.001 |
| 12 | PITPTGHVFQ | 0.001 |
| 9 | MRNPITPTGH | 0.001 |

TABLE XIX-V9

HLA-B7-10mers-24P4C12
Each peptide is a portion of
SEQ ID NO: 19; each start position
is specified, the length of peptide
is 10 amino acids, and the end
position for each peptide is the
start position plus nine.

| Start | Subsequence | Score |
|---|---|---|
| 9 | YPLPTQPATL | 80.000 |
| 13 | TQPATLGYVL | 4.000 |
| 7 | ALYPLPTQPA | 0.450 |
| 11 | LPTQPATLGY | 0.400 |
| 14 | QPATLGYVLW | 0.400 |
| 2 | YWAMTALYPL | 0.400 |
| 18 | LGYVLWASNI | 0.400 |
| 4 | AMTALYPLPT | 0.300 |
| 3 | WAMTALYPLP | 0.090 |
| 16 | ATLGYVLWAS | 0.060 |
| 6 | TALYPLPTQP | 0.030 |
| 15 | PATLGYVLWA | 0.030 |
| 12 | PTQPATLGYV | 0.020 |
| 17 | TLGYVLWASN | 0.020 |
| 5 | MTALYPLPTQ | 0.015 |
| 8 | LYPLPTQPAT | 0.010 |
| 1 | AYWAMTALYP | 0.003 |
| 19 | GYVLWASNIS | 0.002 |
| 10 | PLPTQPATLG | 0.002 |

TABLE XX-V1

HLA-B35-9meres-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 66 | YPRNSTGAY | 120.000 |
| 683 | RPYYMSKSL | 40.000 |
| 15 | KPVKYDPSF | 40.000 |
| 344 | ASKAVGQMM | 30.000 |
| 437 | RSVFNLQIY | 20.000 |
| 679 | GSLDRPYYM | 20.000 |
| 357 | YPLVTFVLL | 20.000 |
| 255 | GPLVLVLIL | 20.000 |
| 631 | SPHLNYYWL | 20.000 |
| 83 | KPYLLYFNI | 16.000 |
| 687 | MSKSLLKIL | 15.000 |

TABLE XX-V1-continued

HLA-B35-9meres-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 396 | SPGCEKVPI | 12.000 |
| 69 | NSTGAYCGM | 10.000 |
| 573 | SAKNAFMLL | 9.000 |
| 533 | VARCIMCCF | 9.000 |
| 213 | NARDISVKI | 7.200 |
| 465 | LAGAFASFY | 6.000 |
| 11 | EAYGKPVKY | 6.000 |
| 333 | RIRIAIALL | 6.000 |
| 343 | EASKAVGQM | 6.000 |
| 489 | SAFIRTLRY | 6.000 |
| 79 | ENKDKPYLL | 6.000 |
| 379 | LATSGQPQY | 6.000 |
| 558 | NAYIMIAIY | 6.000 |
| 630 | KSPHLNYYW | 5.000 |
| 381 | TSGQPQYVL | 5.000 |
| 217 | ISVKIFEDF | 5.000 |
| 132 | FSQTVGEVF | 5.000 |
| 242 | LSLLFILLL | 5.000 |
| 406 | TSCNPTAHL | 5.000 |
| 572 | VSAKNAFML | 5.000 |
| 316 | LAVLEAILL | 4.500 |
| 593 | KVTDLLLFF | 4.000 |
| 514 | IARVILEYI | 3.600 |
| 287 | GASISQLGF | 3.000 |
| 238 | VALVLSLLF | 3.000 |
| 311 | AALIVLAVL | 3.000 |
| 275 | YCWEEYRVL | 3.000 |
| 253 | VAGPLVLVL | 3.000 |
| 651 | IASGFFSVF | 3.000 |
| 647 | GAYVIASGF | 3.000 |
| 225 | FAQSWYWIL | 3.000 |
| 174 | SAPALGRCF | 3.000 |
| 234 | VALGVALVL | 3.000 |
| 369 | IAYWAMTAL | 3.000 |
| 141 | YTKNRNFCL | 3.000 |

TABLE XX-V1-continued

HLA-B35-9meres-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 494 | TLRYHTGSL | 3.000 |
| 678 | NGSLDRPYY | 3.000 |
| 249 | LLRLVAGPL | 3.000 |
| 117 | VSSCPEDPW | 2.500 |
| 282 | VLRDKGASI | 2.400 |
| 28 | KNRSCTDVI | 2.400 |
| 317 | AVLEAILLL | 2.000 |
| 266 | LGVLAYGIY | 2.000 |
| 363 | VLLLICIAY | 2.000 |
| 267 | GVLAYGIYY | 2.000 |
| 25 | GPIKNRSGT | 2.000 |
| 415 | VNSSCPGLM | 2.000 |
| 50 | VVGIVAWLY | 2.000 |
| 589 | VVLDKVTDL | 2.000 |
| 272 | GIYYCWEEY | 2.000 |
| 188 | TPPALPGIT | 2.000 |
| 432 | KGLIQRSVF | 2.000 |
| 152 | VPWNMTVIT | 2.000 |
| 192 | LPGITNDTT | 2.000 |
| 531 | NPVARCIMC | 2.000 |
| 583 | RNIVRVVVL | 2.000 |
| 366 | LICIAYWAM | 2.000 |
| 546 | WCLEKFIKF | 2.000 |
| 554 | FLNRNAYIM | 2.000 |
| 513 | QIARVILEY | 2.000 |
| 92 | FSCILSSNI | 2.000 |
| 530 | QNPVARCIM | 2.000 |
| 133 | SQTVGEVFY | 2.000 |
| 251 | RLVAGPLVL | 2.000 |
| 409 | NPTAHLVNS | 2.000 |
| 347 | AVGQMMSTM | 2.000 |
| 634 | LNYYWLPIM | 2.000 |
| 621 | RIPGLGKDF | 2.000 |
| 643 | TSILGAYVI | 2.000 |
| 482 | IPTFPLISA | 2.000 |
| 110 | CPTPQVCVS | 2.000 |

TABLE XX-V1-continued

HLA-B35-9meres-24P4C12
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 641 | IMTSILGAY | 2.000 |
| 677 | NNGSLDRPY | 2.000 |
| 421 | GLMCVFQGY | 2.000 |
| 162 | LQQELCPSF | 2.000 |
| 149 | LPGVPWNMT | 2.000 |
| 263 | LGVLGVLAY | 2.000 |
| 167 | CPSFLLPSA | 2.000 |
| 148 | CLPGVPWNM | 2.000 |
| 571 | CVSAKNAFM | 2.000 |
| 112 | TPQVCVSSC | 2.000 |
| 384 | QPQYVLWAS | 2.000 |
| 500 | GSLAFGALI | 2.000 |
| 349 | GQMMSTMFY | 2.000 |
| 653 | SGFFSVFGM | 2.000 |
| 4 | KQRDEDDEA | 1.800 |
| 660 | GMCVDTLFL | 1.500 |
| 30 | RSCTDVICC | 1.500 |
| 430 | SSKGLIQRS | 1.500 |

TABLE XX-V3

HLA-B35-9mers-24P4C12
Each peptide is a portion of
SEQ ID NO: 7; each start position
is specified, the length of peptide
is 9 amino acids, and the end
position for each peptide is the
start position plus eight.

| Start | Subsequence | Score |
|---|---|---|
| 6 | WTNITPPAL | 1.000 |
| 9 | ITPPALPGI | 0.400 |
| 4 | FPWTNITPP | 0.200 |
| 2 | RCFPWTNIT | 0.200 |
| 1 | GRCFPWTNI | 0.040 |
| 7 | TNITPPALP | 0.010 |
| 8 | NITPPALPG | 0.010 |
| 3 | CFPWTNITP | 0.001 |
| 5 | PWTNITPPA | 0.001 |

TABLE XX-V5

HLA-B35-9mers-24P4C12
Each peptide is a portion of
SEQ ID NO: 11; each start position
is specified, the length of peptide
is 9 amino acids, and the end
position for each peptide is the
start position plus eight.

| Start | Subsequence | Score |
|---|---|---|
| 3 | EAILLLVLI | 1.200 |
| 5 | ILLLVLIFL | 1.000 |
| 4 | AILLLVLIF | 1.000 |
| 9 | VLIFLRQRI | 0.400 |
| 2 | LEAILLLVL | 0.100 |
| 1 | VLEAILLLV | 0.060 |
| 6 | LLLVLIFLR | 0.010 |
| 7 | LLVLIFLRQ | 0.010 |
| 8 | LVLIFLRQR | 0.010 |

TABLE XX-V6

HLA-B35-9mers-26P4C12
Each peptide is a portion of
SEQ ID NO: 13; each start position
is specified, the length of peptide
is 9 amino acids, and the end
position for each peptide is the
start position plus eight.

| Start | Subsequence | Score |
|---|---|---|
| 5 | KGLIPRSVF | 2.000 |
| 3 | SSKGLIPRS | 1.500 |
| 7 | LIPRSVFNL | 1.000 |
| 8 | IPRSVFNLQ | 0.600 |
| 6 | GLIPRSVFN | 0.100 |
| 2 | YSSKGLIPR | 0.050 |
| 4 | SKGLIPRSV | 0.020 |
| 9 | PRSVFNLQI | 0.004 |
| 1 | GYSSKGLIP | 0.001 |

TABLE XX-V7

HLA-B35-9mers-24P4C12
Each peptide is a portion of
SEQ ID NO: 15; each start position
is specified, the length of peptide
is 9 amino acids, and the end
position for each peptide is the
start position plus eight.

| Start | Subsequence | Score |
|---|---|---|
| 8 | AVGQMMSTM | 2.000 |
| 5 | ILVAVGQMM | 2.000 |
| 4 | WILVAVGQM | 2.000 |

TABLE XX-V7-continued

HLA-B35-9mers-24P4C12
Each peptide is a portion of
SEQ ID NO: 15; each start position
is specified, the length of peptide
is 9 amino acids, and the end
position for each peptide is the
start position plus eight.

| Start | Subsequence | Score |
|---|---|---|
| 7 | VAVGQMMST | 0.300 |
| 6 | LVAVGQMMS | 0.100 |
| 1 | SWYWILVAV | 0.020 |
| 3 | YWILVAVGQ | 0.001 |
| 2 | WYWILVAVG | 0.001 |

TABLE XX-V8

HLA-B35-9mers-24P4C12
Each peptide is a portion of
SEQ ID NO: 17; each start position
is specified, the length of peptide
is 9 amino acids, and the end
position for each peptide is the
start position plus eight.

| Start | Subsequence | Score |
|---|---|---|
| 10 | NPITPTGHV | 4.000 |
| 13 | TPTGHVFQT | 2.000 |
| 19 | FQTSILGAY | 2.000 |
| 5 | LPIMRNPIT | 2.000 |
| 15 | TGHVFQTSI | 0.400 |
| 4 | WLPIMRNPI | 0.400 |
| 7 | IMRNPITPT | 0.300 |
| 20 | QTSILGAYV | 0.200 |
| 11 | PITPTGHVF | 0.100 |
| 16 | GHVFQTSIL | 0.100 |
| 9 | RNPITPTGH | 0.020 |
| 2 | YYWLPIMRN | 0.010 |
| 18 | VFQTSILGA | 0.010 |
| 14 | PTGHVFQTS | 0.010 |
| 17 | HVFQTSILG | 0.010 |
| 12 | ITPTGHVFQ | 0.010 |
| 6 | PIMRNPITP | 0.001 |
| 3 | YWLPIMRNP | 0.001 |
| 8 | MRNPITPTG | 0.001 |
| 1 | NYYWLPIMR | 0.001 |

TABLE XX-V9

HLA-B35-9mers-24P4C12
Each peptide is a portion of
SEQ ID NO: 19; each start position
is specified, the length of peptide
is 9 amino acids, and the end
position for each peptide is the
start position plus eight.

| Start | Subsequence | Score |
|---|---|---|
| 13 | QPATLGYVL | 20.000 |
| 2 | WAMTALYPL | 3.000 |
| 8 | YPLPTQPAT | 2.000 |
| 11 | PTQPATLGY | 0.200 |
| 12 | TQPATLGYV | 0.200 |
| 10 | LPTQPATLG | 0.200 |
| 14 | PATLGYVLW | 0.150 |
| 15 | ATLGYVLWA | 0.100 |
| 4 | MTALYPLPT | 0.100 |
| 16 | TLGYVLWAS | 0.100 |
| 17 | LGYVLWASN | 0.100 |
| 9 | PLPTQPATL | 0.100 |
| 18 | GYVLWASNI | 0.040 |
| 5 | TALYPLPTQ | 0.030 |
| 7 | LYPLPTQPA | 0.010 |
| 3 | AMTALYPLP | 0.010 |
| 6 | ALYPLPTQP | 0.010 |
| 1 | YWAMTALYP | 0.001 |

TABLE XXI-V1

HLA-B35-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 478 | KPQDIPTFPL | 80.000 |
| 83 | KPYLLYFNIF | 40.000 |
| 683 | RPYYMSKSLL | 40.000 |
| 4 | KQRDEDDEAY | 36.000 |
| 123 | DPWTVGKNEF | 20.000 |
| 482 | IPTEPLISAF | 20.000 |
| 357 | YPLVTFVLLL | 20.000 |
| 213 | NARDISVKIF | 18.000 |
| 573 | SAKNAFMLLM | 18.000 |
| 346 | KAVGQMMSTM | 12.000 |
| 79 | ENKDKPYLLY | 12.000 |

TABLE XXI-V1-continued

HLA-B35-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 652 | ASGFFSVFGM | 10.000 |
| 488 | ISAFIRTLRY | 10.000 |
| 132 | FSQTVGEVFY | 10.000 |
| 175 | APALGRCFPW | 10.000 |
| 630 | KSPHLNYYWL | 10.000 |
| 192 | LPGITNDTTI | 8.000 |
| 551 | FIKFLNRNAY | 6.000 |
| 625 | LGKDFKSPHL | 6.000 |
| 331 | RQRIRIAIAL | 6.000 |
| 343 | EASKAVGQMM | 6.000 |
| 60 | DPRQVLYPRN | 6.000 |
| 66 | YPRNSTGAYC | 6.000 |
| 369 | IAYWAMTALY | 6.000 |
| 572 | VSAKNAFMLL | 5.000 |
| 227 | QSWYWILVAL | 5.000 |
| 500 | GSLAFGALIL | 5.000 |
| 417 | SSCPGLMCVF | 5.000 |
| 290 | ISQLGFTTNL | 5.000 |
| 76 | GMGENKDKPY | 4.000 |
| 68 | RNSTGAYCGM | 4.000 |
| 317 | AVLEAILLLM | 4.000 |
| 557 | RNAYIMIAIY | 4.000 |
| 149 | LPGVPWNMTV | 4.000 |
| 676 | RNNGSLDRPY | 4.000 |
| 310 | LAALIVLAVL | 3.000 |
| 316 | LAVLEAILLL | 3.000 |
| 320 | EAILLLMLIF | 3.000 |
| 467 | GAFASFYWAF | 3.000 |
| 395 | SSPGCEKVPI | 3.000 |
| 647 | GAYVIASGFF | 3.000 |
| 677 | NNGSLDRPYY | 3.000 |
| 502 | LAFGALILTL | 3.000 |
| 430 | SSKGLIQRSV | 3.000 |
| 381 | TSGQPQYVLW | 2.500 |
| 362 | FVLLLICIAY | 2.000 |

TABLE XXI-V1-continued

HLA-B35-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 39 | VLFLLFILGY | 2.000 |
| 188 | TPPALPGITN | 2.000 |
| 152 | VPWNMTVITS | 2.000 |
| 348 | VGQMMSTMFY | 2.000 |
| 31 | SCTDVICCVL | 2.000 |
| 384 | QPQYVLWASN | 2.000 |
| 409 | NPTAHLVNSS | 2.000 |
| 613 | LSFFFFSGRI | 2.000 |
| 220 | KIFEDFAQSW | 2.000 |
| 110 | CPTPQVCVSS | 2.000 |
| 546 | WCLEKFIKFL | 2.000 |
| 271 | YGIYYCWEEY | 2.000 |
| 30 | RSCTDVICCV | 2.000 |
| 172 | LPSAPALGRC | 2.000 |
| 162 | LQQELCPSFL | 2.000 |
| 396 | SPGCEKVPIN | 2.000 |
| 266 | LGVLAYGIYY | 2.000 |
| 402 | VPINTSCNPT | 2.000 |
| 378 | YLATSGPQY | 2.000 |
| 365 | LLICIAYWAM | 2.000 |
| 293 | LGFTTNLSAY | 2.000 |
| 262 | ILGVLGVLAY | 2.000 |
| 286 | KGASISQLGF | 2.000 |
| 529 | VQNPVARCIM | 2.000 |
| 678 | NGSLDRPYYM | 2.000 |
| 49 | IVVGIVAWLY | 2.000 |
| 147 | FCLPGVPWNM | 2.000 |
| 265 | VLGVLAYGIY | 2.000 |
| 304 | SVQETWLAAL | 2.000 |
| 464 | VLAGAFASFY | 2.000 |
| 20 | DPSFRGPIKN | 2.000 |
| 661 | MCVDTLFLCF | 2.000 |
| 92 | FSCILSSNII | 2.000 |
| 512 | VQIARVILEY | 2.000 |
| 182 | FPWTNVTPPA | 2.000 |

TABLE XXI-V1-continued

HLA-B35-10mers-24P4C12
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 639 | LPIMTSILGA | 2.000 |
| 570 | FCVSAKNAFM | 2.000 |
| 493 | RTLRYHTGSL | 2.000 |
| 633 | HLNYYWLPIM | 2.000 |
| 531 | NPVARCIMCC | 2.000 |
| 622 | IPGLGKDFKS | 2.000 |
| 485 | FPLISAFIRT | 2.000 |
| 542 | KCCLWCLEKF | 2.000 |
| 589 | VVLDKVTDLL | 2.000 |
| 517 | VILEYIDHKL | 2.000 |
| 414 | LVNSSCPGLM | 2.000 |
| 344 | ASKAVGQMMS | 1.500 |
| 465 | LAGAFASFYW | 1.500 |
| 300 | SAYQSVQETW | 1.500 |
| 659 | FGMCVDTLFL | 1.500 |
| 315 | VLAVLEAILL | 1.500 |
| 118 | SSCPEDPWTV | 1.500 |
| 576 | NAFMLLMRNI | 1.200 |
| 435 | IQRSVFNLQI | 1.200 |

TABLE XXI-V3

HLA-B35-10mers-24P4C12
Each peptide is a portion of
SEQ ID NO: 7; each start position
is specified, the length of peptide
is 10 amino acids, and the end
position for each peptide is the
start position plus nine.

| Start | Subsequence | Score |
|---|---|---|
| 5 | FPWTNITPPA | 2.000 |
| 1 | LGRCFPWTNI | 1.200 |
| 9 | NITPPALPGI | 0.400 |
| 10 | ITPPALPGIT | 0.100 |
| 3 | RCFPWTNITP | 0.020 |
| 8 | TNITPPALPG | 0.010 |
| 6 | PWTNITPPAL | 0.010 |
| 7 | WTNITPPALP | 0.010 |

TABLE XXI-V3-continued

HLA-B35-10mers-24P4C12
Each peptide is a portion of
SEQ ID NO: 7; each start position
is specified, the length of peptide
is 10 amino acids, and the end
position for each peptide is the
start position plus nine.

| Start | Subsequence | Score |
|---|---|---|
| 2 | GRCFPWTNIT | 0.010 |
| 4 | CFPWTNITPP | 0.001 |

TABLE XXI-V5

HLA-B35-10mers-24P4C12
Each peptide is a portion of
SEQ ID NO: 11; each start position
is specified, the length of peptide
is 10 amino acids, and the end
position for each peptide is the
start position plus nine.

| Start | Subsequence | Score |
|---|---|---|
| 4 | EAILLLVLIF | 3.000 |
| 5 | AILLLVLIFL | 1.000 |
| 9 | LVLIFLRQRI | 0.400 |
| 1 | AVLEAILLLV | 0.400 |
| 2 | VLEAILLLVL | 0.300 |
| 3 | LEAILLLVLI | 0.040 |
| 6 | ILLLVLIFLR | 0.010 |
| 10 | VLIFLRQRIR | 0.010 |
| 7 | LLLVLIFLRQ | 0.010 |
| 8 | LLVLIFLRQR | 0.010 |

TABLE XXI-V6

HLA-B35-10mers-24P4C12
Each peptide is a portion of
SEQ ID NO: 13; each start position
is specified, the length of peptide
is 10 amino acids, and the end
position for each peptide is the
start position plus nine.

| Start | Subsequence | Score |
|---|---|---|
| 9 | IPRSVFNLQI | 24.000 |
| 4 | SSKGLIPRSV | 3.000 |
| 7 | GLIPRSVFNL | 1.000 |
| 3 | YSSKGLIPRS | 0.500 |
| 6 | KGLIPRSVFN | 0.200 |
| 5 | SKGLIPRSVF | 0.100 |
| 10 | PRSVFNLQIY | 0.020 |
| 8 | LIPRSVFNLQ | 0.010 |
| 1 | QGYSSKGLIP | 0.010 |

TABLE XXI-V6-continued

HLA-B35-10mers-24P4C12
Each peptide is a portion of
SEQ ID NO: 13; each start position
is specified, the length of peptide
is 10 amino acids, and the end
position for each peptide is the
start position plus nine.

| Start | Subsequence | Score |
|---|---|---|
| 2 | GYSSKGLIPR | 0.001 |

TABLE XXI-V7

HLA-B35-10mers-24P4C12
Each peptide is a portion of
SEQ ID NO: 15; each start position
is specified, the length of peptide
is 10 amino acids, and the end
position for each peptide is the
start position plus nine.

| Start | Subsequence | Score |
|---|---|---|
| 8 | VAVGQMMSTM | 6.000 |
| 5 | WILVAVGQMM | 2.000 |
| 9 | AVGQMMSTMF | 1.000 |
| 1 | QSWYWILVAV | 1.000 |
| 4 | YWILVAVGQM | 0.200 |
| 6 | ILVAVGQMMS | 0.100 |
| 7 | LVAVGQMMST | 0.100 |
| 2 | SWYWILVAVG | 0.001 |
| 3 | WYWILVAVGQ | 0.001 |

TABLE XXI-V8

HLA-B35-10mers-24P4C12
Each peptide is a portion of
SEQ ID NO: 17; each start position
is specified, the length of peptide
is 10 amino acids, and the end
position for each peptide is the
start position plus nine.

| Start | Subsequence | Score |
|---|---|---|
| 14 | TPTGHVFQTS | 2.000 |
| 16 | TGHVFQTSIL | 1.000 |
| 21 | QTSILGAYVI | 0.400 |
| 10 | RNPITPTGHV | 0.400 |
| 6 | LPIMRNPITP | 0.200 |
| 20 | FQTSILGAYV | 0.200 |
| 19 | VFQTSILGAY | 0.200 |
| 13 | ITPTGHVFQT | 0.100 |
| 18 | HVFQTSILGA | 0.100 |
| 5 | WLPIMRNPIT | 0.100 |

TABLE XXI-V8-continued

HLA-B35-10mers-24P4C12
Each peptide is a portion of
SEQ ID NO: 17; each start position
is specified, the length of peptide
is 10 amino acids, and the end
position for each peptide is the
start position plus nine.

| Start | Subsequence | Score |
|---|---|---|
| 15 | PTGHVFQTSI | 0.040 |
| 4 | YWLPIMRNPI | 0.040 |
| 8 | IMRNPITPTG | 0.030 |
| 2 | NYYWLPIMRN | 0.010 |
| 7 | PIMRNPITPT | 0.010 |
| 1 | LNYYWLPIMR | 0.010 |
| 17 | GHVFQTSILG | 0.001 |
| 3 | YYWLPIMRNP | 0.001 |
| 12 | PITPTGHVFQ | 0.001 |
| 9 | MRNPITPTGH | 0.001 |

TABLE XXI-V9

HLA-B35-10mers-24P4C12
Each peptide is a portion of
SEQ ID NO: 19; each start position
is specified, the length of peptide
is 10 amino acids, and the end
position for each peptide is the
start position plus nine.

| Start | Subsequence | Score |
|---|---|---|
| 2 | YWAMTALYPL | 1.000 |
| 13 | TQPATLGYVL | 1.000 |
| 9 | YPLPTQPATL | 1.000 |
| 18 | LGYVLWASNI | 1.000 |
| 14 | QPATLGYVLW | 0.500 |
| 11 | LPTQPATLGY | 0.200 |
| 16 | ATLGYVLWAS | 0.150 |
| 19 | GYVLWASNIS | 0.100 |
| 4 | AMTALYPLPT | 0.100 |
| 8 | LYPLPTQPAT | 0.100 |
| 17 | TLGYVLWASN | 0.100 |
| 7 | ALYPLPTQPA | 0.100 |
| 3 | WAMTALYPLP | 0.050 |
| 12 | PTQPATLGYV | 0.020 |
| 6 | TALYPLPTQP | 0.010 |
| 5 | MTALYPLPTQ | 0.010 |
| 15 | PATLGYVLWA | 0.010 |
| 1 | AYWAMTALYP | 0.010 |

TABLE XXI-V9-continued

HLA-B35-10mers-24P4C12
Each peptide is a portion of
SEQ ID NO: 19; each start position
is specified, the length of peptide
is 10 amino acids, and the end
position for each peptide is the
start position plus nine.

| Start | Subsequence | Score |
|---|---|---|
| 10 | PLPTQPATLG | 0.005 |

Tables XXII-XLIX:

TABLE XXII-V1

HLA-A1-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 80 | NKDKPYLLY | 34 |
| 58 | YGDPRQVLY | 33 |
| 222 | FEDFAQSSWY | 26 |
| 5 | QRDEDDEAY | 25 |
| 77 | MGENKDKPY | 25 |
| 263 | LGVLGVLAY | 24 |
| 489 | SAFIRTLRY | 23 |
| 513 | QIARVILEY | 23 |
| 628 | DFKSPHLNY | 22 |
| 40 | LFLLEILGY | 21 |
| 267 | GVLAYGIYY | 21 |
| 363 | VLLLICIAY | 21 |
| 421 | GLMCVFQGY | 21 |
| 50 | VVGIVAWLY | 20 |
| 318 | VLEAILLLM | 20 |
| 629 | FKSPHLNYY | 20 |
| 133 | SQTVGEVFY | 19 |
| 437 | RSVFNLQIY | 19 |
| 662 | CVDTLFLCF | 19 |
| 11 | EAYGKPVKY | 18 |
| 370 | AYWAMTALY | 18 |
| 18 | KYDPSFRGP | 17 |
| 32 | CTDVICCVL | 17 |
| 66 | YPRNSTGAY | 17 |
| 277 | WEEYRVLRD | 17 |
| 379 | LATSGQPQY | 17 |

TABLE XXII-V1-continued

HLA-A1-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 594 | VTDLLLFFG | 17 |
| 165 | ELCPSFLLP | 16 |
| 353 | STMFYPLVT | 16 |
| 398 | GCEKVPINT | 16 |
| 552 | IKFLNRNAY | 16 |
| 590 | VLDKVTDLL | 16 |
| 678 | NGSLDRPYY | 16 |

TABLE XXII-V3

HLA-A1-9mers-24P4C12
Each peptide is a portion of
SEQ ID NO: 7; each start position
is specified, the length of peptide
is 9 amino acids, and the end
position for each peptide is the
start position plus eight.

| Pos | 123456789 | score |
|---|---|---|
| 8 | NITPPALPG | 11 |
| 9 | ITPPALPGI | 10 |
| 6 | WTNITPPAL | 6 |
| 3 | CFPWTNITP | 5 |

TABLE XXII-V5

HLA-A1-9mers-26P4C12
Each peptide is a portion of
SEQ ID NO: 11; each start position
is specified, the length of peptide
is 9 amino acids, and the end
position for each peptide is the
start position plus eight.

| Pos | 123456789 | score |
|---|---|---|
| 1 | VLEAILLLV | 20 |
| 7 | LLVLIFLRQ | 10 |

TABLE XXII-V6

HLA-A1-9mers-24P4C12
Each peptide is a portion of
SEQ ID NO: 13; each start position
is specified, the length of peptide
is 9 amino acids, and the end
position for each peptide is the
start position plus eight.

| Pos | 123456789 | score |
|---|---|---|
| 2 | YSSSKGLIPR | 12 |
| 1 | GYYSSKGLIP | 7 |
| 3 | SSSKGLIPRS | 7 |
| 8 | IPRSVFNLQ | 7 |
| 9 | PRSVFNLQI | 7 |
| 6 | GLIPRSVFN | 5 |

TABLE XXII-V7

HLA-A1-9mers-24P4C12
Each peptide is a portion of
SEQ ID NO: 15; each start position
is specified, the length of peptide
is 9 amino acids, and the end
position for each peptide is the
start position plus eight.

| Pos | 123456789 | score |
|---|---|---|
| 5 | ILVAVGQMM | 5 |
| 3 | YWILVAVGQ | 4 |
| 7 | VAVGQMMST | 4 |
| 6 | LVAVGQMMS | 3 |
| 1 | SWYWILVAV | 2 |
| 2 | WYWILVAVG | 2 |

TABLE XXII-V8

HLA-A1-9mers-24P4C12
Each peptide is a portion of
SEQ ID NO: 17; each start position
is specified, the length of peptide
is 9 amino acids, and the end
position for each peptide is the
start position plus eight.

| Pos | 123456789 | score |
|---|---|---|
| 19 | FQTSILGAY | 16 |
| 14 | PTGHVFQTS | 11 |
| 12 | ITPTGHVFQ | 8 |
| 18 | VFQTSILGA | 7 |
| 20 | QTSILGAYV | 7 |

TABLE XXII-V9

HLA-A1-9mers-24P4C12
Each peptide is a portion of
SEQ ID NO: 19; each start position
is specified, the length of peptide
is 9 amino acids, and the end
position for each peptide is the
start position plus eight.

| Pos | 123456789 | score |
|---|---|---|
| 11 | PTQPATLGY | 31 |
| 15 | ATTLGYVLWA | 16 |

TABLE XXIII-V1

HLA-A0201-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 260 | VLILGVLGV | 31 |
| 244 | LLFILLLRL | 29 |
| 580 | LLMRNIVRV | 29 |
| 95 | ILSSNIISV | 28 |
| 204 | GISGLIDSL | 28 |
| 261 | LILGVLGVL | 28 |
| 322 | ILLLMLIFL | 28 |
| 506 | ALILTLVQI | 28 |
| 170 | FLLPSAPAL | 27 |
| 252 | LVAGPLVLV | 27 |
| 449 | GLFWTLNWV | 27 |
| 487 | LISAFIRTL | 27 |
| 604 | LLVVGGVGV | 27 |
| 45 | ILGYIVVGI | 26 |
| 232 | ILVALGVAL | 26 |
| 233 | LVALGVALV | 26 |
| 315 | VLAVLEAIL | 26 |
| 501 | SLAFGALIL | 26 |
| 521 | YIDHKLRGV | 26 |
| 42 | LLFILGYIV | 25 |
| 107 | GLQCPTPQV | 25 |
| 200 | TIQQGISGL | 25 |
| 211 | SLNARDISV | 25 |
| 239 | ALVLSLLFI | 25 |
| 257 | LVLVLILGV | 25 |
| 258 | VLVLILGVL | 25 |
| 282 | VLRDKGASI | 25 |
| 317 | AVLEAILLL | 25 |

TABLE XXIII-V1-continued

HLA-A0201-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|-----|-----------|-------|
| 457 | VLALGQCVL | 25 |
| 598 | LLFFGKLLV | 25 |
| 650 | VIASGFFSV | 25 |
| 686 | YMSKSLLKI | 25 |
| 41  | FLLFILGYI | 24 |
| 49  | IVVGIVAWL | 24 |
| 310 | LAALIVLAV | 24 |
| 311 | AALIVLAVL | 24 |
| 333 | RIRIAIALL | 24 |
| 434 | LIQRSVFNL | 24 |
| 509 | LTLVQIARV | 24 |
| 525 | KLRGVQNPV | 24 |
| 564 | AIYGKNFCV | 24 |
| 581 | LMRNIVRVV | 24 |
| 596 | DLLLFFGKL | 24 |
| 605 | LVVGGVGVL | 24 |
| 35  | VICCVLFLL | 23 |
| 56  | WLYGDPRQV | 23 |
| 240 | LVLSLLFIL | 23 |
| 251 | RLVAGPLVL | 23 |
| 253 | VAGPLVLVL | 23 |
| 309 | WLAALIVLA | 23 |
| 340 | LLKEASKAV | 23 |
| 358 | PLVTFVLLL | 23 |
| 494 | TLRYHTGSL | 23 |
| 518 | ILEYIDHKL | 23 |
| 547 | CLEKFIKFL | 23 |
| 589 | VVLDKVTDL | 23 |
| 590 | VLDKVTDLL | 23 |
| 597 | LLLFFGKLL | 23 |
| 100 | IISVAENGL | 22 |
| 241 | VLSLLFILL | 22 |
| 248 | LLLRLVAGP | 22 |
| 249 | LLRLVAGPL | 22 |
| 265 | VLGVLAYGI | 22 |

TABLE XXIII-V1-continued

HLA-A0201-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|-----|-----------|-------|
| 446 | GVLGLFWTL | 22 |
| 452 | WTLNWVLAL | 22 |
| 578 | FMLLMRNIV | 22 |
| 638 | WLPIMTSIL | 22 |
| 660 | GMCVDTLFL | 22 |
| 158 | VITSLQQEL | 21 |
| 187 | VTPPALPGI | 21 |
| 191 | ALPGITNDT | 21 |
| 237 | GVALVLSLL | 21 |
| 247 | ILLRLVAG  | 21 |
| 313 | LIVLAVLEA | 21 |
| 314 | IVLAVLEAI | 21 |
| 442 | LQIYGVLGL | 21 |
| 507 | LILTLVQIA | 21 |
| 537 | IMGCFKCCL | 21 |
| 599 | LFFGKLLVV | 21 |
| 693 | KILGKKNEA | 21 |
| 34  | DVICCVLFL | 20 |
| 38  | CVLFLLFIL | 20 |
| 44  | FILGYIVVG | 20 |
| 207 | GLIDSLNAR | 20 |
| 228 | SWYWILVAL | 20 |
| 234 | VALGVALVL | 20 |
| 236 | LGVALVLSL | 20 |
| 242 | LSLLFILLL | 20 |
| 319 | LEAILLLML | 20 |
| 326 | MLIFLRQRI | 20 |
| 339 | ALLKEASKA | 20 |
| 364 | LLLICIAYW | 20 |
| 417 | SSCPGLMCV | 20 |
| 503 | AFGALILTL | 20 |
| 633 | HLNYYWLPI | 20 |
| 644 | SILGAYVIA | 20 |
| 673 | DLERNNGSL | 20 |
| 690 | SLLKILGKK | 20 |

TABLE XXIII-V1-continued

HLA-A0201-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 48  | YIVVGIVAW | 19 |
| 245 | LFILLLRLV | 19 |
| 255 | GPLVLVLIL | 19 |
| 262 | ILGVLGVLA | 19 |
| 268 | VLAYGIYYC | 19 |
| 291 | SQLGFTTNL | 19 |
| 318 | VLEAILLLM | 19 |
| 323 | LLLMLIFLR | 19 |
| 329 | FLRQRIRIA | 19 |
| 351 | MMSTMFYPL | 19 |
| 365 | LLICIAYWA | 19 |
| 414 | LVNSSCPGL | 19 |
| 464 | VLAGAFASF | 19 |
| 544 | CLWCLEKFI | 19 |
| 617 | FFSGRIPGL | 19 |
| 666 | LFLCFLEDL | 19 |
| 86  | LLYFNIFSC | 18 |
| 231 | WILVALGVA | 18 |
| 235 | ALGVALVLS | 18 |
| 243 | SLLFILLLR | 18 |
| 336 | IAIALLKEA | 18 |
| 355 | MFYPLVTFV | 18 |
| 369 | IAYWAMTAL | 18 |
| 380 | ATSGQPQYV | 18 |
| 394 | ISSPGCEKV | 18 |
| 439 | VFNLQIYGV | 18 |
| 459 | ALGQCVLAG | 18 |
| 510 | TLVQIARVI | 18 |
| 511 | LVQIARVIL | 18 |
| 514 | IARVILEYI | 18 |
| 517 | VILEYIDHK | 18 |
| 583 | RNIVRVVVL | 18 |
| 602 | GKLLVVGGV | 18 |
| 645 | ILGAYVIAS | 18 |
| 46  | LGYIVVGIV | 17 |

TABLE XXIII-V1-continued

HLA-A0201-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 128 | GKNEFSQTV | 17 |
| 154 | WNMTVITSL | 17 |
| 177 | ALGRCFPWT | 17 |
| 184 | WTNVTPPAL | 17 |
| 213 | NARDISVKI | 17 |
| 246 | FILLLRLVA | 17 |
| 289 | SISQLGFTT | 17 |
| 300 | SAYQSVQET | 17 |
| 305 | VQETWLAAL | 17 |
| 312 | ALIVLAVLE | 17 |
| 325 | LMLIFLRQR | 17 |
| 335 | RIAIALLKE | 17 |
| 354 | TMFYPLVTF | 17 |
| 359 | LVTFVLLLI | 17 |
| 453 | TLNWVLALG | 17 |
| 456 | WVLALGQCV | 17 |
| 502 | LAFGALILT | 17 |
| 504 | FGALILTLV | 17 |
| 513 | QIARVILEY | 17 |
| 554 | FLNRNAYIM | 17 |
| 560 | YIMIAIYGK | 17 |
| 586 | VRVVVLDKV | 17 |
| 642 | MTSILGAYV | 17 |
| 658 | VFGMCVDTL | 17 |
| 31  | SCTDVICCV | 16 |
| 43  | LFILGYIVV | 16 |
| 64  | VLYPRNSTG | 16 |
| 90  | NIFSCILSS | 16 |
| 119 | SCPEDPWTV | 16 |
| 144 | NRNFCLPGV | 16 |
| 148 | CLPGVPWNM | 16 |
| 161 | SLQQELCPS | 16 |
| 230 | YWILVALGV | 16 |
| 254 | AGPLVLVLI | 16 |
| 308 | TWLAALIVL | 16 |

TABLE XXIII-V1-continued

HLA-A0201-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 316 | LAVLEAILL | 16 |
| 320 | EAILLLMLI | 16 |
| 357 | YPLVTFVLL | 16 |
| 362 | FVLLLICIA | 16 |
| 373 | AMTALYLAT | 16 |
| 376 | ALYLATSGQ | 16 |
| 407 | SCNPTAHLV | 16 |
| 458 | LALGQCVLA | 16 |
| 637 | YWLPIMTSI | 16 |
| 640 | PIMTSILGA | 16 |
| 52 | GIVAWLYGD | 15 |
| 141 | YTKNRNFCL | 15 |
| 225 | FAQSWYWIL | 15 |
| 250 | LRLVAGPLV | 15 |
| 264 | GVLGVLAYG | 15 |
| 275 | YCWEEYRVL | 15 |
| 366 | LICIAYWAM | 15 |
| 368 | CIAYWAMTA | 15 |
| 371 | YWAMTALYL | 15 |
| 374 | MTALYLATS | 15 |
| 406 | TSCNPTAHL | 15 |
| 433 | GLIQRSVFN | 15 |
| 443 | QIYGVLGLF | 15 |
| 491 | FIRTLRYHT | 15 |
| 573 | SAKNAFMLL | 15 |
| 657 | SVFGMCVDT | 15 |
| 663 | VDTLFLCFL | 15 |

TABLE XXIII-V3

HLA-A0201-9mers-24P4C12
Each peptide is a portion of
SEQ ID NO: 7; each start position
is specified, the length of peptide
is 9 amino acids, and the end
position for each peptide is the
start position plus eight.

| Pos | 123456789 | score |
|---|---|---|
| 9 | ITPPALPGI | 22 |

TABLE XXIII-V3-continued

HLA-A0201-9mers-24P4C12
Each peptide is a portion of
SEQ ID NO: 7; each start position
is specified, the length of peptide
is 9 amino acids, and the end
position for each peptide is the
start position plus eight.

| Pos | 123456789 | score |
|---|---|---|
| 6 | WTNITPPAL | 17 |
| 8 | NITPPALPG | 11 |
| 2 | RCFPWTNIT | 10 |

TABLE XXIII-V5

HLA-A0201-9mers-24P4C12
Each peptide is a portion of
SEQ ID NO: 11; each start position
is specified, the length of peptide
is 9 amino acids, and the end
position for each peptide is the
start position plus eight.

| Pos | 123456789 | score |
|---|---|---|
| 5 | ILLLVLIFL | 28 |
| 1 | VLEAILLLV | 25 |
| 9 | VLIFLRQRI | 21 |
| 2 | LEAILLLVL | 20 |
| 6 | LLLVLIFLR | 19 |
| 3 | EAILLLVLI | 18 |
| 4 | AILLLVLIF | 18 |
| 7 | LLVLIFLRQ | 13 |
| 8 | LVLIFLRQR | 13 |

TABLE XXIII-V6

HLA-A0201-9mers-24P4C12
Each peptide is a portion of
SEQ ID NO: 13; each start position
is specified, the length of peptide
is 9 amino acids, and the end
position for each peptide is the
start position plus eight.

| Pos | 123456789 | score |
|---|---|---|
| 2 | YSSKGLIPR | 12 |
| 1 | GYSSKGLIP | 7 |
| 3 | SSKGLIPRS | 7 |
| 8 | IPRSVFNLQ | 7 |
| 9 | PRSVFNLQI | 7 |
| 6 | GLIPRSVFN | 5 |

TABLE XXIII-V7

HLA-A0201-9mers-24P4C12
Each peptide is a portion of SEQ ID NO: 15; each start position is specified, the length of peptide is 9 amino acids, and the end position for each peptide is the start position plus eight.

| Pos | 123456789 | score |
|---|---|---|
| 1 | SWYWILVAV | 20 |
| 4 | WILVAVGQM | 18 |
| 5 | ILVAVGQMM | 16 |
| 7 | VAVGQMMST | 13 |
| 8 | AVGQMMSTM | 12 |
| 6 | LVAVGQMMS | 10 |

TABLE XXIII-V8

HLA-A0201-9mers-24P4C12
Each peptide is a portion of SEQ ID NO: 17; each start position is specified, the length of peptide is 9 amino acids, and the end position for each peptide is the start position plus eight.

| Pos | 123456789 | score |
|---|---|---|
| 4 | WLPIMRNPI | 19 |
| 7 | IMRNPITPT | 19 |
| 20 | QTSILGAYV | 17 |
| 10 | NPITPTGHV | 15 |
| 16 | GHVFQTSIL | 12 |
| 15 | TGHVFQTSI | 11 |
| 18 | VFQTSILGA | 11 |
| 12 | ITPTGHVFQ | 10 |
| 5 | LPIMRNPIT | 9 |
| 13 | TPTGHVFQT | 9 |

TABLE XXIII-V9

HLA-A0201-9mers-24P4C12
Each peptide is a portion of SEQ ID NO: 19; each start position is specified, the length of peptide is 9 amino acids, and the end position for each peptide is the start position plus eight.

| Pos | 123456789 | score |
|---|---|---|
| 9 | PLPTQPATL | 21 |
| 2 | WAMTALYPL | 20 |
| 15 | ATLGYVLWA | 20 |
| 6 | ALYPLPTQP | 16 |
| 12 | TQPATLGYV | 14 |
| 13 | QPATLGYVL | 14 |

TABLE XXIII-V9-continued

HLA-A0201-9mers-24P4C12
Each peptide is a portion of SEQ ID NO: 19; each start position is specified, the length of peptide is 9 amino acids, and the end position for each peptide is the start position plus eight.

| Pos | 123456789 | score |
|---|---|---|
| 16 | TLGYVLWAS | 14 |
| 5 | TALYPLPTQ | 13 |
| 4 | MTALYPLPT | 12 |
| 8 | YPLPTQPAT | 12 |
| 3 | AMTALYPLP | 11 |

TABLE XXIV-V1

HLA-A0203-9mers-24P4C12

| Pos | 1234567890 | score |
|---|---|---|
| No Results Found. | | |

TABLE XXIV-V3

HLA-A0203-9mers-24P4C12

| Pos | 1234567890 | score |
|---|---|---|
| No Results Found. | | |

TABLE XXIV-V5

HLA-A0203-9mers-24P4C12

| Pos | 1234567890 | score |
|---|---|---|
| No Results Found. | | |

TABLE XXIV-V6

HLA-A0203-9mers-24P4C12

| Pos | 1234567890 | score |
|---|---|---|
| No Results Found. | | |

TABLE XXIV-V7

HLA-A0203-9mers-24P4C12

| Pos | 1234567890 | score |
|---|---|---|
| No Results Found. | | |

TABLE XXIV-V8

HLA-A0203-9mers-24P4C12

| Pos | 1234567890 | score |
|---|---|---|
| No Results Found. | | |

TABLE XXIV-V9

HLA-A0203-9mers-24P4C12

| Pos | 1234567890 | score |
|---|---|---|
| No Results Found. | | |

TABLE XXV-V1

HLA-A3-9mers-24P

Each peptide is a portion of SEQ ID NO: 3; each start position is specified, the length of peptide is 9 amino acids, and the end position for each peptide is the start position plus eight.

| Pos | 123456789 | score |
|---|---|---|
| 585 | IVRVVVLDK | 29 |
| 424 | CVFQGYSSK | 27 |
| 64 | VLYPRNSTG | 26 |
| 135 | TVGEVFYTK | 26 |
| 251 | RLVAGPLVL | 26 |
| 506 | ALILTLVQI | 24 |
| 513 | QIARVILEY | 24 |
| 603 | KLLVVGGVG | 24 |
| 690 | SLLKILGKK | 24 |
| 267 | GVLAYGIYY | 23 |
| 282 | VLRDKGASI | 23 |
| 312 | ALIVLAVLE | 23 |
| 334 | IRIAIALLK | 23 |
| 102 | SVAENGLQC | 22 |
| 232 | ILVALGVAL | 22 |
| 247 | ILLLRLVAG | 22 |
| 443 | QIYGVLGLF | 22 |
| 464 | VLAGAFASF | 22 |
| 516 | RVILEYIDH | 22 |
| 579 | MLLMRNIVR | 22 |
| 50 | VVGIVAWLY | 21 |
| 212 | LNARDISVK | 21 |
| 281 | RVLRDKGAS | 21 |
| 321 | AILLLMLIF | 21 |
| 338 | IALLKEASK | 21 |

TABLE XXV-V1-continued

HLA-A3-9mers-24P

Each peptide is a portion of SEQ ID NO: 3; each start position is specified, the length of peptide is 9 amino acids, and the end position for each peptide is the start position plus eight.

| Pos | 123456789 | score |
|---|---|---|
| 339 | ALLKEASKA | 21 |
| 376 | ALYLATSGQ | 21 |
| 393 | NISSPGCEK | 21 |
| 517 | VILEYIDHK | 21 |
| 593 | KVTDLLLFF | 21 |
| 619 | SGRIPGLGK | 21 |
| 621 | RIPGLGKDF | 21 |
| 44 | FILGYIVVG | 20 |
| 56 | WLYGDPRQV | 20 |
| 243 | SLLFILLLR | 20 |
| 259 | LVLILGVLG | 20 |
| 347 | AVGQMMSTM | 20 |
| 363 | VLLLICIAY | 20 |
| 463 | CVLAGAFAS | 20 |
| 501 | SLAFGALIL | 20 |
| 606 | VVGGVGVLS | 20 |
| 689 | KSLLKILGK | 20 |
| 16 | PVKYDPSFR | 19 |
| 170 | FLLPSAPAL | 19 |
| 186 | NVTPPALPG | 19 |
| 207 | GLIDSLNAR | 19 |
| 246 | FILLLRLVA | 19 |
| 249 | LLRLVAGPL | 19 |
| 260 | VLILGVLGV | 19 |
| 262 | ILGVLGVLA | 19 |
| 298 | NLSAYQSVQ | 19 |
| 317 | AVLEAILLL | 19 |
| 333 | RIRIAIALL | 19 |
| 433 | GLIQRSVFN | 19 |
| 508 | ILTLVQIAR | 19 |
| 525 | KLRGVQNPV | 19 |
| 560 | YIMIAIYGK | 19 |
| 588 | VVVLDKVTD | 19 |
| 604 | LLVVGGVGV | 19 |
| 605 | LVVGGVGVL | 19 |
| 681 | LDRPYYMSK | 19 |

TABLE XXV-V1-continued

HLA-A3-9mers-24P
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 11 | EAYGKPVKY | 18 |
| 49 | IVVGIVAWL | 18 |
| 73 | AYCGMGENK | 18 |
| 220 | KIFEDFAQS | 18 |
| 248 | LLLRLVAGP | 18 |
| 261 | LILGVLGVL | 18 |
| 264 | GVLGVLAYG | 18 |
| 272 | GIYYCWEEY | 18 |
| 278 | EEYRVLRDK | 18 |
| 314 | IVLAVLEAI | 18 |
| 432 | KGLIQRSVF | 18 |
| 441 | NLQIYGVLG | 18 |
| 446 | GVLGLFWTL | 18 |
| 457 | VLALGQCVL | 18 |
| 564 | AIYGKNFCV | 18 |
| 587 | RVVVLDKVT | 18 |
| 649 | YVIASGFFS | 18 |
| 10 | DEAYGKPVK | 17 |
| 63 | QVLYPRNST | 17 |
| 121 | PEDPWTVGK | 17 |
| 177 | ALGRCFPWT | 17 |
| 211 | SLNARDISV | 17 |
| 233 | LVALGVALV | 17 |
| 235 | ALGVALVLS | 17 |
| 239 | ALVLSLLFI | 17 |
| 252 | LVAGPLVLV | 17 |
| 309 | WLAALIVLA | 17 |
| 335 | RIAIALLKE | 17 |
| 365 | LLICIAYWA | 17 |
| 368 | CIAYWAMTA | 17 |
| 401 | KVPINTSCN | 17 |
| 421 | GLMCVFQGY | 17 |
| 456 | WVLALGQCV | 17 |
| 459 | ALGQCVLAG | 17 |
| 510 | TLVQIARVI | 17 |

TABLE XXV-V1-continued

HLA-A3-9mers-24P
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 542 | KCCLWCLEK | 17 |
| 562 | MIAIYGKNF | 17 |
| 580 | LLMRNIVRV | 17 |
| 583 | RNIVRVVVL | 17 |
| 644 | SILGAYVIA | 17 |
| 657 | SVFGMCVDT | 17 |
| 662 | CVDTLFLCF | 17 |
| 26 | PIKNRSCTD | 16 |
| 34 | DVICCVLFL | 16 |
| 45 | ILGYIVVGI | 16 |
| 86 | LLYFNIFSC | 16 |
| 157 | TVITSLQQE | 16 |
| 165 | ELCPSFLLP | 16 |
| 237 | GVALVLSLL | 16 |
| 258 | VLVLILGVL | 16 |
| 289 | SISQLGFTT | 16 |
| 304 | SVQETWLAA | 16 |
| 323 | LLLMLIFLR | 16 |
| 364 | LLLICIAYW | 16 |
| 470 | ASFYWAFHK | 16 |
| 494 | TLRYHTGSL | 16 |
| 511 | LVQIARVIL | 16 |
| 554 | FLNRNAYIM | 16 |
| 571 | CVSAKNAFM | 16 |
| 584 | NIVRVVVLD | 16 |
| 673 | DLERNNGSL | 16 |
| 693 | KILGKKNEA | 16 |
| 698 | KNEAPPDNK | 16 |
| 20 | DPSFRGPIK | 15 |
| 48 | YIVVGIVAW | 15 |
| 58 | YGDPRQVLY | 15 |
| 99 | NIISVAENG | 15 |
| 151 | GVPWNMTVI | 15 |
| 191 | ALPGITNDT | 15 |
| 231 | WILVALGVA | 15 |
| 234 | VALGVALVL | 15 |

TABLE XXV-V1-continued

HLA-A3-9mers-24P
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 257 | LVLVLILGV | 15 |
| 318 | VLEAILLLM | 15 |
| 322 | ILLLMLIFL | 15 |
| 327 | LIFLRQRIR | 15 |
| 329 | FLRQRIRIA | 15 |
| 532 | PVARCIMCC | 15 |
| 589 | VVLDKVTDL | 15 |
| 597 | LLLFFGKLL | 15 |
| 598 | LLFFGKLLV | 15 |
| 622 | IPGLGKDFK | 15 |
| 645 | ILGAYVIAS | 15 |
| 651 | IASGFFSVF | 15 |
| 680 | SLDRPYYMS | 15 |
| 691 | LLKILGKKN | 15 |
| 7 | DEDDEAYGK | 14 |
| 42 | LLFILGYIV | 14 |
| 53 | IVAWLYGDP | 14 |
| 81 | KDKPYLLYF | 14 |
| 95 | ILSSNIISV | 14 |
| 148 | CLPGVPWNM | 14 |
| 171 | LLPSAPALG | 14 |
| 244 | LLFILLLRL | 14 |
| 311 | AALIVLAVL | 14 |
| 315 | VLAVLEAIL | 14 |
| 324 | LLMLIFLRQ | 14 |
| 326 | MLIFLRQRI | 14 |
| 337 | AIALLKEAS | 14 |
| 359 | LVTFVLLLI | 14 |
| 370 | AYWAMTALY | 14 |
| 378 | YLATSGQPQ | 14 |
| 388 | VLWASNISS | 14 |
| 453 | TLNWVLALG | 14 |
| 465 | LAGAFASFY | 14 |
| 487 | LISAFIRTL | 14 |
| 496 | RYHTGSLAF | 14 |

TABLE XXV-V1-continued

HLA-A3-9mers-24P
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 523 | DHKLRGVQN | 14 |
| 527 | RGVQNPVAR | 14 |
| 528 | GVQNPVARC | 14 |
| 534 | ARCIMCCFK | 14 |
| 558 | NAYIMIAIY | 14 |
| 567 | GKNFCVSAK | 14 |
| 596 | DLLLFFGKL | 14 |
| 609 | GVGVLSFFF | 14 |
| 638 | WLPIMTSIL | 14 |
| 647 | GAYVIASGF | 14 |
| 665 | TLFLCFLED | 14 |
| 685 | YYMSKSLLK | 14 |
| 694 | ILGKKNEAP | 14 |
| 699 | NEAPPDNKK | 14 |
| 701 | APPDNKKRK | 14 |

TABLE XXV-V3

HLA-A3-9mers-24P4C12
Each peptide is a portion of
SEQ ID NO: 7; each start position
is specified, the length of peptide
is 9 amino acids, and the end
position for each peptide is the
start position plus eight.

| Pos | 123456789 | score |
|---|---|---|
| 8 | NITPPALPG | 17 |

TABLE XXV-V5

HLA-A3-9mers-24P4C12
Each peptide is a portion of
SEQ ID NO: 11; each start position
is specified, the length of peptide
is 9 amino acids, and the end
position for each peptide is the
start position plus eight.

| Pos | 123456789 | score |
|---|---|---|
| 4 | AILLLVLIF | 21 |
| 8 | LVLIFLRQR | 20 |
| 5 | ILLLVLIFL | 16 |
| 6 | LLLVLIFLR | 16 |
| 1 | VLEAILLLV | 15 |

TABLE XXV-V5-continued

HLA-A3-9mers-24P4C12
Each peptide is a portion of
SEQ ID NO: 11; each start position
is specified, the length of peptide
is 9 amino acids, and the end
position for each peptide is the
start position plus eight.

| Pos | 123456789 | score |
|---|---|---|
| 7 | LLVLIFLRQ | 14 |
| 9 | VLIFLRQRI | 14 |

TABLE XXV-V6

HLA-A3-9mers-24P4C12
Each peptide is a portion of
SEQ ID NO: 13; each start position
is specified, the length of peptide
is 9 amino acids, and the end
position for each peptide is the
start position plus eight.

| Pos | 123456789 | score |
|---|---|---|
| 6 | GLIPRSVFN | 22 |
| 5 | KGLIPRSVF | 18 |
| 7 | LIPRSVFNL | 11 |

TABLE XXV-V7

HLA-A3-9mers-24P4C12
Each peptide is a portion of
SEQ ID NO: 15; each start position
is specified, the length of peptide
is 9 amino acids, and the end
position for each peptide is the
start position plus eight.

| Pos | 123456789 | score |
|---|---|---|
| 8 | AVGQMMSTM | 20 |
| 5 | ILVAVGQMM | 19 |
| 6 | LVAVGQMMS | 15 |
| 4 | WILVAVGQM | 14 |
| 3 | YWILVAVGQ | 12 |
| 1 | SWYWILVAV | 10 |

TABLE XXV-V8

HLA-A3-9mers-24P4C12
Each peptide is a portion of
SEQ ID NO: 17; each start position
is specified, the length of peptide
is 9 amino acids, and the end
position for each peptide is the
start position plus eight.

| Pos | 123456789 | score |
|---|---|---|
| 11 | PITPTGHVF | 22 |
| 6 | PIMRNPITP | 16 |
| 4 | WLPIMRNPI | 12 |

TABLE XXV-V8-continued

HLA-A3-9mers-24P4C12
Each peptide is a portion of
SEQ ID NO: 17; each start position
is specified, the length of peptide
is 9 amino acids, and the end
position for each peptide is the
start position plus eight.

| Pos | 123456789 | score |
|---|---|---|
| 9 | RNPITPTGH | 11 |
| 1 | NYYWLPIMR | 10 |
| 17 | HVFQTSILG | 10 |

TABLE XXV-V9

HLA-A3-9mers-24P4C12
Each peptide is a portion of
SEQ ID NO: 19; each start position
is specified, the length of peptide
is 9 amino acids, and the end
position for each peptide is the
start position plus eight.

| Pos | 123456789 | score |
|---|---|---|
| 6 | ALYPLPTQP | 25 |
| 9 | PLPTQPATL | 18 |
| 11 | PTQPATLGY | 12 |
| 16 | TLGYVLWAS | 12 |

TABLE XXVI-V1

HLA-A26-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 34 | DVICCVLFL | 35 |
| 49 | IVVGIVAWL | 28 |
| 483 | PTFPLISAF | 28 |
| 605 | LVVGGVGVL | 27 |
| 593 | KVTDLLLFF | 26 |
| 317 | AVLEAILLL | 25 |
| 592 | DKVTDLLLF | 25 |
| 138 | EVFYTKNRN | 24 |
| 240 | LVLSLLFIL | 24 |
| 589 | VVLDKVTDL | 24 |
| 38 | CVLFLLFIL | 23 |
| 237 | GVALVLSLL | 23 |
| 11 | EAYGKPVKY | 22 |

TABLE XXVI-V1-continued

HLA-A26-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 267 | GVLAYGIYY | 22 |
| 285 | DKGASISQL | 22 |
| 452 | WTLNWVLAL | 22 |
| 50 | VVGIVAWLY | 20 |
| 79 | ENKDKPYLL | 20 |
| 157 | TVITSLQQE | 20 |
| 263 | LGVLGVLAY | 20 |
| 446 | GVLGLFWTL | 20 |
| 628 | DFKSPHLNY | 20 |
| 641 | IMTSILGAY | 20 |
| 662 | CVDTLFLCF | 20 |
| 236 | LGVALVLSL | 19 |
| 258 | VLVLILGVL | 19 |
| 307 | ETWLAALIV | 19 |
| 320 | EAILLLMLI | 19 |
| 414 | LVNSSCPGL | 19 |
| 437 | RSVFNLQIY | 19 |
| 513 | QIARVILEY | 19 |
| 609 | GVGVLSFFF | 19 |
| 673 | DLERNNGSL | 19 |
| 32 | CTDVICCVL | 18 |
| 198 | DTTIQQGIS | 18 |
| 200 | TIQQGISGL | 18 |
| 204 | GISGLIDSL | 18 |
| 244 | LLFILLLRL | 18 |
| 294 | GFTTNLSAY | 18 |
| 354 | TMFYPLVTF | 18 |
| 360 | VTFVLLLIC | 18 |
| 400 | EKVPINTSC | 18 |
| 511 | LVQIARVIL | 18 |
| 596 | DLLLFFGKL | 18 |
| 102 | SVAENGLQC | 17 |
| 184 | WTNVTPPAL | 17 |
| 216 | DISVKIFED | 17 |
| 261 | LILGVLGVL | 17 |

TABLE XXVI-V1-continued

HLA-A26-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 358 | PLVTFVLLL | 17 |
| 438 | SVFNLQIYG | 17 |
| 442 | LQIYGVLGL | 17 |
| 443 | QIYGVLGLF | 17 |
| 487 | LISAFIRTL | 17 |
| 608 | GGVGVLSFF | 17 |
| 664 | DTLFLCFLE | 17 |

TABLE XXVI-V3

HLA-A26-9mers-24P4C12
Each peptide is a portion of
SEQ ID NO: 7; each start position
is specified, the length of peptide
is 9 amino acids, and the end
position for each peptide is the
start position plus eight.

| Pos | 123456789 | score |
|---|---|---|
| 6 | WTNITPPAL | 17 |
| 9 | ITPPALPGI | 13 |

TABLE XXVI-V5

HLA-A26-9mers-24P4C12
Each peptide is a portion of
SEQ ID NO: 11; each start position
is specified, the length of peptide
is 9 amino acids, and the end
position for each peptide is the
start position plus eight.

| Pos | 123456789 | score |
|---|---|---|
| 3 | EAILLLVLI | 19 |
| 4 | AILLLVLIF | 18 |
| 8 | LVLIFLRQR | 15 |
| 2 | LEAILLLVL | 14 |
| 5 | ILLLVLIFL | 13 |

TABLE XXVI-V6

HLA-A26-9mers-24P4C12
Each peptide is a portion of
SEQ ID NO: 13; each start position
is specified, the length of peptide
is 9 amino acids, and the end
position for each peptide is the
start position plus eight.

| Pos | 123456789 | score |
|---|---|---|
| 7 | LIPRSVFNL | 16 |
| 5 | KGLIPRSVF | 9 |

TABLE XXVI-V7

HLA-A26-9mers-24P4C12
Each peptide is a portion of
SEQ ID NO: 15; each start position
is specified, the length of peptide
is 9 amino acids, and the end
position for each peptide is the
start position plus eight.

| Pos | 123456789 | score |
|---|---|---|
| 8 | AVGQMMSTM | 12 |
| 6 | LVAVGQMMS | 11 |
| 4 | WILVAVGQM | 10 |
| 1 | SWYWILVAV | 8 |
| 5 | ILVAVGQMM | 6 |
| 2 | WYWILVAVG | 5 |
| 7 | VAVGQMMST | 5 |

TABLE XXVI-V8

HLA-A26-9mers-24P4C12
Each peptide is a portion of
SEQ ID NO: 17; each start position
is specified, the length of peptide
is 9 amino acids, and the end
position for each peptide is the
start position plus eight.

| Pos | 123456789 | score |
|---|---|---|
| 19 | FQTSILGAY | 20 |
| 11 | PITPTGHVF | 15 |
| 17 | HVFQTSILG | 15 |
| 16 | GHVFQTSIL | 13 |
| 20 | QTSILGAYV | 10 |
| 14 | PTGHVFQTS | 9 |

TABLE XXVI-V9

HLA-A26-9mers-24P4C12
Each peptide is a portion of
SEQ ID NO: 19; each start position
is specified, the length of peptide
is 9 amino acids, and the end
position for each peptide is the
start position plus eight.

| Pos | 123456789 | score |
|---|---|---|
| 11 | PTQPATLGY | 20 |
| 15 | ATLGYVLWA | 13 |
| 2 | WAMTALYPL | 12 |
| 13 | QPATLGYVL | 10 |
| 4 | MTALYPLPT | 9 |
| 9 | PLPTQPATL | 9 |

TABLE XXVII-V1

HLA-B0702-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 255 | GPLVLVLIL | 23 |
| 357 | YPLVTFVLL | 23 |
| 683 | RPYYMSKSL | 21 |
| 149 | LPGVPWNMT | 20 |
| 396 | SPGCEKVPI | 20 |
| 482 | IPTFPLISA | 20 |
| 631 | SPHLNYYWL | 20 |
| 15 | KPVKYDPSF | 19 |
| 152 | VPWNMTVIT | 19 |
| 167 | CPSFLLPSA | 19 |
| 25 | GPIKNRSCT | 18 |
| 172 | LPSAPALGR | 18 |
| 83 | KPYLLYFNI | 17 |
| 188 | TPPALPGIT | 17 |
| 192 | LPGITNDTT | 17 |
| 57 | LYGDPRQVL | 16 |
| 232 | ILVALGVAL | 16 |
| 253 | VAGPLVLVL | 16 |
| 479 | PQDIPTFPL | 16 |
| 503 | AFGALILTL | 16 |
| 49 | IVVGIVAWL | 15 |
| 120 | CPEDPWTVG | 15 |
| 175 | APALGRCFP | 15 |
| 189 | PPALPGITN | 15 |
| 234 | VALGVALVL | 15 |
| 251 | RLVAGPLVL | 15 |

TABLE XXVII-V1-continued

HLA-B0702-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 381 | TSGQPQYVL | 15 |
| 406 | TSCNPTAHL | 15 |
| 583 | RNIVRVVVL | 15 |
| 617 | FFSGRIPGL | 15 |
| 20 | DPSFRGPIK | 14 |
| 34 | DVICCVLFL | 14 |
| 66 | YPRNSTGAY | 14 |
| 204 | GISGLIDSL | 14 |
| 236 | LGVALVLSL | 14 |
| 252 | LVAGPLVLV | 14 |
| 291 | SQLGFTTNL | 14 |
| 311 | AALIVLAVL | 14 |
| 317 | AVLEAILLL | 14 |
| 333 | RIRIAIALL | 14 |
| 351 | MMSTMFYPL | 14 |
| 419 | CPGLMCVFQ | 14 |
| 452 | WTLNWVLAL | 14 |
| 499 | TGSLAFGAL | 14 |
| 605 | LWGGVGVL | 14 |
| 660 | GMCVDTLFL | 14 |
| 60 | DPRQVLYPR | 13 |
| 100 | IISVAENGL | 13 |
| 110 | CPTPQVCVS | 13 |
| 164 | QELCPSFLL | 13 |
| 170 | FLLPSAPAL | 13 |
| 182 | FPWTNVTPP | 13 |
| 228 | SWYWILVAL | 13 |
| 241 | VLSLLFILL | 13 |
| 249 | LLRLVAGPL | 13 |
| 261 | LILGVLGVL | 13 |
| 302 | YQSVQETWL | 13 |
| 319 | LEAILLLML | 13 |
| 358 | PLVTFVLLL | 13 |
| 369 | IAYWAMTAL | 13 |
| 371 | YWAMTALYL | 13 |

TABLE XXVII-V1-continued

HLA-B0702-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 409 | NPTAHLVNS | 13 |
| 442 | LQIYGVLGL | 13 |
| 446 | GVLGLFWTL | 13 |
| 478 | KPQDIPTFP | 13 |
| 487 | LISAFIRTL | 13 |
| 494 | TLRYHTGSL | 13 |
| 501 | SLAFGALIL | 13 |
| 511 | LVQIARVIL | 13 |
| 590 | VLDKVTDLL | 13 |
| 622 | IPGLKDFK | 13 |
| 651 | IASGFFSVF | 13 |
| 32 | CTDVICCVL | 12 |
| 78 | GENKDKPYL | 12 |
| 154 | WNMTVITSL | 12 |
| 184 | WTNVTPPAL | 12 |
| 242 | LSLLFILLL | 12 |
| 244 | LLFILLLRL | 12 |
| 285 | DKGASISQL | 12 |
| 305 | VQETWLAAL | 12 |
| 308 | TWLAALIVL | 12 |
| 315 | VLAVLEAIL | 12 |
| 322 | ILLLMLIFL | 12 |
| 356 | FYPLVTFVL | 12 |
| 373 | AMTALYLAT | 12 |
| 380 | ATSGQPQYV | 12 |
| 457 | VLALGQCVL | 12 |
| 525 | KLRGVQNPV | 12 |
| 547 | CLEKEIKEL | 12 |
| 572 | VSAKNAFML | 12 |
| 589 | VVLDKVTDL | 12 |
| 591 | LDKVTDLLL | 12 |
| 626 | GKDFKSPHL | 12 |
| 658 | VFGMCVDTL | 12 |
| 701 | APPDNKKRK | 12 |
| 28 | KNRSCTDVI | 11 |

TABLE XXVII-V1-continued

HLA-B0702-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 45 | ILGYIVVGI | 11 |
| 79 | ENKDKPYLL | 11 |
| 104 | AENGLQCPT | 11 |
| 107 | GLQCPTPQV | 11 |
| 109 | QCPTPQVCV | 11 |
| 112 | TPQVGVSSC | 11 |
| 123 | DPWTVGKNE | 11 |
| 163 | QQELCPSFL | 11 |
| 169 | SFLLPSAPA | 11 |
| 177 | ALGRCFPWT | 11 |
| 191 | ALPGITNDT | 11 |
| 237 | GVALVLSLL | 11 |
| 239 | ALVLSLLFI | 11 |
| 258 | VLVLILGVL | 11 |
| 262 | ILGVLGVLA | 11 |
| 275 | YGWEEYRVL | 11 |
| 310 | LAALIVLAV | 11 |
| 332 | QRIRIAIAL | 11 |
| 343 | EASKAVGQM | 11 |
| 354 | TMFYPLVTF | 11 |
| 384 | QPQYVLWAS | 11 |
| 414 | LVNSSCPGL | 11 |
| 426 | FQGYSSKGL | 11 |
| 434 | LIQRSVFNL | 11 |
| 440 | FNLQIYGVL | 11 |
| 450 | LFWTLNWVL | 11 |
| 464 | VLAGAFASF | 11 |
| 518 | ILEYIDHKL | 11 |
| 531 | NPVARCIMC | 11 |
| 537 | IMCCFKCCL | 11 |
| 571 | CVSAKNAFM | 11 |
| 573 | SAKNAFMLL | 11 |
| 574 | AKNAFMLLM | 11 |
| 596 | DLLLFFGKL | 11 |
| 597 | LLLFFGKLL | 11 |

TABLE XXVII-V1-continued

HLA-B0702-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 599 | LFFGKLLVV | 11 |
| 638 | WLPIMTSIL | 11 |
| 663 | VDTLFLCFL | 11 |
| 686 | YMSKSLLKI | 11 |
| 702 | PPDNKKRKK | 11 |

TABLE XXVII-V3

HLA-B0702-9mers-24P4C12
Each peptide is a portion of
SEQ ID NO: 7; each start position
is specified, the length of peptide
is 9 amino acids, and the end
position for each peptide is the
start position plus eight.

| Pos | 123456789 | score |
|---|---|---|
| 4 | FPWTNITPP | 12 |
| 6 | WTNITPPAL | 12 |
| 1 | GRCFPWTNI | 10 |
| 2 | RCFPWTNIT | 9 |
| 5 | PWTNITPPA | 9 |
| 9 | ITPPALPGI | 9 |
| 8 | NITPPALPG | 7 |

TABLE XXVII-V5

HLA-B0702-9mers-24P4C12
Each peptide is a portion of
SEQ ID NO: 11; each start position
is specified, the length of peptide
is 9 amino acids, and the end
position for each peptide is the
start position plus eight.

| Pos | 123456789 | score |
|---|---|---|
| 2 | LEAILLLVL | 14 |
| 5 | ILLLVLIFL | 12 |
| 4 | AILLLVLIF | 11 |
| 1 | VLEAILLLV | 9 |
| 3 | EAILLLVLI | 9 |
| 9 | VLIFLRQRI | 7 |

TABLE XXVII-V6

HLA-B0702-9mers-24P4C12

Each peptide is a portion of SEQ ID NO: 13; each start position is specified, the length of peptide is 9 amino acids, and the end position for each peptide is the start position plus eight.

| Pos | 123456789 | score |
|---|---|---|
| 8 | IPRSVFNLQ | 14 |
| 5 | KGLIPRSVF | 12 |
| 7 | LIPRSVFNL | 11 |
| 9 | PRSVFNLQI | 10 |
| 4 | SKGLIPRSV | 7 |

TABLE XXVII-V7

HLA-B0702-9mers-24P4C12
Each peptide is a portion of SEQ ID NO: 15; each start position is specified, the length of peptide is 9 amino acids, and the end position for each peptide is the start position plus eight.

| Pos | 123456789 | score |
|---|---|---|
| 1 | SWYWILVAV | 9 |
| 5 | ILVAVGQMM | 9 |
| 8 | AVGQMMSTM | 9 |
| 7 | VAVGQMMST | 8 |
| 4 | WILVAVGQM | 7 |

TABLE XXVII-V8

HLA-B0702-9mers-24P4C12
Each peptide is a portion of SEQ ID NO: 17; each start position is specified, the length of peptide is 9 amino acids, and the end position for each peptide is the start position plus eight.

| Pos | 123456789 | score |
|---|---|---|
| 19 | FQTSILGAY | 20 |
| 11 | PITPTGHVF | 15 |
| 17 | HVFQTSILG | 15 |
| 16 | GHVFQTSIL | 13 |
| 20 | QTSILGAYV | 10 |
| 14 | PTGHVFQTS | 9 |

TABLE XXVII-V9

HLA-B0702-9mers-24P4C12
Each peptide is a portion of SEQ ID NO: 19; each start position is specified, the length of peptide is 9 amino acids, and the end position for each peptide is the start position plus eight.

| Pos | 123456789 | score |
|---|---|---|
| 13 | QPATLGYVL | 23 |
| 8 | YPLPTQPAT | 19 |
| 10 | LPTQPATLG | 14 |
| 15 | ATLGYVLWA | 13 |
| 2 | WAMTALYPL | 12 |
| 7 | LYPLPTQPA | 11 |
| 9 | PLPTQPATL | 11 |

TABLE XXVIII-V1

HLA-B08-9mers
Each peptide is a portion of SEQ ID NO: 3; each start position is specified, the length of peptide is 9 amino acids, and the end position for each peptide is the start position plus eight.

| Pos | 123456789 | score |
|---|---|---|
| 79 | ENKDKPYLL | 32 |
| 141 | YTKNRNFCL | 29 |
| 282 | VLRDKGASI | 29 |
| 573 | SAKNAFMLL | 26 |
| 249 | LLRLVAGPL | 23 |
| 494 | TLRYHTGSL | 23 |
| 26 | PIKNRSCTD | 22 |
| 329 | FLRQRIRIA | 22 |
| 589 | VVLDKVTDL | 22 |
| 333 | RIRIAIALL | 21 |
| 583 | RNIVRVWL | 21 |
| 591 | LDKVTDLLL | 21 |
| 626 | GKDFKSPHL | 21 |
| 687 | MSKSLLKIL | 21 |
| 340 | LLKEASKAV | 20 |
| 474 | WAFHKPQDI | 20 |
| 523 | DHKLRGVQN | 20 |
| 540 | CFKCCLWCL | 20 |
| 617 | FFSGRIPGL | 20 |
| 2 | GGKQRDEDD | 19 |
| 232 | ILVALGVAL | 19 |

TABLE XXVIII-V1-continued

HLA-B08-9mers
Each peptide is a portion of SEQ ID NO: 3; each start position is specified, the length of peptide is 9 amino acids, and the end position for each peptide is the start position plus eight.

| Pos | 123456789 | score |
|---|---|---|
| 255 | GPLVLVLIL | 19 |
| 631 | SPHLNYYWL | 19 |
| 694 | ILGKKNEAP | 19 |
| 139 | VFYTKNRNF | 18 |
| 170 | FLLPSAPAL | 18 |
| 241 | VLSLLFILL | 18 |
| 247 | ILLLRLVAG | 18 |
| 258 | VLVLILGVL | 18 |
| 315 | VLAVLEAIL | 18 |
| 322 | ILLLMLIFL | 18 |
| 357 | YPLVTFVLL | 18 |
| 457 | VLALGQCVL | 18 |
| 501 | SLAFGALIL | 18 |
| 514 | IARVILEYI | 18 |
| 518 | ILEYIDHKL | 18 |
| 546 | WCLEKFIKF | 18 |
| 547 | CLEKFIKFL | 18 |
| 683 | RPYYMSKSL | 18 |
| 11 | EAYGKPVKY | 17 |
| 213 | NARDISVKI | 17 |
| 216 | DISVKIFED | 17 |
| 358 | PLVTFVLLL | 17 |
| 533 | VARCIMCCF | 17 |
| 590 | VLDKVTDLL | 17 |
| 596 | DLLLFFGKL | 17 |
| 597 | LLLFFGKLL | 17 |
| 673 | DLERNNGSL | 17 |
| 691 | LLKILGKKN | 17 |
| 45 | ILGYIVVGI | 16 |
| 64 | VLYPRNSTG | 16 |
| 81 | KDKPYLLYF | 16 |
| 100 | IISVAENGL | 16 |
| 158 | VITSLQQEL | 16 |
| 204 | GISGLIDSL | 16 |
| 211 | SLNARDISV | 16 |
| 244 | LLFILLLRL | 16 |
| 251 | RLVAGPLVL | 16 |
| 253 | VAGPLVLVL | 16 |
| 338 | IALLKEASK | 16 |
| 369 | IAYWAMTAL | 16 |
| 433 | GLIQRSVFN | 16 |
| 551 | FIKFLNRNA | 16 |
| 638 | WLPIMTSIL | 16 |
| 702 | PPDNKKRKK | 16 |
| 35 | VICCVLFLL | 15 |
| 200 | TIQQGISGL | 15 |
| 225 | FAQSWYWIL | 15 |
| 234 | VALGVALVL | 15 |
| 316 | LAVLEAILL | 15 |
| 331 | RQRIRIAIA | 15 |
| 396 | SPGCEKVPI | 15 |
| 434 | LIQRSVFNL | 15 |
| 487 | LISAFIRTL | 15 |
| 553 | KFLNRNAYI | 15 |
| 564 | AIYGKNFCV | 15 |
| 579 | MLLMRNIVR | 15 |
| 693 | KILGKKNEA | 15 |

TABLE XXVIII-V3

HLA-B08-9mers-24P4C12
Each peptide is a portion of SEQ ID NO: 7; each start position is specified, the length of peptide is 9 amino acids, and the end position for each peptide is the start position plus eight.

| Pos | 123456789 | score |
|---|---|---|
| 6 | WTNITPPAL | 11 |
| 4 | FPWTNITPP | 8 |
| 1 | GRCFPWTNI | 7 |
| 9 | ITPPALPGI | 7 |

TABLE XXVIII-V5

B08-9mers-24P4C12
Each peptide is a portion of
SEQ ID NO: 11; each start position
is specified, the length of peptide
is 9 amino acids, and the end
position for each peptide is the
start position plus eight.

| Pos | 123456789 | score |
|---|---|---|
| 5 | ILLLVLIFL | 18 |
| 3 | EAILLLVLI | 14 |
| 9 | VLIFLRQRI | 13 |
| 4 | AILLLVLIF | 12 |
| 2 | LEAILLLVL | 10 |
| 6 | LLLVLIFLR | 8 |

TABLE XXVIII-V6

HLA-B08-9mers-24P4C12
Each peptide is a portion of
SEQ ID NO: 13; each start position
is specified, the length of peptide
is 9 amino acids, and the end
position for each peptide is the
start position plus eight.

| Pos | 123456789 | score |
|---|---|---|
| 6 | GLIPRSVFN | 16 |
| 7 | LIPRSVFNL | 15 |
| 3 | SSKGLIPRS | 13 |
| 8 | IPRSVFNLQ | 13 |
| 1 | GYSSKGLIP | 11 |
| 9 | PRSVFNLQI | 8 |

TABLE XXVIII-V7

HLA-B08-9mers-24P4C12
Each peptide is a portion of
SEQ ID NO: 15; each start position
is specified, the length of peptide
is 9 amino acids, and the end
position for each peptide is the
start position plus eight.

| Pos | 123456789 | score |
|---|---|---|
| 5 | ILVAVGQMM | 7 |
| 4 | WILVAVGQM | 6 |
| 7 | VAVGQMMST | 5 |
| 1 | SWYWILVAV | 4 |

TABLE XXVIII-V8

HLA-B08-9mers-24P4C12
Each peptide is a portion of
SEQ ID NO: 17; each start position
is specified, the length of peptide
is 9 amino acids, and the end
position for each peptide is the
start position plus eight.

| Pos | 123456789 | score |
|---|---|---|
| 5 | LPIMRNPIT | 15 |
| 4 | WLPIMRNPI | 12 |
| 16 | GHVFQTSIL | 11 |
| 11 | PITPTGHVF | 10 |
| 7 | IMRNPITPT | 8 |
| 13 | TPTGHVFQT | 7 |
| 15 | TGHVFQTSI | 7 |

TABLE XXVIII-V9

HLA-B08-9mers-24P4C12
Each peptide is a portion of
SEQ ID NO: 19; each start position
is specified, the length of peptide
is 9 amino acids, and the end
position for each peptide is the
start position plus eight.

| Pos | 123456789 | score |
|---|---|---|
| 9 | PLPTQPATL | 16 |
| 13 | QPATLGYVL | 16 |
| 2 | WAMTALYPL | 14 |
| 16 | TLGYVLWAS | 8 |
| 18 | GYVLWASNI | 8 |
| 8 | YPLPTQPAT | 7 |

TABLE XXIX-V1

HLA-B1510-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 275 | YCWEEYRVL | 16 |
| 583 | RNIVRVVVL | 16 |
| 57 | LYGDPRQVL | 15 |
| 232 | ILVALGVAL | 15 |
| 253 | VAGPLVLVL | 15 |
| 381 | TSGQPQYVL | 15 |
| 487 | LISAFIRTL | 15 |
| 605 | LVVGGVGVL | 15 |
| 49 | IVVGIVAWL | 14 |
| 78 | GENKDKPYL | 14 |
| 100 | IISVAENGL | 14 |

TABLE XXIX-V1-continued

HLA-B1510-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 170 | FLLPSAPAL | 14 |
| 184 | WTNVTPPAL | 14 |
| 200 | TIQQGISGL | 14 |
| 204 | GISGLIDSL | 14 |
| 251 | RLVAGPLVL | 14 |
| 357 | YPLVTFVLL | 14 |
| 369 | IAYWAMTAL | 14 |
| 457 | VLALGQCVL | 14 |
| 617 | FFSGRIPGL | 14 |
| 32 | CTDVICCVL | 13 |
| 79 | ENKDKPYLL | 13 |
| 228 | SWYWILVAL | 13 |
| 234 | VALGVALVL | 13 |
| 255 | GPLVLVLIL | 13 |
| 261 | LILGVLGVL | 13 |
| 302 | YQSVQETWL | 13 |
| 308 | TWLAALIVL | 13 |
| 440 | FNLQIYGVL | 13 |
| 446 | GVLGLFWTL | 13 |
| 499 | TGSLAFGAL | 13 |
| 511 | LVQIARVIL | 13 |
| 518 | ILEYIDHKL | 13 |
| 537 | IMCCFKCCL | 13 |
| 547 | CLEKFIKFL | 13 |
| 572 | VSAKNAFML | 13 |
| 163 | QQELCPSFL | 12 |
| 237 | GVALVLSLL | 12 |
| 244 | LLFILLLRL | 12 |
| 258 | VLVLILGVL | 12 |
| 305 | VQETWLAAL | 12 |
| 311 | AALIVLAVL | 12 |
| 315 | VLAVLEAIL | 12 |
| 317 | AVLEAILLL | 12 |
| 322 | ILLLMLIFL | 12 |
| 356 | FYPLVTFVL | 12 |

TABLE XXIX-V1-continued

HLA-B1510-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 371 | YWAMTALYL | 12 |
| 406 | TSCNPTAHL | 12 |
| 412 | AHLVNSSCP | 12 |
| 442 | LQIYGVLGL | 12 |
| 450 | LFWTLNWVL | 12 |
| 452 | WTLNWVLAL | 12 |
| 476 | FHKPQDIPT | 12 |
| 497 | YHTGSLAFG | 12 |
| 501 | SLAFGALIL | 12 |
| 503 | AFGALILTL | 12 |
| 523 | DHKLRGVQN | 12 |
| 589 | VVLDKVTDL | 12 |
| 626 | GKDFKSPHL | 12 |
| 651 | IASGFFSVF | 12 |
| 658 | VFGMCVDTL | 12 |
| 660 | GMCVDTLFL | 12 |
| 673 | DLERNNGSL | 12 |
| 34 | DVICCVLFL | 11 |
| 88 | YFNIFSCIL | 11 |
| 141 | YTKNRNFCL | 11 |
| 154 | WNMTVITSL | 11 |
| 158 | VITSLQQEL | 11 |
| 164 | QELCPSFLL | 11 |
| 236 | LGVALVLSL | 11 |
| 241 | VLSLLFILL | 11 |
| 242 | LSLLFILLL | 11 |
| 285 | DKGASISQL | 11 |
| 291 | SQLGFTTNL | 11 |
| 319 | LEAILLLML | 11 |
| 332 | QRIRIAIAL | 11 |
| 333 | RIRIAIALL | 11 |
| 351 | MMSTMFYPL | 11 |
| 354 | TMFYPLVTF | 11 |
| 358 | PLVTFVLLL | 11 |
| 414 | LVNSSGPGL | 11 |

TABLE XXIX-V1-continued

HLA-B1510-9mers-24P4C12
Each peptide is a portion of SEQ ID NO: 3; each start position is specified, the length of peptide is 9 amino acids, and the end position for each peptide is the start position plus eight.

| Pos | 123456789 | score |
|---|---|---|
| 434 | LIQRSVFNL | 11 |
| 479 | PQDIPTFPL | 11 |
| 494 | TLRYHTGSL | 11 |
| 590 | VLDKVTDLL | 11 |
| 591 | LDKVTDLLL | 11 |
| 631 | SPHLNYYWL | 11 |
| 684 | PYYMSKSLL | 11 |
| 35 | VICCVLFLL | 10 |
| 38 | CVLFLLFIL | 10 |
| 124 | PWTVGKNEF | 10 |
| 225 | FAQSWYWIL | 10 |
| 240 | LVLSLLFIL | 10 |
| 249 | LLRLVAGPL | 10 |
| 316 | LAVLEAILL | 10 |
| 343 | EASKAVGQM | 10 |
| 418 | SCPGLMCVF | 10 |
| 426 | FQGYSSKGL | 10 |
| 477 | HKPQDIPTF | 10 |
| 483 | PTFPLISAF | 10 |
| 540 | CFKCCLWCL | 10 |
| 573 | SAKNAFMLL | 10 |
| 596 | DLLLFFGKL | 10 |
| 597 | LLLFFGKLL | 10 |
| 632 | PHLNYYWLP | 10 |
| 638 | WLPIMTSIL | 10 |
| 663 | VDTLFLCFL | 10 |
| 666 | LFLCFLEDL | 10 |
| 683 | RPYYMSKSL | 10 |
| 687 | MSKSLLKIL | 10 |
| 33 | TDVICCVLF | 9 |
| 36 | ICCVLFLLF | 9 |
| 217 | ISVKIFEDF | 9 |
| 347 | AVGQMMSTM | 9 |
| 432 | KGLIQRSVF | 9 |
| 461 | GQCVLAGAF | 9 |

TABLE XXIX-V1-continued

HLA-B1510-9mers-24P4C12
Each peptide is a portion of SEQ ID NO: 3; each start position is specified, the length of peptide is 9 amino acids, and the end position for each peptide is the start position plus eight.

| Pos | 123456789 | score |
|---|---|---|
| 607 | VGGVGVLSF | 9 |
| 679 | GSLDRPYYM | 9 |
| 15 | KPVKYDPSF | 8 |
| 81 | KDKPYLLYF | 8 |
| 132 | FSQTVGEVF | 8 |
| 139 | VFYTKNRNF | 8 |
| 148 | CLPGVPWNM | 8 |
| 162 | LQQELCPSE | 8 |
| 174 | SAPALGRCF | 8 |
| 287 | GASISQLGF | 8 |
| 415 | VNSSCPGLM | 8 |
| 464 | VLAGAFASF | 8 |
| 468 | AFASFYWAF | 8 |
| 496 | RYHTGSLAF | 8 |
| 530 | QNPVARCIM | 8 |
| 570 | FCVSAKNAF | 8 |
| 608 | GGVGVLSFF | 8 |
| 609 | GVGVLSFFF | 8 |
| 647 | GAYVIASGF | 8 |
| 48 | YIVVGIVAW | 7 |
| 69 | NSTGAYCGM | 7 |
| 214 | ARDISVKIF | 7 |
| 238 | VALVLSLLF | 7 |
| 318 | VLEAILLLM | 7 |
| 321 | AILLLMLIF | 7 |
| 366 | LICIAYWAM | 7 |
| 443 | QIYGVLGLF | 7 |
| 533 | VARCIMCCF | 7 |
| 546 | WCLEKFIKF | 7 |
| 554 | FLNRNAYIM | 7 |
| 562 | MIAIYGKNF | 7 |
| 571 | CVSAKNAFM | 7 |
| 574 | AKNAFMLLM | 7 |
| 593 | KVTDLLLFF | 7 |
| 621 | RIPGLGKDF | 7 |

TABLE XXIX-V1-continued

HLA-B1510-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 634 | LNYYWLPIM | 7 |
| 653 | SGFFSVFGM | 7 |

TABLE XXIX-V3

HLA-B1510-9mers-24P4C12
Each peptide is a portion of
SEQ ID NO: 7; each start position
is specified, the length of peptide
is 9 amino acids, and the end
position for each peptide is the
start position plus eight.

| Pos | 123456789 | score |
|---|---|---|
| 6 | WTNITPPAL | 13 |

TABLE XXIX-V5

B1510-9mers-24P4C12
Each peptide is a portion of
SEQ ID NO: 11; each start position
is specified, the length of peptide
is 9 amino acids, and the end
position for each peptide is the
start position plus eight.

| Pos | 123456789 | score |
|---|---|---|
| 2 | LEAILLLVL | 13 |
| 5 | ILLLVLIFL | 12 |

TABLE XXIX-V6

B1510-9mers-24P4C12
Each peptide is a portion of
SEQ ID NO: 13; each start position
is specified, the length of peptide
is 9 amino acids, and the end
position for each peptide is the
start position plus eight.

| Pos | 123456789 | score |
|---|---|---|
| 7 | LIPRSVFNL | 11 |
| 5 | KGLIPRSVF | 10 |
| 3 | SSKGLIPRS | 5 |
| 6 | GLIPRSVFN | 5 |

TABLE XXIX-V7

B1510-9mers-24P4C12
Each peptide is a portion of
SEQ ID NO: 15; each start position
is specified, the length of peptide
is 9 amino acids, and the end
position for each peptide is the
start position plus eight.

| Pos | 123456789 | score |
|---|---|---|
| 8 | AVGQMMSTM | 9 |
| 4 | WILVAVGQM | 8 |
| 5 | ILVAVGQMM | 8 |
| 1 | SWYWILVAV | 3 |
| 2 | WYWILVAVG | 3 |
| 3 | YWILVAVGQ | 3 |
| 6 | LVAVGQMMS | 3 |

TABLE XXIX-V8

B1510-9mers-24P4C12
Each peptide is a portion of
SEQ ID NO: 17; each start position
is specified, the length of peptide
is 9 amino acids, and the end
position for each peptide is the
start position plus eight.

| Pos | 123456789 | score |
|---|---|---|
| 16 | GHVFQTSIL | 21 |
| 11 | PITPTGHVF | 10 |
| 13 | QPATLGYVL | 13 |
| 9 | PLPTQPATL | 12 |
| 2 | WAMTALYPL | 10 |

TABLE XXIX-V9

B1510-9mers-24P4C12
Each peptide is a portion of
SEQ ID NO: 19; each start position
is specified, the length of peptide
is 9 amino acids, and the end
position for each peptide is the
start position plus eight.

| Pos | 123456789 | score |
|---|---|---|
| 13 | QPATLGYVL | 13 |
| 9 | PLPTQPATL | 12 |
| 2 | WAMTALYPL | 10 |

TABLE XXX-V1

B2705-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 334 | IRIAIALLK | 26 |
| 332 | QRIRIAIAL | 25 |

TABLE XXX-V1-continued

B2705-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 675 | ERNNGSLDR | 24 |
| 214 | ARDISVKIF | 23 |
| 534 | ARCIMCCEK | 21 |
| 620 | GRIPGLGKD | 21 |
| 5 | QRDEDDEAY | 20 |
| 204 | GISGLIDSL | 20 |
| 446 | GVLGLFWTL | 20 |
| 689 | KSLLKILGK | 20 |
| 251 | RLVAGPLVL | 19 |
| 424 | CVFQGYSSK | 19 |
| 436 | QRSVFNLQI | 19 |
| 483 | PTFPLISAF | 19 |
| 583 | RNIVRVVVL | 19 |
| 608 | GGVGVLSFF | 19 |
| 15 | KPVKYDPSF | 18 |
| 22 | SFRGPIKNR | 18 |
| 179 | GRCFPWVNV | 18 |
| 200 | TIQQGISGL | 18 |
| 207 | GLIDSLNAR | 18 |
| 234 | VALGVALVL | 18 |
| 244 | LLFILLLRL | 18 |
| 255 | GPLVLVLIL | 18 |
| 291 | SQLGFTTNL | 18 |
| 317 | AVLEAILLL | 18 |
| 330 | LRQRIRIAI | 18 |
| 333 | RIRIAIALL | 18 |
| 496 | RYHTGSLAF | 18 |
| 527 | RGVQNPVAR | 18 |
| 647 | GAYVIASGF | 18 |
| 668 | LCFLEDLER | 18 |
| 683 | RPYYMSKSL | 18 |
| 690 | SLLKILGKK | 18 |
| 49 | IVVGIVAWL | 17 |
| 78 | GENKDKPYL | 17 |
| 154 | WNMTVITSL | 17 |

TABLE XXX-V1-continued

B2705-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 237 | GVALVLSLL | 17 |
| 242 | LSLLFILLL | 17 |
| 261 | LILGVLGVL | 17 |
| 287 | GASISQLGF | 17 |
| 311 | AALIVLAVL | 17 |
| 338 | IALLKEASK | 17 |
| 354 | TMFYPLVTF | 17 |
| 381 | TSGQPQYVL | 17 |
| 429 | YSSKGLIQR | 17 |
| 477 | HKPQDIPTF | 17 |
| 503 | AFGALILTL | 17 |
| 516 | RVILEYIDH | 17 |
| 546 | WCLEKFIKF | 17 |
| 549 | EKFIKFLNR | 17 |
| 605 | LWGGVGVL | 17 |
| 621 | RIPGLGKDF | 17 |
| 11 | EAYGKPVKY | 16 |
| 23 | FRGPIKNRS | 16 |
| 137 | GEVFYTKNR | 16 |
| 139 | VFYTKNRNF | 16 |
| 170 | FLLPSAPAL | 16 |
| 283 | LRDKGASIS | 16 |
| 285 | DKGASISQL | 16 |
| 321 | AILLLMLIF | 16 |
| 322 | ILLLMLIFL | 16 |
| 323 | LLLMLIFLR | 16 |
| 327 | LIFLRQRIR | 16 |
| 432 | KGLIQRSVF | 16 |
| 440 | FNLQIYGVL | 16 |
| 442 | LQIYGVLGL | 16 |
| 443 | QIYGVLGLF | 16 |
| 457 | VLALGQCVL | 16 |
| 508 | ILTLVQIAR | 16 |
| 517 | VILEYIDHK | 16 |
| 589 | VVLDKVTDL | 16 |

TABLE XXX-V1-continued

B2705-9mers-24P4C12
Each peptide is a portion of SEQ ID NO: 3; each start position is specified, the length of peptide is 9 amino acids, and the end position for each peptide is the start position plus eight.

| Pos | 123456789 | score |
|-----|-----------|-------|
| 617 | FFSGRIPGL | 16 |
| 626 | GKDFKSPHL | 16 |
| 699 | NEAPPDNKK | 16 |
| 10  | DEAYGKPVK | 15 |
| 40  | LFLLFILGY | 15 |
| 60  | DPRQVLYPR | 15 |
| 73  | AYCGMGENK | 15 |
| 81  | KDKPYLLYF | 15 |
| 124 | PWTVGKNEF | 15 |
| 212 | LNARDISVK | 15 |
| 217 | ISVKIFEDF | 15 |
| 228 | SWYWILVAL | 15 |
| 236 | LGVALVLSL | 15 |
| 238 | VALVLSLLF | 15 |
| 243 | SLLFILLLR | 15 |
| 253 | VAGPLVLVL | 15 |
| 258 | VLVLILGVL | 15 |
| 308 | TWLAALIVL | 15 |
| 316 | LAVLEAILL | 15 |
| 369 | IAYWAMTAL | 15 |
| 461 | GQCVLAGAF | 15 |
| 470 | ASFYWAFHK | 15 |
| 518 | ILEYIDHKL | 15 |
| 542 | KCCLWCLEK | 15 |
| 543 | CCLWCLEKF | 15 |
| 547 | CLEKFIKFL | 15 |
| 567 | GKNFCVSAK | 15 |
| 579 | MLLMRNIVR | 15 |
| 586 | VRVVVLDKV | 15 |
| 593 | KVTDLLLFF | 15 |
| 596 | DLLLFFGKL | 15 |
| 607 | VGGVGVLSF | 15 |
| 609 | GVGVLSFFF | 15 |
| 622 | IPGLGKDFK | 15 |
| 651 | IASGFFSVF | 15 |

TABLE XXX-V1-continued

B2705-9mers-24P4C12
Each peptide is a portion of SEQ ID NO: 3; each start position is specified, the length of peptide is 9 amino acids, and the end position for each peptide is the start position plus eight.

| Pos | 123456789 | score |
|-----|-----------|-------|
| 684 | PYYMSKSLL | 15 |
| 698 | KNEAPPDNK | 15 |
| 34  | DVICCVLFL | 14 |
| 38  | CVLFLLFIL | 14 |
| 61  | PRQVLYPRN | 14 |
| 75  | CGMGENKDK | 14 |
| 83  | KPYLLYFNI | 14 |
| 84  | PYLLYFNIF | 14 |
| 135 | TVGEVFYTK | 14 |
| 148 | CLPGVPWNM | 14 |
| 158 | VITSLQQEL | 14 |
| 162 | LQQELCPSF | 14 |
| 164 | QELCPSFLL | 14 |
| 232 | ILVALGVAL | 14 |
| 240 | LVLSLLFIL | 14 |
| 263 | LGVLGVLAY | 14 |
| 267 | GVLAYGIYY | 14 |
| 272 | GIYYCWEEY | 14 |
| 278 | EEYRVLRDK | 14 |
| 325 | LMLIFLRQR | 14 |
| 379 | LATSGQPQY | 14 |
| 418 | SCPGLMCVF | 14 |
| 434 | LIQRSVFNL | 14 |
| 437 | RSVFNLQIY | 14 |
| 450 | LFWTLNWVL | 14 |
| 452 | WTLNWVLAL | 14 |
| 464 | VLAGAFASF | 14 |
| 485 | FPLISAFIR | 14 |
| 487 | LISAFIRTL | 14 |
| 488 | ISAFIRTLR | 14 |
| 489 | SAFIRTLRY | 14 |
| 501 | SLAFGALIL | 14 |
| 513 | QIARVILEY | 14 |
| 515 | ARVILEYID | 14 |
| 552 | IKFLNRNAY | 14 |

TABLE XXX-V1-continued

B2705-9mers-24P4C12
Each peptide is a portion of SEQ ID NO: 3; each start position is specified, the length of peptide is 9 amino acids, and the end position for each peptide is the start position plus eight.

| Pos | 123456789 | score |
|-----|-----------|-------|
| 556 | NRNAYIMIA | 14 |
| 558 | NAYIMIAIY | 14 |
| 560 | YIMIAIYGK | 14 |
| 575 | KNAFMLLMR | 14 |
| 585 | IVRVVVLDK | 14 |
| 595 | TDLLLFFGK | 14 |
| 613 | LSFFFFSGR | 14 |
| 643 | TSILGAYVI | 14 |
| 659 | FGMCVDTLF | 14 |
| 660 | GMCVDTLFL | 14 |
| 679 | GSLDRPYYM | 14 |
| 700 | EAPPDNKKR | 14 |
| 701 | APPDNKKRK | 14 |
| 702 | PPDNKKRKK | 14 |
| 7 | DEDDEAYGK | 13 |
| 36 | ICCVLFLLF | 13 |
| 172 | LPSAPALGR | 13 |
| 241 | VLSLLFILL | 13 |
| 249 | LLRLVAGPL | 13 |
| 250 | LRLVAGPLV | 13 |
| 273 | IYYCWEEYR | 13 |
| 275 | YCWEEYRVL | 13 |
| 280 | YRVLRDKGA | 13 |
| 294 | GFTTNLSAY | 13 |
| 319 | LEAILLLML | 13 |
| 347 | AVGQMMSTM | 13 |
| 348 | VGQMMSTMF | 13 |
| 349 | GQMMSTMFY | 13 |
| 356 | FYPLVTFVL | 13 |
| 357 | YPLVTFVLL | 13 |
| 358 | PLVTFVLLL | 13 |
| 363 | VLLLICIAY | 13 |
| 492 | IRTLRYHTG | 13 |
| 495 | LRYHTGSLA | 13 |
| 506 | ALILTLVQI | 13 |

TABLE XXX-V1-continued

B2705-9mers-24P4C12
Each peptide is a portion of SEQ ID NO: 3; each start position is specified, the length of peptide is 9 amino acids, and the end position for each peptide is the start position plus eight.

| Pos | 123456789 | score |
|-----|-----------|-------|
| 526 | LRGVQNPVA | 13 |
| 545 | LWCLEKFIK | 13 |
| 570 | FCVSAKNAF | 13 |
| 572 | VSAKNAFML | 13 |
| 582 | MRNIVRVVV | 13 |
| 590 | VLDKVTDLL | 13 |
| 592 | DKVTDLLLF | 13 |
| 610 | VGVLSFFFF | 13 |
| 637 | YWLPIMTSI | 13 |
| 648 | AYVIASGFF | 13 |
| 653 | SGFFSVFGM | 13 |
| 666 | LFLCFLEDL | 13 |
| 681 | LDRPYYMSK | 13 |
| 682 | DRPYYMSKS | 13 |
| 685 | YYMSKSLLK | 13 |
| 686 | YMSKSLLKI | 13 |
| 29 | NRSCTDVIC | 12 |
| 32 | CTDVICCVL | 12 |
| 33 | TDVICCVLF | 12 |
| 35 | VICCVLFLL | 12 |
| 57 | LYGDPRQVL | 12 |
| 58 | YGDPRQVLY | 12 |
| 79 | ENKDKPYLL | 12 |
| 80 | NKDKPYLLY | 12 |
| 93 | SCILSSNII | 12 |
| 100 | IISVAENGL | 12 |
| 121 | PEDPWTVGK | 12 |
| 132 | FSQTVGEVF | 12 |
| 144 | NRNFCLPGV | 12 |
| 151 | GVPWNMTVI | 12 |
| 163 | QQELCPSFL | 12 |
| 190 | PALPGITND | 12 |
| 193 | PGITNDTTI | 12 |
| 239 | ALVLSLLFI | 12 |
| 276 | CWEEYRVLR | 12 |

TABLE XXX-V1-continued

B2705-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 302 | YQSVQETWL | 12 |
| 305 | VQETWLAAL | 12 |
| 315 | VLAVLEAIL | 12 |
| 320 | EAILLLMLI | 12 |
| 328 | EFLRQRIRI | 12 |
| 343 | EASKAVGQM | 12 |
| 371 | YWAMTALYL | 12 |
| 386 | QYVLWASNI | 12 |
| 393 | NISSPGCEK | 12 |
| 406 | TSCNPTAHL | 12 |
| 414 | LVNSSCPGL | 12 |
| 421 | GLMCVFQGY | 12 |
| 426 | FQGYSSKGL | 12 |
| 468 | AFASFYWAF | 12 |
| 490 | AFIRTLRYH | 12 |
| 500 | GSLAFGALI | 12 |
| 510 | TLVQIARVI | 12 |
| 519 | LEYIDHKLR | 12 |
| 537 | IMCCFKCCL | 12 |
| 540 | CFKCCLWCL | 12 |
| 553 | KFLNRNAYI | 12 |
| 557 | RNAYIMIAI | 12 |
| 562 | MIAIYGKNF | 12 |
| 591 | LDKVTDLLL | 12 |
| 597 | LLLFFGKLL | 12 |
| 614 | SFFFFSGRI | 12 |
| 619 | SGRIPGLGK | 12 |
| 628 | DFKSPHLNY | 12 |
| 631 | SPHLNYYWL | 12 |
| 634 | LNYYWLPIM | 12 |
| 658 | VFGMCVDTL | 12 |
| 662 | CVDTLFLCF | 12 |
| 663 | VDTLFLCFL | 12 |
| 673 | DLERNNGSL | 12 |
| 687 | MSKSLLKIL | 12 |

TABLE XXX-V3

HLA-B2705-9mers-24P4C12
Each peptide is a portion of
SEQ ID NO: 7; each start position
is specified, the length of peptide
is 9 amino acids, and the end
position for each peptide is the
start position plus eight.

| Pos | 123456789 | score |
|---|---|---|
| 1 | GRCFPWTNI | 24 |
| 6 | WTNITPPAL | 11 |

TABLE XXX-V5

HLA-B2705-9mers-24P4C12
Each peptide is a portion of
SEQ ID NO: 11; each start position
is specified, the length of peptide
is 9 amino acids, and the end
position for each peptide is the
start position plus eight.

| Pos | 123456789 | score |
|---|---|---|
| 4 | AILLLVLIF | 17 |
| 5 | ILLLVLIFL | 17 |
| 6 | LLLVLIFLR | 16 |
| 2 | LEAILLLVL | 14 |
| 8 | LVLIFLRQR | 14 |
| 3 | EAILLLVLI | 12 |
| 9 | VLIFLRQRI | 11 |

TABLE XXX-V6

HLA-B2705-9mers-24P4C12
Each peptide is a portion of
SEQ ID NO: 13; each start position
is specified, the length of peptide
is 9 amino acids, and the end
position for each peptide is the
start position plus eight.

| Pos | 123456789 | score |
|---|---|---|
| 9 | PRSVFNLQI | 19 |
| 5 | KGLIPRSVF | 17 |
| 2 | YSSKGLIPR | 16 |
| 7 | LIPRSVFNL | 14 |
| 3 | SSKGLIPRS | 9 |

TABLE XXX-V7

HLA-B2705-9mers-24P4C12
Each peptide is a portion of
SEQ ID NO: 15; each start position
is specified, the length of peptide
is 9 amino acids, and the end
position for each peptide is the
start position plus eight.

| Pos | 123456789 | score |
|---|---|---|
| 8 | AVGQMMSTM | 13 |
| 4 | WILVAVGQM | 12 |
| 5 | ILVAVGQMM | 11 |
| 3 | YWILVAVGQ | 6 |

TABLE XXX-V8

HLA-B2705-9mers-24P4C12
Each peptide is a portion of
SEQ ID NO: 17; each start position
is specified, the length of peptide
is 9 amino acids, and the end
position for each peptide is the
start position plus eight.

| Pos | 123456789 | score |
|---|---|---|
| 16 | GHVFQTSIL | 15 |
| 1 | NYYWLPIMR | 14 |
| 8 | MRNPITPTG | 14 |
| 9 | RNPITPTGH | 14 |
| 11 | PITPTGHVF | 12 |
| 15 | TGHVFQTSI | 11 |
| 19 | FQTSILGAY | 10 |
| 2 | YYWLPIMRN | 8 |
| 4 | WLPIMRNPI | 7 |
| 7 | IMRNPITPT | 7 |
| 17 | HVFQTSILG | 7 |

TABLE XXX-V9

HLA-B2705-9mers-24P4C12
Each peptide is a portion of
SEQ ID NO: 19; each start position
is specified, the length of peptide
is 9 amino acids, and the end
position for each peptide is the
start position plus eight.

| Pos | 123456789 | score |
|---|---|---|
| 18 | GYVLWASNI | 15 |
| 13 | QPATLGYVL | 13 |
| 2 | WAMTALYPL | 12 |
| 9 | PLPTQPATL | 12 |
| 11 | PTQPATLGY | 10 |
| 6 | ALYPLPTQP | 8 |

TABLE XXX-V9-continued

HLA-B2705-9mers-24P4C12
Each peptide is a portion of
SEQ ID NO: 19; each start position
is specified, the length of peptide
is 9 amino acids, and the end
position for each peptide is the
start position plus eight.

| Pos | 123456789 | score |
|---|---|---|
| 15 | ATLGYVLWA | 7 |

TABLE XXXI-V1

HLA-B2709-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 332 | QRIRIAIAL | 23 |
| 179 | GRCFPWTNV | 22 |
| 250 | LRLVAGPLV | 21 |
| 214 | ARDISVKIF | 20 |
| 436 | QRSVFNLQI | 20 |
| 144 | NRNFCLPGV | 19 |
| 330 | LRQRIRIAI | 19 |
| 582 | MRNIVRVVV | 19 |
| 586 | VRVVVLDKV | 19 |
| 255 | GPLVLVLIL | 17 |
| 583 | RNIVRVVVL | 17 |
| 251 | RLVAGPLVL | 16 |
| 683 | RPYYMSKSL | 16 |
| 78 | GENKDKPYL | 15 |
| 170 | FLLPSAPAL | 15 |
| 334 | IRIAIALLK | 15 |
| 446 | GVLGLFWTL | 15 |
| 620 | GRIPGLGKD | 15 |
| 647 | GAYVIASGE | 15 |
| 660 | GMCVDTLFL | 15 |
| 49 | IVVGIVAWL | 14 |
| 228 | SWYWILVAL | 14 |
| 234 | VALGVALVL | 14 |
| 244 | LLFILLLRL | 14 |
| 317 | AVLEAILLL | 14 |
| 333 | RIRIAIALL | 14 |

TABLE XXXI-V1-continued

HLA-B2709-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|-----|-----------|-------|
| 452 | WTLNWVLAL | 14 |
| 602 | GKLLVVGGV | 14 |
| 626 | GKDFKSPHL | 14 |
| 679 | GSLDRPYYM | 14 |
| 23  | FRGPIKNRS | 13 |
| 34  | DVICCVLFL | 13 |
| 83  | KPYLLYFNI | 13 |
| 107 | GLQCPTPQV | 13 |
| 204 | GISGLIDSL | 13 |
| 232 | ILVALGVAL | 13 |
| 236 | LGVALVLSL | 13 |
| 237 | GVALVLSLL | 13 |
| 240 | LVLSLLFIL | 13 |
| 242 | LSLLFILLL | 13 |
| 253 | VAGPLVLVL | 13 |
| 291 | SQLGFTTNL | 13 |
| 311 | AALIVLAVL | 13 |
| 322 | ILLLMLIFL | 13 |
| 357 | YPLVTFVLL | 13 |
| 358 | PLVTFVLLL | 13 |
| 369 | IAYWAMTAL | 13 |
| 440 | FNLQIYGVL | 13 |
| 442 | LQIYGVLGL | 13 |
| 449 | GLFWTLNWV | 13 |
| 496 | RYHTGSLAF | 13 |
| 500 | GSLAFGALI | 13 |
| 515 | ARVILEYID | 13 |
| 557 | RNAYIMIAI | 13 |
| 589 | VVLDKVTDL | 13 |
| 15  | KPVKYDPSF | 12 |
| 38  | CVLFLLFIL | 12 |
| 45  | ILGYIVVGI | 12 |
| 56  | WLYGDPRQV | 12 |
| 61  | PRQVLYPRN | 12 |
| 81  | KDKPYLLYF | 12 |

TABLE XXXI-V1-continued

HLA-B2709-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|-----|-----------|-------|
| 158 | VITSLQQEL | 12 |
| 164 | QELCPSFLL | 12 |
| 258 | VLVLILGVL | 12 |
| 261 | LILGVLGVL | 12 |
| 287 | GASISQLGF | 12 |
| 308 | TWLAALIVL | 12 |
| 316 | LAVLEAILL | 12 |
| 321 | AILLLMLIF | 12 |
| 328 | IFLRQRIRI | 12 |
| 355 | MFYPLVTFV | 12 |
| 371 | YWAMTALYL | 12 |
| 414 | LVNSSCPGL | 12 |
| 432 | KGLIQRSVF | 12 |
| 434 | LIQRSVFNL | 12 |
| 461 | GQCVLAGAF | 12 |
| 492 | IRTLRYHTG | 12 |
| 495 | LRYHTGSLA | 12 |
| 501 | SLAFGALIL | 12 |
| 503 | AFGALILTL | 12 |
| 506 | ALILTLVQI | 12 |
| 518 | ILEYIDHKL | 12 |
| 553 | KFLNRNAYI | 12 |
| 593 | KVTDLLLFF | 12 |
| 596 | DLLLFFGKL | 12 |
| 597 | LLLFFGKLL | 12 |
| 605 | LVVGGVGVL | 12 |
| 608 | GGVGVLSFF | 12 |
| 621 | RIPGLGKDF | 12 |
| 637 | YWLPIMTSI | 12 |
| 666 | LFLCFLEDL | 12 |
| 684 | PYYMSKSLL | 12 |
| 5   | QRDEDDEAY | 11 |
| 28  | KNRSCTDVI | 11 |
| 29  | NRSCTDVIC | 11 |
| 32  | CTDVICCVL | 11 |

TABLE XXXI-V1-continued

HLA-B2709-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 41 | FLLFILGYI | 11 |
| 42 | LLFILGYIV | 11 |
| 46 | LGYIVVGIV | 11 |
| 67 | PRNSTGAYC | 11 |
| 79 | ENKDKPYLL | 11 |
| 87 | LYFNIFSCI | 11 |
| 100 | IISVAENGL | 11 |
| 128 | GKNEFSQTV | 11 |
| 139 | VFYTKNRNF | 11 |
| 151 | GVPWNMTVI | 11 |
| 184 | WTNVTPPAL | 11 |
| 217 | ISVKIFEDF | 11 |
| 225 | FAQSWYWIL | 11 |
| 230 | YWILVALGV | 11 |
| 238 | VALVLSLLF | 11 |
| 239 | ALVLSLLFI | 11 |
| 249 | LLRLVAGPL | 11 |
| 2S7 | LVLVLILGV | 11 |
| 260 | VLILGVLGV | 11 |
| 280 | YRVLRDKGA | 11 |
| 283 | LRDKGASIS | 11 |
| 285 | DKGASISQL | 11 |
| 297 | TNLSAYQSV | 11 |
| 310 | LAALIVLAV | 11 |
| 314 | IVLAVLEAI | 11 |
| 319 | LEAILLLML | 11 |
| 351 | MMSTMFYPL | 11 |
| 354 | TMFYPLVTF | 11 |
| 381 | TSGQPQYVL | 11 |
| 386 | QYVLWASNI | 11 |
| 427 | QGYSSKGLI | 11 |
| 480 | QDIPTFPLI | 11 |
| 483 | PTFPLISAF | 11 |
| 509 | LTLVQIARV | 11 |
| 510 | TLVQIARVI | 11 |

TABLE XXXI-V1-continued

HLA-B2709-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 511 | LVQIARVIL | 11 |
| 526 | LRGVQNPVA | 11 |
| 534 | ARCIMCCFK | 11 |
| 537 | IMCGFKCCL | 11 |
| 564 | AIYGKNFCV | 11 |
| 572 | VSAKNAFML | 11 |
| 591 | LDKVTDLLL | 11 |
| 592 | DKVTDLLLF | 11 |
| 598 | LLFFGKLLV | 11 |
| 599 | LFFGKLLVV | 11 |
| 609 | GVGVLSFFF | 11 |
| 614 | SFFFFSGRI | 11 |
| 617 | FFSGRIPGL | 11 |
| 631 | SPHLNYYWL | 11 |
| 634 | LNYYWLPIM | 11 |
| 643 | TSILGAYVI | 11 |
| 653 | SGFFSVFGM | 11 |
| 658 | VFGMCVDTL | 11 |
| 663 | VDTLFLCFL | 11 |
| 675 | ERNNGSLDR | 11 |
| 687 | MSKSLLKIL | 11 |

TABLE XXXI-V3

HLA-B2709-9mers-24P4C12
Each peptide is a portion of
SEQ ID NO: 7; each start position
is specified, the length of peptide
is 9 amino acids, and the end
position for each peptide is the
start position plus eight.

| Pos | 123456789 | score |
|---|---|---|
| 1 | GRGFPWFNI | 22 |
| 6 | WTNITPPAL | 11 |
| 9 | ITPPALPGI | 11 |

TABLE XXXI-V5

B2709-9mers-24P4C12
Each peptide is a portion of
SEQ ID NO: 11; each start position is specified, the length of peptide is 9 amino acids, and the end position for each peptide is the start position plus eight.

| Pos | 123456789 | score |
|---|---|---|
| 4 | AILLLVLIF | 13 |
| 5 | ILLLVLIFL | 13 |
| 2 | LEAILLLVL | 11 |
| 1 | VLEAILLLV | 10 |
| 3 | EAILLLVLI | 10 |
| 9 | VLIFLRQRI | 10 |

TABLE XXXI-V6

HLA-B2709-9mers-24P4C12
Each peptide is a portion of SEQ ID NO: 13; each start position is specified, the length of peptide is 9 amino acids, and the end position for each peptide is the start position plus eight.

| Pos | 123456789 | score |
|---|---|---|
| 9 | PRSVFNLQI | 20 |
| 5 | KGLIPRSVF | 12 |
| 7 | LIPRSVFNL | 12 |
| 4 | SKGLIPRSV | 9 |

TABLE XXXI-V7

HLA-B2709-9mers-24P4C12
Each peptide is a portion of SEQ ID NO: 15; each start position is specified, the length of peptide is 9 amino acids, and the end position for each peptide is the start position plus eight.

| Pos | 123456789 | score |
|---|---|---|
| 1 | SWYWILVAV | 12 |
| 4 | WILVAVGQM | 12 |
| 5 | ILVAVGQMM | 10 |
| 8 | AVGQMMSTM | 9 |

TABLE XXXI-V8

HLA-B2709-9mers-24P4C12
Each peptide is a portion of SEQ ID NO: 17; each start position is specified, the length of peptide is 9 amino acids, and the end position for each peptide is the start position plus eight.

| Pos | 123456789 | score |
|---|---|---|
| 16 | GHVFQTSIL | 14 |
| 8 | MRNPITPTG | 13 |

TABLE XXXI-V8-continued

HLA-B2709-9mers-24P4C12
Each peptide is a portion of SEQ ID NO: 17; each start position is specified, the length of peptide is 9 amino acids, and the end position for each peptide is the start position plus eight.

| Pos | 123456789 | score |
|---|---|---|
| 11 | PITPTGHVF | 10 |
| 10 | NPITPTGHV | 9 |
| 4 | WLPIMRNPI | 8 |
| 15 | TGHVFQTSI | 8 |
| 20 | QTSILGAYV | 8 |

TABLE XXXI-V9

HLA-B2709-9mers-24P4C12
Each peptide is a portion of SEQ ID NO: 19; each start position is specified, the length of peptide is 9 amino acids, and the end position for each peptide is the start position plus eight.

| Pos | 123456789 | score |
|---|---|---|
| 18 | GYVLWASNI | 14 |
| 2 | WAMTALYPL | 11 |
| 13 | QPATLGYVL | 11 |
| 9 | PLPTQPATL | 10 |
| 12 | TQPATLGYV | 8 |

TABLE XXXII-V1

HLA-B4402-9mers-24P4C12
Each peptide is a portion of SEQ ID NO: 3; each start position is specified, the length of peptide is 9 amino acids, and the end position for each peptide is the start position plus eight.

| Pos | 123456789 | score |
|---|---|---|
| 164 | QELCPSFLL | 22 |
| 319 | LEAILLLML | 22 |
| 222 | FEDFAQSWY | 21 |
| 78 | GENKDKPYL | 20 |
| 306 | QETWLAALI | 20 |
| 483 | PTFPLISAF | 20 |
| 317 | AVLEAILLL | 19 |
| 332 | QRIRIAIAL | 19 |
| 503 | AFGALILTL | 18 |
| 506 | ALILTLVQI | 18 |
| 552 | IKFLNRNAY | 18 |

TABLE XXXII-V1-continued

HLA-B4402-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 58 | YGDPRQVLY | 17 |
| 170 | FLLPSAPAL | 17 |
| 214 | ARDISVKIF | 17 |
| 242 | LSLLFILLL | 17 |
| 583 | RNIVRVVVL | 17 |
| 11 | EAYGKPVKY | 16 |
| 40 | LELLEILGY | 16 |
| 48 | YIVVGIVAW | 16 |
| 81 | KDKPYLLYF | 16 |
| 121 | PEDPWTVGK | 16 |
| 228 | SWYWILVAL | 16 |
| 253 | VAGPLVLVL | 16 |
| 254 | AGPLVLVLI | 16 |
| 311 | AALIVLAVL | 16 |
| 320 | EAILLLMLI | 16 |
| 321 | AILLLMLIF | 16 |
| 363 | VLLICIAY | 16 |
| 382 | SGQPQYVLW | 16 |
| 452 | WTLNWVLAL | 16 |
| 480 | QDIPTFPLI | 16 |
| 487 | LISAFIRTL | 16 |
| 489 | SAFIRTLRY | 16 |
| 617 | FFSGRIPGL | 16 |
| 629 | FKSPHLNYY | 16 |
| 699 | NEAPPDNKK | 16 |
| 34 | DVICCVLFL | 15 |
| 79 | ENKDKPYLL | 15 |
| 130 | NEFSQTVGE | 15 |
| 154 | WNMTVITSL | 15 |
| 204 | GISGLIDSL | 15 |
| 234 | VALGVALVL | 15 |
| 241 | VLSLLFILL | 15 |
| 263 | LGVLGVLAY | 15 |
| 278 | EEYRVLRDK | 15 |
| 294 | GFTTNLSAY | 15 |
| 354 | TMFYPLVTF | 15 |
| 370 | AYWAMTALY | 15 |
| 399 | CEKVPINTS | 15 |
| 442 | LQIYGVLGL | 15 |
| 468 | AFASFYWAF | 15 |
| 477 | HKPQDIPTF | 15 |
| 499 | TGSLAFGAL | 15 |
| 513 | QIARVILEY | 15 |
| 547 | CLEKFIKFL | 15 |
| 66 | YPRNSTGAY | 14 |
| 80 | NKDKPYLLY | 14 |
| 84 | PYLLYFNIF | 14 |
| 93 | SCILSSNII | 14 |
| 104 | AENGLQCPT | 14 |
| 193 | PGITNDTTI | 14 |
| 223 | EDFAQSWYW | 14 |
| 239 | ALVLSLLFI | 14 |
| 244 | LLFILLLRL | 14 |
| 258 | VLVLILGVL | 14 |
| 261 | LILGVLGVL | 14 |
| 285 | DKGASISQL | 14 |
| 291 | SQLGFTTNL | 14 |
| 301 | AYQSVQETW | 14 |
| 305 | VQETWLAAL | 14 |
| 308 | TWLAALIVL | 14 |
| 316 | LAVLEAILL | 14 |
| 322 | ILLLMLIFL | 14 |
| 330 | LRQRIRIAI | 14 |
| 333 | RIRIAIALL | 14 |
| 356 | FYPLVTFVL | 14 |
| 357 | YPLVTFVLL | 14 |
| 358 | PLVTFVLLL | 14 |
| 364 | LLLICIAYW | 14 |
| 418 | SCPGLMCVF | 14 |
| 432 | KGLIQRSVF | 14 |

TABLE XXXII-V1-continued

HLA-B4402-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 446 | GVLGLFWTL | 14 |
| 496 | RYHTGSLAF | 14 |
| 546 | WCLEKFIKF | 14 |
| 558 | NAYIMIAIY | 14 |
| 573 | SAKNAFMLL | 14 |
| 577 | AFMLLMRNI | 14 |
| 592 | DKVTDLLLF | 14 |
| 593 | KVTDLLLFF | 14 |
| 596 | DLLLFFGKL | 14 |
| 597 | LLLFFGKLL | 14 |
| 621 | RIPGLGKDF | 14 |
| 641 | IMTSILGAY | 14 |
| 643 | TSILGAYVI | 14 |
| 651 | IASGFFSVF | 14 |
| 662 | CVDTLFLCF | 14 |
| 671 | LEDLERNNG | 14 |
| 678 | NGSLDRPYY | 14 |
| 5 | QRDEDDEAY | 13 |
| 7 | DEDDEAYGK | 13 |
| 32 | CTDVICCVL | 13 |
| 36 | ICCVLFLLF | 13 |
| 49 | IVVGIVAWL | 13 |
| 57 | LYGDPRQVL | 13 |
| 77 | MGENKDKPY | 13 |
| 87 | LYFNIFSCI | 13 |
| 137 | GEVFYTKNR | 13 |
| 146 | NFCLPGVPW | 13 |
| 174 | SAPALGRCF | 13 |
| 176 | PALGRCFPW | 13 |
| 184 | WTNVTPPAL | 13 |
| 187 | VTPPALPGI | 13 |
| 200 | TIQQGISGL | 13 |
| 209 | IDSLNARDI | 13 |
| 213 | NARDISVKI | 13 |
| 232 | ILVALGVAL | 13 |

TABLE XXXII-V1-continued

HLA-B4402-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 237 | GVALVLSLL | 13 |
| 238 | VALVLSLLF | 13 |
| 251 | RLVAGPLVL | 13 |
| 255 | GPLVLVLIL | 13 |
| 277 | WEEYRVLRD | 13 |
| 342 | KEASKAVGQ | 13 |
| 351 | MMSTMFYPL | 13 |
| 440 | FNLQIYGVL | 13 |
| 443 | QIYGVLGLF | 13 |
| 448 | LGLFWTLNW | 13 |
| 461 | GQCVLAGAF | 13 |
| 466 | AGAFASFYW | 13 |
| 501 | SLAFGALIL | 13 |
| 518 | ILEYIDHKL | 13 |
| 519 | LEYIDHKLR | 13 |
| 529 | VQNPVARCI | 13 |
| 543 | CCLWCLEKF | 13 |
| 570 | FCVSAKNAF | 13 |
| 589 | VVLDKVTDL | 13 |
| 590 | VLDKVTDLL | 13 |
| 605 | LVVGGVGVL | 13 |
| 631 | SPHLNYYWL | 13 |
| 637 | YWLPIMTSI | 13 |
| 648 | AYVIASGFF | 13 |
| 674 | LERNNGSLD | 13 |
| 687 | MSKSLLKIL | 13 |
| 33 | TDVICCVLF | 12 |
| 35 | VICCVLFLL | 12 |
| 38 | CVLFLLFIL | 12 |
| 50 | WGIVAWLY | 12 |
| 100 | IISVAENGL | 12 |
| 132 | FSQTVGEVF | 12 |
| 133 | SQTVGEVFY | 12 |
| 139 | VFYTKNRNF | 12 |
| 141 | YTKNRNFCL | 12 |

TABLE XXXII-V1-continued

HLA-B4402-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 163 | QQELCPSEL | 12 |
| 217 | ISVKIFEDF | 12 |
| 221 | IFEDFAQSW | 12 |
| 236 | LGVALVLSL | 12 |
| 240 | LVLSLLFIL | 12 |
| 249 | LLRLVAGPL | 12 |
| 267 | GVLAYGIYY | 12 |
| 269 | LAYGIYYCW | 12 |
| 275 | YCWEEYRVL | 12 |
| 287 | GASISQLGE | 12 |
| 314 | IVLAVLEAI | 12 |
| 326 | MLIFLRQRI | 12 |
| 328 | IFLRQRIRI | 12 |
| 349 | GQMMSTMFY | 12 |
| 369 | IAYWAMTAL | 12 |
| 371 | YWAMTALYL | 12 |
| 406 | TSCNPTAHL | 12 |
| 421 | GLMCVFQGY | 12 |
| 426 | FQGYSSKGL | 12 |
| 434 | LIQRSVFNL | 12 |
| 437 | RSVFNLQIY | 12 |
| 450 | LFWTLNWVL | 12 |
| 457 | VLALGQCVL | 12 |
| 464 | VLAGAFASF | 12 |
| 479 | PQDIPTFPL | 12 |
| 510 | TLVQIARVI | 12 |
| 511 | LVQIARVIL | 12 |
| 548 | LEKFIKFLN | 12 |
| 553 | KFLNRNAYI | 12 |
| 557 | RNAYIMIAI | 12 |
| 562 | MIAIYGKNF | 12 |
| 572 | VSAKNAFML | 12 |
| 591 | LDKVTDLLL | 12 |
| 607 | VGGVGVLSF | 12 |
| 608 | GGVGVLSFF | 12 |
| 610 | VGVLSFFFF | 12 |
| 630 | KSPHLNYYW | 12 |
| 638 | WLPIMTSIL | 12 |
| 647 | GAYVIASGF | 12 |
| 658 | VFGMCVDTL | 12 |
| 659 | FGMCVDTLF | 12 |
| 660 | GMCVDTLFL | 12 |
| 663 | VDTLFLCFL | 12 |
| 666 | LFLCFLEDL | 12 |
| 673 | DLERNNGSL | 12 |
| 677 | NNGSLDRPY | 12 |
| 683 | RPYYMSKSL | 12 |
| 686 | YMSKSLLKI | 12 |
| 10 | DEAYGKPVK | 11 |
| 15 | KPVKYDPSF | 11 |
| 28 | KNRSCTDVI | 11 |
| 37 | CCVLFLLFI | 11 |
| 41 | FLLFILGYI | 11 |
| 45 | ILGYIVVGI | 11 |
| 117 | VSSCPEDPW | 11 |
| 124 | PWTVGKNEF | 11 |
| 151 | GVPWNMTVI | 11 |
| 197 | NDTTIQQGI | 11 |
| 201 | IQQGISGLI | 11 |
| 266 | LGVLAYGIY | 11 |
| 302 | YQSVQETWL | 11 |
| 359 | LVTFVLLLI | 11 |
| 361 | TFVLLLICI | 11 |
| 379 | LATSGQPQY | 11 |
| 381 | TSGQPQYVL | 11 |
| 436 | QRSVFNLQI | 11 |
| 444 | IYGVLGLFW | 11 |
| 465 | LAGAFASFY | 11 |
| 474 | WAFHKPQDI | 11 |
| 484 | TFPLISAFI | 11 |

TABLE XXXII-V1-continued

HLA-B4402-9mers-24P4C12
Each peptide is a portion of SEQ ID NO: 3; each start position is specified, the length of peptide is 9 amino acids, and the end position for each peptide is the start position plus eight.

| Pos | 123456789 | score |
|---|---|---|
| 494 | TLRYHTGSL | 11 |
| 533 | VARCIMCCF | 11 |
| 538 | MCCFKCCLW | 11 |
| 540 | CFKCCLWCL | 11 |
| 614 | SFFFFSGRI | 11 |
| 626 | GKDFKSPHL | 11 |
| 628 | DFKSPHLNY | 11 |
| 684 | PYYMSKSLL | 11 |
| 19 | YDPSFRGPI | 10 |
| 83 | KPYLLYFNI | 10 |
| 88 | YFNIFSCIL | 10 |
| 158 | VITSLQQEL | 10 |
| 162 | LQQELCPSF | 10 |
| 225 | FAQSWYWIL | 10 |
| 272 | GIYYCWEEY | 10 |
| 315 | VLAVLEAIL | 10 |
| 348 | VGQMMSTMF | 10 |
| 386 | QYVLWASNI | 10 |
| 396 | SPGCEKVPI | 10 |
| 414 | LVNSSCPGL | 10 |
| 500 | GSLAFGALI | 10 |
| 514 | IARVILEYI | 10 |
| 537 | IMCCFKCCL | 10 |
| 544 | CLWCLEKFI | 10 |
| 555 | LNRNAYIMI | 10 |
| 609 | GVGVLSFFF | 10 |

TABLE XXXII-V3

HLA-B4402-9mers-24P4C12
Each peptide is a portion of SEQ ID NO: 7; each start position is specified, the length of peptide is 9 amino acids, and the end position for each peptide is the start position plus eight.

| Pos | 123456789 | score |
|---|---|---|
| 6 | WTNITPPAL | 13 |

TABLE XXXII-V3-continued

HLA-B4402-9mers-24P4C12
Each peptide is a portion of SEQ ID NO: 7; each start position is specified, the length of peptide is 9 amino acids, and the end position for each peptide is the start position plus eight.

| Pos | 123456789 | score |
|---|---|---|
| 9 | ITPPALPGI | 13 |
| 1 | GRCFPWTNI | 8 |
| 2 | RCFPWTNIT | 7 |
| 7 | TNITPPALP | 6 |
| 8 | NITPPALPG | 6 |

TABLE XXXII-V5

HLA-B4402-9mers-24P4C12
Each peptide is a portion of SEQ ID NO: 11; each start position is specified, the length of peptide is 9 amino acids, and the end position for each peptide is the start position plus eight.

| Pos | 123456789 | score |
|---|---|---|
| 2 | LEAILLLVL | 23 |
| 3 | EAILLLVLI | 17 |
| 4 | AILLLVLIF | 17 |
| 5 | ILLLVLIFL | 14 |
| 9 | VLIFLRQRI | 12 |

TABLE XXXII-V6

HLA-B4402-9mers-24P4C12
Each peptide is a portion of SEQ ID NO: 13; each start position is specified, the length of peptide is 9 amino acids, and the end position for each peptide is the start position plus eight.

| Pos | 123456789 | score |
|---|---|---|
| 5 | KGLIPRSVF | 14 |
| 7 | LIPRSVFNL | 13 |
| 9 | PRSVFNLQI | 11 |
| 6 | GLIPRSVFN | 8 |

TABLE XXXII-V7

HLA-B4402-9mers-24P4C12
Each peptide is a portion of
SEQ ID NO: 15; each start position
is specified, the length of peptide
is 9 amino acids, and the end
position for each peptide is the
start position plus eight.

| Pos | 123456789 | score |
|---|---|---|
| 1 | SWYWILVAV | 6 |
| 3 | YWILVAVGQ | 6 |
| 8 | AVGQMMSTM | 4 |
| 4 | WILVAVGQM | 3 |
| 2 | WYWILVAVG | 2 |

TABLE XXXII-V8

HLA-B4402-9mers-24P4C12
Each peptide is a portion of
SEQ ID NO: 17; each start position
is specified, the length of peptide
is 9 amino acids, and the end
position for each peptide is the
start position plus eight.

| Pos | 123456789 | score |
|---|---|---|
| 11 | PITPTGHVF | 15 |
| 19 | FQTSILGAY | 14 |
| 4 | WLPIMRNPI | 11 |
| 16 | GHVFQTSIL | 11 |
| 15 | TGHVFQTSI | 8 |

TABLE XXXII-V9

HLA-B4402-9mers-24P4C12
Each peptide is a portion of
SEQ ID NO: 19; each start position
is specified, the length of peptide
is 9 amino acids, and the end
position for each peptide is the
start position plus eight.

| Pos | 123456789 | score |
|---|---|---|
| 11 | PTQPATLGY | 15 |
| 9 | PLPTQPATL | 14 |
| 2 | WAMTALYPL | 13 |
| 14 | PATLGYVLW | 13 |
| 13 | QPATLGYVL | 12 |
| 18 | GYVLWASNI | 10 |
| 6 | ALYPLPTQP | 8 |
| 15 | ATLGYVLWA | 7 |

TABLE XXXIII-V1

HLA-B5101-9mers-24P4C12
Each peptide is a portion of
SEQ ID NO: 3; each start position
is specified, the length of peptide
is 9 amino acids, and the end
position for each peptide is the
start position plus eight.

| Pos | 123456789 | score |
|---|---|---|
| 234 | VALGVALVL | 27 |
| 213 | NARDISVKI | 25 |
| 46 | LGYIVVGIV | 24 |
| 83 | KPYLLYFNI | 24 |
| 311 | AALIVLAVL | 24 |
| 253 | VAGPLVLVL | 23 |
| 310 | LAALIVLAV | 23 |
| 357 | YPLVTFVLL | 23 |
| 369 | IAYWAMTAL | 23 |
| 474 | WAFHKPQDI | 23 |
| 514 | IARVILEYI | 23 |
| 683 | RPYYMSKSL | 22 |
| 254 | AGPLVLVLI | 21 |
| 255 | GPLVLVLIL | 21 |
| 320 | EAILLLMLI | 21 |
| 396 | SPGCEKVPI | 21 |
| 427 | QGYSSKGLI | 21 |
| 11 | EAYGKPVKY | 20 |
| 193 | PGITNDTTI | 20 |
| 316 | LAVLEAILL | 20 |
| 123 | DPWTVGKNE | 19 |
| 236 | LGVALVLSL | 18 |
| 314 | IVLAVLEAI | 18 |
| 599 | LFFGKLLVV | 18 |
| 686 | YMSKSLLKI | 18 |
| 60 | DPRQVLYPR | 17 |
| 150 | PGVPWNMTV | 17 |
| 225 | FAQSWYWIL | 17 |
| 261 | LILGVLGVL | 17 |
| 269 | LAYGIYYCW | 17 |
| 300 | SAYQSVQET | 17 |
| 504 | FGALILTLV | 17 |
| 558 | NAYIMIAIY | 17 |
| 573 | SAKNAFMLL | 17 |
| 651 | IASGFFSVF | 17 |
| 182 | FPWTNVTPP | 16 |
| 192 | LPGITNDTT | 16 |

| 313 | | | | 314 | | |
|---|---|---|---|---|---|---|
| 328 | IFLRQRIRI | 16 | | 230 | YWILVALGV | 14 |
| 355 | MFYPLVTFV | 16 | | 238 | VALVLSLLF | 14 |
| 359 | LVTFVLLLI | 16 | | 257 | LVLVLILGV | 14 |
| 458 | LALGQCVLA | 16 | | 409 | NPTAHLVNS | 14 |
| 502 | LAFGALILT | 16 | | 411 | TAHLVNSSC | 14 |
| 505 | GALILTLVQ | 16 | | 450 | LFWTLNWVL | 14 |
| 510 | TLVQIARVI | 16 | | 465 | LAGAFASFY | 14 |
| 581 | LMRNIVRVV | 16 | | 467 | GAFASFYWA | 14 |
| 631 | SPHLNYYWL | 16 | | 482 | IPTEPLISA | 14 |
| 9 | DDEAYGKPV | 15 | | 499 | TGSLAFGAL | 14 |
| 45 | ILGYIVVGI | 15 | | 509 | LTLVQIARV | 14 |
| 56 | WLYGDPRQV | 15 | | 576 | NAFMLLMRN | 14 |
| 110 | CPTPQVCVS | 15 | | 586 | VRVVVLDKV | 14 |
| 120 | CPEDPWTVG | 15 | | 589 | VVLDKVTDL | 14 |
| 151 | GVPWNMTVI | 15 | | 602 | GKLLVVGGV | 14 |
| 172 | LPSAPALGR | 15 | | 605 | LVVGGVGVL | 14 |
| 224 | DFAQSWYWI | 15 | | 639 | LPIMTSILG | 14 |
| 275 | YCWEEYRVL | 15 | | 701 | APPDNKKRK | 14 |
| 308 | TWLAALIVL | 15 | | 702 | PPDNKKRKK | 14 |
| 336 | IAIALLKEA | 15 | | 19 | YDPSFRGPI | 13 |
| 338 | IALLKEASK | 15 | | 28 | KNRSCTDVI | 13 |
| 375 | TALYLATSG | 15 | | 34 | DVICCVLFL | 13 |
| 485 | EPLISAFIR | 15 | | 54 | VAWLYGDPR | 13 |
| 529 | VQNPVARCI | 15 | | 66 | YPRNSTGAY | 13 |
| 564 | AIYGKNFCV | 15 | | 112 | TPQVCVSSC | 13 |
| 582 | MRNIVRVVV | 15 | | 149 | LPGVPWNMT | 13 |
| 596 | DLLLFFGKL | 15 | | 174 | SAPALGRCF | 13 |
| 637 | YWLPIMTSI | 15 | | 176 | PALGRCFPW | 13 |
| 643 | TSILGAYVI | 15 | | 187 | VTPPALPGI | 13 |
| 647 | GAYVIASGF | 15 | | 189 | PPALPGITN | 13 |
| 700 | EAPPDNKKR | 15 | | 201 | IQQGISGLI | 13 |
| 20 | DPSFRGPIK | 14 | | 239 | ALVLSLLFI | 13 |
| 41 | FLLFILGYI | 14 | | 252 | LVAGPLVLV | 13 |
| 43 | LFILGYIVV | 14 | | 282 | VLRDKGASI | 13 |
| 72 | GAYGGMGEN | 14 | | 285 | DKGASISQL | 13 |
| 87 | LYFNIFSCI | 14 | | 293 | LGFTTNLSA | 13 |
| 119 | SCPEDPWTV | 14 | | 322 | ILLLMLIFL | 13 |
| 152 | VPWNMTVIT | 14 | | 330 | LRQRIRIAI | 13 |
| 188 | TPPALPGIT | 14 | | 340 | LLKEASKAV | 13 |
| 190 | PALPGITND | 14 | | 343 | EASKAVGQM | 13 |
| 209 | IDSLNARDI | 14 | | 356 | FYPLVTFVL | 13 |

| 361 | TFVLLLIGI | 13 |
| 384 | QPQYVLWAS | 13 |
| 478 | KPQDIPTFP | 13 |
| 487 | LISAFIRTL | 13 |
| 489 | SAFIRTLRY | 13 |
| 500 | GSLAFGALI | 13 |
| 506 | ALILTLVQI | 13 |
| 521 | YIDHKLRGV | 13 |
| 531 | NPVARCIMC | 13 |
| 553 | KFLNRNAYI | 13 |
| 555 | LNRNAYIMI | 13 |
| 563 | IAIYGKNFC | 13 |
| 578 | FMLLMRNIV | 13 |
| 580 | LLMRNIVRV | 13 |

TABLE XXXIII-V3

HLA-B5101-9mers-24P4C12
Each peptide is a portion of SEQ ID NO: 7; each start position is specified, the length of peptide is 9 amino acids, and the end position for each peptide is the start position plus eight.

| Pos | 123456789 | score |
|---|---|---|
| 4 | FPWTNITPP | 15 |
| 9 | ITPPALPGI | 14 |
| 1 | GRCFPWTNI | 11 |
| 6 | WTNITPPAL | 8 |

TABLE XXXIII-V5

HLA-B5101-9mers-24P4C12
Each peptide is a portion of SEQ ID NO: 11; each start position is specified, the length of peptide is 9 amino acids, and the end position for each peptide is the start position plus eight.

| Pos | 123456789 | score |
|---|---|---|
| 3 | EAILLLVLI | 22 |
| 5 | ILLLVLIFL | 14 |
| 2 | LEAILLLVL | 13 |
| 1 | VLEAILLLV | 12 |
| 9 | VLIFLRQRI | 12 |

TABLE XXXIII-V6

HLA-B5101-9mers-24P4C12
Each peptide is a portion of SEQ ID NO: 13; each start position is specified, the length of peptide is 9 amino acids, and the end position for each peptide is the start position plus eight.

| Pos | 123456789 | score |
|---|---|---|
| 8 | IPRSVFNLQ | 16 |
| 7 | LIPRSVFNL | 12 |
| 9 | PRSVFNLQI | 12 |
| 5 | KGLIPRSVF | 11 |
| 4 | SKGLIPRSV | 10 |

TABLE XXXIII-V7

HLA-B5101-9mers-24P4C12
Each peptide is a portion of SEQ ID NO: 15; each start position is specified, the length of peptide is 9 amino acids, and the end position for each peptide is the start position plus eight.

| Pos | 123456789 | score |
|---|---|---|
| 1 | SWYWILVAV | 14 |
| 7 | VAVGQMMST | 12 |
| 2 | WYWILVAVG | 6 |
| 3 | YWILVAVGQ | 6 |

TABLE XXXIII-V8

HLA-B5101-9mers-24P4C12
Each peptide is a portion of SEQ ID NO: 17; each start position is specified, the length of peptide is 9 amino acids, and the end position for each peptide is the start position plus eight.

| Pos | 123456789 | score |
|---|---|---|
| 10 | NPITPTGHV | 21 |
| 15 | TGHVFQTSI | 18 |
| 13 | TPTGHVFQT | 14 |
| 4 | WLPIMRNPI | 13 |
| 5 | LPIMRNPIT | 13 |

TABLE XXXIII-V9

HLA-B5101-9mers-24P4C12
Each peptide is a portion of SEQ ID NO: 19; each start position is specified, the length of peptide is 9 amino acids, and the end position for each peptide is the start position plus eight.

| Pos | 123456789 | score |
|---|---|---|
| 13 | QPATLGYVL | 20 |
| 2 | WAMTALYPL | 18 |
| 5 | TALYPLPTQ | 16 |

TABLE XXXIII-V9-continued

HLA-B5101-9mers-24P4C12
Each peptide is a portion of SEQ ID NO: 19;
each start position is specified, the length
of peptide is 9 amino acids, and the end
position for each peptide is the start
position plus eight.

| Pos | 123456789 | score |
|---|---|---|
| 8 | YPLPTQPAT | 15 |
| 10 | LPTQPATLG | 14 |
| 12 | TQPATLGYV | 13 |
| 17 | LGYVLWASN | 12 |
| 9 | PLPTQPATL | 11 |
| 14 | PATLGYVLW | 11 |
| 18 | GYVLWASNI | 11 |

TABLE XXXIV-V1

HLA-A1-10mers-24P4C12
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 221 | IFEDFAQSWY | 25 |
| 488 | ISAFIRTLRY | 25 |
| 39 | VLFLLFILGY | 23 |
| 58 | YGDPRQVLYP | 23 |
| 79 | ENKDKPYLLY | 23 |
| 262 | ILGVLGVLAY | 23 |
| 512 | VQIARVILEY | 22 |
| 627 | KDFKSPHLNY | 21 |
| 132 | FSQTVGEVFY | 20 |
| 266 | LGVLAYGIYY | 20 |
| 362 | FVLLLICIAY | 20 |
| 590 | VLDKVTDLLL | 20 |
| 594 | VTDLLLFFGK | 20 |
| 318 | VLEAILLLML | 19 |
| 32 | CTDVICCVLF | 18 |
| 49 | IVVGIVAWLY | 18 |
| 378 | YLATSGQPQY | 18 |
| 420 | PGLMCVFQGY | 18 |
| 464 | VLAGAFASFY | 18 |
| 10 | DEAYGKPVKY | 17 |
| 57 | LYGDPRQVLY | 17 |

TABLE XXXIV-V1-continued

HLA-A1-10mers-24P4C12
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 121 | PEDPWTVGKN | 17 |
| 265 | VLGVLAYGIY | 17 |
| 271 | YGIYYCWEEY | 17 |
| 276 | CWEEYRVLRD | 17 |
| 369 | IAYWAMTALY | 17 |
| 551 | FIKFLNRNAY | 17 |
| 80 | NKDKPYLLYF | 16 |
| 348 | VGQMMSTMFY | 16 |
| 676 | RNNGSLDRPY | 16 |
| 677 | NNGSLDRPYY | 16 |
| 4 | KQRDEDDEAY | 15 |
| 18 | KYDPSFRGPI | 15 |
| 65 | LYPRNSTGAY | 15 |
| 76 | GMGENKDKPY | 15 |
| 214 | ARDISVKIFE | 15 |
| 293 | LGFTTNLSAY | 15 |
| 436 | QRSVFNLQIY | 15 |
| 479 | PQDIPTFPLI | 15 |
| 557 | RNAYIMIAIY | 15 |
| 628 | DFKSPHLNYY | 15 |
| 640 | PIMTSILGAY | 15 |
| 664 | DTLFLCFLED | 15 |
| 283 | LRDKGASISQ | 14 |
| 521 | YIDHKLRGVQ | 14 |
| 673 | DLERNNGSLD | 14 |
| 141 | YTKNRNFCLP | 13 |
| 305 | VQETWLAALI | 13 |
| 382 | SGQPQYVLWA | 13 |
| 407 | SCNPTAHLVN | 13 |
| 518 | ILEYIDHKLR | 13 |
| 547 | CLEKFIKFLN | 13 |
| 670 | FLEDLERNNG | 13 |
| 680 | SLDRPYYMSK | 13 |
| 7 | DEDDEAYGKP | 12 |
| 35 | VICCVLFLLF | 12 |
| 159 | ITSLQQELCP | 12 |

TABLE XXXIV-V1-continued

HLA-A1-10mers-24P4C12
Each peptide is a portion of SEQ ID NO: 3; each start position is specified, the length of peptide is 10 amino acids, and the end position for each peptide is the start position plus nine.

| Pos | 1234567890 | score |
|---|---|---|
| 163 | QQELGPSFLL | 12 |
| 242 | LSLLFILLLR | 12 |
| 618 | FSGRIPGLGK | 12 |
| 626 | GKDFKSPHLN | 12 |
| 698 | KNEAPPDNKK | 12 |

TABLE XXXIV-V3

HLA-A1-10mers-24P4C12
Each peptide is a portion of SEQ ID NO: 7; each start position is specified, the length of peptide is 10 amino acids, and the end position for each peptide is the start position plus nine.

| Pos | 1234567890 | score |
|---|---|---|
| 10 | ITPPALPGIT | 10 |
| 3 | RCFPWTNITP | 9 |
| 7 | WTNITPPALP | 8 |
| 8 | TNITPPALPG | 6 |
| 9 | NITPPALPGI | 4 |

TABLE XXXIV-V5

HLA-A1-10mers-24P4C12
Each peptide is a portion of SEQ ID NO: 11; each start position is specified, the length of peptide is 10 amino acids, and the end position for each peptide is the start position plus nine.

| Pos | 1234567890 | score |
|---|---|---|
| 2 | VLEAILLLVL | 19 |
| 7 | LLLVLIFLRQ | 10 |
| 1 | AVLEAILLLV | 9 |

TABLE XXXIV-V6

HLA-A1-10mers-24P4C12
Each peptide is a portion of SEQ ID NO: 13; each start position is specified, the length of peptide is 10 amino acids, and the end position for each peptide is the start position plus nine.

| Pos | 1234567890 | score |
|---|---|---|
| 10 | PRSVFNLQIY | 15 |

TABLE XXXIV-V6-continued

HLA-A1-10mers-24P4C12
Each peptide is a portion of SEQ ID NO: 13; each start position is specified, the length of peptide is 10 amino acids, and the end position for each peptide is the start position plus nine.

| Pos | 1234567890 | score |
|---|---|---|
| 1 | QGYSSKGLIP | 7 |
| 4 | SSKGLIPRSV | 7 |
| 9 | IPRSVFNLQI | 7 |

TABLE XXXIV-V7

HLA-A1-10mers-24P4C12
Each peptide is a portion of SEQ ID NO: 15; each start position is specified, the length of peptide is 10 amino acids, and the end position for each peptide is the start position plus nine.

| Pos | 1234567890 | score |
|---|---|---|
| 1 | QSWYWILVAV | 4 |
| 2 | SWYWILVAVG | 4 |
| 4 | YWILVAVGQM | 3 |
| 5 | WILVAVGQMM | 2 |
| 6 | ILVAVGQMMS | 2 |
| 8 | VAVGQMMSTM | 2 |
| 9 | AVGQMMSTMF | 2 |

TABLE XXXIV-V8

HLA-A1-10mers-24P4C12
Each peptide is a portion of SEQ ID NO: 17; each start position is specified, the length of peptide is 10 amino acids, and the end position for each peptide is the start position plus nine.

| Pos | 1234567890 | score |
|---|---|---|
| 19 | VFQTSILGAY | 16 |
| 4 | YWLPIMRNPI | 7 |
| 13 | ITPTGHVFQT | 7 |
| 21 | QTSILGAYVI | 7 |

TABLE XXXIV-V9

HLA-A1-10mers-24P4C12
Each peptide is a portion of
SEQ ID NO: 19; each start position
is specified, the length of peptide
is 10 amino acids, and the end
position for each peptide is the
start position plus nine.

| Pos | 1234567890 | score |
|---|---|---|
| 11 | LPTQPATLGY | 21 |
| 12 | PTQPATLGYV | 10 |

TABLE XXXV-V1

HLA-A0201-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 235 | ALGVALVLSL | 29 |
| 44 | FILGYIVVGI | 28 |
| 232 | ILVALGVALV | 28 |
| 243 | SLLFILLLRL | 28 |
| 309 | WLAALIVLAV | 28 |
| 579 | MLLMRNIVRV | 28 |
| 244 | LLFILLLRLV | 27 |
| 260 | VLILGVLGVL | 27 |
| 433 | GLIQRSVFNL | 27 |
| 508 | ILTLVQIARV | 27 |
| 580 | LLMRNIVRVV | 27 |
| 598 | LLFFGKLLVV | 27 |
| 48 | YIVVGIVAWL | 26 |
| 94 | CILSSNIISV | 26 |
| 239 | ALVLSLLFIL | 26 |
| 241 | VLSLLFILLL | 26 |
| 251 | RLVAGPLVLV | 26 |
| 321 | AILLLMLIFL | 26 |
| 441 | NLQIYGVLGL | 26 |
| 502 | LAFGALILTL | 26 |
| 517 | VILEYIDHKL | 26 |
| 603 | KLLVGGVGV | 26 |
| 604 | LLVGGVGVL | 26 |
| 45 | ILGYIVVGIV | 25 |
| 252 | LVAGPLVLVL | 25 |
| 304 | SVQETWLAAL | 25 |

TABLE XXXV-V1-continued

HLA-A0201-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 312 | ALIVLAVLEA | 25 |
| 318 | VLEAILLLML | 25 |
| 486 | PLISAFIRTL | 25 |
| 657 | SVFGMCVDTL | 25 |
| 665 | TLFLCFLEDL | 25 |
| 248 | LLLRLVAGPL | 24 |
| 259 | LVLILGVLGV | 24 |
| 310 | LAALIVLAVL | 24 |
| 339 | ALLKEASKAV | 24 |
| 597 | LLLFFGKLLV | 24 |
| 41 | FLLFILGYIV | 23 |
| 42 | LLFILGYIVV | 23 |
| 56 | WLYGDPRQVL | 23 |
| 231 | WILVALGVAL | 23 |
| 249 | LLRLVAGPLV | 23 |
| 256 | PLVLVLILGV | 23 |
| 313 | LIVLAVLEAI | 23 |
| 315 | VLAVLEAILL | 23 |
| 438 | SVFNLQIYGV | 23 |
| 459 | ALGQCVLAGA | 23 |
| 686 | YMSKSLLKIL | 23 |
| 99 | NIISVAENGL | 22 |
| 257 | LVLVLILGVL | 22 |
| 354 | TMFYPLVTFV | 22 |
| 413 | HLVNSSCPGL | 22 |
| 449 | GLFWTLNWVL | 22 |
| 506 | ALILTLVQIA | 22 |
| 510 | TLVQIARVIL | 22 |
| 513 | QIARVILEYI | 22 |
| 581 | LMRNIVRVVV | 22 |
| 585 | IVRVVLDKV | 22 |
| 590 | VLDKVTDLLL | 22 |
| 199 | TTIQQGISGL | 21 |
| 247 | ILLLRLVAGP | 21 |
| 253 | VAGPLVLVLI | 21 |

TABLE XXXV-V1-continued

HLA-A0201-10mers-24P4C12
Each peptide is a portion of SEQ ID NO: 3; each start position is specified, the length of peptide is 10 amino acids, and the end position for each peptide is the start position plus nine.

| Pos | 1234567890 | score |
|---|---|---|
| 316 | LAVLEAILLL | 21 |
| 501 | SLAFGALILT | 21 |
| 505 | GALILTLVQI | 21 |
| 641 | IMTSILGAYV | 21 |
| 86 | LLYFNIFSCI | 20 |
| 95 | ILSSNIISVA | 20 |
| 191 | ALPGITNDTT | 20 |
| 238 | VALVLSLLFI | 20 |
| 261 | LILGVLGVLA | 20 |
| 314 | IVLAVLEAIL | 20 |
| 325 | LMLIFLRQRI | 20 |
| 329 | FLRQRIRIAI | 20 |
| 350 | QMMSTMFYPL | 20 |
| 358 | PLVTFVLLLI | 20 |
| 368 | CIAYWAMTAL | 20 |
| 393 | NISSPGCEKV | 20 |
| 554 | FLNRNAYIMI | 20 |
| 596 | DLLLFFGKLL | 20 |
| 645 | ILGAYVIASG | 20 |
| 649 | YVIASGFFSV | 20 |
| 34 | DVICCVLFLL | 19 |
| 64 | VLYPRNSTGA | 19 |
| 85 | YLLYFNIFSC | 19 |
| 186 | NVTPPALPGI | 19 |
| 233 | LVALGVALVL | 19 |
| 264 | GVLGVLAYGI | 19 |
| 317 | AVLEAILLLM | 19 |
| 327 | LIFLRQRIRI | 19 |
| 335 | RIAIALLKEA | 19 |
| 351 | MMSTMFYPLV | 19 |
| 357 | YPLVTFVLLL | 19 |
| 363 | VLLLICIAYW | 19 |
| 364 | LLLICIAYWA | 19 |
| 365 | LLICIAYWAM | 19 |
| 380 | ATSGQPQYVL | 19 |
| 457 | VLALGQCVLA | 19 |
| 536 | CIMCCFKCCL | 19 |
| 588 | VVVLDKVTDL | 19 |
| 633 | HLNYYWLPIM | 19 |
| 644 | SILGAYVIAS | 19 |
| 39 | VLFLLFILGY | 18 |
| 157 | TVITSLQQEL | 18 |
| 203 | QGISGLIDSL | 18 |
| 208 | LIDSLNARDI | 18 |
| 240 | LVLSLLFILL | 18 |
| 246 | FILLLRLVAG | 18 |
| 262 | ILGVLGVLAY | 18 |
| 281 | RVLRDKGASI | 18 |
| 322 | ILLLMLIFLR | 18 |
| 332 | QRIRIAIALL | 18 |
| 360 | VTFVLLLICI | 18 |
| 388 | VLWASNISSP | 18 |
| 448 | LGLFWTLNWV | 18 |
| 493 | RTLRYHTGSL | 18 |
| 525 | KLRGVQNPVA | 18 |
| 589 | VVLDKVTDLL | 18 |
| 616 | FFFSGRIPGL | 18 |
| 662 | CVDTLFLCFL | 18 |
| 685 | YYMSKSLLKI | 18 |
| 130 | NEFSQTVGEV | 17 |
| 143 | KNRNFCLPGV | 17 |
| 148 | CLPGVPWNMT | 17 |
| 170 | FLLPSAPALG | 17 |
| 211 | SLNARDISVK | 17 |
| 227 | QSWYWILVAL | 17 |
| 254 | AGPLVLVLIL | 17 |
| 296 | TTNLSAYQSV | 17 |
| 324 | LLMLIFLRQR | 17 |
| 373 | AMTALYLATS | 17 |
| 481 | DIPTEPLISA | 17 |

TABLE XXXV-V1-continued

HLA-A0201-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|-----|------------|-------|
| 546 | WCLEKFIKFL | 17 |
| 563 | IAIYGKNFCV | 17 |
| 582 | MRNIVRVVVL | 17 |
| 40 | LFLLFILGYI | 16 |
| 108 | LQCPTPQVCV | 16 |
| 118 | SSCPEDPWTV | 16 |
| 169 | SFLLPSAPAL | 16 |
| 200 | TIQQGISGLI | 16 |
| 207 | GLIDSLNARD | 16 |
| 212 | LNARDISVKI | 16 |
| 236 | LGVALVLSLL | 16 |
| 292 | QLGFTTNLSA | 16 |
| 307 | ETWLAALIVL | 16 |
| 319 | LEAILLLMLI | 16 |
| 337 | AIALLKEASK | 16 |
| 366 | LICIAYWAMT | 16 |
| 405 | NTSGNPTAHL | 16 |
| 451 | FWTLNWVLAL | 16 |
| 456 | WVLALGQCVL | 16 |
| 458 | LALGQCVLAG | 16 |
| 503 | AFGALILTLV | 16 |
| 509 | LTLVQIARVI | 16 |
| 637 | YWLPIMTSIL | 16 |
| 33 | TDVICCVLFL | 15 |
| 36 | ICCVLFLLFI | 15 |
| 90 | NIFSCILSSN | 15 |
| 161 | SLQQELCPSF | 15 |
| 225 | FAQSWYWILV | 15 |
| 234 | VALGVALVLS | 15 |
| 250 | LRLVAGPLVL | 15 |
| 284 | RDKGASISQL | 15 |
| 323 | LLLMLIFLRQ | 15 |
| 340 | LLKEASKAVG | 15 |
| 378 | YLATSGQPQY | 15 |
| 379 | LATSGQPQYV | 15 |

TABLE XXXV-V1-continued

HLA-A0201-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|-----|------------|-------|
| 430 | SSKGLIQRSV | 15 |
| 464 | VLAGAFASFY | 15 |
| 498 | HTGSLAFGAL | 15 |
| 520 | EYIDHKLRGV | 15 |
| 539 | CCFKCCLWGL | 15 |
| 601 | FGKLLVVGGV | 15 |
| 690 | SLLKILGKKN | 15 |
| 26 | PIKNRSCTDV | 14 |
| 30 | RSCTDVICCV | 14 |
| 37 | CCVLFLLFIL | 14 |
| 102 | SVAENGLQCP | 14 |
| 149 | LPGVPWNMTV | 14 |
| 153 | PWNMTVITSL | 14 |
| 162 | LQQELCPSFL | 14 |
| 165 | ELCPSFLLPS | 14 |
| 171 | LLPSAPALGR | 14 |
| 177 | ALGRCFPWTN | 14 |
| 220 | KIFEDFAQSW | 14 |
| 273 | IYYCWEEYRV | 14 |
| 338 | IALLKEASKA | 14 |
| 353 | STMFYPLVTF | 14 |
| 370 | AYWAMTALYL | 14 |
| 395 | SSPGCEKVPI | 14 |
| 416 | NSSCPGLMCV | 14 |
| 445 | YGVLGLFWTL | 14 |
| 483 | PTFPLISAFI | 14 |
| 500 | GSLAFGALIL | 14 |
| 571 | CVSAKNAFML | 14 |
| 577 | AFMLLMRNIV | 14 |
| 595 | TDLLLFFGKL | 14 |
| 606 | VVGGVGVLSF | 14 |
| 639 | LPIMTSILGA | 14 |
| 680 | SLDRPYYMSK | 14 |
| 693 | KILGKKNEAP | 14 |
| 694 | ILGKKNEAPP | 14 |

TABLE XXXV-V1-continued

HLA-A0201-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|

TABLE XXXV-V3

HLA-A0201-10mers-24P4C12
Each peptide is a portion of
SEQ ID NO: 7; each start position
is specified, the length of peptide
is 10 amino acids, and the end
position for each peptide is the
start position plus nine.

| Pos | 1234567890 | score |
|---|---|---|
| 9 | NITPPALPGI | 23 |
| 10 | ITPPALPGIT | 12 |

TABLE XXXV-V5

HLA-A0201-10mers-24P4C12
Each peptide is a portion of
SEQ ID NO: 11; each start position
is specified, the length of peptide
is 10 amino acids, and the end
position for each peptide is the
start position plus nine.

| Pos | 1234567890 | score |
|---|---|---|
| 5 | AILLLVLIFL | 26 |
| 1 | AVLEAILLLV | 25 |
| 2 | VLEAILLLVL | 25 |
| 3 | LEAILLLVLI | 18 |
| 6 | ILLLVLIFLR | 18 |
| 8 | LLVLIFLRQR | 16 |
| 9 | LVLIFLRQRI | 16 |
| 7 | LLLVLIFLRQ | 15 |
| 10 | VLIFLRQRIR | 12 |

TABLE XXXV-V6

HLA-A0201-10mers-24P4C12
Each peptide is a portion of
SEQ ID NO: 13; each start position
is specified, the length of peptide
is 10 amino acids, and the end
position for each peptide is the
start position plus nine.

| Pos | 1234567890 | score |
|---|---|---|
| 7 | GLIPRSVFNL | 29 |
| 4 | SSKGLIPRSV | 15 |

TABLE XXXV-V7

HLA-A0201-10mers-24P4C12
Each peptide is a portion of
SEQ ID NO: 15; each start position
is specified, the length of peptide
is 10 amino acids, and the end
position for each peptide is the
start position plus nine.

| Pos | 1234567890 | score |
|---|---|---|
| 1 | QSWYWILVAV | 4 |
| 2 | SWYWILVAVG | 4 |
| 4 | YWILVAVGQM | 3 |
| 5 | WILVAVGQMM | 2 |
| 6 | ILVAVGQMMS | 2 |
| 8 | VAVGQMMSTM | 2 |
| 9 | AVGQMMSTMF | 2 |

TABLE XXXV-V8

HLA-A0201-10mers-24P4C12
Each peptide is a portion of
SEQ ID NO: 17; each start position
is specified, the length of peptide
is 10 amino acids, and the end
position for each peptide is the
start position plus nine.

| Pos | 1234567890 | score |
|---|---|---|
| 4 | YWLPIMRNPI | 15 |
| 5 | WLPIMRNPIT | 15 |
| 18 | HVFQTSILGA | 15 |
| 7 | PIMRNPITPT | 14 |
| 13 | ITPTGHVFQT | 14 |
| 8 | IMRNPITPTG | 13 |
| 21 | QTSILGAYVI | 13 |
| 20 | FQTSILGAYV | 12 |
| 15 | PTGHVFQTSI | 11 |
| 10 | RNPITPTGHV | 10 |
| 16 | TGHVFQTSIL | 10 |
| 12 | PITPTGHVFQ | 8 |

TABLE XXXV-V9

HLA-A0201-10mers-24P4C12
Each peptide is a portion of
SEQ ID NO: 19; each start position
is specified, the length of peptide
is 10 amino acids, and the end
position for each peptide is the
start position plus nine.

| Pos | 1234567890 | score |
|---|---|---|
| 9 | YPLPTQPATL | 20 |
| 2 | YWAMTALYPL | 19 |

TABLE XXXV-V9-continued

HLA-A0201-10mers-24P4C12
Each peptide is a portion of
SEQ ID NO: 19; each start position
is specified, the length of peptide
is 10 amino acids, and the end
position for each peptide is the
start position plus nine.

| Pos | 1234567890 | score |
|---|---|---|
| 7 | ALYPLPTQPA | 19 |
| 12 | PTQPATLGYV | 17 |
| 16 | ATLGYVLWAS | 15 |
| 4 | AMTALYPLPT | 14 |
| 5 | MTALYPLPTQ | 13 |
| 17 | TLGYVLWASN | 13 |
| 13 | TQPATLGYVL | 11 |
| 18 | LGYVLWASNI | 11 |
| 15 | PATLGYVLWA | 9 |

TABLE XXXVI-V1

HLA-A0203-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 303 | QSVQETWLAA | 19 |
| 168 | PSFLLPSAPA | 18 |
| 330 | LRQRIRIAIA | 18 |
| 459 | ALGQCVLAGA | 18 |
| 461 | GQCVLAGAFA | 18 |
| 304 | SVQETWLAAL | 17 |
| 3 | GKQRDEDDEA | 10 |
| 46 | LGYIVVGIVA | 10 |
| 64 | VLYPRNSTGA | 10 |
| 95 | ILSSNIISVA | 10 |
| 166 | LCPSFLLPSA | 10 |
| 182 | FPWTNVTPPA | 10 |
| 205 | ISGLIDSLNA | 10 |
| 217 | ISVKIFEDFA | 10 |
| 226 | AQSWYWILVA | 10 |
| 230 | YWILVALGVA | 10 |
| 245 | LFILLLRLVA | 10 |
| 261 | LILGVLGVLA | 10 |

TABLE XXXVI-V1-continued

HLA-A0203-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 279 | EYRVLRDKGA | 10 |
| 292 | QLGFTTNLSA | 10 |
| 302 | YQSVQETWLA | 10 |
| 308 | TWLAALIVLA | 10 |
| 312 | ALIVLAVLEA | 10 |
| 328 | IFLRQRIRIA | 10 |
| 335 | RIAIALLKEA | 10 |
| 338 | IALLKEASKA | 10 |
| 361 | TFVLLLICIA | 10 |
| 364 | LLLICIAYWA | 10 |
| 367 | ICIAYWAMTA | 10 |
| 371 | YWAMTALYLA | 10 |
| 382 | SGQPQYVLWA | 10 |
| 403 | PINTSCNPTA | 10 |
| 450 | LFWTLNWVLA | 10 |
| 457 | VLALGQCVLA | 10 |
| 466 | AGAFASFYWA | 10 |
| 481 | DIPTFPLISA | 10 |
| 494 | TLRYHTGSLA | 10 |
| 497 | YHTGSLAFGA | 10 |
| 506 | ALILTLVQIA | 10 |
| 525 | KLRGVQNPVA | 10 |
| 550 | KFIKFLNRNA | 10 |
| 555 | LNRNAYIMIA | 10 |
| 565 | IYGKNFCVSA | 10 |
| 568 | KNFCVSAKNA | 10 |
| 639 | LPIMTSILGA | 10 |
| 643 | TSILGAYVIA | 10 |
| 692 | LKILGKKNEA | 10 |
| 4 | KQRDEDDEAY | 9 |
| 47 | GYIVVGIVAW | 9 |
| 65 | LYPRNSTGAY | 9 |
| 96 | LSSNIISVAE | 9 |
| 167 | CPSFLLPSAP | 9 |
| 169 | SFLLPSAPAL | 9 |

TABLE XXXVI-V1-continued

HLA-A0203-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 183 | PWTNVTPPAL | 9 |
| 206 | SGLIDSLNAR | 9 |
| 218 | SVKIFEDFAQ | 9 |
| 227 | QSWYWILVAL | 9 |
| 231 | WILVALGVAL | 9 |
| 246 | FILLLRLVAG | 9 |
| 262 | ILGVLGVLAY | 9 |
| 280 | YRVLRDKGAS | 9 |
| 293 | LGFTTNLSAY | 9 |
| 309 | WLAALIVLAV | 9 |
| 313 | LIVLAVLEAI | 9 |
| 329 | FLRQRIRIAI | 9 |
| 331 | RQRIRIAIAL | 9 |
| 336 | IAIALLKEAS | 9 |
| 339 | ALLKEASKAV | 9 |
| 362 | FVLLLICIAY | 9 |
| 365 | LLICIAYWAM | 9 |
| 368 | CIAYWAMTAL | 9 |
| 372 | WAMTALYLAT | 9 |
| 383 | GQPQYVLWAS | 9 |
| 404 | INTSCNPTAH | 9 |
| 451 | FWTLNWVLAL | 9 |
| 458 | LALGQCVLAG | 9 |
| 460 | LGQCVLAGAF | 9 |
| 462 | QCVLAGAFAS | 9 |
| 467 | GAFASFYWAF | 9 |
| 482 | IPTEPLISAF | 9 |
| 495 | LRYHTGSLAF | 9 |
| 498 | HTGSLAFGAL | 9 |
| 507 | LILTLVQIAR | 9 |
| 526 | LRGVQNPVAR | 9 |
| 551 | FIKFLNRNAY | 9 |
| 556 | NRNAYIMIAI | 9 |
| 566 | YGKNFCVSAK | 9 |
| 569 | NFCVSAKNAF | 9 |

TABLE XXXVI-V1-continued

HLA-A0203-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 640 | PIMTSILGAY | 9 |
| 644 | SILGAYVIAS | 9 |
| 693 | KILGKKNEAP | 9 |

TABLE XXXVI-V3

HLA-A0203-10mers-24P4C12
Each peptide is a portion of
SEQ ID NO: 7; each start position
is specified, the length of peptide
is 10 amino acids, and the end
position for each peptide is the
start position plus nine.

| Pos | 1234567890 | score |
|---|---|---|
| 5 | FPWTNITPPA | 10 |
| 6 | PWTNITPPAL | 9 |
| 7 | WTNITPPALP | 8 |

TABLE XXXVI-V5

HLA-A0203-10mers-24P4C12

| Pos | 1234567890 | score |
|---|---|---|

No Results Found.

TABLE XXXVI-V6

HLA-A0203-10mers-24P4C12

| Pos | 1234567890 | score |
|---|---|---|

No Results Found.

TABLE XXXVI-V7

HLA-A0203-10mers-24P4C12
Each peptide is a portion of SEQ ID NO: 15;
each start position is specified, the length
of peptide is 10 amino acids, and the end
position for each peptide is the start
position plus nine.

| Pos | 1234567890 | score |
|---|---|---|
| 1 | QSWYWILVAV | 9 |
| 2 | SWYWILVAVG | 8 |

TABLE XXXVI-V8

HLA-A0203-10mers-24P4C12

Each peptide is a portion of SEQ ID NO: 17; each start position is specified, the length of peptide is 10 amino acids, and the end position for each peptide is the start position plus nine.

| Pos | 1234567890 | score |
|---|---|---|
| 18 | HVFQTSILGA | 10 |
| 19 | VFQTSILGAY | 9 |
| 20 | FQTSILGAYV | 8 |

TABLE XXXVI-V9

HLA-A0203-10mers-24P4C12
Each peptide is a portion of SEQ ID NO: 19; each start position is specified, the length of peptide is 10 amino acids, and the end position for each peptide is the start position plus nine.

| Pos | 1234567890 | score |
|---|---|---|
| 7 | ALYPLPTQPA | 10 |
| 15 | PATLGYVLWA | 10 |
| 8 | LYPLPTQPAT | 9 |
| 16 | ATLGYVLWAS | 9 |
| 9 | YPLPTQPATL | 8 |
| 17 | TLGYVLWASN | 8 |

TABLE XXXVII-V1

HLA-A3-10mers-24P4C12
Each peptide is a portion of SEQ ID NO: 3; each start position is specified, the length of peptide is 10 amino acids, and the end position for each peptide is the start position plus nine.

| Pos | 1234567890 | score |
|---|---|---|
| 333 | RIRIAIALLK | 32 |
| 211 | SLNARDISVK | 30 |
| 337 | AIALLKEASK | 28 |
| 516 | RVILEYIDHK | 28 |
| 281 | RVLRDKGASI | 27 |
| 680 | SLDRPYYMSK | 27 |
| 464 | VLAGAFASFY | 25 |
| 584 | NIVRVVVLDK | 24 |
| 621 | RIPGLGKDFK | 24 |
| 49 | IVVGIVAWLY | 23 |
| 463 | CVLAGAFASF | 23 |
| 233 | LVALGVALVL | 22 |
| 262 | ILGVLGVLAY | 22 |
| 376 | ALYLATSGQP | 22 |
| 443 | QIYGVLGLFW | 22 |

TABLE XXXVII-V1-continued

HLA-A3-10mers-24P4C12
Each peptide is a portion of SEQ ID NO: 3; each start position is specified, the length of peptide is 10 amino acids, and the end position for each peptide is the start position plus nine.

| Pos | 1234567890 | score |
|---|---|---|
| 525 | KLRGVQNPVA | 22 |
| 587 | RVVVLDKVTD | 22 |
| 603 | KLLVVGGVGV | 22 |
| 56 | WLYGDPRQVL | 21 |
| 63 | QVLYPRNSTG | 21 |
| 177 | ALGRCFPWTN | 21 |
| 564 | AIYGKNFCVS | 21 |
| 606 | VVGGVGVLSF | 21 |
| 39 | VLFLLFILGY | 20 |
| 53 | IVAWLYGDPR | 20 |
| 171 | LLPSAPALGR | 20 |
| 251 | RLVAGPLVLV | 20 |
| 252 | LVAGPLVLVL | 20 |
| 282 | VLRDKGASIS | 20 |
| 362 | FVLLLICIAY | 20 |
| 378 | YLATSGQPQY | 20 |
| 544 | CLWCLEKFIK | 20 |
| 650 | VIASGFFSVF | 20 |
| 95 | ILSSNIISVA | 19 |
| 170 | FLLPSAPALG | 19 |
| 191 | ALPGITNDTT | 19 |
| 237 | GVALVLSLLF | 19 |
| 248 | LLLRLVAGPL | 19 |
| 260 | VLILGVLGVL | 19 |
| 261 | LILGVLGVLA | 19 |
| 298 | NLSAYQSVQE | 19 |
| 312 | ALIVLAVLEA | 19 |
| 314 | IVLAVLEAIL | 19 |
| 317 | AVLEAILLLM | 19 |
| 322 | ILLLMLIFLR | 19 |
| 340 | LLKEASKAVG | 19 |
| 347 | AVGQMMSTMF | 19 |
| 494 | TLRYHTGSLA | 19 |
| 605 | LVVGGVGVLS | 19 |
| 618 | FSGRIPGLGK | 19 |

TABLE XXXVII-V1-continued

HLA-A3-10mers-24P4C12
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 645 | ILGAYVIASG | 19 |
| 673 | DLERNNGSLD | 19 |
| 6 | RDEDDEAYGK | 18 |
| 64 | VLYPRNSTGA | 18 |
| 134 | QTVGEVFYTK | 18 |
| 231 | WILVALGVAL | 18 |
| 235 | ALGVALVLSL | 18 |
| 247 | ILLLRLVAGP | 18 |
| 258 | VLVLILGVLG | 18 |
| 324 | LLMLIFLRQR | 18 |
| 456 | WVLALGQCVL | 18 |
| 532 | PVARCIMCCF | 18 |
| 72 | GAYCGMGENK | 17 |
| 86 | LLYFNIFSCI | 17 |
| 161 | SLQQELCPSF | 17 |
| 207 | GLIDSLNARD | 17 |
| 220 | KIFEDFAQSW | 17 |
| 232 | ILVALGVALV | 17 |
| 249 | LLRLVAGPLV | 17 |
| 257 | LVLVLILGVL | 17 |
| 264 | GVLGVLAYGI | 17 |
| 265 | VLGVLAYGIY | 17 |
| 292 | QLGFTTNLSA | 17 |
| 309 | WLAALIVLAV | 17 |
| 326 | MLIFLRQRIR | 17 |
| 364 | LLLICIAYWA | 17 |
| 388 | VLWASNISSP | 17 |
| 392 | SNISSPGCEK | 17 |
| 486 | PLISAFIRTL | 17 |
| 506 | ALILTLVQIA | 17 |
| 551 | FIKFLNRNAY | 17 |
| 580 | LLMRNIVRVV | 17 |
| 598 | LLFFGKLLVV | 17 |
| 612 | VLSFFFFSGR | 17 |
| 624 | GLGKDFKSPH | 17 |
| 649 | YVIASGFFSV | 17 |
| 657 | SVFGMCVDTL | 17 |
| 667 | FLCFLEDLER | 17 |
| 684 | PYYMSKSLLK | 17 |
| 689 | KSLLKILGKK | 17 |
| 9 | DDEAYGKPVK | 16 |
| 44 | FILGYIVVGI | 16 |
| 126 | TVGKNEFSQT | 16 |
| 165 | ELCPSFLLPS | 16 |
| 243 | SLLFILLLRL | 16 |
| 246 | FILLLRLVAG | 16 |
| 259 | LVLILGVLGV | 16 |
| 272 | GIYYCWEEYR | 16 |
| 304 | SVQETWLAAL | 16 |
| 318 | VLEAILLLML | 16 |
| 339 | ALLKEASKAV | 16 |
| 363 | VLLLICIAYW | 16 |
| 453 | TLNWVLALGQ | 16 |
| 457 | VLALGQCVLA | 16 |
| 459 | ALGQCVLAGA | 16 |
| 487 | LISAFIRTLR | 16 |
| 508 | ILTLVQIARV | 16 |
| 518 | ILEYIDHKLR | 16 |
| 559 | AYIMIAIYGK | 16 |
| 566 | YGKNFCVSAK | 16 |
| 571 | CVSAKNAFML | 16 |
| 579 | MLLMRNIVRV | 16 |
| 596 | DLLLFFGKLL | 16 |
| 640 | PIMTSILGAY | 16 |
| 690 | SLLKILGKKN | 16 |
| 693 | KILGKKNEAP | 16 |
| 35 | VICCVLFLLF | 15 |
| 41 | FLLFILGYIV | 15 |
| 42 | LLFILGYIVV | 15 |
| 107 | GLQCPTPQVC | 15 |
| 120 | CPEDPWTVGK | 15 |

TABLE XXXVII-V1-continued

HLA-A3-10mers-24P4C12
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 180 | RCFPWTNVTP | 15 |
| 323 | LLLMLIFLRQ | 15 |
| 329 | FLRQRIRIAI | 15 |
| 367 | ICIAYWAMTA | 15 |
| 369 | IAYWAMTALY | 15 |
| 423 | MCVFQGYSSK | 15 |
| 446 | GVLGLFWTLN | 15 |
| 491 | FIRTLRYHTG | 15 |
| 507 | LILTLVQIAR | 15 |
| 510 | TLVQIARVIL | 15 |
| 585 | IVRVVVLDKV | 15 |
| 597 | LLLFFGKLLV | 15 |
| 604 | LLVVGGVGVL | 15 |
| 688 | SKSLLKILGK | 15 |
| 694 | ILGKKNEAPP | 15 |
| 697 | KKNEAPPDNK | 15 |
| 698 | KNEAPPDNKK | 15 |

TABLE XXXVII-V3

HLA-A3-10mers-24P4C12
Each peptide is a portion of SEQ ID NO: 7; each start position
is specified, the length of peptide
is 10 amino acids, and the end
position for each peptide is the
start position plus nine.

| Pos | 1234567890 | score |
|---|---|---|
| 3 | RCFPWTNITP | 11 |
| 9 | NITPPALPGI | 11 |
| 8 | TNITPPALPG | 9 |
| 10 | ITPPALPGIT | 7 |
| 7 | WTNITPPALP | 5 |

TABLE XXXVII-V5

HLA-A3-10mers-24P4C12
Each peptide is a portion of
SEQ ID NO: 11; each start position
is specified, the length of peptide
is 10 amino acids, and the end
position for each peptide is the
start position plus nine.

| Pos | 1234567890 | score |
|---|---|---|
| 1 | AVLEAILLLV | 19 |
| 2 | VLEAILLLVL | 19 |
| 6 | ILLLVLIFLR | 19 |
| 8 | LLVLIFLRQR | 18 |
| 10 | VLIFLRQRIR | 17 |
| 7 | LLLVLIFLRQ | 15 |
| 5 | AILLLVLIFL | 14 |
| 9 | LVLIFLRQRI | 14 |
| 4 | EAILLLVLIF | 11 |

TABLE XXXVII-V6

HLA-A3-10mers-24P4C12
Each peptide is a portion of
SEQ ID NO: 13; each start position
is specified, the length of peptide
is 10 amino acids, and the end
position for each peptide is the
start position plus nine.

| Pos | 1234567890 | score |
|---|---|---|
| 7 | GLIPRSVFNL | 16 |
| 5 | SKGLIPRSVF | 14 |
| 1 | QGYSSKGLIP | 12 |
| 8 | LIPRSVFNLQ | 11 |
| 9 | IPRSVFNLQI | 11 |
| 6 | KGLIPRSVFN | 10 |
| 4 | SSKGLIPRSV | 7 |

TABLE XXXVII-V7

HLA-A3-10mers-24P4C12
Each peptide is a portion of
SEQ ID NO: 15; each start position
is specified, the length of peptide
is 10 amino acids, and the end
position for each peptide is the
start position plus nine.

| Pos | 1234567890 | score |
|---|---|---|
| 9 | AVGQMMSTMF | 19 |
| 6 | ILVAVGQMMS | 16 |
| 5 | WILVAVGQMM | 14 |
| 7 | LVAVGQMMST | 14 |
| 2 | SWYWILVAVG | 12 |

TABLE XXXVII-V7-continued

HLA-A3-10mers-24P4C12
Each peptide is a portion of
SEQ ID NO: 15; each start position
is specified, the length of peptide
is 10 amino acids, and the end
position for each peptide is the
start position plus nine.

| Pos | 1234567890 | score |
|---|---|---|
| 8 | VAVGQMMSTM | 9 |

TABLE XXXVII-V8

HLA-A3-10mers-24P4C12
Each peptide is a portion of
SEQ ID NO: 17; each start position
is specified, the length of peptide
is 10 amino acids, and the end
position for each peptide is the
start position plus nine.

| Pos | 1234567890 | score |
|---|---|---|
| 12 | PITPTGHVFQ | 15 |
| 11 | NPITPTGHVF | 14 |
| 18 | HVFQTSILGA | 13 |
| 7 | PIMRNPITPT | 12 |
| 5 | WLPIMRNPIT | 11 |
| 1 | LNYYWLPIMR | 10 |
| 8 | IMRNPITPTG | 10 |
| 21 | QTSILGAYVI | 10 |
| 9 | MRNPITPTGH | 9 |
| 6 | LPIMRNPITP | 8 |
| 19 | VFQTSILGAY | 8 |

TABLE XXXVII-V9

HLA-A3-10mers-24P4C12
Each peptide is a portion of
SEQ ID NO: 19; each start position
is specified, the length of peptide
is 10 amino acids, and the end
position for each peptide is the
start position plus nine.

| Pos | 1234567890 | score |
|---|---|---|
| 7 | ALYPLPTQPA | 20 |
| 17 | TLGYVLWASN | 15 |
| 10 | PLPTQPATLG | 14 |
| 9 | YPLPTQPATL | 13 |
| 1 | AYWAMTALYP | 11 |
| 18 | LGYVLWASNI | 10 |
| 4 | AMTALYPLPT | 9 |
| 11 | LPTQPATLGY | 9 |

TABLE XXXVII-V9-continued

HLA-A3-10mers-24P4C12
Each peptide is a portion of
SEQ ID NO: 19; each start position
is specified, the length of peptide
is 10 amino acids, and the end
position for each peptide is the
start position plus nine.

| Pos | 1234567890 | score |
|---|---|---|
| 13 | TQPATLGYVL | 9 |

TABLE XXXVIII-V1

HLA-A26-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 34 | DVIGCVLFLL | 34 |
| 138 | EVFYTKNRNF | 32 |
| 307 | ETWLAALIVL | 31 |
| 657 | SVFGMCVDTL | 28 |
| 199 | TTIQQGISGL | 26 |
| 304 | SVQETWLAAL | 26 |
| 588 | VVVLDKVTDL | 26 |
| 592 | DKVTDLLLFF | 25 |
| 49 | IVVGIVAWLY | 24 |
| 606 | VVGGVGVLSF | 24 |
| 157 | TVITSLQQEL | 23 |
| 252 | LVAGPLVLVL | 23 |
| 257 | LVLVLILGVL | 23 |
| 320 | EAILLLMLIF | 23 |
| 628 | DFKSPHLNYY | 23 |
| 79 | ENKDKPYLLY | 22 |
| 353 | STMFYPLVTF | 22 |
| 362 | FVLLLICIAY | 22 |
| 662 | CVDThFLCFL | 22 |
| 672 | EDLERNNGSL | 22 |
| 48 | YIVVGIVAWL | 20 |
| 198 | DTTIQQGISG | 20 |
| 216 | DISVKIFEDF | 20 |
| 240 | LVLSLLFILL | 20 |
| 293 | LGFTTNLSAY | 20 |
| 640 | PIMTSILGAY | 20 |
| 10 | DEAYGKPVKY | 19 |

TABLE XXXVIII-V1-continued

HLA-A26-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 39 | VLFLLFILGY | 19 |
| 131 | EFSQTVGEVF | 19 |
| 233 | LVALGVALVL | 19 |
| 237 | GVALVLSLLF | 19 |
| 347 | AVGQMMSTMF | 19 |
| 438 | SVFNLQIYGV | 19 |
| 463 | CVLAGAFASF | 19 |
| 498 | HTGSLAFGAL | 19 |
| 512 | VQIARVILEY | 19 |
| 520 | EYIDHKLRGV | 19 |
| 571 | CVSAKNAFML | 19 |
| 589 | VVLDKVTDLL | 19 |
| 33 | TDVICCVLFL | 18 |
| 203 | QGISGLIDSL | 18 |
| 314 | IVLAVLEAIL | 18 |
| 456 | WVLALGQCVL | 18 |
| 481 | DIPTEPLISA | 18 |
| 486 | PLISAFIRTL | 18 |
| 493 | RTLRYHTGSL | 18 |
| 502 | LAFGALILTL | 18 |
| 516 | RVILEYIDHK | 18 |
| 532 | PVARCIMCCF | 18 |
| 549 | EKFIKFLNRN | 18 |
| 609 | GVGVLSFFFF | 18 |
| 99 | NIISVAENGL | 17 |
| 102 | SVAENGLQCP | 17 |
| 156 | MTVITSLQQE | 17 |
| 236 | LGVALVLSLL | 17 |
| 260 | VLILGVLGVL | 17 |
| 316 | LAVLEAILLL | 17 |
| 317 | AVLEAILLLM | 17 |
| 321 | AILLLMLIFL | 17 |
| 360 | VTFVLLLICI | 17 |
| 442 | LQIYGVLGLF | 17 |
| 596 | DLLLFFGKLL | 17 |

TABLE XXXVIII-V1-continued

HLA-A26-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 604 | LLWGGVGVL | 17 |
| 616 | FFFSGRIPGL | 17 |
| 664 | DTLFLCFLED | 17 |
| 665 | TLFLCFLEDL | 17 |
| 682 | DRPYYMSKSL | 17 |
| 32 | CTDVICCVLF | 16 |
| 37 | CCVLFLLFIL | 16 |
| 123 | DPWTVGKNEF | 16 |
| 165 | ELCPSFLLPS | 16 |
| 186 | NVTPPALPGI | 16 |
| 224 | DFAQSWYWIL | 16 |
| 239 | ALVLSLLFIL | 16 |
| 262 | ILGVLGVLAY | 16 |
| 266 | LGVLAYGIYY | 16 |
| 332 | QRIRIAIALL | 16 |
| 359 | LVTFVLLLIC | 16 |
| 380 | ATSGQPQYVL | 16 |
| 400 | EKVPINTSCN | 16 |
| 405 | NTSCNPTAHL | 16 |
| 424 | CVFQGYSSKG | 16 |
| 433 | GLIQRSVFNL | 16 |
| 539 | CCFKCCLWCL | 16 |
| 593 | KVTDLLLFFG | 16 |

TABLE XXXVIII-V3

HLA-A26-10mers-24P4C12
Each peptide is a portion of
SEQ ID NO: 7; each start position
is specified, the length of peptide
is 10 amino acids, and the end
position for each peptide is the
start position plus nine.

| Pos | 1234567890 | score |
|---|---|---|
| 6 | PWTNITPPAL | 10 |
| 9 | NITPPALPGI | 10 |
| 10 | ITPPALPGIT | 10 |
| 7 | WTNITPPALP | 8 |

TABLE XXXVIII-V3-continued

HLA-A26-10mers-24P4C12
Each peptide is a portion of
SEQ ID NO: 7; each start position
is specified, the length of peptide
is 10 amino acids, and the end
position for each peptide is the
start position plus nine.

| Pos | 1234567890 | score |
|---|---|---|
| 3 | RCFPWTNITP | 7 |
| 8 | TNITPPALPG | 6 |
| 4 | CFPWTNITPP | 4 |

TABLE XXXVIII-V5

HLA-A26-10mers-24P4C12
Each peptide is a portion of
SEQ ID NO: 11; each start position
is specified, the length of peptide
is 10 amino acids, and the end
position for each peptide is the
start position plus nine.

| Pos | 1234567890 | score |
|---|---|---|
| 4 | EAILLLVLIF | 27 |
| 1 | AVLEAILLLV | 17 |
| 5 | AILLLVLIFL | 17 |
| 2 | VLEAILLLVL | 13 |

TABLE XXXVIII-V6

HLA-A26-10mers-24P4C12
Each peptide is a portion of
SEQ ID NO: 13; each start position
is specified, the length of peptide
is 10 amino acids, and the end
position for each peptide is the
start position plus nine.

| Pos | 1234567890 | score |
|---|---|---|
| 7 | GLIPRSVFNL | 17 |
| 10 | PRSVFNLQIY | 14 |
| 5 | SKGLIPRSVF | 10 |

TABLE XXXVIII-V7

HLA-A26-10mers-24P4C12
Each peptide is a portion of
SEQ ID NO: 15; each start position
is specified, the length of peptide
is 10 amino acids, and the end
position for each peptide is the
start position plus nine.

| Pos | 1234567890 | score |
|---|---|---|
| 9 | AVGQMMSTMF | 19 |
| 7 | LVAVGQMMST | 11 |
| 4 | YWILVAVGQM | 10 |

TABLE XXXVIII-V8

HLA-A26-10mers-24P4C12
Each peptide is a portion of
SEQ ID NO: 17; each start position
is specified, the length of peptide
is 10 amino acids, and the end
position for each peptide is the
start position plus nine.

| Pos | 1234567890 | score |
|---|---|---|
| 18 | HVFQTSILGA | 19 |
| 19 | VFQTSILGAY | 16 |
| 11 | NPITPTGHVF | 13 |
| 13 | ITPTGHVFQT | 13 |
| 16 | TGHVFQTSIL | 10 |
| 15 | PTGHVFQTSI | 9 |

TABLE XXXVIII-V9

HLA-A26-10mers-24P4C12
Each peptide is a portion of
SEQ ID NO: 19; each start position
is specified, the length of peptide
is 10 amino acids, and the end
position for each peptide is the
start position plus nine.

| Pos | 1234567890 | score |
|---|---|---|
| 12 | PTQPATLGYV | 14 |
| 5 | MTALYPLPTQ | 13 |
| 16 | ATLGYVLWAS | 13 |
| 2 | YWAMTALYPL | 12 |
| 11 | LPTQPATLGY | 12 |
| 9 | YPLPTQPATL | 10 |
| 13 | TQPATLGYVL | 10 |
| 15 | PATLGYVLWA | 6 |

TABLE XXXIX-V1

HLA-B0702-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 357 | YPLVTFVLLL | 23 |
| 478 | KPQDIPTFPL | 23 |
| 683 | RPYYMSKSLL | 21 |
| 182 | FPWTNVTPPA | 19 |
| 83 | KPYLLYFNIF | 18 |
| 192 | LPGITNDTTI | 18 |
| 482 | IPTFPLISAF | 18 |

TABLE XXXIX-V1-continued

HLA-B0702-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|-----|------------|-------|
| 639 | LPIMTSILGA | 18 |
| 149 | LPGVPWNMTV | 17 |
| 252 | LVAGPLVLVL | 17 |
| 380 | ATSGQPQYVL | 17 |
| 402 | VPINTSCNPT | 17 |
| 485 | FPLISAFIRT | 17 |
| 123 | DPWTVGKNEF | 16 |
| 235 | ALGVALVLSL | 16 |
| 254 | AGPLVLVLIL | 15 |
| 370 | AYWAMTALYL | 15 |
| 659 | FGMCVDTLFL | 15 |
| 33  | TDVICCVLFL | 14 |
| 56  | WLYGDPRQVL | 14 |
| 175 | APALGRCFPW | 14 |
| 233 | LVALGVALVL | 14 |
| 241 | VLSLLFILLL | 14 |
| 331 | RQRIRIAIAL | 14 |
| 405 | NTSCNPTAHL | 14 |
| 451 | FWTLNWVLAL | 14 |
| 502 | LAFGALILTL | 14 |
| 582 | MRNIVRVVVL | 14 |
| 590 | VLDKVTDLLL | 14 |
| 15  | KPVKYDPSFR | 13 |
| 60  | DPRQVLYPRN | 13 |
| 66  | YPRNSTGAYC | 13 |
| 110 | CPTPQVCVSS | 13 |
| 120 | CPEDPWTVGK | 13 |
| 167 | CPSFLLPSAP | 13 |
| 172 | LPSAPALGRC | 13 |
| 226 | AQSWYWILVA | 13 |
| 227 | QSWYWILVAL | 13 |
| 231 | WILVALGVAL | 13 |
| 250 | LRLVAGPLVL | 13 |
| 284 | RDKGASISQL | 13 |
| 290 | ISQLGFTTNL | 13 |
| 301 | AYQSVQETWL | 13 |
| 310 | LAALIVLAVL | 13 |
| 314 | IVLAVLEAIL | 13 |
| 318 | VLEAILLLML | 13 |
| 321 | AILLLMLIFL | 13 |
| 350 | QMMSTMFYPL | 13 |
| 355 | MFYPLVTFVL | 13 |
| 356 | FYPLVTFVLL | 13 |
| 368 | CIAYWAMTAL | 13 |
| 396 | SPGCEKVPIN | 13 |
| 441 | NLQIYGVLGL | 13 |
| 498 | HTGSLAFGAL | 13 |
| 500 | GSLAFGALIL | 13 |
| 510 | TLVQIARVIL | 13 |
| 525 | KLRGVQNPVA | 13 |
| 571 | CVSAKNAFML | 13 |
| 572 | VSAKNAFMLL | 13 |
| 657 | SVFGMCVDTL | 13 |
| 686 | YMSKSLLKIL | 13 |
| 20  | DPSFRGPIKN | 12 |
| 48  | YIVVGIVAWL | 12 |
| 169 | SFLLPSAPAL | 12 |
| 183 | PWTNVTPPAL | 12 |
| 189 | PPALPGITND | 12 |
| 239 | ALVLSLLFIL | 12 |
| 243 | SLLFILLLRL | 12 |
| 304 | SVQETWLAAL | 12 |
| 307 | ETWLAALIVL | 12 |
| 309 | WLAALIVLAV | 12 |
| 316 | LAVLEAILLL | 12 |
| 409 | NPTAHLVNSS | 12 |
| 419 | CPGLMCVFQG | 12 |
| 425 | VFQGYSSKGL | 12 |
| 456 | WVLALGQCVL | 12 |
| 493 | RTLRYHTGSL | 12 |

TABLE XXXIX-V1-continued

HLA-B0702-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 581 | LMRNIVRVVV | 12 |
| 588 | VVVLDKVTDL | 12 |
| 604 | LLVVGGVGVL | 12 |
| 606 | VVGGVGVLSF | 12 |
| 622 | IPGLGKDFKS | 12 |
| 637 | YWLPIMTSIL | 12 |
| 662 | CVDTLFLCFL | 12 |
| 701 | APPDNKKRKK | 12 |
| 18 | KYDPSFRGPI | 11 |
| 25 | GPIKNRSCTD | 11 |
| 31 | SCTDVICCVL | 11 |
| 44 | FILGYIVVGI | 11 |
| 77 | MGENKDKPYL | 11 |
| 78 | GENKDKPYLL | 11 |
| 140 | FYTKNRNFCL | 11 |
| 152 | VPWNMTVITS | 11 |
| 153 | PWNMTVITSL | 11 |
| 162 | LQQELCPSFL | 11 |
| 188 | TPPALPGITN | 11 |
| 224 | DFAQSWYWIL | 11 |
| 236 | LGVALVLSLL | 11 |
| 240 | LVLSLLFILL | 11 |
| 248 | LLLRLVAGPL | 11 |
| 257 | LVLVLILGVL | 11 |
| 260 | VLILGVLGVL | 11 |
| 274 | YYCWEEYRVL | 11 |
| 312 | ALIVLAVLEA | 11 |
| 315 | VLAVLEAILL | 11 |
| 332 | QRIRIAIALL | 11 |
| 384 | QPQYVLWASN | 11 |
| 395 | SSPGCEKVPI | 11 |
| 413 | HLVNSSCPGL | 11 |
| 433 | GLIQRSVFNL | 11 |
| 435 | IQRSVFNLQI | 11 |
| 439 | VFNLQIYGVL | 11 |

TABLE XXXIX-V1-continued

HLA-B0702-10mers-24P4C12
Each peptide is a portion of
SEQ ID NO: 3; each start position
is specified, the length of peptide
is 10 amino acids, and the end
position for each peptide is the
start position plus nine.

| Pos | 1234567890 | score |
|---|---|---|
| 445 | YGVLGLFWTL | 11 |
| 449 | GLFWTLNWVL | 11 |
| 503 | AFGALILTLV | 11 |
| 531 | NPVARCIMCC | 11 |
| 536 | CIMCCFKCCL | 11 |
| 539 | CCFKCCLWCL | 11 |
| 546 | WCLEKFIKFL | 11 |
| 565 | IYGKNFCVSA | 11 |
| 589 | VVLDKVTDLL | 11 |
| 595 | TDLLLFFGKL | 11 |
| 616 | FFFSGRIPGL | 11 |
| 625 | LGKDFKSPHL | 11 |
| 630 | KSPHLNYYWL | 11 |
| 672 | EDLERNNGSL | 11 |

TABLE XXXIX-V3

HLA-B0702-10mers-24P4C12
Each peptide is a portion of
SEQ ID NO: 7; each start position
is specified, the length of peptide
is 10 amino acids, and the end
position for each peptide is the
start position plus nine.

| Pos | 1234567890 | score |
|---|---|---|
| 5 | FPWTNITPPA | 19 |
| 6 | PWTNITPPAL | 12 |
| 1 | LGRCFPWTNI | 9 |

TABLE XXXIX-V5

HLA-B0702-10mers-24P4C12
Each peptide is a portion of
SEQ ID NO: 11; each start position
is specified, the length of peptide
is 10 amino acids, and the end
position for each peptide is the
start position plus nine.

| Pos | 1234567890 | score |
|---|---|---|
| 2 | VLEAILLLVL | 14 |
| 5 | AILLLVLIFL | 13 |
| 1 | AVLEAILLLV | 10 |

TABLE XXXIX-V5-continued

HLA-B0702-10mers-24P4C12
Each peptide is a portion of
SEQ ID NO: 11; each start position
is specified, the length of peptide
is 10 amino acids, and the end
position for each peptide is the
start position plus nine.

| Pos | 1234567890 | score |
|---|---|---|
| 4 | EAILLLVLIF | 10 |
| 3 | LEAILLLVLI | 9 |
| 9 | LVLIFLRQRI | 7 |

TABLE XXXIX-V6

HLA-B0702-10mers-24P4C12
Each peptide is a portion of
SEQ ID NO: 13; each start position
is specified, the length of peptide
is 10 amino acids, and the end
position for each peptide is the
start position plus nine.

| Pos | 1234567890 | score |
|---|---|---|
| 9 | IPRSVFNLQI | 21 |
| 7 | GLIPRSVFNL | 12 |

TABLE XXXIX-V7

HLA-B0702-10mers-24P4C12
Each peptide is a portion of
SEQ ID NO: 15; each start position
is specified, the length of peptide
is 10 amino acids, and the end
position for each peptide is the
start position plus nine.

| Pos | 1234567890 | score |
|---|---|---|
| 9 | AVGQMMSTMF | 10 |
| 1 | QSWYWILVAV | 9 |
| 8 | VAVGQMMSTM | 8 |
| 4 | YWILVAVGQM | 7 |
| 7 | LVAVGQMMST | 7 |
| 5 | WILVAVGQMM | 6 |

TABLE XXXIX-V8

HLA-B0702-10mers-24P4C12
Each peptide is a portion of
SEQ ID NO: 17; each start position
is specified, the length of peptide
is 10 amino acids, and the end
position for each peptide is the
start position plus nine.

| Pos | 1234567890 | score |
|---|---|---|
| 11 | NPITPTGHVF | 17 |
| 14 | TPTGHVFQTS | 13 |
| 16 | TGHVFQTSIL | 11 |

TABLE XXXIX-V8-continued

HLA-B0702-10mers-24P4C12
Each peptide is a portion of
SEQ ID NO: 17; each start position
is specified, the length of peptide
is 10 amino acids, and the end
position for each peptide is the
start position plus nine.

| Pos | 1234567890 | score |
|---|---|---|
| 6 | LPIMRNPITP | 10 |
| 4 | YWLPIMRNPI | 9 |
| 7 | PIMRNPITPT | 9 |
| 21 | QTSILGAYVI | 9 |
| 10 | RNPITPTGHV | 8 |
| 13 | ITPTGHVFQT | 8 |
| 15 | PTGHVFQTSI | 8 |
| 18 | HVFQTSILGA | 8 |

TABLE XXXIX-V9

HLA-B0702-10mers-24P4C12
Each peptide is a portion of
SEQ ID NO: 19; each start position
is specified, the length of peptide
is 10 amino acids, and the end
position for each peptide is the
start position plus nine.

| Pos | 1234567890 | score |
|---|---|---|
| 9 | YPLPTQPATL | 22 |
| 11 | LPTQPATLGY | 13 |
| 14 | QPATLGYVLW | 13 |
| 2 | YWAMTALYPL | 12 |
| 4 | AMTALYPLPT | 12 |
| 13 | TQPATLGYVL | 12 |
| 7 | ALYPLPTQPA | 11 |

TABLE XL-V1

HLA-B08-10mers-24P4C12

| Pos | 1234567890 | score |
|---|---|---|
| No Results Found. | | |

TABLE XL-V3

HLA-B08-10mers-24P4C12

| Pos | 1234567890 | score |
|---|---|---|
| No Results Found. | | |

TABLE XL-V5

| HLA-B08-10mers-24P4C12 | | |
|---|---|---|
| Pos | 1234567890 | score |
| No Results Found. | | |

TABLE XL-V6

| HLA-B08-10mers-24P4C12 | | |
|---|---|---|
| Pos | 1234567890 | score |
| No Results Found. | | |

TABLE XL-V7

| HLA-B08-10mers-24P4C12 | | |
|---|---|---|
| Pos | 1234567890 | score |
| No Results Found. | | |

TABLE XL-V8

| HLA-B08-10mers-24P4C12 | | |
|---|---|---|
| Pos | 1234567890 | score |
| No Results Found. | | |

TABLE XL-V9

| HLA-B08-10mers-24P4C12 | | |
|---|---|---|
| Pos | 1234567890 | score |
| No Results Found. | | |

TABLE XLI-V1

| HLA-B1510-10mers-24P4C12 | | |
|---|---|---|
| Pos | 1234567890 | score |
| No Results Found. | | |

TABLE XLI-V3

| HLA-B1510-10mers-24P4C12 | | |
|---|---|---|
| Pos | 1234567890 | score |
| No Results Found. | | |

TABLE XLI-V5

| HLA-B1510-10mers-24P4C12 | | |
|---|---|---|
| Pos | 1234567890 | score |
| No Results Found. | | |

TABLE XLI-V6

| HLA-B1510-10mers-24P4C12 | | |
|---|---|---|
| Pos | 1234567890 | score |
| No Results Found. | | |

TABLE XLI-V7

| HLA-B1510-10mers-24P4C12 | | |
|---|---|---|
| Pos | 1234567890 | score |
| No Results Found. | | |

TABLE XLI-V8

| HLA-B1510-10mers-24P4C12 | | |
|---|---|---|
| Pos | 1234567890 | score |
| No Results Found. | | |

TABLE XLI-V9

| HLA-B1510-10mers-24P4C12 | | |
|---|---|---|
| Pos | 1234567890 | score |
| No Results Found. | | |

TABLE XLII-V1

| HLA-B2705-10mers-24P4C12 | | |
|---|---|---|
| Pos | 1234567890 | score |
| No Results Found. | | |

TABLE XLII-V3

| HLA-B2705-10mers-24P4C12 | | |
|---|---|---|
| Pos | 1234567890 | score |
| No Results Found. | | |

TABLE XLII-V5

| HLA-B2705-10mers-24P4C12 | | |
|---|---|---|
| Pos | 1234567890 | score |
| No Results Found. | | |

TABLE XLII-V6

| HLA-B2705-10mers-24P4C12 | | |
|---|---|---|
| Pos | 1234567890 | score |
| No Results Found. | | |

TABLE XLII-V7

| | |
|---|---|
| HLA-B2705-10mers-24P4C12 | |
| Pos  1234567890 | score |
| No Results Found. | |

TABLE XLII-V8

| | |
|---|---|
| HLA-B2705-10mers-24P4C12 | |
| Pos  1234567890 | score |
| No Results Found. | |

TABLE XLII-V9

| | |
|---|---|
| HLA-B2705-10mers-24P4C12 | |
| Pos  1234567890 | score |
| No Results Found. | |

TABLE XLIII-V1

| | |
|---|---|
| HLA-B2709-10mers-24P4C12 | |
| Pos  1234567890 | score |
| No Results Found. | |

TABLE XLIII-V3

| | |
|---|---|
| HLA-B2709-10mers-24P4C12 | |
| Pos  1234567890 | score |
| No Results Found. | |

TABLE XLIII-V5

| | |
|---|---|
| HLA-B2709-10mers-24P4C12 | |
| Pos  1234567890 | score |
| No Results Found. | |

TABLE XLIII-V6

| | |
|---|---|
| HLA-B2709-10mers-24P4C12 | |
| Pos  1234567890 | score |
| No Results Found. | |

TABLE XLIII-V7

| | |
|---|---|
| HLA-B2709-10mers-24P4C12 | |
| Pos  1234567890 | score |
| No Results Found. | |

TABLE XLIII-V8

| | |
|---|---|
| HLA-B2709-10mers-24P4C12 | |
| Pos  1234567890 | score |
| No Results Found. | |

TABLE XLIII-V9

| | |
|---|---|
| HLA-B2709-10mers-24P4C12 | |
| Pos  1234567890 | score |
| No Results Found. | |

TABLE XLIV-V1

| | | |
|---|---|---|
| HLA-B4402-10mers-24P4C12 Each peptide is a portion of SEQ ID NO: 3; each start position is specified, the length of peptide is 10 amino acids, and the end position for each peptide is the start position plus nine. | | |
| Pos | 1234567890 | score |
| 10 | DEAYGKPVKY | 23 |
| 78 | GENKDKPYLL | 22 |
| 222 | FEDFAQSWYW | 21 |
| 319 | LEAILLLMLI | 20 |
| 47 | GYIVVGIVAW | 19 |
| 332 | QRIRIAIALL | 18 |
| 486 | PLISAFIRTL | 18 |
| 502 | LAFGALILTL | 18 |
| 620 | GRIPGLGKDF | 18 |
| 39 | VLFLLFILGY | 17 |
| 241 | VLSLLFILLL | 17 |
| 254 | AGPLVLVLIL | 17 |
| 320 | EAILLLMLIF | 17 |
| 321 | AILLLMLIFL | 17 |
| 476 | FHKPQDIPTF | 17 |
| 512 | VQIARVILEY | 17 |
| 699 | NEAPPDNKKR | 17 |
| 121 | PEDPWTVGKN | 16 |
| 169 | SFLLPSAPAL | 16 |
| 199 | TTIQQGISGL | 16 |
| 203 | QGISGLIDSL | 16 |
| 260 | VLILGVLGVL | 16 |
| 293 | LGFTTNLSAY | 16 |
| 307 | ETWLAALIVL | 16 |
| 316 | LAVLEAILLL | 16 |
| 380 | ATSGQPQYVL | 16 |

TABLE XLIV-V1-continued

HLA-B4402-10mers-24P4C12
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 546 | WCLEKFIKFL | 16 |
| 657 | SVFGMCVDTL | 16 |
| 34 | DVICCVLFLL | 15 |
| 65 | LYPRNSTGAY | 15 |
| 79 | ENKDKPYLLY | 15 |
| 99 | NIISVAENGL | 15 |
| 104 | AENGLQCPTP | 15 |
| 138 | EVFYTKNRNF | 15 |
| 213 | NARDISVKIF | 15 |
| 235 | ALGVALVLSL | 15 |
| 239 | ALVLSLLFIL | 15 |
| 278 | EEYRVLRDKG | 15 |
| 284 | RDKGASISQL | 15 |
| 353 | STMFYPLVTF | 15 |
| 355 | MFYPLVTFVL | 15 |
| 356 | FYPLVTFVLL | 15 |
| 362 | FVLLLICIAY | 15 |
| 363 | VLLLICIAYW | 15 |
| 370 | AYWAMTALYL | 15 |
| 417 | SSCPGLMCVF | 15 |
| 442 | LQIYGVLGLF | 15 |
| 451 | FWTLNWVLAL | 15 |
| 482 | IPTFPLISAF | 15 |
| 561 | IMIAIYGKNF | 15 |
| 596 | DLLLFFGKLL | 15 |
| 616 | FFFSGRIPGL | 15 |
| 637 | YWLPIMTSIL | 15 |
| 640 | PIMTSILGAY | 15 |
| 4 | KQRDEDDEAY | 14 |
| 18 | KYDPSFRGPI | 14 |
| 80 | NKDKPYLLYF | 14 |
| 83 | KPYLLYFNIF | 14 |
| 130 | NEFSQTVGEV | 14 |
| 131 | EFSQTVGEVF | 14 |
| 157 | TVITSLQQEL | 14 |
| 164 | QELCPSFLLP | 14 |

TABLE XLIV-V1-continued

HLA-B4402-10mers-24P4C12
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 173 | PSAPALGRCF | 14 |
| 175 | APALGRCFPW | 14 |
| 183 | PWTNVTPPAL | 14 |
| 220 | KIFEDFAQSW | 14 |
| 227 | QSWYWILVAL | 14 |
| 231 | WILVALGVAL | 14 |
| 233 | LVALGVALVL | 14 |
| 240 | LVLSLLFILL | 14 |
| 243 | SLLFILLLRL | 14 |
| 250 | LRLVAGPLVL | 14 |
| 252 | LVAGPLVLVL | 14 |
| 253 | VAGPLVLVLI | 14 |
| 262 | ILGVLGVLAY | 14 |
| 304 | SVQETWLAAL | 14 |
| 331 | RQRIRIAIAL | 14 |
| 357 | YPLVTFVLLL | 14 |
| 431 | SKGLIQRSVF | 14 |
| 433 | GLIQRSVFNL | 14 |
| 467 | GAFASFYWAF | 14 |
| 542 | KCCLWGLEKF | 14 |
| 545 | LWCLEKFIKF | 14 |
| 551 | FIKFLNRNAY | 14 |
| 569 | NFCVSAKNAF | 14 |
| 589 | VVLDKVTDLL | 14 |
| 595 | TDLLLFFGKL | 14 |
| 627 | KDFKSPHLNY | 14 |
| 629 | FKSPHLNYYW | 14 |
| 665 | TLFLCFLEDL | 14 |
| 686 | YMSKSLLKIL | 14 |
| 7 | DEDDEAYGKP | 13 |
| 31 | SCTDVICCVL | 13 |
| 32 | CTDVICCVLF | 13 |
| 35 | VICCVLFLLF | 13 |
| 49 | IVVGIVAWLY | 13 |
| 56 | WLYGDPRQVL | 13 |

TABLE XLIV-V1-continued

HLA-B4402-10mers-24P4C12
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 57 | LYGDPRQVLY | 13 |
| 87 | LYFNIFSCIL | 13 |
| 145 | RNFCLPGVPW | 13 |
| 153 | PWNMTVITSL | 13 |
| 186 | NVTPPALPGI | 13 |
| 237 | GVALVLSLLF | 13 |
| 248 | LLLRLVAGPL | 13 |
| 257 | LVLVLILGVL | 13 |
| 271 | YGIYYCWEEY | 13 |
| 301 | AYQSVQETWL | 13 |
| 310 | LAALIVLAVL | 13 |
| 315 | VLAVLEAILL | 13 |
| 327 | LIFLRQRIRI | 13 |
| 342 | KEASKAVGQM | 13 |
| 347 | AVGQMMSTMF | 13 |
| 405 | NTSCNPTAHL | 13 |
| 425 | VFQGYSSKGL | 13 |
| 441 | NLQIYGVLGL | 13 |
| 445 | YGVLGLFWTL | 13 |
| 447 | VLGLFWTLNW | 13 |
| 449 | GLFWTLNWVL | 13 |
| 460 | LGQCVLAGAF | 13 |
| 478 | KPQDIPTFPL | 13 |
| 483 | PTFPLISAFI | 13 |
| 493 | RTLRYHTGSL | 13 |
| 495 | LRYHTGSLAF | 13 |
| 498 | HTGSLAFGAL | 13 |
| 500 | GSLAFGALIL | 13 |
| 517 | VILEYIDHKL | 13 |
| 539 | CCFKCCLWCL | 13 |
| 557 | RNAYIMIAIY | 13 |
| 582 | MRNIVRVVVL | 13 |
| 590 | VLDKVTDLLL | 13 |
| 591 | LDKVTDLLLF | 13 |
| 592 | DKVTDLLLFF | 13 |
| 606 | VVGGVGVLSF | 13 |

TABLE XLIV-V1-continued

HLA-B4402-10mers-24P4C12
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 659 | FGMCVDTLFL | 13 |
| 661 | MCVDTLFLCF | 13 |
| 662 | CVDTLELCFL | 13 |
| 671 | LEDLERNNGS | 13 |
| 672 | EDLERNNGSL | 13 |
| 682 | DRPYYMSKSL | 13 |
| 33 | TDVICCVLFL | 12 |
| 37 | CCVLFLLFIL | 12 |
| 44 | FILGYIVVGI | 12 |
| 76 | GMGENKDKPY | 12 |
| 123 | DPWTVGKNEF | 12 |
| 132 | FSQTVGEVFY | 12 |
| 150 | PGVPWNMTVI | 12 |
| 163 | QQELCPSFLL | 12 |
| 216 | DISVKIFEDF | 12 |
| 223 | EDFAQSWYWI | 12 |
| 236 | LGVALVLSLL | 12 |
| 266 | LGVLAYGIYY | 12 |
| 274 | YYCWEEYRVL | 12 |
| 277 | WEEYRVLRDK | 12 |
| 286 | KGASISQLGF | 12 |
| 290 | ISQLGFTTNL | 12 |
| 300 | SAYQSVQETW | 12 |
| 306 | QETWLAALIV | 12 |
| 313 | LIVLAVLEAI | 12 |
| 318 | VLEAILLLML | 12 |
| 329 | FLRQRIRIAI | 12 |
| 350 | QMMSTMFYPL | 12 |
| 358 | PLVTFVLLLI | 12 |
| 360 | VTFVLLLICI | 12 |
| 368 | CIAYWAMTAL | 12 |
| 369 | IAYWAMTALY | 12 |
| 378 | YLATSGQPQY | 12 |
| 381 | TSGQPQYVLW | 12 |
| 395 | SSPGCEKVPI | 12 |

TABLE XLIV-V1-continued

HLA-B4402-10mers-24P4C12
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 420 | PGLMCVFQGY | 12 |
| 436 | QRSVFNLQIY | 12 |
| 439 | VFNLQIYGVL | 12 |
| 443 | QIYGVLGLFW | 12 |
| 456 | WVLALGQCVL | 12 |
| 463 | CVLAGAFASF | 12 |
| 464 | VLAGAFASFY | 12 |
| 488 | ISAFIRTLRY | 12 |
| 505 | GALILTLVQI | 12 |
| 509 | LTLVQIARVI | 12 |
| 510 | TLVQIARVIL | 12 |
| 548 | LEKFIKFLNR | 12 |
| 556 | NRNAYIMIAI | 12 |
| 571 | CVSAKNAFML | 12 |
| 572 | VSAKNAFMLL | 12 |
| 576 | NAFMLLMRNI | 12 |
| 588 | VVVLDKVTDL | 12 |
| 604 | LLVVGGVGVL | 12 |
| 628 | DFKSPHLNYY | 12 |
| 630 | KSPHLNYYWL | 12 |
| 650 | VIASGFFSVF | 12 |
| 674 | LERNNGSLDR | 12 |
| 676 | RNNGSLDRPY | 12 |
| 677 | NNGSLDRPYY | 12 |
| 685 | YYMSKSLLKI | 12 |
| 14 | GKPVKYDPSF | 11 |
| 27 | IKNRSCTDVI | 11 |
| 40 | LFLLFILGYI | 11 |
| 48 | YIVVGIVAWL | 11 |
| 77 | MGENKDKPYL | 11 |
| 116 | CVSSCPEDPW | 11 |
| 137 | GEVFYTKNRN | 11 |
| 161 | SLQQELCPSF | 11 |
| 162 | LQQELCPSFL | 11 |
| 208 | LIDSLNARDI | 11 |
| 212 | LNARDISVKI | 11 |
| 221 | IFEDFAQSWY | 11 |
| 238 | VALVLSLLFI | 11 |
| 264 | GVLGVLAYGI | 11 |
| 305 | VQETWLAALI | 11 |
| 314 | IVLAVLEAIL | 11 |
| 348 | VGQMMSTMFY | 11 |
| 413 | HLVNSSCPGL | 11 |
| 479 | PQDIPTFPLI | 11 |
| 499 | TGSLAFGALI | 11 |
| 519 | LEYIDHKLRG | 11 |
| 528 | GVQNPVARCI | 11 |
| 532 | PVARCIMCCF | 11 |
| 536 | CIMCCFKCCL | 11 |
| 537 | IMCCFKCCLW | 11 |
| 543 | CCLWCLEKFI | 11 |
| 552 | IKFLNRNAYI | 11 |
| 607 | VGGVGVLSFF | 11 |
| 608 | GGVGVLSFFF | 11 |
| 609 | GVGVLSFFFF | 11 |
| 625 | LGKDFKSPHL | 11 |
| 632 | PHLNYYWLPI | 11 |
| 642 | MTSILGAYVI | 11 |
| 646 | LGAYVIASGF | 11 |
| 658 | VFGMCVDTLF | 11 |
| 683 | RPYYMSKSLL | 11 |

TABLE XLIV

V3-HLA-B4402-10mers-24P4C12
Each peptide is a portion of
SEQ ID NO: 7; each start position
is specified, the length of peptide
is 10 amino acids, and the end
position for each peptide is the
start position plus nine.

| Pos | 1234567890 | score |
|---|---|---|
| 6 | PWTNITPPAL | 14 |
| 9 | NITPPALPGI | 13 |
| 1 | LGRCFPWTNI | 8 |

TABLE XLIV-continued

V3-HLA-B4402-10mers-24P4C12
Each peptide is a portion of
SEQ ID NO: 7; each start position
is specified, the length of peptide
is 10 amino acids, and the end
position for each peptide is the
start position plus nine.

| Pos | 1234567890 | score |
|---|---|---|
| 3 | RCFPWTNITP | 7 |
| 8 | TNITPPALPG | 6 |

TABLE XLIV

V5-HLA-B4402-10mers-24P4C12
Each peptide is a portion of
SEQ ID NO: 11; each start position
is specified, the length of peptide
is 10 amino acids, and the end
position for each peptide is the
start position plus nine.

| Pos | 1234567890 | score |
|---|---|---|
| 3 | LEAILLLVLI | 21 |
| 4 | EAILLLVLIF | 18 |
| 5 | AILLLVLIFL | 17 |
| 2 | VLEAILLLVL | 13 |
| 9 | LVLIFLRQRI | 10 |

TABLE XLIV

V6-HLA-B4402-10mers-24P4C12
Each peptide is a portion of
SEQ ID NO: 13; each start position
is specified, the length of peptide
is 10 amino acids, and the end
position for each peptide is the
start position plus nine.

| Pos | 1234567890 | score |
|---|---|---|
| 7 | GLIPRSVFNL | 17 |
| 5 | SKGLIPRSVF | 14 |
| 10 | PRSVFNLQIY | 12 |
| 9 | IPRSVFNLQI | 10 |

TABLE XLIV

V7-HLA-B4402-10mers-24P4C12
Each peptide is a portion of
SEQ ID NO: 15; each start position
is specified, the length of peptide
is 10 amino acids, and the end
position for each peptide is the
start position plus nine.

| Pos | 1234567890 | score |
|---|---|---|
| 9 | AVGQMMSTMF | 13 |
| 4 | YWILVAVGQM | 6 |

TABLE XLIV

V8-HLA-B4402-10mers-24P4C12
Each peptide is a portion of
SEQ ID NO: 17; each start position
is specified, the length of peptide
is 10 amino acids, and the end
position for each peptide is the
start position plus nine.

| Pos | 1234567890 | score |
|---|---|---|
| 11 | NPITPTGHVF | 17 |
| 4 | YWLPIMRNPI | 14 |
| 19 | VFQTSILGAY | 14 |
| 16 | TGHVFQTSIL | 11 |
| 21 | QTSILGAYVI | 11 |
| 15 | PTGHVFQTSI | 8 |

TABLE XLIV

V9-HLA-B4402-10mers-24P4C12
Each peptide is a portion of
SEQ ID NO: 19; each start position
is specified, the length of peptide
is 10 amino acids, and the end
position for each peptide is the
start position plus nine.

| Pos | 1234567890 | score |
|---|---|---|
| 9 | YPLPTQPATL | 16 |
| 14 | QPATLGYVLW | 13 |
| 11 | LPTQPATLGY | 12 |
| 13 | TQPATLGYVL | 12 |
| 2 | YWAMTALYPL | 11 |
| 18 | LGYVLWASNI | 9 |
| 16 | ATLGYVLWAS | 8 |
| 7 | ALYPLPTQPA | 7 |

TABLE XLV

V1-HLA-B5101-10mers-24P4C12

| Pos | 1234567890 | score |
|---|---|---|
| No Results Found. | | |

TABLE XLV-V3

HLA-B5101-10mers-24P4C12

| Pos | 1234567890 | score |
|---|---|---|
| No Results Found. | | |

TABLE XLV-V5

HLA-B5101-10mers-24P4C12

| Pos | 1234567890 | score |
|---|---|---|
| No Results Found. | | |

TABLE XLV-V6

HLA-B5101-10mers-24P4C12

| Pos | 1234567890 | score |
|---|---|---|
| No Results Found. | | |

TABLE XLV-V7

HLA-B5101-10mers-24P4C12

| Pos | 1234567890 | score |
|---|---|---|
| No Results Found. | | |

TABLE XLV-V8

HLA-B5101-10mers-24P4C12

| Pos | 1234567890 | score |
|---|---|---|
| No Results Found. | | |

TABLE XLV-V9

HLA-B5101-10mers-24P4C12

| Pos | 1234567890 | score |
|---|---|---|
| No Results Found. | | |

TABLE XLVI

V1-HLA-DRB1-0101-15mers-24P4C12
Each peptide is a portion of SEQ ID NO: 3; each start position is specified, the length of peptide is 15 amino acids, and the end position for each peptide is the start position plus fourteen.

| Pos | 123456789012345 | score |
|---|---|---|
| 227 | QSWYWILVALGVALV | 39 |
| 206 | SGLIDSLNARDISVK | 33 |
| 247 | ILLLRLVAGPLVLVL | 33 |
| 313 | LIVLAVLEAILLLML | 33 |
| 601 | FGKLLVVGGVGVLSF | 33 |
| 246 | FILLLRLVAGPLVLV | 32 |
| 262 | ILGVLGVLAYGIYYC | 32 |
| 353 | STMFYPLVTFVLLLI | 32 |
| 368 | CIAYWAMTALYLATS | 32 |
| 652 | ASGFFSVFGMCVDTL | 32 |
| 39 | VLFLLFILGYIVVWGI | 31 |
| 181 | CFPWTNVTPPALPGI | 31 |
| 277 | WEEYRVLRDKGASIS | 31 |
| 559 | AYIMIAIYGKNFCVS | 31 |
| 639 | LPIMTSILGAYVIAS | 31 |
| 85 | YLLYFNIFSCILSSN | 30 |
| 89 | FNIFSCILSSNIISV | 30 |
| 257 | LVLVLILGVLGVLAY | 30 |
| 259 | LVLILGVLGVLAYGI | 30 |
| 635 | NYYWLPIMTSILGAY | 30 |
| 646 | LGAYVIASGFFSVFG | 30 |
| 235 | ALGVALVLSLLFILL | 29 |
| 345 | SKAVGQMMSTMFYPL | 29 |
| 40 | LFLLFILGYIVVGIV | 28 |
| 242 | LSLLFILLLRLVAGP | 28 |
| 359 | LVTFVLLLICIAYWA | 28 |
| 453 | TLNWVLALGQCVLAG | 28 |
| 612 | VLSFFFFSGRIPGLG | 28 |
| 640 | PIMTSILGAYVIASG | 28 |
| 167 | CPSFLLPSAPALGRC | 27 |
| 243 | SLLFILLLRLVAGPL | 27 |
| 280 | YRVLRDKGASISQLG | 27 |
| 362 | FVLLLICIAYWAMTA | 27 |
| 423 | MCVFQGYSSKGLIQR | 27 |
| 501 | SLAFGALILTLVQIA | 27 |
| 575 | KNAFMLLMRNIVRVV | 27 |
| 129 | KNEFSQTVGEVFYTK | 26 |
| 230 | YWILVALGVALVLSL | 26 |
| 254 | AGPLVLVLILGVLGV | 26 |
| 384 | QPQYVLWASNISSPG | 26 |
| 436 | QRSVFNLQIYGVLGL | 26 |
| 437 | RSVFNLQIYGVLGLF | 26 |
| 448 | LGLFWTLNWVLALGQ | 26 |
| 492 | IRTLRYHTGSLAFGA | 26 |

TABLE XLVI-continued

V1-HLA-DRB1-0101-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 551 | FIKELNANAYIMIAI | 26 |
| 594 | VTDLLLFFGKLLVVG | 26 |
| 633 | HLNYYWLPIMTSILG | 26 |
| 688 | SKSLLKILGKKNEAP | 26 |
| 44 | FILGYIVVGIVAWLY | 25 |
| 53 | IVAWLYGDPRQVLYP | 25 |
| 62 | RQVLYPRNSTGAYCG | 25 |
| 90 | NIFSCILSSNIISVA | 25 |
| 228 | SWYWILVALGVALVL | 25 |
| 231 | WILVALGVALVLSLL | 25 |
| 239 | ALVLSLLFILLLRLV | 25 |
| 293 | LGFTTNLSAYQSVQE | 25 |
| 299 | LSAYQSVQETWLAAL | 25 |
| 304 | SVQETWLAALIVLAV | 25 |
| 319 | LEAILLLMLIFLRQR | 25 |
| 326 | MLIFLRQRIRIAIAL | 25 |
| 337 | AIALLKEASKAVGQM | 25 |
| 354 | TMFYPLVTFVLLLIC | 25 |
| 371 | YWAMTALYLATSGQP | 25 |
| 399 | CEKVPINTSCNPTAH | 25 |
| 451 | FWTLNWVLALGQCVL | 25 |
| 454 | LNWVLALGQCVLAGA | 25 |
| 471 | SFYWAFHKPQDIPTF | 25 |
| 482 | IPTFPLISAFIRTLR | 25 |
| 526 | LRGVQNPVARCIMCC | 25 |
| 583 | RNIVRVVVLDKVTDL | 25 |
| 603 | KLLVVGGVGVLSFFF | 25 |
| 51 | VGIVAWLYGDPRQVL | 24 |
| 97 | SSNIISVAENGLQCP | 24 |
| 229 | WYWILVALGVALVLS | 24 |
| 238 | VALVLSLLFILLLRL | 24 |
| 255 | GPLVLVLILGVLGVL | 24 |
| 256 | PLVLVLILGVLGVLA | 24 |
| 279 | EYRVLRDKGASISQL | 24 |
| 307 | ETWLAALIVLAVLEA | 24 |
| 310 | LAALIVLAVLEAILL | 24 |
| 383 | GQPQYVLWASNISSP | 24 |
| 420 | PGLMCVFQGYSSKGL | 24 |
| 459 | ALGQCVLAGAFASFY | 24 |
| 506 | ALILTLVQIARVILE | 24 |
| 523 | DHKLRGVQNPVARCI | 24 |
| 569 | NFCVSAKNAFMLLMR | 24 |
| 579 | MLLMRNIVRVVVLDK | 24 |
| 588 | VVVLDKVTDLLLFFG | 24 |
| 607 | VGGVGVLSFFFFSGR | 24 |
| 644 | SILGAYVIASGFFSV | 24 |
| 660 | GMCVDTLFLCFLEDL | 24 |
| 47 | GYIVVGIVAWLYGDP | 23 |
| 59 | GDPRQVLYPRNSTGA | 23 |
| 165 | ELCPSFLLPSAPALG | 23 |
| 166 | LCPSFLLPSAPALGR | 23 |
| 241 | VLSLLFILLLRLVAG | 23 |
| 374 | MTALYLATSGQPQYV | 23 |
| 412 | AHLVNSSCPGLMCVF | 23 |
| 507 | LILTLVQIARVILEY | 23 |
| 508 | ILTLVQIARVILEYI | 23 |
| 566 | YGKNFGVSAKNAFML | 23 |
| 604 | LLVVGGVGVLSFFFF | 23 |
| 636 | YYWLPIMTSILGAYV | 23 |
| 33 | TDVICCVLFLLFILG | 22 |
| 43 | LFILGYIVVGIVAWL | 22 |
| 86 | LLYFNIFSCILSSNI | 22 |
| 160 | TSLQQELCPSFLLPS | 22 |
| 198 | DTTIQQGISGLIDSL | 22 |
| 312 | ALIVLAVLEAILLLM | 22 |
| 316 | LAVLEAILLLMLIFL | 22 |
| 349 | GQMMSTMFYPLVTFV | 22 |
| 363 | VLLLICIAYWAMTAL | 22 |
| 419 | CPGLMCVFQGYSSKG | 22 |
| 439 | VFNLQIYGVLGLFWT | 22 |

TABLE XLVI-continued

V1-HLA-DRB1-0101-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 441 | NLQIYGVLGLFWTLN | 22 |
| 458 | LALGQCVLAGAFASF | 22 |
| 481 | DIPTFPLISAFIRTL | 22 |
| 511 | LVQIARVILEYIDHK | 22 |
| 587 | RVVVLDKVTDLLLFF | 22 |
| 598 | LLFFGKLLVVGGVGV | 22 |
| 655 | FFSVFGMCVDTLFLC | 22 |
| 689 | KSLLKILGKKNEAPP | 22 |
| 138 | EVFYTKNRNFCLPGV | 21 |
| 151 | GVPWNMTVITSLQQE | 21 |
| 153 | PWNMTVITSLQQELC | 21 |
| 203 | QGISGLIDSLNARDI | 21 |
| 300 | SAYQSVQETWLAALI | 21 |
| 329 | FLRQRIRIAIALLKE | 21 |
| 331 | RQRIRIAIALLKEAS | 21 |
| 409 | NPTAHLVNSSCPGLM | 21 |
| 518 | ILEYIDHKLRGVQNP | 21 |
| 548 | LEKFIKFLNRNAYIM | 21 |
| 606 | VVGGVGVLSFFFFSG | 21 |
| 10 | DEAYGKPVKYDPSFR | 20 |
| 20 | DPSFRGPIKNRSCTD | 20 |
| 272 | GIYYCWEEYRVLRDK | 20 |
| 333 | RIRIAIALLKEASKA | 20 |
| 449 | GLFWTLNWVLALGQC | 20 |
| 476 | FHKPQDIPTFPLISA | 20 |
| 543 | CCLWCLEKFIKFLNR | 20 |
| 563 | IAIYGKNFCVSAKNA | 20 |
| 599 | LFFGKLLVVGGVGVL | 20 |
| 614 | SFFFFSGRIPGLGKD | 20 |
| 634 | LNYYWLPIMTSILGA | 20 |
| 645 | ILGAYVIASGFFSVF | 20 |
| 656 | FSVFGMCVDTLFLGF | 20 |
| 657 | SVFGMCVDTLFLCFL | 20 |
| 37 | CCVLFLLFILGYIVV | 19 |
| 38 | CVLFLLFILGYIVVG | 19 |

TABLE XLVI-continued

V1-HLA-DRB1-0101-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 82 | DKPYLLYFNIFSCIL | 19 |
| 122 | EDPWTVGKNEFSQTV | 19 |
| 179 | GRCFPWTNVTPPALP | 19 |
| 184 | WTNVTPPALPGITND | 19 |
| 245 | LFILLLRLVAGPLVL | 19 |
| 271 | YGIYYCWEEYRVLRD | 19 |
| 317 | AVLEAILLLMLIFLR | 19 |
| 323 | LLLMLIFLRQRIRIA | 19 |
| 336 | IAIALLKEASKAVGQ | 19 |
| 369 | IAYWAMTALYLATSG | 19 |
| 411 | TAHLVNSSCPGLMCV | 19 |
| 442 | LQIYGVLGLFWTLNW | 19 |
| 460 | LGQCVLAGAFASFYW | 19 |
| 495 | LRYHTGSLAFGALIL | 19 |
| 503 | AFGALILTLVQIARV | 19 |
| 557 | RNAYIMIAIYGKNFC | 19 |
| 586 | VRVVVLDKVTDLLLF | 19 |
| 683 | RPYYMSKSLLKILGK | 19 |
| 684 | PYYMSKSLLKILGKK | 19 |

TABLE XLVI

V3-HLA-DRB1-0101-15mers-24P4C12
Each peptide is a portion of
SEQ ID NO: 7; each start position
is specified, the length of peptide
is 15 amino acids, and the end
position for each peptide is the
start position plus fourteen.

| Pos | 123456789012345 | score |
|---|---|---|
| 9 | CFPWTNITPPALPGI | 31 |
| 7 | GRCFPWTNITPPALP | 19 |
| 12 | WTNITPPALPGITND | 19 |
| 10 | FPWTNITPPALPGIT | 18 |
| 14 | NITPPALPGITNDTT | 16 |

TABLE XLVI

V5-HLA-DRB1-0101-15mers-24P4C12
Each peptide is a portion of
SEQ ID NO: 11; each start position

TABLE XLVI

V6-HLA-DRB1-0101-15mers-24P4C12
Each peptide is a portion of
SEQ ID NO: 13; each start position
is specified, the length of peptide
is 15 amino acids, and the end
position for each peptide is the
start position plus fourteen.

| Pos | 123456789012345 | score |
|---|---|---|
| 2 | LIVLAVLEAILLLVL | 33 |
| 8 | LEAILLLVLIFLRQR | 25 |
| 15 | VLIFLRQRIRIAIAL | 25 |
| 1 | ALIVLAVLEAILLLV | 22 |
| 5 | LAVLEAILLLVLIFL | 22 |
| 6 | AVLEAILLLVLIFLR | 19 |
| 12 | LLLVLIFLRQRIRIA | 19 |
| 13 | LLVLIFLRQRIRIAI | 18 |
| 7 | VLEAILLLVLIFLRQ | 17 |
| 11 | ILLLVLIFLRQRIRI | 17 |
| 14 | LVLIFLRQRIRIAIA | 17 |
| 4 | VLAVLEAILLLVLIF | 16 |
| 10 | AILLLVLIFLRQRIR | 16 |

TABLE XLVI

V6-HLA-DRB1-0101-15mers-24P4C12
Each peptide is a portion of
SEQ ID NO: 13; each start position
is specified, the length of peptide
is 15 amino acids, and the end
position for each peptide is the
start position plus fourteen.

| Pos | 123456789012345 | score |
|---|---|---|
| 2 | MCVFQGYSSKGLIPR | 27 |
| 15 | PRSVFNLQIYGVLGL | 26 |
| 7 | GYSSKGLIPRSVFNL | 24 |
| 4 | VFQGYSSKGLIPRSV | 16 |
| 10 | SKGLIPRSVFNLQIY | 16 |
| 12 | GLIPRSVFNLQIYGV | 16 |
| 1 | LMCVFQGYSSKGLIP | 15 |
| 8 | YSSKGLIPRSVFNLQ | 15 |

TABLE XLVI

V7-HLA-DRB1-0101-15mers-24P4C12
Each peptide is a portion of
SEQ ID NO: 15; each start position
is specified, the length of peptide
is 15 amino acids, and the end
position for each peptide is the
start position plus fourteen.

| Pos | 123456789012345 | score |
|---|---|---|
| 6 | QSWYWILVAVGQMMS | 31 |
| 12 | LVAVGQMMSTMFYPL | 29 |

TABLE XLVI-continued

V7-HLA-DRB1-0101-15mers-24P4C12
Each peptide is a portion of
SEQ ID NO: 15; each start position
is specified, the length of peptide
is 15 amino acids, and the end
position for each peptide is the
start position plus fourteen.

| Pos | 123456789012345 | score |
|---|---|---|
| 7 | SWYWILVAVGQMMST | 25 |
| 8 | WYWILVAVGQMMSTM | 24 |
| 9 | YWILVAVGQMMSTMF | 24 |
| 1 | FEDFAQSWYWILVAV | 18 |
| 5 | AQSWYWILVAVGQMM | 16 |
| 11 | ILVAVGQMMSTMFYP | 15 |

TABLE XLVI

V8-HLA-DRB1-0101-15mers-24P4C12
Each peptide is a portion of
SEQ ID NO: 17; each start position
is specified, the length of peptide
is 15 amino acids, and the end
position for each peptide is the
start position plus fourteen.

| Pos | 123456789012345 | score |
|---|---|---|
| 24 | VFQTSILGAYVIASG | 28 |
| 7 | NYYWLPIMRNPITPT | 24 |
| 23 | HVFQTSILGAYVIAS | 23 |
| 6 | LNYYWLPIMRNPITP | 20 |
| 5 | HLNYYWLPIMRNPIT | 18 |
| 21 | TGHVFQTSILGAYVI | 18 |
| 3 | SPHLNYYWLPIMRNP | 17 |
| 8 | YYWLPIMRNPITPTG | 17 |
| 13 | IMRNPITPTGHVFQT | 17 |
| 11 | LPIMRNPITPTGHVF | 16 |
| 12 | PIMRNPITPTGHVFQ | 16 |
| 14 | MRNPITPTGHVFQTS | 16 |
| 26 | QTSILGAYVIASGFF | 16 |
| 9 | YWLPIMRNPITPTGH | 15 |
| 18 | ITPTGHVFQTSILGA | 15 |
| 19 | TPTGHVFQTSILGAY | 14 |
| 20 | PTGHVFQTSILGAYV | 14 |

TABLE XLVI

V9-HLA-DRB1-0101-15mers-24P4C12
Each peptide is a portion of
SEQ ID NO: 19; each start position
is specified, the length of peptide
is 15 amino acids, and the end

| Pos | 123456789012345 | score |
|---|---|---|
| 4 | CIAYWAMTALYPLPT | 32 |
| 10 | MTALYPLPTQPATLG | 30 |
| 22 | TLGYVLWASNISSPG | 26 |
| 21 | ATLGYVLWASNISSP | 24 |
| 7 | YWAMTALYPLPTQPA | 23 |
| 13 | LYPLPTQPATLGYVL | 23 |
| 5 | IAYWAMTALYPLPTQ | 19 |
| 2 | LICIAYWAMTALYPL | 17 |
| 1 | LLICIAYWAMTALYP | 16 |
| 16 | LPTQPATLGYVLWAS | 16 |
| 23 | LGYVLWASNISSPGC | 16 |
| 24 | GYVLWASNISSPGCE | 16 |
| 9 | AMTALYPLPTQPATL | 15 |

TABLE XLVII

V1-HLA-DRB1-0301-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 54 | VAWLYGDPRQVLYPR | 36 |
| 586 | VRVVVLDKVTDLLLF | 31 |
| 667 | FLCFLEDLERNNGSL | 29 |
| 312 | ALIVLAVLEAILLLM | 28 |
| 97 | SSNIISVAENGLQCP | 27 |
| 155 | NMTVITSLQQELCPS | 27 |
| 454 | LNWVALGQCVLAGA | 27 |
| 549 | EKFIKFLNRNAYIMI | 27 |
| 136 | VGEVFYTKNRNFCLP | 26 |
| 508 | ILTLVQIARVILEYI | 26 |
| 622 | IPGLGKDFKSPHLNY | 26 |
| 376 | ALYLATSGQPQYVLW | 25 |
| 447 | VLGLFWTLNWVALG | 25 |
| 279 | EYRVLRDKGASISQL | 24 |
| 534 | ARCIMCCFKCCLWCL | 24 |
| 567 | GKNFCVSAKNAFMLL | 24 |
| 229 | WYWILVALGVALVLS | 23 |
| 238 | VALVLSLLFILLLRL | 23 |

TABLE XLVII-continued

V1-HLA-DRB1-0301-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 14 | GKPVKYDPSFRGPIK | 22 |
| 218 | SVKIFEDFAQSWYWI | 22 |
| 219 | VKIFEDFAQSWYWIL | 22 |
| 235 | ALGVALVLSLLFILL | 22 |
| 241 | VLSLLFILLLRLVAG | 22 |
| 360 | VTFVLLLICIAYWAM | 22 |
| 515 | ARVILEYIDHKLRGV | 22 |
| 594 | VTDLLLFFGKLLVVG | 22 |
| 33 | TDVICCVLFLLFILG | 21 |
| 167 | CPSFLLPSAPALGRC | 21 |
| 192 | LPGITNDTTIQQGIS | 21 |
| 237 | GVALVLSLLFILLLR | 21 |
| 239 | ALVLSLLFILLLRLV | 21 |
| 260 | VLILGVLGVLAYGIY | 21 |
| 302 | YQSVQETWLAALIVL | 21 |
| 319 | LEAILLLMLIFLRQR | 21 |
| 431 | SKGLIQRSVFNLQIY | 21 |
| 461 | GQCVLAGAFASFYWA | 21 |
| 587 | RVVVLDKVTDLLLFF | 21 |
| 590 | VLDKVTDLLLFFGKL | 21 |
| 595 | TDLLLFFGKLLVVGG | 21 |
| 658 | VFGMCVDTLFLCFLE | 21 |
| 32 | GTDVICCVLFLLFIL | 20 |
| 37 | CCVLFLLFILGYIVV | 20 |
| 46 | LGYIVVGIVAWLYGD | 20 |
| 47 | GYIVVGIVAWLYGDP | 20 |
| 74 | YCGMGENKDKPYLLY | 20 |
| 76 | GMGENKDKPYLLYFN | 20 |
| 231 | WILVALGVALVLSLL | 20 |
| 233 | LVALGVALVLSLLFI | 20 |
| 246 | FILLLRLVAGPLVLV | 20 |
| 250 | LRLVAGPLVLVLILG | 20 |
| 255 | GPLVLVLILGVLGVL | 20 |
| 258 | VLVLILGVLGVLAYG | 20 |
| 313 | LIVLAVLEAILLLML | 20 |

TABLE XLVII-continued

V1-HLA-DRB1-0301-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 316 | LAVLEAILLLMLIFL | 20 |
| 323 | LLLMLIFLRQRIRIA | 20 |
| 338 | IALLKEASKAVGQMM | 20 |
| 411 | TAHLVNSSCPGLMCV | 20 |
| 439 | VFNLQIYGVLGLFWT | 20 |
| 484 | TFPLISAFIRTLRYH | 20 |
| 559 | AYIMIAIYGKNFCVS | 20 |
| 588 | VVVLDKVTDLLLFFG | 20 |
| 602 | GKLLVVGGVGVLSFF | 20 |
| 604 | LLVVGGVGVLSFFFF | 20 |
| 691 | LLKILGKKNEAPPDN | 20 |
| 156 | MTVITSLQQELCPSF | 19 |
| 159 | ITSLQQELCPSFLLP | 19 |
| 205 | ISGLIDSLNARDISV | 19 |
| 335 | RIAIALLKEASKAVG | 19 |
| 348 | VGQMMSTMFYPLVTF | 19 |
| 366 | LICIAYWAMTALYLA | 19 |
| 385 | PQYVLWASNISSPGC | 19 |
| 505 | GALILTLVQIARVIL | 19 |
| 576 | NAFMLLMRNIVRVVV | 19 |
| 607 | VGGVGVLSFFFFSGR | 19 |
| 626 | GKDFKSPHLNYYWLP | 19 |
| 638 | WLPIMTSILGAYVIA | 19 |
| 648 | AYVIASGFFSVFGMC | 19 |
| 663 | VDTLELCFLEDLERN | 19 |
| 668 | LCFLEDLERNNGSLD | 19 |
| 684 | PYYMSKSLLKILGKK | 19 |
| 689 | KSLLKILGKKNEAPP | 19 |
| 3 | GKQRDEDDEAYGKPV | 18 |
| 61 | PRQVLYPRNSTGAYC | 18 |
| 98 | SNIISVAENGLQCPT | 18 |
| 114 | QVCVSSCPEDPWTVG | 18 |
| 214 | ARDISVKIFEDFAQS | 18 |
| 243 | SLLFILLLRLVAGPL | 18 |
| 263 | LGVLGVLAYGIYYCW | 18 |

TABLE XLVII-continued

V1-HLA-DRB1-0301-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 327 | LIFLRQRIRIAIALL | 18 |
| 345 | SKAVGQMMSTMFYPL | 18 |
| 462 | QCVLAGAFASFYWAF | 18 |
| 530 | QNPVARCIMCCFKCC | 18 |
| 560 | YIMIAIYGKNFCVSA | 18 |
| 569 | NECVSAKNAFMLLMR | 18 |
| 579 | MLLMRNIVRVVVLDK | 18 |
| 585 | IVRVVVLDKVTDLLL | 18 |
| 655 | FFSVEGMCVDTLFLG | 18 |
| 656 | FSVFGMCVDTLFLCF | 18 |
| 660 | GMCVDTLFLCFLEDL | 18 |
| 664 | DTLFLCFLEDLERNN | 18 |
| 284 | RDKGASISQLGFTTN | 17 |
| 290 | ISQLGFTTNLSAYQS | 17 |
| 324 | LLMLIFLRQRIRIAI | 17 |
| 325 | LMLIFLRQRIRIAIA | 17 |
| 353 | STMFYPLVTFVLLLI | 17 |
| 423 | MCVFQGYSSKGLIQR | 17 |
| 437 | RSVFNLQIYGVLGLF | 17 |
| 485 | FPLISAFIRTLRYHT | 17 |
| 517 | VILEYIDHKLRGVQN | 17 |
| 519 | LEYIDHKLRGVQNPV | 17 |
| 523 | DHKLRGVQNPVARCI | 17 |
| 542 | KCCLWCLEKFIKFLN | 17 |
| 545 | LWCLEKFIKFLNRNA | 17 |
| 548 | LEKFIKFLNRNAYIM | 17 |
| 614 | SFFFFSGRIPGLGKD | 17 |
| 619 | SGRIPGLGKDFKSPH | 17 |
| 670 | FLEDLERNNGSLDRP | 17 |
| 692 | LKILGKKNEAPPDNK | 17 |

TABLE XLVII

V3-HLA-DRB1-0301-15mers-24P4C12
Each peptide is a portion of
SEQ ID NO: 7; each start position
is specified, the length of peptide
is 15 amino acids, and the end

TABLE XLVII (cont.)

position for each peptide is the start position plus fourteen.

| Pos | 123456789012345 | score |
|---|---|---|
| 12 | WTNITPPALPGITND | 12 |
| 3 | APALGRCFPWTNITP | 10 |
| 9 | CFPWTNITPPALPGI | 10 |
| 7 | GRCFPWTNITPPALP | 8 |
| 6 | LGRCFPWTNITPPAL | 7 |

TABLE XLVII

V5-HLA-DRB1-0301-15mers-24P4C12
Each peptide is a portion of SEQ ID NO: 11; each start position is specified, the length of peptide is 15 amino acids, and the end position for each peptide is the start position plus fourteen.

| Pos | 123456789012345 | score |
|---|---|---|
| 1 | ALIVLAVLEAILLLV | 28 |
| 8 | LEAILLLVLIFLRQR | 21 |
| 2 | LIVLAVLEAILLLVL | 20 |
| 5 | LAVLEAILLLVLIFL | 20 |
| 12 | LLLVLIFLRQRIRIA | 20 |
| 13 | LLVLIFLRQRIRIAI | 17 |
| 14 | LVLIFLRQRIRIAIA | 17 |
| 4 | VLAVLEAILLLVLIF | 15 |
| 9 | EAILLLVLIFLRQRI | 15 |
| 10 | AILLLVLIFLRQRIR | 13 |

TABLE XLVII

V6-HLA-DRB1-0301-15mers-24P4C12
Each peptide is a portion of SEQ ID NO: 13; each start position is specified, the length of peptide is 15 amino acids, and the end position for each peptide is the start position plus fourteen.

| Pos | 123456789012345 | score |
|---|---|---|
| 10 | SKGLIPRSVFNLQIY | 22 |
| 2 | MCVFQGYSSKGLIPR | 17 |
| 8 | YSSKGLIPRSVFNLQ | 16 |
| 11 | KGLIPRSVFNLQIYG | 12 |
| 1 | LMCVFQGYSSKGLIP | 11 |
| 15 | PRSVFNLQIYGVLGL | 10 |

TABLE XLVII

V7-HLA-DRB1-0301-15mers-24P4C12
Each peptide is a portion of SEQ ID NO: 15; each start position is specified, the length of peptide is 15 amino acids, and the end position for each peptide is the start position plus fourteen.

| Pos | 123456789012345 | score |
|---|---|---|
| 9 | YWILVAVGQMMSTMF | 18 |
| 12 | LVAVGQMMSTMFYPL | 18 |
| 1 | FEDFAQSWYWILVAV | 16 |
| 8 | WYWILVAVGQMMSTM | 13 |
| 10 | WILVAVGQMMSTMFY | 10 |
| 13 | VAVGQMMSTMFYPLV | 10 |

TABLE XLVII

V8-HLA-DRB1-0301-15mers-24P4C12
Each peptide is a portion of SEQ ID NO: 17; each start position is specified, the length of peptide is 15 amino acids, and the end position for each peptide is the start position plus fourteen.

| Pos | 123456789012345 | score |
|---|---|---|
| 22 | GHVFQTSILGAYVIA | 17 |
| 8 | YYWLPIMRNPITPTG | 16 |
| 15 | RNPITPTGHVFQTSI | 14 |
| 26 | QTSILGAYVIASGFF | 13 |
| 21 | TGHVFQTSILGAYVI | 12 |
| 10 | WLPIMRNPITPTGHV | 11 |
| 11 | LPIMRNPITPTGHVF | 11 |
| 3 | SPHLNYYWLPIMRNP | 10 |
| 7 | NYYWLPIMRNPITPT | 10 |
| 14 | MRNPITPTGHVFQTS | 9 |
| 19 | TPTGHVFQTSILGAY | 8 |

TABLE XLVII

V9-HLA-DRB1-0301-15mers-24P4C12
Each peptide is a portion of SEQ ID NO: 19; each start position is specified, the length of peptide is 15 amino acids, and the end position for each peptide is the start position plus fourteen.

| Pos | 123456789012345 | score |
|---|---|---|
| 2 | LICIAYWAMTALYPL | 19 |
| 23 | LGYVLWASNISSPGC | 19 |
| 10 | MTALYPLPTQPATLG | 13 |
| 7 | YWAMTALYPLPTQPA | 12 |
| 12 | ALYPLPTQPATLGYV | 12 |
| 13 | LYPLPTQPATLGYVL | 12 |

TABLE XLVII-continued

V9-HLA-DRB1-0301-15mers-24P4C12
Each peptide is a portion of
SEQ ID NO: 19; each start position
is specified, the length of peptide
is 15 amino acids, and the end
position for each peptide is the
start position plus fourteen.

| Pos | 123456789012345 | score |
|---|---|---|
| 20 | PATLGYVLWASNISS | 12 |
| 3 | ICIAYWAMTALYPLP | 10 |
| 14 | YPLPTQPATLGYVLW | 10 |
| 24 | GYVLWASNISSPGCE | 10 |
| 5 | IAYWAMTALYPLPTQ | 9 |
| 16 | LPTQPATLGYVLWAS | 9 |

TABLE XLVIII

V1-DR1-0401-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 85 | YLLYFNIFSCILSSN | 28 |
| 89 | FNIFSCILSSNIISV | 28 |
| 243 | SLLFILLLRLVAGPL | 28 |
| 353 | STMFYPLVTFVLLLI | 28 |
| 469 | FASFYWAFHKPQDIP | 28 |
| 548 | LEKFIKFLNRNAYIM | 28 |
| 575 | KNAFMLLMRNIVRVV | 28 |
| 635 | NYYWLPIMTSILGAY | 28 |
| 54 | VAWLYGDPRQVLYPR | 26 |
| 98 | SNIISVAENGLQCPT | 26 |
| 153 | PWNMTVITSLQQELC | 26 |
| 189 | PPALPGITNDTTIQQ | 26 |
| 192 | LPGITNDTTIQQGIS | 26 |
| 323 | LLLMLIFLRQRIRIA | 26 |
| 337 | AIALLKEASKAVGQM | 26 |
| 385 | PQYVLWASNISSPGC | 26 |
| 419 | CPGLMCVFQGYSSKG | 26 |
| 454 | LNWVLALGQCVLAGA | 26 |
| 508 | ILTLVQIARVILEYI | 26 |
| 523 | DHKLRGVQNPVARCI | 26 |
| 579 | MLLMRNIVRVVVLDK | 26 |

TABLE XLVIII-continued

V1-DR1-0401-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 16 | PVKYDPSFRGPIKNR | 22 |
| 38 | CVLFLLFILGYIVVG | 22 |
| 82 | DKPYLLYFNIFSCIL | 22 |
| 86 | LLYFNIFSCILSSNI | 22 |
| 122 | EDPWTVGKNEFSQTV | 22 |
| 138 | EVFYTKNRNFCLPGV | 22 |
| 181 | CFPWTNVTPPALPGI | 22 |
| 219 | VKIFEDFAQSWYWIL | 22 |
| 227 | QSWYWILVALGVALV | 22 |
| 228 | SWYWILVALGVALVL | 22 |
| 272 | GIYYCWEEYRVLRDK | 22 |
| 277 | WEEYRVLRDKGASIS | 22 |
| 292 | QLGFTTNLSAYQSVQ | 22 |
| 299 | LSAYQSVQETWLAAL | 22 |
| 306 | QETWLAALIVLAVLE | 22 |
| 354 | TMFYPLVTFVLLLIC | 22 |
| 359 | LVTFVLLLICIAYWA | 22 |
| 384 | QPQYVLWASNISSPG | 22 |
| 423 | MCVFQGYSSKGLIQR | 22 |
| 442 | LQIYGVLGLFWTLNW | 22 |
| 448 | LGLFWTLNWVLALGQ | 22 |
| 453 | TLNWVLALGQCVLAG | 22 |
| 488 | ISAFIRTLRYHTGSL | 22 |
| 501 | SLAFGALILTLVQIA | 22 |
| 557 | RNAYIMIAIYGKNFC | 22 |
| 633 | HLNYYWLPIMTSILG | 22 |
| 646 | LGAYVIASGFFSVFG | 22 |
| 652 | ASGFFSVFGMCVDTL | 22 |
| 667 | FLCFLEDLERNNGSL | 22 |
| 682 | DRPYYMSKSLLKILG | 22 |
| 14 | GKPVKYDPSFRGPIK | 20 |
| 39 | VLFLLFILGYIVVGI | 20 |
| 40 | LFLLFILGYIWGIV | 20 |
| 43 | LFILGYIWGIVAWL | 20 |
| 97 | SSNIISVAENGLQCP | 20 |

TABLE XLVIII-continued

V1-DR1-0401-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 133 | SQTVGEVFYTKNRNF | 20 |
| 146 | NFCLPGVPWNMTVIT | 20 |
| 149 | LPGVPWNMTVITSLQ | 20 |
| 155 | NMTVITSLQQELCPS | 20 |
| 156 | MTVITSLQQELCPSF | 20 |
| 198 | DTTIQQGISGLIDSL | 20 |
| 202 | QQGISGLIDSLNARD | 20 |
| 206 | SGLIDSLNARDISVK | 20 |
| 216 | DISVKIFEDFAQSWY | 20 |
| 229 | WYWILVALGVALVLS | 20 |
| 230 | YWILVALGVALVLSL | 20 |
| 233 | LVALGVALVLSLLFI | 20 |
| 235 | ALGVALVLSLLFILL | 20 |
| 238 | VALVLSLLFILLLRL | 20 |
| 239 | ALVLSLLFILLLRLV | 20 |
| 241 | VLSLLFILLLRLVAG | 20 |
| 242 | LSLLFILLLRLVAGP | 20 |
| 246 | FILLLRLVAGPLVLV | 20 |
| 247 | ILLLRLVAGPLVLVL | 20 |
| 254 | AGPLVLVLILGVLGV | 20 |
| 255 | GPLVLVLILGVLGVL | 20 |
| 257 | LVLVLILGVLGVLAY | 20 |
| 259 | LVLILGVLGVLAYGI | 20 |
| 262 | ILGVLGVLAYGIYYC | 20 |
| 279 | EYRVLRDKGASISQL | 20 |
| 287 | GASISQLGFTTNLSA | 20 |
| 290 | ISQLGFTTNLSAYQS | 20 |
| 307 | ETWLAALIVLAVLEA | 20 |
| 310 | LAALIVLAVLEAILL | 20 |
| 311 | AALIVLAVLEAILLL | 20 |
| 312 | ALIVLAVLEAILLLM | 20 |
| 313 | LIVLAVLEAILLLML | 20 |
| 315 | VLAVLEAILLLMLIF | 20 |
| 316 | LAVLEAILLLMLIFL | 20 |
| 319 | LEAILLLMLIFLRQR | 20 |

TABLE XLVIII-continued

V1-DR1-0401-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 321 | AILLLMLIFLRQRIR | 20 |
| 324 | LLMLIFLRQRIRIAI | 20 |
| 331 | RQRIRIAIALLKEAS | 20 |
| 333 | RIRIAIALLKEASKA | 20 |
| 335 | RIAIALLKEASKAVG | 20 |
| 356 | FYPLVTFVLLLICIA | 20 |
| 363 | VLLLICIAYWAMTAL | 20 |
| 364 | LLLIGIAYWAMTALY | 20 |
| 371 | YWAMTALYLATSGQP | 20 |
| 374 | MTALYLATSGQPQYV | 20 |
| 401 | KVPINTSCNPTAHLV | 20 |
| 420 | PGLMCVFQGYSSKGL | 20 |
| 436 | QRSVFNLQIYGVLGL | 20 |
| 444 | IYGVLGLFWTLNWVL | 20 |
| 445 | YGVLGLFWTLNWVLA | 20 |
| 447 | VLGLFWTLNWVLALG | 20 |
| 4S1 | FWTLNWVLALGQGVL | 20 |
| 479 | PQDIPTEPLISAFIR | 20 |
| 484 | TFPLISAFIRTLRYH | 20 |
| 485 | FPLISAFIRTLRYHT | 20 |
| 505 | GALILTLVQIARVIL | 20 |
| 506 | ALILTLVQIARVILE | 20 |
| 511 | LVQIARVILEYIDHK | 20 |
| 514 | IARVILEYIDHKLRG | 20 |
| 516 | RVILEYIDHKLRGVQ | 20 |
| 542 | KCCLWCLEKFIKFLN | 20 |
| 545 | LWCLEKFIKFLNRNA | 20 |
| 549 | EKFIKFLNRNAYIMI | 20 |
| 558 | NAYIMIAIYGKNFCV | 20 |
| 582 | MRNIVRVWLDKVTD | 20 |
| 583 | RNIVRVVLDKVTDL | 20 |
| 586 | VRVVVLDKVTDLLLF | 20 |
| 588 | VVVLDKVTDLLLFFG | 20 |
| 594 | VTDLLLFFGKLLVVG | 20 |
| 595 | TDLLLFFGKLLVVGG | 20 |

TABLE XLVIII-continued

V1-DR1-0401-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 601 | FGKLLVVGGVGVLSF | 20 |
| 619 | SGRIPGLGKDFKSPH | 20 |
| 639 | LPIMTSILGAYVIAS | 20 |
| 642 | MTSILGAYVIASGFF | 20 |
| 660 | GMCVDTLFLCFLEDL | 20 |
| 668 | LCFLEDLERNNGSLD | 20 |
| 688 | SKSLLKILGKKNEAP | 20 |
| 90 | NIFSCILSSNIISVA | 18 |
| 125 | WTVGKNEFSQTVGEV | 18 |
| 152 | VPWNMTVITSLQQEL | 18 |
| 166 | LCPSFLLPSAPALGR | 18 |
| 195 | ITNDTTIQQGISGLI | 18 |
| 203 | QGISGLIDSLNARDI | 18 |
| 210 | DSLNARDISVKIFED | 18 |
| 289 | SISQLGFTTNLSAYQ | 18 |
| 295 | FFTNLSAYQSVQETW | 18 |
| 342 | KEASKAVGQMMSTMF | 18 |
| 373 | AMTALYLATSGQPQY | 18 |
| 398 | GCEKVPINTSCNPTA | 18 |
| 428 | GYSSKGLIQRSVFNL | 18 |
| 433 | GLIQRSVFNLQIYGV | 18 |
| 476 | FHKPQDIPTFPLISA | 18 |
| 481 | DIPTFPLISAFIRTL | 18 |
| 502 | LAFGALILTLVQIAR | 18 |
| 527 | RGVQNPVARCIMCCF | 18 |
| 568 | KNFCVSAKNAFMLLM | 18 |
| 611 | GVLSFFFFSGRIPGL | 18 |
| 623 | PGLGKDFKSPHLNYY | 18 |
| 657 | SVFGMCVDTLFLCFL | 18 |
| 669 | CFLEDLERNNGSLDR | 18 |
| 20 | DPSFRGPIKNRSCTD | 16 |
| 45 | ILGYIVVGIVAWLYG | 16 |
| 53 | IVAWLYGDPRQVLYP | 16 |
| 55 | AWLYGDPRQVLYPRN | 16 |
| 63 | QVLYPRNSTGAYCGM | 16 |

TABLE XLVIII-continued

V1-DR1-0401-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 144 | NRNFCLPGVPWNMTV | 16 |
| 151 | GVPWNMTVITSLQQE | 16 |
| 167 | CPSFLLPSAPALGRC | 16 |
| 222 | FEDFAQSWYWILVAL | 16 |
| 226 | AQSWYWILVALGVAL | 16 |
| 271 | YGIYYCWEEYRVLRD | 16 |
| 326 | MLIFLRQRIRIAIAL | 16 |
| 368 | CIAYWAMTALYLATS | 16 |
| 369 | IAYWAMTALYLATSG | 16 |
| 375 | TALYLATSGQPQYVL | 16 |
| 387 | YVLWASNISSPGCEK | 16 |
| 437 | RSVFNLQIYGVLGLF | 16 |
| 449 | GLFWTLNWVLALGQC | 16 |
| 466 | AGAFASFYWAFHKPQ | 16 |
| 470 | ASFYWAFHKPQDIPT | 16 |
| 471 | SFYWAFHKPQDIPTF | 16 |
| 473 | YWAFHKPQDIPTFPL | 16 |
| 482 | IPTFPLISAFIRTLR | 16 |
| 518 | ILEYIDHKLRGVQNP | 16 |
| 543 | CCLWCLEKFIKFLNR | 16 |
| 563 | IAIYGKNFCVSAKNA | 16 |
| 598 | LLFFGKLLVVGGVGV | 16 |
| 612 | VLSFFFFSGRIPGLG | 16 |
| 613 | LSFFFFSGRIPGLGK | 16 |
| 614 | SFFFFSGRIPGLGKD | 16 |
| 634 | LNYYWLPIMTSILGA | 16 |
| 653 | SGFFSVFGMCVDTLF | 16 |
| 664 | DTLFLGFLEDLERNN | 16 |
| 62 | RQVLYPRNSTGAYCG | 15 |
| 325 | LMLIFLRQRIRIAIA | 15 |
| 327 | LIFLRQRIRIAIALL | 15 |
| 519 | LEYIDHKLRGVQNPV | 15 |
| 587 | RVVVLDKVTDLLLFF | 15 |
| 32 | CTDVICCVLFLLFIL | 14 |
| 33 | TDVICCVLFLLFILG | 14 |

TABLE XLVIII-continued

V1-DR1-0401-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 36 | ICCVLFLLFILGYIV | 14 |
| 37 | CCVLFLLFILGYIVV | 14 |
| 42 | LLFILGYIVVGIVAW | 14 |
| 46 | LGYIVVGIVAWLYGD | 14 |
| 47 | GYIVVGIVAWLYGDP | 14 |
| 48 | YIVVGIVAWLYGDPR | 14 |
| 51 | VGIVAWLYGDPRQVL | 14 |
| 61 | PRQVLYPRNSTGAYC | 14 |
| 83 | KPYLLYFNIFSCILS | 14 |
| 84 | PYLLYFNIFSCILSS | 14 |
| 88 | YFNIFSCILSSNIIS | 14 |
| 92 | FSCILSSNIISVAEN | 14 |
| 93 | SCILSSNIISVAENG | 14 |
| 124 | PWTVGKNEFSQTVGE | 14 |
| 136 | VGEVFYTKNRNFCLP | 14 |
| 159 | ITSLQQELCPSFLLP | 14 |
| 163 | QQELCPSFLLPSAPA | 14 |
| 169 | SFLLPSAPALGRCFP | 14 |
| 175 | APALGRCFPWTNVTP | 14 |
| 184 | WTNVTPPALPGITND | 14 |
| 205 | ISGLIDSLNARDISV | 14 |
| 218 | SVKIFEDFAQSWYWI | 14 |
| 231 | WILVALGVALVLSLL | 14 |
| 237 | GVALVLSLLFILLLR | 14 |
| 244 | LLFILLLRLVAGPLV | 14 |
| 249 | LLRLVAGPLVLVLIL | 14 |
| 250 | LRLVAGPLVLVLILG | 14 |
| 256 | PLVLVLILGVLGVLA | 14 |
| 258 | VLVLILGVLGVLAYG | 14 |
| 260 | VLILGVLGVLAYGIY | 14 |
| 263 | LGVLGVLAYGIYYCW | 14 |
| 296 | TTNLSAYQSVQETWL | 14 |
| 302 | YQSVQETWLAALIVL | 14 |
| 322 | ILLLMLIFLRQRIRI | 14 |
| 338 | IALLKEASKAVGQMM | 14 |
| 345 | SKAVGQMMSTMFYPL | 14 |
| 348 | VGQMMSTMFYPLVTF | 14 |
| 349 | GQMMSTMFYPLVTFV | 14 |
| 352 | MSTMFYPLVTFVLLL | 14 |
| 357 | YPLVTFVLLLICIAY | 14 |
| 360 | VTFVLLLICIAYWAM | 14 |
| 361 | TFVLLLICIAYWAMT | 14 |
| 362 | FVLLLICIAYWAMTA | 14 |
| 366 | LICIAYWAMTALYLA | 14 |
| 376 | ALYLATSGQPQYVLW | 14 |
| 391 | ASNISSPGCEKVPIN | 14 |
| 399 | CEKVPINTSCNPTAH | 14 |
| 411 | TAHLVNSSCPGLMCV | 14 |
| 412 | AHLVNSSCPGLMCVF | 14 |
| 422 | LMCVFQGYSSKGLIQ | 14 |
| 432 | KGLIQRSVFNLQIYG | 14 |
| 439 | VFNLQIYGVLGLFWT | 14 |
| 441 | NLQIYGVLGLFWTLN | 14 |
| 455 | NWVLALGQCVLAGAF | 14 |
| 457 | VLALGQCVLAGAFAS | 14 |
| 462 | QCVLAGAFASFYWAF | 14 |
| 489 | SAFIRTLRYHTGSLA | 14 |
| 492 | IRTLRYHTGSLAFGA | 14 |
| 499 | TGSLAFGALILTLVQ | 14 |
| 504 | FGALILTLVQIARVI | 14 |
| 509 | LTLVQIARVILEYID | 14 |
| 515 | ARVILEYIDHKLRGV | 14 |
| 526 | LRGVQNPVARCIMCC | 14 |
| 534 | ARCIMCCFKCCLWCL | 14 |
| 535 | RCIMCCFKCCLWCLE | 14 |
| 552 | IKFLNRNAYIMIAIY | 14 |
| 559 | AYIMIAIYGKNFCVS | 14 |
| 576 | NAFMLLRNIVRVVV | 14 |
| 578 | FMLLMRNIVRVVVLD | 14 |
| 585 | IVRVVVLDKVTDLLL | 14 |

TABLE XLVIII-continued

V1-DR1-0401-15mers-24P4C12
Each peptide is a portion of
SEQ ID NO: 3; each start position
is specified, the length of peptide
is 15 amino acids, and the end
position for each peptide is the
start position plus fourteen.

| Pos | 123456789012345 | score |
|---|---|---|
| 591 | LDKVTDLLLFFGKLL | 14 |
| 596 | DLLLFFGKLLVVGGV | 14 |
| 602 | GKLLVVGGVGVLSFF | 14 |
| 603 | KLLVVGGVGVLSFFF | 14 |
| 604 | LLVVGGVGVLSFFFF | 14 |
| 607 | VGGVGVLSFFFFSGR | 14 |
| 609 | GVGVLSFFFFSGRIP | 14 |
| 610 | VGVLSFFFFSGRIPG | 14 |
| 622 | IPGLGKDFKSPHLNY | 14 |
| 631 | SPHLNYYWLPIMTSI | 14 |
| 636 | YYWLPIMTSILGAYV | 14 |
| 647 | GAYVIASGFFSVFGM | 14 |
| 655 | FFSVFGMCVDTLFLC | 14 |
| 658 | VFGMCVDTLFLCFLE | 14 |
| 663 | VDTLFLCFLEDLERN | 14 |
| 665 | TLFLCFLEDLERNNG | 14 |
| 678 | NGSLDRPYYMSKSLL | 14 |
| 684 | PYYMSKSLLKILGKK | 14 |
| 689 | KSLLKILGKKNEAPP | 14 |

TABLE XLVIII

V3-HLA-DR1-0401-15mers-24P4C12
Each peptide is a portion of
SEQ ID NO: 7; each start position
is specified, the length of peptide
is 15 amino acids, and the end
position for each peptide is the
start position plus fourteen.

| Pos | 123456789012345 | score |
|---|---|---|
| 9 | CFPWTNITPPALPGI | 22 |
| 3 | APALGRCFPWTNITP | 14 |
| 12 | WTNITPPALPGITND | 14 |
| 4 | PALGRCFPWTNITPP | 12 |
| 5 | ALGRCFPWTNITPPA | 12 |
| 8 | RCFPWTNITPPALPG | 12 |
| 13 | TNITPPALPGITNDT | 12 |
| 14 | NITPPALPGITNDTT | 12 |
| 7 | GRCFPWTNITPPALP | 10 |

TABLE XLVIII-continued

V3-HLA-DR1-0401-15mers-24P4C12
Each peptide is a portion of
SEQ ID NO: 7; each start position
is specified, the length of peptide
is 15 amino acids, and the end
position for each peptide is the
start position plus fourteen.

| Pos | 123456789012345 | score |
|---|---|---|

TABLE XLVIII

V5-DR1-0401-15mers-24P4C12
Each peptide is a portion of
SEQ ID NO: 11; each start position
is specified, the length of peptide
is 15 amino acids, and the end
position for each peptide is the
start position plus fourteen.

| Pos | 123456789012345 | score |
|---|---|---|
| 12 | LLLVLIFLRQRIRIA | 26 |
| 1 | ALIVLAVLEAILLLV | 20 |
| 2 | LIVLAVLEAILLLVL | 20 |
| 4 | VLAVLEAILLLVLIF | 20 |
| 5 | LAVLEAILLLVLIFL | 20 |
| 8 | LEAILLLVLIFLRQR | 20 |
| 10 | AILLLVLIFLRQRIR | 20 |
| 13 | LLVLIFLRQRIRIAI | 20 |
| 15 | VLIFLRQRIRIAIAL | 16 |
| 14 | LVLIFLRQRIRIAIA | 15 |
| 9 | EAILLLVLIFLRQRI | 14 |
| 11 | ILLLVLIFLRQRIRI | 14 |
| 3 | IVLAVLEAILLLVLI | 12 |
| 6 | AVLEAILLLVLIFLR | 12 |

TABLE XLVIII-V6

HLA-DR1-0401-15mers-24P4C12
Each peptide is a portion of
SEQ ID NO: 13; each start position
is specified, the length of peptide
is 15 amino acids, and the end
position for each peptide is the
start position plus fourteen.

| Pos | 123456789012345 | score |
|---|---|---|
| 2 | MCVFQGYSSKGLIPR | 22 |
| 15 | PRSVFNLQIYGVLGL | 20 |
| 12 | GLIPRSVFNLQIYGV | 18 |
| 1 | LMCVFQGYSSKGLIP | 14 |
| 11 | KGLIPRSVFNLQIYG | 14 |
| 7 | GYSSKGLIPRSVFNL | 12 |

TABLE XLVIII-V6-continued

HLA-DR1-0401-15mers-24P4C12
Each peptide is a portion of
SEQ ID NO: 13; each start position
is specified, the length of peptide
is 15 amino acids, and the end
position for each peptide is the
start position plus fourteen.

| Pos | 123456789012345 | score |
|---|---|---|
| 8 | YSSKGLIPRSVFNLQ | 12 |
| 9 | SSKGLIPRSVFNLQI | 12 |

TABLE XLVIII-V7

HLA-DR1-0401-15mers-24P4C12
Each peptide is a portion of
SEQ ID NO: 15; each start position
is specified, the length of peptide
is 15 amino acids, and the end
position for each peptide is the
start position plus fourteen.

| Pos | 123456789012345 | score |
|---|---|---|
| 9 | YWILVAVGQMMSTMF | 26 |
| 6 | QSWYWILVAVGQMMS | 22 |
| 7 | SWYWILVAVGQMMST | 22 |
| 8 | WYWILVAVGQMMSTM | 20 |
| 1 | FEDFAQSWYWILVAV | 16 |
| 5 | AQSWYWILVAVGQMM | 16 |
| 10 | WILVAVGQMMSTMFY | 14 |
| 12 | LVAVGQMMSTMFYPL | 14 |

TABLE XLVIII-V8

HLA-DR1-0401-15mers-24P4C12
Each peptide is a portion of
SEQ ID NO: 3; each start position
is specified, the length of peptide
is 17 amino acids, and the end
position for each peptide is the
start position plus fourteen.

| Pos | 123456789012345 | score |
|---|---|---|
| 7 | NYYWLPIMRNPITPT | 28 |
| 5 | HLNYYWLPIMRNPIT | 22 |
| 8 | YYWLPIMRNPITPTG | 20 |
| 15 | RNPITPTGHVFQTSI | 20 |
| 26 | QTSILGAYVIASGFF | 20 |
| 18 | ITPTGHVFQTSILGA | 18 |
| 19 | TPTGHVFQTSILGAY | 18 |
| 3 | SPHLNYYWLPIMRNP | 14 |
| 10 | WLPIMRNPITPTGHV | 14 |
| 11 | LPIMRNPITPTGHVF | 14 |
| 21 | TGHVFQTSILGAYVI | 14 |

TABLE XLVIII-V8-continued

HLA-DR1-0401-15mers-24P4C12
Each peptide is a portion of
SEQ ID NO: 3; each start position
is specified, the length of peptide
is 17 amino acids, and the end
position for each peptide is the
start position plus fourteen.

| Pos | 123456789012345 | score |
|---|---|---|

TABLE XLVIII-V9

HLA-DR1-0401-15mers-24P4C12
Each peptide is a portion of
SEQ ID NO: 19; each start position
is specified, the length of peptide
is 15 amino acids, and the end
position for each peptide is the
start position plus fourteen.

| Pos | 123456789012345 | score |
|---|---|---|
| 10 | MTALYPLPTQPATLG | 26 |
| 23 | LGYVLWASNISSPGC | 26 |
| 11 | TALYPLPTQPATLGY | 22 |
| 22 | TLGYVLWASNISSPG | 22 |
| 7 | YWAMTALYPLPTQPA | 20 |
| 20 | PATLGYVLWASNISS | 20 |
| 5 | IAYWAMTALYPLPTQ | 16 |
| 2 | LICIAYWAMTALYPL | 14 |
| 3 | ICIAYWAMTALYPLP | 12 |
| 15 | PLPTQPATLGYVLWA | 12 |
| 21 | ATLGYVLWASNISSP | 12 |

TABLE XLIX-V1

DRB1-1101-15mers-24P4C12
Each peptide is a portion of SEQ ID NO: 3;
each start position is specified, the length
of peptide is 15 amino acids, and the end
position for each peptide is the start
position plus fourteen.

| Pos | 123456789012345 | score |
|---|---|---|
| 243 | SLLFILLLRLVAGPL | 31 |
| 10 | DEAYGKPVKYDPSFR | 26 |
| 20 | DPSFRGPIKNRSCTD | 26 |
| 668 | LCFLEDLERNNGSLD | 26 |
| 575 | KNAFMLLMRNIVRVV | 25 |
| 613 | LSFFFFSGRIPGLGK | 25 |
| 226 | AQSWYWILVALGVAL | 23 |
| 228 | SWYWILVALGVALVL | 23 |
| 277 | WEEYRVLRDKGASIS | 23 |
| 359 | LVTFVLLLICIAYWA | 23 |

TABLE XLIX-V1-continued

DRB1-1101-15mers-24P4C12
Each peptide is a portion of SEQ ID NO: 3;
each start position is specified, the length
of peptide is 15 amino acids, and the end
position for each peptide is the start
position plus fourteen.

| Pos | 123456789012345 | score |
|---|---|---|
| 448 | LGLFWTLNWVLALGQ | 23 |
| 579 | MLLMRNIVRVVVLDK | 23 |
| 598 | LLFFGKLLVVGGVGV | 22 |
| 633 | HLNYYWLPIMTSILG | 22 |
| 276 | CWEEYRVLRDKGASI | 21 |
| 338 | IALLKEASKAVGQMM | 21 |
| 508 | ILTLVQIARVILEYI | 21 |
| 516 | RVILEYIDHKLRGVQ | 21 |
| 542 | KCCLWCLEKFIKFLN | 21 |
| 585 | IVRVVVLDKVTDLLL | 21 |
| 685 | YYMSKSLLKILGKKN | 21 |
| 172 | LPSAPALGRCFPWTN | 20 |
| 334 | IRIAIALLKEASKAV | 20 |
| 371 | YWAMTALYLATSGQP | 20 |
| 549 | EKFIKFLNRNAYIMI | 20 |
| 591 | LDKVTDLLLFFGKLL | 20 |
| 619 | SGRIPGLGKDFKSPH | 20 |
| 689 | KSLLKILGKKNEAPP | 20 |
| 36 | ICCVLFLLFILGYIV | 19 |
| 122 | EDPWTVGKNEFSQTV | 19 |
| 256 | PLVLVLILGVLGVLA | 19 |
| 259 | LVLILGVLGVLAYGI | 19 |
| 310 | LAALIVLAVLEAILL | 19 |
| 353 | STMFYPLVTFVLLLI | 19 |
| 523 | DHKLRGVQNPVARCI | 19 |
| 567 | GKNFCVSAKNAFMLL | 19 |
| 612 | VLSFFFFSGRIPGLG | 19 |
| 636 | YYWLPIMTSILGAYV | 19 |
| 16 | PVKYDPSFRGPIKNR | 18 |
| 48 | YIVVGIVAWLYGDPR | 18 |
| 85 | YLLYFNIFSCILSSN | 18 |
| 137 | GEVFYTKNRNFCLPG | 18 |
| 181 | CFPWTNVTPPALPGI | 18 |
| 227 | QSWYWILVALGVALV | 18 |
| 244 | LLFILLLRLVAGPLV | 18 |

TABLE XLIX-V1-continued

DRB1-1101-15mers-24P4C12
Each peptide is a portion of SEQ ID NO: 3;
each start position is specified, the length
of peptide is 15 amino acids, and the end
position for each peptide is the start
position plus fourteen.

| Pos | 123456789012345 | score |
|---|---|---|
| 326 | MLIFLRQRIRIAIAL | 18 |
| 419 | CPGLMCVFQGYSSKG | 18 |
| 469 | FASFYWAFHKPQDIP | 18 |
| 470 | ASFYWAFHKPQDIPT | 18 |
| 488 | ISAFIRTLRYHTGSL | 18 |
| 489 | SAFIRTLRYHTGSLA | 18 |
| 597 | LLLFFGKLLVVGGVG | 18 |
| 41 | FLLFILGYIVVGIVA | 17 |
| 45 | ILGYIVVGIVAWLYG | 17 |
| 71 | TGAYCGMGENKDKPY | 17 |
| 86 | LLYFNIFSCILSSNI | 17 |
| 306 | QETWLAALIVLAVLE | 17 |
| 325 | LMLIFLRQRIRIAIA | 17 |
| 354 | TMFYPLVTFVLLLIC | 17 |
| 369 | IAYWAMTALYLATSG | 17 |
| 384 | QPQYVLWASNISSPG | 17 |
| 442 | LQIYGVLGLFWTLNW | 17 |
| 482 | IPTFPLISAFIRTLR | 17 |
| 501 | SLAFGALILTLVQIA | 17 |
| 548 | LEKFIKFLNRNAYIM | 17 |
| 615 | FFFFSGRIPGLGKDF | 17 |
| 635 | NYYWLPIMTSILGAY | 17 |
| 652 | ASGFFSVFGMCVDTL | 17 |
| 82 | DKPYLLYFNIFSCIL | 16 |
| 89 | FNIFSCILSSNIISV | 16 |
| 179 | GRCFPWTNVTPPALP | 16 |
| 253 | VAGPLVLVLILGVLG | 16 |
| 299 | LSAYQSVQETWLAAL | 16 |
| 323 | LLLMLIFLRQRIRIA | 16 |
| 368 | CIAYWAMTALYLATS | 16 |
| 387 | YVLWASNISSPGCEK | 16 |
| 490 | AFIRTLRYHTGSLAF | 16 |
| 494 | TLRYHTGSLAFGALI | 16 |
| 506 | ALILTLVQIARVILE | 16 |
| 517 | VILEYIDHKLRGVQN | 16 |
| 557 | RNAYIMIAIYGKNFC | 16 |

TABLE XLIX-V1-continued

DRB1-1101-15mers-24P4C12
Each peptide is a portion of SEQ ID NO: 3;
each start position is specified, the length
of peptide is 15 amino acids, and the end
position for each peptide is the start
position plus fourteen.

| Pos | 123456789012345 | score |
|---|---|---|
| 563 | IAIYGKNFCVSAKNA | 16 |
| 583 | RNIVRVVVLDKVTDL | 16 |
| 646 | LGAYVIASGFFSVFG | 16 |
| 43 | LFILGYIVVGIVAWL | 15 |
| 44 | FILGYIVVGIVAWLY | 15 |
| 47 | GYIVVGIVAWLYGDP | 15 |
| 54 | VAWLYGDPRQVLYPR | 15 |
| 73 | AYCGMGENKDKPYLL | 15 |
| 153 | PWNMTVITSLQQELC | 15 |
| 156 | MTVITSLQQELCPSF | 15 |
| 195 | ITNDTTIQQGISGLI | 15 |
| 207 | GLIDSLNARDISVKI | 15 |
| 242 | LSLLFILLLRLVAGP | 15 |
| 357 | YPLVTFVLLLICIAY | 15 |
| 429 | YSSKGLIQRSVFNLQ | 15 |
| 485 | FPLISAFIRTLRYHT | 15 |
| 519 | LEYIDHKLRGVQNPV | 15 |
| 527 | RGVQNPVARCIMCCF | 15 |
| 545 | LWCLEKFIKFLNRNA | 15 |
| 595 | TDLLLFFGKLLVVGG | 15 |
| 600 | FFGKLLVVGGVGVLS | 15 |
| 603 | KLLVVGGVGVLSFFF | 15 |
| 681 | LDRPYYMSKSLLKIL | 15 |

TABLE XLIX

V3-HLA-DRB1-1101-15mers-24P4C12
Each peptide is a portion of
SEQ ID NO: 7; each start position
is specified, the length of peptide
is 15 amino acids, and the end
position for each peptide is the
start position plus fourteen.

| Pos | 123456789012345 | score |
|---|---|---|
| 9 | CFPWTNITPPALPGI | 18 |
| 7 | GRCFPWTNITPPALP | 16 |
| 12 | WTNITPPALPGITND | 8 |

TABLE XLIX-V5

HLA-DRB1-1101-15mers-24P4C12
Each peptide is a portion of
SEQ ID NO: 11; each start position
is specified, the length of peptide
is 15 amino acids, and the end
position for each peptide is the
start position plus fourteen.

| Pos | 123456789012345 | score |
|---|---|---|
| 15 | VLIFLRQRIRIAIAL | 18 |
| 14 | LVLIFLRQRIRIAIA | 17 |
| 12 | LLLVLIFLRQRIRIA | 16 |
| 10 | AILLLVLIFLRQRIR | 15 |
| 2 | LIVLAVLEAILLLVL | 14 |
| 8 | LEAILLLVLIFLRQR | 14 |
| 13 | LLVLIFLRQRIRIAI | 14 |
| 1 | ALIVLAVLEAILLLV | 13 |
| 5 | LAVLEAILLLVLIFL | 13 |
| 9 | EAILLLVLIFLRQRI | 13 |
| 11 | ILLLVLIFLRQRIRI | 13 |

TABLE XLIX-V6

HLA-DRB1-1101-15mers-24P4C12
Each peptide is a portion of
SEQ ID NO: 13; each start position
is specified, the length of peptide
is 15 amino acids, and the end
position for each peptide is the
start position plus fourteen.

| Pos | 123456789012345 | score |
|---|---|---|
| 8 | YSSKGLIPRSVFNLQ | 15 |
| 1 | LMCVFQGYSSKGLIP | 14 |
| 15 | PRSVFNLQIYGVLGL | 13 |
| 2 | MCVFQGYSSKGLIPR | 10 |
| 5 | FQGYSSKGLIPRSVF | 10 |
| 3 | CVFQGYSSKGLIPRS | 9 |
| 11 | KGLIPRSVFNLQIYG | 9 |
| 6 | QGYSSKGLIPRSVFN | 8 |
| 4 | VFQGYSSKGLIPRSV | 7 |
| 7 | GYSSKGLIPRSVFNL | 7 |

TABLE XLIX-V7

HLA-DRB1-1101-15mers-24P4C12
Each peptide is a portion of SEQ ID NO: 15; each start position is specified, the length of peptide is 15 amino acids, and the end position for each peptide is the start position plus fourteen.

| Pos | 123456789012345 | score |
|---|---|---|
| 5 | AQSWYWILVAVGQMM | 23 |
| 6 | QSWYWILVAVGQMMS | 18 |
| 9 | YWILVAVGQMMSTMF | 18 |
| 7 | SWYWILVAVGQMMST | 16 |
| 12 | LVAVGQMMSTMFYPL | 12 |
| 1 | FEDFAQSWYWILVAV | 11 |

TABLE XLIX-V8

HLA-DRB1-1101-15mers-24P4C12
Each peptide is a portion of SEQ ID NO: 17; each start position is specified, the length of peptide is 15 amino acids, and the end position for each peptide is the start position plus fourteen.

| Pos | 123456789012345 | score |
|---|---|---|
| 7 | NYYWLPIMRNPITPT | 24 |
| 5 | HLNYYWLPIMRNPIT | 18 |
| 6 | LNYYWLPIMRNPITP | 17 |
| 15 | RNPITPTGHVFQTSI | 16 |
| 8 | YYWLPIMRNPITPTG | 13 |
| 21 | TGHVFQTSILGAYVI | 13 |

TABLE XLIX-V9

HLA-DRB1-1101-15mers-24P4C12
Each peptide is a portion of SEQ ID NO: 19; each start position is specified, the length of peptide is 15 amino acids, and the end position for each peptide is the start position plus fourteen.

| Pos | 123456789012345 | score |
|---|---|---|
| 4 | CIAYWAMTALYPLPT | 22 |
| 10 | MTALYPLPTQPATLG | 18 |
| 22 | TLGYVLWASNISSPG | 17 |
| 7 | YWAMTALYPLPTQPA | 14 |
| 13 | LYPLPTQPATLGYVL | 13 |
| 20 | PATLGYVLWASNISS | 12 |
| 23 | LGYVLWASNISSPGC | 12 |
| 24 | GYVLWASNISSPGCE | 12 |
| 5 | IAYWAMTALYPLPTQ | 10 |
| 11 | TALYPLPTQPATLGY | 10 |

TABLE L

Properties of 24P4C12

| | Bioinformatic Program | URL | Outcome |
|---|---|---|---|
| ORF | ORF finder | | 6 to 2138 |
| Protein length | | | 710aa |
| Transmembrane region | TM Pred | located on the World Wide Wide at ch.embnet.org/ | 11TM, 39-59, 86-104, 231-250, 252-273, 309-330, 360-380, 457-474, 497-515, 559-581, 604-626, 641-663 |
| | HMMTop | located on the World Wide Wide at enzim.hu/hmmtop/ | 11TM, 35-59 84-104 231-250 257-277 308-330 355-377 456-475 500-519 550-572 597-618 649-671 |
| | Sosui | located on the World Wide Wide at genome.ad.jp/SOSui/ | 13TM, 34-65, 86-108, 145-167, 225-247, 307-329, 357-379, 414-436, 447-469, 501-523, 564-586, 600-622, 644-666 |
| | TMHMM | located on the World Wide Wide at cbs.dtu.dk/services/TMHMM | 10TM, 36-58, 228-250, 252-274, 308-330, 356-378, 454-476, 497-519, 559-581, 597-619 |
| Signal Peptide | Signal P | located on the World Wide Wide at cbs.dtu.dk/services/Signal P/ | no |

TABLE L-continued

Properties of 24P4C12

| | Bioinformatic Program | URL | Outcome |
|---|---|---|---|
| pI | pI/MW tool | located on the World Wide Wide at expasy.ch/tools/ | 8.9 pI |
| Molecular weight | pI/MW tool | located on the World Wide Wide at expasy.ch/tools/ | 79.3 kD |
| Localization | PSORT | located on the World Wide Wide at psort.nibb.ac.jp/ | 80% Plasma Membrane, 40% Golgi |
| | PSORT II | located on the World Wide Wide at psort.nibb.ac.jp/ | 65% Plasma Membrane, 38% endoplasmic reticulum |
| Motifs | Pfam | located on the World Wide Wide at sanger.ac.uk/Pfam/ | DUF580, unknown function |
| | Prints | located on the World Wide Wide at biochem.ucl.ac.uk/ | |
| | Blocks | located on the World Wide Wide at blocks.fhcrc.org/ | Anion exchanger family 313-359 |
| | Prosite | located on the World Wide Wide at prosite.org/ | CYS-RICH 536-547 |

TABLE LI

Exon compositions of 24P4C12 v.1

| Exon number | Start | End | Length |
|---|---|---|---|
| 1 | 1 | 45 | 45 |
| 2 | 46 | 94 | 49 |
| 3 | 95 | 168 | 74 |
| 4 | 169 | 247 | 79 |
| 5 | 248 | 347 | 100 |
| 6 | 348 | 473 | 126 |
| 7 | 474 | 534 | 61 |
| 8 | 535 | 622 | 88 |
| 9 | 623 | 706 | 84 |
| 10 | 707 | 942 | 236 |
| 11 | 943 | 1042 | 100 |
| 12 | 1043 | 1135 | 93 |
| 13 | 1136 | 1238 | 103 |
| 14 | 1239 | 1492 | 254 |
| 15 | 1493 | 1587 | 95 |
| 16 | 1588 | 1691 | 104 |
| 17 | 1692 | 1765 | 74 |
| 18 | 1766 | 1836 | 71 |
| 19 | 1837 | 1931 | 95 |
| 20 | 1932 | 2016 | 85 |
| 21 | 2017 | 2573 | 557 |

TABLE LII

Nucleotide sequence of transcript variant 24P4C12 v.7 (SEQ ID NO: 94)

```
gagccatggg gggaaagcag cgggacgagg atgacgaggc          60
ctacgggaag ccagtcaaat acgacccctc ctttcgaggc cccatcaaga acagaagctg         120
cacagatgtc atctgctgcg tcctcttcct gctcttcatt ctaggttaca tcgtggtggg         180
gattgtggcc tggttgtatg gagaccccg gcaagtcctc taccccagga actctactgg          240
ggcctactgt ggcatggggg agaacaaaga taagccgtat ctcctgtact tcaacatctt         300
cagctgcatc ctgtccagca acatcatctc agttgctgag aacggcctac agtgccccac         360
accccaggtg tgtgtgtcct cctgcccgga ggacccatgg actgtgggaa aaaacgagtt         420
```

TABLE LII-continued

Nucleotide sequence of transcript variant 24P4C12 v.7 (SEQ ID NO: 94)

```
ctcacagact gttggggaag tcttctatac aaaaaacagg aactttttgtc tgccaggggt         480
accctggaat atgacggtga tcacaagcct gcaacaggaa ctctgcccca gtttcctcct         540
cccctctgct ccagctctgg ggcgctgctt tccatggacc aacgttactc caccggcgct         600
cccagggatc accaatgaca ccaccataca gcagggatc agcggtctta ttgacagcct          660
caatgcccga gacatcagtg ttaagatctt tgaagatttt gcccagtcct ggtattggat         720
tcttgtggct gtgggacaga tgatgtctac catgttctac ccactggtca cctttgtcct         780
cctcctcatc tgcattgcct actgggccat gactgctctg tacctggcta catcggggca         840
accccagtat gtgctctggg catccaacat cagctccccc ggctgtgaga aagtgccaat         900
aaatacatca tgcaacccca cggcccacct tgtgaactcc tcgtgcccag ggctgatgtg         960
cgtcttccag ggctactcat ccaaaggcct aatccaacgt tctgtcttca atctgcaaat        1020
ctatgggtc ctggggctct tctggaccct taactgggta ctggccctgg gccaatgcgt        1080
cctcgctgga gcctttgcct ccttctactg ggccttccac aagcccagg acatccctac         1140
cttccccctta atctctgcct tcatccgcac actccgttac cacactgggt cattggcatt        1200
tggagccctc atcctgaccc ttgtgcagat agcccgggtc atcttggagt atattgacca        1260
caagctcaga ggagtgcaga accctgtagc ccgctgcatc atgtgctgtt tcaagtgctg        1320
cctctggtgt ctggaaaaat ttatcaagtt cctaaaccgc aatgcataca tcatgatcgc        1380
catctacggg aagaatttct
```

TABLE LII-continued

Nucleotide sequence of transcript variant 24P4C12 v.7 (SEQ ID NO: 94)

| | | | | |
|---|---|---|---|---|
| gtgtctcagc | caaaaatgcg | ttcatgctac | tcatgcgaaa | 1440 |
| cattgtcagg | gtggtcgtcc | | | |
| tggacaaagt | cacagacctg | ctgctgttct | ttgggaagct | 1500 |
| gctggtggtc | ggaggcgtgg | | | |
| gggtcctgtc | cttcttttt | ttctccggtc | gcatcccggg | 1560 |
| gctgggtaaa | gactttaaga | | | |
| gcccccacct | caactattac | tggctgccca | tcatgacctc | 1620 |
| catcctgggg | gcctatgtca | | | |
| tcgccagcgg | cttcttcagc | gttttcggca | tgtgtgtgga | 1680 |
| cacgctcttc | ctctgcttcc | | | |
| tggaagacct | ggagcggaac | aacggctccc | tggaccggcc | 1740 |
| ctactacatg | tccaagagcc | | | |
| ttctaaagat | tctgggcaag | aagaacgagg | cgcccccgga | 1800 |
| caacaagaag | aggaagaagt | | | |
| gacagctccg | gccctgatcc | aggactgcac | cccacccca | 1860 |
| ccgtccagcc | atccaacctc | | | |
| acttcgcctt | acaggtctcc | attttgtggt | aaaaaaaggt | 1920 |
| tttaggccag | gcgccgtggc | | | |
| tcacgcctgt | aatccaacac | tttgagaggc | tgaggcgggc | 1980 |
| ggatcacctg | agtcaggagt | | | |
| tcgagaccag | cctggccaac | atggtgaaac | ctccgtctct | 2040 |
| attaaaaata | caaaaattag | | | |
| ccgagagtgg | tggcatgcac | ctgtcatccc | agctactcgg | 2100 |
| gaggctgagg | caggagaatc | | | |
| gcttgaaccc | gggaggcaga | ggttgcagtg | agccgagatc | 2160 |
| gcgccactgc | actccaacct | | | |
| gggtgacaga | ctctgtctcc | aaaacaaaac | aaacaaacaa | 2220 |
| aaagatttta | tttgttaact | | | |
| tttgttaact | cagtaaaaaa | aaaaaaaaaa | a | 2251 |

TABLE LIII

Nucleotide sequence alignment of 24P4C12v.1 v.1 (SEQ ID NO: 95) and 24P4C12 v.7 (SEQ ID NO: 96).

Score = 1358 bits (706), Expect = 0.0 Identities = 706/706 (100%) Strand = Plus/Plus

```
24P4C12v.1:    1  gagccatggggggaaagcagcgggacgaggatgacgaggcctacgggaagccagtcaaat   60
                  ||||||||||||||||||||||||||||||||||||||||||||||||||||||||||||
24P4C12v.7:    1  gagccatggggggaaagcagcgggacgaggatgacgaggcctacgggaagccagtcaaat   60

24P4C12v.1:   61  acgacccctcctttcgaggccccatcaagaacagaagctgcacagatgtcatctgctgcg  120
                  ||||||||||||||||||||||||||||||||||||||||||||||||||||||||||||
24P4C12v.7:   61  acgacccctcctttcgaggccccatcaagaacagaagctgcacagatgtcatctgctgcg  120

24P4C12v.1:  121  tcctcttcctgctcttcattctaggttacatcgtggtggggattgtggcctggttgtatg  180
                  ||||||||||||||||||||||||||||||||||||||||||||||||||||||||||||
24P4C12v.7:  121  tcctcttcctgctcttcattctaggttacatcgtggtggggattgtggcctggttgtatg  180

24P4C12v.1:  181  gagaccccggcaagtcctctaccccaggaactctactggggcctactgtggcatggggg   240
                  ||||||||||||||||||||||||||||||||||||||||||||||||||||||||||||
24P4C12v.7:  181  gagaccccggcaagtcctctaccccaggaactctactggggcctactgtggcatggggg   240

24P4C12v.1:  241  agaacaaagataagccgtatctcctgtacttcaacatcttcagctgcatcctgtccagca  300
                  ||||||||||||||||||||||||||||||||||||||||||||||||||||||||||||
24P4C12v.7:  241  agaacaaagataagccgtatctcctgtacttcaacatcttcagctgcatcctgtccagca  300

24P4C12v.1:  301  acatcatctcagttgctgagaacggcctacagtgccccacaccccaggtgtgtgtgtcct  360
                  ||||||||||||||||||||||||||||||||||||||||||||||||||||||||||||
24P4C12v.7:  301  acatcatctcagttgctgagaacggcctacagtgccccacaccccaggtgtgtgtgtcct  360

24P4C12v.1:  361  cctgcccggaggacccatggactgtgggaaaaaacgagttctcacagactgttggggaag  420
                  ||||||||||||||||||||||||||||||||||||||||||||||||||||||||||||
24P4C12v.7:  361  cctgcccggaggacccatggactgtgggaaaaaacgagttctcacagactgttggggaag  420

24P4C12v.1:  421  tcttctatacaaaaaacaggaacttttgtctgccaggggtaccctggaatatgacggtga  480
                  ||||||||||||||||||||||||||||||||||||||||||||||||||||||||||||
24P4C12v.7:  421  tcttctatacaaaaaacaggaacttttgtctgccaggggtaccctggaatatgacggtga  480

24P4C12v.1:  481  tcacaagcctgcaacaggaactctgccccagtttcctcctcccctctgctccagctctgg  540
                  ||||||||||||||||||||||||||||||||||||||||||||||||||||||||||||
24P4C12v.7:  481  tcacaagcctgcaacaggaactctgccccagtttcctcctcccctctgctccagctctgg  540

24P4C12v.1:  541  ggcgctgctttcatggaccaacgttactccaccggcgctcccagggatcaccaatgaca  600
                  ||||||||||||||||||||||||||||||||||||||||||||||||||||||||||||
24P4C12v.7:  541  ggcgctgctttcatggaccaacgttactccaccggcgctcccagggatcaccaatgaca  600
```

TABLE LIII-continued

Nucleotide sequence alignment of 24P4C12v.1 v.1 (SEQ ID NO: 95) and
24P4C12 v.7 (SEQ ID NO: 96).

```
24P4C12v.1:   601  ccaccatacagcaggggatcagcggtcttattgacagcctcaatgcccgagacatcagtg  660
                   ||||||||||||||||||||||||||||||||||||||||||||||||||||||||||||
24P4C12v.7:   601  ccaccatacagcaggggatcagcggtcttattgacagcctcaatgcccgagacatcagtg  660

24P4C12v.1:   661  ttaagatctttgaagattttgcccagtcctggtattggattcttgt                706
                   ||||||||||||||||||||||||||||||||||||||||||||||
24P4C12v.7:   661  ttaagatctttgaagattttgcccagtcctggtattggattcttgt                706

Score = 2971 bits (1545), Expect = 0.0Identities = 1545/1545 (100%) Strand = Plus/Plus 24P4C12v.1:  1043  ggctgtgggacagatgatgtctaccatgttctacccactggtcacctttgtcctcctcct 1102
                   ||||||||||||||||||||||||||||||||||||||||||||||||||||||||||||
24P4C12v.7:   707  ggctgtgggacagatgatgtctaccatgttctacccactggtcacctttgtcctcctcct  766

24P4C12v.1:  1103  catctgcattgcctactgggccatgactgctctgtacctggctacatcggggcaacccca 1162
                   ||||||||||||||||||||||||||||||||||||||||||||||||||||||||||||
24P4C12v.7:   767  catctgcattgcctactgggccatgactgctctgtacctggctacatcggggcaacccca  826

24P4C12v.1:  1163  gtatgtgctctgggcatccaacatcagctccccggctgtgagaaagtgccaataaatac  1222
                   ||||||||||||||||||||||||||||||||||||||||||||||||||||||||||||
24P4C12v.7:   827  gtatgtgctctgggcatccaacatcagctccccggctgtgagaaagtgccaataaatac   886

24P4C12v.1:  1223  atcatgcaaccccacggcccaccttgtgaactcctcgtgcccagggctgatgtgcgtctt 1282
                   ||||||||||||||||||||||||||||||||||||||||||||||||||||||||||||
24P4C12v.7:   887  atcatgcaaccccacggcccaccttgtgaactcctcgtgcccagggctgatgtgcgtctt  946

24P4C12v.1:  1283  ccagggctactcatccaaaggcctaatccaacgttctgtcttcaatctgcaaatctatgg 1342
                   ||||||||||||||||||||||||||||||||||||||||||||||||||||||||||||
24P4C12v.7:   947  ccagggctactcatccaaaggcctaatccaacgttctgtcttcaatctgcaaatctatgg 1006

24P4C12v.1:  1343  ggtcctggggctcttctggacccttaactgggtactggccctgggccaatgcgtcctcgc 1402
                   ||||||||||||||||||||||||||||||||||||||||||||||||||||||||||||
24P4C12v.7:  1007  ggtcctggggctcttctggacccttaactgggtactggccctgggccaatgcgtcctcgc 1066

24P4C12v.1:  1403  tggagcctttgcctccttctactgggccttccacaagccccaggacatccctaccttccc 1462
                   ||||||||||||||||||||||||||||||||||||||||||||||||||||||||||||
24P4C12v.7:  1067  tggagcctttgcctccttctactgggccttccacaagccccaggacatccctaccttccc 1126

24P4C12v.1:  1463  cttaatctctgccttcatccgcacactccgttaccacactgggtcattggcatttggagc 1522
                   ||||||||||||||||||||||||||||||||||||||||||||||||||||||||||||
24P4C12v.7:  1127  cttaatctctgccttcatccgcacactccgttaccacactgggtcattggcatttggagc 1186

24P4C12v.1:  1523  cctcatcctgacccttgtgcagatagcccgggtcatcttggagtatattgaccacaagct 1582
                   ||||||||||||||||||||||||||||||||||||||||||||||||||||||||||||
24P4C12v.7:  1187  cctcatcctgacccttgtgcagatagcccgggtcatcttggagtatattgaccacaagct 124

24P4C12v.1:  1583  cagaggagtgcagaaccctgtagcccgctgcatcatgtgctgtttcaagtgctgcctctg 1642
                   ||||||||||||||||||||||||||||||||||||||||||||||||||||||||||||
24P4C12v.7:  1247  cagaggagtgcagaaccctgtagcccgctgcatcatgtgctgtttcaagtgctgcctctg 1306

24P4C12v.1:  1643  gtgtctggaaaaatttatcaagttcctaaaccgcaatgcatacatcatgatcgccatcta 1702
                   ||||||||||||||||||||||||||||||||||||||||||||||||||||||||||||
24P4C12v.7:  1307  gtgtctggaaaaatttatcaagttcctaaaccgcaatgcatacatcatgatcgccatcta 1366

24P4C12v.1:  1703  cgggaagaatttctgtgtctcagccaaaaatgcgttcatgctactcatgcgaaacattgt 1762
                   ||||||||||||||||||||||||||||||||||||||||||||||||||||||||||||
24P4C12v.7:  1367  cgggaagaatttctgtgtctcagccaaaaatgcgttcatgctactcatgcgaaacattgt 1426

24P4C12v.1:  1763  cagggtggtcgtcctggacaaagtcacagacctgctgctgttctttgggaagctgctggt 1822
                   ||||||||||||||||||||||||||||||||||||||||||||||||||||||||||||
24P4C12v.7:  1427  cagggtggtcgtcctggacaaagtcacagacctgctgctgttctttgggaagctgctggt 1486

24P4C12v.1:  1823  ggtcggaggcgtgggggtcctgtccttcttttttttctccggtcgcatcccggggctggg 1882
                   ||||||||||||||||||||||||||||||||||||||||||||||||||||||||||||
24P4C12v.7:  1487  ggtcggaggcgtgggggtcctgtccttcttttttttctccggtcgcatcccggggctggg 1546

24P4C12v.1:  1883  taaagactttaagagcccccacctcaactattactggctgccatcatgacctccatcct  1942
                   ||||||||||||||||||||||||||||||||||||||||||||||||||||||||||||
24P4C12v.7:  1547  taaagactttaagagcccccacctcaactattactggctgccatcatgacctccatcct  1606

24P4C12v.1:  1943  gggggcctatgtcatcgccagcggcttcttcagcgttttcggcatgtgtgtggacacgct 1002
                   ||||||||||||||||||||||||||||||||||||||||||||||||||||||||||||
24P4C12v.7:  1607  gggggcctatgtcatcgccagcggcttcttcagcgttttcggcatgtgtgtggacacgct 1666
```

TABLE LIII-continued

Nucleotide sequence alignment of 24P4C12v.1 v.1 (SEQ ID NO: 95) and 24P4C12 v.7 (SEQ ID NO: 96).

```
24P4C12v.1:  2003  cttcctctgcttcctggaagacctggagcggaacaacggctccctggaccggccctacta  2062
                   ||||||||||||||||||||||||||||||||||||||||||||||||||||||||||||
24P4C12v.7:  1667  cttcctctgcttcctggaagacctggagcggaacaacggctccctggaccggccctacta  1726

24P4C12v.1:  2063  catgtccaagagccttctaaagattctgggcaagaagaacgaggcgccccggacaacaa   2122
                   ||||||||||||||||||||||||||||||||||||||||||||||||||||||||||||
24P4C12v.7:  1727  catgtccaagagccttctaaagattctgggcaagaagaacgaggcgccccggacaacaa   1786

24P4C12v.1:  2123  gaagaggaagaagtgacagctccggccctgatccaggactgcaccccaccccaccgtcc   2182
                   ||||||||||||||||||||||||||||||||||||||||||||||||||||||||||||
24P4C12v.7:  1787  gaagaggaagaagtgacagctccggccctgatccaggactgcaccccaccccaccgtcc   1846

24P4C12v.1:  2183  agccatccaacctcacttcgccttacaggtctccattttgtggtaaaaaaaggttttagg  2242
                   ||||||||||||||||||||||||||||||||||||||||||||||||||||||||||||
24P4C12v.7:  1847  agccatccaacctcacttcgccttacaggtctccattttgtggtaaaaaaaggttttagg  1906

24P4C12v.1:  2243  ccaggcgccgtggctcacgcctgtaatccaacactttgagaggctgaggcgggcggatca  2302
                   ||||||||||||||||||||||||||||||||||||||||||||||||||||||||||||
24P4C12v.7:  1907  ccaggcgccgtggctcacgcctgtaatccaacactttgagaggctgaggcgggcggatca  1966

24P4C12v.1:  2303  cctgagtcaggagttcgagaccagcctggccaacatggtgaaaccctcgtctctattaaa  2362
                   ||||||||||||||||||||||||||||||||||||||||||||||||||||||||||||
24P4C12v.7:  1967  cctgagtcaggagttcgagaccagcctggccaacatggtgaaaccctcgtctctattaaa  2026

24P4C12v.1:  2363  aatacaaaaattagccgagagtggtggcatgcacctgtcatcccagctactcgggaggct  2422
                   ||||||||||||||||||||||||||||||||||||||||||||||||||||||||||||
24P4C12v.7:  2027  aatacaaaaattagccgagagtggtggcatgcacctgtcatcccagctactcgggaggct  2086

24P4C12v.1:  2423  gaggcaggagaatcgcttgaacccgggaggcagaggttgcagtgagccgagatcgcgcca  2482
                   ||||||||||||||||||||||||||||||||||||||||||||||||||||||||||||
24P4C12v.7:  2087  gaggcaggagaatcgcttgaacccgggaggcagaggttgcagtgagccgagatcgcgcca  2146

24P4C12v.1:  2483  ctgcactccaacctgggtgacagactctgtctccaaaacaaaacaaacaaacaaaaagat  2542
                   ||||||||||||||||||||||||||||||||||||||||||||||||||||||||||||
24P4C12v.7:  2147  ctgcactccaacctgggtgacagactctgtctccaaaacaaaacaaacaaacaaaaagat  2206

24P4C12v.1:  2543  tttattaaagatattttgttaactcagtaaaaaaaaaaaaaaaaa                2587
                   |||||||||||||||||||||||||||||||||||||||||||||
24P4C12v.7:  2207  tttattaaagatattttgttaactcagtaaaaaaaaaaaaaaaaa                2251
```

TABLE LIV

Peptide sequences of protein coded by 24P4C12 v.7 (SEQ ID NO: 97)

| | | | | |
|---|---|---|---|---|
| MGGKQRDEDD | EAYGKPVKYD | PSFRGPIKNR | SCTDVICCVL | 60 |
| FLLFILGYIV | VGIVAWLYGD | | | |
| PRQVLYPRNS | TGAYCGMGEN | KDKPYLLYFN | IFSCILSSNI | 120 |
| ISVAENGLQC | PTPQVCVSSC | | | |
| PEDPWTVGKN | EFSQTVGEVF | YTKNRNFCLP | GVPWNMTVIT | 180 |
| SLQQELCPSF | LLPSAPALGR | | | |
| CFPWTNVTPP | ALPGITNDTT | IQQGISGLID | SLNARDISVK | 240 |
| IFEDFAQSWY | WILVAVGQMM | | | |
| STMFYPLVTF | VLLLICIAYW | AMTALYLATS | GQPQYVLWAS | 300 |
| NISSPGCEKV | PINTSCNPTA | | | |
| HLVNSSCPGL | MCVFQGYSSK | GLIQRSVFNL | QIYGVLGLFW | 360 |
| TLNWVLALGQ | CVLAGAFASF | | | |
| YWAFHKPQDI | PTFPLISAFI | RTLRYHTGSL | AFGALILTLV | 420 |
| QIARVILEYI | DHKLRGVQNP | | | |
| VARCIMCCFK | CCLWCLEKFI | KFLNRNAYIM | IAIYGKNFCV | 480 |
| SAKNAFMLLM | RNIVRVVVLD | | | |
| KVTDLLLFFG | KLLVVGGVGV | LSFFFFSGRI | PGLGKDFKSP | 540 |
| HLNYYWLPIM | TSILGAYVIA | | | |
| SGFFSVFGMC | VDTLFLCFLE | DLERNNQSLD | RPYYMSKSLL | 598 |
| KILGKKNEAP | PDNKKRKK | | | |

TABLE LV

Amnino acid sequence alignment of 24P4C12v.1 v.1 (SEQ ID NO: 98) and 24P4C12 v.7 (SEQ ID NO: 99).

```
Score = 1195 bits (3091), Expect = 0.0 Identities = 598/710 (84%),
Positives = 598/710 (84%), Gaps = 112/710 (15%)
24P4C12v.1:  1 MGGKQRDEDDEAYGKPVKYDPSFRGPIKNRSCTDVICCVLFLLFILGYIVVGIVAWLYGD   60
               MGGKQRDEDDEAYGKPVKYDPSFRGPIKNRSCTDVICCVLFLLFILGYIVVGIVAWLYGD
```

TABLE LV-continued

Amnino acid sequence alignment of 24P4C12v.1 v.1 (SEQ ID NO: 98)
and 24P4C12 v.7 (SEQ ID NO: 99).

```
24P4C12v.7:   1MGGKQRDEDDEAYGKPVKYDPSFRGPIKNRSCTDVICCVLFLLFILGYIVVGIVAWLYGD   60

24P4C12v.1:  61PRQVLYPRNSTGAYCGMGENKDKPYLLYFNIFSCILSSNIISVAENGLQCPTPQVCVSSC  120
              PRQVLYPRNSTGAYCGMGENKDKPYLLYFNIFSCILSSNIISVAENGLQCPTPQVCVSSC
24P4C12v.7:  61PRQVLYPRNSTGAYCGMGENKDKPYLLYFNIFSCILSSNIISVAENGLQCPTPQVCVSSC  120

24P4C12v.1: 121PEDPWTVGKNEFSQTVGEVFYTKNRNFCLPGVPWNMTVITSLQQELCPSFLLPSAPALGR  180
              PEDPWTVGKNEFSQTVGEVFYTKNRNFCLPGVPWNMTVITSLQQELCPSFLLPSAPALGR
24P4C12v.7: 121PEDPWTVGKNEFSQTVGEVFYTKNRNFCLPGVPWNMTVITSLQQELCPSFLLPSAPALGR  180

24P4C12v.1: 181CFPWTNVTPPALPGITNDTTIQQGISGLIDSLNARDISVKIFEDFAQSWYWILVALGVAL  240
              CFPWTNVTPPALPGITNDTTIQQGISGLIDSLNARDISVKIFEDFAQSWYWILVA
24P4C12v.7: 181CFPWTNVTPPALPGITNDTTIQQGISGLIDSLNARDISVKIFEDFAQSWYWILVA-----  235

24P4C12v.1: 241VLSLLFILLLRLVAGPLVLVLILGVLGVLAYGIYYCWEEYRVLRDKGASISQLGFTTNLS  300
24P4C12v.7: 235------------------------------------------------------------  235

24P4C12v.1: 301AYQSVQETWLAALIVLAVLEAILLLMLIFLRQRIRIAIALLKEASKAVGQMMSTMFYPLV  360
                                                            VGQMMSTMFYPLV
24P4C12v.7: 236-----------------------------------------------VGQMMSTMFYPLV  248

24P4C12v.1: 361TFVLLLICIAYWAMTALYLATSGQPQYVLWASNISSPGCEKVPINTSCNPTAHLVNSSCP  420
              TFVLLLICIAYWAMTALYLA SGQPQYVLWASNISSPGCEKVPINTSCNPTAHLVNSSCP
24P4C12v.7: 249TFVLLLICIAYWAMTALYLAPSGQPQYVLWASNISSPGCEKVPINTSCNPTAHLVNSSCP  308

24P4C12v.1: 421GLMCVFQGYSSKGLIQRSVFNLQIYGVLGLFWTLNWVLALGQCVLAGAFASFYWAFHKPQ  480
              GLMCVFQGYSSKGLIQRSVFNLQIYGVLGLFWTLNWVLALGQCVLAGAFASFYWAFHKPQ
24P4C12v.7: 309GLMCVFQGYSSKGLIQRSVFNLQIYGVLGLFWTLNWVLALGQCVLAGAFASFYWAFHKPQ  368

24P4C12v.1: 481DIPTFPLISAFIRTLRYHTGSLAFGALILTLVQIARVILEYIDHKLRGVQNPVARCIMCC  540
              DIPTFPLISAFIRTLRYHTGSLAFGALILTLVQIARVILEYIDHKLRGVQNPVARCIMCC
24P4C12v.7: 369DIPTFPLISAFIRTLRYHTGSLAFGALILTLVQIARVILEYIDHKLRGVQNPVARCIMCC  428

24P4C12v.1: 541FKCCLWCLEKFIKFLNRNAYIMIAIYGKNFCVSAKNAFMLLMRNIVRVVVLDKVTDLLLF  600
              FKCCLWCLEKFIKFLNRNAYIMIAIYGKNFCVSAKNAFMLLMRNIVRVVVLDKVTDLLLF
24P4C12v.7: 429FKCCLWCLEKFIKFLNRNAYIMIAIYGKNFCVSAKNAFMLLMRNIVRVVVLDKVTDLLLF  488

24P4C12v.1: 601FGKLLVVGGVGVLSFFFFSGRIPGLGKDFKSPHLNYYWLPIMTSILGAYVIASGFFSVFG  660
              FGKLLVVGGVGVLSFFFFSGRIPGLGKDFKSPHLNYYWLPIMTSILGAYVIASGFFSVFG
24P4C12v.7: 489FGKLLVVGGVGVLSFFFFSGRIPGLGKDFKSPHLNYYWLPIMTSILGAYVIASGFFSVFG  548

24P4C12v.1: 661MCVDTLFLCFLEDLERNNGSLDRPYYMSKSLLKILGKKNEAPPDNKKRKK           710
              MCVDTLFLC LEDLERNNGSLDRPYYMSKSLLKILGKKNEAPPDNKKRKK
24P4C12v.7: 549MCVDTLFLCELEDLERNNGSLDRPYYMSKSLLKILGKKNEAPPDNKKRKK           598
```

TABLE LVI

Nucleotide sequence of transcript variant
24P4C12 v.8 (SEQ ID NO: 100)

```
gagccatggg gggaaagcag cgggacgagg atgacgaggc    60
ctacgggaag ccagtcaaat
acgacccctc ctttcgaggc cccatcaaga acagaagctg   120
cacagatgtc atctgctgcg
tcctcttcct gctcttcatt ctaggttaca tcgtggtggg   180
gattgtggcc tggttgtatg
gagaccccg gcaagtcctc taccccagga actctactgg    240
ggcctactgt ggcatggggg
agaacaaaga taagccgtat ctcctgtact tcaacatctt   300
cagctgcatc ctgtccagca
acatcatctc agttgctgag aacggcctac agtgccccac   360
accccaggtg tgtgtgtcct
cctgccccga ggacccatgg actgtgggaa aaaacgagtt   420
ctcacagact gttggggaag
tcttctatac aaaaaacagg aacttttgtc tgccaggggt   480
accctggaat atgacggtga
```

TABLE LVI-continued

Nucleotide sequence of transcript variant
24P4C12 v.8 (SEQ ID NO: 100)

```
tcacaagcct gcaacaggaa ctctgcccca gtttcctcct   540
cccctctgct ccagctctgg
ggcgctgctt tccatggacc aacgttactc caccggcgct   600
cccaggatc accaatgaca
ccaccataca gcaggggatc agcggtctta ttgacagcct   660
caatgcccga gacatcagtg
ttaagatctt tgaagatttt gcccagtcct ggtattggat   720
tcttgttgcc ctgggggtgg
ctctggtctt gagcctactg tttatcttgc ttctgcgcct   780
ggtggctggg ccctggtgc
tggtgctgat cctgggagtg ctgggcgtgc tggcatacgg   840
catctactac tgctgggagg
agtaccgagt gctgcgggac aagggcgcct ccatctccca   900
gctgggtttc accaccaacc
tcagtgccta ccagagcgtg caggagacct ggctggccgc   960
```

TABLE LVI-continued

Nucleotide sequence of transcript variant
24P4C12 v.8 (SEQ ID NO: 100)

| | |
|---|---|
| cctgatcgtg ttggcggtgc | |
| ttgaagccat cctgctgctg atgctcatct tcctgcggca gcggattcgt attgccatcg | 1020 |
| ccctcctgaa ggaggccagc aaggctgtgg acagatgat gtctaccatg ttctacccac | 1080 |
| tggtcacctt tgtcctcctc ctcatctgca ttgcctactg ggccatgact gctctgtacc | 1140 |
| tggctacatc ggggcaaccc cagtatgtgc tctgggcatc caacatcagc tcccccggct | 1200 |
| gtgagaaagt gccaataaat acatcatgca accccacggc ccaccttgtg aactcctcgt | 1260 |
| gcccagggct gatgtgcgtc ttccagggct actcatccaa aggcctaatc caacgttctg | 1320 |
| tcttcaatct gcaaatctat ggggtcctgg ggctcttctg gacccttaac tgggtactgg | 1380 |
| ccctgggcca atgcgtcctc gctggagcct ttgcctcctt ctactgggcc ttccacaagc | 1440 |
| cccaggacat ccctaccttc cccttaatct ctgccttcat ccgcacactc cgttaccaca | 1500 |
| ctgggtcatt ggcatttgga gccctcatcc tgacccttgt gcagatagcc cgggtcatct | 1560 |
| tggagtatat tgaccacaag ctcagaggag tgcagaaccc tgtagcccgc tgcatcatgt | 1620 |
| gctgtttcaa gtgctgcctc tggtgtctgg aaaaatttat caagttccta aaccgcaatg | 1680 |
| catacatcat gatcgccatc tacgggaaga atttctgtgt ctcagccaaa aatgcgttca | 1740 |
| tgctactcat gcgaaacatt gtcagggtgg tcgtcctgga caaagtcaca gacctgctgc | 1800 |

TABLE LVI-continued

Nucleotide sequence of transcript variant
24P4C12 v.8 (SEQ ID NO: 100)

| | |
|---|---|
| tgttctttgg gaagctgctg gtggtcggag cgtgggggt cctgtccttc ttttttttct | 1860 |
| ccggtcgcat cccggggctg ggtaaagact ttaagagccc ccacctcaac tattactggc | 1920 |
| tgcccatcat gaggaaccca ataaccccaa cgggtcatgt cttccagacc tccatcctgg | 1980 |
| gggcctatgt catcgccagc ggcttcttca gcgttttcgg catgtgtgtg gacacgctct | 2040 |
| tcctctgctt cctggaagac ctggagcgga caacggctc cctggaccgg ccctactaca | 2100 |
| tgtccaagag ccttctaaag attctgggca agaagaacga ggcgccccg gacaacaaga | 2160 |
| agaggaagaa gtgacagctc cggccctgat ccaggactgc accccacccc caccgtccag | 2220 |
| ccatccaacc tcacttcgcc ttacaggtct ccattttgtg gtaaaaaaag gttttaggcc | 2280 |
| aggcgccgtg gctcacgcct gtaatccaac actttgagag gctgaggcgg gcggatcacc | 2340 |
| tgagtcagga gttcgagacc agcctggcca acatggtgaa acctccgtct ctattaaaaa | 2400 |
| tacaaaaatt agccgagagt ggtggcatgc acctgtcatc ccagctactc gggaggctga | 2460 |
| ggcaggagaa tcgcttgaac ccgggaggca gaggttgcag tgagccgaga tcgcgccact | 2520 |
| gcactccaac ctgggtgaca gactctgtct ccaaaacaaa acaaacaaac aaaaagattt | 2580 |
| tattaaagat attttgttaa ctcagtaaaa aaaaaaaaa aaa | 2623 |

TABLE LVII

Nucleotide sequence alignment of 24P4C12v.1 v.1 (SEQ ID NO: 101) and
24P4C12 v.8 (SEQ ID NO: 102)

Score = 3715 bits (1932) , Expect = 0.0Identities = 1932/1932 (100%) Strand = Plus/Plus

```
24P4C12v.1:    1 gagccatggggggaaagcagcgggacgaggatgacgaggcctacgggaagccagtcaaat   60
                 ||||||||||||||||||||||||||||||||||||||||||||||||||||||||||||
24P4C12v.8:    1 gagccatggggggaaagcagcgggacgaggatgacgaggcctacgggaagccagtcaaat   60

24P4C12v.1:   61 acgacccctcctttcgaggccccatcaagaacagaagctgcacagatgtcatctgctgcg  120
                 ||||||||||||||||||||||||||||||||||||||||||||||||||||||||||||
24P4C12v.8:   61 acgacccctcctttcgaggccccatcaagaacagaagctgcacagatgtcatctgctgcg  120

24P4C12v.1:  121 tcctcttcctgctcttcattctaggttacatcgtggtggggattgtggcctggttgtatg  180
                 ||||||||||||||||||||||||||||||||||||||||||||||||||||||||||||
24P4C12v.8:  121 tcctcttcctgctcttcattctaggttacatcgtggtggggattgtggcctggttgtatg  180

24P4C12v.1:  181 gagaccccggcaagtcctctaccccaggaactctactggggcctactgtggcatggggg  240
                 ||||||||||||||||||||||||||||||||||||||||||||||||||||||||||||
24P4C12v.8:  181 gagaccccggcaagtcctctaccccaggaactctactggggcctactgtggcatggggg  240

24P4C12v.1:  241 agaacaaagataagccgtatctcctgtacttcaacatcttcagctgcatcctgtccagca  300
                 ||||||||||||||||||||||||||||||||||||||||||||||||||||||||||||
24P4C12v.8:  241 agaacaaagataagccgtatctcctgtacttcaacatcttcagctgcatcctgtccagca  300

24P4C12v.1:  301 acatcatctcagttgctgagaacgcctacagtgccccacaccccaggtgtgtgtgtcct  360
                 ||||||||||||||||||||||||||||||||||||||||||||||||||||||||||||
24P4C12v.8:  301 acatcatctcagttgctgagaacggcctacagtgccccacaccccaggtgtgtgtgtcct  360
```

TABLE LVII-continued

Nucleotide sequence alignment of 24P4C12v.1 v.1 (SEQ ID NO: 101) and
24P4C12 v.8 (SEQ ID NO: 102)

```
24P4C12v.1:  361  cctgcccggaggacccatggactgtgggaaaaaacgagttctcacagactgttggggaag  420
                  ||||||||||||||||||||||||||||||||||||||||||||||||||||||||||||
24P4C12v.8:  361  cctgcccggaggacccatggactgtgggaaaaaacgagttctcacagactgttggggaag  420

24P4C12v.1:  421  tcttctatacaaaaaacaggaacttttgtctgccaggggtaccctggaatatgacggtga  480
                  ||||||||||||||||||||||||||||||||||||||||||||||||||||||||||||
24P4C12v.8:  421  tcttctatacaaaaaacaggaacttttgtctgccaggggtaccctggaatatgacggtga  480

24P4C12v.1:  481  tcacaagcctgcaacaggaactctgccccagtttcctcctccctctgctccagctctgg  540
                  ||||||||||||||||||||||||||||||||||||||||||||||||||||||||||||
24P4C12v.8:  481  tcacaagcctgcaacaggaactctgccccagtttcctcctccctctgctccagctctgg  540

24P4C12v.1:  541  ggcgctgctttccatggaccaacgttactccaccggcgctcccagggatcaccaatgaca  600
                  ||||||||||||||||||||||||||||||||||||||||||||||||||||||||||||
24P4C12v.8:  541  ggcgctgctttccatggaccaacgttactccaccggcgctcccagggatcaccaatgaca  600

24P4C12v.1:  601  ccaccatacagcaggggatcagcggtcttattgacagcctcaatgcccgagacatcagtg  660
                  ||||||||||||||||||||||||||||||||||||||||||||||||||||||||||||
24P4C12v.8:  601  ccaccatacagcaggggatcagcggtcttattgacagcctcaatgcccgagacatcagtg  660

24P4C12v.1:  661  ttaagatctttgaagattttgcccagtcctggtattggattcttgttgccctggggtgg  720
                  ||||||||||||||||||||||||||||||||||||||||||||||||||||||||||||
24P4C12v.8:  661  ttaagatctttgaagattttgcccagtcctggtattggattcttgttgccctggggtgg  720

24P4C12v.1:  721  ctctggtcttgagcctactgtttatcttgcttctgcgcctggtggctgggcccctggtgc  780
                  ||||||||||||||||||||||||||||||||||||||||||||||||||||||||||||
24P4C12v.8:  721  ctctggtcttgagcctactgtttatcttgcttctgcgcctggtggctgggcccctggtgc  780

24P4C12v.1:  781  tggtgctgatcctgggagtgctgggcgtgctggcatacggcatctactactgctgggagg  840
                  ||||||||||||||||||||||||||||||||||||||||||||||||||||||||||||
24P4C12v.8:  781  tggtgctgatcctgggagtgctgggcgtgctggcatacggcatctactactgctgggagg  840

24P4C12v.1:  841  agtaccgagtgctgcgggacaagggcgcctccatctcccagctgggtttcaccaccaacc  900
                  ||||||||||||||||||||||||||||||||||||||||||||||||||||||||||||
24P4C12v.8:  841  agtaccgagtgctgcgggacaagggcgcctccatctcccagctgggtttcaccaccaacc  900

24P4C12v.1:  901  tcagtgcctaccagagcgtgcaggagacctggctggccgccctgatcgtgttggcggtgc  960
                  ||||||||||||||||||||||||||||||||||||||||||||||||||||||||||||
24P4C12v.8:  901  tcagtgcctaccagagcgtgcaggagacctggctggccgccctgatcgtgttggcggtgc  960

24P4C12v.1:  961  ttgaagccatcctgctgctgatgctcatcttcctgcggcagcggattcgtattgccatcg  1020
                  ||||||||||||||||||||||||||||||||||||||||||||||||||||||||||||
24P4C12v.8:  961  ttgaagccatcctgctgctgatgctcatcttcctgcggcagcggattcgtattgccatcg  1020

24P4C12v.1: 1021  ccctcctgaaggaggccagcaaggctgtgggacagatgatgtctaccatgttctacccac  1080
                  ||||||||||||||||||||||||||||||||||||||||||||||||||||||||||||
24P4C12v.8: 1021  ccctcctgaaggaggccagcaaggctgtgggacagatgatgtctaccatgttctacccac  1080

24P4C12v.1: 1081  tggtcacctttgtcctcctcctcatctgcattgcctactgggccatgactgctctgtacc  1140
                  ||||||||||||||||||||||||||||||||||||||||||||||||||||||||||||
24P4C12v.8: 1081  tggtcacctttgtcctcctcctcatctgcattgcctactgggccatgactgctctgtacc  1140

24P4C12v.1: 1141  tggctacatcggggcaaccccagtatgtgctctgggcatccaacatcagctcccccggct  1200
                  ||||||||||||||||||||||||||||||||||||||||||||||||||||||||||||
24P4C12v.8: 1141  tggctacatcggggcaaccccagtatgtgctctgggcatccaacatcagctcccccggct  1200

24P4C12v.1: 1201  gtgagaaagtgccaataaatacatcatgcaaccccacggcccaccttgtgaactcctcgt  1260
                  ||||||||||||||||||||||||||||||||||||||||||||||||||||||||||||
24P4C12v.8: 1201  gtgagaaagtgccaataaatacatcatgcaaccccacggcccaccttgtgaactcctcgt  1260

24P4C12v.1: 1321  tcttcaatctgcaaatctatggggtcctggggctcttctggacccttaactgggtactgg  1380
                  ||||||||||||||||||||||||||||||||||||||||||||||||||||||||||||
24P4C12v.8: 1321  tcttcaatctgcaaatctatggggtcctggggctcttctggacccttaactgggtactgg  1380

24P4C12v.1: 1261  gcccagggctgatgtgcgtcttccagggctactcatccaaaggcctaatccaacgttctg  1320
                  ||||||||||||||||||||||||||||||||||||||||||||||||||||||||||||
24P4C12v.8: 1261  gcccagggctgatgtgcgtcttccagggctactcatccaaaggcctaatccaacgttctg  1320

24P4C12v.1: 1381  ccctgggccaatgcgtcctcgctggagcctttgcctccttctactgggccttccacaagc  1440
                  ||||||||||||||||||||||||||||||||||||||||||||||||||||||||||||
24P4C12v.8: 1381  ccctgggccaatgcgtcctcgctggagcctttgcctccttctactgggccttccacaagc  1440
```

TABLE LVII-continued

Nucleotide sequence alignment of 24P4C12v.1 v.1 (SEQ ID NO: 101) and
24P4C12 v.8 (SEQ ID NO: 102)

```
24P4C12v.1:  1441  cccaggacatccctaccttccccttaatctctgccttcatccgcacactccgttaccaca  1500
                   ||||||||||||||||||||||||||||||||||||||||||||||||||||||||||||
24P4C12v.8:  1441  cccaggacatccctaccttccccttaatctctgccttcatccgcacactccgttaccaca  1500

24P4C12v.1:  1501  ctgggtcattggcatttggagccctcatcctgacccttgtgcagatagcccgggtcatct  1560
                   ||||||||||||||||||||||||||||||||||||||||||||||||||||||||||||
24P4C12v.8:  1501  ctgggtcattggcatttggagccctcatcctgacccttgtgcagatagcccgggtcatct  1560

24P4C12v.1:  1561  tggagtatattgaccacaagctcagaggagtgcagaaccctgtagcccgctgcatcatgt  1620
                   ||||||||||||||||||||||||||||||||||||||||||||||||||||||||||||
24P4C12v.8:  1561  tggagtatattgaccacaagctcagaggagtgcagaaccctgtagcccgctgcatcatgt  1620

24P4C12v.1:  1621  gctgtttcaagtgctgcctctggtgtctggaaaaatttatcaagttcctaaaccgcaatg  1680
                   ||||||||||||||||||||||||||||||||||||||||||||||||||||||||||||
24P4C12v.8:  1621  gctgtttcaagtgctgcctctggtgtctggaaaaatttatcaagttcctaaaccgcaatg  1680

24P4C12v.1:  1681  catacatcatgatcgccatctacgggaagaatttctgtgtctcagccaaaaatgcgttca  1740
                   ||||||||||||||||||||||||||||||||||||||||||||||||||||||||||||
24P4C12v.8:  1681  catacatcatgatcgccatctacgggaagaatttctgtgtctcagccaaaaatgcgttca  1740

24P4C12v.1:  1741  tgctactcatgcgaaacattgtcagggtggtcgtcctggacaaagtcacagacctgctgc  1800
                   ||||||||||||||||||||||||||||||||||||||||||||||||||||||||||||
24P4C12v.8:  1741  tgctactcatgcgaaacattgtcagggtggtcgtcctggacaaagtcacagacctgctgc  1800

24P4C12v.1:  1801  tgttctttgggaagctgctggtggtcggaggcgtgggggtcctgtccttctttttttttct  1860
                   ||||||||||||||||||||||||||||||||||||||||||||||||||||||||||||
24P4C12v.8:  1801  tgttctttgggaagctgctggtggtcggaggcgtgggggtcctgtccttctttttttttct  1860

24P4C12v.1:  1861  ccggtcgcatcccggggctgggtaaagactttaagagcccccacctcaactattactggc  1920
                   ||||||||||||||||||||||||||||||||||||||||||||||||||||||||||||
24P4C12v.8:  1861  ccggtcgcatcccggggctgggtaaagactttaagagcccccacctcaactattactggc  1920

24P4C12v.1:  1921  tgcccatcatga                                                  1932
                   ||||||||||||
24P4C12v.8:  1921  tgcccatcatga                                                  1932
Score = 1263 bits (657), Expect = 0.0Identities = 657/657 (100%) Strand = Plus/Plus 24P4C12v.1:  1931  gacctccatcctgggggcctatgtcatcgccagcggcttcttcagcgttttcggcatgtg  1990
                   ||||||||||||||||||||||||||||||||||||||||||||||||||||||||||||
24P4C12v.8:  1967  gacctccatcctgggggcctatgtcatcgccagcggcttcttcagcgttttcggcatgtg  2026

24P4C12v.1:  1991  tgtggacacgctcttcctctgcttcctggaagacctggagcggaacaacggctccctgga  2050
                   ||||||||||||||||||||||||||||||||||||||||||||||||||||||||||||
24P4C12v.8:  2027  tgtggacacgctcttcctctgcttcctggaagacctggagcggaacaacggctccctgga  2086

24P4C12v.1:  2051  ccggccctactacatgtccaagagccttctaaagattctgggcaagaagaacgaggcgcc  2110
                   ||||||||||||||||||||||||||||||||||||||||||||||||||||||||||||
24P4C12v.8:  2087  ccggccctactacatgtccaagagccttctaaagattctgggcaagaagaacgaggcgcc  2146

24P4C12v.1:  2111  cccggacaacaagaagaggaagaagtgacagctccggccctgatccaggactgcacccca  2170
                   ||||||||||||||||||||||||||||||||||||||||||||||||||||||||||||
24P4C12v.8:  2147  cccggacaacaagaagaggaagaagtgacagctccggccctgatccaggactgcacccca  2206

24P4C12v.1:  2171  cccccaccgtccagccatccaacctcacttcgccttacaggtctccattttgtggtaaaa  2230
                   ||||||||||||||||||||||||||||||||||||||||||||||||||||||||||||
24P4C12v.8:  2207  cccccaccgtccagccatccaacctcacttcgccttacaggtctccattttgtggtaaaa  2266

24P4C12v.1:  2231  aaaggttttaggccaggcgccgtggctcacgcctgtaatcccaacactttgagaggctgag  2290
                   ||||||||||||||||||||||||||||||||||||||||||||||||||||||||||||
24P4C12v.8:  2267  aaaggttttaggccaggcgccgtggctcacgcctgtaatcccaacactttgagaggctgag  2326

24P4C12v.1:  2291  gcgggcggatcacctgagtcaggagttcgagaccagcctggccaacatggtgaaacctcc  2250
                   ||||||||||||||||||||||||||||||||||||||||||||||||||||||||||||
24P4C12v.8:  2327  gcgggcggatcacctgagtcaggagttcgagaccagcctggccaacatggtgaaacctcc  2386

24P4C12v.1:  2351  gtctctattaaaaatacaaaaattagccgagagtggtggcatgcacctgtcatcccagct  2410
                   ||||||||||||||||||||||||||||||||||||||||||||||||||||||||||||
24P4C12v.8:  2387  gtctctattaaaaatacaaaaattagccgagagtggtggcatgcacctgtcatcccagct  2446

24P4C12v.1:  2411  actcgggaggctgaggcaggagaatcgcttgaacccgggaggcagaggttgcagtgagcc  2470
                   ||||||||||||||||||||||||||||||||||||||||||||||||||||||||||||
24P4C12v.9:  2447  actcgggaggctgaggcaggagaatcgcttgaacccgggaggcagaggttgcagtgagcc  2506
```

TABLE LVII-continued

Nucleotide sequence alignment of 24P4C12v.1 v.1 (SEQ ID NO: 101) and
24P4C12 v.8 (SEQ ID NO: 102)

```
24P4C12v.1:  2471 gagatcgcgccactgcactccaacctgggtgacagactctgtctccaaaacaaaacaaac  2530
                  ||||||||||||||||||||||||||||||||||||||||||||||||||||||||||||
24P4C12v.9:  2507 gagatcgcgccactgcactccaacctgggtgacagactctgtctccaaaacaaaacaaac  2566

24P4C12v.1:  2531 aaacaaaaagattttattaaagatattttgttaactcagtaaaaaaaaaaaaaaaaaaa   2587
                  |||||||||||||||||||||||||||||||||||||||||||||||||||||||||||
24P4C12v.9:  2567 aaacaaaaagattttattaaagatattttgttaactcagtaaaaaaaaaaaaaaaaaaaa  2623
```

TABLE LVIII

Peptide sequences of protein coded by
24P4C12 v.8 (SEQ ID NO: 103)

| | | | | |
|---|---|---|---|---|
| MGGKQRDEDD | EAYGKPVKYD | PSFRGPIKNR | SCTDVICCVL | 60 |
| FLLFILGYIV | VGIVAWLYGD | | | |
| PRQVLYPRNS | TGAYCGMGEN | KDKPYLLYFN | IFSCILSSNI | 120 |
| ISVAENGLQC | PTPQVCVSSC | | | |
| PEDPWTVGKN | EFSQTVGEVF | YTKNRNFCLP | GVPWNMTVIT | 180 |
| SLQQELCPSF | LLPSAPALGR | | | |
| CFPWTNVTPP | ALPGITNDTT | IQQGISGLID | SLNARDISVK | 240 |
| IFEDFAQSWY | WILVALGVAL | | | |
| VLSLLFILLL | RLVAGPLVLV | LILGVLGVLA | YGIYYCWEEY | 300 |
| RVLRDKGASI | SQLGFTTNLS | | | |
| AYQSVQETWL | AALIVLAVLE | AILLLMLIFL | RQRIRIAIAL | 360 |
| LKEASKAVGQ | MMSTMFYPLV | | | |
| TFVLLLICIA | YWAMTALYLA | TSGQPQYVLW | ASNISSPGCE | 420 |
| KVPINTSCNP | TAHLVNSSCP | | | |
| GLMCVFQGYS | SKGLIQRSVF | NLQIYGVLGL | FWTLNWVLAL | 480 |
| GQCVLAGAFA | SFYWAFHKPQ | | | |
| DIPTFPLISA | FIRTLRYHTG | SLAFGALILT | LVQIARVILE | 540 |
| YIDHKLRGVQ | NPVARCIMCC | | | |
| FKCCLWCLEK | FIKFLNRNAY | IMIAIYGKNF | CVSAKNAFML | 600 |
| LMRNIVRVVV | LDKVTDLLLF | | | |
| FGKLLVVGGV | GVLSFFFFSG | RIPGLGKDFK | SPHLNYYWLP | 660 |
| IMRNPITPTG | HVFQTSILGA | | | |
| YVIASGFFSV | FGMCVDTLFL | CFLEDLERNN | GSLDRPYYMS | 720 |
| KSLLKILGKK | NEAPPDNKKR | | | |
| KK | | | | 722 |

TABLE LIX

Amino acid sequence alignmant of 24P4C12v.2. v.1 (SEQ ID NO: 104)
and 24P4C12 v.8 (SEQ ID NO: 105)

```
Score = 1438 bits (3722), Expect = 0.0  Identities = 710/722 (98%),
Positives = 710/722 (98%), Gaps = 12/722 (1%)
24P4C12v.1:    1 MGGKQRDEDDEAYGKPVKYDPSFRGPIKNRSCTDVICCVLFLLFILGYIVVGIVAWLYGD    60
                 MGGKQRDEDDEAYGKPVKYDPSFRGPIKNRSCTDVICCVLFLLFILGYIVVGIVAWLYGD
24P4C12v.8:    1 MGGKQRDEDDEAYGKPVKYDPSFRGPIKNRSCTDVICCVLFLLFILGYIVVGIVAWLYGD    60

24P4C12v.1:   61 PRQVLYPRNSTGAYCGMGENKDKPYLLYFNIFSCILSSNIISVAENGLQCPTPQVCVSSC   120
                 PRQVLYPRNSTGAYCGMGENKDKPYLLYFNIFSCILSSNIISVAENGLQCPTPQVCVSSC
24P4C12v.8:   61 PRQVLYPRNSTGAYCGMGENKDKPYLLYFNIFSCILSSNIISVAENGLQCPTPQVCVSSC   120

24P4C12v.1:  121 PEDPWTVGKNEFSQTVGEVFYTKNRNFCLPGVPWNMTVITSLQQELCPSFLLPSAPALGR   180
                 PEDPWTVGKNEFSQTVGEVFYTKNRNFCLPGVPWNMTVITSLQQELCPSFLLPSAPALGR
24P4C12v.8:  121 PEDPWTVGKNEFSQTVGEVFYTKNRNFCLPGVPWNMTVITSLQQELCPSFLLPSAPALGR   180

24P4C12v.1:  181 CFPWTNVTPPALPGITNDTTIQQGISGLIDSLNARDISVKIFEDFAQSWYWILVALGVAL   240
                 CFPWTNVTPPALPGITNDTTIQQGISGLIDSLNARDISVKIFEDFAQSWYWILVALGVAL
24P4C12v.8:  181 CFPWTNVTPPALPGITNDTTIQQGISGLIDSLNARDISVKIFEDFAQSWYWILVALGVAL   240

24P4C12v.1:  241 VLSLLFILLLRLVAGPLVLVLILGVLGVLAYGIYYCWEEYRVLRDKGASISQLGFTTNLS   300
                 VLSLLFILLLRLVAGPLVLVLILGVLGVLAYGIYYCWEEYRVLRDKGASISQLGFTTNLS
24P4C12v.8:  241 VLSLLFILLLRLVAGPLVLVLILGVLGVLAYGIYYCWEEYRVLRDKGASISQLGFTTNLS   300

24P4C12v.1:  301 AYQSVQETWLAALIVLAVLEAILLLMLIFLRQRIRIAIALLKEASKAVGQMMSTMFYPLV   360
                 AYQSVQETWLAALIVLAVLEAILLLMLIFLRQRIRIAIALLKEASKAVGQMMSTMFYPLV
24P4C12v.8:  301 AYQSVQETWLAALIVLAVLEAILLLMLIFLRQRIRIAIALLKEASKAVGQMMSTMFYPLV   360

24P4C12v.1:  361 TFVLLLICIAYWAMTALYLATSGQPQYVLWASNISSPGCEKVPINTSCNPTAHLVNSSCP   420
                 TFVLLLICIAYWAMTALYLATSGQPQYVLWASNISSP CCEKVPINTSCNPTAHLVNSSCP
24P4C12v.8:  361 TFVLLLICIAYWAMTALYLATSGQPQYVLWASNISSPCCEKVPINTSCNPTAHLVNSSCP   420

24P4C12v.1:  421 GLMCVFQGYSSKGLIQRSVFNLQIYGVLGLFWTLNWVLALGQCVLACAFASFYWAFHKPQ   480
                 GLMCVFQGYSSKGLIQRSVFNLQIYGVLGLFWTLNWVLA GQCVLAGAFASFYWAFHKPQ
24P4C12v.8:  421 GLMCVFQGYSSKGLIQRSVFNLQIYGVLGLFWTLNWVLALGQCVLAGAFASFYWAFHKPQ   480

24P4C12v.1:  481 DIPTFPLISAFIRTLRYHTGSLAFGALILTLVQIARVILEYIDHKLRGVQNPVARCIMCC   540
```

TABLE LIX-continued

Amino acid sequence alignmant of 24P4C12v.2. v.1 (SEQ ID NO: 104)
and 24P4C12 v.8 (SEQ ID NO: 105)

```
                 DIPTFPPLISAFIRTLRYHTGSLAFGALILTLVQIARVILEYIDHKLRGVQNPVARCIMCC
24P4C12v.8:  481 DIPTFPPLISAFIRTLRYHTGSLAFGALILTLVQIARVILEYIDHKLRGVQNPVARCIMCC 540

24P4C12v.1:  541 FKCCLWCLEKFIKFLNRNAYIMIAIYGKNFCVSAKNAFMLLMRNIVRVVVLDKVTDLLLF  600
                 FKCCLWCLEKFIKFLNRNAYIMIAIYGKNFCVSAKNAFMLLMRNIVRVVVLDKVTDLLLF
24P4C12v.8:  541 FKCCLWCLEKFIKFLNRNAYIMIAIYGKNFCVSAKNAFMLLMRNIVRVVVLDKVTDLLLF  600

24p4C12v.1:  601 FGKLLVVGGVGVLSFFFFSGRIPGLGKDFKSPHLNYYWLPIM------------TSILGA  648
                 FGKLLVVGGVGVLSFFFFSGRIPGLGKDFKSPHLNYYWLPIM            TSILGA
24P4C12v.8:  601 FGKLLVVGGVGVLSFFFFSGRIPGLGKDFKSPHLNYYWLPIMRNPITPTGHVFQTSILGA  660

24P4C12v.1:  649 YVIASGFFSVFGMCVDTLFLCFLEDLERNNGSLDRPYYMSKSLLKILGKKNEAPPDNKKR  708
                 YVIASGFFSVFGMCVDTLFLCFLEDLERNNGSLDRPYYMSKSLLKILGKKNEAPPDNKKR
24P4C12v.8:  661 YVIASGFFSVFGMCVDTLFLCFLEDLERNNGSLDRPYYMSKSLLKILGKKNEAPPDNKKR  720

24P4C12v.1:  709 KK                                                           710
                 KK
24p4C12v.8:  721 KK                                                           722
```

TABLE LX

Nucleotide sequence of transcript variant
24P4C12 v.9 (SEQ ID NO: 106)

```
gagccatggg gggaaagcag cgggacgagg atgacgaggc        60
ctacgggaag ccagtcaaat
acgacccctc ctttcgaggc cccatcaaga acagaagctg       120
cacagatgtc atctgctgcg
tcctcttcct gctcttcatt ctaggttaca tcgtggtggg       180
gattgtggcc tggttgtatg
gagaccccg gcaagtcctc tacccccagga actctactgg       240
ggcctactgt ggcatggggg
agaacaaaga taagccgtat ctcctgtact tcaacatctt       300
cagctgcatc ctgtccagca
acatcatctc agttgctgag aacggcctac agtgccccac       360
accccagtg tgtgtgtcct
cctgcccgga ggacccatgg actgtgggaa aaacgagtt        420
ctcacagact gttggggaag
tcttctatac aaaaaacagg aacttttgtc tgccaggggt       480
accctggaat atgacggtga
tcacaagcct gcaacaggaa ctctgcccca gtttcctcct       540
cccctctgct ccagctctgg
ggcgctgctt tccatggacc aacgttactc caccggcgct       600
cccagggatc accaatgaca
ccaccataca gcaggggatc agcggtctta ttgacagcct       660
caatgcccga gacatcagtg
ttaagatctt tgaagatttt gcccagtcct ggtattggat       720
tcttgttgcc ctggggggtgg
ctctggtctt gagcctactg tttatcttgc ttctgcgcct       780
ggtgctgggc ccctggtgc
tggtgctgat cctgggagtg ctgggcgtgc tggcatacgg       840
catctactac tgctgggagg
agtaccgagt gctgcgggac aagggcgcct ccatctccca       900
gctgggtttc accaccaacc
tcagtgccta ccagagcgtg caggagacct ggctggccgc       960
cctgatcgtg ttggcggtgc
ttgaagccat cctgctgctg atgctcatct tcctgcggca      1020
gcggattcgt attgccatcg
```

TABLE LX-continued

Nucleotide sequence of transcript variant
24P4C12 v.9 (SEQ ID NO: 106)

```
ccctcctgaa ggaggccagc aaggctgtgg gacagatgat      1080
gtctaccatg ttctacccac
tggtcaccct tgtcctcctc ctcatctgca ttgcctactg      1140
ggccatgact gctctgtatc
ctctgcccac gcagccagcc actcttggat atgtgctctg      1200
ggcatccaac atcagctccc
ccggctgtga gaaagtgcca ataaatacat catgcaaccc      1260
cacggcccac cttgtgaact
cctcgtgccc agggctgatg tgcgtcttcc agggctactc      1320
atccaaaggc ctaatccaac
gttctgtctt caatctgcaa atctatgggg tcctggggct      1380
cttctggacc cttaactggg
tactggccct gggccaatgc gtcctcgctg gagcctttgc      1440
ctccttctac tgggccttcc
acaagcccca ggacatccct accttcccct taatctctgc      1500
cttcatccgc acactccgtt
accacactgg gtcattggca tttggagccc tcatcctgac      1560
ccttgtgcag atagcccggg
tcatcttgga gtatattgac acaagctca gaggagtgca       1620
gaaccctgta gcccgctgca
tcatgtgctg tttcaagtgc tgcctctggt gtctggaaaa      1680
atttatcaag ttcctaaacc
gcaatgcata catcatgatc gccatctacg gaagaattt       1740
ctgtgtctca gccaaaaatg
cgttcatgct actcatgcga acattgtca gggtggtcgt       1800
cctggacaaa gtcacagacc
tgctgctgtt cttgggaag ctgctggtgg tcggaggcgt       1860
gggggtcctg tccttctttt
ttttctccgg tcgcatcccg ggctgggta aagactttaa        1920
gagccccac ctcaactatt
actggctgcc catcatgacc tccatcctgg gggcctatgt      1980
catcgccagc ggcttcttca
gcgttttcgg catgtgtgtg gacacgctct tcctctgctt      2040
```

TABLE LX-continued

Nucleotide sequence of transcript variant
24P4C12 v.9 (SEQ ID NO: 106)

```
cctggaagac ctggagcgga acaacggctc cctggaccgg ccctactaca tgtccaagag    2100
ccttctaaag attctgggca agaagaacga ggcgcccccg gacaacaaga agaggaagaa    2160
gtgacagctc cggccctgat ccaggactgc accccacccc caccgtccag ccatccaacc    2220
tcacttcgcc ttacaggtct ccattttgtg gtaaaaaaag gttttaggcc aggcgccgtg    2280
gctcacgcct gtaatccaac actttgagag gctgaggcgg gcggatcacc tgagtcagga    2340
gttcgagacc agcctggcca acatggtgaa aacctccgtct ctattaaaaa tacaaaaatt    2400
agccgagagt ggtggcatgc acctgtcatc ccagctactc gggaggctga ggcaggagaa    2460
tcgcttgaac ccgggaggca gaggttgcag tgagccgaga tcgcgccact gcactccaac    2520
ctgggtgaca gactctgtct ccaaaacaaa acaaacaaac aaaaagattt tattaaagat    2580
attttgttaa ctcagtaaaa aaaaaaaaaa aaa                                  2593
```

TABLE LXI

Nucleotide sequence alignment of 24P4C12v.1 v.1 (SEQ ID NO: 107) and
24P4C12 v.9 (SEQ ID NO: 108)

Score = 2188 bits (1138), Expect = 0.0 Identities = 1138/1138 (100%) Strand = Plus/Plus

```
24P4C12v.1:    1 gagccatggggggaaagcagcgggacgaggatgacgaggcctacgggaagccagtcaaat    60
                 ||||||||||||||||||||||||||||||||||||||||||||||||||||||||||||
24P4C12v.9:    1 aaacaaaaagattttattaaagatattttgttaactcagtaaaaaaaaaaaaaaaaaaaa    60

24P4C12v.1:   61 acgacccctcctttcgaggccccatcaagaacagaagctgcacagatgtcatctgctgcg   120
                 ||||||||||||||||||||||||||||||||||||||||||||||||||||||||||||
24P4C12v.9:   61 acgacccctcctttcgaggccccatcaagaacagaagctgcacagatgtcatctgctgcg   120

24P4C12v.1:  121 tcctcttcctgctcttcattctaggttacatcgtggtggggattgtggcctggttgtatg   190
                 ||||||||||||||||||||||||||||||||||||||||||||||||||||||||||||
24P4C12v.9:  121 tcctcttcctgctcttcattctaggttacatcgtggtggggattgtggcctggttgtatg   190

24P4C12v.1:  181 gagaccccggcaagtcctctaccccaggaactctactggggcctactgtggcatgggggg   240
                 ||||||||||||||||||||||||||||||||||||||||||||||||||||||||||||
24P4C12v.9:  181 gagaccccggcaagtcctctaccccaggaactctactggggcctactgtggcatgggggg   240

24P4C12v.1:  241 agaacaaagataagccgtatctcctgtacttcaacatcttcagctgcatcctgtccagca   300
                 ||||||||||||||||||||||||||||||||||||||||||||||||||||||||||||
24P4C12v.9:  241 agaacaaagataagccgtatctcctgtacttcaacatcttcagctgcatcctgtccagca   300

24P4C12v.1:  301 acatcatctcagttgctgagaacggcctacagtgccccacaccccaggtgtgtgtgtcct   360
                 ||||||||||||||||||||||||||||||||||||||||||||||||||||||||||||
24P4C12v.9:  301 acatcatctcagttgctgagaacggcctacagtgccccacaccccaggtgtgtgtgtcct   360

24P4C12v.1:  361 cctgcccggaggacccatggactgtgggaaaaaacgagttctcacagactgttggggaag   420
                 ||||||||||||||||||||||||||||||||||||||||||||||||||||||||||||
24P4C12v.9:  361 cctgcccggaggacccatggactgtgggaaaaaacgagttctcacagactgttggggaag   420

24P4C12v.1:  421 tcttctatacaaaaaacaggaacttttgtctgccaggggtaccctggaatatgacggtga   480
                 ||||||||||||||||||||||||||||||||||||||||||||||||||||||||||||
24P4C12v.9:  421 tcttctatacaaaaaacaggaacttttgtctgccaggggtaccctggaatatgacggtga   480

24P4C12v.1:  481 tcacaagcctgcaacaggaactctgccccagtttcctcctcccctctgctccagctctgg   540
                 ||||||||||||||||||||||||||||||||||||||||||||||||||||||||||||
24P4C12v.9:  481 tcacaagcctgcaacaggaactctgccccagtttcctcctcccctctgctccagctctgg   540

24P4C12v.1:  541 ggcgctgctttccatggaccaacgttactccaccggcgctcccagggatcaccaatgaca   600
                 ||||||||||||||||||||||||||||||||||||||||||||||||||||||||||||
24P4C12v.9:  541 ggcgctgctttccatggaccaacgttactccaccggcgctcccagggatcaccaatgaca   600

24P4C12v.1:  601 ccaccatacagcaggggatcagcggtcttattgacagcctcaatgcccgagacatcagtg   660
                 ||||||||||||||||||||||||||||||||||||||||||||||||||||||||||||
24P4C12v.9:  601 ccaccatacagcaggggatcagcggtcttattgacagcctcaatgcccgagacatcagtg   660

24P4C12v.1:  661 ttaagatctttgaagattttgcccagtcctggtattggattcttgttgccctgggggtgg   720
                 ||||||||||||||||||||||||||||||||||||||||||||||||||||||||||||
24P4C12v.9:  661 ttaagatctttgaagattttgcccagtcctggtattggattcttgttgccctgggggtgg   720
```

TABLE LXI-continued

Nucleotide sequence alignment of 24P4C12v.1 v.1 (SEQ ID NO: 107) and 24P4C12 v.9 (SEQ ID NO: 108)

```
24P4C12v.1:   721  ctctggtcttgagcctactgtttatcttgcttctgcgcctggtggctgggcccctggtgc  780
                   ||||||||||||||||||||||||||||||||||||||||||||||||||||||||||||
24P4C12v.9:   721  ctctggtcttgagcctactgtttatcttgcttctgcgcctggtggctgggcccctggtgc  780

24P4C12v.1:   781  tggtgctgatcctgggagtgctgggcgtgctggcatacggcatctactactgctgggagg  840
                   ||||||||||||||||||||||||||||||||||||||||||||||||||||||||||||
24P4C12v.9:   781  tggtgctgatcctgggagtgctgggcgtgctggcatacggcatctactactgctgggagg  840

24P4C12v.1:   841  agtaccgagtgctgcgggacaagggcgcctccatctcccagctgggtttcaccaccaacc  900
                   ||||||||||||||||||||||||||||||||||||||||||||||||||||||||||||
24P4C12v.9:   841  agtaccgagtgctgcgggacaagggcgcctccatctcccagctgggtttcaccaccaacc  900

24P4C12v.1:   901  tcagtgcctaccagagcgtgcaggagacctggctggccgccctgatcgtgttggcggtgc  960
                   ||||||||||||||||||||||||||||||||||||||||||||||||||||||||||||
24P4C12v.9:   901  tcagtgcctaccagagcgtgcaggagacctggctggccgccctgatcgtgttggcggtgc  960

24P4C12v.1:  1021  ccctcctgaaggaggccagcaaggctgtgggacagatgatgtctaccatgttctacccac  1080
                   ||||||||||||||||||||||||||||||||||||||||||||||||||||||||||||
24P4C12v.9:  1021  ccctcctgaaggaggccagcaaggctgtgggacagatgatgtctaccatgttctacccac  1080

24P4C12v.1:  1081  tggtcacctttgtcctcctcctcatctgcattgcctactgggccatgactgctctgta   1138
                   ||||||||||||||||||||||||||||||||||||||||||||||||||||||||||
24P4C12v.9:  1081  tggtcacctttgtcctcctcctcatctgcattgcctactgggccatgactgctctgta   1138
```

Score = 2738 bits (1424), Expect = 0.0 Identities = 1424/1424 (100%) Strand = Plus/Plus

```
24P4C12v.1:  1164  tatgtgctctgggcatccaacatcagctcccccggctgtgagaaagtgccaataaataca  1223
                   ||||||||||||||||||||||||||||||||||||||||||||||||||||||||||||
24P4C12v.9:  1170  tatgtgctctgggcatccaacatcagctcccccggctgtgagaaagtgccaataaataca  1229

24P4C12v.1:  1224  tcatgcaaccccacggcccaccttgtgaactcctcgtgcccagggctgatgtgcgtcttc  1283
                   ||||||||||||||||||||||||||||||||||||||||||||||||||||||||||||
24P4C12v.9:  1230  tcatgcaaccccacggcccaccttgtgaactcctcgtgcccagggctgatgtgcgtcttc  1289

24P4C12v.1:  1284  cagggctactcatccaaaggcctaatccaacgttctgtcttcaatctgcaaatctatggg  1343
                   ||||||||||||||||||||||||||||||||||||||||||||||||||||||||||||
24P4C12v.9:  1290  tcatgcaaccccacggcccaccttgtgaactcctcgtgcccagggctgatgtgcgtcttc  1349

24P4C12v.1:  1344  gtcctggggctcttctggaccccttaactgggtactggccctgggccaatgcgtcctcgct  1403
                   ||||||||||||||||||||||||||||||||||||||||||||||||||||||||||||
24P4C12v.9:  1350  gtcctggggctcttctggaccccttaactgggtactggccctgggccaatgcgtcctcgct  1409

24P4C12v.1:  1404  ggagcctttgcctccttctactgggccttccacaagccccaggacatccctaccttcccc  1463
                   ||||||||||||||||||||||||||||||||||||||||||||||||||||||||||||
24P4C12v.9:  1410  ggagcctttgcctccttctactgggccttccacaagccccaggacatccctaccttcccc  1469

24P4C12v.1:  1464  ttaatctctgccttcatccgcacactccgttaccacactgggtcattggcatttggagcc  1523
                   ||||||||||||||||||||||||||||||||||||||||||||||||||||||||||||
24P4C12v.9:  1470  ttaatctctgccttcatccgcacactccgttaccacactgggtcattggcatttggagcc  1529

24P4C12v.1:  1524  ctcatcctgacccttgtgcagatagcccgggtcatcttggagtatattgaccacaagctc  1583
                   ||||||||||||||||||||||||||||||||||||||||||||||||||||||||||||
24P4C12v.9:  1530  ctcatcctgacccttgtgcagatagcccgggtcatcttggagtatattgaccacaagctc  1589

24P4C12v.1:  1584  agaggagtgcagaaccctgtagcccgctgcatcatgtgctgtttcaagtgctgcctctgg  1643
                   ||||||||||||||||||||||||||||||||||||||||||||||||||||||||||||
24P4C12v.9:  1590  agaggagtgcagaaccctgtagcccgctgcatcatgtgctgtttcaagtgctgcctctgg  1649

24P4C12v.1:  1704  gggaagaatttctgtgtctcagccaaaaatgcgttcatgctactcatgcgaaacattgtc  1763
                   ||||||||||||||||||||||||||||||||||||||||||||||||||||||||||||
24P4C12v.9:  1710  gggaagaatttctgtgtctcagccaaaaatgcgttcatgctactcatgcgaaacattgtc  1769

24P4C12v.1:  1644  tgtctggaaaaatttatcaagttcctaaaccgcaatgcatacatcatgatcgccatctac  1703
                   ||||||||||||||||||||||||||||||||||||||||||||||||||||||||||||
24P4C12v.9:  1650  tgtctggaaaaatttatcaagttcctaaaccgcaatgcatacatcatgatcgccatctac  1709

24P4C12v.1:  1764  agggtggtcgtcctggacaaagtcacagacctgctgctgttctttgggaagctgctggtg  1823
                   ||||||||||||||||||||||||||||||||||||||||||||||||||||||||||||
24P4C12v.9:  1770  agggtggtcgtcctggacaaagtcacagacctgctgctgttctttgggaagctgctggtg  1829

24P4C12v.1:  1824  gtcggaggcgtgggggtcctgtccttctttttttttctccggtcgcatcccggggctgggt  1883
                   ||||||||||||||||||||||||||||||||||||||||||||||||||||||||||||
24P4C12v.9:  1830  gtcggaggcgtgggggtcctgtccttctttttttttctccggtcgcatcccggggctgggt  1889
```

TABLE LXI-continued

Nucleotide sequence alignment of 24P4C12v.1 v.1 (SEQ ID NO: 107) and 24P4C12 v.9 (SEQ ID NO: 108)

```
24P4C12v.1: 1884 aaagactttaagagccccacctcaactattactggctgcccatcatgacctccatcctg 1943
                 ||||||||||||||||||||||||||||||||||||||||||||||||||||||||||||
24P4C12v.9: 1890 aaagactttaagagccccacctcaactattactggctgcccatcatgacctccatcctg 1949

24P4C12v.1: 1944 ggggcctatgtcatcgccagcggcttcttcagcgttttcggcatgtgtgtggacacgctc 2003
                 ||||||||||||||||||||||||||||||||||||||||||||||||||||||||||||
24P4C12v.9: 1950 ggggcctatgtcatcgccagcggcttcttcagcgttttcggcatgtgtgtggacacgctc 2009

24P4C12v.1: 2004 ttcctctgcttcctggaagacctggagcggaacaacggctccctggaccggccctactac 2063
                 ||||||||||||||||||||||||||||||||||||||||||||||||||||||||||||
24P4C12v.9: 2010 ttcctctgcttcctggaagacctggagcggaacaacggctccctggaccggccctactac 2069

24P4C12v.1: 2064 atgtccaagagccttctaaagattctgggcaagaagaacgaggcgccccggacaacaag 2123
                 ||||||||||||||||||||||||||||||||||||||||||||||||||||||||||||
24P4C12v.9: 2070 atgtccaagagccttctaaagattctgggcaagaagaacgaggcgccccggacaacaag 2129

24P4C12v.1: 2124 aagaggaagaagtgacagctccggccctgatccaggactgcaccccaccccaccgtcca 2183
                 ||||||||||||||||||||||||||||||||||||||||||||||||||||||||||||
24P4C12v.9: 2130 aagaggaagaagtgacagctccggccctgatccaggactgcaccccaccccaccgtcca 2189

24P4C12v.1: 2184 gccatccaacctcacttcgccttacaggtctccattttgtggtaaaaaaaggttttaggc 2243
                 ||||||||||||||||||||||||||||||||||||||||||||||||||||||||||||
24P4C12v.9: 2190 gccatccaacctcacttcgccttacaggtctccattttgtggtaaaaaaaggttttaggc 2249

24P4C12v.1: 2244 caggcgccgtggctcacgcctgtaatcccaacactttgagaggctgaggcgggcggatcac 2303
                 ||||||||||||||||||||||||||||||||||||||||||||||||||||||||||||
24P4C12v.9: 2250 caggcgccgtggctcacgcctgtaatcccaacactttgagaggctgaggcgggcggatcac 2309

24P4C12v.1: 2304 ctgagtcaggagttcgagaccagcctggccaacatggtgaaacctccgtctctattaaaa 2363
                 ||||||||||||||||||||||||||||||||||||||||||||||||||||||||||||
24P4C12v.9: 2310 ctgagtcaggagttcgagaccagcctggccaacatggtgaaacctccgtctctattaaaa 2369

24P4C12v.1: 2364 atacaaaaattagccgagagtggtggcatgcacctgtcatcccagctactcgggaggctg 2423
                 ||||||||||||||||||||||||||||||||||||||||||||||||||||||||||||
24P4C12v.9: 2370 atacaaaaattagccgagagtggtggcatgcacctgtcatcccagctactcgggaggctg 2429

24P4C12v.1: 2484 aggcaggagaatcgcttgaacccgggaggcagaggttgcagtgagccgagatcgcgccac 2483
                 ||||||||||||||||||||||||||||||||||||||||||||||||||||||||||||
24P4C12v.9: 2430 aggcaggagaatcgcttgaacccgggaggcagaggttgcagtgagccgagatcgcgccac 2489

24P4C12v.1: 2484 tgcactccaacctgggtgacagactctgtctccaaaacaaaacaaacaaacaaaaagatt 2543
                 ||||||||||||||||||||||||||||||||||||||||||||||||||||||||||||
24P4C12v.9: 2490 tgcactccaacctgggtgacagactctgtctccaaaacaaaacaaacaaacaaaaagatt 2549

24P4C12v.1: 2544 ttattaaagatattttgttaactcagtaaaaaaaaaaaaaaaaa 2587
                 |||||||||||||||||||||||||||||||||||||||||||||
24P4C12v.9: 2550 ttattaaagatattttgttaactcagtaaaaaaaaaaaaaaaaaa 2593
```

TABLE LXII

Peptide sequences of protein coded by 24P4C12 v.9 (SEQ ID NO: 109)

| | |
|---|---|
| MGGKQRDEDD EAYGKPVKYD PSFRGPIKNR SCTDVICCVL FLLFILGYIV VGIVAWLYGD | 60 |
| PRQVLYPRNS TGAYCGMGEN KDKPYLLYFN IFSCILSSNI ISVAENGLQC PTPQVCVSSC | 120 |
| PEDPWTVGKN EFSQTVGEVF YTKNRNFCLP GVPWNMTVIT SLQQELCPSF LLPSAPALGR | 180 |
| CFPWTNVTPP ALPGITNDTT IQQGISGLID SLNARDISVK IFEDFAQSWY WILVALGVAL | 240 |
| VLSLLFILLL RLVAGPLVLV LILGVLGVLA YGIYYCWEEY RVLRDKGASI SQLGFTTNLS | 300 |
| AYQSVQETWL AALIVLAVLE AILLLMLIFL RQRIRIAIAL LKEASKAVGQ MMSTMFYPLV | 360 |
| TFVLLLICIA YWAMTALYPL PTQPATLGYV LWASNISSPG CEKVPINTSC NPTAHLVNSS | 420 |
| CPGLMCVFQG YSSKGLIQRS VFNLQIYGVL GLFWTLNWVL ALGQCVLAGA FASFYWAFHK | 480 |
| PQDIPTFPLI SAFIRTLRYH TGSLAFGALI LTLVQIARVI LEYIDHKLRG VQNPVARCIM | 540 |
| CCFKCCLWCL EKFIKFLNRN AYIMIAIYGK NFCVSAKNAF MLLMRNIVRV VVLDKVTDLL | 600 |
| LFFGKLLVVG GVGVLSFFFF SGRIPGLGKD FKSPHLNYYW LPIMTSILGA YVIASGFFSV | 660 |
| FGMCVDTLFL CFLEDLERNN GSLDRPYYMS KSLLKILGKK NEAPPDNKKR KK | 712 |

TABLE LXIII

Amino acid sequence alignment of 24P4C12v.1 v.1 (SEQ ID NO: 110) and 24P4C12 v.9 (SEQ ID NO: 111)

```
Score = 1424 bits (3686), Expect = 0.0 Identities = 704/713 (98%),
Positives = 705/713 (98%), Gaps = 4/713 (0%)
24P4C12v.1:   1 MGGKQRDEDDEAYGKPVKYDPSFRGPIKNRSCTDVICCVLFLLFILGYIVVGIVAWLYGD  60
                MGGKQRDEDDEAYGKPVKYDPSFRGPIKNRSCTDVICCVLFLLFILGYIVVGIVAWLYGD
24P4C12v.9:   1 MGGKQRDEDDEAYGKPVKYDPSFRGPIKNRSCTDVICCVLFLLFILGYIVVGIVAWLYGD  60

24P4C12v.1:  61 PRQVLYPRNSTGAYCGMGENKDKPYLLYFNIFSCILSSNIISVAENGLQCPTPQVCVSSC 120
                PRQVLYPRNSTGAYCGMGENKDKPYLLYFNIFSCILSSNIISVAENGLQCPTPQVCVSSC
24P4C12v.9:  61 PRQVLYPRNSTGAYCGMGENKDKPYLLYFNIFSCILSSNIISVAENGLQCPTPQVCVSSC 120

24P4C12v.1: 121 PEDPWTVGKNEFSQTVGEVFYTKNRNFCLPGVPWNMTVITSLQQELCPSFLLPSAPALGR 180
                PEDPWTVGKNEFSQTVGEVFYTKNRNFCLPGVPWNMTVITSLQQELCPSFLLPSAPALGR
24P4C12v.9: 121 PEDPWTVGKNEFSQTVGEVFYTKNRNFCLPGVPWNMTVITSLQQELCPSFLLPSAPALGR 180

24P4C12v.1: 181 CFPWTNVTPPALPGITNDTTIQQGISGLIDSLNARDISVKIFEDFAQSWYWILVALGVAL 240
                CFPWTNVTPPALPGITNDTTIQQGISGLIDSLNARDISVKIFEDFAQSWYWILVALGVAL
24P4C12v.9: 181 CFPWTNVTPPALPGITNDTTIQQGISGLIDSLNARDISVKIFEDFAQSWYWILVALGVAL 240

24P4C12v.1: 241 VLSLLFILLLRLVAGPLVLVLILGVLGVLAYGIYYCWEEYRVLRDKGASISQLGFTTNLS 300
                VLSLLFILLLRLVAGPLVLVLILGVLGVLAYGIYYCWEEYRVLRDKGASISQLGFTTNLS
24P4C12v.9: 241 VLSLLFILLLRLVAGPLVLVLILGVLGVLAYGIYYCWEEYRVLRDKGASISQLGFTTNLS 300

24p4C12v.1: 301 AYQSVQETWLAALIVLAVLEAILLLMLIFLRQRIRIAIALLKEASKAVGQMMSTMFYPLV 360
                AYQSVQETWLAALIVLAVLEAILLLMLIFLRQRIRIAIALLKEASKAVGQMMSTMFYPLV
24P4C12v.9: 301 AYQSVQETWLAALIVLAVLEAILLLMLIFLRQRIRIAIALLKEASKAVGQMMSTMFYPLV 360

24P4C12v.1: 361 TFVLLLICIAYWAMTALYLATSGQPQ---YVLWASNISSPGCEKVPINTSCNPTAHLVNS 417
                TFVLLLICIAYWAMTALY  + QP    YVLWASNISSPGCEKVPINTSCNPTAHLVNS
24P4C12v.9: 361 TFVLLLICIAYWAMTALYPLPT-QPATLGYVLWASNISSPGCEKVPINTSCNPTAHLVNS 419

24P4C12v.1: 418 SCPGLMCVFQGYSSKGLIQRSVFNLQIYGVLGLFWTLNWVLALGQCVLAGAFASFYWAFH 477
                SCPGLMCVFQGYSSKGLIQRSVFNLQIYGVLGLFWTLNWVLALGQCVLAGAFASFYWAFH
24P4C12v.9: 420 SCPGLMCVFQGYSSKGLIQRSVFNLQIYGVLGLFWTLNWVLALGQCVLAGAFASFYWAFH 479

24P4C12v.1: 478 KPQDIPTFPLISAFIRTLRYHTGSLAFGALILTLVQIARVILEYIDHKLRGVQNPVARCI 537
                KPQDIPTFPLISAFIRTLRYHTGSLAFGALILTLVQIARVILEYIDHKLRGVQNPVARCI
24P4C12v.9: 480 KPQDIPTFPLISAFIRTLRYHTGSLAFGALILTLVQIARVILEYIDHKLRGVQNPVARCI 539

24P4C12v.1: 538 MCCFKCCLWCLEKFIKFLNRNAYIMIAIYGKNFCVSAKNAFMLLMRNIVRVVVLDKVTDL 597
                MCCFKCCLWCLEKFIKFLNRNAYIMIAIYGKNFCVSAKNAFMLLMRNIVRVVVLDKVTDL
24P4C12v.9: 540 MCCFKCCLWCLEKFIKFLNRNAYIMIAIYGKNFCVSAKNAFMLLMRNIVRVVVLDKVTDL 599

24P4C12v.1: 598 LLFFGKLLVVGGVGVLSFFFFSGRIPGLGKDFKSPHLNYYWLPIMTSILGAYVIASGFFS 657
                LLFFGKLLVVGGVGVLSFFFFSGRIPGLGKDFKSPHLNYYWLPIMTSILGAYVIASGFFS
24P4C12v.9: 600 LLFFGKLLVVGGVGVLSFFFFSGRIPGLGKDFKSPHLNYYWLPIMTSILGAYVIASGFFS 659

24P4C12v.1: 658 VFGMCVDTLFLCFLEDLERNNGSLDRPYYMSKSLLKILGKKNEAPPDNKKRKK         710
                VFGMCVDTLFLCFLEDLERNNGSLDRPYYMSKSLLKILGKKNEAPPDNKKRKK
24P4C12v.9: 660 VFGMCVDTLFLCFLEDLERNNGSLDRPYYMSKSLLKILGKKNEAPPDNKKRKK         712
```

The invention claimed is:

1. A method for detecting malignancy in pancreas, lung or ovary tissue which method comprises:
   contacting a histological test sample of said tissue with an antibody or fragment thereof that specifically binds to the amino acid sequence shown in SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19; and,
   observing any positive amounts of a complex of the antibody or fragment with any protein in said samples, whereby positive amounts of said complex observed in said sample shows that said tissue is malignant.

2. The method of claim 1, wherein said test sample has been obtained from a subject who has, or who is suspected of having, cancer of said tissue.

3. A method for detecting malignancy in prostate tissue which method comprises:
   contacting a test histological sample of said tissue with an antibody or fragment thereof that specifically binds to the amino acid sequence shown in SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19;
   contacting a control histological sample of prostate tissue known to be normal with said antibody or fragment;

observing any positive amounts of a complex of the antibody or fragment with any protein in the samples;

whereby positive amounts of said complex mainly around the cell membrane in the test sample as compared to the control sample indicates that the tissue is malignant.

4. The method of claim 3, wherein said test sample has been obtained from a subject who has, or who is suspected of having, cancer of said tissue.

5. A method for detecting malignancy in breast or tissue which method comprises:

contacting a histological test sample of said tissue with an antibody or fragment thereof that specifically binds to the amino acid sequence shown in SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19; and, observing any positive amounts of a complex of the antibody or fragment with any protein in said samples, whereby positive amounts of said complex observed in said sample shows that said tissue is malignant.

6. The method of claim 5, wherein said test sample has been obtained from a subject who has, or who is suspected of having, cancer of said tissue.

* * * * *

SEQUENCE LISTING

<160> NUMBER OF SEQ ID NOS: 112

<210> SEQ ID NO 1
<211> LENGTH: 160
<212> TYPE: DNA
<213> ORGANISM: Homo Sapiens

<400> SEQUENCE: 1

```
gatcagggcg gccagccagg tctcctgcac gctctggtag gcactgaggt tggtggtgaa    60
acccagctgg gagatggagg cgccctcgtc ccgcagcact cggtactcct cccagcagta   120
gtagatgcca tatgccagca cgcccagcac tcccaggatc                         160
```

<210> SEQ ID NO 2
<211> LENGTH: 2587
<212> TYPE: DNA

-continued

<213> ORGANISM: Homo Sapiens

<400> SEQUENCE: 2

| | | | | | |
|---|---|---|---|---|---|
| gagccatggg | gggaaagcag | cgggacgagg | atgacgaggc | ctacgggaag | ccagtcaaat | 60 |
| acgacccctc | ctttcgaggc | cccatcaaga | acagaagctg | cacagatgtc | atctgctgcg | 120 |
| tcctcttcct | gctcttcatt | ctaggttaca | tcgtggtggg | gattgtggcc | tggttgtatg | 180 |
| gagaccccg | gcaagtcctc | taccccagga | actctactgg | ggcctactgt | ggcatggggg | 240 |
| agaacaaaga | taagccgtat | ctcctgtact | tcaacatctt | cagctgcatc | ctgtccagca | 300 |
| acatcatctc | agttgctgag | aacggcctac | agtgccccac | accccaggtg | tgtgtgtcct | 360 |
| cctgcccgga | ggacccatgg | actgtgggaa | aaaacgagtt | ctcacagact | gttggggaag | 420 |
| tcttctatac | aaaaaacagg | aacttttgtc | tgccaggggt | accctggaat | atgacggtga | 480 |
| tcacaagcct | gcaacaggaa | ctctgcccca | gtttcctcct | cccctctgct | ccagctctgg | 540 |
| ggcgctgctt | tccatggacc | aacgttactc | caccggcgct | cccagggatc | accaatgaca | 600 |
| ccaccataca | gcagggatc | agcggtctta | ttgacagcct | caatgcccga | gacatcagtg | 660 |
| ttaagatctt | tgaagatttt | gcccagtcct | ggtattggat | tcttgttgcc | ctggggtgg | 720 |
| ctctggtctt | gagcctactg | tttatcttgc | ttctgcgcct | ggtggctggg | ccctggtgc | 780 |
| tggtgctgat | cctgggagtg | ctgggcgtgc | tggcatacgg | catctactac | tgctgggagg | 840 |
| agtaccgagt | gctgcgggac | aagggcgcct | ccatctccca | gctgggtttc | accaccaacc | 900 |
| tcagtgccta | ccagagcgtg | caggagacct | ggctggccgc | cctgatcgtg | ttggcggtgc | 960 |
| ttgaagccat | cctgctgctg | atgctcatct | tcctgcggca | gcggattcgt | attgccatcg | 1020 |
| ccctcctgaa | ggaggccagc | aaggctgtgg | acagatgat | gtctaccatg | ttctacccac | 1080 |
| tggtcacctt | tgtcctcctc | ctcatctgca | ttgcctactg | ggccatgact | gctctgtacc | 1140 |
| tggctacatc | ggggcaaccc | cagtatgtgc | tctgggcatc | caacatcagc | tcccccggct | 1200 |
| gtgagaaagt | gccaataaat | acatcatgca | accccacggc | ccaccttgtg | aactcctcgt | 1260 |
| gcccagggct | gatgtgcgtc | ttccagggct | actcatccaa | aggcctaatc | caacgttctg | 1320 |
| tcttcaatct | gcaaatctat | ggggtcctgg | ggctcttctg | gacccttaac | tgggtactgg | 1380 |
| ccctgggcca | atgcgtcctc | gctggagcct | ttgcctcctt | ctactgggcc | ttccacaagc | 1440 |
| cccaggacat | ccctaccttc | cccttaatct | ctgccttcat | ccgcacactc | cgttaccaca | 1500 |
| ctgggtcatt | ggcatttgga | gccctcatcc | tgacccttgt | gcagatagcc | cgggtcatct | 1560 |
| tggagtatat | tgaccacaag | ctcagaggag | tgcagaaccc | tgtagcccgc | tgcatcatgt | 1620 |
| gctgtttcaa | gtgctgcctc | tggtgtctgg | aaaaatttat | caagttccta | aaccgcaatg | 1680 |
| catacatcat | gatcgccatc | tacgggaaga | atttctgtgt | ctcagccaaa | aatgcgttca | 1740 |
| tgctactcat | gcgaaacatt | gtcagggtgg | tcgtcctgga | caaagtcaca | gacctgctgc | 1800 |
| tgttcttttgg | gaagctgctg | gtggtcgagg | gcgtgggggt | cctgtccttc | ttttttttct | 1860 |
| ccggtcgcat | cccggggctg | ggtaaagact | ttaagagccc | ccacctcaac | tattactggc | 1920 |
| tgcccatcat | gacctccatc | ctgggggcct | atgtcatcgc | cagcggcttc | ttcagcgttt | 1980 |
| tcggcatgtg | tgtggacacg | ctcttcctct | gcttcctgga | agacctggag | cggaacaacg | 2040 |
| gctccctgga | ccgcctac | tacatgtcca | agagccttct | aaagattctg | gcaagaaga | 2100 |
| acgaggcgcc | cccggacaac | aagaagagga | agaagtgaca | gctccggccc | tgatccagga | 2160 |
| ctgcacccca | ccccaccgt | ccagccatcc | aacctcactt | cgccttacag | gtctccattt | 2220 |
| tgtggtaaaa | aaaggtttta | ggccaggcgc | cgtggctcac | gcctgtaatc | caacactttg | 2280 |

-continued

```
agaggctgag gcgggcggat cacctgagtc aggagttcga gaccagcctg gccaacatgg    2340
tgaaacctcc gtctctatta aaaatacaaa aattagccga gagtggtggc atgcacctgt    2400
catcccagct actcgggagg ctgaggcagg agaatcgctt gaacccggga ggcagaggtt    2460
gcagtgagcc gagatcgcgc cactgcactc caacctgggg gacagactct gtctccaaaa    2520
caaaacaaac aaacaaaaag attttattaa agatattttg ttaactcagt aaaaaaaaaa    2580
aaaaaaa                                                              2587
```

<210> SEQ ID NO 3
<211> LENGTH: 710
<212> TYPE: PRT
<213> ORGANISM: Homo Sapiens

<400> SEQUENCE: 3

| Met | Gly | Gly | Lys | Gln | Arg | Asp | Glu | Asp | Glu | Ala | Tyr | Gly | Lys | Pro |
|---|---|---|---|---|---|---|---|---|---|---|---|---|---|---|
| 1 | | | | 5 | | | | | 10 | | | | | 15 |

| Val | Lys | Tyr | Asp | Pro | Ser | Phe | Arg | Gly | Pro | Ile | Lys | Asn | Arg | Ser | Cys |
|---|---|---|---|---|---|---|---|---|---|---|---|---|---|---|---|
| | | | 20 | | | | | 25 | | | | | 30 | | |

| Thr | Asp | Val | Ile | Cys | Cys | Val | Leu | Phe | Leu | Leu | Phe | Ile | Leu | Gly | Tyr |
|---|---|---|---|---|---|---|---|---|---|---|---|---|---|---|---|
| | | | 35 | | | | 40 | | | | | 45 | | | |

| Ile | Val | Val | Gly | Ile | Val | Ala | Trp | Leu | Tyr | Gly | Asp | Pro | Arg | Gln | Val |
|---|---|---|---|---|---|---|---|---|---|---|---|---|---|---|---|
| | 50 | | | | | 55 | | | | | 60 | | | | |

| Leu | Tyr | Pro | Arg | Asn | Ser | Thr | Gly | Ala | Tyr | Cys | Gly | Met | Gly | Glu | Asn |
|---|---|---|---|---|---|---|---|---|---|---|---|---|---|---|---|
| 65 | | | | | 70 | | | | | 75 | | | | | 80 |

| Lys | Asp | Lys | Pro | Tyr | Leu | Leu | Tyr | Phe | Asn | Ile | Phe | Ser | Cys | Ile | Leu |
|---|---|---|---|---|---|---|---|---|---|---|---|---|---|---|---|
| | | | | 85 | | | | | 90 | | | | | 95 | |

| Ser | Ser | Asn | Ile | Ile | Ser | Val | Ala | Glu | Asn | Gly | Leu | Gln | Cys | Pro | Thr |
|---|---|---|---|---|---|---|---|---|---|---|---|---|---|---|---|
| | | | 100 | | | | | 105 | | | | | 110 | | |

| Pro | Gln | Val | Cys | Val | Ser | Ser | Cys | Pro | Glu | Asp | Pro | Trp | Thr | Val | Gly |
|---|---|---|---|---|---|---|---|---|---|---|---|---|---|---|---|
| | | 115 | | | | | 120 | | | | | 125 | | | |

| Lys | Asn | Glu | Phe | Ser | Gln | Thr | Val | Gly | Glu | Val | Phe | Tyr | Thr | Lys | Asn |
|---|---|---|---|---|---|---|---|---|---|---|---|---|---|---|---|
| | 130 | | | | | 135 | | | | | 140 | | | | |

| Arg | Asn | Phe | Cys | Leu | Pro | Gly | Val | Pro | Trp | Asn | Met | Thr | Val | Ile | Thr |
|---|---|---|---|---|---|---|---|---|---|---|---|---|---|---|---|
| 145 | | | | | 150 | | | | | 155 | | | | | 160 |

| Ser | Leu | Gln | Gln | Glu | Leu | Cys | Pro | Ser | Phe | Leu | Leu | Pro | Ser | Ala | Pro |
|---|---|---|---|---|---|---|---|---|---|---|---|---|---|---|---|
| | | | | 165 | | | | | 170 | | | | | 175 | |

| Ala | Leu | Gly | Arg | Cys | Phe | Pro | Trp | Thr | Asn | Val | Thr | Pro | Pro | Ala | Leu |
|---|---|---|---|---|---|---|---|---|---|---|---|---|---|---|---|
| | | | 180 | | | | | 185 | | | | | 190 | | |

| Pro | Gly | Ile | Thr | Asn | Asp | Thr | Thr | Ile | Gln | Gln | Gly | Ile | Ser | Gly | Leu |
|---|---|---|---|---|---|---|---|---|---|---|---|---|---|---|---|
| | | 195 | | | | | 200 | | | | | 205 | | | |

| Ile | Asp | Ser | Leu | Asn | Ala | Arg | Asp | Ile | Ser | Val | Lys | Ile | Phe | Glu | Asp |
|---|---|---|---|---|---|---|---|---|---|---|---|---|---|---|---|
| | 210 | | | | | 215 | | | | | 220 | | | | |

| Phe | Ala | Gln | Ser | Trp | Tyr | Trp | Ile | Leu | Val | Ala | Leu | Gly | Val | Ala | Leu |
|---|---|---|---|---|---|---|---|---|---|---|---|---|---|---|---|
| 225 | | | | | 230 | | | | | 235 | | | | | 240 |

| Val | Leu | Ser | Leu | Leu | Phe | Ile | Leu | Leu | Leu | Arg | Leu | Val | Ala | Gly | Pro |
|---|---|---|---|---|---|---|---|---|---|---|---|---|---|---|---|
| | | | | 245 | | | | | 250 | | | | | 255 | |

| Leu | Val | Leu | Val | Leu | Ile | Leu | Gly | Val | Leu | Gly | Val | Leu | Ala | Tyr | Gly |
|---|---|---|---|---|---|---|---|---|---|---|---|---|---|---|---|
| | | | 260 | | | | | 265 | | | | | 270 | | |

| Ile | Tyr | Tyr | Cys | Trp | Glu | Glu | Tyr | Arg | Val | Leu | Arg | Asp | Lys | Gly | Ala |
|---|---|---|---|---|---|---|---|---|---|---|---|---|---|---|---|
| | | 275 | | | | | 280 | | | | | 285 | | | |

| Ser | Ile | Ser | Gln | Leu | Gly | Phe | Thr | Thr | Asn | Leu | Ser | Ala | Tyr | Gln | Ser |
|---|---|---|---|---|---|---|---|---|---|---|---|---|---|---|---|
| | 290 | | | | | 295 | | | | | 300 | | | | |

| Val | Gln | Glu | Thr | Trp | Leu | Ala | Ala | Leu | Ile | Val | Leu | Ala | Val | Leu | Glu |
|---|---|---|---|---|---|---|---|---|---|---|---|---|---|---|---|
| 305 | | | | | 310 | | | | | 315 | | | | | 320 |

```
Ala Ile Leu Leu Leu Met Leu Ile Phe Leu Arg Gln Arg Ile Arg Ile
            325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Ile Cys
        355                 360                 365

Ile Ala Tyr Trp Ala Met Thr Ala Leu Tyr Leu Ala Thr Ser Gly Gln
        370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
            405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
            435                 440                 445

Gly Leu Phe Trp Thr Leu Asn Trp Val Leu Ala Leu Gly Gln Cys Val
            450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
            485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
            515                 520                 525

Val Gln Asn Pro Val Ala Arg Cys Ile Met Cys Cys Phe Lys Cys Cys
530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
            565                 570                 575

Ala Phe Met Leu Leu Met Arg Asn Ile Val Arg Val Val Val Leu Asp
            580                 585                 590

Lys Val Thr Asp Leu Leu Leu Phe Phe Gly Lys Leu Leu Val Val Gly
            595                 600                 605

Gly Val Gly Val Leu Ser Phe Phe Phe Ser Gly Arg Ile Pro Gly
            610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
            645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
            675                 680                 685

Lys Ser Leu Leu Lys Ile Leu Gly Lys Lys Asn Glu Ala Pro Pro Asp
            690                 695                 700

Asn Lys Lys Arg Lys Lys
705                 710

<210> SEQ ID NO 4
<211> LENGTH: 2587
<212> TYPE: DNA
<213> ORGANISM: Homo Sapiens
```

```
<400> SEQUENCE: 4
gagccatggg gggaaagcag cgggacgagg atgacgaggc ctacgggaag ccagtcaaat      60 acgaccctc ctttcgaggc cccatcaaga acagaagctg cacagatgtc atctgctgcg     120
tcctcttcct gctcttcatt ctaggttaca tcgtggtggg gattgtggcc tggttgtatg     180 gagaccccg gcaagtcctc tacccagga actctactgg ggcctactgt ggcatggggg     240
agaacaaaga taagccgtat ctcctgtact tcaacatctt cagctgcatc ctgtccagca     300
acatcatctc agttgctgag aacggcctac agtgccccac accccaggtg tgtgtgtcct     360
cctgcccgga ggacccatgg actgtgggaa aaacgagtt ctcacagact gttggggaag     420
tcttctatac aaaaaacagg aacttttgtc tgccaggggt accctggaat atgacggtga     480
tcacaagcct gcaacaggaa ctctgcccca gtttcctcct cccctctgct ccagctctgg     540
gacgctgctt tccatggacc aacgttactc caccggcgct cccagggatc accaatgaca     600
ccaccataca gcagggatc agcggtctta ttgacagcct caatgcccga gacatcagtg     660
ttaagatctt tgaagatttt gcccagtcct ggtattggat tcttgttgcc ctgggggtgg     720
ctctggtctt gagcctactg tttatcttgc ttctgcgcct ggtggctggg ccctggtgc     780 tggtgctgat cctgggagtg ctgggcgtgc tggcatacgg catctactac tgctgggagg     840
agtaccgagt gctgcgggac aagggcgcct ccatctccca gctgggtttc accaccaacc     900
tcagtgccta ccagagcgtg caggagacct ggctggccgc cctgatcgtg ttggcggtgc     960
ttgaagccat cctgctgctg atgctcatct tcctgcggca gcggattcgt attgccatcg    1020
ccctcctgaa ggaggccagc aaggctgtgg acagatgat gtctaccatg ttctacccac    1080
tggtcacctt tgtcctcctc ctcatctgca ttgcctactg ggccatgact gctctgtacc    1140
tggctacatc ggggcaaccc cagtatgtgc tctgggcatc caacatcagc tcccccggct    1200
gtgagaaagt gccaataaat acatcatgca accccacggc ccaccttgtg aactcctcgt    1260
gcccagggct gatgtgcgtc ttccagggct actcatccaa aggcctaatc caacgttctg    1320
tcttcaatct gcaaatctat ggggtcctgg ggctcttctg gacccttaac tgggtactgg    1380
ccctgggcca atgcgtcctc gctggagcct ttgcctcctt ctactgggcc ttccacaagc    1440
cccaggacat ccctaccttc cccttaatct ctgccttcat ccgcacactc cgttaccaca    1500
ctgggtcatt ggcatttgga ccctcatcc tgaccttgt gcagatagcc cgggtcatct    1560
tggagtatat tgaccacaag ctcagaggag tgcagaaccc tgtagcccgc tgcatcatgt    1620
gctgtttcaa gtgctgcctc tggtgtctgg aaaaatttat caagttccta aaccgcaatg    1680
catacatcat gatcgccatc tacgggaaga atttctgtgt ctcagccaaa aatgcgttca    1740
tgctactcat gcgaaacatt gtcaggtgg tcgtcctgga caaagtcaca gacctgctgc    1800
tgttctttgg gaagctgctg gtggtcgag gcgtgggggt cctgtccttc tttttttct    1860 ccggtcgcat cccggggctg ggtaaagact ttaagagccc ccacctcaac tattactggc    1920
tgcccatcat gacctccatc ctgggggcct atgtcatcgc cagcggcttc ttcagcgttt    1980
tcggcatgtg tgtggacacg ctcttcctct gcttcctgga agacctggag cggaacaacg    2040
gctccctgga ccggccctac tacatgtcca agagccttct aaagattctg ggcaagaaga    2100
acgaggcgcc cccggacaac aagaagagga agaagtgaca gctccggccc tgatccagga    2160 ctgcaccca cccccaccgt ccagccatcc aacctcactt cgccttacag gtctccattt    2220
tgtggtaaaa aaaggtttta ggccaggcgc cgtggctcac gcctgtaatc caacactttg    2280
agaggctgag gcgggcggat caccctgagtc aggagttcga gaccagcctg gccaacatgg    2340
```

```
tgaaacctcc gtctctatta aaaatacaaa aattagccga gagtggtggc atgcacctgt    2400
catcccagct actcgggagg ctgaggcagg agaatcgctt gaacccggga ggcagaggtt    2460
gcagtgagcc gagatcgcgc cactgcactc caacctgggt gacagactct gtctccaaaa    2520
caaaacaaac aaacaaaaag attttattaa agatattttg ttaactcagt aaaaaaaaaa    2580
aaaaaaa                                                              2587

<210> SEQ ID NO 5
<211> LENGTH: 710
<212> TYPE: PRT
<213> ORGANISM: Homo Sapiens

<400> SEQUENCE: 5

Met Gly Gly Lys Gln Arg Asp Glu Asp Glu Ala Tyr Gly Lys Pro
 1               5                  10                  15

Val Lys Tyr Asp Pro Ser Phe Arg Gly Pro Ile Lys Asn Arg Ser Cys
             20                  25                  30

Thr Asp Val Ile Cys Cys Val Leu Phe Leu Leu Phe Ile Leu Gly Tyr
             35                  40                  45

Ile Val Val Gly Ile Val Ala Trp Leu Tyr Gly Asp Pro Arg Gln Val
 50                  55                  60

Leu Tyr Pro Arg Asn Ser Thr Gly Ala Tyr Cys Gly Met Gly Glu Asn
65                   70                  75                  80

Lys Asp Lys Pro Tyr Leu Leu Tyr Phe Asn Ile Phe Ser Cys Ile Leu
                 85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
            115                 120                 125

Lys Asn Glu Phe Ser Gln Thr Val Gly Glu Val Phe Tyr Thr Lys Asn
            130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
            195                 200                 205

Ile Asp Ser Leu Asn Ala Arg Asp Ile Ser Val Lys Ile Phe Glu Asp
            210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
            275                 280                 285

Ser Ile Ser Gln Leu Gly Phe Thr Thr Asn Leu Ser Ala Tyr Gln Ser
            290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
```

```
                    325                 330                 335
Ala Ile Ala Leu Leu Lys Glu Ala Ser Lys Ala Val Gly Gln Met Met
                340                 345                 350

Ser Thr Met Phe Tyr Pro Leu Val Thr Phe Val Leu Leu Leu Ile Cys
                355                 360                 365

Ile Ala Tyr Trp Ala Met Thr Ala Leu Tyr Leu Ala Thr Ser Gly Gln
                370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
                420                 425                 430

Gly Leu Ile Gln Arg Ser Val Phe Asn Leu Gln Ile Tyr Gly Val Leu
                435                 440                 445

Gly Leu Phe Trp Thr Leu Asn Trp Val Leu Ala Leu Gly Gln Cys Val
                450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
                500                 505                 510

Gln Ile Ala Arg Val Ile Leu Glu Tyr Ile Asp His Lys Leu Arg Gly
                515                 520                 525

Val Gln Asn Pro Val Ala Arg Cys Ile Met Cys Cys Phe Lys Cys Cys
                530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
                580                 585                 590

Lys Val Thr Asp Leu Leu Leu Phe Phe Gly Lys Leu Leu Val Val Gly
                595                 600                 605

Gly Val Gly Val Leu Ser Phe Phe Phe Ser Gly Arg Ile Pro Gly
                610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
                660                 665                 670

Asp Leu Glu Arg Asn Asn Gly Ser Leu Asp Arg Pro Tyr Tyr Met Ser
                675                 680                 685

Lys Ser Leu Leu Lys Ile Leu Gly Lys Lys Asn Glu Ala Pro Pro Asp
                690                 695                 700

Asn Lys Lys Arg Lys Lys
705                 710

<210> SEQ ID NO 6
<211> LENGTH: 2587
<212> TYPE: DNA
<213> ORGANISM: Homo Sapiens
```

```
<400> SEQUENCE: 6
gagccatggg gggaaagcag cgggacgagg atgacgaggc ctacgggaag ccagtcaaat      60
acgacccctc ctttcgaggc cccatcaaga acagaagctg cacagatgtc atctgctgcg     120
tcctcttcct gctcttcatt ctaggttaca tcgtggtggg gattgtgccc tggttgtatg     180
gagacccccg gcaagtcctc taccccagga actctactgg ggcctactgt ggcatggggg     240
agaacaaaga taagccgtat ctcctgtact tcaacatctt cagctgcatc ctgtccagca     300
acatcatctc agttgctgag aacggcctac agtgccccac accccaggtg tgtgtgtcct     360
cctgcccgga ggacccatgg actgtgggaa aaaacgagtt ctcacagact gttggggaag     420
tcttctatac aaaaaacagg aacttttgtc tgccaggggt accctggaat atgacggtga     480
tcacaagcct gcaacaggaa ctctgcccca gtttcctcct cccctctgct ccagctctgg     540
ggcgctgctt tccatggacc aacattactc caccggcgct cccagggatc accaatgaca     600
ccaccataca gcggggatc agcggtctta ttgacagcct caatgcccga gacatcagtg     660
ttaagatctt tgaagatttt gcccagtcct ggtattggat tcttgttgcc ctgggggtgg     720
ctctggtctt gagcctactg tttatcttgc ttctgcgcct ggtggctggg cccctggtgc     780
tggtgctgat cctgggagtg ctgggcgtgc tggcatacgg catctactac tgctgggagg     840
agtaccgagt gctgcgggac aagggcgcct ccatctccca gctgggtttc accaccaacc     900
tcagtgccta ccagagcgtg caggagacct ggctggccgc cctgatcgtg ttggcggtgc     960
ttgaagccat cctgctgctg atgctcatct tcctgcggca gcggattcgt attgccatcg    1020
ccctcctgaa ggaggccagc aaggctgtgg gacagatgat gtctaccatg ttctacccac    1080
tggtcacctt tgtcctcctc ctcatctgca ttgcctactg gccatgact gctctgtacc     1140 tggctacatc ggggcaaccc cagtatgtgc tctgggcatc caacatcagc tcccccggct    1200
gtgagaaagt gccaataaat acatcatgca accccacggc ccaccttgtg aactcctcgt    1260
gcccagggct gatgtgcgtc ttccagggct actcatccaa aggcctaatc caacgttctg    1320
tcttcaatct gcaaatctat ggggtcctgg ggctcttctg gacccttaac tgggtactgg    1380
ccctgggcca atgcgtcctc gctggagcct ttgcctcctt ctactgggcc ttccacaagc    1440
cccaggacat ccctaccttc cccttaatct ctgccttcat ccgcacactc cgttaccaca    1500
ctgggtcatt ggcatttgga gccctcatcc tgacccttgt gcagatagcc cgggtcatct    1560
tggagtatat tgaccacaag ctcagaggag tgcagaaccc tgtagcccgc tgcatcatgt    1620
gctgtttcaa gtgctgcctc tggtgtctgg aaaaatttat caagttccta aaccgcaatg    1680
catacatcat gatcgccatc tacgggaaga attctgtgt ctcagccaaa aatgcgttca    1740
tgctactcat gcgaaacatt gtcagggtgg tcgtcctgga caaagtcaca gacctgctgc    1800
tgttctttgg gaagctgctg gtggtcggag gcgtgggggt cctgtccttc tttttttct    1860 ccggtcgcat cccggggctg ggtaaagact taagagccc ccacctcaac tattactggc    1920
tgcccatcat gacctccatc ctgggggcct atgtcatcgc cagcggcttc ttcagcgttt    1980
tcggcatgtg tgtggacacg ctcttcctct gcttcctgga agacctggag cggaacaacg    2040
gctccctgga ccggccctac tacatgtcca agagccttct aaagattctg gcaagaaga    2100 acgaggcgcc cccggacaac aagaagagga gaagtgaca gctccggccc tgatccagga    2160
ctgcacccca cccccaccgt ccagccatcc aacctcactt cgccttacag gtctccattt    2220
tgtggtaaaa aaaggtttta ggccaggcgc cgtggctcac gcctgtaatc caacactttg    2280
agaggctgag gcgggcggat cacctgagtc aggagttcga gaccagcctg gccaacatgg    2340
```

-continued

```
tgaaacctcc gtctctatta aaaatacaaa aattagccga gagtggtggc atgcacctgt    2400
catcccagct actcgggagg ctgaggcagg agaatcgctt gaacccggga ggcagaggtt    2460
gcagtgagcc gagatcgcgc cactgcactc caacctgggt gacagactct gtctccaaaa    2520
caaaacaaac aaacaaaaag attttattaa agatattttg ttaactcagt aaaaaaaaaa    2580
aaaaaaa                                                               2587
```

<210> SEQ ID NO 7
<211> LENGTH: 710
<212> TYPE: PRT
<213> ORGANISM: Homo Sapiens

<400> SEQUENCE: 7

```
Met Gly Gly Lys Gln Arg Asp Glu Asp Asp Glu Ala Tyr Gly Lys Pro
 1               5                  10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Ile Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335
```

Ala Ile Ala Leu Leu Lys Glu Ala Ser Lys Ala Val Gly Gln Met Met
        340                 345                 350

Ser Thr Met Phe Tyr Pro Leu Thr Phe Val Leu Leu Leu Ile Cys
        355                 360                 365

Ile Ala Tyr Trp Ala Met Thr Ala Leu Tyr Leu Ala Thr Ser Gly Gln
370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
                420                 425                 430

Gly Leu Ile Gln Arg Ser Val Phe Asn Leu Gln Ile Tyr Gly Val Leu
                435                 440                 445

Gly Leu Phe Trp Thr Leu Asn Trp Val Leu Ala Leu Gly Gln Cys Val
450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
                500                 505                 510

Gln Ile Ala Arg Val Ile Leu Glu Tyr Ile Asp His Lys Leu Arg Gly
                515                 520                 525

Val Gln Asn Pro Val Ala Arg Cys Ile Met Cys Cys Phe Lys Cys Cys
                530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Val Leu Asp
                580                 585                 590

Lys Val Thr Asp Leu Leu Phe Gly Lys Leu Leu Val Val Gly
                595                 600                 605

Gly Val Gly Val Leu Ser Phe Phe Phe Ser Gly Arg Ile Pro Gly
610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
                660                 665                 670

Asp Leu Glu Arg Asn Asn Gly Ser Leu Asp Arg Pro Tyr Tyr Met Ser
                675                 680                 685

Lys Ser Leu Leu Lys Ile Leu Gly Lys Lys Asn Glu Ala Pro Pro Asp
                690                 695                 700

Asn Lys Lys Arg Lys Lys
705                 710

<210> SEQ ID NO 8
<211> LENGTH: 2587
<212> TYPE: DNA
<213> ORGANISM: Homo Sapiens

<400> SEQUENCE: 8

-continued

```
gagccatggg gggaaagcag cgggacgagg atgacgaggc ctacgggaag ccagtcaaat      60
acgacccctc ctttcgaggc cccatcaaga acagaagctg cacagatgtc atctgctgcg     120
tcctcttcct gctcttcatt ctaggttaca tcgtggtggg gattgtggcc tggttgtatg     180 gagaccccg gcaagtcctc taccccagga actctactgg ggcctactgt ggcatggggg     240
agaacaaaga taagccgtat ctcctgtact tcaacatctt cagctgcatc ctgtccagca     300
acatcatctc agttgctgag aacggcctac agtgccccac accccaggtg tgtgtgtcct     360
cctgcccgga ggacccatgg actgtgggaa aaaacgagtt ctcacagact gttggggaag     420
tcttctatac aaaaaacagg aacttttgtc tgccagggt accctggaat atgacggtga     480
tcacaagcct gcaacaggaa ctctgcccca gtttcctcct cccctctgct ccagctctgg     540
ggcgctgctt tccatggacc aacgttactc caccggcgct cccagggatc accaatgaca     600
ccaccataca gcagggatc agcggtctta ttgacagcct caatgcccga gacatcagtg     660
ttaagatctt tgaagatttt gcccagtcct ggtattggat tcttgttgcc ctggggtgg     720 ctctggtctt gagcctactg tttatcttgc ttctgcgcct ggtggctggg ccctggtgc     780 tggtgctgat cctgggagtg ctgggcgtgc tggcatatgg catctactac tgctgggagg     840
agtaccgagt gctgcgggac aagggcgcct ccatctccca gctgggttc accaccaacc     900 tcagtgccta ccagagcgtg caggagacct ggctggccgc cctgatcgtg ttggcggtgc     960
ttgaagccat cctgctgctg atgctcatct tcctgcggca gcggattcgt attgccatcg    1020
ccctcctgaa ggaggccagc aaggctgtgg acagatgat gtctaccatg ttctacccac    1080
tggtcacctt tgtcctcctc ctcatctgca ttgcctactg ggccatgact gctctgtacc    1140
tggctacatc ggggcaaccc cagtatgtgc tctgggcatc aacatcagc tcccccggct    1200 gtgagaaagt gccaataaat acatcatgca accccacggc ccaccttgtg aactcctcgt    1260
gcccagggct gatgtgcgtc ttccagggct actcatccaa aggcctaatc caacgttctg    1320
tcttcaatct gcaaatctat ggggtcctgg ggctcttctg gacccttaac tgggtactgg    1380
ccctgggcca atgcgtcctc gctggagcct ttgcctcctt ctactgggcc ttccacaagc    1440
cccaggacat ccctaccttc cccttaatct ctgccttcat ccgcacactc cgttaccaca    1500
ctgggtcatt ggcatttgga gccctcatcc tgacccttgt gcagatagcc cgggtcatct    1560
tggagtatat tgaccacaag ctcagaggag tgcagaaccc tgtagcccgc tgcatcatgt    1620
gctgtttcaa gtgctgcctc tggtgtctgg aaaaatttat caagttccta aaccgcaatg    1680
catacatcat gatcgccatc tacgggaaga atttctgtgt ctcagccaaa aatgcgttca    1740
tgctactcat gcgaaacatt gtcagggtgg tcgtcctgga caaagtcaca gacctgctgc    1800
tgttctttgg gaagctgctg tggtcggag cgtggggt cctgtccttc ttttttttct    1860
ccggtcgcat cccggggctg ggtaaagact ttaagagccc ccacctcaac tattactggc    1920
tgcccatcat gacctccatc ctgggggcct atgtcatcgc cagcggcttc ttcagcgttt    1980
tcggcatgtg tgtggacacg ctcttcctct gcttcctgga agacctggag cggaacaacg    2040
gctccctgga ccggccctac tacatgtcca agagccttct aaagattctg ggcaagaaga    2100
acgaggcgcc cccggacaac aagaagagga gaagtgaca gctccggccc tgatccagga    2160 ctgcaccca cccccaccgt ccagccatcc aacctcactt cgccttacag gtctccattt    2220
tgtggtaaaa aaaggtttta ggccaggcgc cgtggctcac gcctgtaatc caacactttg    2280
agaggctgag gcgggcggat cacctgagtc aggagttcga gaccagcctg gccaacatgg    2340 tgaaaccctcc gtctctatta aaaatacaaa aattagccga gagtggtggc atgcacctgt    2400
```

-continued

```
catcccagct actcgggagg ctgaggcagg agaatcgctt gaacccggga ggcagaggtt      2460
gcagtgagcc gagatcgcgc cactgcactc caacctgggt gacagactct gtctccaaaa      2520
caaaacaaac aaacaaaaag attttattaa agatattttg ttaactcagt aaaaaaaaaa      2580
aaaaaaa                                                                2587
```

<210> SEQ ID NO 9
<211> LENGTH: 710
<212> TYPE: PRT
<213> ORGANISM: Homo Sapiens

<400> SEQUENCE: 9

```
Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
                35                  40                  45

Ile Val Val Gly Ile Val Ala Trp Leu Tyr Gly Asp Pro Arg Gln Val
50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335
```

```
Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Leu Ile Cys
        355                 360                 365

Ile Ala Tyr Trp Ala Met Thr Ala Leu Tyr Leu Ala Thr Ser Gly Gln
    370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
        435                 440                 445

Gly Leu Phe Trp Thr Leu Asn Trp Val Leu Ala Leu Gly Gln Cys Val
    450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
        515                 520                 525

Val Gln Asn Pro Val Ala Arg Cys Ile Met Cys Cys Phe Lys Cys Cys
    530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Val Leu Asp
            580                 585                 590

Lys Val Thr Asp Leu Leu Leu Phe Phe Gly Lys Leu Leu Val Val Gly
        595                 600                 605

Gly Val Gly Val Leu Ser Phe Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
        675                 680                 685

Lys Ser Leu Leu Lys Ile Leu Gly Lys Lys Asn Glu Ala Pro Pro Asp
    690                 695                 700

Asn Lys Lys Arg Lys Lys
705                 710

<210> SEQ ID NO 10
<211> LENGTH: 2587
<212> TYPE: DNA
<213> ORGANISM: Homo Sapiens

<400> SEQUENCE: 10

```

```
gagccatggg gggaaagcag cgggacgagg atgacgaggc ctacgggaag ccagtcaaat      60
acgacccctc ctttcgaggc cccatcaaga acagaagctg cacagatgtc atctgctgcg     120
tcctcttcct gctcttcatt ctaggttaca tcgtggtggg gattgtggcc tggttgtatg     180
gagacccccg gcaagtcctc taccccagga actctactgg ggcctactgt ggcatggggg     240
agaacaaaga taagccgtat ctcctgtact tcaacatctt cagctgcatc ctgtccagca     300
acatcatctc agttgctgag aacggctac agtgccccac accccaggtg tgtgtgtcct      360
cctgcccgga ggacccatgg actgtgggaa aaacgagtt ctcacagact gttggggaag      420
tcttctatac aaaaaacagg aacttttgtc tgccaggggt accctggaat atgacggtga     480
tcacaagcct gcaacaggaa ctctgcccca gtttcctcct ccctctgct ccagctctgg      540 ggcgctgctt tccatggacc aacgttactc caccggcgct cccagggatc accaatgaca     600
ccaccataca gcagggatc agcggtctta ttgacagcct caatgcccga gacatcagtg      660
ttaagatctt tgaagatttt gcccagtcct ggtattggat tcttgttgcc ctggggtgg      720 ctctggtctt gagcctactg tttatcttgc ttctgcgcct ggtggctggg ccctggtgc      780 tggtgctgat cctgggagtg ctgggcgtgc tggcatacgg catctactac tgctgggagg     840
agtaccgagt gctgcgggac aagggcgcct ccatctccca gctgggtttc accaccaacc     900
tcagtgccta ccagagcgtg caggagacct ggctggccgc cctgatcgtg ttggcggtgc     960
ttgaagccat cctgctgctg gtgctcatct tcctgcggca gcggattcgt attgccatcg    1020
ccctcctgaa ggaggccagc aaggctgtgg acagatgat gtctaccatg ttctacccac     1080
tggtcaccct tgtcctcctc ctcatctgca ttgcctactg ggccatgact gctctgtacc    1140
tggctacatc ggggcaaccc cagtatgtgc tctgggcatc caacatcagc tcccccggct    1200
gtgagaaagt gccaataaat acatcatgca accccacggc ccaccttgtg aactcctcgt    1260
gcccagggct gatgtgcgtc ttccagggct actcatccaa aggcctaatc caacgttctg    1320
tcttcaatct gcaaatctat ggggtcctgg ggctcttctg gacccttaac tgggtactgg    1380
ccctgggcca atgcgtcctc gctggagcct ttgcctcctt ctactgggcc ttccacaagc    1440
cccaggacat ccctaccttc cccttaatct ctgccttcat ccgcacactc cgttaccaca    1500
ctgggtcatt ggcatttgga gccctcatcc tgaccttgt gcagatagcc cgggtcatct    1560
tggagtatat tgaccacaag ctcagaggag tgcagaaccc tgtagcccgc tgcatcatgt    1620
gctgtttcaa gtgctgcctc tggtgtctgg aaaaatttat caagttccta accgcaatg     1680 catacatcat gatcgccatc tacgggaaga atttctgtgt ctcagccaaa aatgcgttca    1740
tgctactcat gcgaaacatt gtcagggtgg tcgtcctgga caaagtcaca gacctgctgc    1800
tgttcttggg gaagctgctg gtggtcgag gcgtgggggt cctgtccttc ttttttttct    1860
ccggtcgcat cccggggctg ggtaaagact ttaagagccc ccacctcaac tattactggc    1920
tgcccatcat gacctccatc ctgggggcct atgtcatcgc cagcggcttc ttcagcgttt    1980
tcggcatgtg tgtggacacg ctcttcctct gcttcctgga agacctggag cggaacaacg    2040
gctccctgga ccgccctac tacatgtcca agagccttct aaagattctg gcaagaaga     2100 acgaggcgcc cccggacaac aagaagagga gaagtgaca gctccggccc tgatccagga    2160
ctgcacccca ccccaccgt ccagccatcc aacctcactt cgccttacag gtctccattt    2220
tgtggtaaaa aaaggtttta ggccaggcgc cgtggctcac gcctgtaatc caacactttg    2280
agaggctgag gcgggcggat cacctgagtc aggagttcga gaccagcctg ccaacatgg    2340 tgaaacctcc gtctctatta aaaatacaaa aattagccga gagtggtggc atgcacctgt    2400
```

-continued

```
catcccagct actcgggagg ctgaggcagg agaatcgctt gaacccggga ggcagaggtt    2460
gcagtgagcc gagatcgcgc cactgcactc caacctggga gacagactct gtctccaaaa    2520 caaacaaac aaacaaaaag attttattaa agatattttg ttaactcagt aaaaaaaaaa     2580
aaaaaaa                                                              2587
```

<210> SEQ ID NO 11
<211> LENGTH: 710
<212> TYPE: PRT
<213> ORGANISM: Homo Sapiens

<400> SEQUENCE: 11

```
Met Gly Gly Lys Gln Arg Asp Glu Asp Glu Ala Tyr Gly Lys Pro
 1               5                  10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Val Leu Ile Phe Leu Arg Gln Arg Ile Arg Ile
                325                 330                 335

Ala Ile Ala Leu Leu Lys Glu Ala Ser Lys Ala Val Gly Gln Met Met
```

```
                    340                 345                 350
Ser Thr Met Phe Tyr Pro Leu Val Thr Phe Val Leu Leu Leu Ile Cys
            355                 360                 365

Ile Ala Tyr Trp Ala Met Thr Ala Leu Tyr Leu Ala Thr Ser Gly Gln
            370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
            405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
            435                 440                 445

Gly Leu Phe Trp Thr Leu Asn Trp Val Leu Ala Leu Gly Gln Cys Val
            450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
            485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
            515                 520                 525

Val Gln Asn Pro Val Ala Arg Cys Ile Met Cys Cys Phe Lys Cys Cys
            530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
            565                 570                 575

Ala Phe Met Leu Leu Met Arg Asn Ile Val Arg Val Val Val Leu Asp
            580                 585                 590

Lys Val Thr Asp Leu Leu Leu Phe Phe Gly Lys Leu Leu Val Val Gly
            595                 600                 605

Gly Val Gly Val Leu Ser Phe Phe Phe Ser Gly Arg Ile Pro Gly
            610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
            645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
            675                 680                 685

Lys Ser Leu Leu Lys Ile Leu Gly Lys Lys Asn Glu Ala Pro Pro Asp
            690                 695                 700

Asn Lys Lys Arg Lys Lys
705                 710

<210> SEQ ID NO 12
<211> LENGTH: 2587
<212> TYPE: DNA
<213> ORGANISM: Homo Sapiens

<400> SEQUENCE: 12
gagccatggg gggaaagcag cgggacgagg atgacgaggc ctacgggaag ccagtcaaat      60
```

```
acgacccctc ctttcgaggc cccatcaaga acagaagctg cacagatgtc atctgctgcg    120
tcctcttcct gctcttcatt ctaggttaca tcgtggtggg gattgtggcc tggttgtatg    180 gagaccccg gcaagtcctc tacccagga actctactgg ggcctactgt ggcatggggg     240
agaacaaaga taagccgtat ctcctgtact tcaacatctt cagctgcatc ctgtccagca    300
acatcatctc agttgctgag aacggcctac agtgccccac accccaggtg tgtgtgtcct    360
cctgcccgga ggacccatgg actgtgggaa aaacgagtt ctcacagact gttggggaag     420
tcttctatac aaaaaacagg aacttttgtc tgccaggggt accctggaat atgacggtga    480
tcacaagcct gcaacaggaa ctctgcccca gtttcctcct ccctctgct ccagctctgg     540 ggcgctgctt tccatggacc aacgttactc caccggcgct cccagggatc accaatgaca    600
ccaccataca gcagggatc agcggtctta ttgacagcct caatgcccga gacatcagtg     660
ttaagatctt tgaagatttt gcccagtcct ggtattggat tcttgttgcc ctggggtgg     720 ctctggtctt gagcctactg tttatcttgc ttctgcgcct ggtggctggg ccctggtgc     780 tggtgctgat cctgggagtg ctgggcgtgc tggcatacgg catctactac tgctgggagg    840
agtaccgagt gctgcgggac aagggcgcct ccatctccca gctgggtttc accaccaacc    900
tcagtgccta ccagagcgtg caggagacct ggctggccgc cctgatcgtg ttggcggtgc    960
ttgaagccat cctgctgctg atgctcatct tcctgcggca gcggattcgt attgccatcg   1020
ccctcctgaa ggaggccagc aaggctgtgg gacagatgat gtctaccatg ttctacccac   1080
tggtcacctt tgtcctcctc ctcatctgca ttgcctactg ggccatgact gctctgtacc   1140
tggctacatc ggggcaaccc cagtatgtgc tctgggcatc caacatcagc tcccccggct   1200
gtgagaaagt gccaataaat acatcatgca accccacggc ccaccttgtg aactcctcgt   1260
gcccagggct gatgtgcgtc ttccagggct actcatccaa aggcctaatc ccacgttctg   1320
tcttcaatct gcaaatctat ggggtcctgg ggctcttctg gaccccttaac tgggtactgg   1380 ccctgggcca atgcgtcctc gctggagcct ttgcctcctt ctactgggcc ttccacaagc   1440
cccaggacat ccctacctt ccttaatct ctgccttcat ccgcacactc cgttaccaca     1500
ctgggtcatt ggcattggga gccctcatcc tgacccttgt gcagatagcc cgggtcatct   1560
tggagtatat tgaccacaag ctcagaggag tgcagaaccc tgtagcccgc tgcatcatgt   1620
gctgtttcaa gtgctgcctc tggtgtctgg aaaaatttat caagttccta aaccgcaatg   1680
catacatcat gatcgccatc tacgggaaga atttctgtgt ctcagccaaa aatgcgttca    1740
tgctactcat gcgaaacatt gtcagggtgg tcgtcctgga caaagtcaca gacctgctgc   1800
tgttctttgg gaagctgctg gtggtcggag gcgtgggggt cctgtccttc tttttttct     1860 ccggtcgcat cccgggggctg ggtaaagact ttaagagccc ccacctcaac tattactggc   1920
tgcccatcat gacctccatc ctgggggcct atgtcatcgc cagcggcttc ttcagcgttt   1980
tcggcatgtg tgtggacacg ctcttcctct gcttcctgga agacctggag cggaacaacg   2040
gctccctgga ccggccctac tacatgtcca agagccttct aaagattctg ggcaagaaga   2100
acgaggcgcc cccggacaac aagaagagga agaagtgaca gctccggccc tgatccagga   2160
ctgcacccca cccccaccgt ccagccatcc aacctcactt cgccttacag gtctccattt   2220
tgtggtaaaa aaaggtttta ggccaggcgc cgtggctcac gcctgtaatc caacactttg   2280
agaggctgag gcgggcggat cacctgagtc aggagttcga gaccagcctg gccaacatgg   2340
tgaaacctcc gtctctatta aaaatacaaa aattagccga gagtggtggc atgcacctgt   2400
catcccagct actcgggagg ctgaggcagg agaatcgctt gaacccggga ggcagaggtt   2460
```

```
gcagtgagcc gagatcgcgc cactgcactc caacctgggt gacagactct gtctccaaaa    2520 caaacaaac  aaacaaaaag attttattaa agatattttg ttaactcagt aaaaaaaaaa    2580
aaaaaaa                                                               2587
```

<210> SEQ ID NO 13
<211> LENGTH: 710
<212> TYPE: PRT
<213> ORGANISM: Homo Sapiens

<400> SEQUENCE: 13

```
Met Gly Gly Lys Gln Arg Asp Glu Asp Glu Ala Tyr Gly Lys Pro
 1               5                  10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
                35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
                100                 105                 110

Pro Gln Val Cys Val Ser Ser Cys Pro Glu Asp Pro Trp Thr Val Gly
                115                 120                 125

Lys Asn Glu Phe Ser Gln Thr Val Gly Glu Val Phe Tyr Thr Lys Asn
        130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
                180                 185                 190

Pro Gly Ile Thr Asn Asp Thr Thr Ile Gln Gln Gly Ile Ser Gly Leu
                195                 200                 205

Ile Asp Ser Leu Asn Ala Arg Asp Ile Ser Val Lys Ile Phe Glu Asp
        210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
                260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
                340                 345                 350
```

```
Ser Thr Met Phe Tyr Pro Leu Val Thr Phe Val Leu Leu Leu Ile Cys
            355                 360                 365

Ile Ala Tyr Trp Ala Met Thr Ala Leu Tyr Leu Ala Thr Ser Gly Gln
        370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Pro Arg Ser Val Phe Asn Leu Gln Ile Tyr Gly Val Leu
        435                 440                 445

Gly Leu Phe Trp Thr Leu Asn Trp Val Leu Ala Leu Gly Gln Cys Val
        450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
        515                 520                 525

Val Gln Asn Pro Val Ala Arg Cys Ile Met Cys Cys Phe Lys Cys Cys
        530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Val Leu Asp
            580                 585                 590

Lys Val Thr Asp Leu Leu Leu Phe Phe Gly Lys Leu Leu Val Val Gly
        595                 600                 605

Gly Val Gly Val Leu Ser Phe Phe Phe Ser Gly Arg Ile Pro Gly
        610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
        675                 680                 685

Lys Ser Leu Leu Lys Ile Leu Gly Lys Lys Asn Glu Ala Pro Pro Asp
        690                 695                 700

Asn Lys Lys Arg Lys Lys
705                 710

<210> SEQ ID NO 14
<211> LENGTH: 2251
<212> TYPE: DNA
<213> ORGANISM: Homo Sapiens

<400> SEQUENCE: 14
gagccatggg gggaaagcag cgggacgagg atgacgaggc ctacgggaag ccagtcaaat     60
```

```
acgacccctc ctttcgaggc cccatcaaga acagaagctg cacagatgtc atctgctgcg    120
tcctcttcct gctcttcatt ctaggttaca tcgtggtggg gattgtggcc tggttgtatg    180 gagaccccg  gcaagtcctc taccccagga actctactgg ggcctactgt ggcatggggg    240
agaacaaaga taagccgtat ctcctgtact tcaacatctt cagctgcatc ctgtccagca    300
acatcatctc agttgctgag aacggcctac agtgccccac accccaggtg tgtgtgtcct    360
cctgcccgga ggacccatgg actgtgggaa aaaacgagtt ctcacagact gttggggaag    420
tcttctatac aaaaaacagg aacttttgtc tgccaggggt accctggaat atgacggtga    480
tcacaagcct gcaacaggaa ctctgcccca gtttcctcct ccctctgct  ccagctctgg    540 ggcgctgctt tccatggacc aacgttactc caccggcgct cccagggatc accaatgaca    600
ccaccataca gcagggatc  agcggtctta ttgacagccc caatgcccga gacatcagtg    660
ttaagatctt tgaagatttt gcccagtcct ggtattggat tcttgtggct gtgggacaga    720
tgatgtctac catgttctac ccactggtca cctttgtcct cctcctcatc tgcattgcct    780
actgggccat gactgctctg tacctggcta catcggggca accccagtat gtgctctggg    840
catccaacat cagctccccc ggctgtgaga aagtgccaat aaatacatca tgcaacccca    900
cggcccacct tgtgaactcc tcgtgcccag ggctgatgtg cgtcttccag ggctactcat    960
ccaaaggcct aatccaacgt tctgtcttca atctgcaaat ctatgggtc  ctggggctct   1020 tctggaccct taactgggta ctggccctgg gccaatgcgt cctcgctgga gcctttgcct   1080
ccttctactg ggccttccac aagccccagg acatccctac cttcccctta atctctgcct   1140
tcatccgcac actccgttac cacactgggt cattggcatt tggagccctc atcctgaccc   1200
ttgtgcagat agcccgggtc atcttggagt atattgacca caagctcaga ggagtgcaga   1260
accctgtagc ccgctgcatc atgtgctgtt tcaagtgctg cctctggtgt ctggaaaaat   1320
ttatcaagtt cctaaaccgc aatgcataca tcatgatcgc catctacggg aagaatttct   1380
gtgtctcagc caaaaatgcg ttcatgctac tcatgcgaaa cattgtcagg gtggtcgtcc   1440
tggacaaagt cacagacctg ctgctgttct ttgggaagct gctggtggtc ggaggcgtgg   1500
gggtcctgtc cttctttttt ttctccggtc gcatcccggg gctgggtaaa gactttaaga   1560
gcccccacct caactattac tggctgccca tcatgacctc catcctgggg gcctatgtca   1620
tcgccagcgg cttcttcagc gttttcggca tgtgtgtgga cacgctcttc ctctgcttcc   1680
tggaagacct ggagcggaac aacggctccc tggaccggcc ctactacatg tccaagagcc   1740
ttctaaagat tctgggcaag aagaacgagg cgccccgga  caacaagaag aggaagaagt   1800
gacagctccg gccctgatcc aggactgcac cccacccca  ccgtccagcc atccaacctc   1860
acttcgcctt acaggtctcc attttgtggt aaaaaaggt  tttaggccag cgccgtggc   1920 tcacgcctgt aatccaacac tttgagaggc tgaggcgggc ggatcacctg agtcaggagt   1980
tcgagaccag cctggccaac atggtgaaac ctccgtctct attaaaaata caaaattag   2040 ccgagagtgg tggcatgcac ctgtcatccc agctactcgg gaggctgagg caggagaatc   2100
gcttgaaccc gggaggcaga ggttgcagtg agccgagatc gcgccactgc actccaacct   2160
gggtgacaga ctctgtctcc aaaacaaaac aaacaaacaa aaagatttta ttaaagatat   2220
tttgttaact cagtaaaaaa aaaaaaaaaa a                                  2251
```

<210> SEQ ID NO 15
<211> LENGTH: 598
<212> TYPE: PRT
<213> ORGANISM: Homo Sapiens -continued

<400> SEQUENCE: 15

```
Met Gly Gly Lys Gln Arg Asp Glu Asp Glu Ala Tyr Gly Lys Pro
 1               5                  10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
 50                  55                  60

Leu Tyr Pro Arg Asn Ser Thr Gly Ala Tyr Cys Gly Met Gly Glu Asn
 65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Val Gly Gln Met Met
225                 230                 235                 240

Ser Thr Met Phe Tyr Pro Leu Val Thr Phe Val Leu Leu Ile Cys
                245                 250                 255

Ile Ala Tyr Trp Ala Met Thr Ala Leu Tyr Leu Ala Thr Ser Gly Gln
            260                 265                 270

Pro Gln Tyr Val Leu Trp Ala Ser Asn Ile Ser Ser Pro Gly Cys Glu
        275                 280                 285

Lys Val Pro Ile Asn Thr Ser Cys Asn Pro Thr Ala His Leu Val Asn
290                 295                 300

Ser Ser Cys Pro Gly Leu Met Cys Val Phe Gln Gly Tyr Ser Ser Lys
305                 310                 315                 320

Gly Leu Ile Gln Arg Ser Val Phe Asn Leu Gln Ile Tyr Gly Val Leu
                325                 330                 335

Gly Leu Phe Trp Thr Leu Asn Trp Val Leu Ala Leu Gly Gln Cys Val
            340                 345                 350

Leu Ala Gly Ala Phe Ala Ser Phe Tyr Trp Ala Phe His Lys Pro Gln
        355                 360                 365

Asp Ile Pro Thr Phe Pro Leu Ile Ser Ala Phe Ile Arg Thr Leu Arg
370                 375                 380

Tyr His Thr Gly Ser Leu Ala Phe Gly Ala Leu Ile Leu Thr Leu Val
385                 390                 395                 400

Gln Ile Ala Arg Val Ile Leu Glu Tyr Ile Asp His Lys Leu Arg Gly
                405                 410                 415
```

```
Val Gln Asn Pro Val Ala Arg Cys Ile Met Cys Cys Phe Lys Cys Cys
            420                 425                 430

Leu Trp Cys Leu Glu Lys Phe Ile Lys Phe Leu Asn Arg Asn Ala Tyr
        435                 440                 445

Ile Met Ile Ala Ile Tyr Gly Lys Asn Phe Cys Val Ser Ala Lys Asn
450                 455                 460

Ala Phe Met Leu Leu Met Arg Asn Ile Val Arg Val Val Leu Asp
465                 470                 475                 480

Lys Val Thr Asp Leu Leu Leu Phe Phe Gly Lys Leu Leu Val Val Gly
                485                 490                 495

Gly Val Gly Val Leu Ser Phe Phe Phe Ser Gly Arg Ile Pro Gly
            500                 505                 510

Leu Gly Lys Asp Phe Lys Ser Pro His Leu Asn Tyr Tyr Trp Leu Pro
        515                 520                 525

Ile Met Thr Ser Ile Leu Gly Ala Tyr Val Ile Ala Ser Gly Phe Phe
530                 535                 540

Ser Val Phe Gly Met Cys Val Asp Thr Leu Phe Leu Cys Phe Leu Glu
545                 550                 555                 560

Asp Leu Glu Arg Asn Asn Gly Ser Leu Asp Arg Pro Tyr Tyr Met Ser
                565                 570                 575

Lys Ser Leu Leu Lys Ile Leu Gly Lys Lys Asn Glu Ala Pro Pro Asp
                580                 585                 590

Asn Lys Lys Arg Lys Lys
            595

<210> SEQ ID NO 16
<211> LENGTH: 2623
<212> TYPE: DNA
<213> ORGANISM: Homo Sapiens

<400> SEQUENCE: 16
gagccatggg gggaaagcag cgggacgagg atgacgaggc ctacgggaag ccagtcaaat      60
acgacccctc ctttcgaggc cccatcaaga acagaagctg cacagatgtc atctgctgcg    120
tcctcttcct gctcttcatt ctaggttaca tcgtggtggg gattgtggcc tggttgtatg    180 gagaccccg gcaagtcctc taccccagga actctactgg ggcctactgt ggcatggggg    240
agaacaaaga taagccgtat ctcctgtact tcaacatctt cagctgcatc ctgtccagca    300
acatcatctc agttgctgag aacggcctac agtgccccac accccaggtg tgtgtgtcct    360
cctgcccgga ggaccatgg actgtgggaa aaaacgagtt ctcacagact gttgggaag     420 tcttctatac aaaaaacagg aacttttgtc tgccagggt accctggaat atgacggtga    480
tcacaagcct gcaacaggaa ctctgccca gtttcctcct ccctctgct ccagctctgg    540 ggcgctgctt tccatggacc aacgttactc caccggcgct cccagggatc accaatgaca    600
ccaccataca gcagggatc agcggtctta ttgacagcct caatgcccga gacatcagtg    660
ttaagatctt tgaagatttt gcccagtcct ggtattggat tcttgttgcc ctgggggtgg    720
ctctggtctt gagcctactg tttatcttgc ttctgcgcct ggtggctggg ccctggtgc    780 tggtgctgat cctgggagtg ctgggcgtgc tggcatacgg catctactac tgctgggagg    840
agtaccgagt gctgcgggac aagggcgcct ccatctccca gctgggtttc accaccaacc    900
tcagtgccta ccagagcgtg caggagacct ggctggccgc cctgatcgtg ttggcggtgc    960
ttgaagccat cctgctgctg atgctcatct tcctgcggca gcggattcgt attgccatcg   1020
ccctcctgaa ggaggccagc aaggctgtgg acagatgat gtctaccatg ttctacccac   1080
```

-continued

```
tggtcacctt tgtcctcctc ctcatctgca ttgcctactg gccatgact gctctgtacc     1140
tggctacatc ggggcaaccc cagtatgtgc tctgggcatc aacatcagc tccccggct      1200
gtgagaaagt gccaataaat acatcatgca accccacggc ccaccttgtg aactcctcgt    1260
gcccagggct gatgtgcgtc ttccagggct actcatccaa aggcctaatc caacgttctg    1320
tcttcaatct gcaaatctat ggggtcctgg ggctcttctg gacccttaac tgggtactgg    1380
ccctgggcca atgcgtcctc gctggagcct ttgcctcctt ctactgggcc ttccacaagc    1440
cccaggacat ccctaccttc cccttaatct ctgccttcat ccgcacactc cgttaccaca    1500
ctgggtcatt ggcatttgga gccctcatcc tgacccttgt gcagatagcc cgggtcatct    1560
tggagtatat tgaccacaag ctcagaggag tgcagaaccc tgtagcccgc tgcatcatgt    1620
gctgtttcaa gtgctgcctc tggtgtctgg aaaaatttat caagttccta aaccgcaatg    1680
catacatcat gatcgccatc tacgggaaga atttctgtgt ctcagccaaa aatgcgttca    1740
tgctactcat gcgaaacatt gtcagggtgg tcgtcctgga caaagtcaca gacctgctgc    1800
tgttctttgg gaagctgctg gtggtcggag gcgtggggt cctgtccttc ttttttttct     1860
ccggtcgcat cccgggggctg ggtaaagact ttaagagccc ccacctcaac tattactggc   1920
tgcccatcat gaggaaccca ataaccccaa cgggtcatgt cttccagacc tccatcctgg    1980
gggcctatgt catcgccagc ggcttcttca gcgttttcgg catgtgtgtg gacacgctct    2040
tcctctgctt cctggaagac ctggagcgga caacggctc cctggaccgg ccctactaca    2100
tgtccaagag ccttctaaag attctgggca agaagaacga ggcgccccg gacaacaaga    2160
agaggaagaa gtgacagctc cggccctgat ccaggactgc accccacccc caccgtccag    2220
ccatccaacc tcacttcgcc ttacaggtct ccattttgtg gtaaaaaag gttttaggcc    2280
aggcgccgtg gctcacgcct gtaatccaac actttgagag gctgaggcgg gcggatcacc    2340
tgagtcagga gttcgagacc agcctggcca acatggtgaa acctccgtct ctattaaaaa    2400
tacaaaaatt agccgagagt ggtggcatgc acctgtcatc ccagctactc gggaggctga    2460
ggcaggagaa tcgcttgaac ccgggaggca gaggttgcag tgagccgaga tcgcgccact    2520
gcactccaac ctgggtgaca gactctgtct ccaaaacaaa acaaacaaac aaaaagattt    2580
tattaaagat attttgttaa ctcagtaaaa aaaaaaaaa aaa                       2623
```

<210> SEQ ID NO 17
<211> LENGTH: 722
<212> TYPE: PRT
<213> ORGANISM: Homo Sapiens

<400> SEQUENCE: 17

```
Met Gly Gly Lys Gln Arg Asp Glu Asp Asp Glu Ala Tyr Gly Lys Pro
 1               5                  10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110
```

-continued

```
Pro Gln Val Cys Val Ser Ser Cys Pro Glu Pro Trp Thr Val Gly
            115                 120                 125
Lys Asn Glu Phe Ser Gln Thr Val Gly Glu Val Phe Tyr Thr Lys Asn
            130                 135                 140
Arg Asn Phe Cys Leu Pro Gly Val Pro Trp Asn Met Thr Val Ile Thr
145                 150                 155                 160
Ser Leu Gln Gln Glu Leu Cys Pro Ser Phe Leu Leu Pro Ser Ala Pro
                165                 170                 175
Ala Leu Gly Arg Cys Phe Pro Trp Thr Asn Val Thr Pro Pro Ala Leu
            180                 185                 190
Pro Gly Ile Thr Asn Asp Thr Thr Ile Gln Gln Gly Ile Ser Gly Leu
            195                 200                 205
Ile Asp Ser Leu Asn Ala Arg Asp Ile Ser Val Lys Ile Phe Glu Asp
            210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Leu Arg Leu Val Ala Gly Pro
                245                 250                 255
Leu Val Leu Val Leu Ile Leu Gly Val Leu Gly Val Leu Ala Tyr Gly
            260                 265                 270
Ile Tyr Tyr Cys Trp Glu Glu Tyr Arg Val Leu Arg Asp Lys Gly Ala
            275                 280                 285
Ser Ile Ser Gln Leu Gly Phe Thr Thr Asn Leu Ser Ala Tyr Gln Ser
            290                 295                 300
Val Gln Glu Thr Trp Leu Ala Ala Leu Ile Val Leu Ala Val Leu Glu
305                 310                 315                 320
Ala Ile Leu Leu Leu Met Leu Ile Phe Leu Arg Gln Arg Ile Arg Ile
                325                 330                 335
Ala Ile Ala Leu Leu Lys Glu Ala Ser Lys Ala Val Gly Gln Met Met
            340                 345                 350
Ser Thr Met Phe Tyr Pro Leu Val Thr Phe Val Leu Leu Ile Cys
            355                 360                 365
Ile Ala Tyr Trp Ala Met Thr Ala Leu Tyr Leu Ala Thr Ser Gly Gln
            370                 375                 380
Pro Gln Tyr Val Leu Trp Ala Ser Asn Ile Ser Ser Pro Gly Cys Glu
385                 390                 395                 400
Lys Val Pro Ile Asn Thr Ser Cys Asn Pro Thr Ala His Leu Val Asn
                405                 410                 415
Ser Ser Cys Pro Gly Leu Met Cys Val Phe Gln Gly Tyr Ser Ser Lys
            420                 425                 430
Gly Leu Ile Gln Arg Ser Val Phe Asn Leu Gln Ile Tyr Gly Val Leu
            435                 440                 445
Gly Leu Phe Trp Thr Leu Asn Trp Val Leu Ala Leu Gly Gln Cys Val
            450                 455                 460
Leu Ala Gly Ala Phe Ala Ser Phe Tyr Trp Ala Phe His Lys Pro Gln
465                 470                 475                 480
Asp Ile Pro Thr Phe Pro Leu Ile Ser Ala Phe Ile Arg Thr Leu Arg
                485                 490                 495
Tyr His Thr Gly Ser Leu Ala Phe Gly Ala Leu Ile Leu Thr Leu Val
            500                 505                 510
Gln Ile Ala Arg Val Ile Leu Glu Tyr Ile Asp His Lys Leu Arg Gly
            515                 520                 525
Val Gln Asn Pro Val Ala Arg Cys Ile Met Cys Cys Phe Lys Cys Cys
```

| | | 530 | | | | 535 | | | | 540 | | | |
|---|---|---|---|---|---|---|---|---|---|---|---|---|---|

Leu Trp Cys Leu Glu Lys Phe Ile Lys Phe Leu Asn Arg Asn Ala Tyr
545             550                 555                 560

Ile Met Ile Ala Ile Tyr Gly Lys Asn Phe Cys Val Ser Ala Lys Asn
            565                 570                 575

Ala Phe Met Leu Leu Met Arg Asn Ile Val Arg Val Val Leu Asp
        580                 585                 590

Lys Val Thr Asp Leu Leu Leu Phe Gly Lys Leu Leu Val Val Gly
            595                 600                 605

Gly Val Gly Val Leu Ser Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Arg Asn Pro Ile Thr Pro Thr Gly His Val Phe Gln Thr Ser
                645                 650                 655

Ile Leu Gly Ala Tyr Val Ile Ala Ser Gly Phe Phe Ser Val Phe Gly
            660                 665                 670

Met Cys Val Asp Thr Leu Phe Leu Cys Phe Leu Glu Asp Leu Glu Arg
            675                 680                 685

Asn Asn Gly Ser Leu Asp Arg Pro Tyr Tyr Met Ser Lys Ser Leu Leu
690                 695                 700

Lys Ile Leu Gly Lys Asn Glu Ala Pro Pro Asp Asn Lys Lys Arg
705                 710                 715                 720

Lys Lys

<210> SEQ ID NO 18
<211> LENGTH: 2593
<212> TYPE: DNA
<213> ORGANISM: Homo Sapiens

<400> SEQUENCE: 18

```
gagccatggg gggaaagcag cgggacgagg atgacgaggc ctacgggaag ccagtcaaat    60
acgacccctc ctttcgaggc cccatcaaga acagaagctg cacagatgtc atctgctgcg   120
tcctcttcct gctcttcatt ctaggttaca tcgtggtggg gattgtggcc tggttgtatg   180
gagacccccg gcaagtcctc taccccagga actctactgg ggcctactgt ggcatggggg   240
agaacaaaga taagccgtat ctcctgtact tcaacatctt cagctgcatc ctgtccagca   300
acatcatctc agttgctgag aacggcctac agtgccccac accccaggtg tgtgtgtcct   360
cctgcccgga ggacccatgg actgtgggaa aaaacgagtt ctcacagact gttggggaag   420
tcttctatac aaaaaacagg aacttttgtc tgccaggggt accctggaat atgacggtga   480
tcacaagcct gcaacaggaa ctctgcccca gtttcctcct ccctctgct ccagctctgg    540
ggcgctgctt ccatggacc aacgttactc caccggcgct cccagggatc accaatgaca    600
ccaccataca gcagggatc agcggtctta ttgacagcct caatgcccga gacatcagtg     660
ttaagatctt tgaagatttt gcccagtcct ggtattggat tcttgttgcc ctgggggtgg   720
ctctggtctt gagcctactg tttatcttgc ttctgcgcct ggtggctggg ccctggtgc    780
tggtgctgat cctgggagtg ctgggcgtgc tggcatacgg catctactac tgctgggagg   840
agtaccgagt gctgcgggac aagggcgcct ccatctccca gctgggtttc accaccaacc   900
tcagtgccta ccagagcgtg caggagacct ggctggccgc cctgatcgtg ttggcggtgc   960
ttgaagccat cctgctgctg atgctcatct tcctgcggca gcgattcgt attgccatcg  1020
ccctcctgaa ggaggccagc aaggctgtgg acagatgat gtctaccatg ttctacccac  1080
```

```
tggtcacctt tgtcctcctc ctcatctgca ttgcctactg ggccatgact gctctgtatc   1140
ctctgcccac gcagccagcc actcttggat atgtgctctg ggcatccaac atcagctccc   1200
ccggctgtga gaaagtgcca ataaatacat catgcaaccc cacggcccac cttgtgaact   1260
cctcgtgccc agggctgatg tgcgtcttcc agggctactc atccaaaggc ctaatccaac   1320
gttctgtctt caatctgcaa atctatgggg tcctggggct cttctggacc cttaactggg   1380 tactggcccct gggccaatgc gtcctcgctg gagcctttgc ctccttctac tgggccttcc   1440
acaagcccca ggacatccct accttcccct taatctctgc cttcatccgc acactccgtt   1500
accacactgg gtcattggca tttggagccc tcatcctgac ccttgtgcag atagcccggg   1560
tcatcttgga gtatattgac cacaagctca gaggagtgca gaaccctgta gcccgctgca   1620
tcatgtgctg tttcaagtgc tgcctctggt gtctggaaaa atttatcaag ttcctaaacc   1680
gcaatgcata catcatgatc gccatctacg gaagaatttt ctgtgtctca gccaaaaatg   1740
cgttcatgct actcatgcga acattgtca gggtggtcgt cctggacaaa gtcacagacc   1800
tgctgctgtt ctttgggaag ctgctggtgg tcggaggcgt gggggtcctg tccttctttt   1860
ttttctccgg tcgcatcccg gggctgggta aagactttaa gagcccccac ctcaactatt   1920
actggctgcc catcatgacc tccatcctgg gggcctatgt catcgccagc ggcttcttca   1980
gcgttttcgg catgtgtgtg gacacgctct tcctctgctt cctggaagac ctggagcgga   2040
acaacggctc cctggaccgg ccctactaca tgtccaagag ccttctaaag attctgggca   2100
agaagaacga ggcgccccg gacaacaaga agaggaagaa gtgacagctc cggccctgat   2160
ccaggactgc acccccaccc caccgtccag ccatccaacc tcacttcgcc ttacaggtct   2220
ccattttgtg gtaaaaaaag gttttaggcc aggcgccgtg gctcacgcct gtaatccaac   2280
actttgagag gctgaggcgg gcggatcacc tgagtcagga gttcgagacc agcctggcca   2340
acatggtgaa acctccgtct ctattaaaaa tacaaaaatt agccgagagt ggtggcatgc   2400
acctgtcatc ccagctactc gggaggctga ggcaggagaa tcgcttgaac ccgggaggca   2460
gaggttgcag tgagccgaga tcgcgccact gcactccaac ctgggtgaca gactctgtct   2520
ccaaaacaaa acaaacaaac aaaaagattt tattaaagat attttgttaa ctcagtaaaa   2580
aaaaaaaaaa aaa                                                        2593
```

<210> SEQ ID NO 19
<211> LENGTH: 712
<212> TYPE: PRT
<213> ORGANISM: Homo Sapiens

<400> SEQUENCE: 19

```
Met Gly Gly Lys Gln Arg Asp Glu Asp Glu Ala Tyr Gly Lys Pro
 1               5                  10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
```

-continued

```
                100                 105                 110
Pro Gln Val Cys Val Ser Ser Cys Pro Glu Asp Pro Trp Thr Val Gly
            115                 120                 125
Lys Asn Glu Phe Ser Gln Thr Val Gly Glu Val Phe Tyr Thr Lys Asn
        130                 135                 140
Arg Asn Phe Cys Leu Pro Gly Val Pro Trp Asn Met Thr Val Ile Thr
145                 150                 155                 160
Ser Leu Gln Gln Glu Leu Cys Pro Ser Phe Leu Pro Ser Ala Pro
                165                 170                 175
Ala Leu Gly Arg Cys Phe Pro Trp Thr Asn Val Thr Pro Pro Ala Leu
            180                 185                 190
Pro Gly Ile Thr Asn Asp Thr Thr Ile Gln Gln Gly Ile Ser Gly Leu
        195                 200                 205
Ile Asp Ser Leu Asn Ala Arg Asp Ile Ser Val Lys Ile Phe Glu Asp
210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Arg Leu Val Ala Gly Pro
                245                 250                 255
Leu Val Leu Val Leu Ile Leu Gly Val Leu Gly Val Leu Ala Tyr Gly
            260                 265                 270
Ile Tyr Tyr Cys Trp Glu Glu Tyr Arg Val Leu Arg Asp Lys Gly Ala
        275                 280                 285
Ser Ile Ser Gln Leu Gly Phe Thr Thr Asn Leu Ser Ala Tyr Gln Ser
    290                 295                 300
Val Gln Glu Thr Trp Leu Ala Ala Leu Ile Val Leu Ala Val Leu Glu
305                 310                 315                 320
Ala Ile Leu Leu Leu Met Leu Ile Phe Leu Arg Gln Arg Ile Arg Ile
                325                 330                 335
Ala Ile Ala Leu Leu Lys Glu Ala Ser Lys Ala Val Gly Gln Met Met
            340                 345                 350
Ser Thr Met Phe Tyr Pro Leu Val Thr Phe Val Leu Leu Leu Ile Cys
        355                 360                 365
Ile Ala Tyr Trp Ala Met Thr Ala Leu Tyr Pro Leu Pro Thr Gln Pro
370                 375                 380
Ala Thr Leu Gly Tyr Val Leu Trp Ala Ser Asn Ile Ser Ser Pro Gly
385                 390                 395                 400
Cys Glu Lys Val Pro Ile Asn Thr Ser Cys Asn Pro Thr Ala His Leu
                405                 410                 415
Val Asn Ser Ser Cys Pro Gly Leu Met Cys Val Phe Gln Gly Tyr Ser
            420                 425                 430
Ser Lys Gly Leu Ile Gln Arg Ser Val Phe Asn Leu Gln Ile Tyr Gly
        435                 440                 445
Val Leu Gly Leu Phe Trp Thr Leu Asn Trp Val Leu Ala Leu Gly Gln
    450                 455                 460
Cys Val Leu Ala Gly Ala Phe Ala Ser Phe Tyr Trp Ala Phe His Lys
465                 470                 475                 480
Pro Gln Asp Ile Pro Thr Phe Pro Leu Ile Ser Ala Phe Ile Arg Thr
                485                 490                 495
Leu Arg Tyr His Thr Gly Ser Leu Ala Phe Gly Ala Leu Ile Leu Thr
            500                 505                 510
Leu Val Gln Ile Ala Arg Val Ile Leu Glu Tyr Ile Asp His Lys Leu
        515                 520                 525
```

```
Arg Gly Val Gln Asn Pro Val Ala Arg Cys Ile Met Cys Cys Phe Lys
        530                 535                 540

Cys Cys Leu Trp Cys Leu Glu Lys Phe Ile Lys Phe Leu Asn Arg Asn
545                 550                 555                 560

Ala Tyr Ile Met Ile Ala Ile Tyr Gly Lys Asn Phe Cys Val Ser Ala
                565                 570                 575

Lys Asn Ala Phe Met Leu Leu Met Arg Asn Ile Val Arg Val Val
                580                 585                 590

Leu Asp Lys Val Thr Asp Leu Leu Phe Phe Gly Lys Leu Leu Val
        595                 600                 605

Val Gly Gly Val Gly Val Leu Ser Phe Phe Phe Ser Gly Arg Ile
610                 615                 620

Pro Gly Leu Gly Lys Asp Phe Lys Ser Pro His Leu Asn Tyr Tyr Trp
625                 630                 635                 640

Leu Pro Ile Met Thr Ser Ile Leu Gly Ala Tyr Val Ile Ala Ser Gly
                645                 650                 655

Phe Phe Ser Val Phe Gly Met Cys Val Asp Thr Leu Phe Leu Cys Phe
                660                 665                 670

Leu Glu Asp Leu Glu Arg Asn Asn Gly Ser Leu Asp Arg Pro Tyr Tyr
                675                 680                 685

Met Ser Lys Ser Leu Leu Lys Ile Leu Gly Lys Lys Asn Glu Ala Pro
690                 695                 700

Pro Asp Asn Lys Lys Arg Lys Lys
705                 710

<210> SEQ ID NO 20
<211> LENGTH: 710
<212> TYPE: PRT
<213> ORGANISM: Homo Sapiens

<400> SEQUENCE: 20

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190
```

-continued

```
Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
        210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Arg Leu Val Ala Gly Pro
        245                 250                 255

Leu Val Leu Val Leu Ile Leu Gly Val Leu Gly Val Leu Ala Tyr Gly
        260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
        290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                    325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Ile Cys
                355                 360                 365

Ile Ala Tyr Trp Ala Met Thr Ala Leu Tyr Leu Ala Thr Ser Gly Gln
        370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                    405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
        435                 440                 445

Gly Leu Phe Trp Thr Leu Asn Trp Val Leu Ala Leu Gly Gln Cys Val
        450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                    485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
        515                 520                 525

Val Gln Asn Pro Val Ala Arg Cys Ile Met Cys Cys Phe Lys Cys Cys
        530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                    565                 570                 575

Ala Phe Met Leu Leu Met Arg Asn Ile Val Arg Val Val Leu Asp
            580                 585                 590

Lys Val Thr Asp Leu Leu Leu Phe Phe Gly Lys Leu Leu Val Val Gly
        595                 600                 605

Gly Val Gly Val Leu Ser Phe Phe Phe Ser Gly Arg Ile Pro Gly
        610                 615                 620
```

```
Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
            645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
            675                 680                 685

Lys Ser Leu Leu Lys Ile Leu Gly Lys Lys Asn Glu Ala Pro Pro Asp
690                 695                 700

Asn Lys Lys Arg Lys Lys
705                 710

<210> SEQ ID NO 21
<211> LENGTH: 710
<212> TYPE: PRT
<213> ORGANISM: Homo Sapiens

<400> SEQUENCE: 21

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
            85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
            165                 170                 175

Ala Leu Gly Arg Cys Phe Pro Trp Thr Asn Ile Thr Pro Pro Ala Leu
        180                 185                 190

Pro Gly Ile Thr Asn Asp Thr Thr Ile Gln Gln Gly Ile Ser Gly Leu
    195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
            245                 250                 255

Leu Val Leu Val Leu Ile Leu Gly Val Leu Gly Val Leu Ala Tyr Gly
        260                 265                 270

Ile Tyr Tyr Cys Trp Glu Glu Tyr Arg Val Leu Arg Asp Lys Gly Ala
275                 280                 285
```

```
Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
                340                 345                 350

Ser Thr Met Phe Tyr Pro Leu Val Thr Phe Val Leu Leu Ile Cys
                355                 360                 365

Ile Ala Tyr Trp Ala Met Thr Ala Leu Tyr Leu Ala Thr Ser Gly Gln
    370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
                420                 425                 430

Gly Leu Ile Gln Arg Ser Val Phe Asn Leu Gln Ile Tyr Gly Val Leu
                435                 440                 445

Gly Leu Phe Trp Thr Leu Asn Trp Val Leu Ala Leu Gly Gln Cys Val
    450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
                500                 505                 510

Gln Ile Ala Arg Val Ile Leu Glu Tyr Ile Asp His Lys Leu Arg Gly
                515                 520                 525

Val Gln Asn Pro Val Ala Arg Cys Ile Met Cys Cys Phe Lys Cys Cys
530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
                580                 585                 590

Lys Val Thr Asp Leu Leu Leu Phe Phe Gly Lys Leu Leu Val Val Gly
                595                 600                 605

Gly Val Gly Val Leu Ser Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
                660                 665                 670

Asp Leu Glu Arg Asn Asn Gly Ser Leu Asp Arg Pro Tyr Tyr Met Ser
                675                 680                 685

Lys Ser Leu Leu Lys Ile Leu Gly Lys Lys Asn Glu Ala Pro Pro Asp
690                 695                 700

Asn Lys Lys Arg Lys Lys
```

-continued

```
                          705                 710

<210> SEQ ID NO 22
<211> LENGTH: 710
<212> TYPE: PRT
<213> ORGANISM: Homo Sapiens

<400> SEQUENCE: 22

Met Gly Gly Lys Gln Arg Asp Glu Asp Glu Ala Tyr Gly Lys Pro
 1               5                  10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
                35                  40                  45

Ile Val Val Gly Ile Val Ala Trp Leu Tyr Gly Asp Pro Arg Gln Val
 50                  55                  60

Leu Tyr Pro Arg Asn Ser Thr Gly Ala Tyr Cys Gly Met Gly Glu Asn
 65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
                100                 105                 110

Pro Gln Val Cys Val Ser Ser Cys Pro Glu Asp Pro Trp Thr Val Gly
            115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
            195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
            275                 280                 285

Ser Ile Ser Gln Leu Gly Phe Thr Thr Asn Leu Ser Ala Tyr Gln Ser
            290                 295                 300

Val Gln Glu Thr Trp Leu Ala Ala Leu Ile Val Leu Ala Val Leu Glu
305                 310                 315                 320

Ala Ile Leu Leu Leu Val Leu Ile Phe Leu Arg Gln Arg Ile Arg Ile
                325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Leu Ile Cys
            355                 360                 365

Ile Ala Tyr Trp Ala Met Thr Ala Leu Tyr Leu Ala Thr Ser Gly Gln
```

```
            370                 375                 380
Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
                420                 425                 430

Gly Leu Ile Gln Arg Ser Val Phe Asn Leu Gln Ile Tyr Gly Val Leu
                435                 440                 445

Gly Leu Phe Trp Thr Leu Asn Trp Val Leu Ala Leu Gly Gln Cys Val
            450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
                500                 505                 510

Gln Ile Ala Arg Val Ile Leu Glu Tyr Ile Asp His Lys Leu Arg Gly
                515                 520                 525

Val Gln Asn Pro Val Ala Arg Cys Ile Met Cys Cys Phe Lys Cys Cys
530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Val Leu Asp
                580                 585                 590

Lys Val Thr Asp Leu Leu Leu Phe Phe Gly Lys Leu Leu Val Val Gly
                595                 600                 605

Gly Val Gly Val Leu Ser Phe Phe Phe Ser Gly Arg Ile Pro Gly
            610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
                660                 665                 670

Asp Leu Glu Arg Asn Asn Gly Ser Leu Asp Arg Pro Tyr Tyr Met Ser
                675                 680                 685

Lys Ser Leu Leu Lys Ile Leu Gly Lys Lys Asn Glu Ala Pro Pro Asp
                690                 695                 700

Asn Lys Lys Arg Lys Lys
705                 710

<210> SEQ ID NO 23
<211> LENGTH: 710
<212> TYPE: PRT
<213> ORGANISM: Homo Sapiens

<400> SEQUENCE: 23

Met Gly Gly Lys Gln Arg Asp Glu Asp Glu Ala Tyr Gly Lys Pro
  1               5                  10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
```

```
                35                  40                  45
Ile Val Val Gly Ile Val Ala Trp Leu Tyr Gly Asp Pro Arg Gln Val
 50                  55                  60

Leu Tyr Pro Arg Asn Ser Thr Gly Ala Tyr Cys Gly Met Gly Glu Asn
 65                  70                  75                  80

Lys Asp Lys Pro Tyr Leu Leu Tyr Phe Asn Ile Phe Ser Cys Ile Leu
                 85                  90                  95

Ser Ser Asn Ile Ile Ser Val Ala Glu Asn Gly Leu Gln Cys Pro Thr
                100                 105                 110

Pro Gln Val Cys Val Ser Ser Cys Pro Glu Asp Pro Trp Thr Val Gly
                115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
                180                 185                 190

Pro Gly Ile Thr Asn Asp Thr Thr Ile Gln Gln Gly Ile Ser Gly Leu
                195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Arg Leu Val Ala Gly Pro
                245                 250                 255

Leu Val Leu Val Leu Ile Leu Gly Val Leu Gly Val Leu Ala Tyr Gly
                260                 265                 270

Ile Tyr Tyr Cys Trp Glu Glu Tyr Arg Val Leu Arg Asp Lys Gly Ala
                275                 280                 285

Ser Ile Ser Gln Leu Gly Phe Thr Thr Asn Leu Ser Ala Tyr Gln Ser
290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
                340                 345                 350

Ser Thr Met Phe Tyr Pro Leu Val Thr Phe Val Leu Leu Ile Cys
                355                 360                 365

Ile Ala Tyr Trp Ala Met Thr Ala Leu Tyr Leu Ala Thr Ser Gly Gln
                370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
                420                 425                 430

Gly Leu Ile Pro Arg Ser Val Phe Asn Leu Gln Ile Tyr Gly Val Leu
                435                 440                 445

Gly Leu Phe Trp Thr Leu Asn Trp Val Leu Ala Leu Gly Gln Cys Val
450                 455                 460
```

```
Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
                500                 505                 510

Gln Ile Ala Arg Val Ile Leu Glu Tyr Ile Asp His Lys Leu Arg Gly
                515                 520                 525

Val Gln Asn Pro Val Ala Arg Cys Ile Met Cys Phe Lys Cys Cys
530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
                580                 585                 590

Lys Val Thr Asp Leu Leu Leu Phe Gly Lys Leu Leu Val Val Gly
                595                 600                 605

Gly Val Gly Val Leu Ser Phe Phe Phe Ser Gly Arg Ile Pro Gly
610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
                660                 665                 670

Asp Leu Glu Arg Asn Asn Gly Ser Leu Asp Arg Pro Tyr Tyr Met Ser
                675                 680                 685

Lys Ser Leu Leu Lys Ile Leu Gly Lys Asn Glu Ala Pro Pro Asp
690                 695                 700

Asn Lys Lys Arg Lys Lys
705                 710

<210> SEQ ID NO 24
<211> LENGTH: 598
<212> TYPE: PRT
<213> ORGANISM: Homo Sapiens

<400> SEQUENCE: 24

Met Gly Gly Lys Gln Arg Asp Glu Asp Glu Ala Tyr Gly Lys Pro
  1               5                  10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
                35                  40                  45

Ile Val Val Gly Ile Val Ala Trp Leu Tyr Gly Asp Pro Arg Gln Val
                50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
                100                 105                 110

Pro Gln Val Cys Val Ser Ser Cys Pro Glu Asp Pro Trp Thr Val Gly
                115                 120                 125
```

```
Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Val Gly Gln Met Met
225                 230                 235                 240

Ser Thr Met Phe Tyr Pro Leu Val Thr Phe Val Leu Leu Ile Cys
                245                 250                 255

Ile Ala Tyr Trp Ala Met Thr Ala Leu Tyr Leu Ala Thr Ser Gly Gln
            260                 265                 270

Pro Gln Tyr Val Leu Trp Ala Ser Asn Ile Ser Ser Pro Gly Cys Glu
        275                 280                 285

Lys Val Pro Ile Asn Thr Ser Cys Asn Pro Thr Ala His Leu Val Asn
290                 295                 300

Ser Ser Cys Pro Gly Leu Met Cys Val Phe Gln Gly Tyr Ser Ser Lys
305                 310                 315                 320

Gly Leu Ile Gln Arg Ser Val Phe Asn Leu Gln Ile Tyr Gly Val Leu
                325                 330                 335

Gly Leu Phe Trp Thr Leu Asn Trp Val Leu Ala Leu Gly Gln Cys Val
            340                 345                 350

Leu Ala Gly Ala Phe Ala Ser Phe Tyr Trp Ala Phe His Lys Pro Gln
        355                 360                 365

Asp Ile Pro Thr Phe Pro Leu Ile Ser Ala Phe Ile Arg Thr Leu Arg
370                 375                 380

Tyr His Thr Gly Ser Leu Ala Phe Gly Ala Leu Ile Leu Thr Leu Val
385                 390                 395                 400

Gln Ile Ala Arg Val Ile Leu Glu Tyr Ile Asp His Lys Leu Arg Gly
                405                 410                 415

Val Gln Asn Pro Val Ala Arg Cys Ile Met Cys Cys Phe Lys Cys Cys
            420                 425                 430

Leu Trp Cys Leu Glu Lys Phe Ile Lys Phe Leu Asn Arg Asn Ala Tyr
        435                 440                 445

Ile Met Ile Ala Ile Tyr Gly Lys Asn Phe Cys Val Ser Ala Lys Asn
450                 455                 460

Ala Phe Met Leu Leu Met Arg Asn Ile Val Arg Val Val Val Leu Asp
465                 470                 475                 480

Lys Val Thr Asp Leu Leu Leu Phe Phe Gly Lys Leu Leu Val Val Gly
                485                 490                 495

Gly Val Gly Val Leu Ser Phe Phe Phe Ser Gly Arg Ile Pro Gly
            500                 505                 510

Leu Gly Lys Asp Phe Lys Ser Pro His Leu Asn Tyr Tyr Trp Leu Pro
        515                 520                 525

Ile Met Thr Ser Ile Leu Gly Ala Tyr Val Ile Ala Ser Gly Phe Phe
530                 535                 540

Ser Val Phe Gly Met Cys Val Asp Thr Leu Phe Leu Cys Phe Leu Glu
545                 550                 555                 560
```

```
Asp Leu Glu Arg Asn Asn Gly Ser Leu Asp Arg Pro Tyr Tyr Met Ser
                565                 570                 575

Lys Ser Leu Leu Lys Ile Leu Gly Lys Lys Asn Glu Ala Pro Pro Asp
            580                 585                 590

Asn Lys Lys Arg Lys Lys
        595

<210> SEQ ID NO 25
<211> LENGTH: 722
<212> TYPE: PRT
<213> ORGANISM: Homo Sapiens

<400> SEQUENCE: 25

Met Gly Gly Lys Gln Arg Asp Glu Asp Glu Ala Tyr Gly Lys Pro
  1               5                  10                  15

Val Lys Tyr Asp Pro Ser Phe Arg Gly Pro Ile Lys Asn Arg Ser Cys
             20                  25                  30

Thr Asp Val Ile Cys Cys Val Leu Phe Leu Phe Ile Leu Gly Tyr
             35                  40                  45

Ile Val Val Gly Ile Val Ala Trp Leu Tyr Gly Asp Pro Arg Gln Val
 50                  55                  60

Leu Tyr Pro Arg Asn Ser Thr Gly Ala Tyr Cys Gly Met Gly Glu Asn
 65                  70                  75                  80

Lys Asp Lys Pro Tyr Leu Leu Tyr Phe Asn Ile Phe Ser Cys Ile Leu
             85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
            115                 120                 125

Lys Asn Glu Phe Ser Gln Thr Val Gly Glu Val Phe Tyr Thr Lys Asn
            130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
            195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
            275                 280                 285

Ser Ile Ser Gln Leu Gly Phe Thr Thr Asn Leu Ser Ala Tyr Gln Ser
            290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335
```

```
Ala Ile Ala Leu Leu Lys Glu Ala Ser Lys Ala Val Gly Gln Met Met
                340                 345                 350

Ser Thr Met Phe Tyr Pro Leu Val Thr Phe Val Leu Leu Leu Ile Cys
            355                 360                 365

Ile Ala Tyr Trp Ala Met Thr Ala Leu Tyr Leu Ala Thr Ser Gly Gln
        370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
        435                 440                 445

Gly Leu Phe Trp Thr Leu Asn Trp Val Leu Ala Leu Gly Gln Cys Val
450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
        515                 520                 525

Val Gln Asn Pro Val Ala Arg Cys Ile Met Cys Cys Phe Lys Cys Cys
530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
            580                 585                 590

Lys Val Thr Asp Leu Leu Phe Phe Gly Lys Leu Leu Val Val Gly
        595                 600                 605

Gly Val Gly Val Leu Ser Phe Phe Ser Gly Arg Ile Pro Gly
610                 615                 620

Leu Gly Lys Asp Phe Lys Ser Pro His Leu Asn Tyr Tyr Trp Leu Pro
625                 630                 635                 640

Ile Met Arg Asn Pro Ile Thr Pro Thr Gly His Val Phe Gln Thr Ser
                645                 650                 655

Ile Leu Gly Ala Tyr Val Ile Ala Ser Gly Phe Phe Ser Val Phe Gly
            660                 665                 670

Met Cys Val Asp Thr Leu Phe Leu Cys Phe Leu Glu Asp Leu Glu Arg
        675                 680                 685

Asn Asn Gly Ser Leu Asp Arg Pro Tyr Tyr Met Ser Lys Ser Leu Leu
690                 695                 700

Lys Ile Leu Gly Lys Lys Asn Glu Ala Pro Pro Asp Asn Lys Lys Arg
705                 710                 715                 720

Lys Lys

<210> SEQ ID NO 26
<211> LENGTH: 712
<212> TYPE: PRT
<213> ORGANISM: Homo Sapiens
```

```
<400> SEQUENCE: 26

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
                100                 105                 110

Pro Gln Val Cys Val Ser Ser Cys Pro Glu Asp Pro Trp Thr Val Gly
            115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
                180                 185                 190

Pro Gly Ile Thr Asn Asp Thr Thr Ile Gln Gln Gly Ile Ser Gly Leu
            195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
                260                 265                 270

Ile Tyr Tyr Cys Trp Glu Glu Tyr Arg Val Leu Arg Asp Lys Gly Ala
                275                 280                 285

Ser Ile Ser Gln Leu Gly Phe Thr Thr Asn Leu Ser Ala Tyr Gln Ser
290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
                340                 345                 350

Ser Thr Met Phe Tyr Pro Leu Val Thr Phe Val Leu Leu Leu Ile Cys
                355                 360                 365

Ile Ala Tyr Trp Ala Met Thr Ala Leu Tyr Pro Leu Pro Thr Gln Pro
370                 375                 380

Ala Thr Leu Gly Tyr Val Leu Trp Ala Ser Asn Ile Ser Ser Pro Gly
385                 390                 395                 400

Cys Glu Lys Val Pro Ile Asn Thr Ser Cys Asn Pro Thr Ala His Leu
                405                 410                 415
```

```
Val Asn Ser Ser Cys Pro Gly Leu Met Cys Val Phe Gln Gly Tyr Ser
            420                 425                 430

Ser Lys Gly Leu Ile Gln Arg Ser Val Phe Asn Leu Gln Ile Tyr Gly
        435                 440                 445

Val Leu Gly Leu Phe Trp Thr Leu Asn Trp Val Leu Ala Leu Gly Gln
    450                 455                 460

Cys Val Leu Ala Gly Ala Phe Ala Ser Phe Tyr Trp Ala Phe His Lys
465                 470                 475                 480

Pro Gln Asp Ile Pro Thr Phe Pro Leu Ile Ser Ala Phe Ile Arg Thr
                485                 490                 495

Leu Arg Tyr His Thr Gly Ser Leu Ala Phe Gly Ala Leu Ile Leu Thr
                500                 505                 510

Leu Val Gln Ile Ala Arg Val Ile Leu Glu Tyr Ile Asp His Lys Leu
            515                 520                 525

Arg Gly Val Gln Asn Pro Val Ala Arg Cys Ile Met Cys Cys Phe Lys
        530                 535                 540

Cys Cys Leu Trp Cys Leu Glu Lys Phe Ile Lys Phe Leu Asn Arg Asn
545                 550                 555                 560

Ala Tyr Ile Met Ile Ala Ile Tyr Gly Lys Asn Phe Cys Val Ser Ala
                565                 570                 575

Lys Asn Ala Phe Met Leu Leu Met Arg Asn Ile Val Arg Val Val Val
                580                 585                 590

Leu Asp Lys Val Thr Asp Leu Leu Phe Gly Lys Leu Leu Val
            595                 600                 605

Val Gly Gly Val Gly Val Leu Ser Phe Phe Phe Ser Gly Arg Ile
    610                 615                 620

Pro Gly Leu Gly Lys Asp Phe Lys Ser Pro His Leu Asn Tyr Tyr Trp
625                 630                 635                 640

Leu Pro Ile Met Thr Ser Ile Leu Gly Ala Tyr Val Ile Ala Ser Gly
                645                 650                 655

Phe Phe Ser Val Phe Gly Met Cys Val Asp Thr Leu Phe Leu Cys Phe
                660                 665                 670

Leu Glu Asp Leu Glu Arg Asn Asn Gly Ser Leu Asp Arg Pro Tyr Tyr
                675                 680                 685

Met Ser Lys Ser Leu Leu Lys Ile Leu Gly Lys Lys Asn Glu Ala Pro
            690                 695                 700

Pro Asp Asn Lys Lys Arg Lys Lys
705                 710

<210> SEQ ID NO 27
<211> LENGTH: 710
<212> TYPE: PRT
<213> ORGANISM: Homo Sapiens

<400> SEQUENCE: 27

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80
```

```
Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Ile Cys
    355                 360                 365

Ile Ala Tyr Trp Ala Met Thr Ala Leu Tyr Leu Ala Thr Ser Gly Gln
    370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
        435                 440                 445

Gly Leu Phe Trp Thr Leu Asn Trp Val Leu Ala Leu Gly Gln Cys Val
    450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
```

```
                    500                 505                 510
Gln Ile Ala Arg Val Ile Leu Glu Tyr Ile Asp His Lys Leu Arg Gly
                515                 520                 525

Val Gln Asn Pro Val Ala Arg Cys Ile Met Cys Cys Phe Lys Cys Cys
            530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
            580                 585                 590

Lys Val Thr Asp Leu Leu Leu Phe Phe Gly Lys Leu Leu Val Val Gly
                595                 600                 605

Gly Val Gly Val Leu Ser Phe Phe Phe Ser Gly Arg Ile Pro Gly
            610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
            675                 680                 685

Lys Ser Leu Leu Lys Ile Leu Gly Lys Asn Glu Ala Pro Pro Asp
690                 695                 700

Asn Lys Lys Arg Lys Lys
705                 710

<210> SEQ ID NO 28
<211> LENGTH: 710
<212> TYPE: PRT
<213> ORGANISM: Homo Sapiens

<400> SEQUENCE: 28

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Ser
    130                 135                 140

Ser Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
```

-continued

```
                165                 170                 175
Ala Leu Gly Arg Cys Phe Pro Trp Thr Asn Ile Thr Pro Ala Leu
            180                 185                 190
Pro Gly Ile Thr Asn Asp Thr Thr Ile Gln Gln Gly Ile Ser Gly Leu
            195                 200                 205
Ile Asp Ser Leu Asn Ala Arg Asp Ile Ser Val Lys Ile Phe Glu Asp
            210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Arg Leu Val Ala Gly Pro
            245                 250                 255
Leu Val Leu Val Leu Ile Leu Gly Val Leu Gly Val Leu Ala Tyr Gly
            260                 265                 270
Ile Tyr Tyr Cys Trp Glu Glu Tyr Arg Val Leu Arg Asp Lys Gly Ala
            275                 280                 285
Ser Ile Ser Gln Leu Gly Phe Thr Thr Asn Leu Ser Ala Tyr Gln Ser
            290                 295                 300
Val Gln Glu Thr Trp Leu Ala Ala Leu Ile Val Leu Ala Val Leu Glu
305                 310                 315                 320
Ala Ile Leu Leu Leu Val Leu Ile Phe Leu Arg Gln Arg Ile Arg Ile
            325                 330                 335
Ala Ile Ala Leu Leu Lys Glu Ala Ser Lys Ala Val Gly Gln Met Met
            340                 345                 350
Ser Thr Met Phe Tyr Pro Leu Val Thr Phe Val Leu Leu Ile Cys
            355                 360                 365
Ile Ala Tyr Trp Ala Met Thr Ala Leu Tyr Leu Ala Thr Ser Gly Gln
            370                 375                 380
Pro Gln Tyr Val Leu Trp Ala Ser Asn Ile Ser Ser Pro Gly Cys Glu
385                 390                 395                 400
Lys Val Pro Ile Asn Thr Ser Cys Asn Pro Thr Ala His Leu Val Asn
            405                 410                 415
Ser Ser Cys Pro Gly Leu Met Cys Val Phe Gln Gly Tyr Ser Ser Lys
            420                 425                 430
Gly Leu Ile Gln Arg Ser Val Phe Asn Leu Gln Ile Tyr Gly Val Leu
            435                 440                 445
Gly Leu Phe Trp Thr Leu Asn Trp Val Leu Ala Leu Gly Gln Cys Val
            450                 455                 460
Leu Ala Gly Ala Phe Ala Ser Phe Tyr Trp Ala Phe His Lys Pro Gln
465                 470                 475                 480
Asp Ile Pro Thr Phe Pro Leu Ile Ser Ala Phe Ile Arg Thr Leu Arg
            485                 490                 495
Tyr His Thr Gly Ser Leu Ala Phe Gly Ala Leu Ile Leu Thr Leu Val
            500                 505                 510
Gln Ile Ala Arg Val Ile Leu Glu Tyr Ile Asp His Lys Leu Arg Gly
            515                 520                 525
Val Gln Asn Pro Val Ala Arg Cys Ile Met Cys Cys Phe Lys Cys Cys
530                 535                 540
Leu Trp Cys Leu Glu Lys Phe Ile Lys Phe Leu Asn Arg Asn Ala Tyr
545                 550                 555                 560
Ile Met Ile Ala Ile Tyr Gly Lys Asn Phe Cys Val Ser Ala Lys Asn
            565                 570                 575
Ala Phe Met Leu Leu Met Arg Asn Ile Val Arg Val Val Leu Asp
            580                 585                 590
```

```
Lys Val Thr Asp Leu Leu Phe Phe Gly Lys Leu Leu Val Val Gly
        595                 600                 605

Gly Val Gly Val Leu Ser Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
                660                 665                 670

Asp Leu Glu Arg Asn Asn Gly Ser Leu Asp Arg Pro Tyr Tyr Met Ser
                675                 680                 685

Lys Ser Leu Leu Lys Ile Leu Gly Lys Lys Asn Glu Ala Pro Pro Asp
    690                 695                 700

Asn Lys Lys Arg Lys Lys
705             710

<210> SEQ ID NO 29
<211> LENGTH: 14
<212> TYPE: PRT
<213> ORGANISM: Tetanus toxoid

<400> SEQUENCE: 29

Gln Tyr Ile Lys Ala Asn Ser Lys Phe Ile Gly Ile Thr Glu
1               5                   10

<210> SEQ ID NO 30
<211> LENGTH: 21
<212> TYPE: PRT
<213> ORGANISM: Plasmodium falciparum

<400> SEQUENCE: 30

Asp Ile Glu Lys Lys Ile Ala Lys Met Glu Lys Ala Ser Ser Val Phe
1               5                   10                  15

Asn Val Val Asn Ser
            20

<210> SEQ ID NO 31
<211> LENGTH: 16
<212> TYPE: PRT
<213> ORGANISM: Streptococcus aureus

<400> SEQUENCE: 31

Gly Ala Val Asp Ser Ile Leu Gly Gly Val Ala Thr Tyr Gly Ala Ala
1               5                   10                  15

<210> SEQ ID NO 32
<211> LENGTH: 13
<212> TYPE: PRT
<213> ORGANISM: Artificial Sequence
<220> FEATURE:
<221> NAME/KEY: VARIANT
<222> LOCATION: 3
<223> OTHER INFORMATION: Xaa = cyclohexylalanine, phenylalanine, or
      tyrosine
<220> FEATURE:
<221> NAME/KEY: VARIANT
<222> LOCATION: 1,13
<223> OTHER INFORMATION: Xaa =  D-alanine or L-alanine
<220> FEATURE:
<223> OTHER INFORMATION: PAN DR-binding epitope

<400> SEQUENCE: 32

Xaa Lys Xaa Val Ala Ala Trp Thr Leu Lys Ala Ala Xaa
1               5                   10
```

```
1               5                   10
```

<210> SEQ ID NO 33
<211> LENGTH: 14
<212> TYPE: DNA
<213> ORGANISM: Artificial Sequence
<220> FEATURE:
<223> OTHER INFORMATION: Primer

<400> SEQUENCE: 33
ttttgatcaa gctt                                                       14

<210> SEQ ID NO 34
<211> LENGTH: 42
<212> TYPE: DNA
<213> ORGANISM: Artificial Sequence
<220> FEATURE:
<223> OTHER INFORMATION: Primer

<400> SEQUENCE: 34
ctaatacgac tcactatagg gctcgagcgg ccgcccgggc ag                        42

<210> SEQ ID NO 35
<211> LENGTH: 12
<212> TYPE: DNA
<213> ORGANISM: Artificial Sequence
<220> FEATURE:
<223> OTHER INFORMATION: Primer

<400> SEQUENCE: 35
gatcctgccc gg                                                         12

<210> SEQ ID NO 36
<211> LENGTH: 40
<212> TYPE: DNA
<213> ORGANISM: Artificial Sequence
<220> FEATURE:
<223> OTHER INFORMATION: Primer

<400> SEQUENCE: 36
gtaatacgac tcactatagg gcagcgtggt cgcggccgag                           40

<210> SEQ ID NO 37
<211> LENGTH: 10
<212> TYPE: DNA
<213> ORGANISM: Artificial Sequence
<220> FEATURE:
<223> OTHER INFORMATION: Primer

<400> SEQUENCE: 37
gatcctcggc                                                            10

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
ctaatacgac tcactatagg gc                                              22

<210> SEQ ID NO 39
<211> LENGTH: 22
<212> TYPE: DNA
<213> ORGANISM: Artificial Sequence
<220> FEATURE:

```
<223> OTHER INFORMATION: Primer

<400> SEQUENCE: 39
tcgagcggcc gcccgggcag ga                                          22

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
agcgtggtcg cggccgagga                                             20

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
atatcgccgc gctcgtcgtc gacaa                                       25

<210> SEQ ID NO 42
<211> LENGTH: 26
<212> TYPE: DNA
<213> ORGANISM: Artificial Sequence
<220> FEATURE:
<223> OTHER INFORMATION: Primer

<400> SEQUENCE: 42
agccacacgc agctcattgt agaagg                                      26

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
agatgaggag gaggacaaag gtg                                         23

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
actgctggga ggagtaccga gtg                                         23

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
gattacaagg atgacgacga taag                                        24

<210> SEQ ID NO 46
```

```
<211> LENGTH: 12
<212> TYPE: PRT
<213> ORGANISM: Homo Sapiens

<400> SEQUENCE: 46

Arg Asn Pro Ile Thr Pro Thr Gly His Val Phe Gln
 1               5                  10

<210> SEQ ID NO 47
<211> LENGTH: 10
<212> TYPE: PRT
<213> ORGANISM: Homo Sapiens

<400> SEQUENCE: 47

Pro Leu Pro Thr Gln Pro Ala Thr Leu Gly
 1               5                  10

<210> SEQ ID NO 48
<211> LENGTH: 4
<212> TYPE: PRT
<213> ORGANISM: Homo Sapiens

<400> SEQUENCE: 48

Asn Arg Ser Cys
 1

<210> SEQ ID NO 49
<211> LENGTH: 4
<212> TYPE: PRT
<213> ORGANISM: Homo Sapiens

<400> SEQUENCE: 49

Asn Ser Thr Gly
 1

<210> SEQ ID NO 50
<211> LENGTH: 4
<212> TYPE: PRT
<213> ORGANISM: Homo Sapiens

<400> SEQUENCE: 50

Asn Met Thr Val
 1

<210> SEQ ID NO 51
<211> LENGTH: 4
<212> TYPE: PRT
<213> ORGANISM: Homo Sapiens

<400> SEQUENCE: 51

Asn Asp Thr Thr
 1

<210> SEQ ID NO 52
<211> LENGTH: 4
<212> TYPE: PRT
<213> ORGANISM: Homo Sapiens

<400> SEQUENCE: 52

Asn Leu Ser Ala
 1

<210> SEQ ID NO 53
<211> LENGTH: 4
<212> TYPE: PRT
<213> ORGANISM: Homo Sapiens
```

```
<400> SEQUENCE: 53

Asn Ile Ser Ser
 1

<210> SEQ ID NO 54
<211> LENGTH: 4
<212> TYPE: PRT
<213> ORGANISM: Homo Sapiens

<400> SEQUENCE: 54

Asn Thr Ser Cys
 1

<210> SEQ ID NO 55
<211> LENGTH: 4
<212> TYPE: PRT
<213> ORGANISM: Homo Sapiens

<400> SEQUENCE: 55

Asn Ser Ser Cys
 1

<210> SEQ ID NO 56
<211> LENGTH: 4
<212> TYPE: PRT
<213> ORGANISM: Homo Sapiens

<400> SEQUENCE: 56

Asn Gly Ser Leu
 1

<210> SEQ ID NO 57
<211> LENGTH: 4
<212> TYPE: PRT
<213> ORGANISM: Homo Sapiens

<400> SEQUENCE: 57

Ser Cys Thr Asp
 1

<210> SEQ ID NO 58
<211> LENGTH: 4
<212> TYPE: PRT
<213> ORGANISM: Homo Sapiens

<400> SEQUENCE: 58

Ser Val Ala Glu
 1

<210> SEQ ID NO 59
<211> LENGTH: 4
<212> TYPE: PRT
<213> ORGANISM: Homo Sapiens

<400> SEQUENCE: 59

Ser Cys Pro Glu
 1

<210> SEQ ID NO 60
<211> LENGTH: 4
<212> TYPE: PRT
<213> ORGANISM: Homo Sapiens

<400> SEQUENCE: 60
```

Thr Val Gly Glu
1

<210> SEQ ID NO 61
<211> LENGTH: 4
<212> TYPE: PRT
<213> ORGANISM: Homo Sapiens

<400> SEQUENCE: 61

Ser Val Gln Glu
1

<210> SEQ ID NO 62
<211> LENGTH: 8
<212> TYPE: PRT
<213> ORGANISM: Homo Sapiens

<400> SEQUENCE: 62

Arg Asp Glu Asp Asp Glu Ala Tyr
1               5

<210> SEQ ID NO 63
<211> LENGTH: 6
<212> TYPE: PRT
<213> ORGANISM: Homo Sapiens

<400> SEQUENCE: 63

Gly Ala Tyr Cys Gly Met
1               5

<210> SEQ ID NO 64
<211> LENGTH: 6
<212> TYPE: PRT
<213> ORGANISM: Homo Sapiens

<400> SEQUENCE: 64

Gly Met Gly Glu Asn Lys
1               5

<210> SEQ ID NO 65
<211> LENGTH: 6
<212> TYPE: PRT
<213> ORGANISM: Homo Sapiens

<400> SEQUENCE: 65

Gly Val Pro Trp Asn Met
1               5

<210> SEQ ID NO 66
<211> LENGTH: 6
<212> TYPE: PRT
<213> ORGANISM: Homo Sapiens

<400> SEQUENCE: 66

Gly Leu Ile Asp Ser Leu
1               5

<210> SEQ ID NO 67
<211> LENGTH: 6
<212> TYPE: PRT
<213> ORGANISM: Homo Sapiens

<400> SEQUENCE: 67

Gly Ile Tyr Tyr Cys Trp
1               5

```
<210> SEQ ID NO 68
<211> LENGTH: 6
<212> TYPE: PRT
<213> ORGANISM: Homo Sapiens

<400> SEQUENCE: 68

Gly Ala Ser Ile Ser Gln
1               5

<210> SEQ ID NO 69
<211> LENGTH: 6
<212> TYPE: PRT
<213> ORGANISM: Homo Sapiens

<400> SEQUENCE: 69

Gly Gln Met Met Ser Thr
1               5

<210> SEQ ID NO 70
<211> LENGTH: 6
<212> TYPE: PRT
<213> ORGANISM: Homo Sapiens

<400> SEQUENCE: 70

Gly Leu Phe Trp Thr Leu
1               5

<210> SEQ ID NO 71
<211> LENGTH: 6
<212> TYPE: PRT
<213> ORGANISM: Homo Sapiens

<400> SEQUENCE: 71

Gly Ala Phe Ala Ser Phe
1               5

<210> SEQ ID NO 72
<211> LENGTH: 3
<212> TYPE: PRT
<213> ORGANISM: Homo Sapiens

<400> SEQUENCE: 72

Gly Lys Lys
1

<210> SEQ ID NO 73
<211> LENGTH: 22
<212> TYPE: PRT
<213> ORGANISM: Homo Sapiens

<400> SEQUENCE: 73

Leu Phe Ile Leu Leu Leu Arg Leu Val Ala Gly Pro Leu Val Leu Val
1               5                   10                  15

Leu Ile Leu Gly Val Leu
            20

<210> SEQ ID NO 74
<211> LENGTH: 12
<212> TYPE: PRT
<213> ORGANISM: Homo Sapiens

<400> SEQUENCE: 74

Cys Ile Met Cys Cys Phe Lys Cys Cys Leu Trp Cys
1               5                   10
```

```
<210> SEQ ID NO 75
<211> LENGTH: 710
<212> TYPE: PRT
<213> ORGANISM: Homo Sapiens

<400> SEQUENCE: 75
```

| | | | | | | | | | | | | | | |
|---|---|---|---|---|---|---|---|---|---|---|---|---|---|---|
| Met | Gly | Gly | Lys | Gln | Arg | Asp | Glu | Asp | Glu | Ala | Tyr | Gly | Lys | Pro |
| 1 | | | | 5 | | | | | 10 | | | | | 15 |
| Val | Lys | Tyr | Asp | Pro | Ser | Phe | Arg | Gly | Pro | Ile | Lys | Asn | Arg | Ser | Cys |
| | | | 20 | | | | | 25 | | | | | 30 | | |
| Thr | Asp | Val | Ile | Cys | Cys | Val | Leu | Phe | Leu | Leu | Phe | Ile | Leu | Gly | Tyr |
| | | | 35 | | | | 40 | | | | | 45 | | | |
| Ile | Val | Val | Gly | Ile | Val | Ala | Trp | Leu | Tyr | Gly | Asp | Pro | Arg | Gln | Val |
| | | 50 | | | | | 55 | | | | | 60 | | | |
| Leu | Tyr | Pro | Arg | Asn | Ser | Thr | Gly | Ala | Tyr | Cys | Gly | Met | Gly | Glu | Asn |
| 65 | | | | | 70 | | | | | 75 | | | | | 80 |
| Lys | Asp | Lys | Pro | Tyr | Leu | Leu | Tyr | Phe | Asn | Ile | Phe | Ser | Cys | Ile | Leu |
| | | | | 85 | | | | | 90 | | | | | 95 | |
| Ser | Ser | Asn | Ile | Ile | Ser | Val | Ala | Glu | Asn | Gly | Leu | Gln | Cys | Pro | Thr |
| | | | 100 | | | | | 105 | | | | | 110 | | |
| Pro | Gln | Val | Cys | Val | Ser | Ser | Cys | Pro | Glu | Asp | Pro | Trp | Thr | Val | Gly |
| | | | 115 | | | | | 120 | | | | | 125 | | |
| Lys | Asn | Glu | Phe | Ser | Gln | Thr | Val | Gly | Glu | Val | Phe | Tyr | Thr | Lys | Asn |
| | 130 | | | | | 135 | | | | | 140 | | | | |
| Arg | Asn | Phe | Cys | Leu | Pro | Gly | Val | Pro | Trp | Asn | Met | Thr | Val | Ile | Thr |
| 145 | | | | | 150 | | | | | 155 | | | | | 160 |
| Ser | Leu | Gln | Gln | Glu | Leu | Cys | Pro | Ser | Phe | Leu | Leu | Pro | Ser | Ala | Pro |
| | | | | 165 | | | | | 170 | | | | | 175 | |
| Ala | Leu | Gly | Arg | Cys | Phe | Pro | Trp | Thr | Asn | Val | Thr | Pro | Pro | Ala | Leu |
| | | | 180 | | | | | 185 | | | | | 190 | | |
| Pro | Gly | Ile | Thr | Asn | Asp | Thr | Thr | Ile | Gln | Gln | Gly | Ile | Ser | Gly | Leu |
| | | | 195 | | | | | 200 | | | | | 205 | | |
| Ile | Asp | Ser | Leu | Asn | Ala | Arg | Asp | Ile | Ser | Val | Lys | Ile | Phe | Glu | Asp |
| | 210 | | | | | 215 | | | | | 220 | | | | |
| Phe | Ala | Gln | Ser | Trp | Tyr | Trp | Ile | Leu | Val | Ala | Leu | Gly | Val | Ala | Leu |
| 225 | | | | | 230 | | | | | 235 | | | | | 240 |
| Val | Leu | Ser | Leu | Leu | Phe | Ile | Leu | Leu | Arg | Leu | Val | Ala | Gly | Pro | |
| | | | | 245 | | | | | 250 | | | | | 255 | |
| Leu | Val | Leu | Val | Leu | Ile | Leu | Gly | Val | Leu | Gly | Val | Leu | Ala | Tyr | Gly |
| | | | 260 | | | | | 265 | | | | | 270 | | |
| Ile | Tyr | Tyr | Cys | Trp | Glu | Glu | Tyr | Arg | Val | Leu | Arg | Asp | Lys | Gly | Ala |
| | | 275 | | | | | 280 | | | | | 285 | | | |
| Ser | Ile | Ser | Gln | Leu | Gly | Phe | Thr | Thr | Asn | Leu | Ser | Ala | Tyr | Gln | Ser |
| | 290 | | | | | 295 | | | | | 300 | | | | |
| Val | Gln | Glu | Thr | Trp | Leu | Ala | Ala | Leu | Ile | Val | Leu | Ala | Val | Leu | Glu |
| 305 | | | | | 310 | | | | | 315 | | | | | 320 |
| Ala | Ile | Leu | Leu | Leu | Met | Leu | Ile | Phe | Leu | Arg | Gln | Arg | Ile | Arg | Ile |
| | | | | 325 | | | | | 330 | | | | | 335 | |
| Ala | Ile | Ala | Leu | Leu | Lys | Glu | Ala | Ser | Lys | Ala | Val | Gly | Gln | Met | Met |
| | | | 340 | | | | | 345 | | | | | 350 | | |
| Ser | Thr | Met | Phe | Tyr | Pro | Leu | Val | Thr | Phe | Val | Leu | Leu | Ile | Cys | |
| | | 355 | | | | | 360 | | | | | 365 | | | |
| Ile | Ala | Tyr | Trp | Ala | Met | Thr | Ala | Leu | Tyr | Leu | Ala | Thr | Ser | Gly | Gln |
| | 370 | | | | | 375 | | | | | 380 | | | | |

-continued

```
Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
        435                 440                 445

Gly Leu Phe Trp Thr Leu Asn Trp Val Leu Ala Leu Gly Gln Cys Val
    450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
        515                 520                 525

Val Gln Asn Pro Val Ala Arg Cys Ile Met Cys Cys Phe Lys Cys Cys
    530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Val Leu Asp
            580                 585                 590

Lys Val Thr Asp Leu Leu Leu Phe Phe Gly Lys Leu Leu Val Val Gly
        595                 600                 605

Gly Val Gly Val Leu Ser Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
        675                 680                 685

Lys Ser Leu Leu Lys Ile Leu Gly Lys Lys Asn Glu Ala Pro Pro Asp
    690                 695                 700

Asn Lys Lys Arg Lys Lys
705                 710

<210> SEQ ID NO 76
<211> LENGTH: 17
<212> TYPE: PRT
<213> ORGANISM: Homo Sapiens

<400> SEQUENCE: 76

Gly Arg Cys Phe Pro Trp Thr Asn Ile Thr Pro Pro Ala Leu Pro Gly
 1               5                   10                  15

Ile

<210> SEQ ID NO 77
<211> LENGTH: 19
<212> TYPE: PRT
```

<213> ORGANISM: Homo Sapiens

<400> SEQUENCE: 77

Leu Gly Arg Cys Phe Pro Trp Thr Asn Ile Thr Pro Pro Ala Leu Pro
1               5                   10                  15

Gly Ile Thr

<210> SEQ ID NO 78
<211> LENGTH: 29
<212> TYPE: PRT
<213> ORGANISM: Homo Sapiens

<400> SEQUENCE: 78

Pro Ser Ala Pro Ala Leu Gly Arg Cys Phe Pro Trp Thr Asn Ile Thr
1               5                   10                  15

Pro Pro Ala Leu Pro Gly Ile Thr Asn Asp Thr Thr Ile
            20                  25

<210> SEQ ID NO 79
<211> LENGTH: 17
<212> TYPE: PRT
<213> ORGANISM: Homo Sapiens

<400> SEQUENCE: 79

Val Leu Glu Ala Ile Leu Leu Val Leu Ile Phe Leu Arg Gln Arg
1               5                   10                  15

Ile

<210> SEQ ID NO 80
<211> LENGTH: 19
<212> TYPE: PRT
<213> ORGANISM: Homo Sapiens

<400> SEQUENCE: 80

Ala Val Leu Glu Ala Ile Leu Leu Val Leu Ile Phe Leu Arg Gln
1               5                   10                  15

Arg Ile Arg

<210> SEQ ID NO 81
<211> LENGTH: 29
<212> TYPE: PRT
<213> ORGANISM: Homo Sapiens

<400> SEQUENCE: 81

Ala Leu Ile Val Leu Ala Val Leu Glu Ala Ile Leu Leu Val Leu
1               5                   10                  15

Ile Phe Leu Arg Gln Arg Ile Arg Ile Ala Ile Ala Leu
            20                  25

<210> SEQ ID NO 82
<211> LENGTH: 17
<212> TYPE: PRT
<213> ORGANISM: Homo Sapiens

<400> SEQUENCE: 82

Gly Tyr Ser Ser Lys Gly Leu Ile Pro Arg Ser Val Phe Asn Leu Gln
1               5                   10                  15

Ile

<210> SEQ ID NO 83
<211> LENGTH: 19
<212> TYPE: PRT

<213> ORGANISM: Homo Sapiens

<400> SEQUENCE: 83

Gln Gly Tyr Ser Ser Lys Gly Leu Ile Pro Arg Ser Val Phe Asn Leu
1               5                   10                  15

Gln Ile Tyr

<210> SEQ ID NO 84
<211> LENGTH: 29
<212> TYPE: PRT
<213> ORGANISM: Homo Sapiens

<400> SEQUENCE: 84

Leu Met Cys Val Phe Gln Gly Tyr Ser Ser Lys Gly Leu Ile Pro Arg
1               5                   10                  15

Ser Val Phe Asn Leu Gln Ile Tyr Gly Val Leu Gly Leu
            20                  25

<210> SEQ ID NO 85
<211> LENGTH: 16
<212> TYPE: PRT
<213> ORGANISM: Homo Sapiens

<400> SEQUENCE: 85

Ser Trp Tyr Trp Ile Leu Val Ala Val Gly Gln Met Met Ser Thr Met
1               5                   10                  15

<210> SEQ ID NO 86
<211> LENGTH: 18
<212> TYPE: PRT
<213> ORGANISM: Homo Sapiens

<400> SEQUENCE: 86

Gln Ser Trp Tyr Trp Ile Leu Val Ala Val Gly Gln Met Met Ser Thr
1               5                   10                  15

Met Phe

<210> SEQ ID NO 87
<211> LENGTH: 28
<212> TYPE: PRT
<213> ORGANISM: Homo Sapiens

<400> SEQUENCE: 87

Phe Glu Asp Phe Ala Gln Ser Trp Tyr Trp Ile Leu Val Ala Val Gly
1               5                   10                  15

Gln Met Met Ser Thr Met Phe Tyr Pro Leu Val Thr
            20                  25

<210> SEQ ID NO 88
<211> LENGTH: 28
<212> TYPE: PRT
<213> ORGANISM: Homo Sapiens

<400> SEQUENCE: 88

Asn Tyr Tyr Trp Leu Pro Ile Met Arg Asn Pro Ile Thr Pro Thr Gly
1               5                   10                  15

His Val Phe Gln Thr Ser Ile Leu Gly Ala Tyr Val
            20                  25

<210> SEQ ID NO 89
<211> LENGTH: 30
<212> TYPE: PRT
<213> ORGANISM: Homo Sapiens

```
<400> SEQUENCE: 89

Leu Asn Tyr Tyr Trp Leu Pro Ile Met Arg Asn Pro Ile Thr Pro Thr
 1               5                  10                  15

Gly His Val Phe Gln Thr Ser Ile Leu Gly Ala Tyr Val Ile
            20                  25                  30

<210> SEQ ID NO 90
<211> LENGTH: 40
<212> TYPE: PRT
<213> ORGANISM: Homo Sapiens

<400> SEQUENCE: 90

Phe Lys Ser Pro His Leu Asn Tyr Tyr Trp Leu Pro Ile Met Arg Asn
 1               5                  10                  15

Pro Ile Thr Pro Thr Gly His Val Phe Gln Thr Ser Ile Leu Gly Ala
            20                  25                  30

Tyr Val Ile Ala Ser Gly Phe Phe
            35                  40

<210> SEQ ID NO 91
<211> LENGTH: 26
<212> TYPE: PRT
<213> ORGANISM: Homo Sapiens

<400> SEQUENCE: 91

Tyr Trp Ala Met Thr Ala Leu Tyr Pro Leu Pro Thr Gln Pro Ala Thr
 1               5                  10                  15

Leu Gly Tyr Val Leu Trp Ala Ser Asn Ile
            20                  25

<210> SEQ ID NO 92
<211> LENGTH: 28
<212> TYPE: PRT
<213> ORGANISM: Homo Sapiens

<400> SEQUENCE: 92

Ala Tyr Trp Ala Met Thr Ala Leu Tyr Pro Leu Pro Thr Gln Pro Ala
 1               5                  10                  15

Thr Leu Gly Tyr Val Leu Trp Ala Ser Asn Ile Ser
            20                  25

<210> SEQ ID NO 93
<211> LENGTH: 38
<212> TYPE: PRT
<213> ORGANISM: Homo Sapiens

<400> SEQUENCE: 93

Leu Leu Ile Cys Ile Ala Tyr Trp Ala Met Thr Ala Leu Tyr Pro Leu
 1               5                  10                  15

Pro Thr Gln Pro Ala Thr Leu Gly Tyr Val Leu Trp Ala Ser Asn Ile
            20                  25                  30

Ser Ser Pro Gly Cys Glu
            35

<210> SEQ ID NO 94
<211> LENGTH: 2251
<212> TYPE: DNA
<213> ORGANISM: Homo Sapiens

<400> SEQUENCE: 94
gagccatggg gggaaagcag cgggacgagg atgacgaggc ctacgggaag ccagtcaaat      60
```

```
acgacccctc ctttcgaggc cccatcaaga acagaagctg cacagatgtc atctgctgcg    120
tcctcttcct gctcttcatt ctaggttaca tcgtggtggg gattgtggcc tggttgtatg    180 gagaccccg  gcaagtcctc tacccagga  actctactgg ggcctactgt ggcatggggg    240
agaacaaaga taagccgtat ctcctgtact tcaacatctt cagctgcatc ctgtccagca    300
acatcatctc agttgctgag aacggcctac agtgccccac accccaggtg tgtgtgtcct    360
cctgcccgga ggacccatgg actgtgggaa aaaacgagtt ctcacagact gttggggaag    420
tcttctatac aaaaaacagg aacttttgtc tgccaggggt accctggaat atgacggtga    480
tcacaagcct gcaacaggaa ctctgcccca gtttcctcct cccctctgct ccagctctgg    540
ggcgctgctt tccatggacc aacgttactc caccggcgct cccagggatc accaatgaca    600
ccaccataca gcagggatc  agcggtctta ttgacagcct caatgcccga gacatcagtg    660
ttaagatctt tgaagatttt gcccagtcct ggtattggat tcttgtggct gtgggacaga    720
tgatgtctac catgttctac ccactggtca cctttgtcct cctcctcatc tgcattgcct    780
actgggccat gactgctctg tacctggcta catcggggca accccagtat gtgctctggg    840
catccaacat cagctccccc ggctgtgaga aagtgccaat aaatacatca tgcaaccccca   900 cggcccacct tgtgaactcc tcgtgcccag ggctgatgtg cgtcttccag ggctactcat    960
ccaaaggcct aatccaacgt tctgtcttca atctgcaaat ctatgggtc  ctggggctct   1020 tctggaccct taactgggta ctggccctgg gccaatgcgt cctcgctgga gcctttgcct   1080
ccttctactg ggccttccac aagccccagg acatccctac cttcccctta atctctgcct   1140
tcatccgcac actccgttac cacactgggt cattggcatt tggagccctc atcctgaccc   1200
ttgtgcagat agcccgggtc atcttggagt atattgacca caagctcaga ggagtgcaga   1260
accctgtagc ccgctgcatc atgtgctgtt tcaagtgctg cctctggtgt ctggaaaaat    1320
ttatcaagtt cctaaaccgc aatgcataca tcatgatcgc catctacggg aagaatttct   1380
gtgtctcagc caaaaatgcg ttcatgctac tcatgcgaaa cattgtcagg gtggtcgtcc   1440
tggacaaagt cacagacctg ctgctgttct ttgggaagct gctggtggtc ggaggcgtgg    1500
gggtcctgtc cttcttttt  ttctccggtc gcatcccggg gctgggtaaa gactttaaga    1560 gccccccacct caactattac tggctgccca tcatgacctc catcctgggg gcctatgtca    1620
tcgccagcgg cttcttcagc gttttcggca tgtgtgtgga cacgctcttc ctctgcttcc    1680
tggaagacct ggagcggaac aacgctccc  tggaccggcc ctactacatg tccaagagcc    1740
ttctaaagat tctgggcaag aagaacgagg cgccccgga  caacaagaag aggaagaagt    1800
gacagctccg gccctgatcc aggactgcac cccacccca  ccgtccagcc atccaacctc    1860
acttcgcctt acaggtctcc attttgtggt aaaaaaaggt tttaggccag cgccgtggc    1920 tcacgcctgt aatccaacac tttgagaggc tgaggcgggc ggatcacctg agtcaggagt    1980
tcgagaccag cctggccaac atggtgaaac ctccgtctct attaaaaata caaaaattag    2040
ccgagagtgg tggcatgcac ctgtcatccc agctactcgg gaggctgagg caggagaatc    2100
gcttgaaccc gggaggcaga ggttgcagtg agccgagatc gcgccactgc actccaacct    2160
gggtgacaga ctctgtctcc aaaacaaaac aaacaaacaa aagattttta ttaaagatat    2220
tttgttaact cagtaaaaaa aaaaaaaaaa a                                   2251
```

<210> SEQ ID NO 95
<211> LENGTH: 2587
<212> TYPE: DNA
<213> ORGANISM: Homo Sapiens

```
<400> SEQUENCE: 95
gagccatggg gggaaagcag cgggacgagg atgacgaggc ctacgggaag ccagtcaaat      60 acgaccccctc ctttcgaggc cccatcaaga acagaagctg cacagatgtc atctgctgcg    120
tcctcttcct gctcttcatt ctaggttaca tcgtggtggg gattgtggcc tggttgtatg    180 gagaccccccg gcaagtcctc taccccagga actctactgg ggcctactgt ggcatgggggg    240 agaacaaaga taagccgtat ctcctgtact tcaacatctt cagctgcatc ctgtccagca    300
acatcatctc agttgctgag aacggcctac agtgccccac accccaggtg tgtgtgtcct    360
cctgcccgga ggacccatgg actgtgggaa aaaacgagtt ctcacagact gttggggaag    420
tcttctatac aaaaaacagg aacttttgtc tgccaggggt accctggaat atgacggtga    480
tcacaagcct gcaacaggaa ctctgcccca gtttcctcct cccctctgct ccagctctgg    540
ggcgctgctt tccatggacc aacgttactc caccggcgct cccagggatc accaatgaca    600
ccaccataca gcagggggatc agcggtctta ttgacagcct caatgcccga gacatcagtg    660
ttaagatctt tgaagatttt gcccagtcct ggtattggat tcttgttgcc ctggggggtgg    720 ctctggtctt gagcctactg tttatcttgc ttctgcgcct ggtggctggg cccctggtgc    780
tggtgctgat cctgggagtg ctgggcgtgc tggcatacgg catctactac tgctgggagg    840
agtaccgagt gctgcgggac aagggcgcct ccatctccca gctgggtttc accaccaacc    900
tcagtgccta ccagagcgtg caggagacct ggctggccgc cctgatcgtg ttggcggtgc    960
ttgaagccat cctgctgctg atgctcatct tcctgcgggca gcggattcgt attgccatcg   1020
ccctcctgaa ggaggccagc aaggctgtgg gacagatgat gtctaccatg ttctacccac   1080
tggtcacctt tgtcctcctc ctcatctgca ttgcctactg ggccatgact gctctgtacc   1140
tggctacatc ggggcaaccc cagtatgtgc tctgggcatc caacatcagc tcccccggct   1200
gtgagaaagt gccaataaat acatcatgca acccccacggc ccaccttgtg aactcctcgt   1260
gcccagggct gatgtgcgtc ttccagggct actcatccaa aggcctaatc caacgttctg   1320
tcttcaatct gcaaatctat ggggtcctgg ggctcttctg gacccttaac tgggtactgg   1380 ccctgggccca atgcgtcctc gctggagcct ttgcctcctt ctactgggcc ttccacaagc   1440
cccaggacat ccctaccttc ccctttaatct ctgccttcat ccgcacactc cgttaccaca   1500
ctgggtcatt ggcatttgga gccctcatcc tgaccctttgt gcagatagcc cgggtcatct   1560
tggagtatat tgaccacaag ctcagaggag tgcagaaccc tgtagcccgc tgcatcatgt   1620
gctgtttcaa gtgctgcctc tggtgtctgg aaaaatttat caagttccta aaccgcaatg   1680
catacatcat gatcgccatc tacgggaaga atttctgtgt ctcagccaaa aatgcgttca   1740
tgctactcat gcgaaacatt gtcagggtgg tcgtcctgga caaagtcaca gacctgctgc   1800 tgttcttttgg gaagctgctg gtggtcgagg cgtgggggt cctgtccttc ttttttttct   1860
ccggtcgcat cccgggggctg ggtaaagact ttaagagccc ccacctcaac tattactggc   1920
tgcccatcat gacctccatc ctgggggcct atgtcatcgc cagcggcttc ttcagcgttt   1980
tcggcatgtg tgtggacacg ctcttcctct gcttcctgga agacctggag cggaacaacg   2040
gctccctgga ccggccctac tacatgtcca gagccttct aaagattctg gcaagaaga    2100 acgaggcgcc cccggacaac aagaaggga agaagtgaca gctccggccc tgatccagga   2160
ctgcacccca cccccaccgt ccagccatcc aacctcactt cgccttacag gtctccattt   2220
tgtggtaaaa aaaggtttta ggccaggcgc cgtggctcac gcctgtaatc caacactttg   2280
agaggctgag gcgggcggat cacctgagtc aggagttcga gaccagcctg gccaacatgg   2340
```

-continued

| | |
|---|---|
| tgaaacctcc gtctctatta aaaatacaaa aattagccga gagtggtggc atgcacctgt | 2400 |
| catcccagct actcgggagg ctgaggcagg agaatcgctt gaacccggga ggcagaggtt | 2460 |
| gcagtgagcc gagatcgcgc cactgcactc caacctgggt gacagactct gtctccaaaa | 2520 |
| caaaacaaac aaacaaaaag attttattaa agatattttg ttaactcagt aaaaaaaaaa | 2580 |
| aaaaaaa | 2587 |

<210> SEQ ID NO 96
<211> LENGTH: 2251
<212> TYPE: DNA
<213> ORGANISM: Homo Sapiens

<400> SEQUENCE: 96

| | |
|---|---|
| gagccatggg gggaaagcag cgggacgagg atgacgaggc ctacgggaag ccagtcaaat | 60 |
| acgacccctc ctttcgaggc cccatcaaga acagaagctg cacagatgtc atctgctgcg | 120 |
| tcctcttcct gctcttcatt ctaggttaca tcgtggtggg gattgtggcc tggttgtatg | 180 |
| gagaccccg gcaagtcctc taccccagga actctactgg ggcctactgt ggcatggggg | 240 |
| agaacaaaga taagccgtat ctcctgtact tcaacatctt cagctgcatc ctgtccagca | 300 |
| acatcatctc agttgctgag aacggcctac agtgccccac accccaggtg tgtgtgtcct | 360 |
| cctgcccgga ggacccatgg actgtgggaa aaaacgagtt ctcacagact gttggggaag | 420 |
| tcttctatac aaaaaacagg aacttttgtc tgccagggt accctggaat atgacggtga | 480 |
| tcacaagcct gcaacaggaa ctctgcccca gtttcctcct cccctctgct ccagctctgg | 540 |
| ggcgctgctt tccatggacc aacgttactc caccggcgct cccagggatc accaatgaca | 600 |
| ccaccataca gcagggatc agcggtctta ttgacagcct caatgcccga gacatcagtg | 660 |
| ttaagatctt tgaagatttt gcccagtcct ggtattggat tcttgtggct gtgggacaga | 720 |
| tgatgtctac catgttctac ccactggtca cctttgtcct cctcctcatc tgcattgcct | 780 |
| actgggccat gactgctctg tacctggcta catcggggca accccagtat gtgctctggg | 840 |
| catccaacat cagctccccc ggctgtgaga aagtgccaat aaatacatca tgcaacccca | 900 |
| cggcccacct tgtgaactcc tcgtgcccag ggctgatgtg cgtcttccag ggctactcat | 960 |
| ccaaaggcct aatccaacgt tctgtcttca atctgcaaat ctatgggtc ctggggctct | 1020 |
| tctggaccct taactgggta ctggccctgg gccaatgcgt cctcgctgga gcctttgcct | 1080 |
| ccttctactg ggccttccac aagccccagg acatccctac cttcccctta atctctgcct | 1140 |
| tcatccgcac actccgttac cacactgggt cattggcatt tggagccctc atcctgaccc | 1200 |
| ttgtgcagat agcccgggtc atcttggagt atattgacca caagctcaga ggagtgcaga | 1260 |
| accctgtagc ccgctgcatc atgtgctgtt tcaagtgctg cctctggtgt ctggaaaaat | 1320 |
| ttatcaagtt cctaaaccgc aatgcataca tcatgatcgc catctacggg aagaatttct | 1380 |
| gtgtctcagc caaaaatgcg ttcatgctac tcatgcgaaa cattgtcagg gtggtcgtcc | 1440 |
| tggacaaagt cacagacctg ctgctgttct ttgggaagct gctggtggtc ggaggcgtgg | 1500 |
| gggtcctgtc cttctttttt ttctccggtc gcatcccggg gctgggtaaa gactttaaga | 1560 |
| gccccaccct caactattac tggctgccca tcatgacctc catcctgggg gcctatgtca | 1620 |
| tcgccagcgg cttcttcagc gttttcggca tgtgtgtgga cacgctcttc ctctgcttcc | 1680 |
| tggaagacct ggagcggaac aacggctccc tggaccggcc ctactacatg tccaagagcc | 1740 |
| ttctaaagat tctgggcaag aagaacgagg cgccccgga caacaagaag aggaagaagt | 1800 |
| gacagctccg gccctgatcc aggactgcac cccacccca ccgtccagcc atccaacctc | 1860 |

-continued

```
acttcgcctt acaggtctcc attttgtggt aaaaaaaggt tttaggccag gcgccgtggc    1920
tcacgcctgt aatccaacac tttgagaggc tgaggcgggc ggatcacctg agtcaggagt    1980
tcgagaccag cctggccaac atggtgaaac ctccgtctct attaaaaata caaaaattag    2040
ccgagagtgg tggcatgcac ctgtcatccc agctactcgg gaggctgagg caggagaatc    2100
gcttgaaccc gggaggcaga ggttgcagtg agccgagatc gcgccactgc actccaacct    2160
gggtgacaga ctctgtctcc aaaacaaaac aaacaaacaa aaagatttta ttaaagatat    2220
tttgttaact cagtaaaaaa aaaaaaaaaa a                                   2251
```

<210> SEQ ID NO 97
<211> LENGTH: 598
<212> TYPE: PRT
<213> ORGANISM: Homo Sapiens

<400> SEQUENCE: 97

```
Met Gly Gly Lys Gln Arg Asp Glu Asp Asp Glu Ala Tyr Gly Lys Pro
 1               5                  10                  15

Val Lys Tyr Asp Pro Ser Phe Arg Gly Pro Ile Lys Asn Arg Ser Cys
             20                  25                  30

Thr Asp Val Ile Cys Cys Val Leu Phe Leu Leu Phe Ile Leu Gly Tyr
         35                  40                  45

Ile Val Val Gly Ile Val Ala Trp Leu Tyr Gly Asp Pro Arg Gln Val
     50                  55                  60

Leu Tyr Pro Arg Asn Ser Thr Gly Ala Tyr Cys Gly Met Gly Glu Asn
 65                  70                  75                  80

Lys Asp Lys Pro Tyr Leu Leu Tyr Phe Asn Ile Phe Ser Cys Ile Leu
                 85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Val Gly Gln Met Met
225                 230                 235                 240

Ser Thr Met Phe Tyr Pro Leu Val Thr Phe Val Leu Leu Ile Cys
                245                 250                 255

Ile Ala Tyr Trp Ala Met Thr Ala Leu Tyr Leu Ala Thr Ser Gly Gln
            260                 265                 270

Pro Gln Tyr Val Leu Trp Ala Ser Asn Ile Ser Ser Pro Gly Cys Glu
        275                 280                 285

Lys Val Pro Ile Asn Thr Ser Cys Asn Pro Thr Ala His Leu Val Asn
    290                 295                 300
```

Ser Ser Cys Pro Gly Leu Met Cys Val Phe Gln Gly Tyr Ser Ser Lys
305                 310                 315                 320

Gly Leu Ile Gln Arg Ser Val Phe Asn Leu Gln Ile Tyr Gly Val Leu
            325                 330                 335

Gly Leu Phe Trp Thr Leu Asn Trp Val Leu Ala Leu Gly Gln Cys Val
            340                 345                 350

Leu Ala Gly Ala Phe Ala Ser Phe Tyr Trp Ala Phe His Lys Pro Gln
            355                 360                 365

Asp Ile Pro Thr Phe Pro Leu Ile Ser Ala Phe Ile Arg Thr Leu Arg
            370                 375                 380

Tyr His Thr Gly Ser Leu Ala Phe Gly Ala Leu Ile Leu Thr Leu Val
385                 390                 395                 400

Gln Ile Ala Arg Val Ile Leu Glu Tyr Ile Asp His Lys Leu Arg Gly
            405                 410                 415

Val Gln Asn Pro Val Ala Arg Cys Ile Met Cys Cys Phe Lys Cys Cys
            420                 425                 430

Leu Trp Cys Leu Glu Lys Phe Ile Lys Phe Leu Asn Arg Asn Ala Tyr
            435                 440                 445

Ile Met Ile Ala Ile Tyr Gly Lys Asn Phe Cys Val Ser Ala Lys Asn
450                 455                 460

Ala Phe Met Leu Leu Met Arg Asn Ile Val Arg Val Val Val Leu Asp
465                 470                 475                 480

Lys Val Thr Asp Leu Leu Phe Phe Gly Lys Leu Leu Val Val Gly
            485                 490                 495

Gly Val Gly Val Leu Ser Phe Phe Phe Ser Gly Arg Ile Pro Gly
            500                 505                 510

Leu Gly Lys Asp Phe Lys Ser Pro His Leu Asn Tyr Tyr Trp Leu Pro
            515                 520                 525

Ile Met Thr Ser Ile Leu Gly Ala Tyr Val Ile Ala Ser Gly Phe Phe
530                 535                 540

Ser Val Phe Gly Met Cys Val Asp Thr Leu Phe Leu Cys Phe Leu Glu
545                 550                 555                 560

Asp Leu Glu Arg Asn Asn Gly Ser Leu Asp Arg Pro Tyr Tyr Met Ser
            565                 570                 575

Lys Ser Leu Leu Lys Ile Leu Gly Lys Lys Asn Glu Ala Pro Pro Asp
            580                 585                 590

Asn Lys Lys Arg Lys Lys
            595

<210> SEQ ID NO 98
<211> LENGTH: 710
<212> TYPE: PRT
<213> ORGANISM: Homo Sapiens

<400> SEQUENCE: 98

Met Gly Gly Lys Gln Arg Asp Glu Asp Glu Ala Tyr Gly Lys Pro
 1               5                  10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65                  70                  75                  80

-continued

```
Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Ile Cys
        355                 360                 365

Ile Ala Tyr Trp Ala Met Thr Ala Leu Tyr Leu Ala Thr Ser Gly Gln
    370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
        435                 440                 445

Gly Leu Phe Trp Thr Leu Asn Trp Val Leu Ala Leu Gly Gln Cys Val
    450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510
```

-continued

```
Gln Ile Ala Arg Val Ile Leu Glu Tyr Ile Asp His Lys Leu Arg Gly
            515                 520                 525
Val Gln Asn Pro Val Ala Arg Cys Ile Met Cys Cys Phe Lys Cys Cys
        530                 535                 540
Leu Trp Cys Leu Glu Lys Phe Ile Lys Phe Leu Asn Arg Asn Ala Tyr
545                 550                 555                 560
Ile Met Ile Ala Ile Tyr Gly Lys Asn Phe Cys Val Ser Ala Lys Asn
                565                 570                 575
Ala Phe Met Leu Leu Met Arg Asn Ile Val Arg Val Val Leu Asp
            580                 585                 590
Lys Val Thr Asp Leu Leu Phe Gly Lys Leu Leu Val Val Gly
        595                 600                 605
Gly Val Gly Val Leu Ser Phe Phe Ser Gly Arg Ile Pro Gly
    610                 615                 620
Leu Gly Lys Asp Phe Lys Ser Pro His Leu Asn Tyr Tyr Trp Leu Pro
625                 630                 635                 640
Ile Met Thr Ser Ile Leu Gly Ala Tyr Val Ile Ala Ser Gly Phe Phe
                645                 650                 655
Ser Val Phe Gly Met Cys Val Asp Thr Leu Phe Leu Cys Phe Leu Glu
                660                 665                 670
Asp Leu Glu Arg Asn Asn Gly Ser Leu Asp Arg Pro Tyr Tyr Met Ser
            675                 680                 685
Lys Ser Leu Leu Lys Ile Leu Gly Lys Asn Glu Ala Pro Pro Asp
        690                 695                 700
Asn Lys Lys Arg Lys Lys
705                 710

<210> SEQ ID NO 99
<211> LENGTH: 598
<212> TYPE: PRT
<213> ORGANISM: Homo Sapiens

<400> SEQUENCE: 99

Met Gly Gly Lys Gln Arg Asp Glu Asp Glu Ala Tyr Gly Lys Pro
  1               5                  10                  15
Val Lys Tyr Asp Pro Ser Phe Arg Gly Pro Ile Lys Asn Arg Ser Cys
                20                  25                  30
Thr Asp Val Ile Cys Cys Val Leu Phe Leu Leu Phe Ile Leu Gly Tyr
            35                  40                  45
Ile Val Val Gly Ile Val Ala Trp Leu Tyr Gly Asp Pro Arg Gln Val
        50                  55                  60
Leu Tyr Pro Arg Asn Ser Thr Gly Ala Tyr Cys Gly Met Gly Glu Asn
65                  70                  75                  80
Lys Asp Lys Pro Tyr Leu Leu Tyr Phe Asn Ile Phe Ser Cys Ile Leu
                85                  90                  95
Ser Ser Asn Ile Ile Ser Val Ala Glu Asn Gly Leu Gln Cys Pro Thr
                100                 105                 110
Pro Gln Val Cys Val Ser Ser Cys Pro Glu Asp Pro Trp Thr Val Gly
            115                 120                 125
Lys Asn Glu Phe Ser Gln Thr Val Gly Glu Val Phe Tyr Thr Lys Asn
        130                 135                 140
Arg Asn Phe Cys Leu Pro Gly Val Pro Trp Asn Met Thr Val Ile Thr
145                 150                 155                 160
Ser Leu Gln Gln Glu Leu Cys Pro Ser Phe Leu Leu Pro Ser Ala Pro
                165                 170                 175
```

```
Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
            195                 200                 205

Ile Asp Ser Leu Asn Ala Arg Asp Ile Ser Val Lys Ile Phe Glu Asp
            210                 215                 220

Phe Ala Gln Ser Trp Tyr Trp Ile Leu Val Ala Val Gly Gln Met Met
225                 230                 235                 240

Ser Thr Met Phe Tyr Pro Leu Val Thr Phe Val Leu Leu Ile Cys
                    245                 250                 255

Ile Ala Tyr Trp Ala Met Thr Ala Leu Tyr Leu Ala Thr Ser Gly Gln
            260                 265                 270

Pro Gln Tyr Val Leu Trp Ala Ser Asn Ile Ser Ser Pro Gly Cys Glu
            275                 280                 285

Lys Val Pro Ile Asn Thr Ser Cys Asn Pro Thr Ala His Leu Val Asn
            290                 295                 300

Ser Ser Cys Pro Gly Leu Met Cys Val Phe Gln Gly Tyr Ser Ser Lys
305                 310                 315                 320

Gly Leu Ile Gln Arg Ser Val Phe Asn Leu Gln Ile Tyr Gly Val Leu
                    325                 330                 335

Gly Leu Phe Trp Thr Leu Asn Trp Val Leu Ala Leu Gly Gln Cys Val
                340                 345                 350

Leu Ala Gly Ala Phe Ala Ser Phe Tyr Trp Ala Phe His Lys Pro Gln
            355                 360                 365

Asp Ile Pro Thr Phe Pro Leu Ile Ser Ala Phe Ile Arg Thr Leu Arg
            370                 375                 380

Tyr His Thr Gly Ser Leu Ala Phe Gly Ala Leu Ile Leu Thr Leu Val
385                 390                 395                 400

Gln Ile Ala Arg Val Ile Leu Glu Tyr Ile Asp His Lys Leu Arg Gly
                    405                 410                 415

Val Gln Asn Pro Val Ala Arg Cys Ile Met Cys Cys Phe Lys Cys Cys
                420                 425                 430

Leu Trp Cys Leu Glu Lys Phe Ile Lys Phe Leu Asn Arg Asn Ala Tyr
            435                 440                 445

Ile Met Ile Ala Ile Tyr Gly Lys Asn Phe Cys Val Ser Ala Lys Asn
            450                 455                 460

Ala Phe Met Leu Leu Met Arg Asn Ile Val Arg Val Val Leu Asp
465                 470                 475                 480

Lys Val Thr Asp Leu Leu Leu Phe Phe Gly Lys Leu Leu Val Val Gly
                    485                 490                 495

Gly Val Gly Val Leu Ser Phe Phe Phe Ser Gly Arg Ile Pro Gly
                500                 505                 510

Leu Gly Lys Asp Phe Lys Ser Pro His Leu Asn Tyr Tyr Trp Leu Pro
            515                 520                 525

Ile Met Thr Ser Ile Leu Gly Ala Tyr Val Ile Ala Ser Gly Phe Phe
            530                 535                 540

Ser Val Phe Gly Met Cys Val Asp Thr Leu Phe Leu Cys Phe Leu Glu
545                 550                 555                 560

Asp Leu Glu Arg Asn Asn Gly Ser Leu Asp Arg Pro Tyr Tyr Met Ser
                    565                 570                 575

Lys Ser Leu Leu Lys Ile Leu Gly Lys Lys Asn Glu Ala Pro Pro Asp
            580                 585                 590

Asn Lys Lys Arg Lys Lys
```

<210> SEQ ID NO 100
<211> LENGTH: 2623
<212> TYPE: DNA
<213> ORGANISM: Homo Sapiens

<400> SEQUENCE: 100

```
gagccatggg gggaaagcag cgggacgagg atgacgaggc ctacgggaag ccagtcaaat      60
acgacccctc ctttcgaggc cccatcaaga acagaagctg cacagatgtc atctgctgcg     120
tcctcttcct gctcttcatt ctaggttaca tcgtggtggg gattgtgcc tggttgtatg      180
gagaccccg gcaagtcctc tacccagga actctactgg ggcctactgt ggcatggggg      240
agaacaaaga taagccgtat ctcctgtact tcaacatctt cagctgcatc ctgtccagca     300
acatcatctc agttgctgag aacggcctac agtgccccac accccaggtg tgtgtgtcct     360
cctgcccgga ggacccatgg actgtgggaa aaaacgagtt ctcacagact gttggggaag     420
tcttctatac aaaaaacagg aacttttgtc tgccaggggt accctggaat atgacggtga     480
tcacaagcct gcaacaggaa ctctgcccca gtttcctcct ccctctgct ccagctctgg      540
ggcgctgctt tccatggacc aacgttactc caccggcgct cccagggatc accaatgaca     600
ccaccataca gcagggatc agcggtctta ttgacagcct caatgcccga gacatcagtg      660
ttaagatctt tgaagatttt gcccagtcct ggtattggat tcttgttgcc ctgggggtgg     720
ctctggtctt gagcctactg tttatcttgc ttctgcgcct ggtggctggg ccctgtgtc     780
tggtgctgat cctgggagtg ctgggcgtgc tggcatacgg catctactac tgctgggagg     840
agtaccgagt gctgcgggac aagggcgcct ccatctccca gctgggtttc accaccaacc     900
tcagtgccta ccagagcgtg caggagacct ggctggccgc cctgatcgtg ttggcggtgc     960
ttgaagccat cctgctgctg atgctcatct tcctgcggca gcggattcgt attgccatcg    1020
ccctcctgaa ggaggccagc aaggctgtgg acagatgat gtctaccatg ttctacccac    1080
tggtcaccct tgtcctcctc ctcatctgca ttgcctactg gccatgact gctctgtacc     1140
tggctacatc ggggcaaccc cagtatgtgc tctgggcatc aacatcagc tcccccggct    1200
gtgagaaagt gccaataaat acatcatgca accccacggc ccaccttgtg aactcctcgt    1260
gcccagggct gatgtgcgtc ttccagggct actcatccaa aggcctaatc caacgttctg    1320
tcttcaatct gcaaatctat ggggtcctgg ggctcttctg gacccttaac tgggtactgg    1380
ccctgggcca atgcgtcctc gctggagcct ttgcctcctt ctactgggcc ttccacaagc    1440
cccaggacat ccctaccttc cccttaatct ctgccttcat ccgcacactc cgttaccaca    1500
ctgggtcatt ggcatttgga gccctcatcc tgacccttgt gcagatagcc cgggtcatct    1560
tggagtatat tgaccacaag ctcagaggag tgcagaaccc tgtagcccgc tgcatcatgt    1620
gctgtttcaa gtgctgcctc tggtgtctgg aaaaatttat caagttccta aaccgcaatg    1680
catacatcat gatcgccatc tacgggaaga atttctgtgt ctcagccaaa aatgcgttca    1740
tgctactcat gcgaaacatt gtcagggtgg tcgtcctgga caaagtcaca gacctgctgc    1800
tgttctttgg gaagctgctg gtggtcggag gcgtgggggt cctgtccttc ttttttttct    1860
ccggtcgcat cccgggggctg ggtaaagact ttaagagccc ccacctcaac tattactggc    1920
tgcccatcat gaggaaccca ataaccccaa cgggtcatgt cttccagacc tccatcctgg    1980
gggcctatgt catcgccagc ggcttcttca gcgttttcgg catgtgtgtg gacacgctct    2040
tcctctgctt cctggaagac ctggagcgga caacggctc cctggaccgg ccctactaca    2100
```

-continued

| | |
|---|---|
| tgtccaagag ccttctaaag attctgggca agaagaacga ggcgccccg gacaacaaga | 2160 |
| agaggaagaa gtgacagctc cggccctgat ccaggactgc accccacccc caccgtccag | 2220 |
| ccatccaacc tcacttcgcc ttacaggtct ccattttgtg gtaaaaaaag gttttaggcc | 2280 |
| aggcgccgtg gctcacgcct gtaatccaac actttgagag gctgaggcgg gcggatcacc | 2340 |
| tgagtcagga gttcgagacc agcctggcca catggtgaa acctccgtct ctattaaaaa | 2400 |
| tacaaaaatt agccgagagt ggtggcatgc acctgtcatc ccagctactc gggaggctga | 2460 |
| ggcaggagaa tcgcttgaac ccggaggca gaggttgcag tgagccgaga tcgcgccact | 2520 |
| gcactccaac ctgggtgaca gactctgtct ccaaaacaaa acaaacaaac aaaaagattt | 2580 |
| tattaaagat attttgttaa ctcagtaaaa aaaaaaaaaa aaa | 2623 |

<210> SEQ ID NO 101
<211> LENGTH: 2587
<212> TYPE: DNA
<213> ORGANISM: Homo Sapiens

<400> SEQUENCE: 101

| | |
|---|---|
| gagccatggg gggaaagcag cgggacgagg atgacgaggc ctacgggaag ccagtcaaat | 60 |
| acgacccctc ctttcgaggc cccatcaaga acagaagctg cacagatgtc atctgctgcg | 120 |
| tcctcttcct gctcttcatt ctaggttaca tcgtggtggg gattgtggcc tggttgtatg | 180 |
| gagacccccg gcaagtcctc tacccagga actctactgg ggcctactgt ggcatggggg | 240 |
| agaacaaaga taagccgtat ctcctgtact tcaacatctt cagctgcatc ctgtccagca | 300 |
| acatcatctc agttgctgag aacggcctac agtgccccac accccaggtg tgtgtgtcct | 360 |
| cctgcccgga ggacccatgg actgtgggaa aaaacgagtt ctcacagact gttggggaag | 420 |
| tcttctatac aaaaaacagg aacttttgtc tgccaggggt accctggaat atgacggtga | 480 |
| tcacaagcct gcaacaggaa ctctgcccca gtttcctcct cccctctgct ccagctctgg | 540 |
| ggcgctgctt tccatggacc aacgttactc caccggcgct cccaggggatc accaatgaca | 600 |
| ccaccataca gcggggatc agcggtctta ttgacagcct caatgcccga gacatcagtg | 660 |
| ttaagatctt tgaagatttt gcccagtcct ggtattggat tcttgttgcc ctgggggtgg | 720 |
| ctctggtctt gagcctactg tttatcttgc ttctgcgcct ggtggctggg cccctggtgc | 780 |
| tggtgctgat cctgggagtg ctgggcgtgc tggcatacgg catctactac tgctgggagg | 840 |
| agtaccgagt gctgcgggac aagggcgcct ccatctccca gctgggtttc accaccaacc | 900 |
| tcagtgccta ccagagcgtg caggagacct ggctggccgc cctgatcgtg ttggcggtgc | 960 |
| ttgaagccat cctgctgctg atgctcatct tcctgcggca gcggattcgt attgccatcg | 1020 |
| ccctcctgaa ggaggccagc aaggctgtgg gacagatgat gtctaccatg ttctacccac | 1080 |
| tggtcacctt tgtcctcctc ctcatctgca ttgcctactg ggccatgact gctctgtacc | 1140 |
| tggctacatc ggggcaaccc cagtatgtgc tctgggcatc aacatcagc tcccccggct | 1200 |
| gtgagaaagt gccaataaat acatcatgca accccacggc ccaccttgtg aactcctcgt | 1260 |
| gcccagggct gatgtgcgtc ttccagggct actcatccaa aggcctaatc caacgttctg | 1320 |
| tcttcaatct gcaaatctat ggggtcctgg ggctcttctg gacccttaac tgggtactgg | 1380 |
| ccctgggcca atgcgtcctc gctggagcct ttgcctcctt ctactgggcc ttccacaagc | 1440 |
| cccaggacat ccctaccttc ccccttaatct ctgccttcat ccgcacactc cgttaccaca | 1500 |
| ctgggtcatt ggcatttgga gccctcatcc tgacccttgt gcagatagcc cgggtcatct | 1560 |
| tggagtatat tgaccacaag ctcagaggag tgcagaaccc tgtagcccgc tgcatcatgt | 1620 |

-continued

```
gctgtttcaa gtgctgcctc tggtgtctgg aaaaatttat caagttccta aaccgcaatg   1680
catacatcat gatcgccatc tacgggaaga atttctgtgt ctcagccaaa aatgcgttca   1740
tgctactcat gcgaaacatt gtcagggtgg tcgtcctgga caaagtcaca gacctgctgc   1800
tgttctttgg gaagctgctg gtggtcggag gcgtgggggg cctgtccttc ttttttttct   1860
ccggtcgcat cccggggctg ggtaaagact ttaagagccc ccacctcaac tattactggc   1920
tgcccatcat gacctccatc ctgggggcct atgtcatcgc cagcggcttc ttcagcgttt   1980
tcggcatgtg tgtggacacg ctcttcctct gcttcctgga agacctggag cggaacaacg   2040
gctccctgga ccgcccctac tacatgtcca agagccttct aaagattctg gcaagaaga   2100 acgaggcgcc cccggacaac aagaagagga agaagtgaca gctccggccc tgatccagga   2160
ctgcacccca cccccaccgt ccagccatcc aacctcactt cgccttacag gtctccattt   2220
tgtggtaaaa aaaggtttta ggccaggcgc cgtggctcac gcctgtaatc caacactttg   2280
agaggctgag gcgggcggat cacctgagtc aggagttcga gaccagcctg ccaacatgg    2340 tgaaacctcc gtctctatta aaaatacaaa aattagccga gagtggtggc atgcacctgt   2400
catcccagct actcgggagg ctgaggcagg agaatcgctt gaacccggga ggcagaggtt   2460
gcagtgagcc gagatcgcgc cactgcactc caacctgggt gacagactct gtctccaaaa   2520
caaaacaaac aaacaaaaag attttattaa agatattttg ttaactcagt aaaaaaaaaa   2580
aaaaaaa                                                            2587
```

<210> SEQ ID NO 102
<211> LENGTH: 2623
<212> TYPE: DNA
<213> ORGANISM: Homo Sapiens

<400> SEQUENCE: 102

```
gagccatggg gggaaagcag cgggacgagg atgacgaggc ctacgggaag ccagtcaaat     60
acgacccctc ctttcgaggc cccatcaaga acagaagctg cacagatgtc atctgctgcg    120
tcctcttcct gctcttcatt ctaggttaca tcgtggtggg gattgtggcc tggttgtatg    180
gagacccccg gcaagtcctc taccccagga actctactgg ggcctactgt ggcatggggg    240
agaacaaaga taagccgtat ctcctgtact tcaacatctt cagctgcatc ctgtccagca    300
acatcatctc agttgctgag aacggcctac agtgccccac accccaggtg tgtgtgtcct    360
cctgcccgga ggacccatgg actgtgggaa aaaacgagtt ctcacagact gttggggaag    420
tcttctatac aaaaaaacagg aacttttgtc tgccaggggt accctggaat atgacggtga    480
tcacaagcct gcaacaggaa ctctgcccca gtttcctcct cccctctgct ccagctctgg    540
ggcgctgctt tccatggacc aacgttactc caccggcgct cccagggatc accaatgaca    600
ccaccataca gcagggatc agcggtctta ttgacagcct caatgcccga gacatcagtg    660
ttaagatctt tgaagatttt gcccagtcct ggtattggat tcttgttgcc ctggggggtgg   720 ctctggtctt gagcctactg tttatcttgc ttctgcgcct ggtggctggg cccctggtgc    780
tggtgctgat cctgggagtg ctgggcgtgc tggcatacgg catctactac tgctgggagg    840
agtaccgagt gctgcgggac aagggcgcct ccatctccca gctgggtttc accaccaacc    900
tcagtgccta ccagagcgtg caggagacct ggctggccgc cctgatcgtg ttggcggtgc    960
ttgaagccat cctgctgctg atgctcatct tcctgcggca gcggattcgt attgccatcg   1020
ccctcctgaa ggaggccagc aaggctgtgg acagatgat gtctaccatg ttctaccccac   1080 tggtcacctt tgtcctcctc ctcatctgca ttgcctactg ggccatgact gctctgtacc   1140
```

-continued

```
tggctacatc ggggcaaccc cagtatgtgc tctgggcatc aacatcagc tccccggct    1200 gtgagaaagt gccaataaat acatcatgca acccacggc ccaccttgtg aactcctcgt    1260
gcccagggct gatgtgcgtc ttccagggct actcatccaa aggcctaatc caacgttctg    1320
tcttcaatct gcaaatctat ggggtcctgg ggctcttctg gacccttaac tgggtactgg    1380
ccctgggcca atgcgtcctc gctggagcct ttgcctcctt ctactgggcc ttccacaagc    1440
cccaggacat ccctaccttc cccttaatct ctgccttcat ccgcacactc cgttaccaca    1500
ctgggtcatt ggcatttgga gccctcatcc tgaccccttgt gcagatagcc cgggtcatct    1560
tggagtatat tgaccacaag ctcagaggag tgcagaaccc tgtagcccgc tgcatcatgt    1620
gctgtttcaa gtgctgcctc tggtgtctgg aaaaatttat caagttccta accgcaatg    1680 catacatcat gatcgccatc tacgggaaga atttctgtgt ctcagccaaa aatgcgttca    1740
tgctactcat gcgaaacatt gtcagggtgg tcgtcctgga caaagtcaca gacctgctgc    1800
tgttctttgg gaagctgctg gtggtcggag cgtgggggt cctgtccttc ttttttttct    1860
ccggtcgcat cccggggctg gtaaagact ttaagagccc ccacctcaac tattactggc    1920
tgcccatcat gaggaaccca ataaccccaa cgggtcatgt cttccagacc tccatcctgg    1980
gggcctatgt catcgccagc ggcttcttca gcgttttcgg catgtgtgtg gacacgctct    2040
tcctctgctt cctggaagac ctggagcgga caacggctc cctggaccgg ccctactaca    2100
tgtccaagag ccttctaaag attctgggca agaagaacga ggcgccccg gacaacaaga    2160 agaggaagaa gtgacagctc cggccctgat ccaggactgc accccacccc caccgtccag    2220
ccatccaacc tcacttcgcc ttacaggtct ccattttgtg gtaaaaaaag gttttaggcc    2280
aggcgccgtg gctcacgcct gtaatccaac actttgagag gctgaggcgg gcggatcacc    2340
tgagtcagga gttcgagacc agcctggcca acatggtgaa acctccgtct ctattaaaaa    2400
tacaaaaatt agccgagagt ggtggcatgc acctgtcatc ccagctactc gggaggctga    2460
ggcaggagaa tcgcttgaac ccgggaggca gaggttgcag tgagccgaga tcgcgccact    2520
gcactccaac ctgggtgaca gactctgtct ccaaaacaaa acaaacaaac aaaagattt    2580 tattaaagat attttgttaa ctcagtaaaa aaaaaaaaaa aaa                     2623
```

<210> SEQ ID NO 103
<211> LENGTH: 722
<212> TYPE: PRT
<213> ORGANISM: Homo Sapiens

<400> SEQUENCE: 103

```
Met Gly Gly Lys Gln Arg Asp Glu Asp Asp Glu Ala Tyr Gly Lys Pro
 1               5                  10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
```

115                 120                 125
Lys Asn Glu Phe Ser Gln Thr Val Gly Glu Val Phe Tyr Thr Lys Asn
            130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                    165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
                    195                 200                 205

Ile Asp Ser Leu Asn Ala Arg Asp Ile Ser Val Lys Ile Phe Glu Asp
            210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Arg Leu Val Ala Gly Pro
                    245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
            275                 280                 285

Ser Ile Ser Gln Leu Gly Phe Thr Thr Asn Leu Ser Ala Tyr Gln Ser
            290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                    325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Leu Ile Cys
            355                 360                 365

Ile Ala Tyr Trp Ala Met Thr Ala Leu Tyr Leu Ala Thr Ser Gly Gln
            370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                    405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
            435                 440                 445

Gly Leu Phe Trp Thr Leu Asn Trp Val Leu Ala Leu Gly Gln Cys Val
            450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                    485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
            515                 520                 525

Val Gln Asn Pro Val Ala Arg Cys Ile Met Cys Cys Phe Lys Cys Cys
            530                 535                 540

-continued

```
Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
            580                 585                 590

Lys Val Thr Asp Leu Leu Leu Phe Phe Gly Lys Leu Leu Val Val Gly
                595                 600                 605

Gly Val Gly Val Leu Ser Phe Phe Phe Ser Gly Arg Ile Pro Gly
        610                 615                 620

Leu Gly Lys Asp Phe Lys Ser Pro His Leu Asn Tyr Tyr Trp Leu Pro
625                 630                 635                 640

Ile Met Arg Asn Pro Ile Thr Pro Thr Gly His Val Phe Gln Thr Ser
                645                 650                 655

Ile Leu Gly Ala Tyr Val Ile Ala Ser Gly Phe Phe Ser Val Phe Gly
                660                 665                 670

Met Cys Val Asp Thr Leu Phe Leu Cys Phe Leu Glu Asp Leu Glu Arg
                675                 680                 685

Asn Asn Gly Ser Leu Asp Arg Pro Tyr Tyr Met Ser Lys Ser Leu Leu
690                 695                 700

Lys Ile Leu Gly Lys Lys Asn Glu Ala Pro Pro Asp Asn Lys Lys Arg
705                 710                 715                 720

Lys Lys

<210> SEQ ID NO 104
<211> LENGTH: 710
<212> TYPE: PRT
<213> ORGANISM: Homo Sapiens

<400> SEQUENCE: 104

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
        130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
```

-continued

```
              195                 200                 205
Ile Asp Ser Leu Asn Ala Arg Asp Ile Ser Val Lys Ile Phe Glu Asp
210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Leu Arg Leu Val Ala Gly Pro
                245                 250                 255
Leu Val Leu Val Leu Ile Leu Gly Val Leu Gly Val Leu Ala Tyr Gly
                260                 265                 270
Ile Tyr Tyr Cys Trp Glu Glu Tyr Arg Val Leu Arg Asp Lys Gly Ala
                275                 280                 285
Ser Ile Ser Gln Leu Gly Phe Thr Thr Asn Leu Ser Ala Tyr Gln Ser
                290                 295                 300
Val Gln Glu Thr Trp Leu Ala Ala Leu Ile Val Leu Ala Val Leu Glu
305                 310                 315                 320
Ala Ile Leu Leu Leu Met Leu Ile Phe Leu Arg Gln Arg Ile Arg Ile
                325                 330                 335
Ala Ile Ala Leu Leu Lys Glu Ala Ser Lys Ala Val Gly Gln Met Met
                340                 345                 350
Ser Thr Met Phe Tyr Pro Leu Val Thr Phe Val Leu Leu Leu Ile Cys
                355                 360                 365
Ile Ala Tyr Trp Ala Met Thr Ala Leu Tyr Leu Ala Thr Ser Gly Gln
                370                 375                 380
Pro Gln Tyr Val Leu Trp Ala Ser Asn Ile Ser Ser Pro Gly Cys Glu
385                 390                 395                 400
Lys Val Pro Ile Asn Thr Ser Cys Asn Pro Thr Ala His Leu Val Asn
                405                 410                 415
Ser Ser Cys Pro Gly Leu Met Cys Val Phe Gln Gly Tyr Ser Ser Lys
                420                 425                 430
Gly Leu Ile Gln Arg Ser Val Phe Asn Leu Gln Ile Tyr Gly Val Leu
                435                 440                 445
Gly Leu Phe Trp Thr Leu Asn Trp Val Leu Ala Leu Gly Gln Cys Val
                450                 455                 460
Leu Ala Gly Ala Phe Ala Ser Phe Tyr Trp Ala Phe His Lys Pro Gln
465                 470                 475                 480
Asp Ile Pro Thr Phe Pro Leu Ile Ser Ala Phe Ile Arg Thr Leu Arg
                485                 490                 495
Tyr His Thr Gly Ser Leu Ala Phe Gly Ala Leu Ile Leu Thr Leu Val
                500                 505                 510
Gln Ile Ala Arg Val Ile Leu Glu Tyr Ile Asp His Lys Leu Arg Gly
                515                 520                 525
Val Gln Asn Pro Val Ala Arg Cys Ile Met Cys Cys Phe Lys Cys Cys
                530                 535                 540
Leu Trp Cys Leu Glu Lys Phe Ile Lys Phe Leu Asn Arg Asn Ala Tyr
545                 550                 555                 560
Ile Met Ile Ala Ile Tyr Gly Lys Asn Phe Cys Val Ser Ala Lys Asn
                565                 570                 575
Ala Phe Met Leu Leu Met Arg Asn Ile Val Arg Val Val Val Leu Asp
                580                 585                 590
Lys Val Thr Asp Leu Leu Phe Gly Lys Leu Leu Val Val Gly
                595                 600                 605
Gly Val Gly Val Leu Ser Phe Phe Phe Ser Gly Arg Ile Pro Gly
                610                 615                 620
```

```
Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
            645                 650                 655

Ser Val Phe Gly Met Cys Val Asp Thr Leu Phe Leu Cys Phe Leu Glu
        660                 665                 670

Asp Leu Glu Arg Asn Asn Gly Ser Leu Asp Arg Pro Tyr Tyr Met Ser
    675                 680                 685

Lys Ser Leu Leu Lys Ile Leu Gly Lys Asn Glu Ala Pro Pro Asp
690                 695                 700

Asn Lys Lys Arg Lys Lys
705             710

<210> SEQ ID NO 105
<211> LENGTH: 722
<212> TYPE: PRT
<213> ORGANISM: Homo Sapiens

<400> SEQUENCE: 105

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Phe Ile Leu Gly Tyr
            35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285
```

```
Ser Ile Ser Gln Leu Gly Phe Thr Thr Asn Leu Ser Ala Tyr Gln Ser
    290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
                340                 345                 350

Ser Thr Met Phe Tyr Pro Leu Val Thr Phe Val Leu Leu Leu Ile Cys
            355                 360                 365

Ile Ala Tyr Trp Ala Met Thr Ala Leu Tyr Leu Ala Thr Ser Gly Gln
    370                 375                 380

Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
    435                 440                 445

Gly Leu Phe Trp Thr Leu Asn Trp Val Leu Ala Leu Gly Gln Cys Val
450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
    515                 520                 525

Val Gln Asn Pro Val Ala Arg Cys Ile Met Cys Cys Phe Lys Cys Cys
530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
            580                 585                 590       Asp

Lys Val Thr Asp Leu Leu Phe Gly Lys Leu Leu Val Val Gly
            595                 600                 605       Gly

Gly Val Gly Val Leu Ser Phe Phe Phe Ser Gly Arg Ile Pro Gly
    610                 615                 620

Leu Gly Lys Asp Phe Lys Ser Pro His Leu Asn Tyr Tyr Trp Leu Pro
625                 630                 635                 640

Ile Met Arg Asn Pro Ile Thr Pro Thr Gly His Val Phe Gln Thr Ser
                645                 650                 655

Ile Leu Gly Ala Tyr Val Ile Ala Ser Gly Phe Phe Ser Val Phe Gly
            660                 665                 670

Met Cys Val Asp Thr Leu Phe Leu Cys Phe Leu Glu Asp Leu Glu Arg
            675                 680                 685

Asn Asn Gly Ser Leu Asp Arg Pro Tyr Tyr Met Ser Lys Ser Leu Leu
    690                 695                 700

Lys Ile Leu Gly Lys Lys Asn Glu Ala Pro Pro Asp Asn Lys Lys Arg
705                 710                 715                 720
```

Lys Lys

<210> SEQ ID NO 106
<211> LENGTH: 2593
<212> TYPE: DNA
<213> ORGANISM: Homo Sapiens

<400> SEQUENCE: 106

```
gagccatggg gggaaagcag cgggacgagg atgacgaggc ctacgggaag ccagtcaaat      60
acgacccctc ctttcgaggc cccatcaaga acagaagctg cacagatgtc atctgctgcg     120
tcctcttcct gctcttcatt ctaggttaca tcgtggtggg gattgtggcc tggttgtatg     180
gagaccccg gcaagtcctc taccccagga actctactgg ggcctactgt ggcatggggg     240
agaacaaaga taagccgtat ctcctgtact tcaacatctt cagctgcatc ctgtccagca     300
acatcatctc agttgctgag aacggcctac agtgccccac accccaggtg tgtgtgtcct     360
cctgcccgga ggacccatgg actgtgggaa aaacgagtt ctcacagact gttggggaag     420
tcttctatac aaaaaacagg aacttttgtc tgccaggggt accctggaat atgacggtga     480
tcacaagcct gcaacaggaa ctctgcccca gtttcctcct cccctctgct ccagctctgg     540
ggcgctgctt tccatggacc aacgttactc caccggcgct cccagggatc accaatgaca     600
ccaccataca gcagggggatc agcggtctta ttgacagcct caatgcccga gacatcagtg     660
ttaagatctt tgaagatttt gcccagtcct ggtattggat tcttgttgcc ctggggtgg     720
ctctggtctt gagcctactg tttatcttgc ttctgcgcct ggtggctggg ccctggtgc     780
tggtgctgat cctgggagtg ctgggcgtgc tggcatacgg catctactac tgctgggagg     840
agtaccgagt gctgcgggac aagggcgcct ccatctccca gctgggtttc accaccaacc     900
tcagtgccta ccagagcgtg caggagacct ggctggccgc cctgatcgtg ttggcggtgc     960
ttgaagccat cctgctgctg atgctcatct ccctgcggca gcggattcgt attgccatcg    1020
ccctcctgaa ggaggccagc aaggctgtgg acagatgat gtctaccatg ttctacccac    1080
tggtcacctt tgtcctcctc ctcatctgca ttgcctactg ggccatgact gctctgtatc    1140
ctctgcccac gcagccagcc actcttggat atgtgctctg ggcatccaac atcagctccc    1200
ccggctgtga gaaagtgcca ataaatacat catgcaaccc cacggcccac cttgtgaact    1260
cctcgtgccc agggctgatg tgcgtcttcc agggctactc atccaaaggc ctaatccaac    1320
gttctgtctt caatctgcaa atctatgggg tcctggggct cttctggacc cttaactggg    1380
tactggcccct gggccaatgc gtcctcgctg agcctttgc ctccttctac tgggccttcc    1440
acaagcccca ggacatccct accttcccct taatctctgc cttcatccgc acactccgtt    1500
accacactgg gtcattggca tttggagccc tcatcctgac ccttgtgcag atagcccggg    1560
tcatcttgga gtatattgac cacaagctca gaggagtgca gaaccctgta gcccgctgca    1620
tcatgtgctg tttcaagtgc tgcctctggt gtctggaaaa atttatcaag ttcctaaacc    1680
gcaatgcata catcatgatc gccatctacg ggaagaattt ctgtgtctca gccaaaaatg    1740
cgttcatgct actcatgcga acattgtca gggtggtcgt cctggacaaa gtcacagacc    1800
tgctgctgtt ctttggaag ctgctggtgg tcggaggcgt gggggtcctg tccttctttt    1860
ttttctccgg tcgcatcccg gggctgggta agacttttaa gagcccccac ctcaactatt    1920
actggctgcc catcatgacc tccatcctgg gggctatgt catcgccagc ggcttcttca    1980
gcgttttcgg catgtgtgtg acacgctct tcctctgctt cctggaagac ctggagcgga    2040
acaacggctc cctggaccgg ccctactaca tgtccaagag ccttctaaag attctgggca    2100
```

```
agaagaacga ggcgcccccg gacaacaaga agaggaagaa gtgacagctc cggccctgat    2160
ccaggactgc accccacccc caccgtccag ccatccaacc tcacttcgcc ttacaggtct    2220
ccattttgtg gtaaaaaaag gttttaggcc aggcgccgtg gctcacgcct gtaatccaac    2280
actttgagag gctgaggcgg gcggatcacc tgagtcagga gttcgagacc agcctggcca    2340
acatggtgaa acctccgtct ctattaaaaa tacaaaaatt agccgagagt ggtggcatgc    2400
acctgtcatc ccagctactc gggaggctga ggcaggagaa tcgcttgaac ccgggaggca    2460
gaggttgcag tgagccgaga tcgcgccact gcactccaac ctgggtgaca gactctgtct    2520
ccaaaacaaa acaaacaaac aaaaagattt tattaaagat attttgttaa ctcagtaaaa    2580
aaaaaaaaaa aaa                                                      2593
```

<210> SEQ ID NO 107  
<211> LENGTH: 2587  
<212> TYPE: DNA  
<213> ORGANISM: Homo Sapiens

<400> SEQUENCE: 107

```
gagccatggg gggaaagcag cgggacgagg atgacgaggc ctacgggaag ccagtcaaat     60
acgacccctc ctttcgaggc cccatcaaga acagaagctg cacagatgtc atctgctgcg    120
tcctcttcct gctcttcatt ctaggttaca tcgtggtggg gattgtgcc tggttgtatg    180 gagacccccg gcaagtcctc tacccagga actctactgg ggcctactgt ggcatggggg    240
agaacaaaga taagccgtat ctcctgtact tcaacatctt cagctgcatc ctgtccagca    300
acatcatctc agttgctgag aacggcctac agtgccccac accccaggtg tgtgtgtcct    360
cctgcccgga ggacccatgg actgtgggaa aaaacgagtt ctcacagact gttggggaag    420
tcttctatac aaaaaacagg aacttttgtc tgccaggggt accctggaat atgacggtga    480
tcacaagcct gcaacaggaa ctctgcccca gtttcctcct cccctctgct ccagctctgg    540
ggcgctgctt tccatggacc aacgttactc caccggcgct cccagggatc accaatgaca    600
ccaccataca gcaggggatc agcggtctta ttgacagcct caatgcccga gacatcagtg    660
ttaagatctt tgaagatttt gcccagtcct ggtattggat tcttgttgcc ctgggggtgg    720
ctctggtctt gagcctactg tttatcttgc ttctgcgcct ggtggctggg cccctggtgc    780
tggtgctgat cctgggagtg ctgggcgtgc tggcatacgg catctactac tgctgggagg    840
agtaccgagt gctgcgggac aagggcgcct ccatctccca gctgggtttc accaccaacc    900
tcagtgccta ccagagcgtg caggagacct ggctggccgc cctgatcgtg ttggcggtgc    960
ttgaagccat cctgctgctg atgctcatct tcctgcggca gcggattcgt attgccatcg   1020
ccctcctgaa ggaggccagc aaggctgtgg gacagatgat gtctaccatg ttctacccac   1080
tggtcacctt tgtcctcctc ctcatctgca ttgcctactg gccatgact gctctgtacc   1140 tggctacatc ggggcaaccc cagtatgtgc tctgggcatc aacatcagc tccccggct   1200 gtgagaaagt gccaataaat acatcatgca accccacggc ccaccttgtg aactcctcgt   1260
gcccagggct gatgtgcgtc ttccagggct actcatccaa aggcctaatc caacgttctg   1320
tcttcaatct gcaaatctat ggggtcctgg ggctcttctg gaccccttaac tgggtactgg   1380 ccctgggcca atgcgtcctc gctggagcct ttgcctcctt ctactgggcc ttccacaagc   1440
cccaggacat ccctacctc cccttaatct ctgccttcat ccgcacactc cgttaccaca   1500
ctgggtcatt ggcatttgga gccctcatcc tgacccttgt gcagatagcc cgggtcatct   1560
tggagtatat tgaccacaag ctcagaggag tgcagaaccc tgtagcccgc tgcatcatgt   1620
```

```
gctgtttcaa gtgctgcctc tggtgtctgg aaaaatttat caagttccta aaccgcaatg      1680
catacatcat gatcgccatc tacgggaaga atttctgtgt ctcagccaaa aatgcgttca      1740
tgctactcat gcgaaacatt gtcagggtgg tcgtcctgga caaagtcaca gacctgctgc      1800
tgttctttgg gaagctgctg gtggtcggag gcgtgggggt cctgtccttc ttttttttct      1860
ccggtcgcat cccggggctg ggtaaagact ttaagagccc ccacctcaac tattactggc      1920
tgcccatcat gacctccatc ctgggggcct atgtcatcgc cagcggcttc ttcagcgttt      1980
tcggcatgtg tgtggacacg ctcttcctct gcttcctgga agacctggag cggaacaacg      2040
gctccctgga ccggccctac tacatgtcca agagccttct aaagattctg ggcaagaaga      2100
acgaggcgcc cccggacaac aagaaggagga gaagtgaca gctccggccc tgatccagga      2160 ctgcaccccca ccccaccgt ccagccatcc aacctcactt cgccttacag gtctccattt      2220
tgtggtaaaa aaaggtttta ggccaggcgc cgtggctcac gcctgtaatc caacactttg      2280
agaggctgag gcgggcggat cacctgagtc aggagttcga gaccagcctg gccaacatgg      2340 tgaaaccctcc gtctctatta aaaatacaaa aattagccga gagtggtggc atgcacctgt      2400
catcccagct actcgggagg ctgaggcagg agaatcgctt gaacccggga ggcagaggtt      2460
gcagtgagcc gagatcgcgc cactgcactc caacctgggt gacagactct gtctccaaaa      2520
caaaacaaac aaacaaaaag attttattaa agatattttg ttaactcagt aaaaaaaaaa      2580
aaaaaaa                                                                2587

<210> SEQ ID NO 108
<211> LENGTH: 2593
<212> TYPE: DNA
<213> ORGANISM: Homo Sapiens

<400> SEQUENCE: 108
gagccatggg gggaaagcag cgggacgagg atgacgaggc ctacgggaag ccagtcaaat        60
acgacccctc ctttcgaggc cccatcaaga acagaagctg cacagatgtc atctgctgcg       120
tcctcttcct gctcttcatt ctaggttaca tcgtggtggg gattgtggcc tggttgtatg       180 gagaccccccg gcaagtcctc tacccctagga actctactgg ggcctactgt ggcatggggg       240
agaacaaaga taagccgtat ctcctgtact tcaacatctt cagctgcatc ctgtccagca       300
acatcatctc agttgctgag aacggcctac agtgccccac accccaggtg tgtgtgtcct       360
cctgcccgga ggacccatgg actgtgggaa aaaacgagtt ctcacagact gttggggaag       420
tcttctatac aaaaaacagg aacttttgtc tgccaggggt accctggaat atgacggtga       480
tcacaagcct gcaacaggaa ctctgccccca gtttcctcct cccctctgct ccagctctgg       540
ggcgctgctt tccatggacc aacgttactc caccggcgct cccagggatc accaatgaca       600
ccaccataca gcagggatc agcggtctta ttgacagcct caatgcccga gacatcagtg       660
ttaagatctt tgaagatttt gcccagtcct ggtattggat tcttgttgcc ctgggggtgg       720
ctctggtctt gagcctactg tttatcttgc ttctgcgcct ggtggctggg ccctggtgc       780 tggtgctgat cctgggagtg ctgggcgtgc tggcatacgg catctactac tgctgggagg       840
agtaccgagt gctgcgggac aagggcgcct ccatctccca gctgggtttc accaccaacc       900
tcagtgccta ccagagcgtg caggagacct ggctggccgc cctgatcgtg ttggcggtgc       960
ttgaagccat cctgctgctg atgctcatct tcctgcggca gcggattcgt attgccatcg      1020 cccctcctgaa ggaggccagc aaggctgtgg gacagatgat gtctaccatg ttctacccac      1080
tggtcacctt tgtcctcctc ctcatctgca ttgcctactg ggccatgact gctctgtatc      1140
```

-continued

```
ctctgcccac gcagccagcc actcttggat atgtgctctg ggcatccaac atcagctccc    1200
ccggctgtga gaaagtgcca ataaatacat catgcaaccc cacggcccac cttgtgaact    1260
cctcgtgccc agggctgatg tgcgtcttcc agggctactc atccaaaggc ctaatccaac    1320
gttctgtctt caatctgcaa atctatgggg tcctggggct cttctggacc cttaactggg    1380
tactggccct gggccaatgc gtcctcgctg gagcctttgc ctccttctac tgggccttcc    1440
acaagcccca ggacatccct accttcccct taatctctgc cttcatccgc acactccgtt    1500
accacactgg gtcattggca tttggagccc tcatcctgac ccttgtgcag atagcccggg    1560
tcatcttgga gtatattgac cacaagctca gaggagtgca gaaccctgta gcccgctgca    1620
tcatgtgctg tttcaagtgc tgcctctggt gtctggaaaa atttatcaag ttcctaaacc    1680
gcaatgcata catcatgatc gccatctacg ggaagaattt ctgtgtctca gccaaaaatg    1740
cgttcatgct actcatgcga aacattgtca gggtggtcgt cctggacaaa gtcacagacc    1800
tgctgctgtt ctttgggaag ctgctggtgg tcggaggcgt gggggtcctg tccttctttt    1860
ttttctccgg tcgcatcccg gggctgggta agactttaa gagccccac ctcaactatt    1920 actggctgcc catcatgacc tccatcctgg ggcctatgt catcgccagc ggcttcttca    1980
gcgttttcgg catgtgtgtg gacacgctct tcctctgctt cctggaagac ctggagcgga    2040
acaacggctc cctggaccgg ccctactaca tgtccaagag ccttctaaag attctgggca    2100
agaagaacga ggcgccccg gacaacaaga gaggaagaa gtgacagctc cggccctgat    2160
ccaggactgc acccccaccc caccgtccag ccatccaacc tcacttcgcc ttacaggtct    2220
ccattttgtg gtaaaaaaag gttttaggcc aggcgccgtg gctcacgcct gtaatccaac    2280
actttgagag gctgaggcgg gcggatcacc tgagtcagga gttcgagacc agcctggcca    2340
acatggtgaa acctccgtct ctattaaaaa tacaaaaatt agccgagagt ggtggcatgc    2400
acctgtcatc ccagctactc gggaggctga ggcaggagaa tcgcttgaac ccggaggca    2460 gaggttgcag tgagccgaga tcgcgccact gcactccaac ctgggtgaca gactctgtct    2520
ccaaaacaaa acaaacaaac aaaagattt tattaaagat atttgtaa ctcagtaaaa    2580 aaaaaaaaaa aaa                                                       2593
```

<210> SEQ ID NO 109
<211> LENGTH: 712
<212> TYPE: PRT
<213> ORGANISM: Homo Sapiens

<400> SEQUENCE: 109

```
Met Gly Gly Lys Gln Arg Asp Glu Asp Asp Glu Ala Tyr Gly Lys Pro
 1               5                  10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110
```

-continued

```
Pro Gln Val Cys Val Ser Ser Cys Pro Glu Asp Pro Trp Thr Val Gly
            115                 120                 125
Lys Asn Glu Phe Ser Gln Thr Val Gly Glu Val Phe Tyr Thr Lys Asn
130                 135                 140
Arg Asn Phe Cys Leu Pro Gly Val Pro Trp Asn Met Thr Val Ile Thr
145                 150                 155                 160
Ser Leu Gln Gln Glu Leu Cys Pro Ser Phe Leu Leu Pro Ser Ala Pro
                165                 170                 175
Ala Leu Gly Arg Cys Phe Pro Trp Thr Asn Val Thr Pro Pro Ala Leu
            180                 185                 190
Pro Gly Ile Thr Asn Asp Thr Thr Ile Gln Gln Gly Ile Ser Gly Leu
        195                 200                 205
Ile Asp Ser Leu Asn Ala Arg Asp Ile Ser Val Lys Ile Phe Glu Asp
210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Leu Arg Leu Val Ala Gly Pro
                245                 250                 255
Leu Val Leu Val Leu Ile Leu Gly Val Leu Gly Val Leu Ala Tyr Gly
            260                 265                 270
Ile Tyr Tyr Cys Trp Glu Glu Tyr Arg Val Leu Arg Asp Lys Gly Ala
        275                 280                 285
Ser Ile Ser Gln Leu Gly Phe Thr Thr Asn Leu Ser Ala Tyr Gln Ser
290                 295                 300
Val Gln Glu Thr Trp Leu Ala Ala Leu Ile Val Leu Ala Val Leu Glu
305                 310                 315                 320
Ala Ile Leu Leu Leu Met Leu Ile Phe Leu Arg Gln Arg Ile Arg Ile
                325                 330                 335
Ala Ile Ala Leu Leu Lys Glu Ala Ser Lys Ala Val Gly Gln Met Met
            340                 345                 350
Ser Thr Met Phe Tyr Pro Leu Val Thr Phe Val Leu Leu Leu Ile Cys
        355                 360                 365
Ile Ala Tyr Trp Ala Met Thr Ala Leu Tyr Pro Leu Pro Thr Gln Pro
370                 375                 380
Ala Thr Leu Gly Tyr Val Leu Trp Ala Ser Asn Ile Ser Ser Pro Gly
385                 390                 395                 400
Cys Glu Lys Val Pro Ile Asn Thr Ser Cys Asn Pro Thr Ala His Leu
                405                 410                 415
Val Asn Ser Ser Cys Pro Gly Leu Met Cys Val Phe Gln Gly Tyr Ser
            420                 425                 430
Ser Lys Gly Leu Ile Gln Arg Ser Val Phe Asn Leu Gln Ile Tyr Gly
        435                 440                 445
Val Leu Gly Leu Phe Trp Thr Leu Asn Trp Val Leu Ala Leu Gly Gln
450                 455                 460
Cys Val Leu Ala Gly Ala Phe Ala Ser Phe Tyr Trp Ala Phe His Lys
465                 470                 475                 480
Pro Gln Asp Ile Pro Thr Phe Pro Leu Ile Ser Ala Phe Ile Arg Thr
                485                 490                 495
Leu Arg Tyr His Thr Gly Ser Leu Ala Phe Gly Ala Leu Ile Leu Thr
            500                 505                 510
Leu Val Gln Ile Ala Arg Val Ile Leu Glu Tyr Ile Asp His Lys Leu
        515                 520                 525
Arg Gly Val Gln Asn Pro Val Ala Arg Cys Ile Met Cys Cys Phe Lys
530                 535                 540
```

```
Cys Cys Leu Trp Cys Leu Glu Lys Phe Ile Lys Phe Leu Asn Arg Asn
545                 550                 555                 560

Ala Tyr Ile Met Ile Ala Ile Tyr Gly Lys Asn Phe Cys Val Ser Ala
            565                 570                 575

Lys Asn Ala Phe Met Leu Leu Met Arg Asn Ile Val Arg Val Val Val
        580                 585                 590

Leu Asp Lys Val Thr Asp Leu Leu Leu Phe Phe Gly Lys Leu Leu Val
    595                 600                 605

Val Gly Gly Val Gly Val Leu Ser Phe Phe Phe Ser Gly Arg Ile
610                 615                 620

Pro Gly Leu Gly Lys Asp Phe Lys Ser Pro His Leu Asn Tyr Tyr Trp
625                 630                 635                 640

Leu Pro Ile Met Thr Ser Ile Leu Gly Ala Tyr Val Ile Ala Ser Gly
                645                 650                 655

Phe Phe Ser Val Phe Gly Met Cys Val Asp Thr Leu Phe Leu Cys Phe
            660                 665                 670

Leu Glu Asp Leu Glu Arg Asn Asn Gly Ser Leu Asp Arg Pro Tyr Tyr
        675                 680                 685

Met Ser Lys Ser Leu Leu Lys Ile Leu Gly Lys Lys Asn Glu Ala Pro
    690                 695                 700

Pro Asp Asn Lys Lys Arg Lys Lys
705                 710

<210> SEQ ID NO 110
<211> LENGTH: 710
<212> TYPE: PRT
<213> ORGANISM: Homo Sapiens

<400> SEQUENCE: 110

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
        35                  40                  45

Ile Val Val Gly Ile Val Ala Trp Leu Tyr Gly Asp Pro Arg Gln Val
    50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
    130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205
```

```
Ile Asp Ser Leu Asn Ala Arg Asp Ile Ser Val Lys Ile Phe Glu Asp
210                 215                 220
Phe Ala Gln Ser Trp Tyr Trp Ile Leu Val Ala Leu Gly Val Ala Leu
225                 230                 235                 240
Val Leu Ser Leu Leu Phe Ile Leu Leu Leu Arg Leu Val Ala Gly Pro
            245                 250                 255
Leu Val Leu Val Leu Ile Leu Gly Val Leu Gly Val Leu Ala Tyr Gly
            260                 265                 270
Ile Tyr Tyr Cys Trp Glu Glu Tyr Arg Val Leu Arg Asp Lys Gly Ala
            275                 280                 285
Ser Ile Ser Gln Leu Gly Phe Thr Thr Asn Leu Ser Ala Tyr Gln Ser
290                 295                 300
Val Gln Glu Thr Trp Leu Ala Ala Leu Ile Val Leu Ala Val Leu Glu
305                 310                 315                 320
Ala Ile Leu Leu Leu Met Leu Ile Phe Leu Arg Gln Arg Ile Arg Ile
                325                 330                 335
Ala Ile Ala Leu Leu Lys Glu Ala Ser Lys Ala Val Gly Gln Met Met
            340                 345                 350
Ser Thr Met Phe Tyr Pro Leu Val Thr Phe Val Leu Leu Leu Ile Cys
            355                 360                 365
Ile Ala Tyr Trp Ala Met Thr Ala Leu Tyr Leu Ala Thr Ser Gly Gln
370                 375                 380
Pro Gln Tyr Val Leu Trp Ala Ser Asn Ile Ser Ser Pro Gly Cys Glu
385                 390                 395                 400
Lys Val Pro Ile Asn Thr Ser Cys Asn Pro Thr Ala His Leu Val Asn
                405                 410                 415
Ser Ser Cys Pro Gly Leu Met Cys Val Phe Gln Gly Tyr Ser Ser Lys
            420                 425                 430
Gly Leu Ile Gln Arg Ser Val Phe Asn Leu Gln Ile Tyr Gly Val Leu
            435                 440                 445
Gly Leu Phe Trp Thr Leu Asn Trp Val Leu Ala Leu Gly Gln Cys Val
            450                 455                 460
Leu Ala Gly Ala Phe Ala Ser Phe Tyr Trp Ala Phe His Lys Pro Gln
465                 470                 475                 480
Asp Ile Pro Thr Phe Pro Leu Ile Ser Ala Phe Ile Arg Thr Leu Arg
                485                 490                 495
Tyr His Thr Gly Ser Leu Ala Phe Gly Ala Leu Ile Leu Thr Leu Val
            500                 505                 510
Gln Ile Ala Arg Val Ile Leu Glu Tyr Ile Asp His Lys Leu Arg Gly
            515                 520                 525
Val Gln Asn Pro Val Ala Arg Cys Ile Met Cys Cys Phe Lys Cys Cys
            530                 535                 540
Leu Trp Cys Leu Glu Lys Phe Ile Lys Phe Leu Asn Arg Asn Ala Tyr
545                 550                 555                 560
Ile Met Ile Ala Ile Tyr Gly Lys Asn Phe Cys Val Ser Ala Lys Asn
                565                 570                 575
Ala Phe Met Leu Leu Met Arg Asn Ile Val Arg Val Val Val Leu Asp
            580                 585                 590
Lys Val Thr Asp Leu Leu Leu Phe Phe Gly Lys Leu Leu Val Val Gly
            595                 600                 605
Gly Val Gly Val Leu Ser Phe Phe Phe Ser Gly Arg Ile Pro Gly
            610                 615                 620
Leu Gly Lys Asp Phe Lys Ser Pro His Leu Asn Tyr Tyr Trp Leu Pro
```

```
                625                 630                 635                 640
Ile Met Thr Ser Ile Leu Gly Ala Tyr Val Ile Ala Ser Gly Phe Phe
                    645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
            675                 680                 685

Lys Ser Leu Leu Lys Ile Leu Gly Lys Lys Asn Glu Ala Pro Pro Asp
            690                 695                 700

Asn Lys Lys Arg Lys Lys
705                 710

<210> SEQ ID NO 111
<211> LENGTH: 712
<212> TYPE: PRT
<213> ORGANISM: Homo Sapiens

<400> SEQUENCE: 111

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
    210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
```

-continued

```
              290                 295                 300
Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
                340                 345                 350

Ser Thr Met Phe Tyr Pro Leu Val Thr Phe Val Leu Leu Leu Ile Cys
                355                 360                 365

Ile Ala Tyr Trp Ala Met Thr Ala Leu Tyr Pro Leu Pro Thr Gln Pro
370                 375                 380

Ala Thr Leu Gly Tyr Val Leu Trp Ala Ser Asn Ile Ser Ser Pro Gly
385                 390                 395                 400

Cys Glu Lys Val Pro Ile Asn Thr Ser Cys Asn Pro Thr Ala His Leu
                405                 410                 415

Val Asn Ser Ser Cys Pro Gly Leu Met Cys Val Phe Gln Gly Tyr Ser
                420                 425                 430

Ser Lys Gly Leu Ile Gln Arg Ser Val Phe Asn Leu Gln Ile Tyr Gly
                435                 440                 445

Val Leu Gly Leu Phe Trp Thr Leu Asn Trp Val Leu Ala Leu Gly Gln
450                 455                 460

Cys Val Leu Ala Gly Ala Phe Ala Ser Phe Tyr Trp Ala Phe His Lys
465                 470                 475                 480

Pro Gln Asp Ile Pro Thr Phe Pro Leu Ile Ser Ala Phe Ile Arg Thr
                485                 490                 495

Leu Arg Tyr His Thr Gly Ser Leu Ala Phe Gly Ala Leu Ile Leu Thr
                500                 505                 510

Leu Val Gln Ile Ala Arg Val Ile Leu Glu Tyr Ile Asp His Lys Leu
                515                 520                 525

Arg Gly Val Gln Asn Pro Val Ala Arg Cys Ile Met Cys Cys Phe Lys
530                 535                 540

Cys Cys Leu Trp Cys Leu Glu Lys Phe Ile Lys Phe Leu Asn Arg Asn
545                 550                 555                 560

Ala Tyr Ile Met Ile Ala Ile Tyr Gly Lys Asn Phe Cys Val Ser Ala
                565                 570                 575

Lys Asn Ala Phe Met Leu Leu Met Arg Asn Ile Val Arg Val Val Val
                580                 585                 590

Leu Asp Lys Val Thr Asp Leu Leu Leu Phe Phe Gly Lys Leu Leu Val
                595                 600                 605

Val Gly Gly Val Gly Val Leu Ser Phe Phe Phe Ser Gly Arg Ile
610                 615                 620

Pro Gly Leu Gly Lys Asp Phe Lys Ser Pro His Leu Asn Tyr Tyr Trp
625                 630                 635                 640

Leu Pro Ile Met Thr Ser Ile Leu Gly Ala Tyr Val Ile Ala Ser Gly
                645                 650                 655

Phe Phe Ser Val Phe Gly Met Cys Val Asp Thr Leu Phe Leu Cys Phe
                660                 665                 670

Leu Glu Asp Leu Glu Arg Asn Asn Gly Ser Leu Asp Arg Pro Tyr Tyr
                675                 680                 685

Met Ser Lys Ser Leu Leu Lys Ile Leu Gly Lys Lys Asn Glu Ala Pro
                690                 695                 700

Pro Asp Asn Lys Lys Arg Lys Lys
705                 710
```

```
<210> SEQ ID NO 112
<211> LENGTH: 710
<212> TYPE: PRT
<213> ORGANISM: Homo sapiens

<400> SEQUENCE: 112

Met Gly Gly Lys Gln Arg Asp Glu Asp Glu Ala Tyr Gly Lys Pro
1               5                   10                  15

Val Lys Tyr Asp Pro Ser Phe Arg Gly Pro Ile Lys Asn Arg Ser Cys
            20                  25                  30

Thr Asp Val Ile Cys Cys Val Leu Phe Leu Leu Phe Ile Leu Gly Tyr
                35                  40                  45

Ile Val Val Gly Ile Val Ala Trp Leu Tyr Gly Asp Pro Arg Gln Val
        50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Val Cys Val Ser Ser Cys Pro Glu Asp Pro Trp Thr Val Gly
        115                 120                 125

Lys Asn Glu Phe Ser Gln Thr Val Gly Glu Val Phe Tyr Thr Lys Asn
130                 135                 140

Arg Asn Phe Cys Leu Pro Gly Val Pro Trp Asn Met Thr Val Ile Thr
145                 150                 155                 160

Ser Leu Gln Gln Glu Leu Cys Pro Ser Phe Leu Leu Pro Ser Ala Pro
                165                 170                 175

Ala Leu Gly Arg Cys Phe Pro Trp Thr Asn Val Thr Pro Pro Ala Leu
            180                 185                 190

Pro Gly Ile Thr Asn Asp Thr Thr Ile Gln Gln Gly Ile Ser Gly Leu
        195                 200                 205

Ile Asp Ser Leu Asn Ala Arg Asp Ile Ser Val Lys Ile Phe Glu Asp
210                 215                 220

Phe Ala Gln Ser Trp Tyr Trp Ile Leu Val Ala Leu Gly Val Ala Leu
225                 230                 235                 240

Val Leu Ser Leu Leu Phe Ile Leu Leu Leu Arg Leu Val Ala Gly Pro
                245                 250                 255

Leu Val Leu Val Leu Ile Leu Gly Val Leu Gly Val Leu Ala Tyr Gly
            260                 265                 270

Ile Tyr Tyr Cys Trp Glu Glu Tyr Arg Val Leu Arg Asp Lys Gly Ala
        275                 280                 285

Ser Ile Ser Gln Leu Gly Phe Thr Thr Asn Leu Ser Ala Tyr Gln Ser
290                 295                 300

Val Gln Glu Thr Trp Leu Ala Ala Leu Ile Val Leu Ala Val Leu Glu
305                 310                 315                 320

Ala Ile Leu Leu Leu Met Leu Ile Phe Leu Arg Gln Arg Ile Arg Ile
                325                 330                 335

Ala Ile Ala Leu Leu Lys Glu Ala Ser Lys Ala Val Gly Gln Met Met
            340                 345                 350

Ser Thr Met Phe Tyr Pro Leu Val Thr Phe Val Leu Leu Leu Ile Cys
        355                 360                 365

Ile Ala Tyr Trp Ala Met Thr Ala Leu Tyr Leu Ala Thr Ser Gly Gln
370                 375                 380
```

-continued

```
Pro Gln Tyr Val Leu Trp Ala Ser Asn Ile Ser Ser Pro Gly Cys Glu
385                 390                 395                 400

Lys Val Pro Ile Asn Thr Ser Cys Asn Pro Thr Ala His Leu Val Asn
                405                 410                 415

Ser Ser Cys Pro Gly Leu Met Cys Val Phe Gln Gly Tyr Ser Ser Lys
            420                 425                 430

Gly Leu Ile Gln Arg Ser Val Phe Asn Leu Gln Ile Tyr Gly Val Leu
            435                 440                 445

Gly Leu Phe Trp Thr Leu Asn Trp Val Leu Ala Leu Gly Gln Cys Val
        450                 455                 460

Leu Ala Gly Ala Phe Ala Ser Phe Tyr Trp Ala Phe His Lys Pro Gln
465                 470                 475                 480

Asp Ile Pro Thr Phe Pro Leu Ile Ser Ala Phe Ile Arg Thr Leu Arg
                485                 490                 495

Tyr His Thr Gly Ser Leu Ala Phe Gly Ala Leu Ile Leu Thr Leu Val
            500                 505                 510

Gln Ile Ala Arg Val Ile Leu Glu Tyr Ile Asp His Lys Leu Arg Gly
            515                 520                 525

Val Gln Asn Pro Val Ala Arg Cys Ile Met Cys Cys Phe Lys Cys Cys
530                 535                 540

Leu Trp Cys Leu Glu Lys Phe Ile Lys Phe Leu Asn Arg Asn Ala Tyr
545                 550                 555                 560

Ile Met Ile Ala Ile Tyr Gly Lys Asn Phe Cys Val Ser Ala Lys Asn
                565                 570                 575

Ala Phe Met Leu Leu Met Arg Asn Ile Val Arg Val Val Leu Asp
            580                 585                 590

Lys Val Thr Asp Leu Leu Leu Phe Phe Gly Lys Leu Leu Val Val Gly
            595                 600                 605

Gly Val Gly Val Leu Ser Phe Phe Phe Ser Gly Arg Ile Pro Gly
610                 615                 620

Leu Gly Lys Asp Phe Lys Ser Pro His Leu Asn Tyr Tyr Trp Leu Pro
625                 630                 635                 640

Ile Met Thr Ser Ile Leu Gly Ala Tyr Val Ile Ala Ser Gly Phe Phe
                645                 650                 655

Ser Val Phe Gly Met Cys Val Asp Thr Leu Phe Leu Cys Phe Leu Glu
            660                 665                 670

Asp Leu Glu Arg Asn Asn Gly Ser Leu Asp Arg Pro Tyr Tyr Met Ser
            675                 680                 685

Lys Ser Leu Leu Lys Ile Leu Gly Lys Lys Asn Glu Ala Pro Pro Asp
    690                 695                 700

Asn Lys Lys Arg Lys Lys
705             710
```